United States Patent
Kessler et al.

(10) Patent No.: US 12,053,473 B2
(45) Date of Patent: *Aug. 6, 2024

(54) BENZYLAMINO SUBSTITUTED QUINAZOLINES AND DERIVATIVES AS SOS1 INHIBITORS

(71) Applicant: Boehringer Ingelheim International GmbH, Ingelheim am Rhein (DE)

(72) Inventors: Dirk Kessler, Vienna (AT); Christiane Kofink, Perchtoldsdorf (AT); Matthew Russell Netherton, Danbury, CT (US); Juergen Ramharter, Vienna (AT); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 439 days.

This patent is subject to a terminal disclaimer.

(21) Appl. No.: 17/077,232

(22) Filed: Oct. 22, 2020

(65) Prior Publication Data
US 2021/0177851 A1 Jun. 17, 2021

Related U.S. Application Data

(63) Continuation of application No. 16/472,433, filed as application No. PCT/EP2017/084265 on Dec. 21, 2017, now Pat. No. 10,898,487.

(30) Foreign Application Priority Data

Dec. 22, 2016 (EP) .................... 16206422

(51) Int. Cl.
*A61K 31/517* (2006.01)
*A61K 9/20* (2006.01)
*A61K 31/337* (2006.01)
*A61K 31/496* (2006.01)
*A61K 31/506* (2006.01)
*A61K 31/519* (2006.01)
*A61K 31/5377* (2006.01)
(Continued)

(52) U.S. Cl.
CPC .......... *A61K 31/517* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 31/337* (2013.01); *A61K 31/496* (2013.01); *A61K 31/506* (2013.01); *A61K 31/519* (2013.01); *A61K 31/5377* (2013.01); *A61K 31/7068* (2013.01); *A61P 35/00* (2018.01); *C07D 239/94* (2013.01); *C07D 401/14* (2013.01); *C07D 403/10* (2013.01); *C07D 405/12* (2013.01); *C07D 405/14* (2013.01); *C07D 409/10* (2013.01); *C07D 413/10* (2013.01); *C07D 487/04* (2013.01)

(58) Field of Classification Search
CPC .. A61K 31/517; A61K 31/337; A61K 31/496; A61K 31/506; A61K 31/519; A61K 31/5377; A61K 31/7068; A61K 9/2009; A61K 9/2018; A61K 9/2027; A61K 9/2054; A61K 9/2059; C07D 239/94; C07D 401/14; C07D 403/10; C07D 405/12; C07D 405/14; C07D 405/4091; C07D 413/10; C07D 487/04
See application file for complete search history.

(56) References Cited

U.S. PATENT DOCUMENTS 5,654,307 A 8/1997 Bridges et al.
6,174,899 B1 1/2001 Shulman
(Continued)

FOREIGN PATENT DOCUMENTS

WO 2008116742 A1 10/2008
WO 2008150118 A2 12/2008
(Continued)

OTHER PUBLICATIONS

Baltanás et al., "Functional Redundancy of Sos1 and Sos2 for Lymphopoiesis and Organismal Homeostasis and Survival", Mol. Cell. Biol., 2013, 33(22), pp. 4562-4578.
(Continued)

*Primary Examiner* — Erich A Leeser
(74) *Attorney, Agent, or Firm* — Philip I. Datlow

(57) ABSTRACT

The present invention encompasses compounds of formula (I)

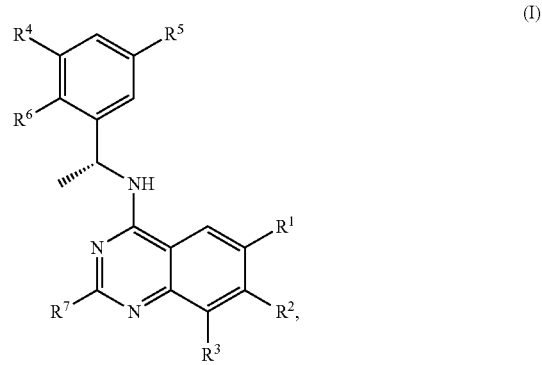

wherein the groups $R^1$ to $R^7$ have the meanings given in the claims and specification, their use as inhibitors of SOS1, pharmaceutical compositions which contain compounds of this kind and their use as medicaments/medical uses, especially as agents for treatment and/or prevention of oncological diseases.

5 Claims, 18 Drawing Sheets

(51) Int. Cl.
| | |
|---|---|
| A61K 31/7068 | (2006.01) |
| A61P 35/00 | (2006.01) |
| C07D 239/94 | (2006.01) |
| C07D 401/14 | (2006.01) |
| C07D 403/10 | (2006.01) |
| C07D 405/12 | (2006.01) |
| C07D 405/14 | (2006.01) |
| C07D 409/10 | (2006.01) |
| C07D 413/10 | (2006.01) |
| C07D 487/04 | (2006.01) |

(56) References Cited

U.S. PATENT DOCUMENTS

| | | | |
|---|---|---|---|
| 10,898,487 B2 * | 1/2021 | Kessler | A61P 9/00 |
| 2011/0136838 A1 | 6/2011 | Atkinson et al. | |
| 2022/0249492 A1 | 8/2022 | Gmachl et al. | |

FOREIGN PATENT DOCUMENTS

| | | |
|---|---|---|
| WO | 2010019637 A1 | 2/2010 |
| WO | 2010060940 A2 | 6/2010 |
| WO | 2011053861 A1 | 5/2011 |
| WO | 2012078677 A2 | 6/2012 |
| WO | 2013016197 A1 | 1/2013 |
| WO | 2013136254 A1 | 9/2013 |
| WO | 2016077793 A1 | 5/2016 |
| WO | 2018115380 A1 | 6/2018 |
| WO | 2018172250 A1 | 9/2018 |
| WO | 2020254451 A1 | 12/2020 |

OTHER PUBLICATIONS

Bid et al., "RAC1: an emerging therapeutic option for targeting cancer angiogenesis and metastasis", Mol. Cancer Ther. 2013, 12(10), pp. 1925-1934.
Buday et al., "Many faces of Ras activation", Biochim. Biophys. Acta., 2008, 1786(2), pp. 178-187.
Burns et al., "Approach for targeting Ras with small molecules that activate SOS-mediated nucleotide exchange", Proc. Natl. Acad. Sci. 2014, 111(9), pp. 3401-3406.
Cancer Genome Atlas Research Network., "Comprehensive molecular profiling of lung adenocarcinoma", Nature, 2014, 511(7511), pp. 543-550.
Chardin et al., "Chromosomal localization of two genes encoding human ras exchange factors: SOS1 maps to the 2p22→p16 region and SOS2 to the 14q21→q22 region of the human genome", Science, 1993, 260(5112), pp. 1338-1343.
Chardin et al., "Human Sos1: a guanine nucleotide exchange factor for Ras that binds to GRB2", Cytogenet. Cell. Genet., 1994, 66(1), pp. 68-69.
Cox et al., "Drugging the undruggable RAS: Mission possible", Nat. Rev. Drug Discov., 2014, 13(11), pp. 828-851.
Denayer et al., "Tumor spectrum in children with Noonan syndrome and SOS1 or RAF1 mutations", Genes Chromosomes Cancer, 2010, 49(3), pp. 242-252.
Eberlein et al., "Acquired Resistance to the Mutant-Selective EGFR Inhibitor AZD9291 Is Associated with Increased Dependence on RAS Signaling in Preclinical Models", Cancer Res., 2015, 75(12), pp. 2489-2500.
Esteban et al., "Ras-guanine nucleotide exchange factor sos2 is dispensable for mouse growth and development", Mol. Cell. Biol., 2000, 20(17), pp. 6410-6413.

Evelyn et al., "Rational design of small molecule inhibitors targeting the Ras GEF, SOS1", Chem. Biol. 2014, 21(12), pp. 1618-1628.
Evelyn et al., "Rational design of small molecule inhibitors targeting the Ras GEF, SOS1", J. Biol. Chem. 2015, 290 (20), pp. 12879-12898.
Freedman et al., "A Ras-induced conformational switch in the Ras activator Son of sevenless", Proc. Natl. Acad. Sci. U S A., 2006, 103(45), pp. 16692-16697.
Hou Ju et al., "Design, synthesis, anti-tumor activity, and molecular modeling of quinazoline and pyrido[2,3-d] byrimidine derivatives targeting epidermal growth factor receptor", European Journal of Medicinal Chemistry, Editions Scientifique Elsevier, Paris, FR, vol. 118, Apr. 20, 2016 (Apr. 20, 2016), pp. 276-289.
Hunter et al., "Biochemical and Structural Analysis of Common Cancer-Associated KRAS Mutations", Mol. Cancer Res., 2015, 13(9), pp. 1325-1335.
Innocenti et al., "Mechanisms through which Sos-1 coordinates the activation of Ras and Rac", J. Cell Biol., 2002, 156 (1), pp. 125-136.
International Search Report and Written Opinion for corresponding application, PCT/EP2017/084265, date of mailing Apr. 23, 2018.
Jeng et al., "Sos-mediated cross-activation of wild-type Ras by oncogenic Ras is essential for tumorigenesis", Nat. Commun., 2012, 3, pp. 1168.
Kardinal et al., "Chronic myelogenous leukemia blast cell proliferation is inhibited by peptides that disrupt Grb2-SoS complexes", Blood, 2001, 98, pp. 1773-1781.
Leto et al., "Primary and acquired resistance to EGFR-targeted therapies in colorectal cancer: impact on future treatment strategies", J. Mol. Med. (Berl). Jul. 2014;92(7), pp. 709-722.
Lu et al., "Inhibitors of Ras-SOS Interactions", ChemMedChem. 2016, 11(8), pp. 814-821.
McCormick et al., "K-Ras protein as a drug target", J. Mol. Med. (Berl)., 2016, 94(3), pp. 253-258.
McCormick et al., "The potential of targeting Ras proteins in lung cancer", Expert Opin. Ther. Targets., 2015, 19(4), pp. 451-454.
Nimnual et al., "The two hats of SOS", Sci. STKE., 2002, 2002(145), p. 36.
Ortiz-Cuaran et al., "Heterogeneous Mechanisms of Primary and Acquired Resistance to Third-Generation EGFR Inhibitors", Clin. Cancer Res., 2016, 22(19), pp. 4837-4847.
Pierre et al., "Understanding SOS (Son of Sevenless)", Biochem. Pharmacol., 2011, 82(9), pp. 1049-1056.
Qian et al., "The Sos1 and Sos2 Ras-specific exchange factors: differences in placental expression and signaling properties.", EMBO J., 2000, 19(4), pp. 642-654.
Rodriguez-Viciana et al., "RalGDS comes of age", Cancer Cell. 2005, 7(3), pp. 205-206.
Salojin et al., "ZAP-70 is essential for the T cell antigen receptor-induced plasma membrane targeting of SOS and Vav in T cells", J. Biol. Chem. 2000, 275(8), pp. 5966-5975.
Sini et al., "Abl-dependent tyrosine phosphorylation of Sos-1 mediates growth-factor-induced Rac activation", Nat. Cell Biol., 2004, 6(3), pp. 268-274.
Timofeeva et al., "Enhanced expression of SOS1 is detected in prostate cancer epithelial cells from African-American men", Int. J. Oncol., 2009, 35(4), pp. 751-760.
Watanabe et al., "Significance of the Grb2 and son of sevenless (Sos) proteins in human bladder cancer cell lines", IUBMB Life., 2000, 49(4), pp. 317-320.
Winter et al., "Small molecule binding sites on the Ras:SOS complex can be exploited for inhibition of Ras activation", J. Med. Chem. 2015, 58(5), pp. 2265-2274.
Young et al., "Ras signaling and therapies", Adv. Cancer Res., 2009, 102, pp. 1-17.

* cited by examiner a)

b)

a)

b)

a)

b)

a)

b)

a)

b)

a)

b)

a)

b)

a)

b)

a)

b)

a)

b)

a)

b)

BENZYLAMINO SUBSTITUTED QUINAZOLINES AND DERIVATIVES AS SOS1 INHIBITORS

FIELD OF THE INVENTION

The present invention relates to new benzylamino substituted quinazolines and derivatives of formula (I)

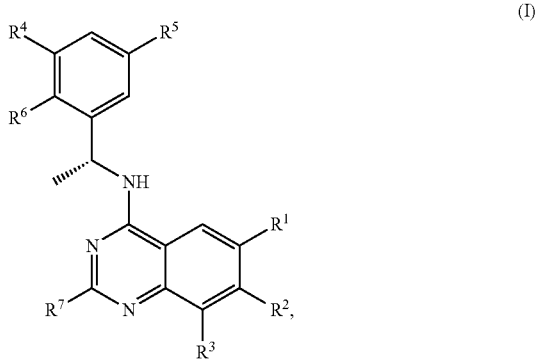

wherein the groups $R^1$ to $R^7$ have the meanings given in the claims and specification, their use as inhibitors of SOS1, pharmaceutical compositions which contain compounds of this kind and their use as medicaments/medical uses, especially as agents for treatment and/or prevention of oncological diseases.

BACKGROUND OF THE INVENTION

RAS-family proteins including KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof are small GTPases that exist in cells in either GTP-bound or GDP-bound states (McCormick et al., J. Mol. Med. (Berl)., 2016, 94(3):253-8; Nimnual et al., Sci. STKE., 2002, 2002 (145):pe36). The RAS-family proteins have a weak intrinsic GTPase activity and slow nucleotide exchange rates (Hunter et al., Mol. Cancer Res., 2015, 13(9):1325-35). Binding of GTPase activating proteins (GAPs) such as NF1 increases the GTPase activity of RAS-family proteins. The binding of guanine nucleotide exchange factors (GEFs) such as SOS1 (Son of Sevenless 1) promote release GDP from RAS-family proteins, enabling GTP binding (Chardin et al., Science, 1993, 260(5112):1338-43). When in the GTP-bound state, RAS-family proteins are active and engage effector proteins including C-RAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RalGDS (Ral guanine nucleotide dissociation stimulator) pathway (McCormick et al., J. Mol. Med. (Berl)., 2016, 94(3):253-8; Rodriguez-Viciana et al., Cancer Cell. 2005, 7(3):205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7(3): 205-6).

Cancer-associated mutations in RAS-family proteins suppress their intrinsic and GAP-induced GTPase activity leading to an increased population of GTP-bound/active RAS-family proteins (McCormick et al., Expert Opin. Ther. Targets., 2015, 19(4):451-4; Hunter et al., Mol. Cancer Res., 2015, 13(9):1325-35). This in turn leads to persistent activation of effector pathways (e.g. MEK/ERK, PI3K/AKT/mTOR, RalGDS pathways) downstream of RAS-family proteins. KRAS mutations (e.g. amino acids G12, G13, Q61, A146) are found in a variety of human cancers including lung cancer, colorectal cancer and pancreatic cancer (Cox et al., Nat. Rev. Drug Discov., 2014, 13(11):828-51). Mutations in HRAS (e.g. amino acids G12, G13, Q61) and NRAS (e.g. amino acids G12, G13, Q61, A146) are also found in a variety of human cancer types however typically at a lower frequency compared to KRAS mutations (Cox et al., Nat. Rev. Drug Discov., 2014, 13(11):828-51). Alterations (e.g. mutation, over-expression, gene amplification) in RAS-family proteins have also been described as a resistance mechanism against cancer drugs such as the EGFR antibodies cetuximab and panitumumab (Leto et al., J. Mol. Med. (Berl). 2014 July; 92(7):709-22) and the EGFR tyrosine kinase inhibitor osimertinib/AZD9291 (Ortiz-Cuaran et al., Clin. Cancer Res., 2016, 22(19):4837-47; Eberlein et al., Cancer Res., 2015, 75(12):2489-500).

Son of Sevenless 1 (SOS1) is a human homologue of the originally identified *Drosophila* protein Son of Sevenless (Pierre et al., Biochem. Pharmacol., 2011, 82(9):1049-56; Chardin et al., Cytogenet. Cell. Genet., 1994, 66(1):68-9). The SOS1 protein consists of 1333 amino acids (150 kDa). SOS1 is a multi-domain protein with two tandem N-terminal histone domains (HD) followed by the Dbl homology domain (DH), a Pleckstrin homology domain (PH), a helical linker (HL), RAS exchanger motif (REM), CDCl25 homology domain and a C-terminal proline rich domain (PR). SOS1 has two binding sites for RAS-family proteins; a catalytic site that binds GDP-bound RAS-family proteins to promote guanine nucleotide exchange and an allosteric site that binds GTP-bound RAS-family proteins which causes a further increase in the catalytic GEF function of SOS1 (Freedman et al., Proc. Natl. Acad. Sci. USA., 2006, 103 (45):16692-7; Pierre et al., Biochem. Pharmacol., 2011, 82(9):1049-56). Published data indicate a critical involvement of SOS1 in mutant KRAS activation and oncogenic signaling in cancer (Jeng et al., Nat. Commun., 2012, 3:1168). Depleting SOS1 levels decreased the proliferation rate and survival of tumor cells carrying a KRAS mutation whereas no effect was observed in KRAS wild type cell lines. The effect of loss of SOS1 could not be rescued by introduction of a catalytic site mutated SOS1, demonstrating the essential role of SOS1 GEF activity in KRAS mutant cancer cells.

SOS1 is critically involved in the activation of RAS-family protein signaling in cancer via mechanisms other than mutations in RAS-family proteins. SOS1 interacts with the adaptor protein Grb2 and the resulting SOS1/Grb2 complex binds to activated/phosphorylated Receptor Tyrosine Kinases (e.g. EGFR, ErbB2, ErbB3, ErbB4, PDGFR-A/B, FGFR1/2/3, IGF1R, INSR, ALK, ROS, TrkA, TrkB, TrkC, RET, c-MET, VEGFR1/2/3, AXL) (Pierre et al., Biochem. Pharmacol., 2011, 82(9):1049-56). SOS1 is also recruited to other phosphorylated cell surface receptors such as the T cell Receptor (TCR), B cell Receptor (BCR) and monocyte colony-stimulating factor receptor (Salojin et al., J. Biol. Chem. 2000, 275(8):5966-75). This localization of SOS1 to the plasma membrane, proximal to RAS-family proteins, enables SOS1 to promote RAS-family protein activation. SOS1-activation of RAS-family proteins can also be mediated by the interaction of SOS1/Grb2 with the BCR-ABL oncoprotein commonly found in chronic myelogenous leukemia (Kardinal et al., 2001, Blood, 98:1773-81; Sini et al., Nat. Cell Biol., 2004, 6(3):268-74).

Furthermore, alterations in SOS1 have been implicated in cancer. SOS1 mutations are found in embryonal rhabdomyosarcomas, sertoli cell testis tumors, granular cell tumors of the skin (Denayer et al., Genes Chromosomes Cancer, 2010, 49(3):242-52) and lung adenocarcinoma (Cancer Genome Atlas Research Network., Nature. 2014, 511(7511):543-50). Meanwhile over-expression of SOS1 has been described in bladder cancer (Watanabe et al., IUBMB Life., 2000, 49(4):317-20) and prostate cancer (Timofeeva et al., Int. J. Oncol., 2009; 35(4):751-60). In addition to cancer, hereditary SOS1 mutations are implicated in the pathogenesis of RASopathies like e.g. Noonan syndrome (NS), cardio-facio-cutaneous syndrome (CFC) and hereditary gingival fibromatosis type 1 (Pierre et al., Biochem. Pharmacol., 2011, 82(9):1049-56).

SOS1 is also a GEF for the activation of the GTPases RAC1 (Ras-related C3 botulinum toxin substrate 1) (Innocenti et al., J. Cell Biol., 2002, 156(1):125-36). RAC1, like RAS-family proteins, is implicated in the pathogenesis of a variety of human cancers and other diseases (Bid et al., Mol. Cancer Ther. 2013, 12(10):1925-34).

Son of Sevenless 2 (SOS2), a homolog of SOS1 in mammalian cells, also acts as a GEF for the activation of RAS-family proteins (Pierre et al., Biochem. Pharmacol., 2011, 82(9):1049-56; Buday et al., Biochim. Biophys. Acta., 2008, 1786(2):178-87). Published data from mouse knockout models suggests a redundant role for SOS1 and SOS2 in homeostasis in the adult mouse. Whilst germline knockout of SOS1 in mice results in lethality during mid-embryonic gestation (Qian et al., EMBO J., 2000, 19(4):642-54), systemic conditional SOS1 knockout adult mice are viable (Baltanns et al., Mol. Cell. Biol., 2013, 33(22):4562-78). SOS2 gene targeting did not result in any overt phenotype in mice (Esteban et al., Mol. Cell. Biol., 2000, 20(17):6410-3). In contrast, double SOS1 and SOS2 knockout leads to rapid lethality in adult mice (Baltanns et al., Mol. Cell. Biol., 2013, 33(22):4562-78). These published data suggest that selective targeting of individual SOS isoforms (e.g. selective SOS1 targeting) may be adequately tolerated to achieve a therapeutic index between SOS1/RAS-family protein driven cancers (or other SOS1/RAS-family protein pathologies) and normal cells and tissues.

Selective pharmacological inhibition of the binding of the catalytic site of SOS1 to RAS-family proteins is expected to prevent SOS1-mediated activation of RAS-family proteins to the GTP-bound form. Such SOS1 inhibitor compounds are be expected to consequently inhibit signaling in cells downstream of RAS-family proteins (e.g. ERK phosphorylation). In cancer cells associated with dependence on RAS-family proteins (e.g. KRAS mutant cancer cell lines), SOS1 inhibitor compounds are be expected to deliver anti-cancer efficacy (e.g. inhibition of proliferation, survival, metastasis etc.). High potency towards inhibition of SOS1:RAS-family protein binding (nanomolar level $IC_{50}$ values) and ERK phosphorylation in cells (nanomolar level $IC_{50}$ values) are desirable characteristics for a SOS1 inhibitor compound. Furthermore, a desirable characteristic of SOS1 inhibitor compound would be the selective inhibition of SOS1 over SOS2. This conclusion is based on the viable phenotype of SOS1 knockout mice and lethality of SOS1/SOS2 double knockout mice, as described above.

These characteristics have not been achieved in previously described SOS1 inhibitor compounds. In the last decades the RAS family proteins-SOS1 protein interaction has gained increasing recognition. Until today several efforts to identify and optimize binders, which target either the effector binding site of RAS or the catalytic binding site of SOS1 (for a selected review see: Lu et al., ChemMedChem. 2016, 11(8):814-21), have been made with limited success.

Recently, small activating molecules have been identified, which bind to a lipophilic pocket of SOS1 in close proximity to the RAS binding site (Burns et al., Proc. Natl. Acad. Sci. 2014, 111(9):3401-6). However, binding of these molecules seems to lead to increased nucleotide exchange and thereby activation of RAS instead of deactivation.

In an effort to stabilize the protein-protein-interaction of RAS-family proteins with SOS1 and to prevent reloading of RAS-family proteins with GTP, several different fragments were subsequently identified (Winter et al., J. Med. Chem. 2015, 58(5):2265-74). However, reversible binding of fragments to SOS1 did not translate into a measurable effect on the nucleotide exchange and only a weak effect was observed for fragments covalently bound to RAS.

Also recently, studies have been conducted to combine rational design and screening platforms to identify small molecule inhibitors of SOS1 (Evelyn et al., Chem. Biol. 2014, 21(12):1618-28; Evelyn et al., J. Biol. Chem. 2015, 290(20):12879-98; Zheng et al., WO 2016/077793), i.e. compounds which bind to SOS1 and inhibit protein-protein interaction with RAS-family proteins. Although compounds with a slight inhibitory effect on SOS1 have been identified, the effects on guanine nucleotide exchange and cellular signal transduction modulation (e.g. ERK phosphorylation) are weak.

Herein we describe novel SOS1 inhibitor compounds, which bind to the SOS1 catalytic site (confirmed by means of crystallography) and simultaneously prevent interactions with and activation of RAS-family proteins. This results in a pronounced inhibitory effect on the interaction of SOS1 with RAS-family proteins, in particular KRAS (with low single digit nanomolar $IC_{50}$ activity) and consequently a significant reduction of ERK phosphorylation in KRAS mutant cancer cell lines The selective SOS1 inhibitor compounds described herein are expected to deliver a pharmacological benefit to patients with cancers that are associated with dependence on RAS-family protein signaling. Such cancers expected to be targeted by a SOS1 inhibitor compound include those exhibiting alterations (mutations, gene amplification, overexpression) of components (proteins, genes) in the RAS-family protein pathway such as KRAS, NRAS, HRAS, receptor tyrosine kinases (e.g. EGFR, ErbB2, ErbB3, ErbB4, PDGFR-A/B, FGFR1/2/3, IGF1R, INSR, ALK, ROS, TrkA, TrkB, TrkC, RET, c-MET, VEGFR1/2/3, AXL), GAPs (e.g. NF1) and SOS1. Additionally, given the role of SOS1 in RAC1 activation, cancers demonstrating dependence on RAC1 are expected to be targeted by SOS1 inhibitor compounds. Furthermore, in other diseases associated with RAS-family protein pathway dysregulation such as the neurofibromatosis, Noonan syndrome (NS), cardio-facio-cutaneous syndrome (CFC) and hereditary gingival fibromatosis type 1, SOS1 inhibitor compounds would also be expected to deliver a pharmacological benefit.

In addition to the inhibitory effect and potency, compounds disclosed herein show good solubility, fine-tuned DMPK properties and good selectivity over kinases of the human kinome.

DETAILED DESCRIPTION OF THE INVENTION

Compounds

It has now been found that, surprisingly, compounds of formula (I) wherein the groups $R^1$ to $R^7$ have the meanings given hereinafter act as inhibitors of the interaction of the catalytic site of SOS1 with RAS-family proteins which is involved in controlling cell proliferation. Thus, the compounds according to the invention may be used for example for the treatment of diseases characterised by excessive or abnormal cell proliferation.

The present invention therefore relates to a compound of formula (I)

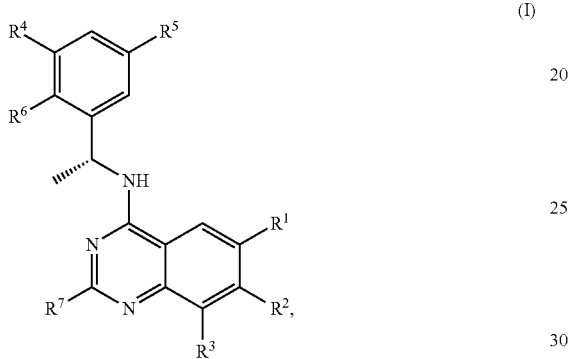

(I)

wherein
[A0]
$R^1$ is —O—$R^4$;
- $R^4$ is selected from the group consisting of $C_{3-10}$cycloalkyl and 3-10 membered heterocyclyl, wherein the $C_{3-10}$cycloalkyl and 3-10 membered heterocyclyl are both optionally substituted by one or more, identical or different $R^{a1}$ and/or $R^{b1}$;
- each $R^{a1}$ is independently selected from the group consisting of $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{b1}$ and/or $R^{c1}$;
- each $R^{b1}$ is independently selected from the group consisting of —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$, —$N(C_{1-4}alkyl)C(O)R^{c1}$ and the bivalent substituent =O, while =O may only be a substituent in non-aromatic ring systems;
- each $R^{c1}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl;

or
$R^1$ is selected from the group consisting of $C_{3-10}$cycloalkyl, $C_{3-10}$cycloalkenyl, $C_{6-10}$aryl, 3-10 membered heterocyclyl and 5-10 membered heteroaryl, wherein the $C_{3-10}$cycloalkyl, $C_{3-10}$cycloalkenyl, $C_{6-10}$aryl, 3-10 membered heterocyclyl and 5-10 membered heteroaryl are all optionally substituted by one or more, identical or different $R^{a2}$ and/or $R^{b2}$;
- each $R^{a2}$ is independently selected from the group consisting of $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{b2}$ and/or $R^{c2}$;
- each $R^{b2}$ is independently selected from the group consisting of —$OR^{c2}$, —$NR^{c2}R^{c2}$, halogen, —CN, —$C(O)R^{c2}$, —$C(O)OR^{c2}$, —$C(O)NR^{c2}R^{c2}$, —OC(O)$R^{c2}$, —$S(O)_2R^{c2}$, —$S(O)_2NR^{c2}R^{c2}$, —$NHC(O)R^{c2}$, —$N(C_{1-4}alkyl)C(O)R^{c2}$, —$NHC(O)OR^{c2}$ and the bivalent substituents =O and =NH, while =O and =NH may only be a substituent in non-aromatic ring systems;
- each $R^{c2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{d2}$ and/or $R^{e2}$;
- each $R^{d2}$ is independently selected from the group consisting of —$OR^{e2}$, —$NR^{e2}R^{e2}$, halogen, —CN, —$C(O)R^{e2}$, —$C(O)OR^{e2}$, —$C(O)NR^{e2}R^{e2}$, —$S(O)_2R^{e2}$, —$S(O)_2NR^{e2}R^{e2}$, —$NHC(O)R^{e2}$, —$N(C_{1-4}alkyl)C(O)R^{e2}$ and the bivalent substituent =O, while =O may only be a substituent in non-aromatic ring systems;
- each $R^{e2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{f2}$ and/or $R^{g2}$;
- each $R^{f2}$ is independently selected from the group consisting of —$OR^{g2}$, —$NR^{g2}R^{g2}$, halogen, —CN, —$C(O)R^{g2}$, —$C(O)OR^{g2}$, —$C(O)NR^{g2}R^{g2}$, —$S(O)_2R^{g2}$, —$S(O)_2NR^{g2}R^{g2}$, —$NHC(O)R^{g2}$, —$N(C_{1-4}alkyl)C(O)R^{g2}$ and the bivalent substituent =O, while =O may only be a substituent in non-aromatic ring systems;
- each $R^{g2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl;

or
$R^1$ is selected from the group consisting of $C_{2-4}$alkyl and $C_{2-4}$alkenyl, wherein the $C_{2-4}$alkyl and $C_{2-4}$alkenyl are both substituted with $R^{b3}$;
- $R^{b3}$ is selected from the group consisting of —$C(O)R^{c3}$, —$C(O)OR^{c3}$, —$C(O)NR^{c3}R^{c3}$, —$C(O)NHOR^{c3}$ and —$C(O)N(C_{1-4}alkyl)OR^{c3}$;
- each $R^{c3}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{d3}$ and/or $R^{e3}$;

each $R^{d3}$ is independently selected from the group consisting of —$OR^{e3}$, —$NR^{e3}R^{e3}$, halogen, —CN, —C(O)$R^{e3}$, —C(O)O$R^{e3}$, —C(O)N$R^{e3}R^{e3}$, —S(O)$_2R^{e3}$, —S(O)$_2NR^{e3}R^{e3}$, —NHC(O)$R^{e3}$, —N(C$_{1-4}$alkyl)C(O)$R^{e3}$ and the bivalent substituent =O, while =O may only be a substituent in non-aromatic ring systems;

each $R^{e3}$ is independently selected from the group consisting of hydrogen, C$_{1-6}$alkyl, C$_{2-6}$alkenyl, C$_{2-6}$alkynyl, C$_{3-10}$cycloalkyl, C$_{6-10}$aryl, 3-10 membered heterocyclyl and 5-10 membered heteroaryl;

[B0]
$R^2$ is selected from the group consisting of hydrogen, C$_{1-4}$alkyl, —O—C$_{1-4}$alkyl, —NH$_2$, —NH(C$_{1-4}$alkyl), —N(C$_{1-4}$alkyl)$_2$ and halogen;

[C0]
$R^3$ is selected from the group consisting of hydrogen, C$_{1-4}$alkyl, —O—C$_{1-4}$alkyl, —NH$_2$, —NH(C$_{1-4}$alkyl), —N(C$_{1-4}$alkyl)$_2$ and halogen;

[D0]
$R^4$ is selected from the group consisting of C$_{1-4}$alkyl, C$_{1-4}$haloalkyl, hydroxy-C$_{1-4}$alkyl, hydroxy-C$_{1-4}$haloalkyl, C$_{3-6}$cycloalkyl, hydroxy-C$_{3-6}$cycloalkyl, 3-6 membered heterocyclyl, 3-6 membered hydroxy-heterocyclyl, halogen and —SO$_2$—C$_{1-4}$alkyl;

[E0]
$R^5$ is selected from the group consisting of hydrogen and —NH$_2$;

[F0]
$R^6$ is selected from the group consisting of hydrogen, C$_{1-4}$alkyl and halogen;

[G0]
$R^7$ is selected from the group consisting of C$_{1-4}$alkyl and C$_{1-4}$haloalkyl;
or a salt thereof.

In one aspect [A1] the invention relates to a compound of formula (I), wherein
$R^1$ is —O—$R^4$;
$R^4$ is selected from the group consisting of C$_{3-10}$cycloalkyl and 3-10 membered heterocyclyl, wherein the C$_{3-10}$cycloalkyl and 3-10 membered heterocyclyl are both optionally substituted by one or more, identical or different $R^{a1}$ and/or $R^{b1}$;
each $R^{a1}$ is independently selected from the group consisting of C$_{1-6}$alkyl, C$_{2-6}$alkenyl, C$_{2-6}$alkynyl, C$_{3-10}$cycloalkyl, C$_{6-10}$aryl, 3-10 membered heterocyclyl and 5-10 membered heteroaryl, wherein the C$_{1-6}$alkyl, C$_{2-6}$alkenyl, C$_{2-6}$alkynyl, C$_{3-10}$cycloalkyl, C$_{6-10}$aryl, 3-10 membered heterocyclyl and 5-10 membered heteroaryl are all optionally substituted by one or more, identical or different $R^{b1}$ and/or $R^{c1}$;
each $R^{b1}$ is independently selected from the group consisting of —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2NR^{c1}R^{c1}$, —NHC(O)$R^{c1}$, —N(C$_{1-4}$alkyl)C(O)$R^{c1}$ and the bivalent substituent =O, while =O may only be a substituent in non-aromatic ring systems;
each $R^{c1}$ is independently selected from the group consisting of hydrogen, C$_{1-6}$alkyl, C$_{2-6}$alkenyl, C$_{2-6}$alkynyl, C$_{3-10}$cycloalkyl, C$_{6-10}$aryl, 3-10 membered heterocyclyl and 5-10 membered heteroaryl;
or a salt thereof.

In another aspect [A2] the invention relates to a compound of formula (I), wherein
$R^1$ is —O—$R^4$;
$R^4$ is 3-10 membered heterocyclyl optionally substituted by one or more, identical or different $R^{a1}$ and/or $R^{b1}$;
each $R^{a1}$ is independently selected from the group consisting of C$_{1-6}$alkyl, C$_{3-10}$cycloalkyl, C$_{6-10}$aryl, 3-10 membered heterocyclyl and 5-10 membered heteroaryl, wherein the C$_{1-6}$alkyl, C$_{3-10}$cycloalkyl, C$_{6-10}$aryl, 3-10 membered heterocyclyl and 5-10 membered heteroaryl are all optionally substituted by one or more, identical or different $R^{b1}$ and/or $R^{c1}$;
each $R^{b1}$ is independently selected from the group consisting of —$OR^{c1}$, —$NR^{c1}R^{c1}$, halogen, —C(O)$R^{c1}$, —C(O)O$R^{c1}$, —C(O)N$R^{c1}R^{c1}$ and the bivalent substituent =O, while =O may only be a substituent in non-aromatic ring systems;
each $R^{c1}$ is independently selected from the group consisting of hydrogen, C$_{1-6}$alkyl, C$_{3-10}$cycloalkyl, C$_{6-10}$aryl, 3-10 membered heterocyclyl and 5-10 membered heteroaryl;
or a salt thereof.

In another aspect [A3] the invention relates to a compound of formula (I), wherein
$R^1$ is —O—$R^4$;
$R^4$ is 3-7 membered heterocyclyl optionally substituted by one or more, identical or different $R^{b1}$;
each $R^{b1}$ is independently selected from the group consisting of —$OR^{c1}$, —$NR^{c1}R^{c1}$, halogen, —C(O)$R^{c1}$, —C(O)O$R^{c1}$, —C(O)N$R^{c1}R^{c1}$ and the bivalent substituent =O;
each $R^{c1}$ is independently selected from the group consisting of hydrogen, C$_{1-6}$alkyl and C$_{3-7}$cycloalkyl;
or a salt thereof.

In another aspect [A4] the invention relates to a compound of formula (I), wherein
$R^1$ is —O—$R^4$;
$R^4$ is selected from the group consisting of tetrahydrofuryl and pyrrolidinyl, wherein the tetrahydrofuryl and pyrrolidinyl are both optionally substituted by one or more, identical or different $R^{b1}$;
each $R^{b1}$ is independently selected from the group consisting of —$OR^{c1}$, —$NR^{c1}R^{c1}$, halogen, —C(O)$R^{c1}$, —C(O)O$R^{c1}$, —C(O)N$R^{c1}R^{c1}$ and the bivalent substituent =O, while =O may only be a substituent in non-aromatic ring systems;
each $R^{c1}$ is independently selected from the group consisting of hydrogen, C$_{1-6}$alkyl and C$_{3-7}$cycloalkyl;
or a salt thereof.

In another aspect [A5] the invention relates to a compound of formula (I), wherein
$R^1$ is —O—$R^4$;
$R^4$ is selected from the group consisting of tetrahydrofuryl and pyrrolidinyl, wherein the tetrahydrofuryl and pyrrolidinyl are both optionally substituted by $R^{b1}$;
$R^{b1}$ is independently selected from the group consisting of —C(O)$R^{c1}$ and —C(O)O$R^{c1}$;
each $R^{c1}$ is independently selected from the group consisting of C$_{1-6}$alkyl and C$_{3-7}$cycloalkyl;
or a salt thereof.

In another aspect [A6] the invention relates to a compound of formula (I), wherein
$R^1$ is —O—$R^4$;
$R^4$ is pyrrolidinyl optionally substituted (preferably on nitrogen) by $R^{b1}$;
$R^{b1}$ is independently selected from the group consisting of —C(O)$R^{c1}$ and —C(O)O$R^{c1}$;
each $R^{c1}$ is independently selected from the group consisting of C$_{1-6}$alkyl and C$_{3-7}$cycloalkyl;
or a salt thereof.

In another aspect [A7] the invention relates to a compound of formula (I), wherein
R¹ is —O—R$^A$;
R$^A$ is tetrahydrofuryl
or a salt thereof.

In another aspect [A8] the invention relates to a compound of formula (I), wherein
R¹ is selected from the group consisting of

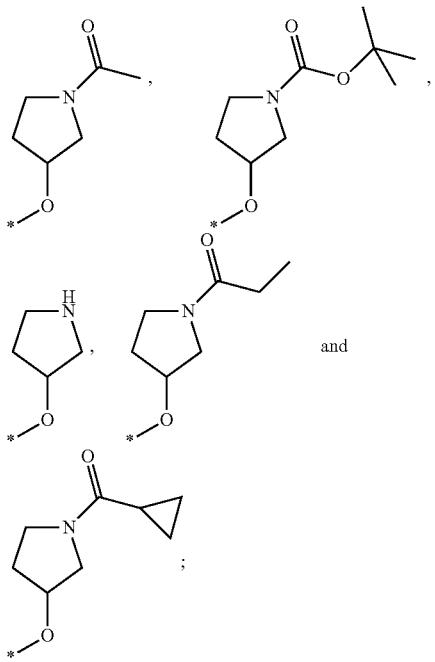

or a salt thereof.

In another aspect [A9] the invention relates to a compound of formula (I), wherein
R¹ is selected from the group consisting of

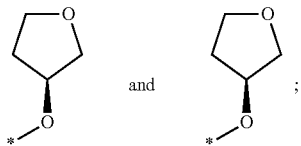 [SMILES: *O[C@H]1CCOC1 ; *O[C@H]1CCOC1]

or a salt thereof.

In another aspect [A10] the invention relates to a compound of formula (I), wherein
R¹ is selected from the group consisting of $C_{3-10}$cycloalkyl, $C_{3-10}$cycloalkenyl, $C_{6-10}$aryl, 3-10 membered heterocyclyl and 5-10 membered heteroaryl, wherein the $C_{3-10}$cycloalkyl, $C_{3-10}$cycloalkenyl, $C_{6-10}$aryl, 3-10 membered heterocyclyl and 5-10 membered heteroaryl are all optionally substituted by one or more, identical or different $R^{a2}$ and/or $R^{b2}$;
each $R^{a2}$ is independently selected from the group consisting of $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{b2}$ and/or $R^{c2}$;
each $R^{b2}$ is independently selected from the group consisting of —OR$^{c2}$, —NR$^{c2}$R$^{c2}$, halogen, —CN, —C(O)R$^{c2}$, —C(O)OR$^{c2}$, —C(O)NR$^{c2}$R$^{c2}$, —OC(O)R$^{c2}$, —S(O)$_2$R$^{c2}$, —S(O)$_2$NR$^{c2}$R$^{c2}$, —NHC(O)R$^{c2}$, —N(C$_{1-4}$alkyl)C(O)R$^{c2}$, —NHC(O)OR$^{c2}$ and the bivalent substituents =O and =NH, while =O and =NH may only be a substituent in non-aromatic ring systems;
each $R^{c2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{d2}$ and/or $R^{e2}$;
each $R^{d2}$ is independently selected from the group consisting of —OR$^{e2}$, —NR$^{e2}$R$^{e2}$, halogen, —CN, —C(O)R$^{e2}$, —C(O)OR$^{e2}$, —C(O)NR$^{e2}$R$^{e2}$, —S(O)$_2$R$^{e2}$, —S(O)$_2$NR$^{e2}$R$^{e2}$, —NHC(O)R$^{e2}$, —N(C$_{1-4}$alkyl)C(O)R$^{e2}$ and the bivalent substituent =O, while =O may only be a substituent in non-aromatic ring systems;
each $R^{e2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{f2}$ and/or $R^{g2}$;
each $R^{f2}$ is independently selected from the group consisting of —OR$^{g2}$, —NR$^{g2}$R$^{g2}$, halogen, —CN, —C(O)R$^{g2}$, —C(O)OR$^{g2}$, —C(O)NR$^{g2}$R$^{g2}$, —S(O)$_2$R$^{g2}$, —S(O)$_2$NR$^{g2}$R$^{g2}$, —NHC(O)R$^{g2}$, —N(C$_{1-4}$alkyl)C(O)R$^{g2}$ and the bivalent substituent =O, while =O may only be a substituent in non-aromatic ring systems;
each $R^{g2}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl;
or a salt thereof.

In another aspect [A11] the invention relates to a compound of formula (I), wherein
R¹ is selected from the group consisting of $C_{3-7}$cycloalkyl, $C_{3-7}$cycloalkenyl, $C_{6-10}$aryl, 3-10 membered heterocyclyl and 5-10 membered heteroaryl, wherein the $C_{3-7}$cycloalkyl, $C_{3-7}$cycloalkenyl, $C_{6-10}$aryl, 3-10 membered heterocyclyl and 5-10 membered heteroaryl are all optionally substituted by one or more, identical or different $R^{a2}$ and/or $R^{b2}$;
each $R^{a2}$ is independently selected from the group consisting of $C_{1-6}$alkyl, $C_{3-7}$cycloalkyl, $C_{6-10}$aryl, 3-7 membered heterocyclyl and 5-6 membered heteroaryl, wherein the $C_{1-6}$alkyl, $C_{3-7}$cycloalkyl, $C_{6-10}$aryl, 3-7 membered heterocyclyl and 5-6 membered heteroaryl are all optionally substituted by one or more, identical or different $R^{b2}$ and/or $R^{c2}$;
each $R^{b2}$ is independently selected from the group consisting of —OR$^{c2}$, —NR$^{c2}$R$^{c2}$, halogen, —CN, —C(O)R$^{c2}$, —C(O)OR$^{c2}$, —C(O)NR$^{c2}$R$^{c2}$, —OC(O)R$^{c2}$, —S(O)$_2$R$^{c2}$, —S(O)$_2$NR$^{c2}$R$^{c2}$, —NHC(O)

R$^{c2}$, —N(C$_{1-4}$alkyl)C(O)R$^{c2}$, —NHC(O)OR$^{c2}$ and the bivalent substituents =O and =NH, while =O and =NH may only be a substituent in non-aromatic ring systems;

each R$^{c2}$ is independently selected from the group consisting of hydrogen, C$_{1-6}$alkyl, C$_{3-7}$cycloalkyl, C$_{6-10}$aryl, 3-7 membered heterocyclyl and 5-6 membered heteroaryl, wherein the C$_{1-6}$alkyl, C$_{3-7}$cycloalkyl, C$_{6-10}$aryl, 3-7 membered heterocyclyl and 5-6 membered heteroaryl are all optionally substituted by one or more, identical or different R$^{d2}$ and/or R$^{e2}$;

each R$^{d2}$ is independently selected from the group consisting of —OR$^{e2}$, —NR$^{e2}$R$^{e2}$, halogen, —CN, —C(O)R$^{e2}$, —C(O)OR$^{e2}$ and —C(O)NR$^{e2}$R$^{e2}$;

each R$^{e2}$ is independently selected from the group consisting of hydrogen, C$_{1-6}$alkyl, C$_{3-7}$cycloalkyl, C$_{6-10}$aryl, 3-7 membered heterocyclyl and 5-6 membered heteroaryl, wherein the C$_{1-6}$alkyl, C$_{3-7}$cycloalkyl, C$_{6-10}$aryl, 3-7 membered heterocyclyl and 5-6 membered heteroaryl are all optionally substituted by one or more, identical or different R$^{f2}$ and/or R$^{g2}$;

each R$^{f2}$ is independently selected from the group consisting of —OR$^{g2}$, —NR$^{g2}$R$^{g2}$, halogen, —CN, —C(O)R$^{g2}$, —C(O)OR$^{g2}$ and —C(O)NR$^{g2}$R$^{g2}$;

each R$^{g2}$ is independently selected from the group consisting of hydrogen, C$_{1-6}$alkyl, C$_{3-7}$cycloalkyl, C$_{6-10}$aryl, 3-7 membered heterocyclyl and 5-6 membered heteroaryl;

or a salt thereof.

In another aspect [A12] the invention relates to a compound of formula (I), wherein R$^1$ is selected from the group consisting of C$_{3-7}$cycloalkyl, C$_{3-7}$cycloalkenyl, C$_{6-10}$aryl, 3-10 membered heterocyclyl and 5-10 membered heteroaryl, wherein the C$_{3-7}$cycloalkyl, C$_{3-7}$cycloalkenyl, C$_{6-10}$aryl, 3-10 membered heterocyclyl and 5-10 membered heteroaryl are all optionally substituted by one or more, identical or different R$^{a2}$ and/or R$^{b2}$;

each R$^{a2}$ is independently selected from the group consisting of C$_{1-6}$alkyl and 3-7 membered heterocyclyl, wherein the C$_{1-6}$alkyl and 3-7 membered heterocyclyl are both optionally substituted by one or more, identical or different R$^{b2}$ and/or R$^{c2}$;

each R$^{b2}$ is independently selected from the group consisting of —OR$^{c2}$, —NR$^{c2}$R$^{c2}$, halogen, —C(O)R$^{c2}$, —C(O)OR$^{c2}$, —C(O)NR$^{c2}$R$^{c2}$, —OC(O)R$^{c2}$, —NHC(O)R$^{c2}$, —N(C$_{1-4}$alkyl)C(O)R$^{c2}$, —NHC(O)OR$^{c2}$ and the bivalent substituents =O and =NH, while =O and =NH may only be a substituent in non-aromatic ring systems;

each R$^{c2}$ is independently selected from the group consisting of hydrogen, C$_{1-6}$alkyl and 3-7 membered heterocyclyl, wherein the C$_{1-6}$alkyl and 3-7 membered heterocyclyl are both optionally substituted by one or more, identical or different R$^{d2}$ and/or R$^{e2}$;

each R$^{d2}$ is independently selected from the group consisting of —OR$^{e2}$, —NR$^{e2}$R$^{e2}$, halogen and —CN;

each R$^{e2}$ is independently selected from the group consisting of hydrogen, C$_{1-6}$alkyl and C$_{6-10}$aryl, wherein the C$_{1-6}$alkyl and C$_{6-10}$aryl are both optionally substituted by one or more, identical or different R$^{f2}$ and/or R$^{g2}$;

each R$^{f2}$ is —OR$^{g2}$;

each R$^{g2}$ is C$_{1-6}$alkyl;

or a salt thereof.

In another aspect [A13] the invention relates to a compound of formula (I), wherein R$^1$ is selected from the group consisting of C$_{3-7}$cycloalkyl, C$_{3-7}$cycloalkenyl and 3-10 membered heterocyclyl, wherein the C$_{3-7}$cycloalkyl, C$_{3-7}$cycloalkenyl and 3-10 membered heterocyclyl are all optionally substituted by one or more, identical or different R$^{a2}$ and/or R$^{b2}$;

each R$^{a2}$ is independently selected from the group consisting of C$_{1-6}$alkyl and 3-7 membered heterocyclyl, wherein the C$_{1-6}$alkyl and 3-7 membered heterocyclyl are both optionally substituted by one or more, identical or different R$^{b2}$ and/or R$^{c2}$;

each R$^{b2}$ is independently selected from the group consisting of —OR$^{c2}$, —C(O)R$^{c2}$, —C(O)OR$^{c2}$, —C(O)NR$^{c2}$R$^{c2}$, —OC(O)R$^{c2}$ and the bivalent substituent =O;

each R$^{c2}$ is independently selected from the group consisting of hydrogen, C$_{1-6}$alkyl and 3-7 membered heterocyclyl, wherein the C$_{1-6}$alkyl and 3-7 membered heterocyclyl are both optionally substituted by one or more, identical or different R$^{d2}$ and/or R$^{e2}$;

each R$^{d2}$ is independently selected from the group consisting of —OR$^{e2}$, —NR$^{e2}$R$^{e2}$, halogen and —CN;

each R$^{e2}$ is independently selected from the group consisting of hydrogen and C$_{1-6}$alkyl, wherein the C$_{1-6}$alkyl is optionally substituted by one or more, identical or different R$^{f2}$ and/or R$^{g2}$;

each R$^{f2}$ is —OR$^{g2}$;

each R$^{g2}$ is C$_{1-6}$alkyl;

or a salt thereof.

In another aspect [A14] the invention relates to a compound of formula (I), wherein R$^1$ is

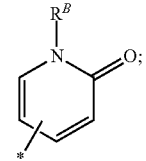

R$^B$ is selected from the group consisting of hydrogen and C$_{1-6}$alkyl, wherein the C$_{1-6}$alkyl is optionally substituted by R$^{b2}$;

R$^{b2}$ is selected from the group consisting of —C(O)OR$^{c2}$ and —C(O)NR$^{c2}$R$^{c2}$;

each R$^{c2}$ is independently selected from the group consisting of hydrogen and C$_{1-6}$alkyl;

or a salt thereof.

In another aspect [A15] the invention relates to a compound of formula (I), wherein R$^1$ is selected from the group consisting of

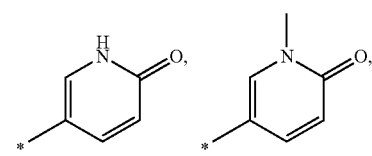

13

-continued

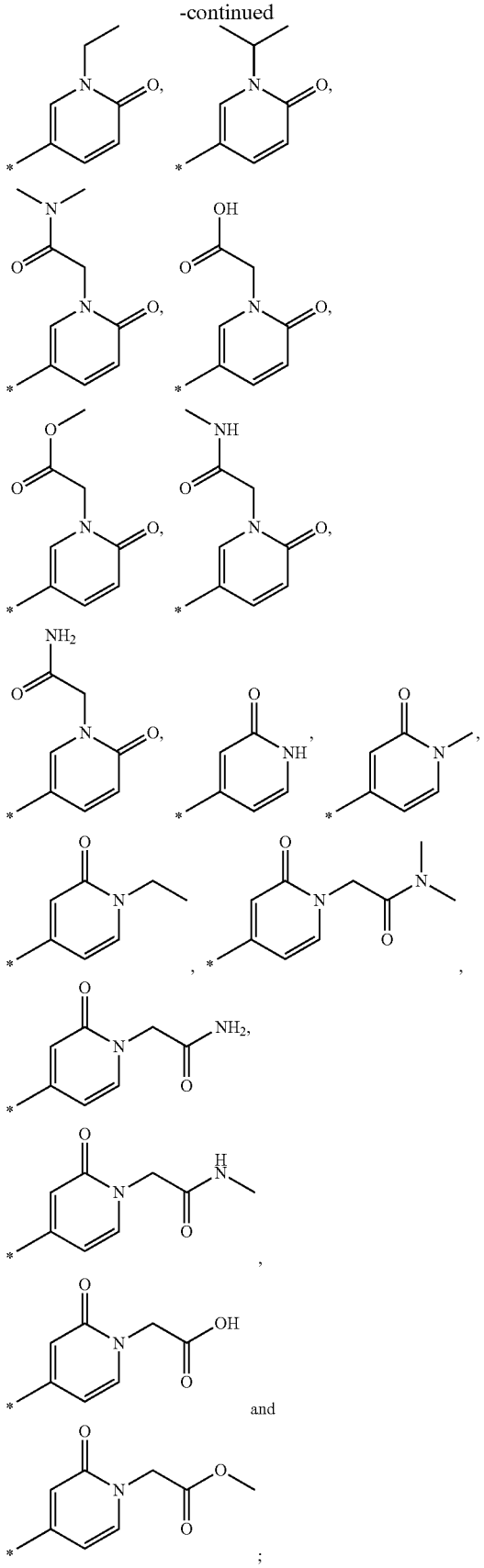

or a salt thereof.

14

In another aspect [A16] the invention relates to a compound of formula (I), wherein
R$^1$ is

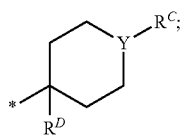

Y is selected from the group consisting of CH and N;
R$^C$ is selected from the group consisting of hydrogen, R$^{a2}$ and R$^{b2}$;
  R$^{a2}$ is selected from the group consisting of C$_{1-6}$alkyl and 3-7 membered heterocyclyl, wherein the C$_{1-6}$alkyl is optionally substituted by C(O)NR$^{c2}$R$^{c2}$ or —C(O)OR$^{c2}$;
  R$^{b2}$ is selected from the group consisting of —OR$^{e2}$, —C(O)R$^{c2}$, —C(O)OR$^{c2}$, —C(O)NR$^{c2}$R$^{c2}$ and —OC(O)R$^{c2}$;
  each R$^{c2}$ is independently selected from the group consisting of hydrogen, C$_{1-6}$alkyl and 3-7 membered heterocyclyl, wherein the C$_{1-6}$alkyl is optionally substituted by one or more, identical or different R$^{d2}$ and/or R$^{e2}$;
  each R$^{d2}$ is independently selected from the group consisting of —OR$^{e2}$, —NR$^{e2}$R$^{e2}$, halogen and —CN;
  each R$^{e2}$ is independently selected from the group consisting of hydrogen and C$_{1-6}$alkyl, wherein the C$_{1-6}$alkyl is optionally substituted by one or more, identical or different R$^{f2}$ and/or R$^{g2}$;
  each R$^{f2}$ is —OR$^{g2}$;
  each R$^{g2}$ is C$_{1-6}$alkyl;
R$^D$ is selected from the group consisting of hydrogen and —OH;
or a salt thereof.

In another aspect [A17] the invention relates to a compound of formula (I), wherein
R$^1$ is selected from the group consisting of

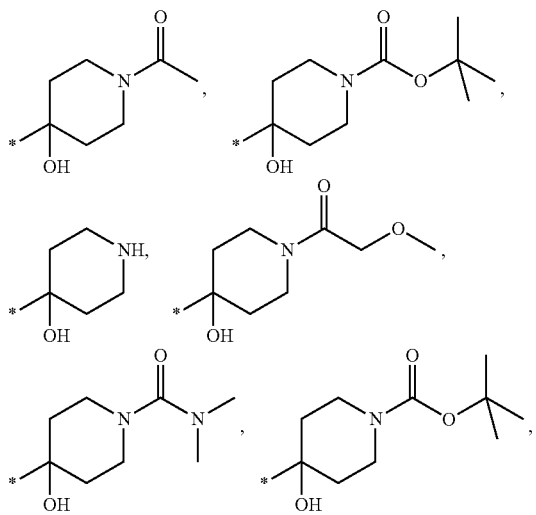

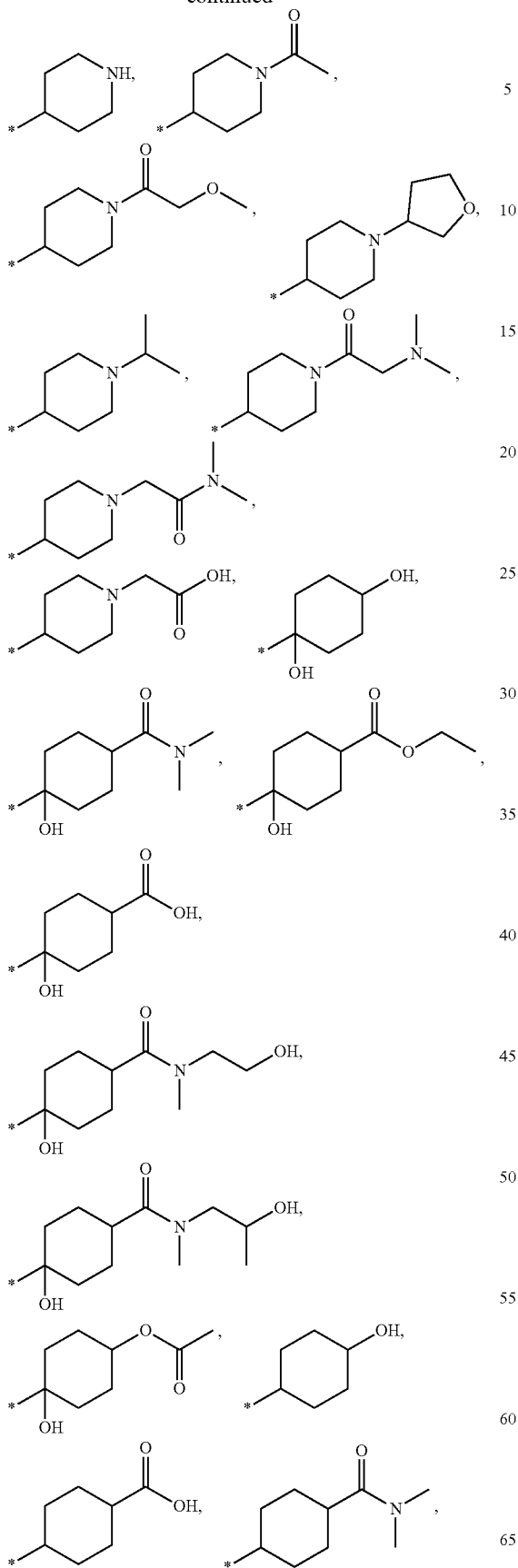
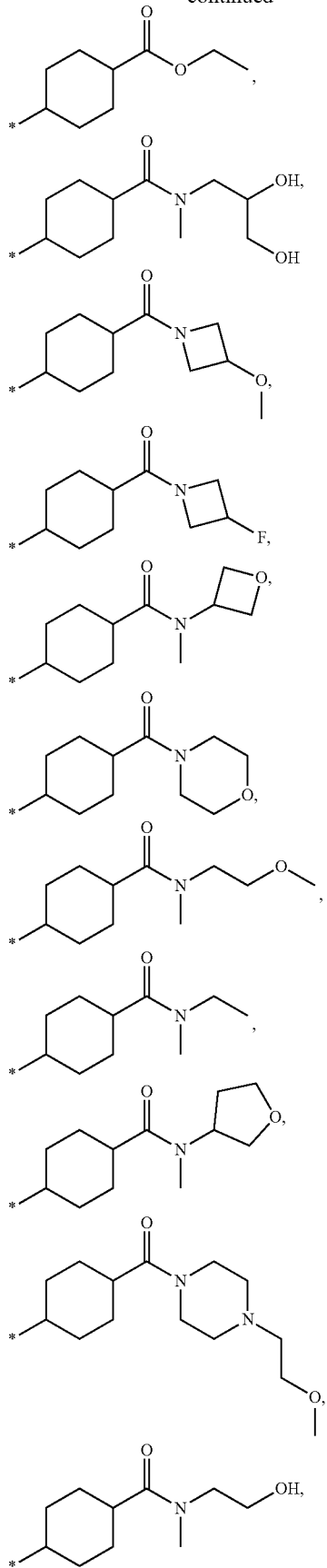

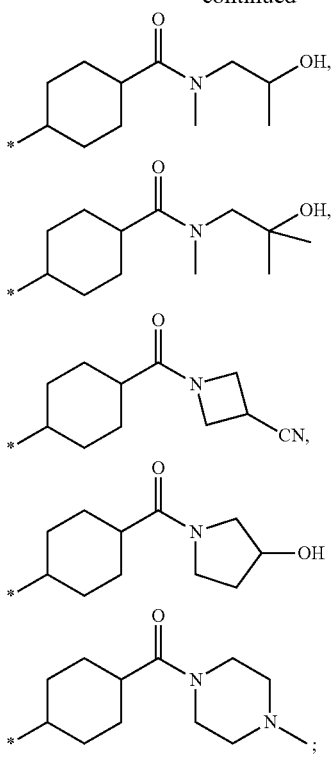

or a salt thereof.

In another aspect [A18] the invention relates to a compound of formula (I), wherein R¹ is

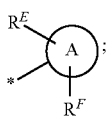

ring A is selected from the group consisting of pyridyl, pyrazolyl and phenyl;

$R^E$ is selected from the group consisting of $R^{a2}$ and $R^{b2}$;

$R^{a2}$ is selected from the group consisting of $C_{1-6}$alkyl and 3-7 membered heterocyclyl, wherein the $C_{1-6}$alkyl and 3-7 membered heterocyclyl are both optionally substituted by —C(O)NR$^{c2}$R$^{c2}$, —C(O)OR$^{c2}$ or —C(O)R$^{c2}$;

$R^{b2}$ is independently selected from the group consisting of —OR$^{c2}$, —C(O)OR$^{c2}$ and —C(O)NR$^{c2}$R$^{c2}$;

each $R^{c2}$ is independently selected from the group consisting of hydrogen, $C_{1-6}$alkyl and 3-7 membered heterocyclyl, wherein the $C_{1-6}$alkyl and 3-7 membered heterocyclyl are both optionally substituted by $R^{d2}$;

$R^{d2}$ is —OR$^{e2}$;

$R^{e2}$ is independently selected from the group consisting of hydrogen and $C_{1-6}$alkyl;

$R^F$ is selected from the group consisting of hydrogen, $C_{1-4}$alkoxy and $C_{1-4}$alkyl; or a salt thereof.

In another aspect [A19] the invention relates to a compound of formula (I), wherein R¹ is selected from the group consisting of

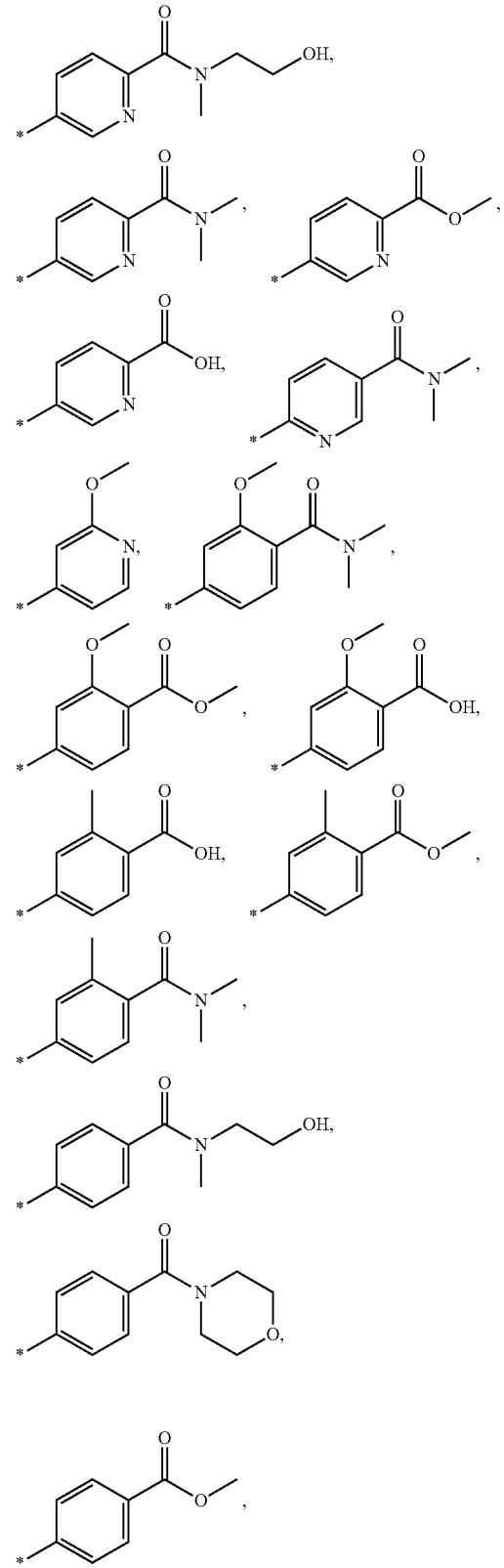

-continued

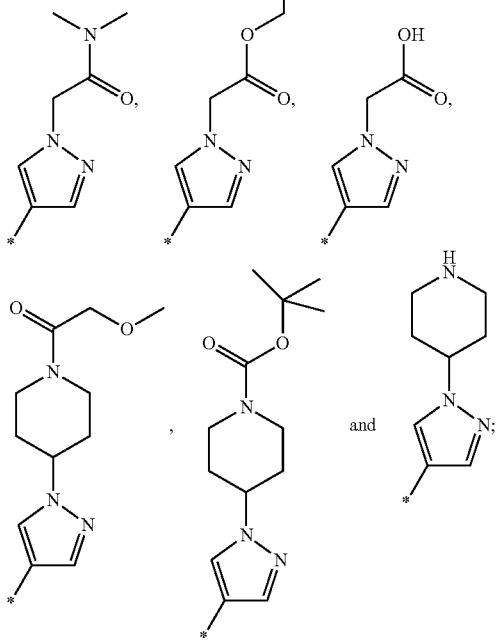

or a salt thereof.

In another aspect [A20] the invention relates to a compound of formula (I), wherein
- $R^1$ is selected from the group consisting of $C_{2-4}$alkyl and $C_{2-4}$alkenyl, wherein the $C_{2-4}$alkyl and $C_{2-4}$alkenyl are both substituted with $R^{b3}$;
- $R^{b3}$ is selected from the group consisting of —C(O)$R^{c3}$, —C(O)O$R^{c3}$, —C(O)NR$^{c3}$R$^{e3}$, —C(O)NHOR$^{c3}$ and —C(O)N(C$_{1-4}$alkyl)OR$^{c3}$;
- each $R^{c3}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl, wherein the $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl are all optionally substituted by one or more, identical or different $R^{d3}$ and/or $R^{e3}$;
- each $R^{d3}$ is independently selected from the group consisting of —OR$^{e3}$, —NR$^e$R$^{e3}$, halogen, —CN, —C(O)R$^{e3}$, —C(O)OR$^{e3}$, —C(O)NR$^{e3}$R$^{e3}$, —S(O)$_2$R$^{e3}$, —S(O)$_2$NR$^{e3}$R$^{e3}$, —NHC(O)R$^{e3}$, —N(C$_{1-4}$alkyl)C(O)R$^{e3}$ and the bivalent substituent =O, while =O may only be a substituent in non-aromatic ring systems;
- each $R^{e3}$ is independently selected from the group consisting of hydrogen, $C_{1-6}$alkyl, $C_{2-6}$alkenyl, $C_{2-6}$alkynyl, $C_{3-10}$cycloalkyl, $C_{6-10}$aryl, 3-10 membered heterocyclyl and 5-10 membered heteroaryl;

or a salt thereof.

In another aspect [A21] the invention relates to a compound of formula (I), wherein
- $R^1$ is selected from the group consisting of $C_{2-4}$alkyl and $C_{2-4}$alkenyl, wherein the $C_{2-4}$alkyl and $C_{2-4}$alkenyl are both substituted with $R^{b3}$;
- $R^{b3}$ is selected from the group consisting of —C(O)$R^{c3}$, —C(O)OR$^{c3}$, —C(O)NR$^{c3}$R$^{e3}$, —C(O)NHOR$^{c3}$ and —C(O)N(C$_{1-4}$alkyl)OR$^{c3}$;
- each $R^{c3}$ is independently selected from the group consisting of hydrogen, $C_{1-6}$alkyl, $C_{3-7}$cycloalkyl, $C_{6-10}$aryl, 3-7 membered heterocyclyl and 5-6 membered heteroaryl, wherein the $C_{1-6}$alkyl, $C_{3-7}$cycloalkyl, $C_{6-10}$aryl, 3-7 membered heterocyclyl and 5-6 membered heteroaryl are all optionally substituted by one or more, identical or different $R^{d3}$ and/or $R^{e3}$;
- each $R^{d3}$ is independently selected from the group consisting of —OR$^{e3}$, —NR$^{e3}$R$^{e3}$, halogen, —CN, —C(O)R$^{e3}$, —C(O)OR$^{e3}$, —C(O)NR$^{e3}$R$^{e3}$, —S(O)$_2$R$^{e3}$, —S(O)$_2$NR$^{e3}$R$^{e3}$, —NHC(O)R$^{e3}$ and —N(C$_{1-4}$alkyl)C(O)R$^{e3}$;
- each $R^{e3}$ is independently selected from the group consisting of hydrogen, $C_{1-6}$alkyl, $C_{3-7}$cycloalkyl, $C_{6-10}$aryl, 3-7 membered heterocyclyl and 5-6 membered heteroaryl;

or a salt thereof.

In another aspect [A22] the invention relates to a compound of formula (I), wherein
- $R^1$ is selected from the group consisting of $C_{2-4}$alkyl and $C_{2-4}$alkenyl, wherein the $C_{2-4}$alkyl and $C_{2-4}$alkenyl are both substituted with $R^{b3}$;
- $R^{b3}$ is selected from the group consisting of —C(O)OR$^{c3}$, —C(O)NR$^{c3}$R$^{e3}$ and —C(O)NHOR$^{c3}$;
- each $R^{c3}$ is independently selected from the group consisting of hydrogen, $C_{1-6}$alkyl, and $C_{3-7}$cycloalkyl, wherein the $C_{1-6}$alkyl and $C_{3-7}$cycloalkyl are both optionally substituted by one or more, identical or different halogen;

or a salt thereof.

In another aspect [A23] the invention relates to a compound of formula (I), wherein
- $R^1$ is selected from the group consisting of

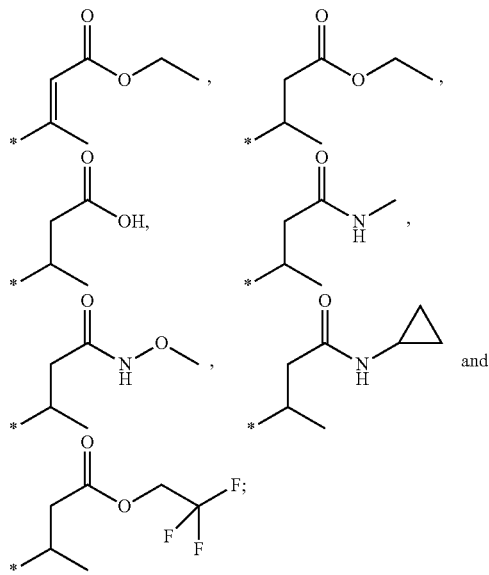

or a salt thereof.

In another aspect [B1] the invention relates to a compound of formula (I), wherein
- $R^2$ is selected from the group consisting of hydrogen, $C_{1-4}$alkyl, —O—$C_{1-4}$alkyl and halogen;

or a salt thereof.

In another aspect [B2] the invention relates to a compound of formula (I), wherein $R^2$ is selected from the group consisting of hydrogen, methyl, methoxy and fluorine;
or a salt thereof.

In another aspect [B3] the invention relates to a compound of formula (I), wherein
$R^2$ is hydrogen;
or a salt thereof.

In another aspect [B4] the invention relates to a compound of formula (I), wherein
$R^2$ is methoxy;
or a salt thereof.

In another aspect [C1] the invention relates to a compound of formula (I), wherein
$R^3$ is selected from the group consisting of hydrogen, $C_{1-4}$alkyl, —O—$C_{1-4}$alkyl and halogen;
or a salt thereof.

In another aspect [C2] the invention relates to a compound of formula (I), wherein
$R^3$ is selected from the group consisting of hydrogen, methyl, methoxy and fluorine;
or a salt thereof.

In another aspect [C3] the invention relates to a compound of formula (I), wherein
$R^3$ is hydrogen;
or a salt thereof.

In another aspect [C4] the invention relates to a compound of formula (I), wherein
$R^3$ is methyl;
or a salt thereof.

In another aspect [D1] the invention relates to a compound of formula (I), wherein
$R^4$ is selected from the group consisting of $C_{1-4}$alkyl, $C_{1-4}$haloalkyl, hydroxy-$C_{1-4}$alkyl, hydroxy-$C_{1-4}$haloalkyl, hydroxy-$C_{3-6}$cycloalkyl, halogen and —$SO_2C_{1-4}$alkyl;
or a salt thereof.

In another aspect [D2] the invention relates to a compound of formula (I), wherein
$R^4$ is selected from the group consisting of methyl, trifluoromethyl, difluoromethyl, hydroxy-ethyl, hydroxy-propyl, hydroxy-difluoroethyl, hydroxy-cyclobutyl, chlorine, iodine, hydroxy-oxetanyl and methylsulfonyl;
or a salt thereof.

In another aspect [D3] the invention relates to a compound of formula (I), wherein
$R^4$ is trifluoromethyl;
or a salt thereof.

In another aspect [D4] the invention relates to a compound of formula (I), wherein
$R^4$ is difluoromethyl;
or a salt thereof.

In another aspect [D5] the invention relates to a compound of formula (I), wherein
$R^4$ is

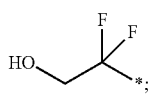

or a salt thereof.

In another aspect [E1] the invention relates to a compound of formula (I), wherein
$R^5$ is hydrogen;
or a salt thereof.

In another aspect [E2] the invention relates to a compound of formula (I), wherein
$R^5$ is —$NH_2$;
or a salt thereof.

In another aspect [F1] the invention relates to a compound of formula (I), wherein
$R^6$ is selected from the group consisting of hydrogen, methyl and fluorine;
or a salt thereof.

In another aspect [F2] the invention relates to a compound of formula (I), wherein
$R^6$ is hydrogen;
or a salt thereof.

In another aspect [F3] the invention relates to a compound of formula (I), wherein
$R^6$ is fluorine;
or a salt thereof.

In another aspect [G1] the invention relates to a compound of formula (I), wherein
$R^1$ is $C_{1-4}$alkyl;
or a salt thereof.

In another aspect [G2] the invention relates to a compound of formula (I), wherein
$R^1$ is methyl;
or a salt thereof.

All the above-mentioned structural aspects [A1] to [A23], [B1] to [B4], [C1] to [C4], [D1] to [D5], [E1] and [E2], [F1] to [F3] and [G1] and [G2] are preferred embodiments of the corresponding aspects [A0], [B0], [C0], [D0], [E0], [F0] and [G0], respectively. The structural aspects [A0] to [A23], [B0] to [B4], [C0] to [C4], [D0] to [D5], [E0] to [E2], [F0] to [F3] and [G0] to [G2] relating to different molecular parts of the compounds (I) according to the invention may be combined with one another as desired in combinations [A][B][C][D][E][F][G] to obtain preferred compounds (I). Each combination [A][B][C][D][E][F][G] represents and defines individual embodiments or generic subsets of compounds (I) according to the invention.

Preferred embodiments of the invention with structure (I) are example compounds I-001 to I-384 and any subset thereof.

All synthetic intermediates generically defined as well as specifically disclosed herein and their salts are also part of the invention.

The present invention further relates to hydrates, solvates, polymorphs, metabolites, derivatives, isomers and prodrugs of a compound of formula (I).

The present invention further relates to a hydrate of a compound of formula (I).

The present invention further relates to a solvate of a compound of formula (I).

Compounds of formula (I) which e.g. bear ester groups are potential prodrugs the ester being cleaved under physiological conditions.

The present invention further relates to a pharmaceutically acceptable salt of a compound of formula (I).

The present invention further relates to a pharmaceutically acceptable salt of a compound of formula (I) with anorganic or organic acids or bases.

Medical Uses—Methods of Treatment

The present invention is directed to SOS1 inhibitor compounds, in particular compounds of formula (I), which are useful in the treatment and/or prevention of a disease and/or condition associated with or modulated by SOS1, especially wherein the inhibition of the interaction of SOS1 and a RAS-family protein and/or RAC1 is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a SOS1 inhibitor compound, in particular a compound of formula (I), —or a pharmaceutically acceptable salt thereof—for use in the treatment and/or prevention of a disease and/or condition wherein the inhibition of the interaction of SOS1 and a RAS-family protein and/or RAC1 is of therapeutic benefit, including but not limited to the treatment and/or prevention of cancer.

In another aspect the invention relates to a SOS1 inhibitor compound, in particular a compound of formula (I), —or a pharmaceutically acceptable salt thereof—for use in the treatment and/or prevention of cancer.

In another aspect the invention relates to a SOS1 inhibitor compound, in particular a compound of formula (I), —or a pharmaceutically acceptable salt thereof—for use in a method of treatment and/or prevention of cancer in the human or animal body.

In another aspect the invention relates to a SOS1 inhibitor compound, in particular a compound of formula (I), —or a pharmaceutically acceptable salt thereof—for use in the treatment and/or prevention of cancer.

In another aspect the invention relates to a SOS1 inhibitor compound, in particular a compound of formula (I), —or a pharmaceutically acceptable salt thereof—for use in a method of treatment and/or prevention of cancer in the human or animal body.

In another aspect the invention relates to a SOS1 inhibitor compound—or a pharmaceutically acceptable salt thereof—for use as hereinbefore defined wherein said SOS1 inhibitor compound is administered before, after or together with at least one other pharmacologically active substance.

In another aspect the invention relates to a compound of formula (I)—or a pharmaceutically acceptable salt thereof—for use as hereinbefore defined wherein said compound is administered before, after or together with at least one other pharmacologically active substance.

In another aspect the invention relates to a SOS1 inhibitor compound—or a pharmaceutically acceptable salt thereof—for use as hereinbefore defined, wherein said SOS1 inhibitor compound is administered in combination with at least one other pharmacologically active substance.

In another aspect the invention relates to a compound of formula (I)—or a pharmaceutically acceptable salt thereof—for use as hereinbefore defined, wherein said compound is administered in combination with at least one other pharmacologically active substance.

In another aspect the invention relates to a pharmacologically active substance prepared for being administered before, after or together with a SOS1 inhibitor compound—or a pharmaceutically acceptable salt thereof—for use as hereinbefore defined for the use of the compound of formula (I).

In another aspect the invention relates to a pharmacologically active substance prepared for being administered before, after or together with a compound of formula (I)—or a pharmaceutically acceptable salt thereof—for use as hereinbefore defined for the use of the compound of formula (I).

In another aspect the invention relates to a SOS1 inhibitor compound, in particular a compound of formula (I), —or a pharmaceutically acceptable salt thereof—for use in the treatment or in a method of treatment as hereinbefore defined.

In another aspect the invention relates to the use of a SOS1 inhibitor compound, in particular a compound of formula (I), —or a pharmaceutically acceptable salt thereof—for preparing a pharmaceutical composition for the treatment and/or prevention of cancer.

In another aspect the invention relates to the use of a SOS1 inhibitor compound—or a pharmaceutically acceptable salt thereof—as hereinbefore defined wherein said SOS1 inhibitor compound is administered before, after or together with at least one other pharmacologically active substance.

In another aspect the invention relates to the use of a compound of formula (I)—or a pharmaceutically acceptable salt thereof—as hereinbefore defined wherein said compound is administered before, after or together with at least one other pharmacologically active substance.

In another aspect the invention relates to the use of a SOS1 inhibitor compound, in particular a compound of formula (I), —or a pharmaceutically acceptable salt thereof—as hereinbefore defined for the treatment.

In another aspect the invention relates to a method for the treatment and/or prevention of a disease and/or condition wherein the inhibition of the interaction of SOS1 and a RAS-family protein or RAC1 is of therapeutic benefit comprising administering a therapeutically effective amount of a SOS1 inhibitor compound, in particular a compound of formula (I), —or a pharmaceutically acceptable salt thereof—to a human being.

In another aspect the invention relates to a method for the treatment and/or prevention of cancer comprising administering a therapeutically effective amount of a SOS1 inhibitor compound, in particular a compound of formula (I), —or a pharmaceutically acceptable salt thereof—to a human being.

In another aspect the invention relates to a method as hereinbefore defined wherein a SOS1 inhibitor compound—or a pharmaceutically acceptable salt thereof—is administered before, after or together with at least one other pharmacologically active substance.

In another aspect the invention relates to a method as hereinbefore defined wherein the compound of formula (I)—or a pharmaceutically acceptable salt thereof—is administered before, after or together with at least one other pharmacologically active substance.

In another aspect the invention relates to a method as hereinbefore defined wherein the SOS1 inhibitor compound—or a pharmaceutically acceptable salt thereof—is administered in combination with a therapeutically effective amount of at least one other pharmacologically active substance.

In another aspect the invention relates to a method as hereinbefore defined wherein the compound of formula (I)—or a pharmaceutically acceptable salt thereof—is administered in combination with a therapeutically effective amount of at least one other pharmacologically active substance.

In another aspect the invention relates to a method for the treatment as hereinbefore defined.

In another aspect the invention relates to a kit comprising
 a first pharmaceutical composition or dosage form comprising a SOS1 inhibitor compound and, optionally, one or more pharmaceutically acceptable carriers, excipients and/or vehicles, and at least a second pharmaceutical composition or dosage form comprising another pharmacologically active substance and, optionally, one or more pharmaceutically acceptable carriers, excipients and/or vehicles.

In another aspect the invention relates to a kit comprising
a first pharmaceutical composition or dosage form comprising a compound of formula (I) and, optionally, one or more pharmaceutically acceptable carriers, excipients and/or vehicles, and
at least a second pharmaceutical composition or dosage form comprising another pharmacologically active substance and, optionally, one or more pharmaceutically acceptable carriers, excipients and/or vehicles.

In another aspect the invention relates to a pharmaceutical composition comprising at least one (preferably one) compound of formula (I)—or a pharmaceutically acceptable salt thereof—and one or more pharmaceutically acceptable excipient(s).

In another aspect the invention relates to a pharmaceutical preparation comprising a compound of formula (I)—or a pharmaceutically acceptable salt thereof—and at least one other pharmacologically active substance.

In another aspect the pharmacologically active substance to be used together/in combination with the SOS1 inhibitor compound, in particular compound of formula (I) (including all individual embodiments or generic subsets of compounds (I)), or in the medical uses, uses, methods of treatment and/or prevention as herein (above and below) defined can be selected from any one or more of the following (preferably there is only one additional pharmacologically active substance used in all these embodiments):

1. Inhibitors of EGFR and/or of Mutants Thereof
   a. e.g. afatinib, erlotinib, gefitinib, lapatinib, cetuximab, panitumumab, osimertinib, olmutinib, EGF-816;
   b. preferred are afatinib, osimertinib and cetuximab;
   c. most preferred is afatinib
2. inhibitors of ErbB2 (Her2) and/or of mutants thereof
   a. e.g. afatinib, lapatinib, trastuzumab, pertuzumab;
   b. preferred are afatinib and trastuzumab;
   c. most preferred is trastuzumab;
3. inhibitors of ALK and/or of mutants thereof
   a. e.g. crizotinib, alectinib, entrectinib, brigatinib;
   b. preferred are crizotinib and alectinib;
   c. most preferred is crizotinib;
4. inhibitors of MEK and/or of mutants thereof
   a. e.g. trametinib, cobimetinib, binimetinib, selumetinib, refametinib;
   b. preferred are trametinib and cobimetinib;
   c. most preferred is trametinib;
5. inhibitors of KRAS G12C
   a. e.g. ARS-853 (compound V-64 in WO 2014/152588), example I-272 in WO 2016/044772;
6. inhibitors of BCR-ABL and/or of mutants thereof
   a. e.g. imatinib, dasatinib, nilotinib;
   b. preferred are imatinib and nilotinib;
   c. most preferred is imatinib;
7. inhibitors of FGFR1 and/or FGFR2 and/or FGFR3 and/or of mutants thereof
   a. e.g. nintedanib;
8. inhibitors of ROS1 and/or of mutants thereof
   a. e.g. crizotinib, entrectinib, lorlatinib, ceritinib, merestinib;
   b. preferred are crizotinib and entrectinib;
   c. most preferred is crizotinib;
9. inhibitors of c-MET and/or of mutants thereof
10. inhibitors of AXL and/or of mutants thereof
11. inhibitors of NTRK1 and/or of mutants thereof
12. inhibitors of RET and/or of mutants thereof
13. taxanes
    a. e.g. paclitaxel, nab-paclitaxel, docetaxel;
    b. preferred is paclitaxel;
14. platinum-containing compounds
    a. e.g. cisplatin, carboplatin, oxaliplatin;
15. anti-metabolites
    a. e.g. 5-fluorouracil, capecitabine, floxuridine, cytarabine, gemcitabine, combination of trifluridine and tipiracil (=TAS102);
    b. preferred is gemcitabine;
16. mitotic kinase inhibitors
    a. e.g. CDK4/6 inhibitors
       i. e.g. palbociclib, ribociclib, abemaciclib;
       ii. preferred are palbociclib and abemaciclib;
       iii. most preferred is abemaciclib;
17. immunotherapeutic agents
    a. e.g. immune checkpoint inhibitors
       i. e.g. anti-CTLA4 mAb, anti-PD1 mAb, anti-PD-1 mAb, anti-PD-L2 mAb, anti-LAG3 mAb, anti-TIM3 mAb;
       ii. preferred are anti-PD1 mAb;
       iii. e.g. ipilimumab, nivolumab, pembrolizumab, atezolizumab, avelumab, durvalumab, pidilizumab, PDR-001 (BAP049-Clone-E disclosed and used in WO 2017/019896);
       iv. preferred are nivolumab, pembrolizumab and PDR-001;
       v. most preferred is pembrolizumab;
18. anti-angiogenic drugs
    a. e.g. bevacizumab, nintedanib;
    b. most preferred is bevacizumab;
19. topoisomerase inhibitors
    a. e.g. irinotecan, liposomal irinotecan, topotecan;
    b. most preferred is irinotecan;
20. inhibitors of A-Raf and/or B-Raf and/or C-Raf and/or of mutants thereof
    a. e.g. RAF-709 (=example 131 in WO 2014/151616), LY-3009120 (=example 1 in WO 2013/134243);
21. inhibitors of ERK and/or of mutants thereof
    a. e.g. ulixertinib;
22. apoptose regulators
    a. e.g. inhibitors of the interaction between p53 (preferably functional p53, most preferably wtp53) and MDM2 ("MDM2 inhibitors");
       i. e.g. HDM-201, NVP-CGM097, RG-7112, MK-8242, RG-7388, SAR405838, AMG-232, DS-3032, RG-7775, APG-115;
       ii. preferred are HDM-201, RG-7388 and AMG-232
    b. e.g. PARP inhibitors;
    c. e.g. MCL-1 inhibitors;
23. inhibitors of mTOR
    a. e.g. rapamycin, temsirolimus, everolimus, ridaforolimus;
24. epigenetic regulators
    a. e.g. BET inhibitors
       i. e.g. JQ-1, GSK 525762, OTX 015 (=MK8628), CPI 0610, TEN-010 (=RO6870810);
    b. e.g. CDK9 inhibitors;
25. inhibitors of IGF1/2 and/or of IGF1-R
    a. e.g. xentuzumab (antibody 60833 in WO 2010/066868), MEDI-573 (=dusigitumab);

Within this invention it is to be understood that the combinations, compositions, kits, methods, uses or compounds for use according to this invention may envisage the simultaneous, concurrent, sequential, successive, alternate or separate administration of the active ingredients or components. It will be appreciated that the SOS1 inhibitor compound (e.g. compound of formula (I)) and the at least one other pharmacologically active substance can be administered either formulated either dependently or independently, such as e.g. the SOS1 inhibitor compound (e.g. compound of formula (I)) and the at least one other pharmacologically active substance may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active ingredient and includes both fixed and non-fixed (e.g. free) combinations (including kits) and uses, such as e.g. the simultaneous, concurrent, sequential, successive, alternate or separate use of the components or ingredients. The term "fixed combination" means that the active ingredients are both administered to a patient simultaneously in the form of a single entity or dosage. The term "non-fixed combination" means that the active ingredients are both administered to a patient as separate entities either simultaneously, concurrently or sequentially with no specific time limits, wherein such administration provides therapeutically effective levels of the two compounds in the body of the patient.

The administration of the SOS1 inhibitor compound (e.g. compound of formula (I)) and the at least one other pharmacologically active substance may take place by co-administering the active components or ingredients, such as e.g. by administering them simultaneously or concurrently in one single or in two or more separate formulations or dosage forms. Alternatively, the administration of the SOS1 inhibitor compound (e.g. compound of formula (I)) and the at least one other pharmacologically active substance may take place by administering the active components or ingredients sequentially or in alternation, such as e.g. in two or more separate formulations or dosage forms.

For example, simultaneous administration includes administration at substantially the same time. This form of administration may also be referred to as "concomitant" administration. Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second and/or additional time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

The elements of the combinations of this invention may be administered (whether dependently or independently) by methods customary to the skilled person, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable carriers, excipients and/or vehicles appropriate for each route of administration.

Accordingly, in one aspect of the invention the invention provides a method for the treatment and/or prevention of cancer comprising administering to a patient in need thereof a therapeutically effective amount of a SOS1 inhibitor compound (e.g. a compound of formula (I)) and a therapeutically effective amount of at least one other pharmacologically active substance, wherein the SOS1 inhibitor compound (e.g. a compound of formula (I)) is administered simultaneously, concurrently, sequentially, successively, alternately or separately with the at least one other pharmacologically active substance.

In another aspect the invention provides a SOS1 inhibitor compound (e.g. a compound of formula (I)) for use in the treatment and/or prevention of cancer, wherein the SOS1 inhibitor compound (e.g. a compound of formula (I)) is administered simultaneously, concurrently, sequentially, successively, alternately or separately with the at least one other pharmacologically active substance.

In another aspect the invention provides a kit comprising
a first pharmaceutical composition or dosage form comprising a SOS1 inhibitor compound (e.g. a compound of formula (I)), and, optionally, one or more pharmaceutically acceptable carriers, excipients and/or vehicles, and
at least a second pharmaceutical composition or dosage form comprising another pharmacologically active substance, and, optionally, one or more pharmaceutically acceptable carriers, excipients and/or vehicles,
for use in the treatment and/or prevention of cancer, wherein the first pharmaceutical composition is to be administered simultaneously, concurrently, sequentially, successively, alternately or separately with the second and/or additional pharmaceutical composition or dosage form.

In a further embodiment of the invention the components (i.e. the combination partners) of the combinations, kits, uses, methods and compounds for use according to the invention (including all embodiments) are administered simultaneously.

In a further embodiment of the invention the components (i.e. the combination partners) of the combinations, kits, uses, methods and compounds for use according to the invention (including all embodiments) are administered concurrently.

In a further embodiment of the invention the components (i.e. the combination partners) of the combinations, kits, uses, methods and compounds for use according to the invention (including all embodiments) are administered sequentially.

In a further embodiment of the invention the components (i.e. the combination partners) of the combinations, kits, uses, methods and compounds for use according to the invention (including all embodiments) are administered successively.

In a further embodiment of the invention the components (i.e. the combination partners) of the combinations, kits, uses, methods and compounds for use according to the invention (including all embodiments) are administered alternately.

In a further embodiment of the invention the components (i.e. the combination partners) of the combinations, kits, uses, methods and compounds for use according to the invention (including all embodiments) are administered separately.

The "therapeutically effective amount" of the active compound(s) to be administered is the minimum amount necessary to prevent, ameliorate, or treat a disease or disorder.

The combinations of this invention may be administered at therapeutically effective single or divided daily doses. The active components of the combination may be administered in such doses which are therapeutically effective in monotherapy, or in such doses which are lower than the doses used in monotherapy, but when combined result in a desired (joint) therapeutically effective amount.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer, colorectal cancer, cholangiocarcinoma, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of pancreatic cancer, lung cancer (preferably non-small cell lung cancer (NSCLC)), cholangiocarcinoma and colorectal cancer.

In another aspect the disease/condition to be treated/prevented with the SOS1 inhibitor compound, SOS1 inhibitor compound for use, compound of formula (I), compound of formula (I) for use, use for preparing and method for the treatment and/or prevention as herein (above and below) defined is a RASopathy, preferably selected from the group consisting of Neurofibromatosis type 1 (NF1), Noonan Syndrome (NS), Noonan Syndrome with Multiple Lentigines (NSML) (also referred to as LEOPARD syndrome), Capillary Malformation-Arteriovenous Malformation Syndrome (CM-AVM), Costello Syndrome (CS), Cardio-Facio-Cutaneous Syndrome (CFC), Legius Syndrome (also known as NF1-like Syndrome) and Hereditary gingival fibromatosis.

In another aspect the disease/condition/cancer to be treated/prevented with the SOS1 inhibitor compound, SOS1 inhibitor compound for use, compound of formula (I), compound of formula (I) for use, use for preparing and method for the treatment and/or prevention as herein (above and below) defined is a disease/condition/cancer defined as exhibiting one or more of the following molecular features:

1. KRAS alterations:
   a. KRAS amplification (wt or mutant);
   b. KRAS overexpression (wt or mutant);
   c. KRAS mutation(s):
      i. G12 mutations (e.g. G12C, G12V, G12S, G12A, G12V, G12R, G12F, G12D);
      ii. G13 mutations (e.g. G13C, G13D, G13R, G13V, G13S, G13A)
      iii. T35 mutation (e.g. T35I);
      iv. I36 mutation (e.g. I36L, I36M);
      v. E49 mutation (e.g. E49K);
      vi. Q61 mutation (e.g. Q61H, Q61R, Q61P, Q61E, Q61K, Q61L, Q61K);
      vii. K117 mutation (e.g. K117N);
      viii. A146 mutation (e.g. A146T, A146V);
2. NRAS alterations:
   a. NRAS amplification (wt or mutant);
   b. NRAS overexpression (wt or mutant);
   c. NRAS mutation(s):
      i. G12 mutations (e.g. G12A, G12V, G12D, G12C, G12S, G12R);
      ii. G13 mutation (e.g. G13V, G13D, G13R, G13S, G13C, G13A);
      iii. Q61 mutation (e.g. Q61K, Q61L, Q61H, Q61P, Q61R);
      iv. A146 mutation (e.g. A146T, A146V);
3. HRAS alterations:
   a. HRAS amplification (wt or mutant);
   b. HRAS overexpression (wt or mutant);
   c. HRAS mutation(s);
      i. G12 mutation (e.g. G12C, G12V, G12S, G12A, G12V, G12R, G12F, G12D);
      ii. G13 mutation (e.g. G13C, G13D, G13R, G13V, G13S, G13A);
      iii. Q61 mutation (e.g. Q61K, Q61L, Q61H, Q61P, Q61R);
4. EGFR alterations:
   a. EGFR amplification (wt or mutant);
   b. EGFR overexpression (wt or mutant);
   c. EGFR mutation(s)
      i. e.g. exon 20 insertion, exon 19 deletion (Del19), G719X (e.g. G719A, G719C, G719S), T790M, C797S, T854A, L858R, L861Q, or any combination thereof;
5. ErbB2 (Her2) alterations:
   a. ErbB2 amplification;
   b. ErbB2 overexpression;
   c. ErbB2 mutation(s)
      i. e.g. R678, G309, L755, D769, D769, V777, P780, V842, R896, c.2264_2278del (L755_T759del), c.2339_2340ins (G778_P780dup), S310;
6. c-MET alterations:
   a. c-MET amplification;
   b. c-MET overexpression;
   c. c-MET mutation(s)
      i. e.g. E168, N375, Q648, A887, E908, T1010, V1088, H1112, R1166, R1188, Y1248, Y1253, M1268, D1304, A1357, P1382;
7. AXL alterations:
   a. AXL amplification;
   b. AXL overexpression;
8. BCR-ABL alterations:
   a. chromosomal rearrangements involving the ABL gene;
9. ALK alterations:
   a. ALK amplification;
   b. ALK overexpression;
   c. ALK mutation(s)
      i. e.g. 1151Tins, L1152R, C1156Y, F1174L, L1196M, L1198F, G1202R, S1206Y, G1269A;
   d. chromosomal rearrangements involving the ALK gene;
10. FGFR1 alterations:
    a. FGFR1 amplification;
    b. FGFR1 overexpression;
11. FGFR2 alterations:
    a. FGFR2 amplification;
    b. FGFR2 overexpression;

12. FGFR3 alterations:
    a. FGFR3 amplification;
    b. FGFR3 overexpression;
    c. chromosomal rearrangement involving the FGFR3 gene;
13. NTRK1 alterations:
    a. chromosomal rearrangements involving the NTRK1 gene;
14. NF1 alterations:
    a. NF1 mutation(s);
15. RET alterations:
    a. RET amplification;
    b. RET overexpression;
    c. chromosomal rearrangements involving the RET gene
16. ROS1 alterations:
    a. ROS1 amplification;
    b. ROS1 overexpression;
    c. ROS1 mutation(s)
        i. e.g. G2032R, D2033N, L2155S;
    d. chromosomal rearrangements involving the ROS1 gene;
17. SOS1 alterations
    a. SOS1 amplification;
    b. SOS1 overexpression;
    c. SOS1 mutation(s);
18. RAC1 alterations
    a. RAC1 amplification;
    b. RAC1 overexpression;
    c. RAC1 mutation(s);
19. MDM2 alterations
    a. MDM2 amplification
    b. MDM2 overexpression
    c. MDM2 amplification in combination with functional p53
    d. MDM2 amplification in combination with wild-type p53
20. RAS wild-type
    a. KRAS wild-type
    a. HRAS wild-type
    b. NRAS wild-type Particularly preferred, the cancer to be treated/prevented with the SOS1 inhibitor compound, SOS1 inhibitor compound for use, compound of formula (I), compound of formula (I) for use, use for preparing and method for the treatment and/or prevention as herein (above and below) defined is selected from the group consisting of:
    lung adenocarcinoma harboring a KRAS mutation selected from the group consisting of G12C, G12V, G12D and G12R;
    colorectal adenocarcinoma harboring a KRAS mutation selected from the group consisting of G12D, G12V, G12C, G12R and G13D; and
    pancreatic adenocarcinoma harboring a KRAS mutation selected from the group consisting of G12D, G12V, G12R, G12C and Q61H.

Any disease/condition/cancer, medical use, use, method of treatment and/or prevention as disclosed or defined herein (including molecular/genetic features) may be treated/performed with any compound of formula (I) as disclosed or defined herein (including all individual embodiments or generic subsets of compounds (I)).

DEFINITIONS

Figure 1:
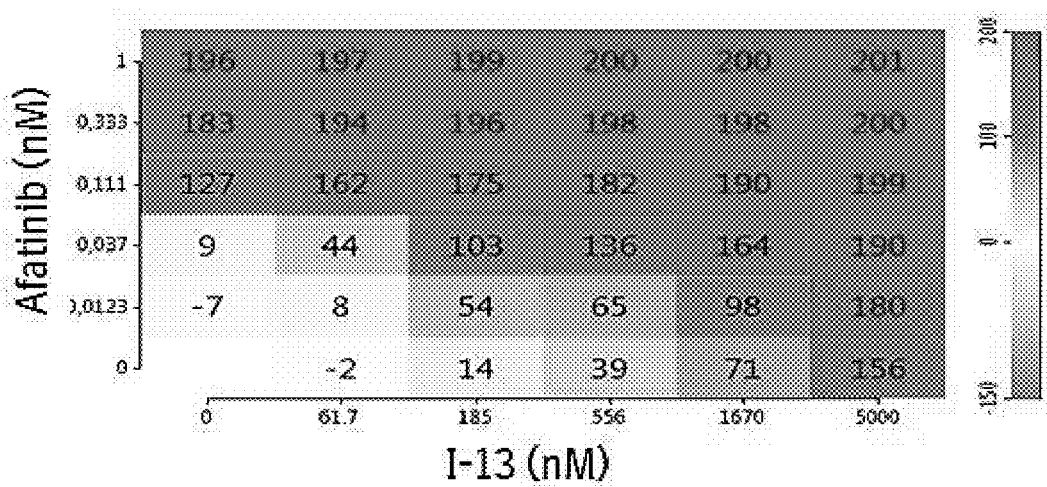
FIG. 1 shows the effect of SOS1 inhibitor compound I-13 and afatinib, alone or in combination, on the in vitro growth of PC-9 cells (EGFR del19; KRAS wt).
Figure 1:
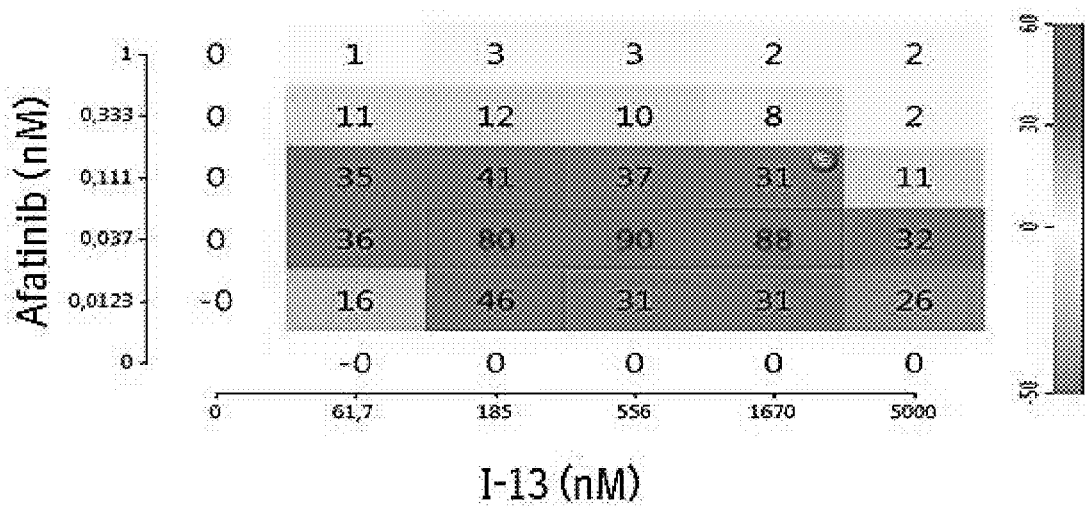

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, $H_2N$, (O)S, $(O)_2S$, NC (cyano), HOOC, $F_3C$ or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH$ $(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)$ $CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH$ $(CH_3)_2$), 2,2-dimethyl-1-propyl (neo-pentyl; —$CH_2$ $C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$), 2,3-dimethyl-1-butyl (—$CH_2CH(CH_3)CH(CH_3)$ $CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_4$alkylene" includes for example —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH (CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH (CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH (CH_3)$—$CH(CH_3))$—, —$(CH_2$—$CH(CH_2CH_3))$—, —$(CH (CH_2CH_3)$—$CH_2)$—, —$(CH(CH_2CH_2CH_3))$—, —$(CH(CH (CH_3))_2)$— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1- enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl,1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —$CHFCHF$— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms in common. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

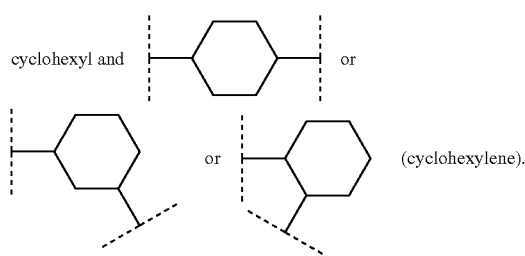

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

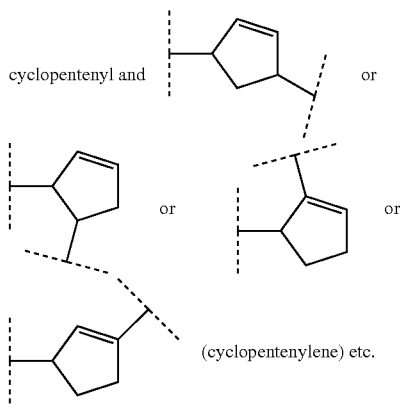

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

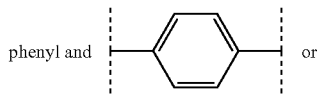

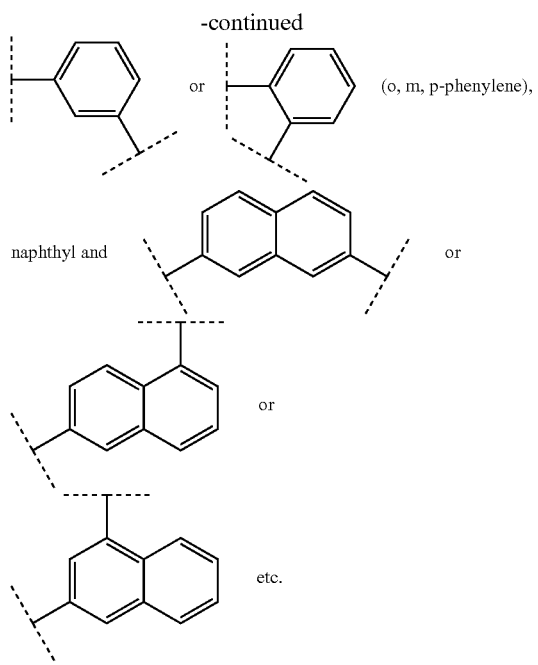

(o, m, p-phenylene), naphthyl and or or etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

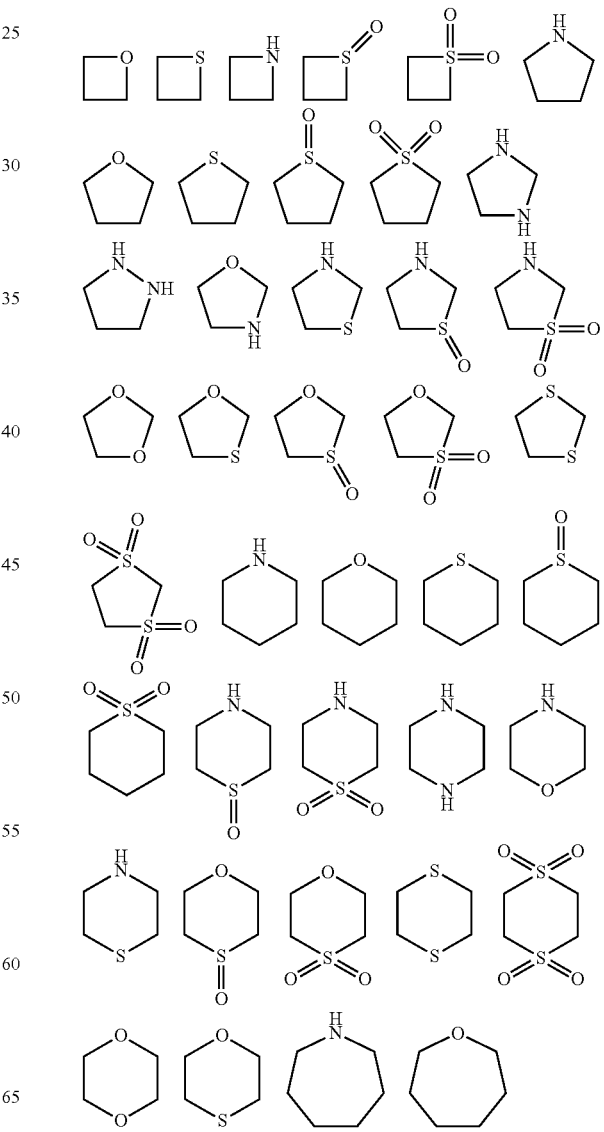

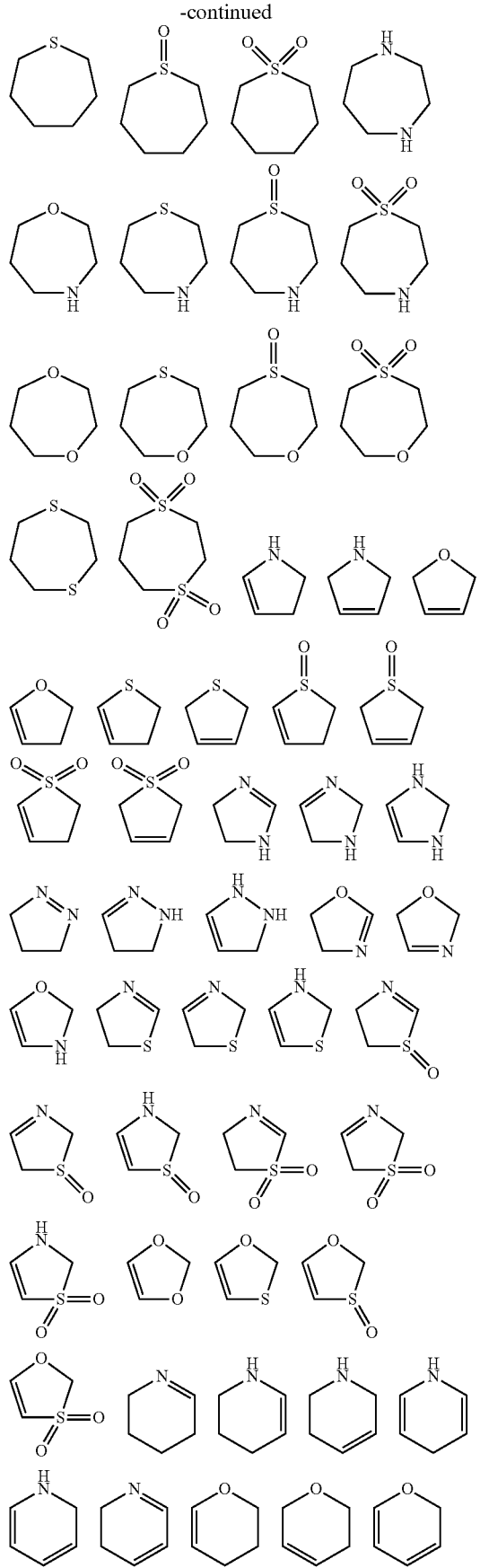
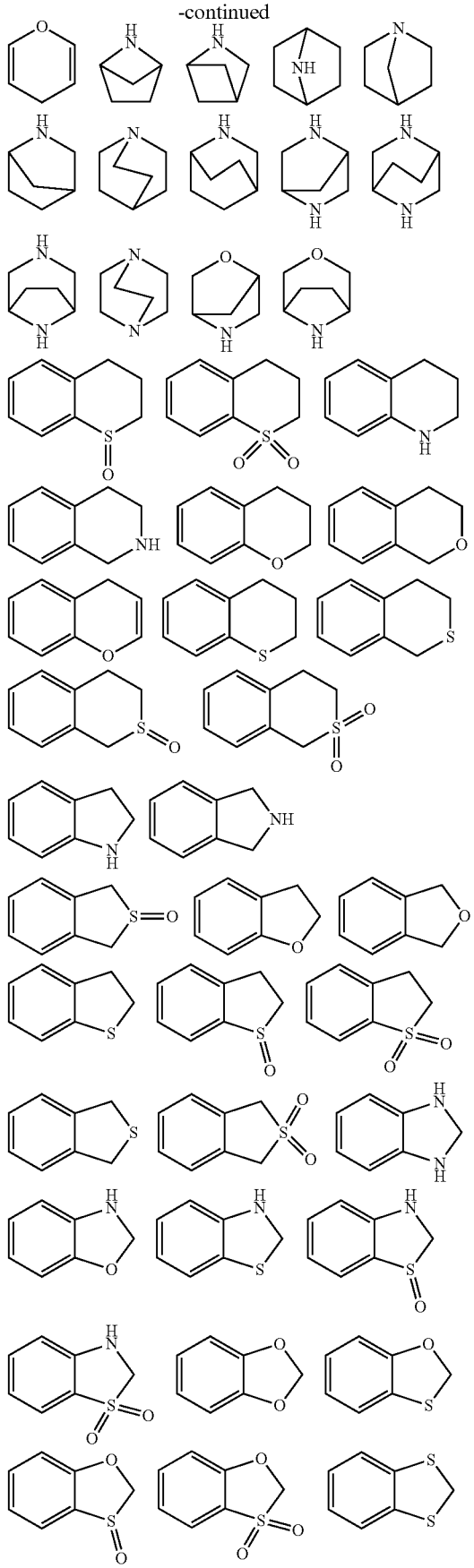

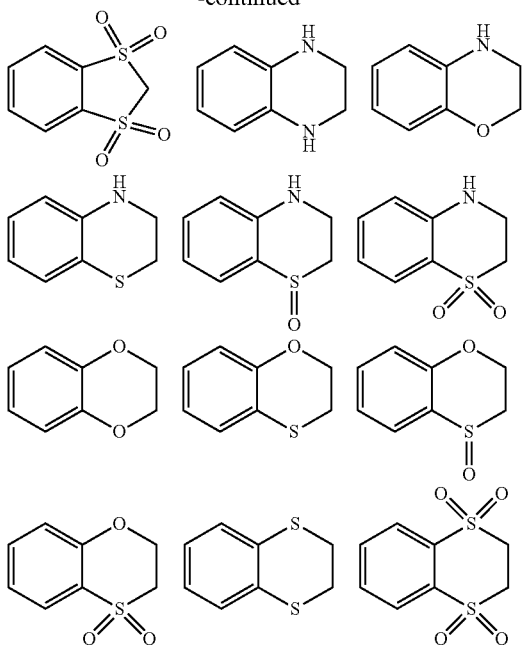

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

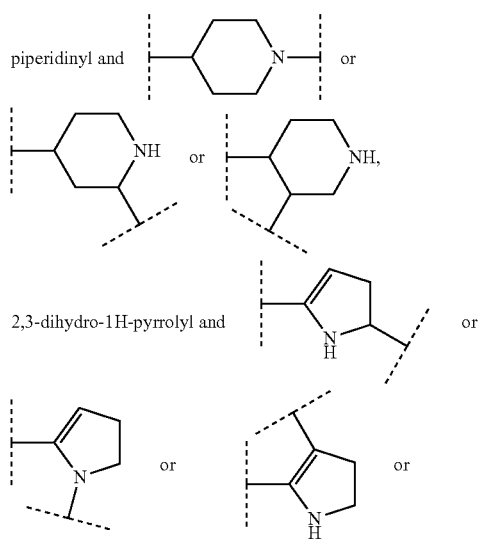

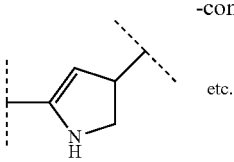

The above definition of heterocyclylene also applies if heterocyclylene is part of another (combined) group as for example in HO-heterocyclyleneamino or H$_2$N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

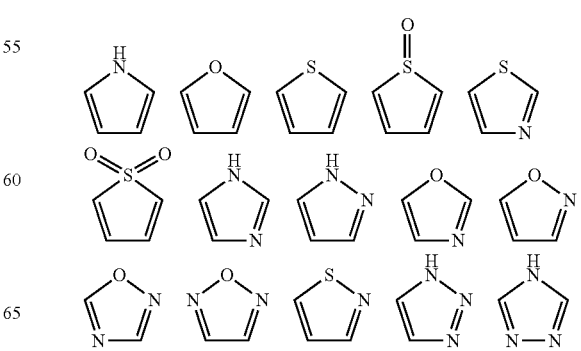

-continued

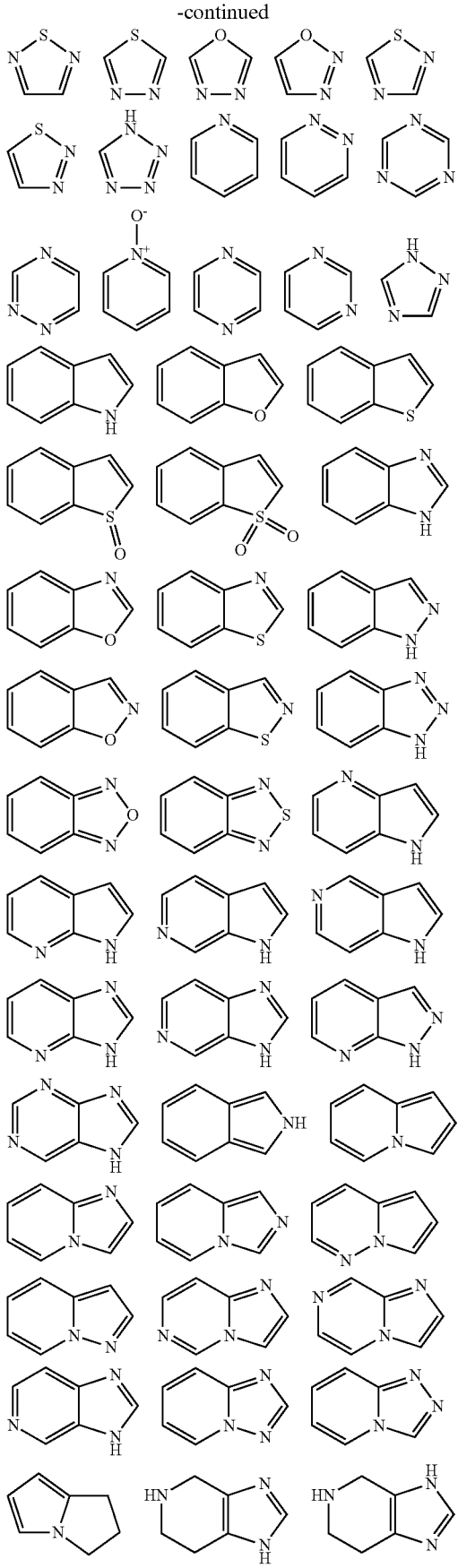
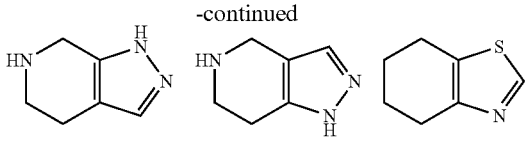

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

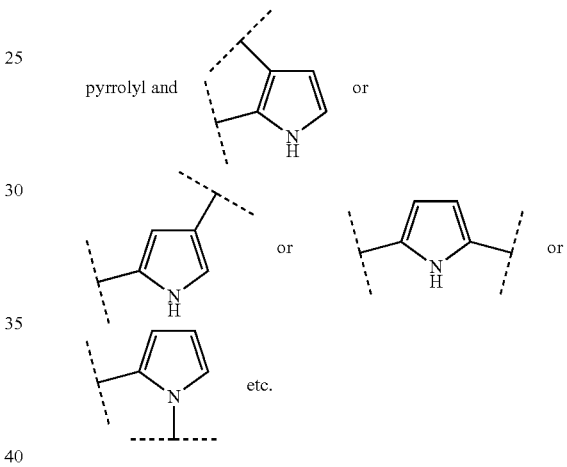

The above definition of heteroarylene also applies if heteroarylene is part of another (combined) group as for example in HO-heteroaryleneamino or $H_2N$-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O group or =NR group only, one or two =O groups possible or, e.g., one =O group and one =NR group, each group replacing a free electron pair) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

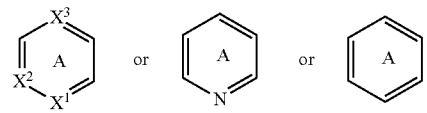

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

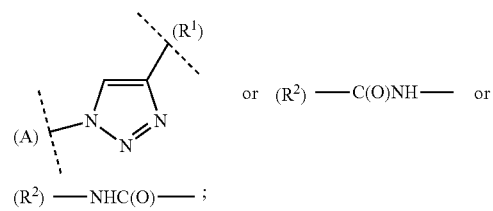

In a representation such as for example

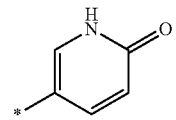

the asterisk designates the point of attachment of the respective group as a substituent.

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

RAS-family proteins are meant to include KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof.

A SOS1 inhibitor compound is a compound, which binds to SOS1 and thereby prevents the SOS1 mediated nucleotide exchange and subsequently reduces the levels of RAS in its GTP bound form. More specifically, a SOS1 inhibitor compound shows a pharmacological inhibition of the binding of the catalytic site of SOS1 to RAS-family proteins. Thus, such a compound interacts with SOS1, e.g. the catalytic site on SOS1, and reduces the level of binding to the RAS-family protein in relation to said binding without addition of a SOS1 inhibitor compound. Accordingly, it is envisaged that a SOS1 inhibitor compound at least reduces the level of binding to the RAS-family protein about 5%, 10%, 20%, 30%, 40%, 50%, 60%, 70%, 80%, 90% or even 100% when compared to the binding that is achieved without the addition of said inhibitor compound. Suitable test systems to measure the binding to the catalytic site of SOS1 are disclosed herein. Said compound may be chemically synthesized (e.g. a small molecule) or microbiologically produced (e.g. a monoclonal antibody) and/or comprised in, for example, samples, e.g., cell extracts from, e.g., plants, animals or microorganisms. Preferably, the SOS1 inhibitor compound is a small molecule.

List of Abbreviations

| | |
|---|---|
| Ac | acetyl |
| AcCN | acetonitrile |
| amphos | bis(di-tert-butyl(4-dimethylaminophenyl)phosphine) |
| aq. | aquatic, aqueous |
| ATP | adenosine triphosphate |
| Bn | benzyl |
| Boc | tert-butyloxycarbonyl |
| Bu | butyl |
| c | concentration |
| Cbz | carboxybenzyl |
| $CH_2Cl_2$ | dichloro methane |
| d | day(s) |
| dba | dibenzylideneacetone |
| TLC | thin layer chromatography |
| DAST | diethylamino sulfurtrifluoride |
| Davephos | 2-dimethylamino-2'-dicyclohexylaminophosphinobiphenyl |
| DBA | dibenzylidene acetone |
| DCE | dichloro ethane |
| DCM | dichloro methane |
| DEA | diethyl amine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| $Et_2O$ | diethyl ether |

-continued

| | |
|---|---|
| EtOAc | ethyl acetate |
| EtOH | ethanol |
| h | hour |
| HATU | O-(7-azabenzotriazol-1-yl)-N,N,N',N'-tetramethyluronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf ($R_f$) | retention factor |
| RP | reversed phase |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyluronium tetrafluoroborate |
| tBu | tert-butyl |
| TEA | triethyl amine |
| temp. | temperature |
| tert | tertiary |
| $T_f$ | trif late |
| TFA | trifluoroacetic acid |
| THF | tetrahydrofuran |
| TMS | trimethylsilyl |
| $t_{Ret}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep C18 OBD™ 5 µm, 30×50 mm or XBridge™ Prep C18, OBD™10 µm, 50×150 mm or XBridge™ Prep C18, OBD™ 5 µm, 30×150 mm or XBridge™ Prep18, OBD™ 5 µm, 30×50 mm) and YMC (names: Actus-Triart Prep C18, 5 µm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following columns: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C2 (250×20 mm, 5 µm).

The analytical HPLC (reaction control) of intermediate and final compounds is carried out using columns made by Waters (names: XBridge™ C18, 2.5 µm, 2.1×20 mm or XBridge™ C18, 2.5 µm, 2.1×30 mm or Aquity UPLC BEH C18, 1.7 µm, 2.1×50 mm) and YMC (names: Triart C18, 3.0 µm, 2.0×30 mm) and Phenomenex (names: Luna C18, 5.0 µm, 2.0×30 mm). The analytical equipment is also equipped with a mass detector in each case.

HPLC-Mass Spectroscopy/UV-Spectrometry

The retention times/MS-ESI$^+$ for characterizing the example compounds according to the invention are produced using an HPLC-MS apparatus (high performance liquid chromatography with mass detector). Compounds that elute at the injection peak are given the retention time $t_{Ret.}$=0.00.

HPLC-Methods (Preparative)

prep. HPLC1
- HPLC: 333 and 334 Pumps
- Column: Waters X-Bridge C18 OBD, 10 µm, 30×100 mm, Part. No. 186003930
- Solvent: A: 10 mM $NH_4HCO_3$ in $H_2O$; B: Acetonitrile (HPLC grade)
- Detection: UV/Vis-155
- Flow: 50 mL/min
- Gradient: 0.00-1.50 min: 1.5% B
  - 1.50-7.50 min: varying
  - 7.50-9.00 min: 100% B prep. HPLC2
- HPLC: 333 and 334 Pumps
- Column: Waters Sunfire C18 OBD, 10 µm, 30×100 mm, Part. No. 186003971
- Solvent: A: $H_2O$+0.2% HCOOH; B: Acetonitrile (HPLC grade)+0.2% HCOOH
- Detection: UV/Vis-155
- Flow: 50 mL/min
- Gradient: 0.00-1.50 min: 1.5% B
  - 1.50-7.50 min: varying
  - 7.50-9.00 min: 100% B HPLC-Methods (analytic)

LCMSBAS1
- HPLC: Agilent 1100 Series
- MS: Agilent LC/MSD SL
- Column: Phenomenex Mercury Gemini C18, 3 µm, 2×20 mm, Part. No. 00M-4439-B0-CE
- Solvent: A: 5 mM $NH_4HCO_3$/20 mM $NH_3$ in $H_2O$; B: acetonitrile (HPLC grade)
- Detection: MS: positive and negative mode
- Mass range: 120-900 m/z
- Flow: 1.00 mL/min
- Column temperature: 40° C.
- Gradient: 0.00-2.50 min: 5% B→95% B
  - 2.50-2.80 min: 95% B
  - 2.81-3.10 min: 95% B→5% B FECB5
- HPLC: Agilent 1100/1200 Series
- MS: Agilent LC/MSD SL
- Column: Waters X-Bridge C18 OBD, 5 µm, 2.1×50 mm
- Solvent: A: 5 mM $NH_4HCO_3$/19 mM $NH_3$ in $H_2O$; B: acetonitrile (HPLC grade)
- Detection: MS: positive and negative mode
- Mass range: 105-1200 m/z
- Flow: 1.20 mL/min
- Column temperature: 35° C.
- Gradient: 0.00-1.25 min: 5% B→95% B
  - 1.25-2.00 min: 95% B
  - 2.00-2.01 min: 95% B→5% B FECBM3ESI
- HPLC: Agilent 1100/1200 Series
- MS: Agilent LC/MSD SL
- Column: Waters X-Bridge C18 OBD, 5 µm, 2.1×50 mm
- Solvent: A: 5 mM $NH_4HCO_3$/19 mM $NH_3$ in $H_2O$; B: acetonitrile (HPLC grade)
- Detection: MS: Multimode ESI positive and negative mode
- Mass range: 105-1200 m/z
- Flow: 1.20 mL/min
- Column temperature: 35° C.
- Gradient: 0.00-1.25 min: 5% B→100% B
  - 1.25-2.00 min: 100% B
  - 2.00-2.01 min: 100% B→5% B VAB
- HPLC: Agilent 1100/1200 Series
- MS: Agilent LC/MSD SL
- Column: Waters X-Bridge BEH C18, 2.5 µm, 2.1×30 mm XP
- Solvent: A: 5 mM $NH_4HCO_3$/19 mM $NH_3$ in $H_2O$; B: acetonitrile (HPLC grade)
- Detection: MS: positive and negative mode
- Mass range: 100-1200 m/z
- Flow: 1.40 mL/min
- Column temperature: 45° C.
- Gradient: 0.00-1.00 min: 5% B→100% B
  - 1.00-1.37 min: 100% B
  - 1.37-1.40 min: 100% B→5% B BFEC
- HPLC: Agilent 1100/1200 Series
- MS: Agilent LC/MSD SL
- Column: Waters X-Bridge BEH C18, 2.5 µm, 2.1×30 mm XP Solvent: A: 5 mM NH₄HCOs/19 mM NH₃ in H₂O; B: acetonitrile (HPLC grade)
Detection: MS: positive and negative mode
Mass range: 50-1000 m/z
Flow: 1.40 mL/min
Column temperature: 45° C.
Gradient: 0.00-1.00 min: 15% B→100% B
1.00-1.30 min: 100% B AFEC
HPLC: Agilent 1100/1200 Series
MS: Agilent LC/MSD SL
Column: Waters Sunfire C18, 5 μm, 2.1×50 mm
Solvent: A: H₂O+0.2% formic acid; B: acetonitrile (HPLC grade)
Detection: MS: positive and negative mode
Mass range: 50-1000 m/z
Flow: 1.40 mL/min
Column temperature: 45° C.
Gradient: 0.00-1.00 min: 15% B→100% B
1.00-1.23 min: 100% B FA-8
HPLC-MS: Waters-Alliance 2996
Column: Symmetryshield C18, 5 μm, 4.6×250 mm
Solvent: A: H₂O+0.1% TFA; B: acetonitrile (HPLC grade)
Detection: MS: positive and negative mode
Mass range: 100-1200 m/z
Flow: 1.00 mL/min
Column temperature: 25° C.
Gradient: 2.00-8.00 min: 20% B→80% B
8.00-19.00 min: 80% B
19.00-20.00 min: 80% B→20% B FSUN2
HPLC: Agilent 1100/1200 Series
MS: Agilent LC/MSD SL
Column: Waters Sunfire C18, 5 μm, 2.1×50 mm
Solvent: A: H₂O+0.2% formic acid; B: acetonitrile (HPLC grade)
Detection: MS: positive and negative mode
Mass range: 105-1200 m/z
Flow: 1.20 mL/min
Column temperature: 35° C.
Gradient: 0.0 min: 5% B
0.0-1.50 min: 5% B→95% B
1.50-2.00 min: 95% B
2.00-2.01 min: 95% B→5% B LCMS A
HPLC-MS: LCMS/MS API 2000 (Applied Biosystem)
Column: Agilent Zorbax Extend C18 4.6×50 mm, 5 micron
Solvent: A: 10 mM NH₄OAc in H₂O; B: acetonitrile (HPLC grade)
Detection: MS: positive and negative mode
Mass range: 100-800 m/z
Flow: 1.20 mL/min
Column temperature: 25° C.
Gradient: 0.0 min: 10% B
0.0-1.50 min: 10% B→30% B
1.50-3.00 min: 30% B→90% B
3.00-4.00 min: 90% B
4.00-5.00 min: 90% B→10% B LCMS B
HPLC-MS: Alliance HT Waters ZQ Mass (Waters)
Column: Agilent Zorbax Extend C18 4.6×50 mm, 5 micron
Solvent: A: 10 mM NH₄OAc in H₂O; B: acetonitrile (HPLC grade)
Detection: MS: positive and negative mode
Mass range: 100-800 m/z
Flow: 1.20 mL/min
Column temperature: 50° C.
Gradient: 0.01 min: 5% B
0.01-0.75 min: 5% B
0.75-1.50 min: 5% B→15% B
1.50-3.00 min: 15% B→90% B
3.00-4.00 min: 90% B
4.00-5.00 min: 90% B→5% B RND-FA-2.6
HPLC: Agilent Infinity-1290 Series
MS: Agilent SQD-6130 (API-ES+/−3000 V)
MSD signal settings: Scan pos 100-1000, Scan neg 100-1000
Column: Aquity BEH C18, 2.1×50 mm, 1.7 μm
Eluent: A: 0.1% formic acid in water; B: 0.1% formic acid in acetonitrile
Detection signal: UV 215 nm (bandwidth 4, reference off)
Spectrum: range: 200-400 nm; step: 2 nm
Peak width: >0.025 min (0.5 S)
Injection: 0.5 μL injection with needle wash at flush port
Flow rate: 0.8 mL/min
Column temperature: 60° C.
Gradient: 0.0-0.2 min: 3% B
0.2-1.5 min: 3% B→95% B
1.5-2.5 min: 95% B
2.5-2.6 min: 95% B→3% B GVK_LCMS_03
HPLC: Agilent RRLC (1200 Series)
MS: Agilent SQD-6130 (API-ES/APCI (Multi Mode)+/−3000 V, Corona Current 4 μA)
MSD signal settings: Scan pos 90-1000, Scan neg 90-1000
Column: X-bridge C18, 4.6×50 mm, 2.5 μm
Eluent: A: 5 mM ammonium acetate; B: acetonitrile
Detection signal: UV 215 nm (bandwidth 4, reference off)
Spectrum: range: 200-400 nm; step: 2 nm
Peak width: >0.1 min (2.0 S)
Injection: 5 μL injection with needle wash
Flow rate: 0.6 mL/min
Column temperature: 35° C.
Gradient: 0.0-1.0 min: 5% B
1.0-1.8 min: 5% B→55% B
1.8-3.5 min: 55% B→98% B
3.5-5.5 min: 98% B
5.5-6.0 min: 98% B→5% B RND-FA-3.2
HPLC: Agilent Infinity-1290 Series
MS: Agilent SQD-6150 (API-ES+/−3000 V)
MSD signal settings: Scan pos 100-1000, Scan neg 100-1000
Column: Aquity BEH C18, 2.1×50 mm, 1.7 μm
Eluent: A: 0.1% formic acid in water; B: 0.1% formic acid in acetonitrile
Detection signal: UV 215 nm (bandwidth 4, reference off)
Spectrum: range: 200-400 nm; step: 2 nm
Peak width: >0.025 min (0.5 S)
Injection: 0.5 μL injection with needle wash at flush port
Flow rate: 0.8 mL/min
Column temperature: 45° C.
Gradient: 0.0-0.2 min: 2% B
0.2-1.5 min: 2% B→98% B
1.5-2.6 min: 98% B
2.6-2.61 min: 98% B→2% B
2.61-3.2 min: 2% B RND-FA-4.5
 HPLC: Waters UPLC
 MS: Waters Micromass Triple Quad (API-ES+/−3500 V, Cone voltage 25 to 50 V)
 MSD signal settings: Scan pos 100-900, Scan neg 100-900
 Column: Aquity BEH C18 2.1×50 mm, 1.7 μm
 Eluent: A: 0.1% formic acid in water; B: 0.1% formic acid in acetonitrile
 Detection signal: UV 215 nm (bandwidth 1, reference off)
 Spectrum: range: 200-400 nm; step: 1 nm
 Peak width: <0.01 min (0.1 s)
 Injection: 0.5 μL standard injection
 Flow rate: 0.4 mL/min
 Column temperature: 35° C.
 Gradient: 0.0-0.5 min: 5% B
  0.5-2.0 min: 5% B→50% B
  2.0-3.5 min: 50% B→100% B
  3.5-5.0 min: 100% B
  5.0-5.1 min: 100% B→5% B GVK_LCMS_05
 LC: Waters UPLC Acquity
 MS: Micromass Quattro Micro™
 MSD signal settings: Scan pos/neg 100-1200
 Column: Kinetex C18, 2.1×100 mm, 1.7 μm
 Eluent: A: water+0.1% formic acid; B: acetonitrile (HPLC grade)+0.1% formic acid
 Detection signal: UV 215/254 nm (bandwidth 4, reference off)
 Spectrum: range: 200-400 nm; Resolution: 1.2 nm
 Sampling rate: 5 points/sec
 Injection: 0.5 μL standard injection
 Flow: 0.4 mL/min
 Column temperature: 35° C.
 Gradient: 0.0-0.3 min: 5% B
  0.3-1.5 min: 5% B→50% B
  1.5-3.0 min: 50% B→100% B
  3.0-4.5 min: 100% B
  4.5-5.0 min: 100% B→5% B
  5.0-6.0 min: 5% B RNDA A6.0
 HPLC: Agilent RRLC (1200 Series)
 MS: Agilent SQD-6130 (API-ES/APCI (Multi Mode)+/−3000 V, Corona Current 4 μA)
 MSD signal settings: Scan pos 90-1000, Scan neg 90-1000
 Column: X-bridge C18, 4.6×50 mm, 2.5 μm
 Eluent: A: 5 mM ammonium acetate; B: acetonitrile
 Detection signal: UV 215 nm (bandwidth 4, reference off)
 Spectrum: range: 200-400 nm; step: 2 nm
 Peak width: >0.1 min (2.0 S)
 Injection: 5 μL injection with needle wash
 Flow rate: 0.6 mL/min
 Column temperature: 35° C.
 Gradient: 0.0-1.0 min: 5% B
  1.0-1.8 min: 5% B→55% B
  1.8-3.5 min: 55% B→98% B
  3.5-5.5 min: 98% B
  5.5-6.0 min: 98% B→5% B RND_XBRIDGE_7
 HPLC: Agilent RRLC (1200 Series)
 MS: Agilent SQD-6130 (API-ES/APCI (Multi Mode)+/−3000 V, Corona Current 4 μA)
 MSD signal settings: Scan pos 90-1000, Scan neg 90-1000
 Column: X-bridge C18, 4.6×75 mm, 3.5 μm
 Eluent: A: 5 mM ammonium acetate in water; B: acetonitrile
 Detection signal: UV 215/254 nm (bandwidth 4, reference off)
 Spectrum: range: 200-400 nm; step: 2 nm
 Peak width: >0.1 min (2.0 S)
 Injection: 5 μL injection with needle wash
 Flow rate: 1.30 mL/min
 Column temperature: 35° C.
 Gradient 0.0-1.0 min: 10% B
  1.0-5.0 min: 10% B→90% B
  5.0-5.5 min: 90% B→98% B
  5.5-7.0 min: 98% B
  7.0-7.01 min: 98% B→10% B GVK_LCMS_11
 HPLC: Agilent Infinity-1290 Series
 MS: Agilent SQD-6130 (API-ES+/−3000 V)
 MSD signal settings: Scan pos 100-1000, Scan neg 100-1000
 Column: Aquity BEH C18, 2.1×50 mm, 1.7 μm
 Eluent: A: 0.1% formic acid in water; B: 0.1% formic acid in acetonitrile
 Detection signal: UV 215 nm (bandwidth 4, reference off)
 Spectrum: range: 200-400 nm; step: 2 nm
 Peak width: >0.025 min (0.5 S)
 Injection: 0.5 μL injection with needle wash at flush port
 Flow rate: 0.6 mL/min
 Column temperature: 25° C.
 Gradient: 0.0-0.4 min: 3% B
  0.4-3.2 min: 3%→98% B
  3.2-3.8 min: 98% B
  3.8-4.2 min: 98%→3% B
  4.2-4.5 min: 3% B GVK_LCMS_15
 HPLC: Agilent RRLC (1200 Series)
 MS: Agilent SQD-6130 (API-ES/APCI (Multi Mode)+3500 V, −2500 V, Corona Current 10 μA)
 MSD signal settings: Scan pos 90-1000, Scan neg 90-1000
 Column: Atlantis® T3, 4.6×250 mm, 5.0 μm
 Eluent: A: 10 mM ammonium acetate; B: acetonitrile
 Detection signal: UV 215 nm/254 nm (bandwidth 4, reference off)
 Spectrum: range: 200-400 nm; step: 2 nm
 Peak width: >0.1 min (2.0 S)
 Injection: 5 μL injection with needle wash
 Flow rate: 1.00 mL/min
 Column temperature: 35° C.
 Gradient: 0.0-2.0 min: 5% B
  2.0-12.0 min: 5% B→95% B
  12.0-18.0 min: 95% B
  18.0-18.1 min: 95% B→5% B
  18.1-20.0 min: 5% B GVK_LCMS_18
 HPLC: Agilent Infinity-1290 Series
 MS: Agilent SQD-6130 (API-ES+3500 V/−3000 V)
 MSD signal settings: Scan pos 100-1200, Scan neg 100-1200
 Column: Aquity BEH C18, 2.1×50 mm, 1.7 μm
 Eluent: A: 0.1% Formic Acid in Acetonitrile; B: 0.1% Formic Acid in water
 Detection signal: UV 215/254 nm (bandwidth 4, reference off)
 Spectrum: range: 200-400 nm; step: 2 nm
 Peak width: >0.025 min (0.5 S)
 Injection: 0.5 μL injection with needle wash at flush port.
 Flow rate: 0.8 mL/min
 Column temperature: 60° C.
 Gradient: 0.0-0.4 min: 97% B 0.4-2.2 min: 97% B→2% B
2.2-2.6 min: 2% B
2.6-2.61 min: 2% B→97% B
2.61-3.0 min: 97% B GVK_LCMS_19
HPLC: Agilent RRLC (1200 Series)
MS: Agilent SQD-6130 (API-ES/APCI (Multi Mode) +3500 V, −2500 V, Corona Current 10 µA)
MSD signal settings: Scan pos 90-1000, Scan neg 90-1000
Column: X-bridge C18, 4.6×75 mm, 3.5 µm
Eluent: A: 10 mM ammonium acetate; B: acetonitrile
Detection signal: UV 215 nm/254 nm (bandwidth 4, reference off)
Spectrum: range: 200-400 nm; step: 2 nm
Peak width: >0.1 min (2.0 S)
Injection: 5 µL injection with needle wash
Flow rate: 2.00 mL/min
Column temperature: 35° C.
Gradient: 0.0-0.2 min: 10% B
0.2-2.5 min: 10%→75% B
2.5-3.0 min: 75%→100% B
3.0-4.8 min: 100% B
4.8-5.0 min: 100%→10% B GVK_LCMS_21
LC: Agilent Infinity 1290 series
MS: Agilent 6130 Quadruple lcms (SQ)
MSD signal settings: Scan pos/neg 80-1200
Column: Aquity BEH C18 2.1×50 mm, 1.7 µm
Eluent: A: water+0.1% formic acid; B: acetonitrile (HPLC grade)+0.1% formic acid
Detection signal: UV 215/254 nm (bandwidth 4, reference off)
Spectrum: range: 200-400 nm; step: 2.0 nm
Peak width: >0.01 min (0.2 s)
Injection: 0.5 µL standard injection
Flow: 0.8 mL/min
Column temperature: 60° C.
Gradient: 0.0-0.2 min: 3% B
0.2-1.5 min 3% B→95% B
1.5-2.5 min 95% B
2.5-2.6 min 95% B→3% B
2.6-3.2 min 3% B GVK_LCMS_22
HPLC: Agilent Infinity-1290 Series
MS: Agilent SQD-6150 (API-ES+/−3000 V)
MSD signal settings: Scan pos 100-1000, Scan neg 100-1000
Column: Aquity BEH C18, 2.1×50 mm, 1.7 µm
Eluent: A: 0.1% formic acid in water; B: 0.1% formic acid in acetonitrile
Detection signal: UV 215 nm (bandwidth 4, reference off)
Spectrum: range: 200-400 nm; step: 2 nm
Peak width: >0.025 min (0.5 S)
Injection: 0.5 µL injection with needle wash at flush port
Flow rate: 0.8 mL/min
Column temperature: 45° C.
Gradient: 0.0-0.2 min: 2% B
0.2-1.5 min: 2% B→98% B
1.5-2.6 min: 98% B
2.6-2.61 min: 98% B→2% B
2.61-3.2 min: 2% B The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein. Substances described in the literature can be prepared according to the published methods of synthesis.

General Reaction Scheme and Summary of the Synthesis Route Towards Compounds (I) According to the Invention

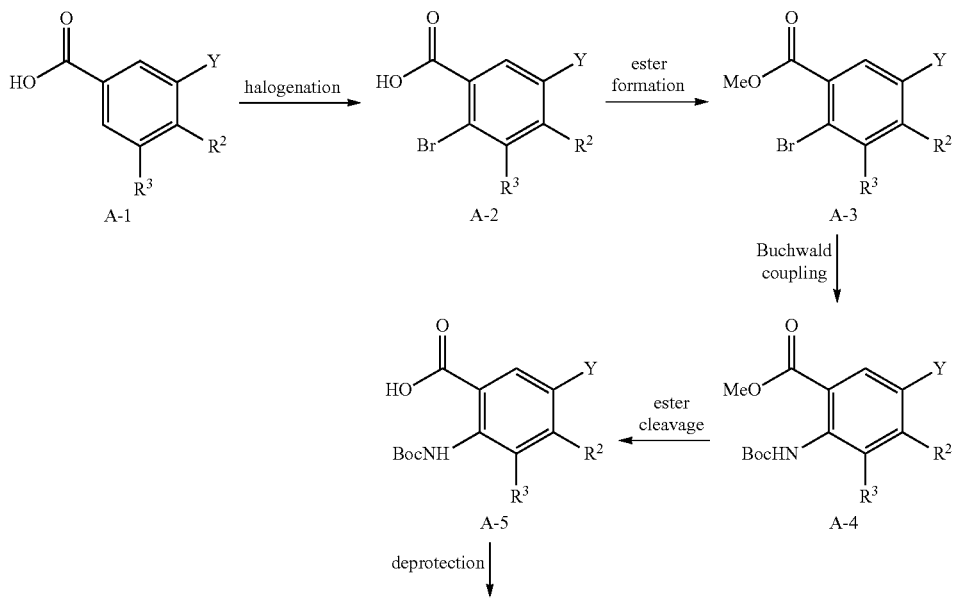

Scheme 1

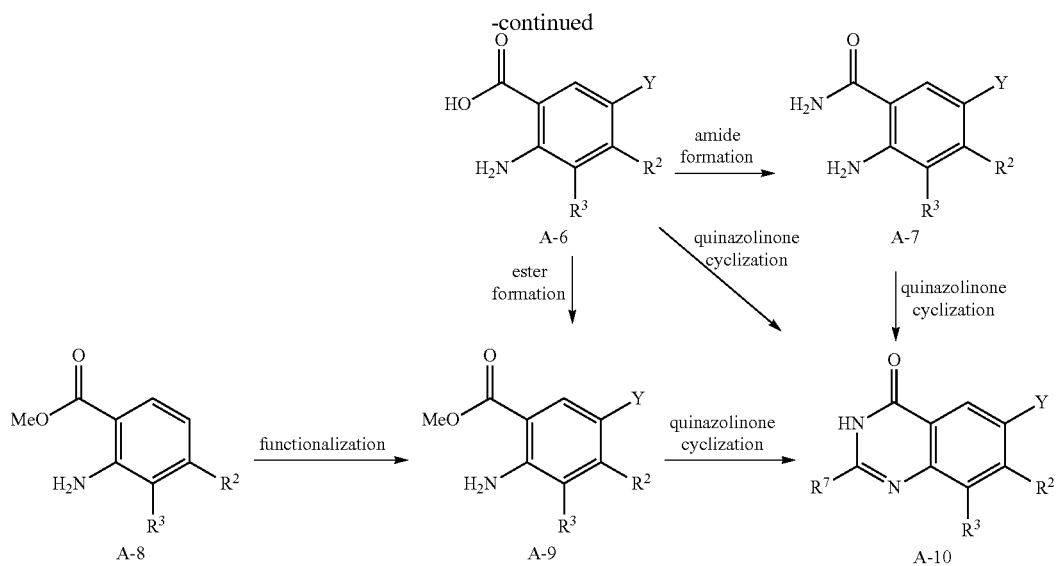

Compounds (1) according to the invention can be prepared stepwise starting with a synthesis depicted in scheme 1 and scheme 2.

Scheme 1 outlines the synthesis towards the first key intermediate A-10:

Key intermediate A-10 can be prepared via cyclization of the corresponding anilines bearing either a carboxylic acid (A-6), a carboxylic ester (A-9) or an amide functionality (A-7).

Anilines A-6 are either commercially available or can be synthesized starting from carboxylic acids A-1. After halogenation (A-2) and transformation of the carboxylic acid to the corresponding carboxylic ester (A-3), the amine is installed via e.g. a BUCHWALD-HARTWIG coupling yielding intermediate A-4. Cleavage of the ester (A-5) and deprotection of the amine lead to intermediate A-6.

The carboxylic esters A-9 can be synthesized via halogenation of the corresponding anilines A-8, which are commercially available, or from carboxylic acids A-6.

Scheme 2

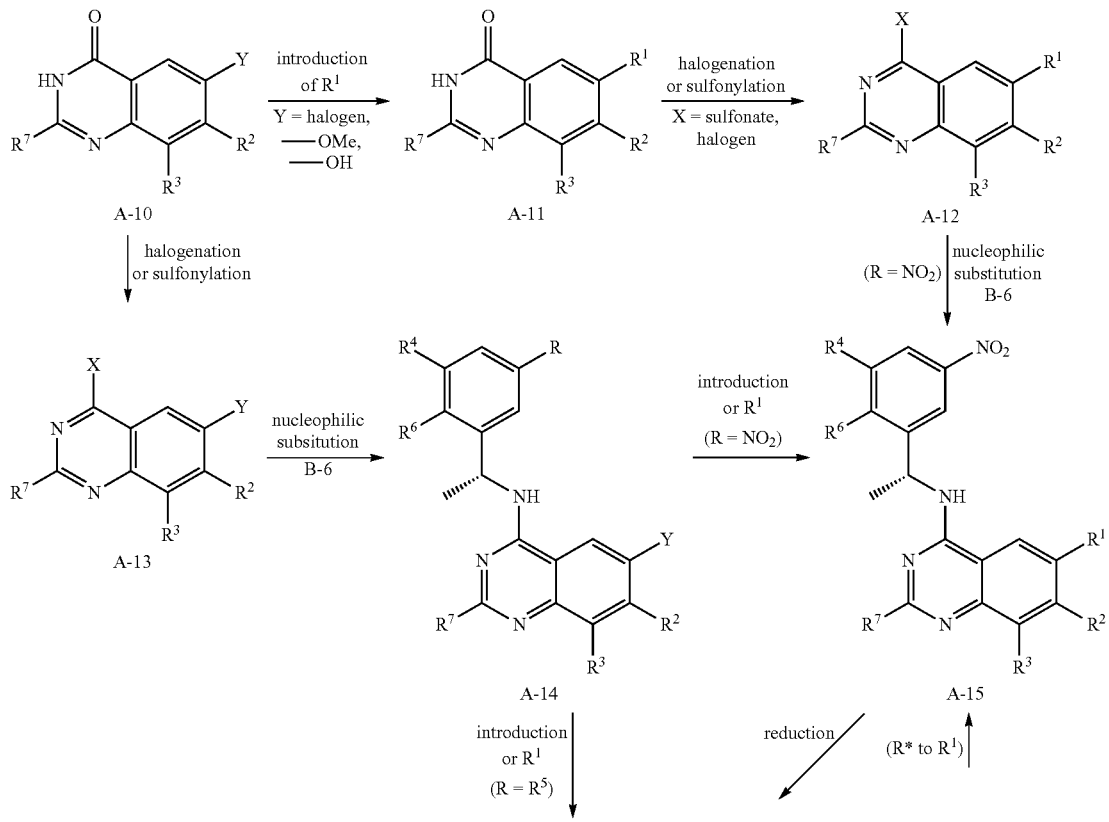

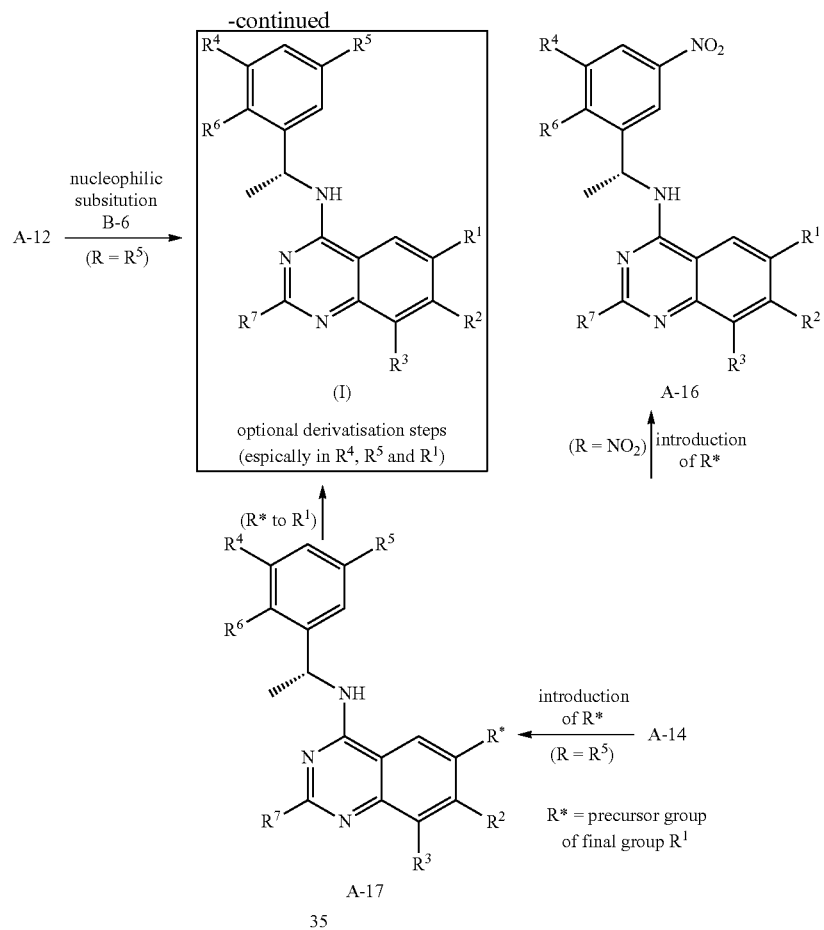

Quinazolinones A-10 (scheme 2) can then be functionalized (introduction of $R^1$) by e.g. nucleophilic substitutions, alkylations or transition metal catalyzed cross couplings, such as SUZUKI or HECK couplings, etc., or by the addition of metal halides such as GRIGNARD additions, etc. leading to quinazolinones A-11. If final compounds (I) bear an ether moiety in $R^1$ then synthesis starts from a dimethoxy quinazoline A-10: Selective ether cleavage followed by nucleophilic substitution of the hydroxy functionality also leads to desired intermediates A-11.

Intermediates A-11 can then be transferred to the corresponding quinazolines A-12 via e.g. halogenation or sulfonylation etc. Nucleophilic substitution of A-12 with benzyl amines B-6 directly leads to final compounds (I) or, alternatively, to nitro intermediates A-15 which in turn can be reduced to the final compounds (I).

An alternative synthesis route towards the final compounds (I) is the transformation of intermediates A-10 via e.g. halogenation or sufonylation etc. to the corresponding functionalized quinazolines A-13. Quinazoline A-13 undergoes a nucleophilic substitution with benzylic amines B-6 leading to quinazolines A-14 that can be further functionalized e.g. with transition metal catalyzed cross couplings, such as SUZUKI or HECK couplings, etc., the addition of metal halides such as GRIGNARD additions, nucleophilic substitutions or alkylations, etc. leading to the final compounds (I). Compounds (I) initially obtained can be further derivatized in optional steps (especially in $R^4$, $R^5$ and $R^1$) not depicted in scheme 2 to obtain further/additional compounds (I).

Scheme 3

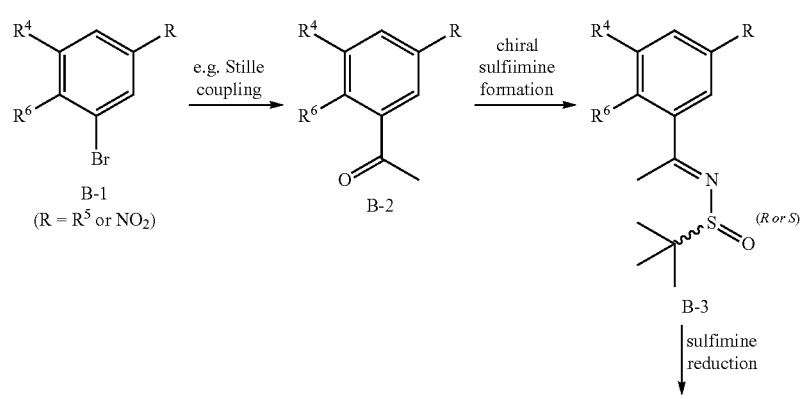

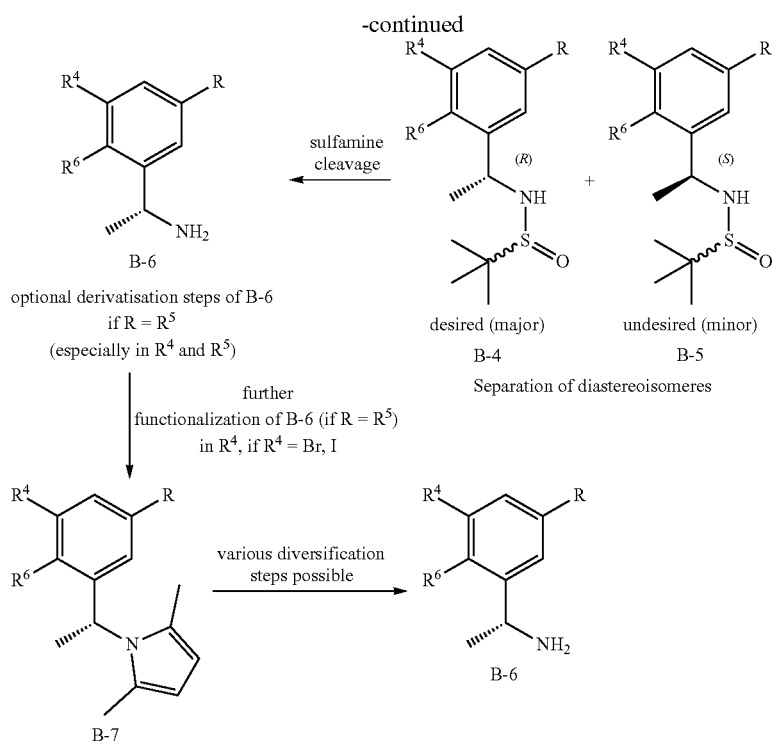

optional derivatisation steps of B-6
if R = R⁵
(especially in R⁴ and R⁵)

further functionalization of B-6 (if R = R⁵) in R⁴, if R⁴ = Br, I

Separation of diastereoisomeres

The required benzylic amines B-6 can be prepared from aromatic bromides B-1 that are transformed via a metal catalyzed cross coupling, e.g. a STILLE coupling, into the corresponding acetophenones B-2. The formation of a chiral sulfimine B-3 followed by the sulfimine reduction, e.g. with sodium borohydride or L-selectride, gives a diastereomeric mixture of B-4 and B-5 that can be separated. Only the desired diastereoisomere B-4 is taken into the next step and gives (after cleavage of the sulfimine) the desired chiral benzylic amine B-6. Depending of the nature of R⁴ chiral benzylic amines B-6 initially obtained can be further modified (after amino protection, e.g. via B-7) using e.g. metal catalyzed cross couplings or organometallic additions leading to further different chiral benzylic amines B-6.

Synthesis of Intermediates A-2

Experimental Procedure for the Synthesis of A-2a

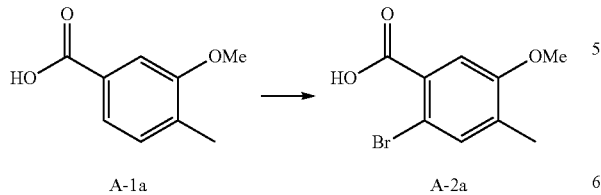

To a stirred solution of 3-methoxy-4-methyl-benzoic acid A-1a (500.0 mg, 3.0 mmol, 1.0 equiv.) in a mixture of acetic acid (3.8 mL) and water (3.8 mL), bromine (578.0 mg, 3.6 mmol, 1.2 equiv.) is added slowly at rt. The reaction is heated to 60° C. for 1 h. Then the reaction mixture is cooled to rt and the precipitate filtered off to give the desired product A-2a (HPLC method: RND-FA-4.5: $t_{ret}$ [min]=1.79; [M+H]⁺=245.0).

Synthesis of Intermediates A-3

Experimental Procedure for the Synthesis of A-3a

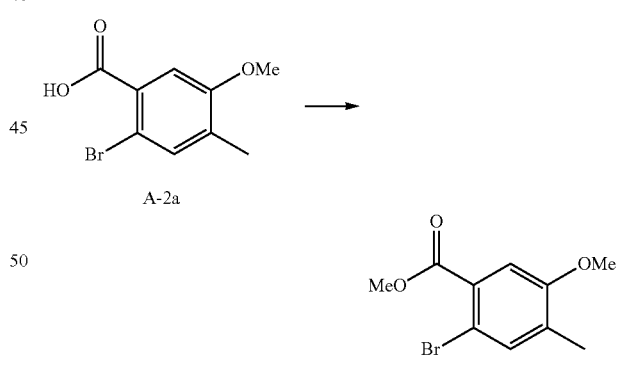

2-Bromo-5-methoxy-4-methyl-benzoic acid (6.2 g, 25.3 mmol, 1.0 equiv.) is dissolved in MeOH (20.0 mL). The solution is cooled to 0° C. and thionyl chloride (4.5 g, 37.9 mmol, 1.5 equiv.) is added slowly. Then the reaction mixture is heated to 80° C. for 4 h. The solvent is removed under reduced pressure, the residue diluted with water and extracted with EtOAc. The combined organic layers are dried over Na₂SO₄, filtered and the solvent is removed in vacuo giving the desired product A-3a (HPLC method: RND-FA-4.5: $t_{ret}$ [min]=2.14; [M+H]⁺=259.0).

Synthesis of Intermediates A-4

Experimental Procedure for the Synthesis of A-4a

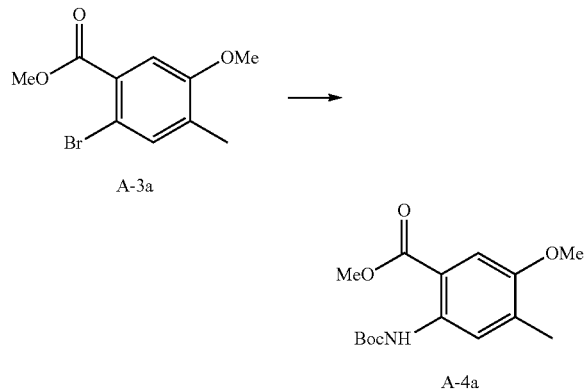

To a solution of 2-bromo-5-methoxy-4-methyl-benzoic acid methyl ester (4.2 g, 16.2 mmol 1.0 equiv.) in dry 1,4-dioxane (40 mL) xantphos (937.0 mg, 17.8 mmol, 10 mol %), tert-butyl carbamate (2.1 g, 17.8 mmol, 1.1 equiv.), cesium carbonate (10.7 g, 32.4 mmol, 2.0 equiv.) and palladium acetate (182 mg, 0.8 mmol, 5.0 mol %) is added and the reaction mixture is refluxed for 16 h. Then the reaction mixture is concentrated in vacuo The crude product is purified by chromatography on silica gel using EtOAc/petrol ether as eluent, giving the desired product A-4a (HPLC method: BFEC: $t_{ret}$ [min]=5.79; [M+H-Boc]$^+$=196.1).

Synthesis of Intermediates A-5

Experimental Procedure for the Synthesis of A-5a

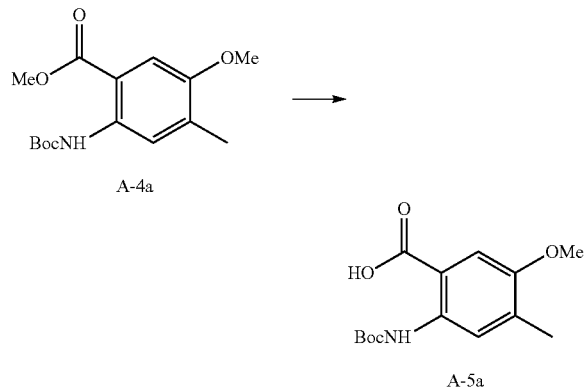

A-4a (4.2 g, 14.2 mmol, 1.0 equiv.) is dissolved in MeOH (7.0 mL) and THF (10.0 mL). Then LiOH (1.2 g, 28.4 mmol, 2.0 equiv.) is added and the reaction mixture stirred for 16 h at rt. The reaction mixture is concentrated in vacuo, the residue diluted with water, acidified with citric acid and extracted with EtOAc. The combined organic layers are dried over Na$_2$SO$_4$, filtered and the solvent is removed in vacuo giving the desired product A-5a (HPLC method: GVK_LCMS_05: $t_{ret}$ [min]=2.47; [M-H]$^+$=280.3).

Synthesis of Intermediates A-6

Experimental Procedure for the Synthesis of A-6a

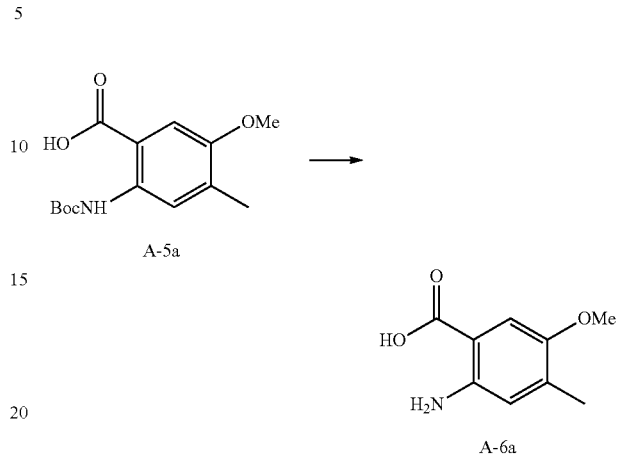

A-5a (3.5 g, 13.1 mmol, 1.0 equiv.) is dissolved in HCl in 1,4-dioxane (40.0 mL) and stirred for 4 h at rt. Then the reaction mixture is concentrated in vacuo, the residue diluted with water, neutralized and extracted with DCM/MeOH (10:1). The combined organic layers are dried over Na$_2$SO$_4$, filtered and the solvent is removed in vacuo giving the desired product A-6a (HPLC method: GVK_LCMS_05: $t_{ret}$ [min]=1.52; [M+H]$^+$=182.3).

Synthesis of Intermediates A-7

Experimental Procedure for the Synthesis of A-7a

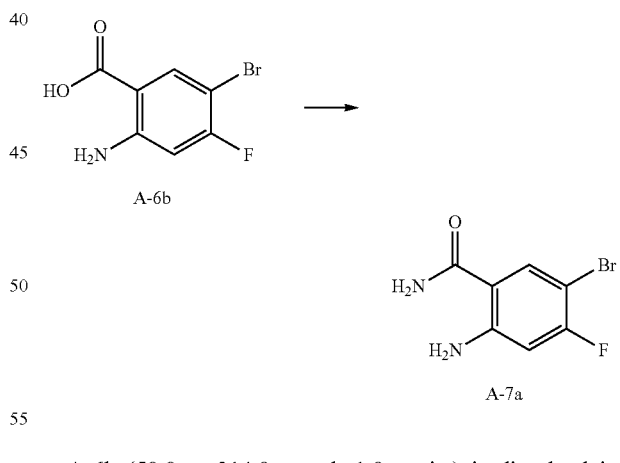

A-6b (50.0 g, 214.0 mmol, 1.0 equiv.) is dissolved in DMF (50 mL) and cooled down to 0° C. HATU (121.8 g, 320.0 mmol, 1.5 equiv.) and DIPEA (191.4 mL, 1068.0 mmol, 5.0 equiv.) is added and the reaction mixture stirred for 20 min at 0° C. Then NH$_4$Cl (57.7 g, 1068.0 mmol, 5.0 equiv.) is added and the reaction mixture stirred for 2 h at rt. The reaction is quenched with ice water and extracted with EtOAc (3×200 mL). The combined organic layer is dried (Na$_2$SO$_4$), filtered and concentrated in vacuo to give product A-7a (HPLC method: GVK_LCMS_05: $t_{ret}$ [min]=1.06; [M+H]$^+$=233.0).

Synthesis of Intermediates A-9

Experimental Procedure for the Synthesis of A-9a

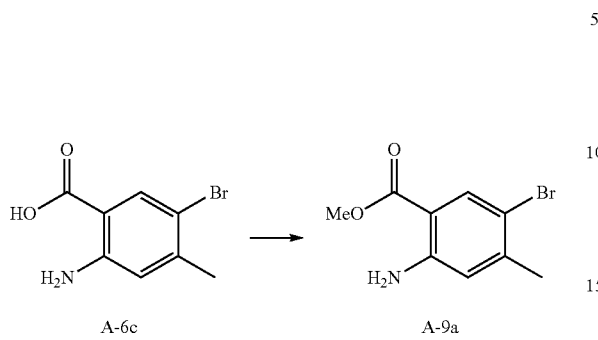

A-6c (5.0 g, 21.7 mmol, 1.0 equiv.) is dissolved in MeOH (50 mL) and cooled down to 0° C. Thionyl chloride (12.9 g, 108.7 mmol, 5.0 equiv.) is added dropwise, then the reaction mixture is stirred for 24 h at 80° C. MeOH is evaporated, water is added to the reaction mixture and extracted with EtOAc. The combined organic layer is dried (MgSO$_4$), filtered and concentrated in vacuo to give product A-9a (HPLC method: GVK_LCMS_05: t$_{ret}$ [min]=1.67; [M+H]$^+$=196.1).

Experimental Procedure for the Synthesis of A-9b

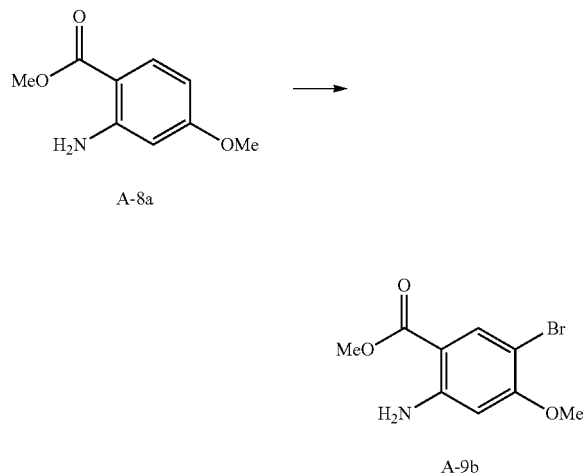 [SMILES: COC(=O)c1ccc(OC)cc1N ; COC(=O)c1cc(Br)c(OC)cc1N]

A-8a (15.0 g, 82.8 mmol, 1.0 equiv.) is dissolved in chloroform (750 mL) and cooled to 0° C. A solution of bromine (4.2 mL, 82.8 mmol, 1.0 equiv.) in chloroform (10 mL) is added dropwise and the reaction mixture stirred for 1 h at rt. Then the reaction mixture is quenched with sodium thiosulphate (aqu.) and extracted with EtOAc. The combined organic layer is washed with saturated NaHCO$_3$ solution, dried over Na$_2$SO$_4$ and concentrated in vacuo. The crude product is washed with hexane to give the final compound A-9b (HPLC method: GVK_LCMS_05: t$_{ret}$ [min]=1.76; [M+H]$^+$=260.0).

Experimental Procedure for the Synthesis of A-9c

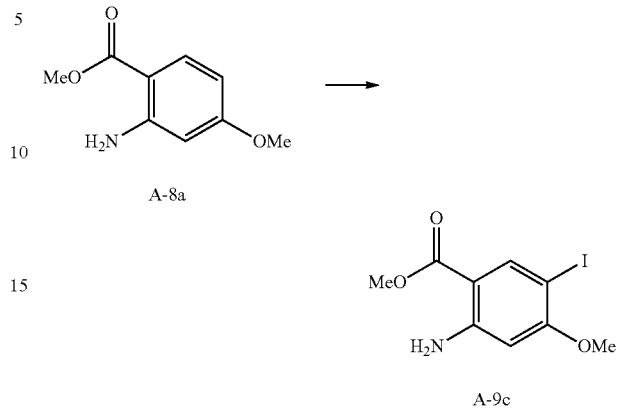

A-8a (20.0 g, 110.4 mmol, 1.0 equiv.) is dissolved in EtOH (80 mL). Water (140 mL) and conc. HCl (32 mL) is added and the reaction mixture cooled to 0° C. A solution of iodine monochloride (19.7 g, 121.4 mmol, 1.1 equiv.) in conc. HCl (10 mL) is added dropwise and the reaction mixture stirred for 16 h at rt. Then the reaction mixture is quenched with water and the precipitate is filtered off. The crude product is washed with n-pentane to give the final compound A-9c (HPLC method: GVK_LCMS_05: t$_{ret}$ [min]=1.98; [M+H]$^+$=308.0).

Synthesis of Intermediates A-10

Experimental Procedure for the Synthesis of A-10a

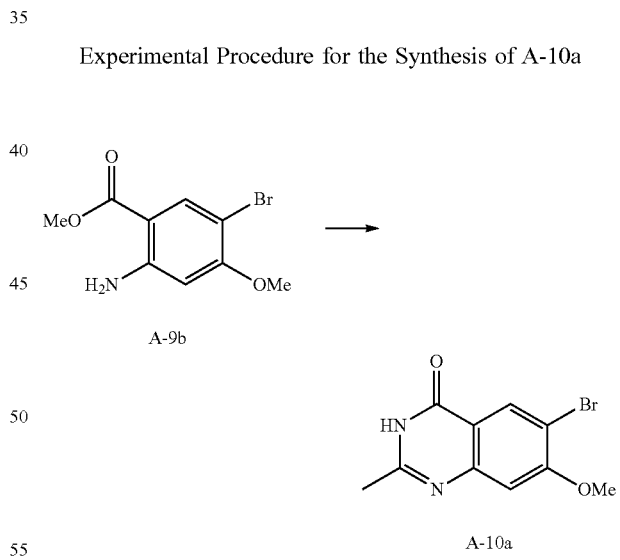

A-9b (12.0 g, 46.1 mmol, 1.0 equiv.) is dissolved in acetonitrile (120 mL) and treated with methane sulfonic acid (24 mL). The reaction mixture is heated in a sealed tube to 100° C. for 16 h. The acetonitrile is evaporated, water and sat. NaOH solution is added to the reaction mixture and the precipitate filtered off to give the desired product A-10a.

The following intermediates A-10 (table 1) are available in an analogous manner starting from different carboxylic esters A-9. The crude product A-10 is purified by chromatography if necessary.

TABLE 1

| # | structure | $t_{ret}$ [min] | $[M + H]^+$ | HPLC method |
|---|---|---|---|---|
| A-10a | 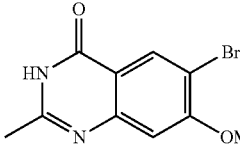 | 1.59 | 269.0 | GVK-LCMS-03 |
| A-10b | 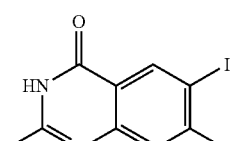 | 1.62 | 317.0 | RND-FA-3.2 |
| A-10c | 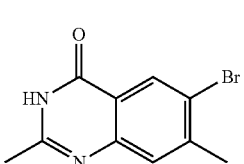 | 1.65 | 253 | GVK_LCMS_22 |
| A-10d | 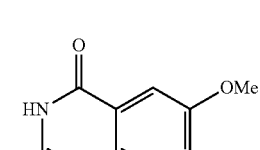 | 2.91 | 221.0 | RND-AA-6.0 |
| A-10e | 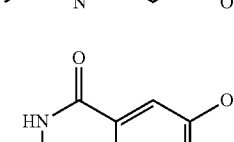 | 1.23 | 209.1 | RND-FA-3.0 |

Experimental Procedure for the Synthesis of A-10f

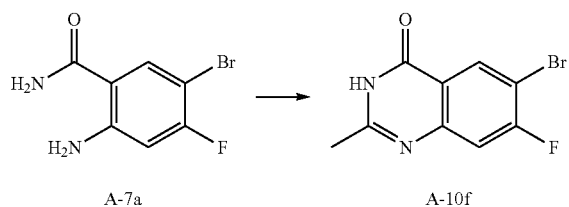

A-7a (35.0 g, 150.0 mmol, 1.0 equiv.) is dissolved in EtOH (350 mL) and treated with trimethyl ortho acetate (180.0 mL, 10.0 equiv.). The reaction mixture is heated in a seal tube to 120° C. for 4 h. Then the reaction mixture is cooled to rt and the precipitate is filtered off. The crude compound is washed with Et$_2$O to give the desired product A-10f.

The following intermediates A-10 (table 2) are available in an analogous manner starting from different aromatic amides A-7. The crude product A-10 is purified by chromatography if necessary.

TABLE 2

| # | structure | $t_{ret}$ [min] | $[M + H]^+$ | HPLC method |
|---|---|---|---|---|
| A-10f | 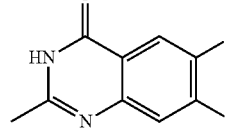 | 1.65 | 257.0 | RND-FA-2.6 |
| A-10g | 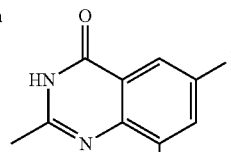 | 2.03 | 253.0 | GVK-LCMS-05 |
| A-10h | 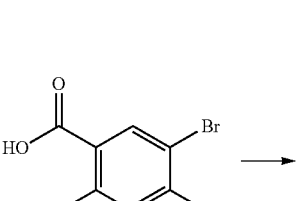 | 1.07 | 301.0 | LCMSBAS-1 |

Experimental Procedure for the Synthesis of A-10i

To a stirred solution of A-6b (75.0 g, 326.0 mmol, 1.0 equiv.) in MeOH (600 mL) is added ammonium acetate (251.0 g, 3.3 mol, 10.0 equiv.) and trimethyl orthoacetate (391.2 g, 3.3 mol, 10.0 equiv.). The reaction mixture is heated in a seal tube to 120° C. for 24 h. The MeOH is evaporated, water is added to the reaction mixture and the precipitate is filtered off. The crude compound is washed with petrol ether and Et$_2$O to give the desired product A-10i.

The following intermediates A-10 (table 3) are available in an analogous manner starting from different carboxylic acids A-6. The crude product A-10 is purified by chromatography if necessary.

TABLE 3

| # | structure | $t_{ret}$ [min] | $[M + H]^+$ | HPLC method |
|---|---|---|---|---|
| A-10i | 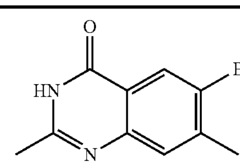 | 1.65 | 253 | GVK_LCMS_22 |

TABLE 3-continued

| # | structure | $t_{ret}$ [min] | [M + H]$^+$ | HPLC method |
|---|---|---|---|---|
| A-10j | (6-Br, 2-Me quinazolin-4(3H)-one) | 1.39 | 240.0 | GVK_LCMS_11 |
| A-10k | (6-I, 2-Me quinazolin-4(3H)-one) | 1.106 | 286.9 | GVK_LCMS_21 |
| A-10l | (6-OMe, 2-Me quinazolin-4(3H)-one) | 1.28 | 191.1 | GVK-LCMS-05 |
| A-10m | (6-OMe, 7-Me, 2-Me quinazolin-4(3H)-one) | 1.48 | 205.27 | GVK_LCMS_05 |

Experimental Procedure for the Synthesis of A-10n

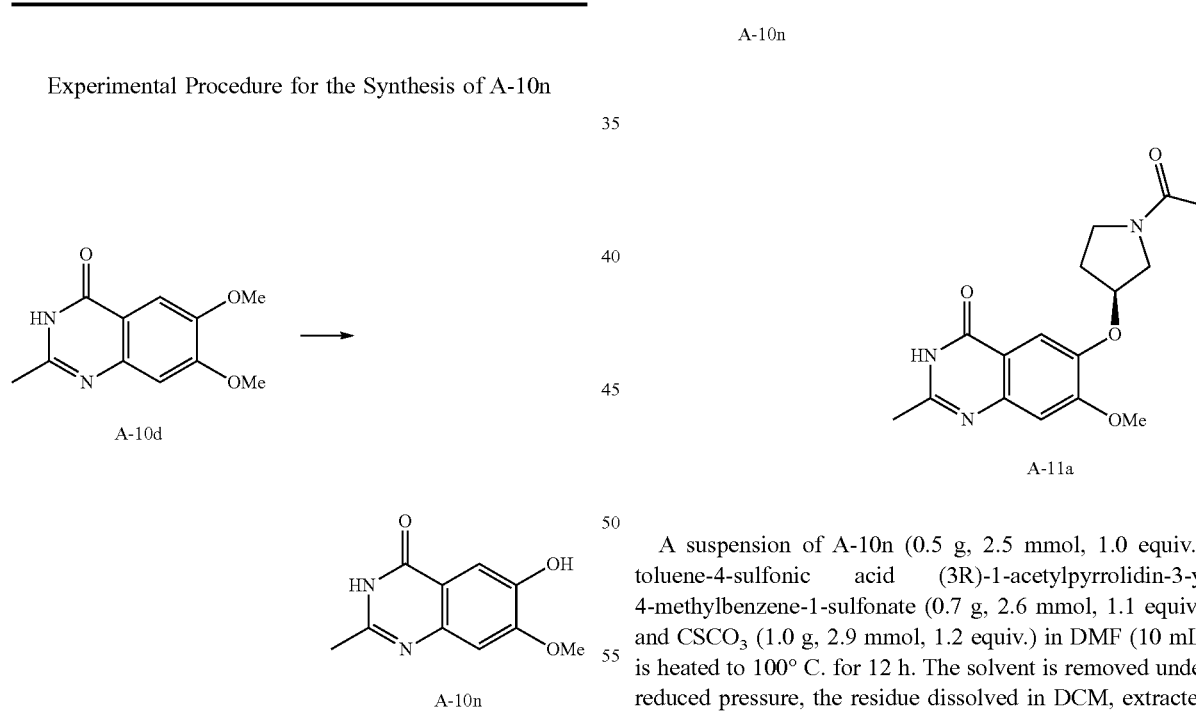

A-10d → A-10n

To a suspension of A-10d (30.0 g, 136.2 mmol, 1.0 equiv.) in methane sulfonic acid (150.0 mL), DL-methionine (30.5 g, 149.2 mmol, 1.5 equiv.) is added at rt. The reaction mixture is heated to 80° C. for 16 h. The reaction mixture is quenched with ice water and basified with 2N NaOH solution. The precipitate is filtered off to give the desired product A-10n (HPLC method: RND-Xbridge 3: $t_{ret}$ [min]=1.11; [M+H]$^+$=207.2).

TABLE 4

| # | structure | $t_{ret}$ [min] | [M + H]$^+$ | HPLC method |
|---|---|---|---|---|
| A-10n | (6-OH, 7-OMe, 2-Me quinazolin-4(3H)-one) | 1.65 | 253 | GVK_LCMS_22 |

Synthesis of Intermediates A-11

Experimental Procedure for the Synthesis of A-11a

A-10n → A-11a

A suspension of A-10n (0.5 g, 2.5 mmol, 1.0 equiv.), toluene-4-sulfonic acid (3R)-1-acetylpyrrolidin-3-yl 4-methylbenzene-1-sulfonate (0.7 g, 2.6 mmol, 1.1 equiv.) and CSCO$_3$ (1.0 g, 2.9 mmol, 1.2 equiv.) in DMF (10 mL) is heated to 100° C. for 12 h. The solvent is removed under reduced pressure, the residue dissolved in DCM, extracted with NaHCO$_3$ (sat.) and the water phase washed with DCM. The combined organic layers are dried over MgSO$_4$, filtered and the solvent removed in vacuo. The crude product is purified by chromatography (DCM:MeOH:NH$_3$, 19:1:0.1) giving the desired product A-11a.

The following intermediates A-11 (table 5) are available in an analogous manner starting from different quinazolinones A-10. The crude product A-11 is purified by chromatography if necessary.

TABLE 5
| # | structure | $t_{ret}$ [min] | $[M + H]^+$ | HPLC method |
|---|---|---|---|---|
| A-11a | | 0.58 | 318.2 | VAB |
| A-11a | | 0.58 | 318.2 | VAB |
| A-11b | 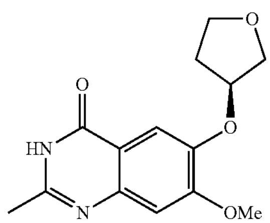 [SMILES: COc1cc2nc(C)[nH]c(=O)c2cc1O[C@H]1CCOC1] | 0.57 | 277.0 | LCMSBAS-1 |
| A-11c | 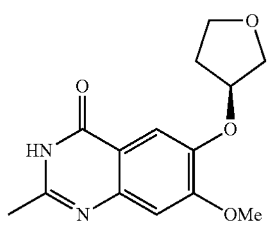 [SMILES: COc1cc2nc(C)[nH]c(=O)c2cc1O[C@H]1CCOC1] | 0.59 | 277.3 | VAB |
Synthesis of Intermediates A-12
Experimental Procedure for the Synthesis of A-12a
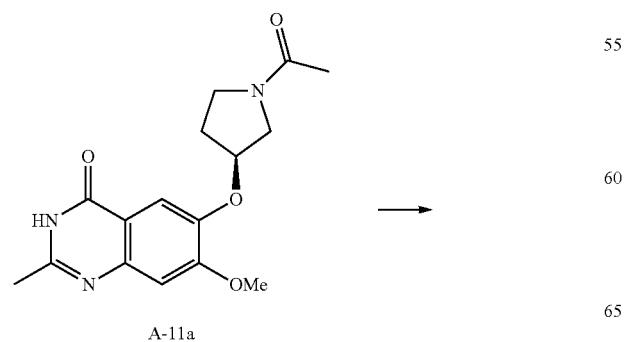
A-11a (250.0 mg, 0.8 mmol, 1.0 equiv.), 2,4,6-triisopropylbenzenesulfonyl chloride (295.0 mg, 1.0 mmol, 1.2 equiv.), and 4-dimethylaminopyridine (13.0 mg, 0.1 mmol, 0.1 equiv.) are suspended in DCM (5.0 mL) and triethyl amine (0.3 mL, 2.4 mmol, 3.0 equiv.). The reaction mixture is stirred at rt for 12 h. The reaction is diluted with DCM, extracted with NaHCO₃ (sat.) and the water phase washed with DCM. The combined organic layers are dried over MgSO₄, filtered and the solvent removed in vacuo. The crude product is purified by chromatography using cyclohexane/EtOAc to give the desired product A-12a.

The following intermediates A-12 (table 6) are available in an analogous manner starting from different quinazolinones A-11. The crude product A-12 is purified by chromatography if necessary.

TABLE 6

| # | structure | $t_{ret}$ [min] | [M + H]⁺ | HPLC method |
|---|---|---|---|---|
| A-12a | 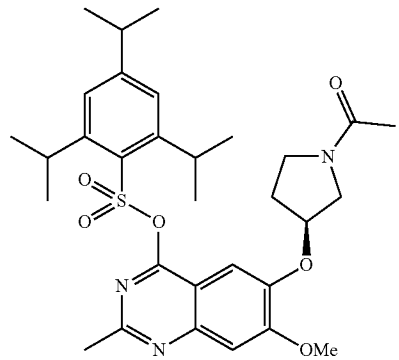 [SMILES: COc1cc2nc(C)nc(OS(=O)(=O)c3c(C(C)C)cc(C(C)C)cc3C(C)C)c2cc1O[C@H]1CCN(C(C)=O)C1] | 1.16 | 584.3 | VAB |
| A-12b | 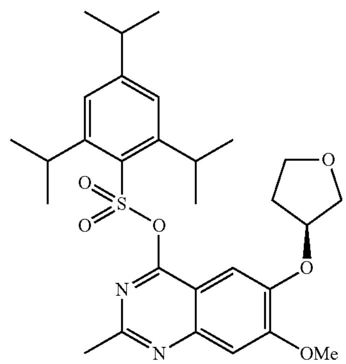 [SMILES: COc1cc2nc(C)nc(OS(=O)(=O)c3c(C(C)C)cc(C(C)C)cc3C(C)C)c2cc1O[C@H]1CCOC1] | 1.70 | 543.0 | LCMSBAS-1 |
| A-12c | 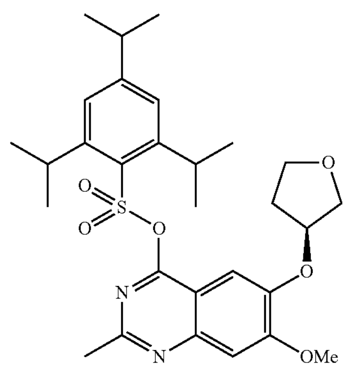 [SMILES: COc1cc2nc(C)nc(OS(=O)(=O)c3c(C(C)C)cc(C(C)C)cc3C(C)C)c2cc1O[C@H]1CCOC1] | 1.70 | 543.0 | LCMSBAS-1 |
| A-12d* | 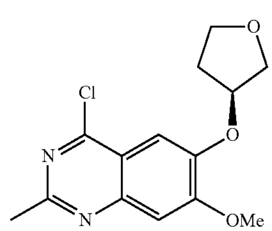 [SMILES: COc1cc2nc(C)nc(Cl)c2cc1O[C@H]1CCOC1] | 1.37 | 295 | BFEC |

*A-12d is synthesized in analogy to A-13a (see below)

Synthesis of Intermediates A-13

Experimental Procedure for the Synthesis of A-13a

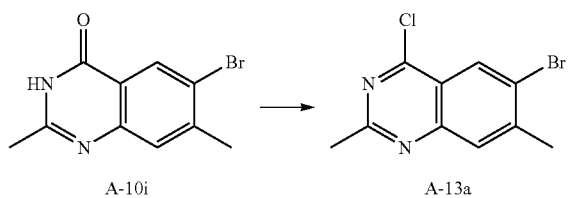

A mixture of A-10i (30.0 g, 119.0 mmol, 1.0 equiv.) in POCl$_3$ (600 mL) is stirred at 140° C. for 4 h. After completion of the reaction POCl$_3$ is removed in vacuo, the reaction mixture is pured on ice water, neutralized with sat. NaHCO$_3$ solution and extracted 3× with EtOAc. The combined organic layers are dried over Na$_2$SO$_4$, filtered and the solvent is removed in vacuo. The crude product is purified by chromatography on silica gel using EtOAc/hexane as eluent giving the desired product A-13a.

The following intermediates A-13 (table 7) are available in an analogous manner starting from different dihydroquinazolin-4-ones A-10. The crude product A-13 is purified by chromatography if necessary.

TABLE 7

| # | structure | $t_{ret}$ [min] | [M + H]$^+$ | HPLC method |
|---|---|---|---|---|
| A-13a | 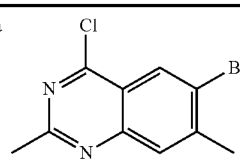 | 1.99 | 271.0 | RND-FA-2.6 |
| A-13b | 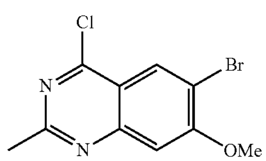 | 2.00 | 287.0 | RND-FA-3.2 |
| A-13c | 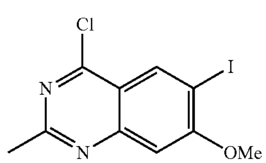 | 2.72 | 334.0 | RND-FA-4.5 |
| A-13d | 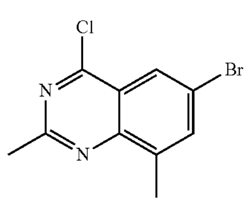 | 2.96 | 271.0 | GVK-LCMS-05 |
| A-13e | 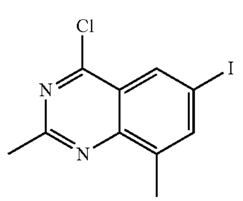 | 0.903 | 315.2 | BFEC |
| A-13f | 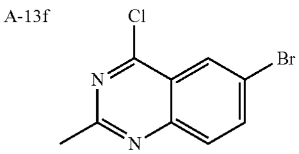 | 2.48 | 256.9 | GVK_LCMS_11 |
| A-13g | 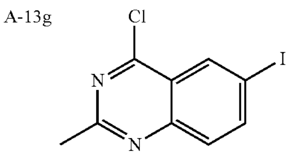 | 2.86 | 304.9 | GVK-LCMS_19 |
| A-13h | 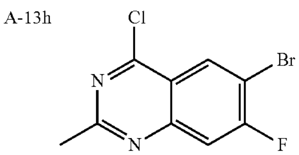 | 1.51 | 274.9 | RND-FA-2.6 |
| A-13i | 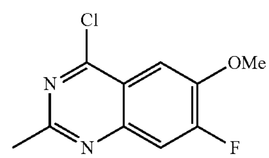 | 1.71 | 227.0 | RND-FA-3.0 |
| A-13j | 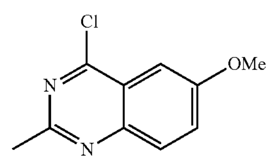 | 2.11 | 209.1 | RND-FA-4.5 |
| A-13k | 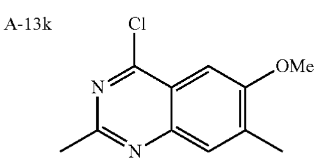 | 4.13 | 223.1 | RND-FA-6 |

Synthesis of Intermediates B-1

Experimental Procedure for the Synthesis of C-2a

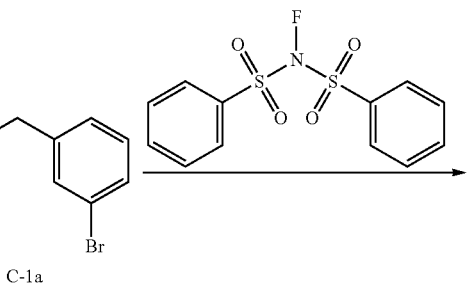

-continued

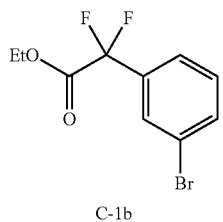

C-1b

A solution C-1a (5.0 g, 21.0 mmol, 1.0 equiv.) in THF (25 mL) is cooled to −78° C. and LiHMDS (40 mL, 42.0 mmol, 2.0 equiv.) is added dropwise at −78° C. The reaction mixture is stirred for 30 min, then a solution of N-fluorobenzene sulfonimide (13.0 g, 42.0 mmol, 2.0 equiv.) in THF (25 mL) is added dropwise. The reaction mixture is slowly allowed to warm to 0° C. and stirred for 1 h. After complete consumption of starting material (monitored by TLC) water is added to the reaction mixture and extracted with EtOAc (2×100 mL). The combined organic layers are washed with water and brine. The organic layer is dried over $Na_2SO_4$ and concentrated under reduced pressure. The crude product is purified by silica gel chromatography giving the desired product C-1b (HPLC method LCMSBAS1: $t_{ret}$ [min]=1.01; $[M+H]^+$=235.0).

Experimental Procedure for the Synthesis of B-1a

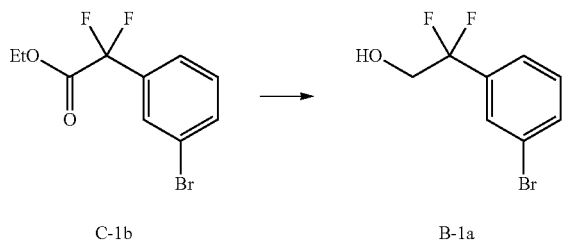 [SMILES: CCOC(=O)C(F)(F)c1cccc(Br)c1 ; OCC(F)(F)c1cccc(Br)c1]

C-1b                B-1a

To a solution of C-1b (250.0 mg, 0.9 mmol, 1.0 equiv.) in EtOH (2.0 mL) is added $NaBH_4$ (65.8 mg, 1.7 mmol, 2.0 equiv.) and the reaction mixture is stirred for 12 h at rt. The reaction is quenched with water and extracted with EtOAc. The combined organic layers are dried over $Na_2SO_4$, filtered and the solvent is removed in vacuo. The crude product is purified by RP-chromatography ($CH_3CN/H_2O$) giving the desired product B-1a (product confirmed by NMR).

Experimental Procedure for the Synthesis of B-1b

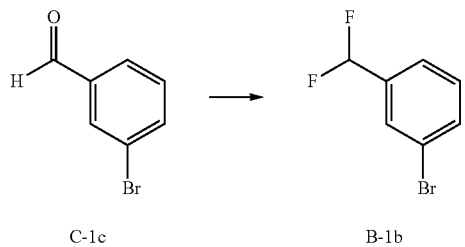 [SMILES: O=Cc1cccc(Br)c1 ; FC(F)c1cccc(Br)c1]

C-1c                B-1b

3-Bromo benzaldehyde C-1c (5.0 g, 27.0 mmol, 1.0 equiv.) is dissolved in DCM (50 mL). Then DAST (7.4 g, 46.0 mmol, 1.7 equiv.) is added slowly and the reaction mixture stirred for 16 h at rt. The progress of the reaction is monitored by TLC. The reaction mixture is quenched with saturated $NaHCO_3$, extracted with DCM, dried over $Na_2SO_4$ and the solvent removed under reduced pressure giving the desired product B-1b (product confirmed by NMR).

Synthesis of Intermediates B-2

Experimental Procedure for the Synthesis of B-2a

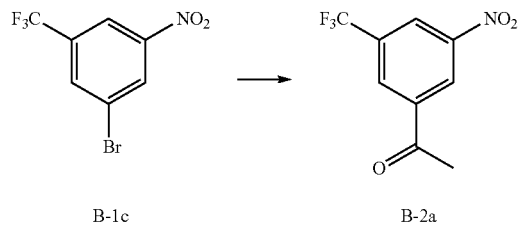 [SMILES: O=[N+]([O-])c1cc(Br)cc(C(F)(F)F)c1 ; CC(=O)c1cc([N+](=O)[O-])cc(C(F)(F)F)c1]

B-1c                B-2a

1-Bromo-3-nitro-5-trifluoromethyl-benzene B-1c (100.0 g 370.0 mmol, 1.0 equiv.) is dissolved in dry 1,4-dioxane (1000 mL). Then $NEt_3$ (103 mL, 20.0 equiv.) is added and the solution purged with argon for 5 min. Tributyl(1-ethoxyvinyl)tin (173.0 g, 4815.0 mmol, 13.0 equiv.) and bis(triphenylphosphine)palladium(II)chloride (26.0 g, 370.0 mmol, 1.0 equiv.) is added and the reaction mixture heated to 80° C. in the autoclave for 12 h. The reaction is quenched with 1N HCl and extracted with EtOAc. The combined organic layers are dried over $Na_2SO_4$, filtered and the solvent is removed in vacuo. The crude product is purified by chromatography on silica gel using EtOAc/petrol ether as eluent giving the desired product B-2a (55.0 g, 236.0 mmol, 64%).

The following intermediates B-2 (table 8) are available in an analogous manner starting from different aromatic bromides B1. The crude product B-2 is purified by chromatography if necessary.

TABLE 8

| # | structure | $t_{ret}$ [min] | $[M + H]^+$ | HPLC method |
|---|---|---|---|---|
| B-2a | F₃C–⟨⟩–NO₂ with COCH₃ | n.a. | n.a. | confirmed by NMR |
| B-2b | F₃C–⟨⟩–NO₂ with F and COCH₃ | n.a. | n.a. | confirmed by NMR |
| B-2c | F₃C–⟨⟩–NO₂ with CH₃ and COCH₃ | n.a. | n.a. | confirmed by NMR |

TABLE 8-continued

| # | structure | $t_{ret}$ [min] | $[M + H]^+$ | HPLC method |
|---|---|---|---|---|
| B-2d | 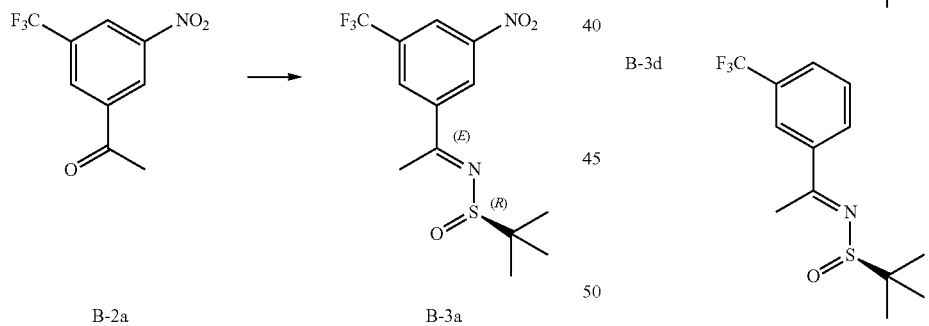 | n.a. | n.a. | confirmed by NMR |
| B-2e | 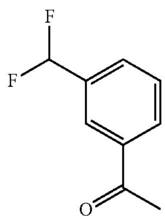 | n.a. | n.a. | confirmed by NMR |
| B-2f | 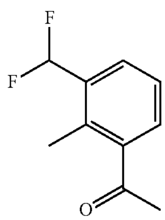 | n.a. | n.a. | confirmed by NMR |

Synthesis of Intermediates B-3

Experimental Procedure for the Synthesis of B-3a

B-2a → B-3a

B-2a (53.0 g, 227.3 mmol; 1.0 equiv.) is dissolved in THF. (R)-(+)-2-methyl-2-propanesulfinamide (41.3 g; 341.0 mmol; 1.5 equiv.) and Ti(OEt)$_4$ (129.6 g, 568.3 mmol; 2.5 equiv.) is added at rt and the resulting reaction mixture heated to 80° C. for 5 h. The reaction mixture is cooled to rt and quenched with ice water. The precipitate is dissolved in EtOAc and filtered through celite. The organic layer is concentrated in vacuo. The crude product is purified by chromatography on silica gel using EtOAc/petrol ether as eluent giving the desired product B-3a.

The following intermediates B-3 (table 9) are available in an analogous manner starting from different acetophenones B-2. The crude product B-3 is purified by chromatography if necessary.

TABLE 9

| # | structure | $t_{ret}$ [min] | $[M + H]^+$ | HPLC method |
|---|---|---|---|---|
| B-3a | 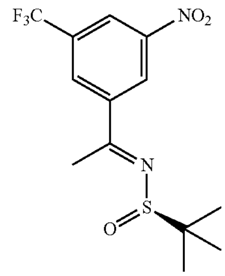 [SMILES: C/C(=N\[S@](=O)C(C)(C)C)c1cc([N+](=O)[O-])cc(C(F)(F)F)c1] | n.a. | n.a. | — |
| B-3b | 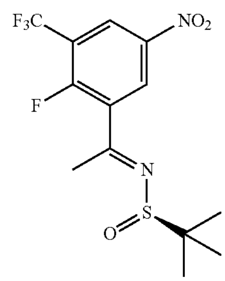 [SMILES: C/C(=N\[S@](=O)C(C)(C)C)c1cc([N+](=O)[O-])cc(C(F)(F)F)c1F] | n.a. | n.a. | — |
| B-3c | 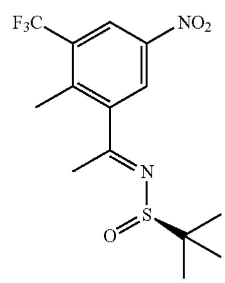 [SMILES: C/C(=N\[S@](=O)C(C)(C)C)c1cc([N+](=O)[O-])cc(C(F)(F)F)c1C] | n.a. | n.a. | — |
| B-3d | 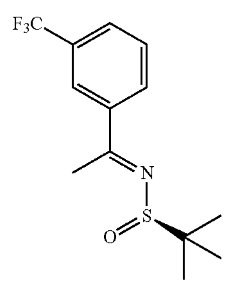 [SMILES: C/C(=N\[S@](=O)C(C)(C)C)c1cccc(C(F)(F)F)c1] | n.a. | n.a. | — |
| B-3e | 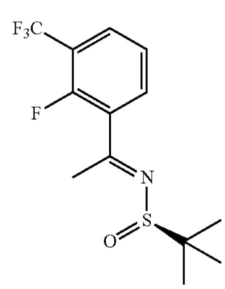 [SMILES: C/C(=N\[S@](=O)C(C)(C)C)c1cccc(C(F)(F)F)c1F] | 2.80 | 310.1 | RND-FA-3.2 |

TABLE 9-continued

| # | structure | $t_{ret}$ [min] | $[M + H]^+$ | HPLC method |
|---|---|---|---|---|
| B-3f | (structure: HO-CH2-CF2-phenyl-C(CH3)=N-S(=O)-tBu) | 3.01 | 302.1 $(M - H)^-$ | RND-FA-3.2 |
| B-3g | (structure: 3-(CHF2)-phenyl-C(CH3)=N-S(=O)-tBu) | 1.91 | 274.1 | RND-FA-3.2 |
| B-3h | (structure: 3-(CHF2)-2-methyl-phenyl-C(CH3)=N-S(=O)-tBu) | n.a. | n.a. | — |

Experimental Procedure for the Synthesis of B-3i

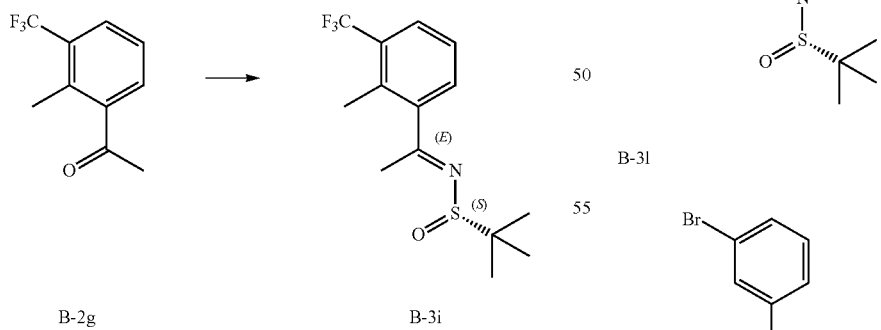

B-2g → B-3i

B-2g (10.0 g; 49.5 mmol, 1.0 equiv.) is dissolved in THF. (S)-(+)-2-methyl-2-propanesulfinamide (9.0 g; 74.2 mmol, 1.5 equiv.) and Ti(OEt)$_4$ (28.2 g, 123.7 mmol, 2.5 equiv.) are added at rt. The resulting reaction mixture is heated to 80° C. for 4 h. The reaction mixture is cooled to rt and quenched with ice water. The precipitate is dissolved in EtOAc and filtered through celite. The organic layer is concentrated in vacuo. The crude product is purified by chromatography on silica gel using EtOAc/petrol ether as eluent giving the desired product B-3i.

The following intermediates B-3 (table 10) are available in an analogous manner starting from different acetophenones B-3. The crude product B-3 is purified by chromatography if necessary.

TABLE 10

| # | structure | $t_{ret}$ [min] | $[M + H]^+$ | HPLC method |
|---|---|---|---|---|
| B-3i | (structure: 3-CF3, 2-methyl-phenyl-C(CH3)=N-S(=O)-tBu) | 1.50 | 306.1 | GVK_LCMS_21 |
| B-3j | (structure: 2-F, 3-methyl-phenyl-C(CH3)=N-S(=O)-tBu) | 1.99 | 256.2 | RND-FA-3.2 |
| B-3k | (structure: 3-I-phenyl-C(CH3)=N-S(=O)-tBu) | n.a. | n.a. | — |
| B-3l | (structure: 3-Br-phenyl-C(CH3)=N-S(=O)-tBu) | n.a. | n.a. | — |

Synthesis of Intermediates B-4 (Together with Undesired B-5)

Experimental Procedure for the Synthesis of B-4a

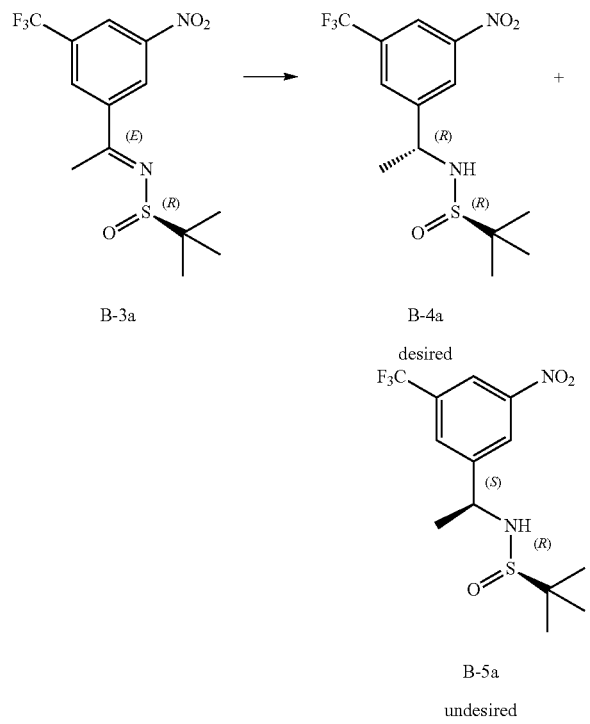

To a stirred solution of B-3a (350.0 g, 1.0 mol, 1.0 equiv.) in THF (3500 mL) and water (70 mL) is added sodium borohydride (61.0 g, 1.8 mol, 1.8 equiv.) at −78° C. The reaction is allowed to warm to rt and is monitored by TLC. The reaction mixture is quenched with ice water, extracted with EtOAc and concentrated in vacuo. The reaction gives a diastereomeric mixture that can be separated by chromatography on silica gel using EtOAc/petrol ether as eluent. The desired diastereoisomere B-4a is the major product.

The following intermediates B-4 (table 11) are available in an analogous manner starting from different sulfimines B-3. The crude product B-4 is purified by chromatography if necessary.

TABLE 11

| # | structure | $t_{ret}$ [min] | $[M+H]^+$ | HPLC method |
|---|---|---|---|---|
| B-4a | 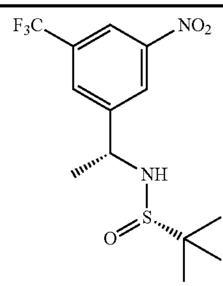 | 1.97 | 339.1 | GVK_LCMS-22 |
| B-4b | 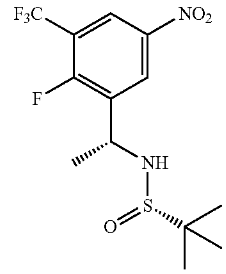 [SMILES: C[C@@H](N[S@@](=O)C(C)(C)C)c1cc([N+](=O)[O-])cc(C(F)(F)F)c1F] | 2.79 | 338.1 | RNA-FA-4.5 min |
| B-4c | 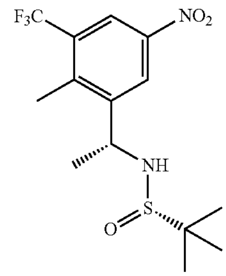 [SMILES: Cc1c([C@@H](C)N[S@@](=O)C(C)(C)C)cc([N+](=O)[O-])cc1C(F)(F)F] | n.a. | n.a. | — |
| B-4d | 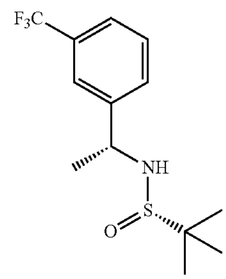 [SMILES: C[C@@H](N[S@@](=O)C(C)(C)C)c1cccc(C(F)(F)F)c1] | n.a. | n.a. | — |
| B-4e | 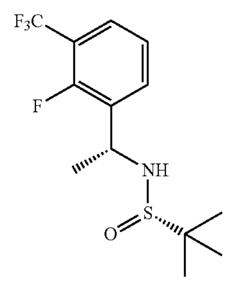 [SMILES: C[C@@H](N[S@@](=O)C(C)(C)C)c1cccc(C(F)(F)F)c1F] | 1.45 | 312.2 | RND-FA-2.6 |
| B-4f | 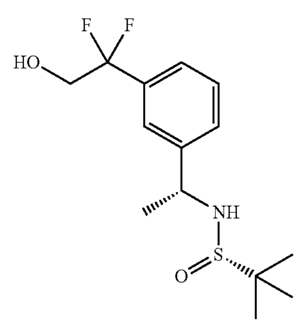 [SMILES: C[C@@H](N[S@@](=O)C(C)(C)C)c1cccc(C(F)(F)CO)c1] | 1.75 | 306.2 | GVK_LCMS_22 |

TABLE 11-continued

| # | structure | $t_{ret}$ [min] | $[M+H]^+$ | HPLC method |
|---|---|---|---|---|
| B-4g | 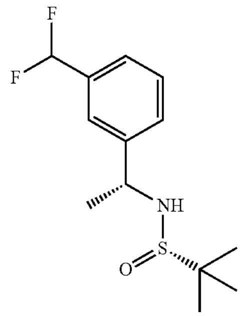 [SMILES: C[C@@H](N[S@@](=O)C(C)(C)C)c1cccc(C(F)F)c1] | 1.88 | 276.2 | RND-FA-3.2 |
| B-4h | 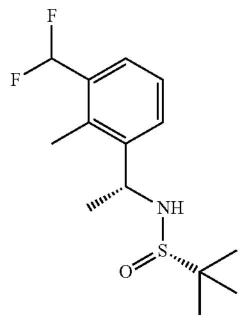 [SMILES: Cc1c(C(F)F)cccc1[C@@H](C)N[S@@](=O)C(C)(C)C] | n.a. | n.a. | — |

Experimental Procedure for the Synthesis of B-4i

To a solution of B-3i (82.0 g, 268.5 mmol, 1.0 equiv.) in THF (1000 mL) is added L-selectride (402.8 mL, 1M in THF, 1.5 equiv.) dropwise at −78° C. and the reaction mixture is stirred for 3 h. The reaction mixture is quenched with ice water, extracted with EtOAc and concentrated in vacuo. The reaction gives a diastereomeric mixture that can be separated by chromatography on silica gel using EtOAc/petrol ether as eluent. The desired diastereoisomere B-4i is the major product.

The following intermediates B-4 (table 12) are available in an analogous manner starting from different sulfimines B-3. The crude product B-4 is purified by chromatography if necessary.

TABLE 12

| # | structure | $t_{ret}$ [min] | $[M+H]^+$ | HPLC method |
|---|---|---|---|---|
| B-4i | 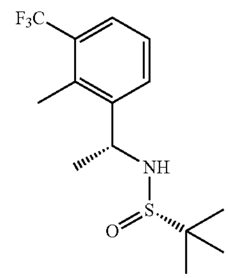 [SMILES: Cc1c([C@@H](C)N[S@@](=O)C(C)(C)C)cccc1C(F)(F)F] | 1.49 | 308.1 | GVK_LCMS_21 |
| B-4j | 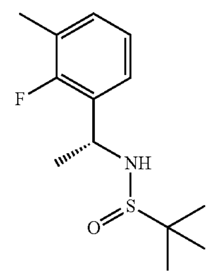 [SMILES: Cc1cccc([C@@H](C)NS(=O)C(C)(C)C)c1F] | n.a. | n.a. | — |
| B-4k | 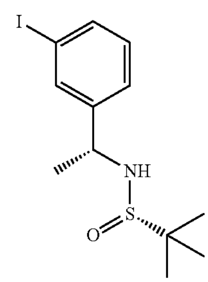 [SMILES: C[C@@H](N[S@@](=O)C(C)(C)C)c1cccc(I)c1] | n.a. | n.a. | confirmed by NMR |
| B-4l | 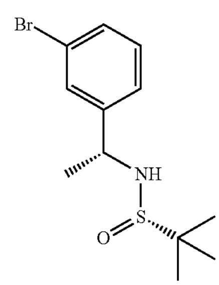 [SMILES: C[C@@H](N[S@@](=O)C(C)(C)C)c1cccc(Br)c1] | 1.94 | 304.1 | GVK_LCMS_22 |

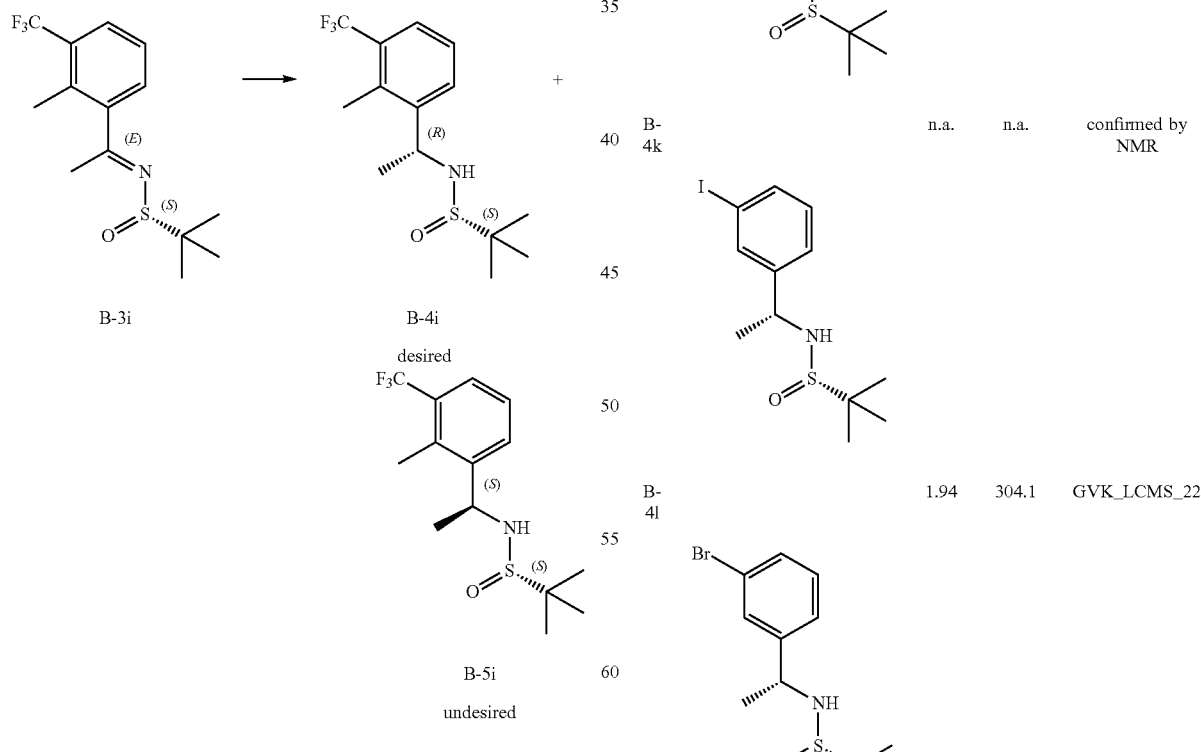

Experimental Procedure for the Synthesis of B-4m

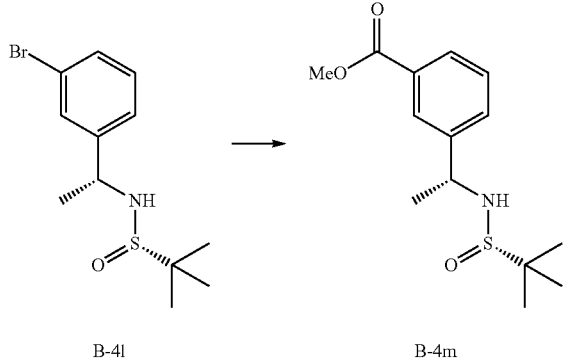 [SMILES: C[C@@H](N[S@@](=O)C(C)(C)C)c1cccc(Br)c1 ; COC(=O)c1cccc([C@@H](C)N[S@@](=O)C(C)(C)C)c1]

B-4l (30.0 g, 98.6 mmol, 1.0 equiv.) is dissolved in MeOH (300 mL), treated with triethyl amine (34.6 mL, 247.0 mmol, 2.5 equiv.) and degased for 20 min using argon gas. [1,1'-Bis(diphenylphosphino) ferrocene]dichloropalladium(II) (8.1 g, 10 mmol, 10 mol %) is dissolved in DCM (10 mL), added to the reaction mixture and the reaction mixture heated to 130° C. under CO atmosphere (200 psi) for 4 h. The reaction mixture is filtered through celite, washed with MeOH and the filtrate is concentrated under reduced pressure. The crude product is purified by column chromatography (silica gel, eluting with 50% EtOAc/hexane) giving the desired product B-4m (product confirmed by NMR).

Synthesis of Intermediates B-6

Experimental Procedure for the Synthesis of B-6a

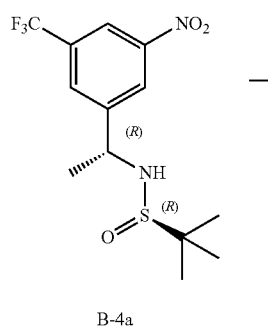

To a stirred solution of B-4a (170.0 g, 502.0 mmol, 1.0 equiv.) in 1,4-dioxan (100 mL) is added 4M HCl in dioxan (100 mL). The reaction is monitored by TLC. After completion the reaction mixture is concentrated in vacuo, filtered and washed with $Et_2$ to obtain the desired product B-6a. The compound is isolated as HCl salt.

The following intermediates B-6 (table 13) are available in an analogous manner starting from different sulfon amines B-4. The crude product B-6 is purified by chromatography if necessary and isolated as HCl salt.

TABLE 13

| # | structure | $t_{ret}$ [min] | $[M + H]^+$ | HPLC method |
|---|---|---|---|---|
| B-6a | $F_3C$—⬡—$NO_2$, $NH_2$ | 1.59 | 235.1 | GVK_LCMS_11 |
| B-6b | $F_3C$—⬡(F)—$NO_2$, $NH_2$ | n.a. | n.a. | — |
| B-6c | $F_3C$—⬡(CH3)—$NO_2$, $NH_2$ | n.a. | n.a. | — |
| B-6d | $F_3C$—⬡—$NH_2$ | 0.88 | 190.1 | GVK_LCMS_21 |
| B-6e | $F_3C$—⬡(F)—, $NH_2$ | 1.41 | 208.1 | GVK_LCMS_22 |
| B-6f | HO—CF$_2$—⬡—, $NH_2$ | 1.13 | 306.2 | GVK_LCMS_22 |
| B-6g | $F_2$HC—⬡—, $NH_2$ | 1.23 | 172.1 | RND-FA-3.2 |

TABLE 13-continued

| # | structure | $t_{ret}$ [min] | $[M+H]^+$ | HPLC method |
|---|---|---|---|---|
| B-6h | (F, F, methyl, CH-NH2 phenyl) | n.a. | n.a. | — |
| B-6i | (F3C, methyl, CH-NH2 phenyl) | 0.96 | 204.1 | GVK_LCMS_21 |
| B-6j | (methyl, F, CH-NH2 phenyl) | 1.28 | 154.1 | GVK_LCMS_22 |
| B-6k | (I, CH-NH2 phenyl) | 1.42 | 248.0 | GVK_LCMS_22 |
| B-6l | (Br, CH-NH2 phenyl) | 1.52 | 200 | RND-FA-4.5 |
| B-6m | (MeO2C, CH-NH2 phenyl) | 1.3 | 180.2 | GVK_LCMS_22 |

Experimental Procedure for the Synthesis of B-6n

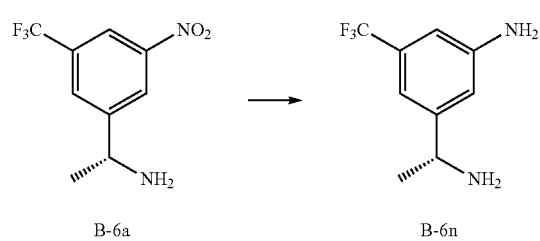 [SMILES: C[C@@H](N)c1cc([N+](=O)[O-])cc(C(F)(F)F)c1 ; C[C@@H](N)c1cc(N)cc(C(F)(F)F)c1]

B-6a (98.0 g, 417.0 mmol, 1.0 equiv.) is dissolved in MeOH (980 mL), 10% palladium carbon (20.0 g) is added and the reaction purged with $H_2$ gas (40 psi). The reaction is monitored by TLC. After completion the reaction mixture is filtered over celite and the filtrate concentrated in vacuo. The residue is washed with water to give the desired product B-6n.

The following intermediates B-6 (table 14) are available in an analogous manner starting from different amines B-6 initially obtained. The crude product B-6 is purified by chromatography if necessary.

TABLE 14

| # | structure | $t_{ret}$ [min] | $[M+H]^+$ | HPLC method |
|---|---|---|---|---|
| B-6n | (F3C, NH2, CH-NH2 phenyl) | 1.34 | 205.1 | RND-FA-3.2 |
| B-6o | (F3C, NH2, F, CH-NH2 phenyl) | 1.38 | 223.1 | RND-FA-3.2 |
| B-6p | (F3C, NH2, methyl, CH-NH2 phenyl) | 1.41 | 219.1 | GVK_LCMS_22 |

Synthesis of Intermediates B-7

Experimental Procedure for the Synthesis of B-7a

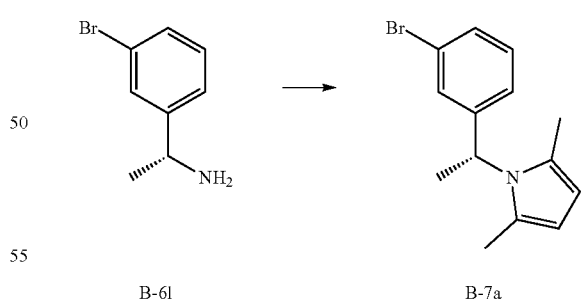

B-6l            B-7a

B-6l (9.5 g, 47.5 mmol, 1.0 equiv.), scandium(III) trifluoromethanesulfonate (0.5 g, 1.0 mmol, 2 mol %) and acetonylacetone (6.5 g, 56.9 mmol, 1.2 equiv.) are stirred at rt for 2 h. The reaction is monitored by TLC. The reaction mixture is quenched with ice water and extracted with EtOAc. The organic layer is dried over $Na_2SO_4$ and the solvent removed under reduced pressure. The crude product is purified by column chromatography (silica gel, eluting with 5% EtOAc/hexane) giving the desired product B-7a.

The following intermediates B-7 (table 15) are available in an analogous manner starting from benzylic amines B-6. The crude product B-7 is purified by chromatography if necessary.

TABLE 15

| # | structure | $t_{ret}$ [min] | $[M+H]^+$ | HPLC method |
|---|---|---|---|---|
| B-7a | 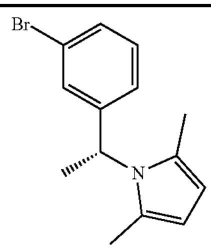 | 2.49 | 278.1 | GVK_LCMS_11 |
| B-7b | 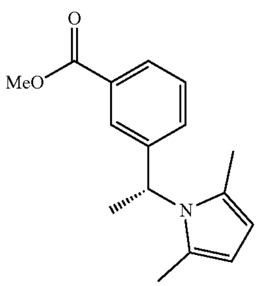 [SMILES: COC(=O)c1cccc([C@@H](C)n2c(C)ccc2C)c1] | n.a. | n.a. | confirmed by NMR |

Experimental Procedure for the Synthesis of B-7c

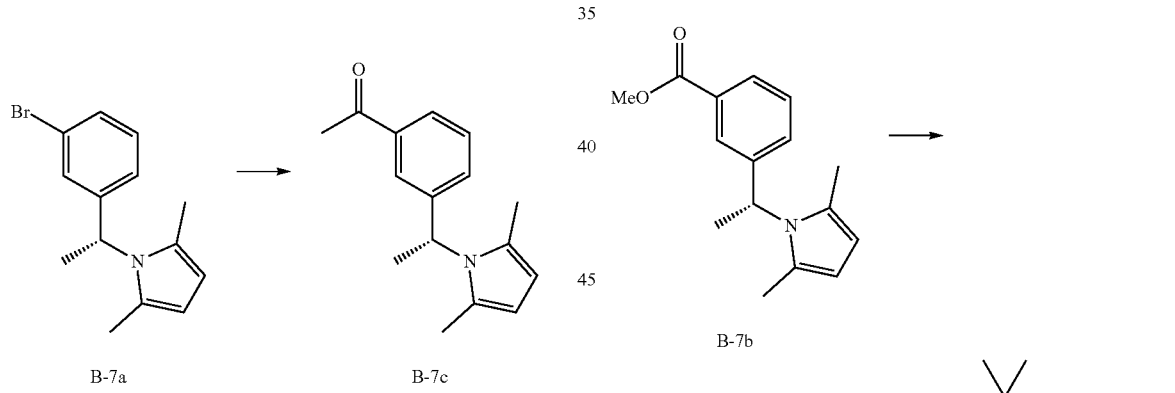

B-7a (2.0 g, 7.2 mmol, 1.0 equiv.) is dissolved in 1,4-dioxane (10 mL), then tributyl(1-ethoxyvinyl)tin (3.3 g, 9.0 mmol, 1.2 equiv.) and triethylamine (1.5 g, 14.4 mmol, 2.0 equiv.) are added. The reaction mixture is purged with argon for 15 min, then bis(triphenylphosphine)palladium(II) chloride (539.0 mg, 1.0 mmol, 10.0 mol %) is added and the reaction mixture heated to 80° C. in a sealed tube for 16 h. Progress of reaction is monitored by TLC. The reaction mixture is cooled to rt and treated with 1N HCl (20 mL). The mixture is stirred at rt for 1 h, then extracted with EtOAc (2×20 mL), washed with brine (10 mL) and dried over $Na_2SO_4$. The reaction mixture is filtered and concentrated under reduced pressure. The crude product is purified by column chromatography (silica gel, eluting with 5% EtOAc/hexane) giving the desired product B-7c (product confirmed by NMR).

Experimental Procedure for the Synthesis of B-7d

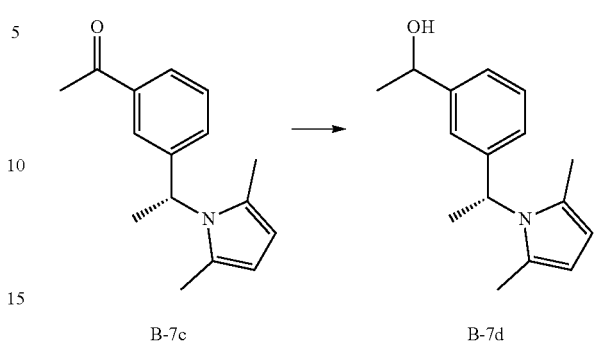

B-7c (800.0 mg, 3.3 mmol, 1.0 equiv.) is dissolved in MeOH (10 mL) and cooled to 0° C. Sodium borohydride (370.0 mg, 9.9 mmol, 3.0 equiv.) is added and the reaction mixture stirred for 16 h at rt. The progress of the reaction is monitored by TLC. The reaction mixture is quenched with saturated aqueous ammonium chloride (10 mL) and extracted with EtOAc (2×50 mL). The combined organic layers are washed with brine (20 mL), dried over $Na_2SO_4$, filtered and concentrated under reduced pressure. The crude product is purified by column chromatography (silica gel, eluting with 40% EtOAc/hexane) giving the desired product B-7d (product confirmed by NMR).

Experimental Procedure for the Synthesis of B-7e

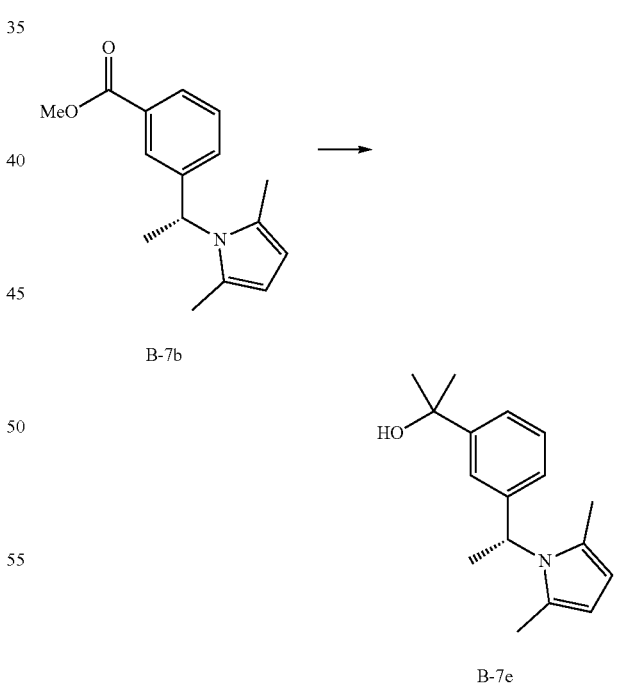

B-7b (10.0 g, 38.8 mmol, 1.0 equiv.) is dissolved in THF (100 mL). MeMgBr (51.8 mL, 155.4 mmol, 3M in $Et_2O$, 5.0 equiv.) is added to the reaction mixture at 0° C. and stirred at rt for 3 h. The reaction is monitored by TLC. The reaction is quenched with saturated ammonium chloride solution, extracted with EtOAc (2×100 mL), the combined organic layers dried over Na₂SO₄ and concentrated under reduced pressure. The crude product is purified by column chromatography (silica gel, eluting with 30% EtOAc/hexane) giving the desired product B-7e (product confirmed by NMR).

TABLE 16

| # | structure | $t_{ret}$ [min] | [M + H]⁺ | HPLC method |
|---|---|---|---|---|
| B-7c | 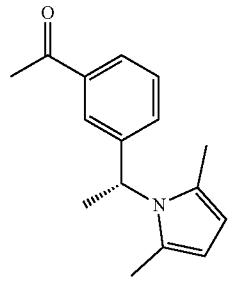 [SMILES: CC(=O)c1cccc([C@@H](C)n2c(C)ccc2C)c1] | n.a. | n.a. | confirmed by NMR |
| B-7d | 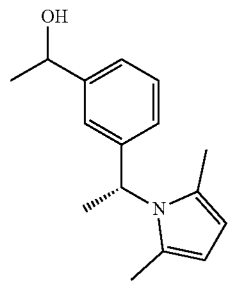 [SMILES: Cc1ccc(C)n1[C@H](C)c1cccc(C(C)O)c1] | n.a. | n.a. | confirmed by NMR |
| B-7e | 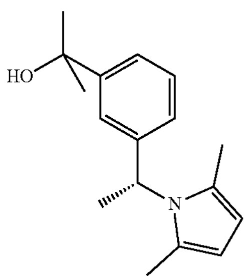 [SMILES: Cc1ccc(C)n1[C@H](C)c1cccc(C(C)(C)O)c1] | n.a. | n.a. | confirmed by NMR |

Experimental Procedure for the Synthesis of B-6q

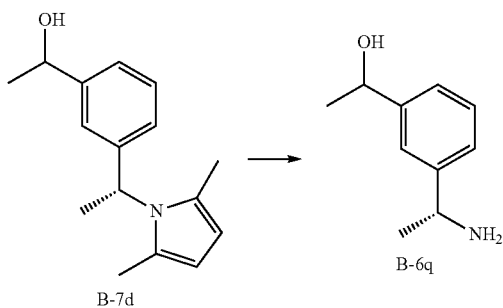 [SMILES: Cc1ccc(C)n1[C@H](C)c1cccc(C(C)O)c1 ; CC(O)c1cccc([C@@H](C)N)c1]

B-7d

B-6q

B-7d (500.0 mg, 1.9 mmol, 1.0 equiv.) is dissolved in a mixture of EtOH (20.0 mL) and water (10.0 mL) and treated with hydroxylamine hydrochloride (1.4 g, 20.5 mmol, 10.0 equiv.) and K₂CO (851.0 mg, 6.2 mmol, 3.0 equiv.). The reaction mixture is heated to 100° C. for 48 h. The reaction mixture is quenched with 2N NaOH solution, extracted with chloroform, the combined organic layers are dried over Na₂SO₄ and concentrated under reduced pressure. The crude product is purified by chromatography giving the desired compound B-6q.

The following intermediates B-6 (table 17) are available in an analogous manner starting from different pyrroles B-7. The crude product B-6 is purified by chromatography if necessary.

TABLE 17

| # | structure | $t_{ret}$ [min] | [M + H]⁺ | HPLC method |
|---|---|---|---|---|
| B-6q | 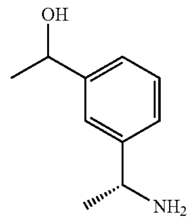 | 7.69 | 166.2 | GVK_LCMS_15 |
| B-6r | 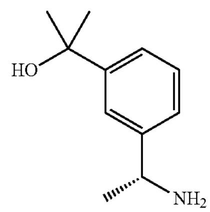 | 1.17 | 180.2 | RND-FA-4.5 |

Synthesis of Intermediates A-14

Experimental Procedure for the Synthesis of A-14a

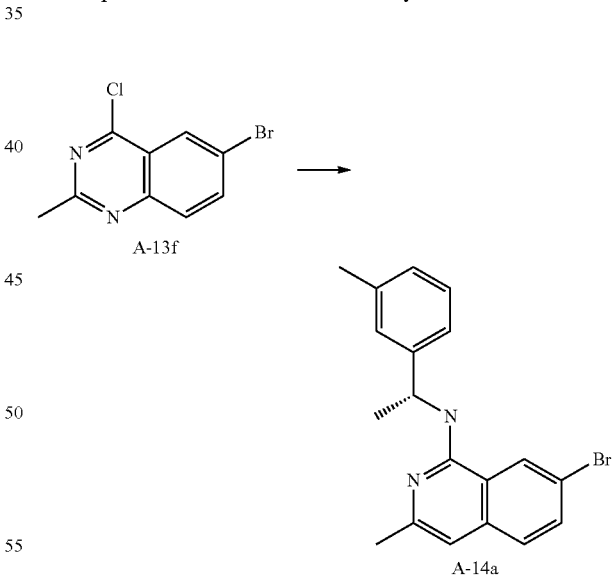

A-13f

A-14a

To a suspension of A-13f (10.0 g, 38.8 mmol, 1.0 equiv.) in EtOH (100 mL) is added (1R)-1-(3-methylphenyl)ethan-1-amine (6.2 g, 50.5 mmol, 1.3 equiv.) and DIPEA (12.5 g, 97.1 mmol, 2.0 equiv.). The resulting reaction mixture is heated to 100° C. in a sealed tube for 16 h. The reaction mixture is cooled to rt and concentrated under reduced pressure. The residue is dissolved in EtOAc and washed with sat. NaHCO₃ solution. The organic layer is concentrated in vacuo and the resulting solid is crystallized using a mixture of EtOAc and hexane.

The following intermediates A-14 (table 18) are available in an analogous manner starting from different quinazolines A-13. The crude product A-14 is purified by chromatography if necessary.

TABLE 18

| # | structure | $t_{ret}$ [min] | $[M + H]^+$ | HPLC method |
|---|---|---|---|---|
| A-14a | 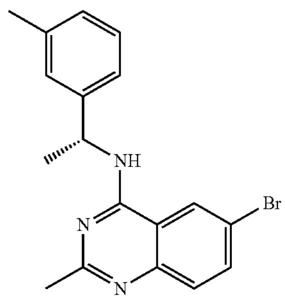 [SMILES: Cc1cccc([C@@H](C)Nc2nc(C)nc3ccc(Br)cc23)c1] | 0.82 | 356.2 | BFEC |
| A-14b | 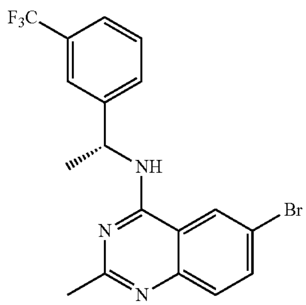 [SMILES: Cc1nc(N[C@H](C)c2cccc(C(F)(F)F)c2)c2cc(Br)ccc2n1] | 1.44 | 410 | LCMSBAS-1 |
| A-14c | 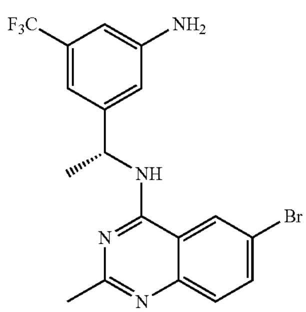 | 1.30 | 425 | LCMSBAS-1 |
| A-14d | 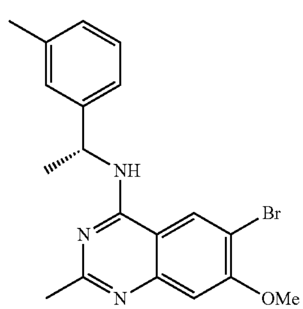 [SMILES: COc1cc2nc(C)nc(N[C@H](C)c3cccc(C)c3)c2cc1Br] | 0.85 | 365.3 | VAB |

TABLE 18-continued

| # | structure | $t_{ret}$ [min] | [M + H]$^+$ | HPLC method |
|---|---|---|---|---|
| A-14e | 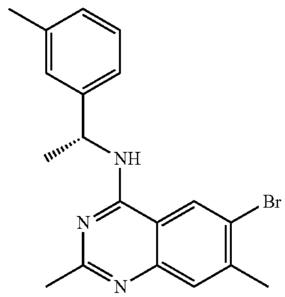 | 0.842 | 370.2 | BFEC |
| A-14f | 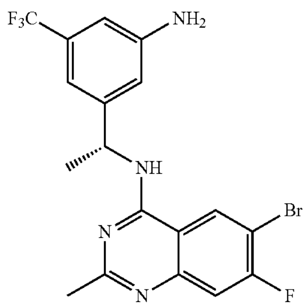 | 1.39 | 443 | LCMSBAS-1 |
| A-14g | 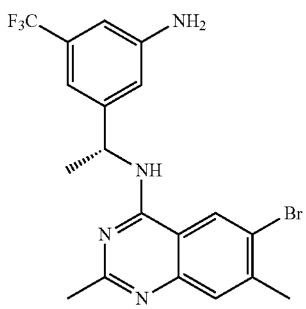 | 0.78 | 439.2 | BFEC |
| A-14h | 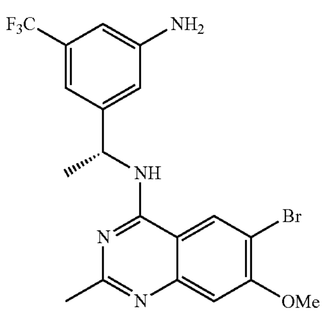 | 1.29 | 455 | LCMSBAS-1 |
| A-14i | 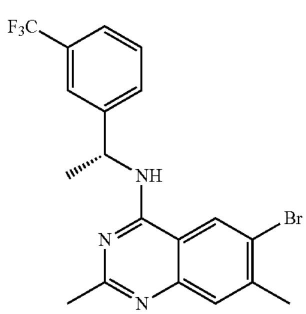 [SMILES: Cc1nc(N[C@H](C)c2cccc(C(F)(F)F)c2)c2cc(Br)c(C)cc2n1] | 1.50 | 424 | LCMSBAS-1 |

TABLE 18-continued

| # | structure | $t_{ret}$ [min] | [M + H]⁺ | HPLC method |
|---|---|---|---|---|
| A-14j | 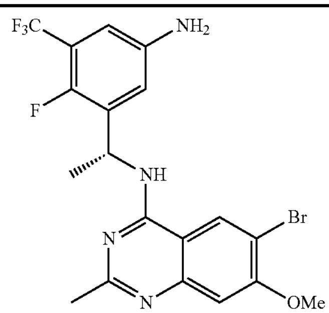 | 1.04 | 475.1 | VAB |
| A-14k | 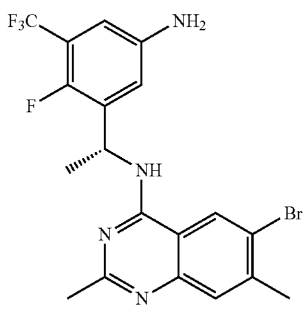 [SMILES: Cc1nc(N[C@H](C)c2cc(N)cc(C(F)(F)F)c2F)c2cc(Br)c(C)cc2n1] | 1.07 | 459.0 | VAB |
| A-14l | 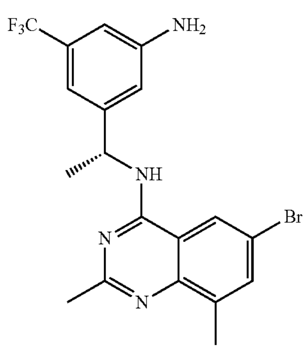 | n.a. | n.a. | — |
| A-14m | 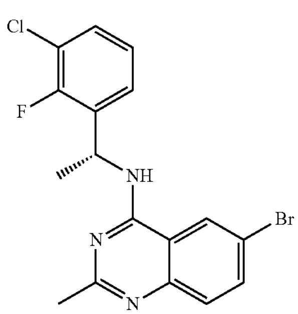 [SMILES: Cc1nc(N[C@H](C)c2cccc(Cl)c2F)c2cc(Br)ccc2n1] | 0.83 | 394.2 | BFEC |
| A-14n | 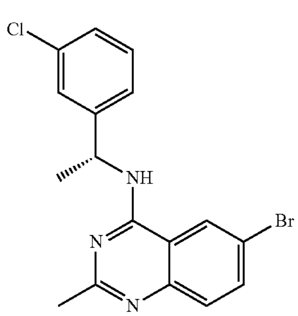 [SMILES: Cc1nc(N[C@H](C)c2cccc(Cl)c2)c2cc(Br)ccc2n1] | 0.82 | 376.2 | BFEC |

TABLE 18-continued
| # | structure | $t_{ret}$ [min] | $[M + H]^+$ | HPLC method |
|---|---|---|---|---|
| A-14o | 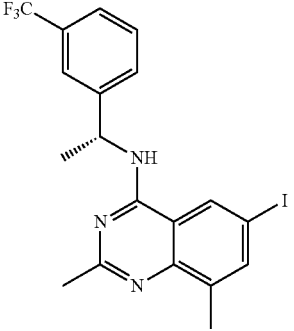 [SMILES: Cc1nc(N[C@H](C)c2cccc(C(F)(F)F)c2)c2cc(I)cc(C)c2n1] | n.a. | n.a. | — |
| A-14p | 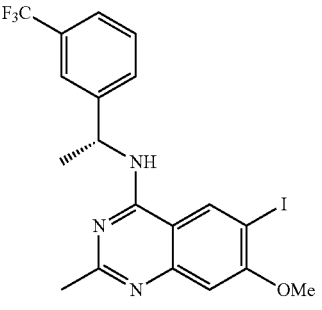 [SMILES: COc1cc2nc(C)nc(N[C@H](C)c3cccc(C(F)(F)F)c3)c2cc1I] | 3.61 | 488. | RND-XBRIDGE_7 |
| A-14q | 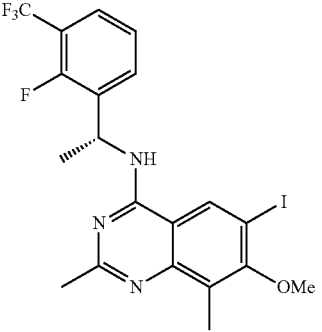 [SMILES: COc1c(I)cc2c(N[C@H](C)c3cccc(C(F)(F)F)c3F)nc(C)nc2c1C] | 0.993 | 520.0 | BFEC |
| A-14r | 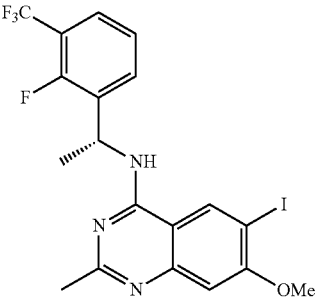 [SMILES: COc1cc2nc(C)nc(N[C@H](C)c3cccc(C(F)(F)F)c3F)c2cc1I] | 0.86 | 506.0 | BFEC |

TABLE 18-continued
| # | structure | t_ret [min] | [M + H]+ | HPLC method |
|---|---|---|---|---|
| A-14s | 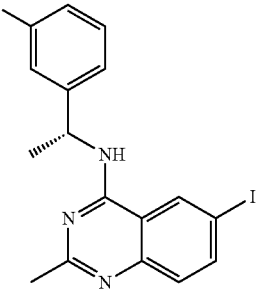 | 1.55 | 458.0 | LCMSBAS_1 |
| A-14t | 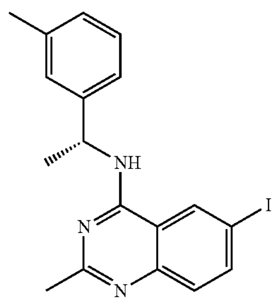 [SMILES: Cc1cccc([C@@H](C)Nc2nc(C)nc3ccc(I)cc23)c1] | 0.83 | 404.2 | BFEC |
| A-14u | 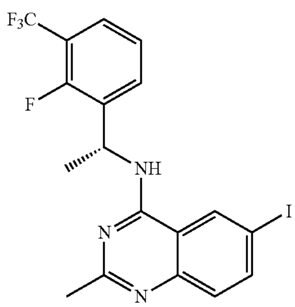 [SMILES: Cc1nc(N[C@H](C)c2cccc(C(F)(F)F)c2F)c2cc(I)ccc2n1] | 0.86 | 476.2 | BFEC |
| A-14v | 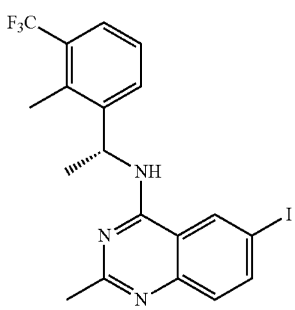 [SMILES: Cc1nc(N[C@H](C)c2cccc(C(F)(F)F)c2C)c2cc(I)ccc2n1] | 0.91 | 472.2 | BFEC |
| A-14w | 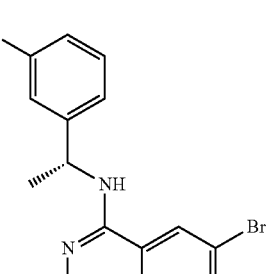 | 3.12 | 439.9 | RND-FA-4.5 |

TABLE 18-continued

| # | structure | $t_{ret}$ [min] | $[M + H]^+$ | HPLC method |
|---|---|---|---|---|
| A-14x | 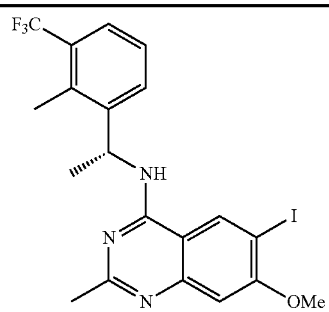 | 0.90 | 502.0 | BFEC |
| A-14y | 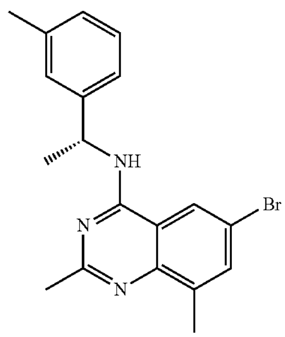 [SMILES: Cc1cccc([C@@H](C)Nc2nc(C)nc3c(C)cc(Br)cc23)c1] | 0.96 | 370.2 | BFEC |
| A-14z | 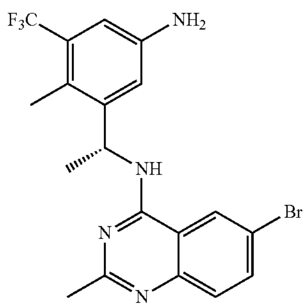 [SMILES: Cc1nc(N[C@H](C)c2cc(N)cc(C(F)(F)F)c2C)c2cc(Br)ccc2n1] | 0.748 | 439.0 | BFEC |
| A-14aa | 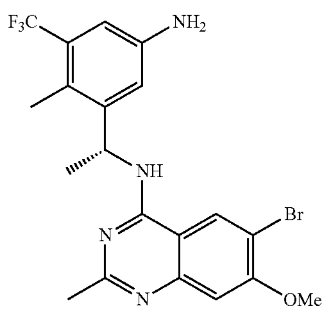 [SMILES: COc1cc2nc(C)nc(N[C@H](C)c3cc(N)cc(C(F)(F)F)c3C)c2cc1Br] | 0.77 | 469.2 | BFEC |
| A-14ab | 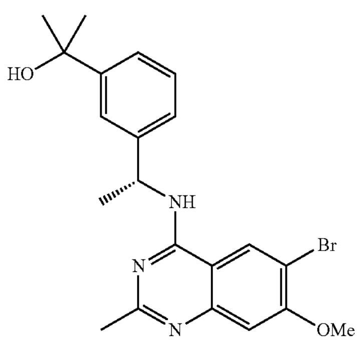 [SMILES: COc1cc2nc(C)nc(N[C@H](C)c3cccc(C(C)(C)O)c3)c2cc1Br] | 0.66 | 430.2 | BFEC |

TABLE 18-continued
| # | structure | t_ret [min] | [M + H]+ | HPLC method |
|---|---|---|---|---|
| A-14ac | 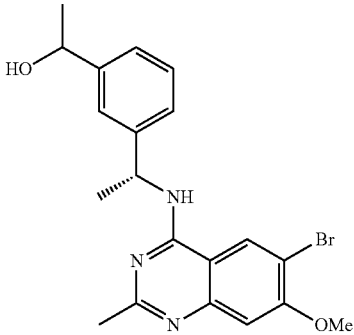 [SMILES: COc1cc2nc(C)nc(N[C@H](C)c3cccc(C(C)O)c3)c2cc1Br] | 0.625 | 416.2 | BFEC |
| A-14ad | 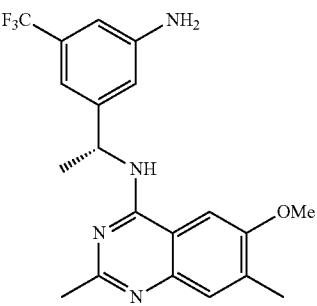 [SMILES: COc1cc2c(N[C@H](C)c3cc(N)cc(C(F)(F)F)c3)nc(C)nc2cc1C] | 1.30 | 391 | LCMSBAS1 |
| A-14ae | 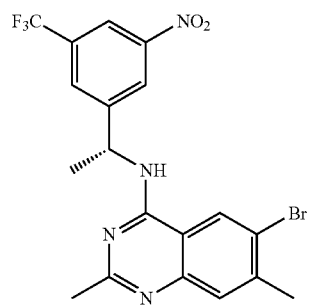 | 0.88 | 469.1 | BFEC |
| A-14af | 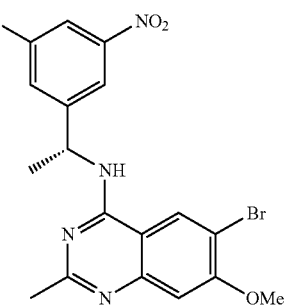 | 0.835 | 485.2 | BFEC |

TABLE 18-continued
| # | structure | $t_{ret}$ [min] | $[M + H]^+$ | HPLC method |
|---|---|---|---|---|
| A-14ag | 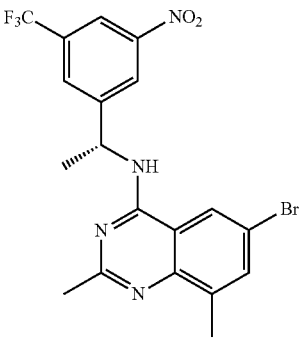 [SMILES: Cc1nc(N[C@H](C)c2cc([N+](=O)[O-])cc(C(F)(F)F)c2)c2cc(Br)cc(C)c2n1] | 0.988 | 469.2 | BFEC |
| A-14ah | 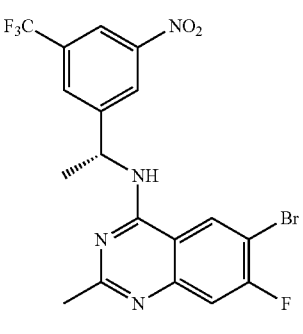 [SMILES: Cc1nc(N[C@H](C)c2cc([N+](=O)[O-])cc(C(F)(F)F)c2)c2cc(Br)c(F)cc2n1] | 0.87 | 473.2 | BFEC |
| A-14ai | 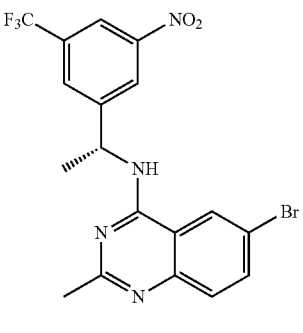 [SMILES: Cc1nc(N[C@H](C)c2cc([N+](=O)[O-])cc(C(F)(F)F)c2)c2cc(Br)ccc2n1] | 0.84 | 455.2 | BFEC |
| A-14aj | 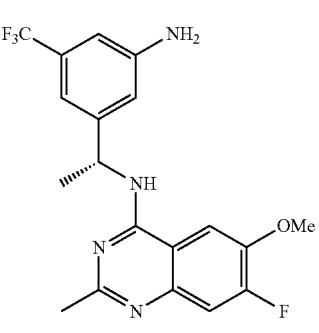 | 1.25 | 395 | LCMSBAS1 |

TABLE 18-continued

| # | structure | $t_{ret}$ [min] | $[M + H]^+$ | HPLC method |
|---|---|---|---|---|
| A-14ak | 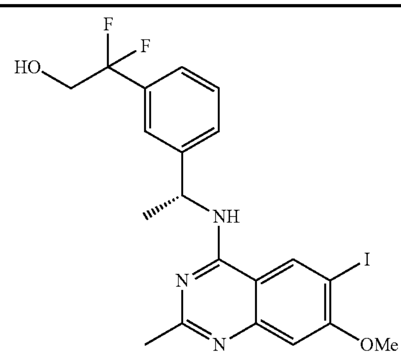 | 0.68 | 500.0 | BFEC |

Experimental Procedure for the Synthesis of A-14al

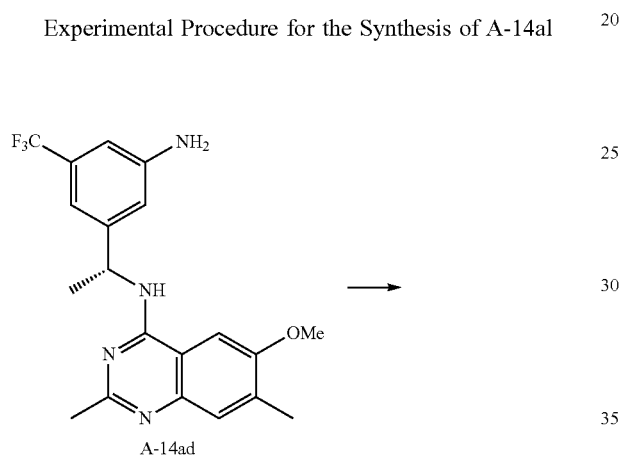

A-14ad (90 mg, 231.0 μmol, 1.0 equiv.) is dissolved in DCE (2.0 mL) and cooled down to 0° C. Then BBr₃ (277.0 μL, 277.0 μmol, 1.2 equiv.) is added dropwise and the reaction mixture stirred 12 h at rt. The solvent is removed under reduced pressure and the crude product is purified by chromatography using acetonitrile/water giving the desired product A-14al.

The following intermediates A-14 (table 19) are available in an analogous manner starting from different quinazolines A-14 initially obtained (table 18). The crude product A-14 is purified by chromatography if necessary.

TABLE 19

| # | structure | $t_{ret}$ [min] | $[M + H]^+$ | HPLC method |
|---|---|---|---|---|
| A-14al | | 0.84 | 377.3 | VAB |
| A-14al | | 0.84 | 377.3 | VAB |
| A-14am | 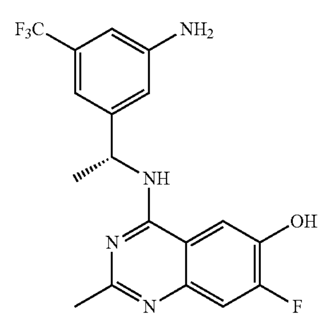 [SMILES: Cc1nc(N[C@H](C)c2cc(N)cc(C(F)(F)F)c2)c2cc(O)c(C)cc2n1] | 0.72 | 381.2 | VAB |

Experimental Procedure for the Synthesis of A-14an

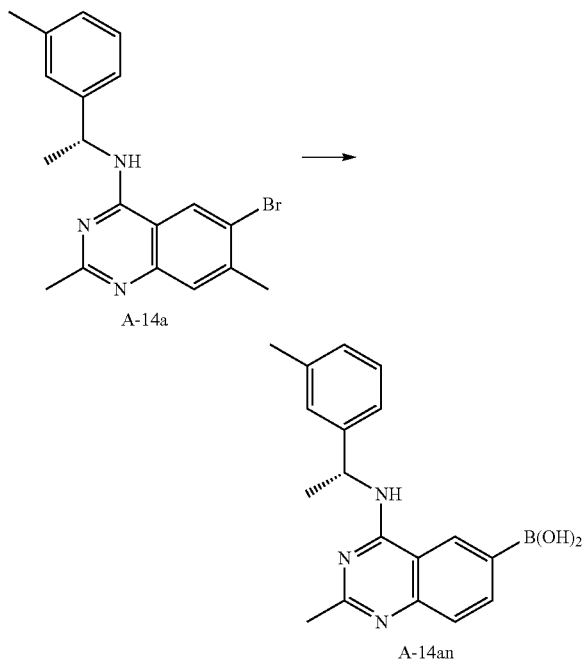

A-14a

A-14an

To a solution of A-14a (5.0 g, 14.0 mmol, 1.0 equiv. in DSO is added bis(pinacolato)diboron (4.6 g, 18.2 mmol, 1.3 equiv.) and potassium acetate (3.5 g, 35.1 mmol, 2.5 equiv.). The reaction is performed under inert atmosphere. Then 11'-bis(diphenylphosphino)ferrocene-palladium-(II)dichloride dichloromethane complex (1.1 g, 1.4 mmol, 0.1 equiv.) is added and reaction mixture heated to 100° C. for 2.5 h. The reaction mixture is cooled to rt and diluted with EtOAc. The solution is filtered through celite and the filtrate washed with water. The organic layer is concentrated under reduced pressure and the residue purified by chromatography giving the desired product A-14an.

The following intermediates A-14 (table 20) are available in an analogous manner starting from different quinazolines A-14 initially obtained. The crude product A-14 is purified by chromatography if necessary.

TABLE 20

| # | structure | $t_{ret}$ [min] | [M + H]$^+$ | HPLC method |
|---|---|---|---|---|
| A-14an | 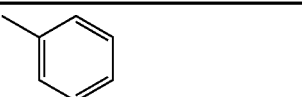 | 0.58 | 322.4 | BFEC |
| A-14ao | F$_3$C- structure | 0.66 | 405.2 | BFEC |
| A-14ap | structure with OMe | 0.60 | 252.2 | BFEC |
| A-14aq | F$_3$C-, NH$_2$ structure with OMe | 0.56 | 421.2 | BFEC |

Synthesis of Intermediates A-15

Experimental Procedure for the Synthesis of A-15a

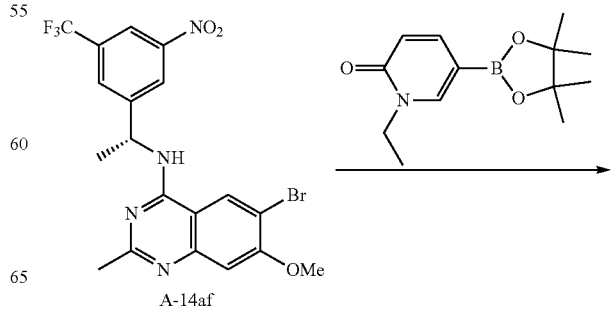

A-14af

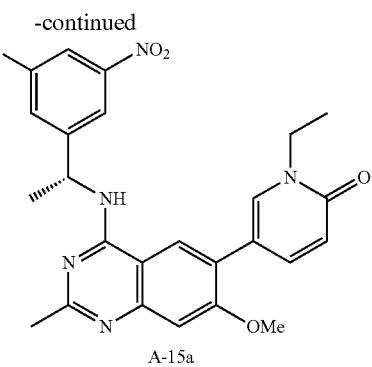

A-15a

A-14af (100.0 mg, 206.0 µmol, 1.0 equiv.), 1-ethyl-5-(tetramethyl-1,3,2-dioxaborolan-2-yl)-1,2-dihydropyridin-2-one (103.0 mg, 412.0 µmol, 2.0 equiv.), Pd(amphos)$_2$Cl$_2$ (15.0 mg, 21.0 µmol, 0.1 equiv.), DCM (17.5 mg, 20.0 µmol, 5 mol %) and Na$_2$CO$_3$ (57.0 mg, 412.0 µmol, 2.0 equiv.) are dissolved in a mixture of dioxane (0.5 mL), water (0.2 mL) and EtOH (0.2 mL) and stirred for 3 h at 50° C. The reaction mixture is filtered through celite, quenched with water and extracted with DCM. The combined organic layers are dried over MgSO$_4$, filtered and the solvent removed in vacuo. The crude product is purified by chromatography giving the desired product A-15a.

The following intermediates A-15 (table 21) are available in an analogous manner starting from different quinazolines A-14 (table 18). The crude product A-15 is purified by chromatography if necessary.

TABLE 21

| # | structure | $t_{ret}$ [min] | [M + H]$^+$ | HPLC method |
|---|---|---|---|---|
| A-15a | 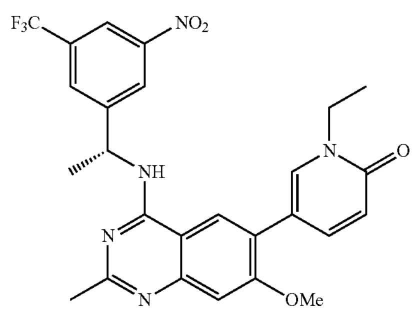 [SMILES: CCn1cc(-c2cc3c(N[C@H](C)c4cc([N+](=O)[O-])cc(C(F)(F)F)c4)nc(C)nc3cc2OC)ccc1=O] | 1.01 | 528.2 | VAB |
| A-15b | 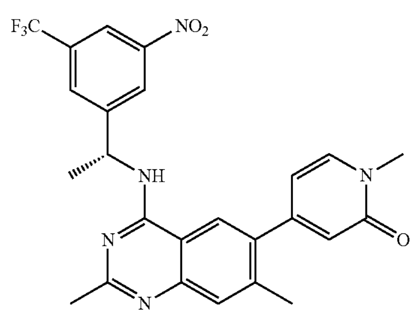 [SMILES: Cc1nc(N[C@H](C)c2cc([N+](=O)[O-])cc(C(F)(F)F)c2)c2cc(-c3ccn(C)c(=O)c3)c(C)cc2n1] | 0.99 | 498.2 | VAB |
| A-15c | 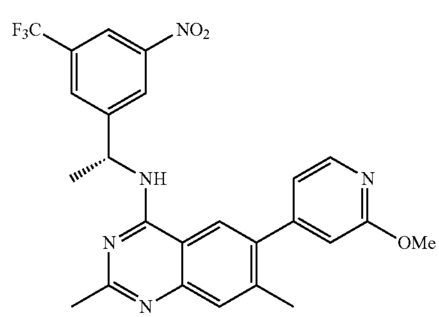 [SMILES: COc1cc(-c2cc3c(N[C@H](C)c4cc([N+](=O)[O-])cc(C(F)(F)F)c4)nc(C)nc3cc2C)ccn1] | 1.02 | 510.0 | VAB |

TABLE 21-continued

| # | structure | $t_{ret}$ [min] | [M + H]+ | HPLC method |
|---|---|---|---|---|
| A-15d | 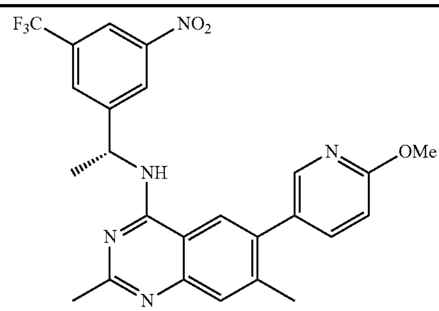 | 1.13 | 498.2 | VAB |
| A-15e | 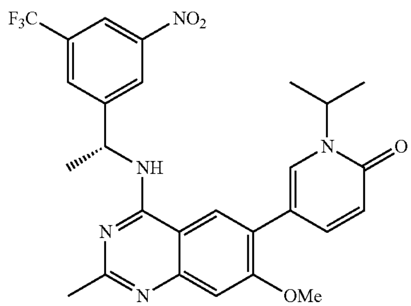 [SMILES: COc1cc2nc(C)nc(N[C@H](C)c3cc([N+](=O)[O-])cc(C(F)(F)F)c3)c2cc1-c1ccc(=O)n(C(C)C)c1] | 1.02 | 542.3 | VAB |
| A-15f | 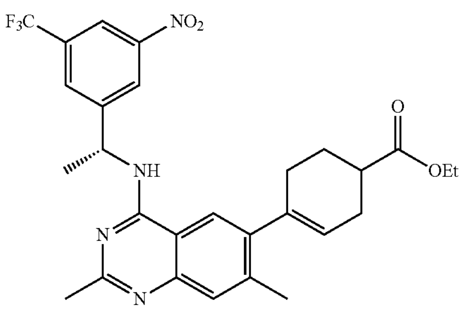 [SMILES: CCOC(=O)C1CC=C(c2cc3c(N[C@H](C)c4cc([N+](=O)[O-])cc(C(F)(F)F)c4)nc(C)nc3cc2C)CC1] | 0.95 | 543 | BFEC |
| A-15g | 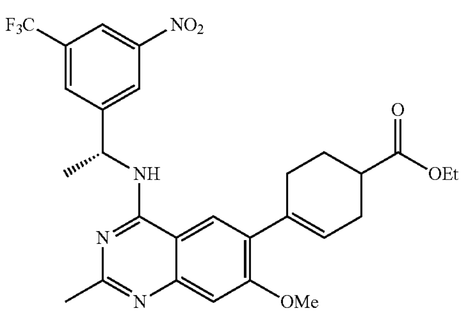 [SMILES: CCOC(=O)C1CC=C(c2cc3c(N[C@H](C)c4cc([N+](=O)[O-])cc(C(F)(F)F)c4)nc(C)nc3cc2OC)CC1] | 0.924 | 559.4 | BFEC |
| A-15h | 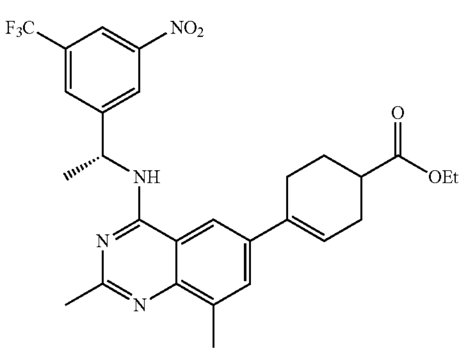 [SMILES: CCOC(=O)C1CC=C(c2cc(C)c3nc(C)nc(N[C@H](C)c4cc([N+](=O)[O-])cc(C(F)(F)F)c4)c3c2)CC1] | 1.037 | 543.4 | BFEC |

TABLE 21-continued

| # | structure | $t_{ret}$ [min] | [M + H]$^+$ | HPLC method |
|---|---|---|---|---|
| A-15i | 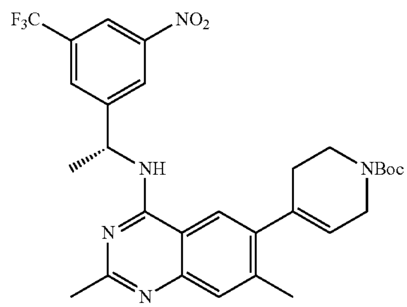 [SMILES: Cc1nc(N[C@H](C)c2cc([N+](=O)[O-])cc(C(F)(F)F)c2)c2cc(C3=CCN(C(=O)OC(C)(C)C)CC3)c(C)cc2n1] | 0.93 | 572 | BFEC |
| A-15j | 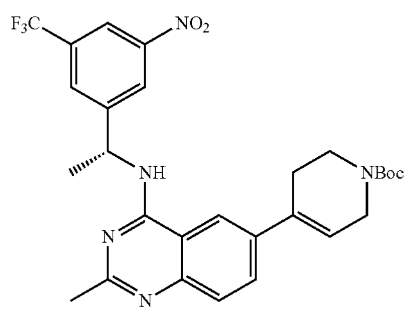 [SMILES: Cc1nc(N[C@H](C)c2cc([N+](=O)[O-])cc(C(F)(F)F)c2)c2cc(C3=CCN(C(=O)OC(C)(C)C)CC3)ccc2n1] | 0.931 | 558.4 | BFEC |
| A-15k | 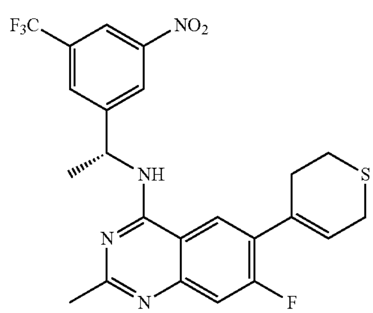 [SMILES: Cc1nc(N[C@H](C)c2cc([N+](=O)[O-])cc(C(F)(F)F)c2)c2cc(C3=CCSCC3)c(F)cc2n1] | 0.90 | 493 | BFEC |
| A-15l | 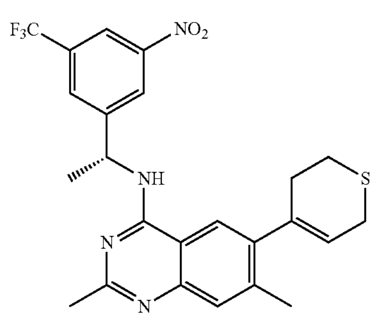 [SMILES: Cc1nc(N[C@H](C)c2cc([N+](=O)[O-])cc(C(F)(F)F)c2)c2cc(C3=CCSCC3)c(C)cc2n1] | 0.91 | 489 | BFEC |

Experimental Procedure for the Synthesis of A-15m

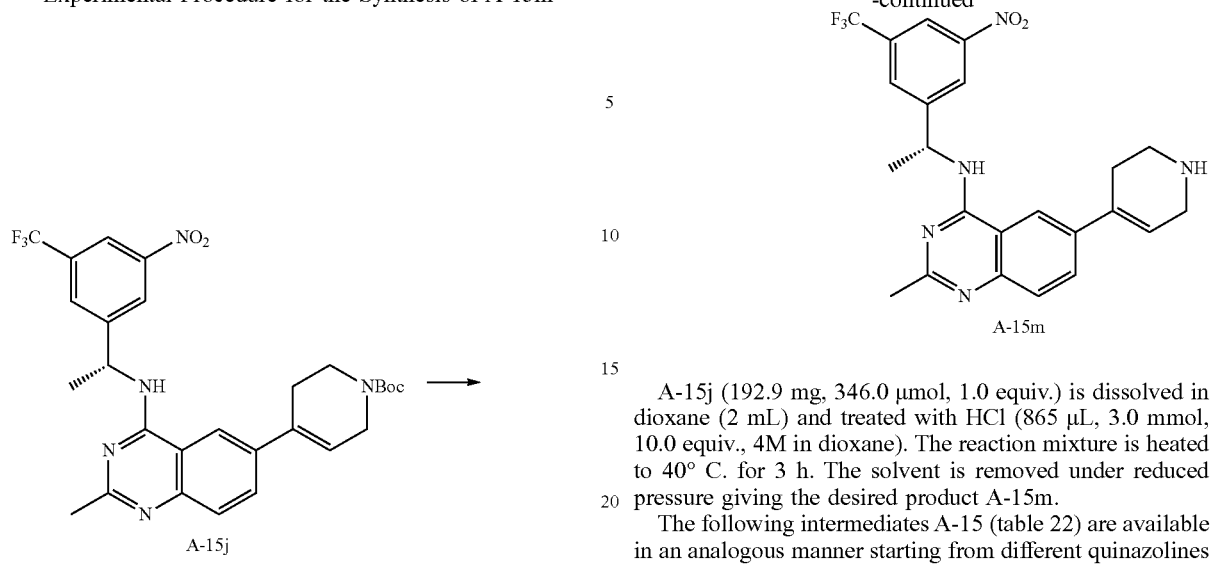

A-15j (192.9 mg, 346.0 μmol, 1.0 equiv.) is dissolved in dioxane (2 mL) and treated with HCl (865 μL, 3.0 mmol, 10.0 equiv., 4M in dioxane). The reaction mixture is heated to 40° C. for 3 h. The solvent is removed under reduced pressure giving the desired product A-15m.

The following intermediates A-15 (table 22) are available in an analogous manner starting from different quinazolines A-15 initially obtained (table 21). The crude product A-15 is purified by chromatography if necessary.

TABLE 22

| # | structure | $t_{ret}$ [min] | $[M + H]^+$ | HPLC method |
|---|---|---|---|---|
| A-15m | 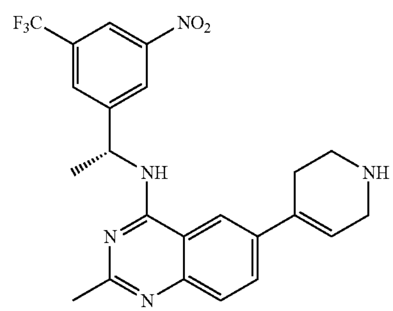 [SMILES: Cc1nc(N[C@H](C)c2cc([N+](=O)[O-])cc(C(F)(F)F)c2)c2cc(C3=CCNCC3)ccc2n1] | 0.68 | 458.4 | BFEC |
| A-15n | 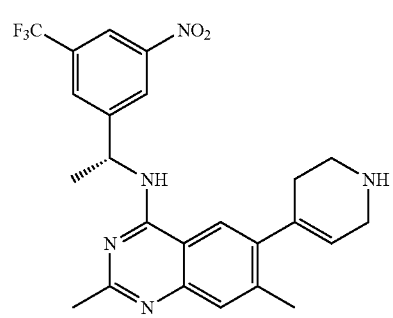 [SMILES: Cc1nc(N[C@H](C)c2cc([N+](=O)[O-])cc(C(F)(F)F)c2)c2cc(C3=CCNCC3)c(C)cc2n1] | 0.687 | 472.4 | BFEC |

Experimental Procedure for the Synthesis of A-15o

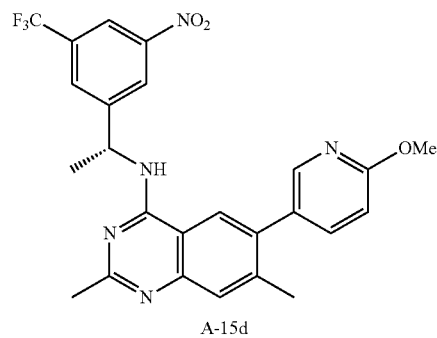

A-15d

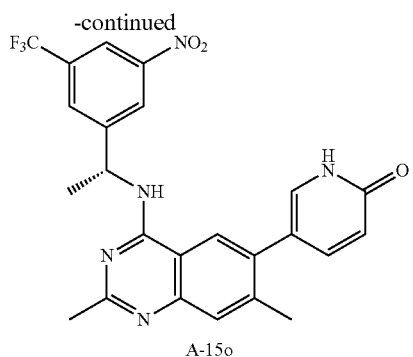

A-15o

A-15d (104.0 mg, 0.2 mmol, 1.0 equiv.), LiOH (44.3 mg, 1.0 mmol, 5.0 equiv.) and p-toluene sulfonic acid (180.0 mg, 1.0 mmol, 5.0 equiv.) are dissolved in DMF (0.5 mL) and stirred at 120° C. for 1 h. The reaction mixture is basified with ammonia and the precipitate is filtered off giving the desired product A-15o.

The following intermediates A-15 (table 23) are available in an analogous manner starting from different quinazolines A-15 initially obtained (table 21). The crude product A-15 is purified by chromatography if necessary.

TABLE 23

| # | structure | $t_{ret}$ [min] | $[M + H]^+$ | HPLC method |
|---|---|---|---|---|
| A-15o | 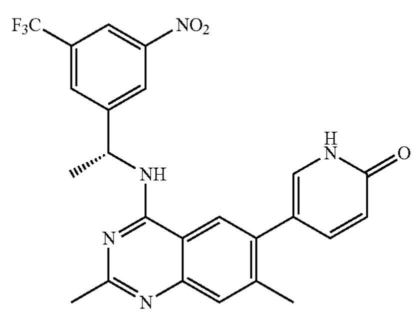 [SMILES: Cc1nc(N[C@H](C)c2cc([N+](=O)[O-])cc(C(F)(F)F)c2)c2cc(-c3ccc(=O)[nH]c3)c(C)cc2n1] | 0.95 | 484.3 | VAB |
| A-15p | 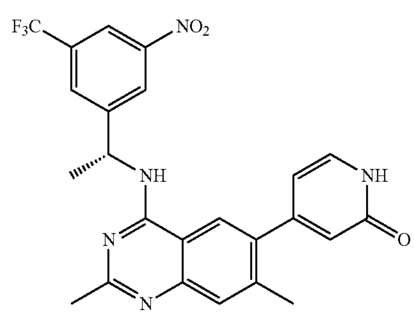 [SMILES: Cc1nc(N[C@H](C)c2cc([N+](=O)[O-])cc(C(F)(F)F)c2)c2cc(-c3cc[nH]c(=O)c3)c(C)cc2n1] | 0.96 | 484.3 | VAB |

Experimental Procedure for the Synthesis of A-15q

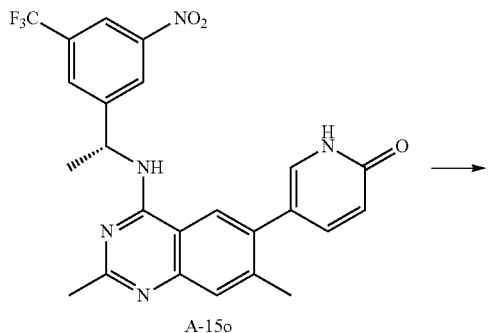

A-15o (94.0 mg, 0.2 mmol, 1.0 equiv.) is dissolved in DMSO (0.5 mL), treated with NaH (11.6 mg, 0.3 mmol, 1.5 equiv.) and stirred at rt for 5 min. Then bromo ethane (16.0 µL, 0.2 mmol, 1.1 equiv.) is added and the reaction mixture stirred for 17 h at rt. The reaction mixture is quenched with MeOH, filtered through celite and purified by chromatography using acetonitrile/water giving the desired product A-15q.

The following intermediates A-15 (table 24) are available in an analogous manner starting from different quinazolines A-15 initially obtained (table 23). The crude product A-15 is purified by chromatography if necessary.

TABLE 24

| # | structure | $t_{ret}$ [min] | $[M + H]^+$ | HPLC method |
|---|---|---|---|---|
| A-15q | 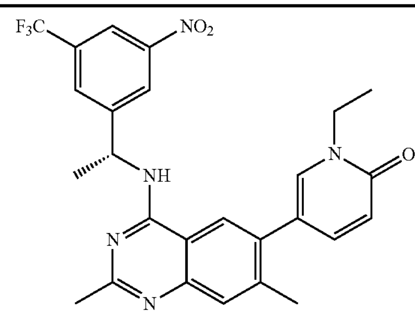 | 1.01 | 512.3 | VAB |
| A-15r | 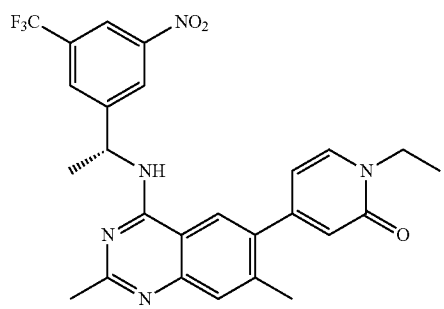 [SMILES: CCn1ccc(-c2cc3c(N[C@H](C)c4cc([N+](=O)[O-])cc(C(F)(F)F)c4)nc(C)nc3cc2C)cc1=O] | 1.02 | 512.3 | VAB |

Experimental Procedure for the Synthesis of A-15s

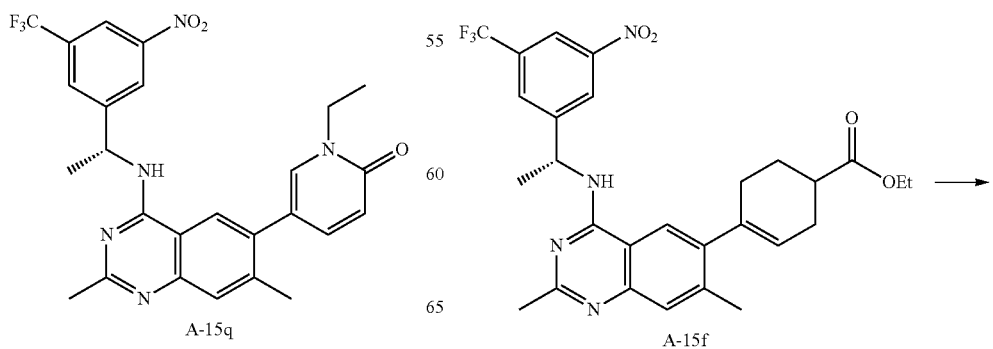

-continued

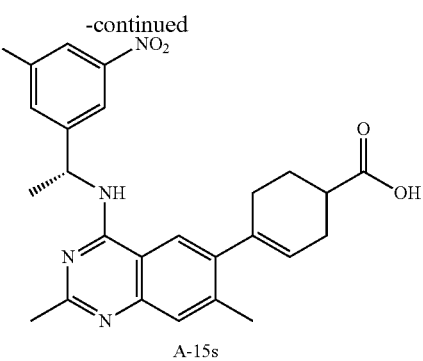
A-15s

A-15f (347.0 mg, 0.6 mmol, 1.0 equiv.) is dissolved in a mixture of THF (2.5 mL) and water (0.5 mL) and treated with LiOH (93.8 mg, 3.8 mmol, 6.0 equiv.). The reaction mixture is stirred for 12 h at rt. Then the solvent is removed under reduced pressure, the residue dissolved in DMF and purified by chromatography using acetonitrile/water giving the desired product A-15s.

The following intermediates A-15 (table 25) are available in an analogous manner starting from different quinazolines A-15 initially obtained (table 21). The crude product A-15 is purified by chromatography if necessary.

TABLE 25

| # | structure | $t_{ret}$ [min] | $[M + H]^+$ | HPLC method |
|---|---|---|---|---|
| A-15s | 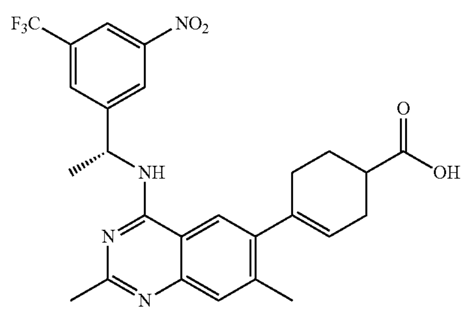 [SMILES: Cc1nc(N[C@H](C)c2cc([N+](=O)[O-])cc(C(F)(F)F)c2)c2cc(C3=CCC(C(=O)O)CC3)c(C)cc2n1] | 0.57 | 515.4 | BFEC |
| A-15t | 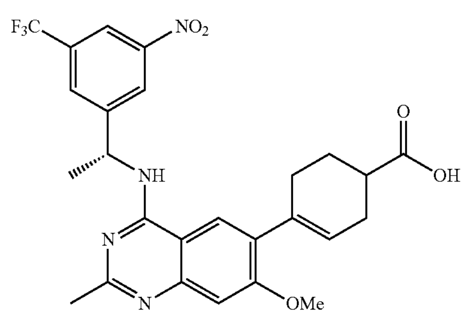 [SMILES: COc1cc2nc(C)nc(N[C@H](C)c3cc([N+](=O)[O-])cc(C(F)(F)F)c3)c2cc1C1=CCC(C(=O)O)CC1] | 0.563 | 531.2 | BFEC |
| A-15u | 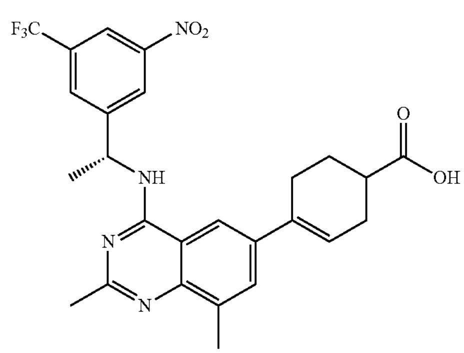 [SMILES: Cc1nc(N[C@H](C)c2cc([N+](=O)[O-])cc(C(F)(F)F)c2)c2cc(C3=CCC(C(=O)O)CC3)cc(C)c2n1] | 0.624 | 515.4 | BFEC |

Experimental Procedure for the Synthesis of A-15v

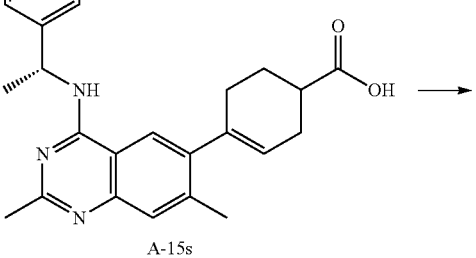

A-15s

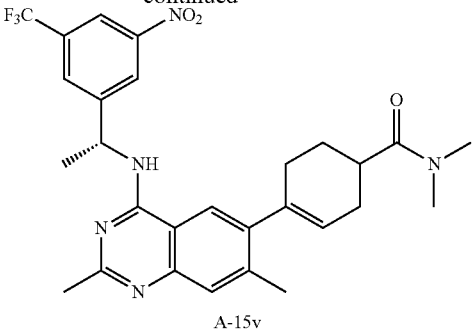

A-15v

A-15s (20.1 mg, 39.0 μmol, 1.0 equiv.) is dissolved in DMF (2.0 mL), DIPEA (25.0 μL, 154.0 μmol, 4.0 equiv.) and HATU (16.0 mg, 42.0 μmol, 1.1 equiv.) are added and the mixture is stirred for 20 min at rt. Then dimethyl amine (40.0 μL, 80.0 μmol, 2.0 equiv.) is added and the reaction mixture stirred for 1 h at rt. The crude product is purified by chromatography using a mixture of acetonitrile/water to give the desired product A-15v.

The following intermediates A-15 (table 26) are available in an analogous manner starting from different quinazolines A-15 initially obtained (table 25). The crude product A-15 is purified by chromatography if necessary.

TABLE 26

| # | structure | $t_{ret}$ [min] | $[M + H]^+$ | HPLC method |
|---|---|---|---|---|
| A-15v | (structure) | 0.80 | 542.2 | BFEC |
| A-15w | (structure) | 0.754 | 613.4 | BFEC |
| A-15x | (structure) | 0.78 | 558.4 | BFEC |

TABLE 26-continued

| # | structure | t_ret [min] | [M + H]+ | HPLC method |
|---|---|---|---|---|
| A-15y | 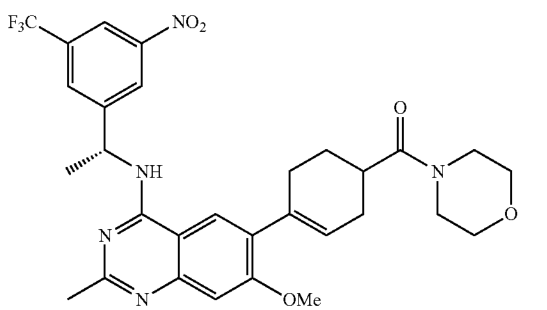 [SMILES: COc1cc2nc(C)nc(N[C@H](C)c3cc([N+](=O)[O-])cc(C(F)(F)F)c3)c2cc1C1=CCC(C(=O)N2CCOCC2)CC1] | 0.765 | 600.4 | BFEC |
| A-15z | 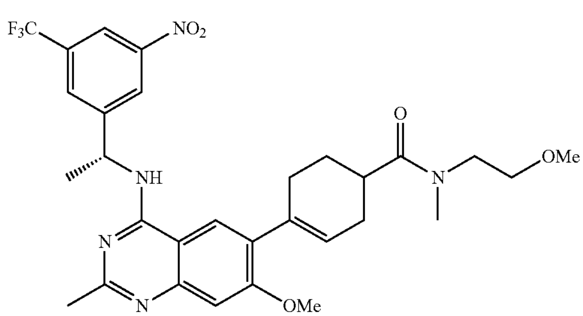 [SMILES: COCCN(C)C(=O)C1CC=C(c2cc3c(N[C@H](C)c4cc([N+](=O)[O-])cc(C(F)(F)F)c4)nc(C)nc3cc2OC)CC1] | 0.785 | 602.4 | BFEC |
| A-15aa | 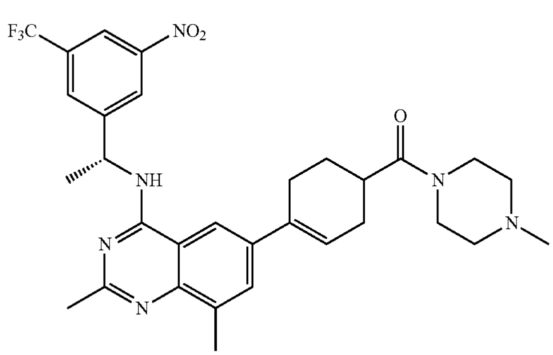 [SMILES: Cc1nc(N[C@H](C)c2cc([N+](=O)[O-])cc(C(F)(F)F)c2)c2cc(C3=CCC(C(=O)N4CCN(C)CC4)CC3)cc(C)c2n1] | 0.866 | 597.4 | BFEC |
| A-15ab | 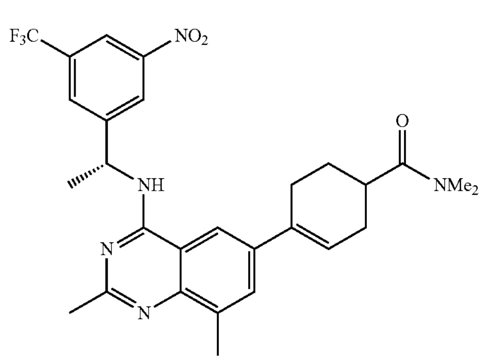 [SMILES: Cc1nc(N[C@H](C)c2cc([N+](=O)[O-])cc(C(F)(F)F)c2)c2cc(C3=CCC(C(=O)N(C)C)CC3)cc(C)c2n1] | 0.894 | 542.4 | BFEC |

TABLE 26-continued

| # | structure | $t_{ret}$ [min] | $[M + H]^+$ | HPLC method |
|---|---|---|---|---|
| A-15ac | 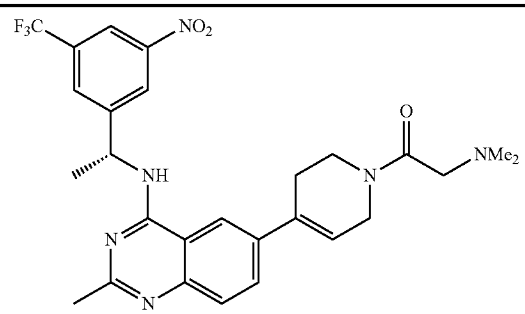 | 0.74 | 543.4 | BFEC |
| A-15ad | 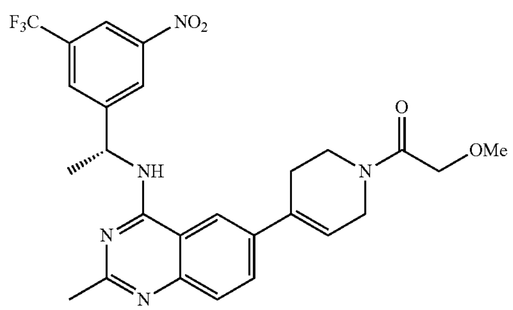 [SMILES: COCC(=O)N1CC=C(c2ccc3nc(C)nc(N[C@H](C)c4cc([N+](=O)[O-])cc(C(F)(F)F)c4)c3c2)CC1] | 0.73 | 530.4 | BFEC |
| A-15ae | 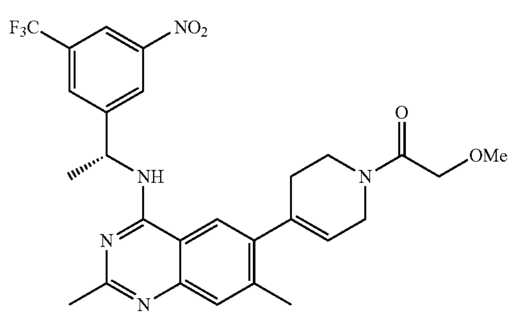 [SMILES: COCC(=O)N1CC=C(c2cc3c(N[C@H](C)c4cc([N+](=O)[O-])cc(C(F)(F)F)c4)nc(C)nc3cc2C)CC1] | 0.743 | 544.4 | BFEC |

Experimental Procedure for the Synthesis of A-15Af

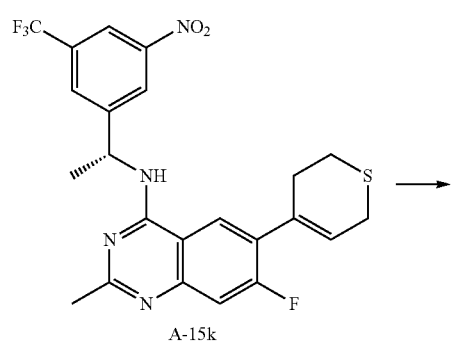

A-15k (208.1 mg, 426.0 µmol, 1.0 equiv.) is dissolved in DCM, cooled to 0° C., treated with 3-chloroperoxybenzoic acid (300.0 mg, 869.0 µmol, 2.0 equiv.) and stirred for 12 h at rt. The reaction mixture is filtered through celite giving the desired product A-15af.

The following intermediates A-15 (table 27) are available in an analogous manner starting from different quinazolines A-15 initially obtained (table 21). The crude product A-15 is purified by chromatography if necessary.

TABLE 27

| # | structure | $t_{ret}$ [min] | $[M + H]^+$ | HPLC method |
|---|---|---|---|---|
| A-15af | 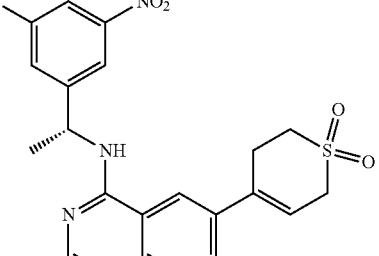 | 0.75 | 525 | BFEC |
| A-15ag | 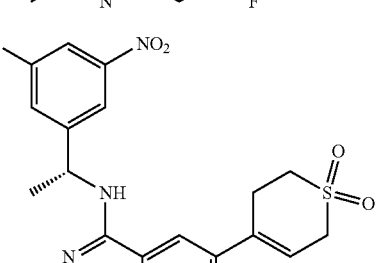 | 0.74 | 521 | BFEC |

Synthesis of Intermediates A-16

Experimental Procedure for the Synthesis of A-16a

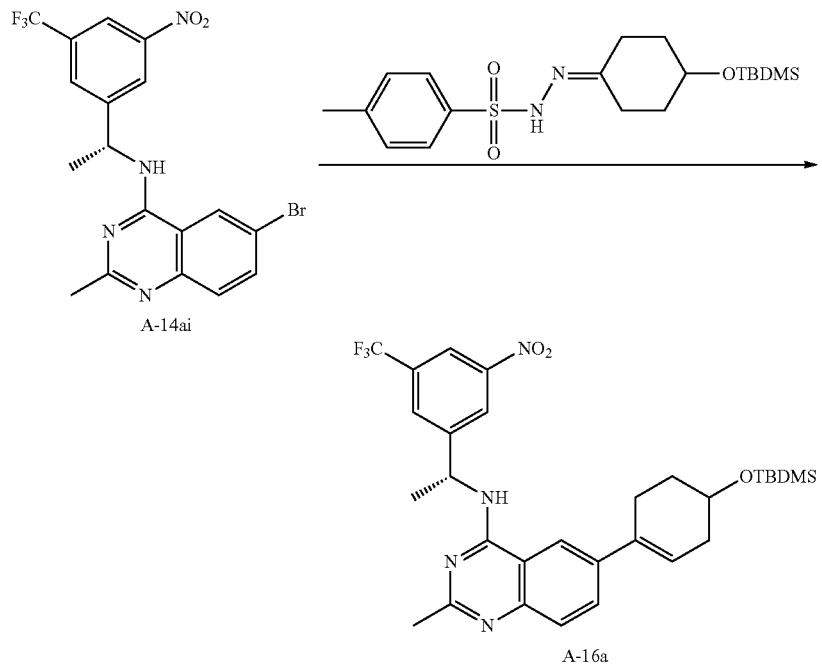

A-14ai (45.0 mg, 99.0 μmol, 0.7 equiv.), N'-{4-[(tert-butyldimethylsilyl)oxy]cyclo-hexylidene}-4-methylbenzene-1-sulfonohydrazide (59.8 mg, 151.0 μmol, 1.0 equiv.) and bis(triphenylphosphine)palladium(II) chloride (3.0 mg, 4.0 μmol, 0.1 equiv.) are dissolved in dry dioxane (3 mL) and heated to 100° C. Then lithium tert-butoxide (25.0 mg, 303.0 μmol, 2.0 equiv.) is added and the reaction mixture stirred at 100° C. for 2 d. The reaction is diluted with water, extracted with DCM, dried over $Na_2SO_4$ filtered and the solvent removed under reduced pressure. The crude product is dissolved in DMF and purified by chromatography using acetonitrile/water giving the desired product A-16a (HPLC method: BFEC: $t_{ret}$ [min]=1.1; $[M+H]^+$=587.4).

Experimental Procedure for the Synthesis of A-16b and A-16c

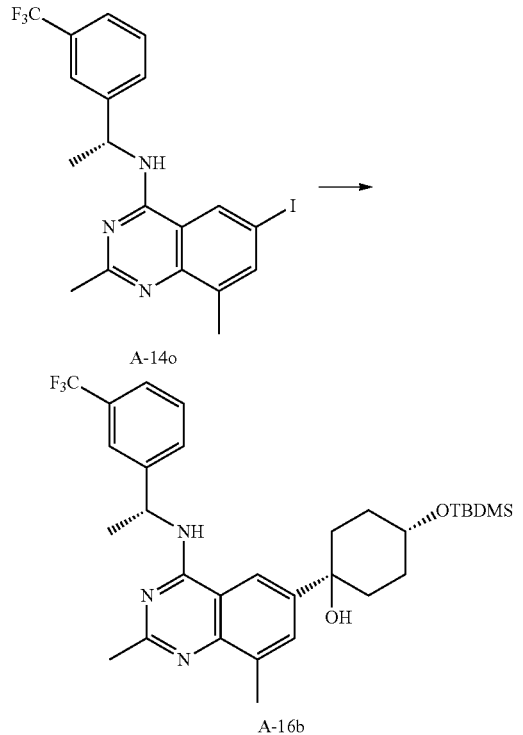

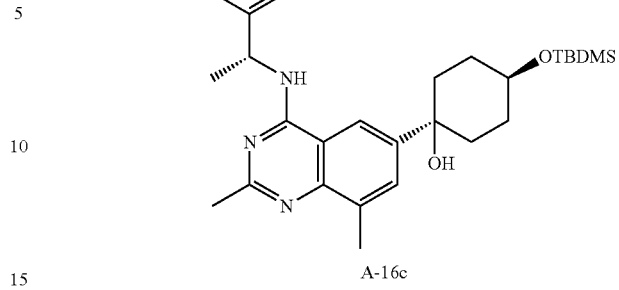

The reaction is performed under inert atmosphere. A-14o (160.0 mg, 0.35 mmol, 1.0 equiv.) is dissolved in dry THF (2 mL) and 1,3-dimethyl-3,4,5,6-tetrahydro-2(1)-pyrimidinone (79.5 μL, 0.7 mmol, 2.0 equiv.) and cooled to −20° C. Then isopropylmagnesium bromid (0.4 mL, 1.2 mmol, 3.5 equiv.) is added dropwise and the reaction mixture stirred for 1 h at −20° C. 4-(Tert-butyldimethylsilyloxy)cyclohexanone (116.3 mg, 0.5 mmol, 1.5 equiv.) is added and the reaction mixture stirred for 12 h at rt. The reaction is quenched with $NH_4Cl$ (sat.) and extracted with DCM. The solvent is removed under reduced pressure and the residue dissolved in DMF. The crude product is purified by chromatography using acetonitrile/water giving the desired products A-16b and A-16c.

The following compounds A-16 (table 28) are available in an analogous manner starting from different quinazolines A-14 initially obtained (table 18). The crude product A-16 is purified by chromatography if necessary.

TABLE 28

| # | structure | $[M + H]^+$ $t_{ret}$ [min] | HPLC method |
|---|---|---|---|
| A-16b | (structure shown) | M + H = 574.4; $t_{ret}$ = 1.124 | BFEC |
| A-16c | (structure shown) | M + H = 574.4; $t_{ret}$ = 1.164 | BFEC |

TABLE 28-continued

| # | structure | [M + H]+ t_ret [min] | HPLC method |
|---|---|---|---|
| A-16d | 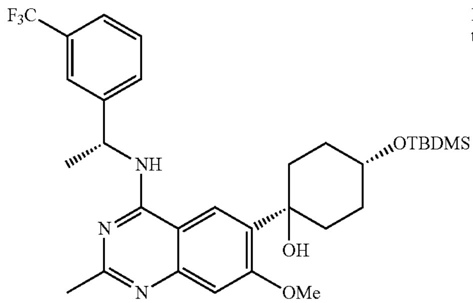 [SMILES: COc1cc2nc(C)nc(N[C@H](C)c3cccc(C(F)(F)F)c3)c2cc1[C@]1(O)CC[C@H](O[Si](C)(C)C(C)(C)C)CC1] | M + H = 590; t_ret = 1.11 | BFEC |
| A-16e | 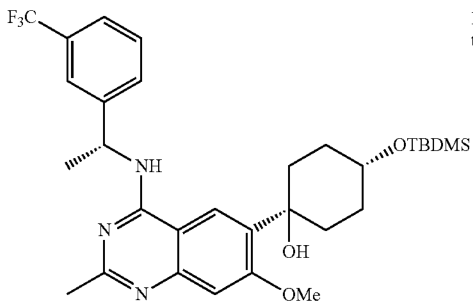 [SMILES: COc1cc2nc(C)nc(N[C@H](C)c3cccc(C(F)(F)F)c3)c2cc1[C@]1(O)CC[C@H](O[Si](C)(C)C(C)(C)C)CC1] | M + H = 590; t_ret = 1.08 | BFEC |
| A-16f | 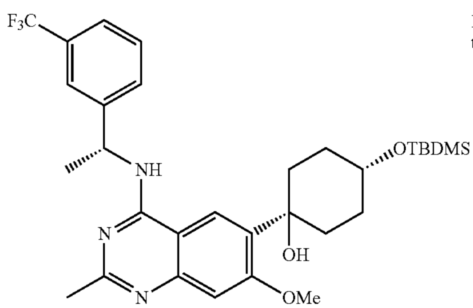 [SMILES: COc1cc2nc(C)nc(N[C@H](C)c3cccc(C(F)(F)F)c3)c2cc1[C@]1(O)CC[C@H](O[Si](C)(C)C(C)(C)C)CC1] | M + H = 608; t_ret = 1.11 | BFEC |
| A-16g | 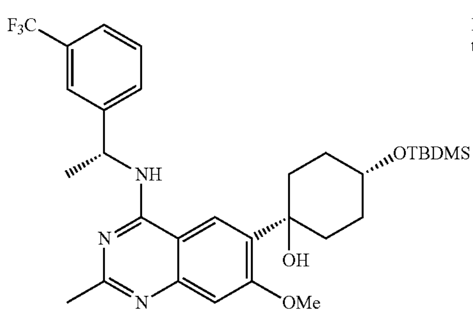 [SMILES: COc1cc2nc(C)nc(N[C@H](C)c3cccc(C(F)(F)F)c3)c2cc1[C@]1(O)CC[C@H](O[Si](C)(C)C(C)(C)C)CC1] | M + H = 608; t_ret = 1.08 | BFEC |
| A-16h | 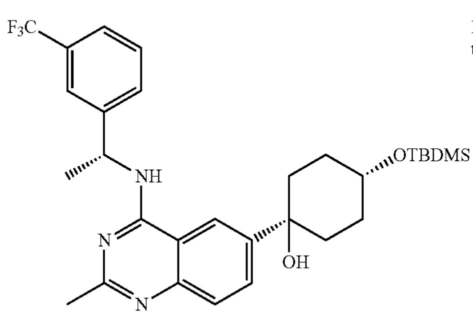 [SMILES: Cc1nc(N[C@H](C)c2cccc(C(F)(F)F)c2)c2cc([C@]3(O)CC[C@H](O[Si](C)(C)C(C)(C)C)CC3)ccc2n1] | M + H = 560; t_ret = 1.05 | BFEC |

TABLE 28-continued

| # | structure | [M + H]⁺ $t_{ret}$ [min] | HPLC method |
|---|---|---|---|
| A-16i | 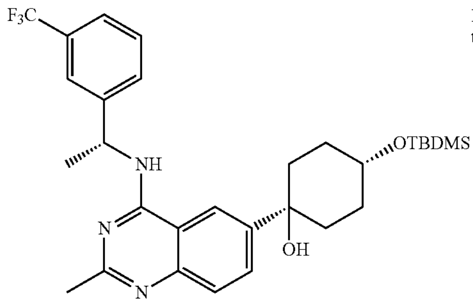 [SMILES: Cc1nc(N[C@H](C)c2cccc(C(F)(F)F)c2)c2cc([C@]3(O)CC[C@H](O[Si](C)(C)C(C)(C)C)CC3)ccc2n1] | M + H = 560; $t_{ret}$ = 1.08 | BFEC |
| A-16j | 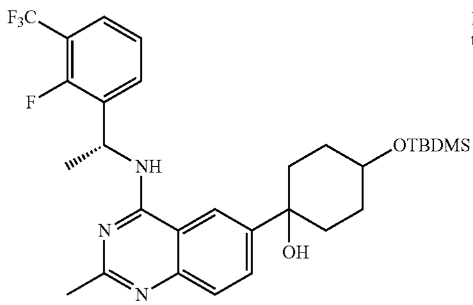 | M + H = 578; $t_{ret}$ = 1.05 | BFEC |
| A-16k | 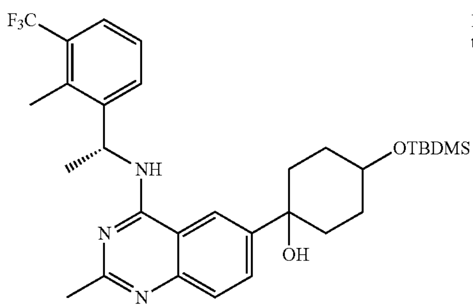 | M + H = 472; $t_{ret}$ = 0.91 | BFEC |

Synthesis of Compounds (I) According to the Invention

Experimental Procedure for the Synthesis of I-1

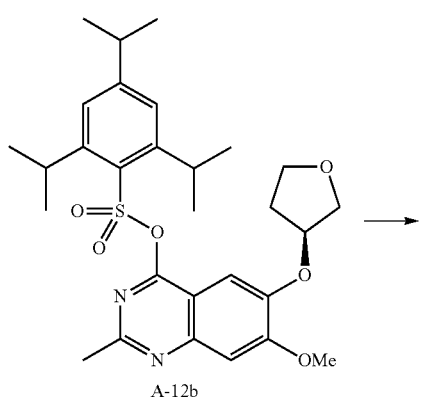

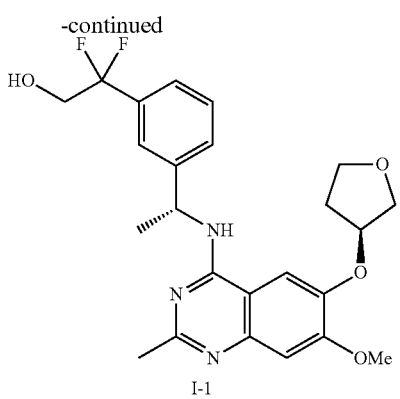

A-12b (50.0 mg, 0.1 mmol, 1.0 equiv.) and B-6f (46.0 mg, 0.14 mmol, 1.5 equiv.) are suspended in DMSO (1 mL) and TEA (0.1 mL) and the reaction mixture is stirred at 90° C. for 12 h. Then the solvent is removed under reduced pressure, the residue dissolved in DCM and extracted with water. The combined organic layers are dried over MgSO₄, filtered and the solvent is removed in vacuo. The crude product is purified by chromatography (DCM:MeOH:NH₃, 19:1:0.1) to give the desired product I-1.

The following compounds (I) (table 29) are available in an analogous manner starting from different quinazolines A-12. The crude product (I) is purified by chromatography if necessary.

TABLE 29

| # | structure | [M + H]⁺ $t_{ret}$ [min] | HPLC method | IC$_{50}$ (SOS1) [nM] |
|---|---|---|---|---|
| I-1 | 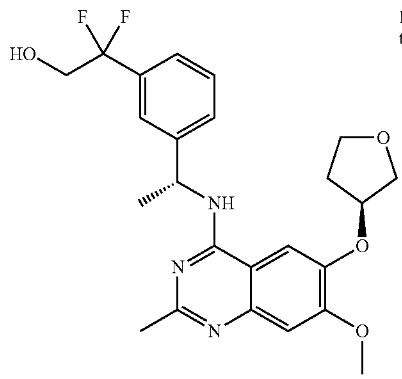 | M + H = 460; $t_{ret}$ = 1.09 | LCMSBAS1 | 3 |
| I-2 | 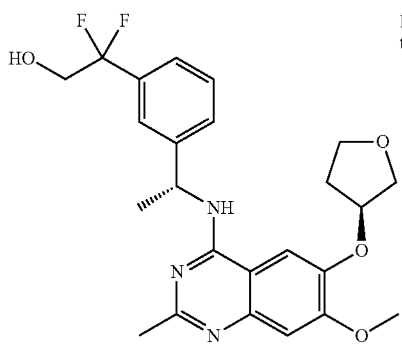 | M + H = 460; $t_{ret}$ = 1.09 | LCMSBAS1 | 3 |
| I-3 | 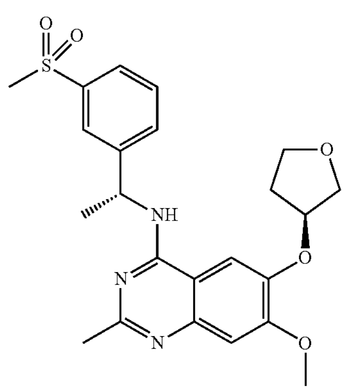 [SMILES: COc1cc2nc(C)nc(N[C@H](C)c3cccc(S(C)(=O)=O)c3)c2cc1O[C@H]1CCOC1] | M + H = 458; $t_{ret}$ = 0.99 | LCMSBAS-1 | 47* |
| I-4 | 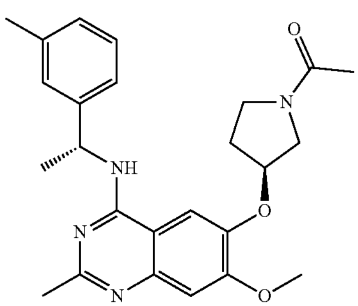 [SMILES: COc1cc2nc(C)nc(N[C@H](C)c3cccc(C)c3)c2cc1O[C@H]1CCN(C(C)=O)C1] | M + H = 435; $t_{ret}$ = 1.14 | LCMSBAS-1 | 30 |

TABLE 29-continued

| # | structure | [M + H]+ t_ret [min] | HPLC method | IC50 (SOS1) [nM] |
|---|---|---|---|---|
| I-5 | 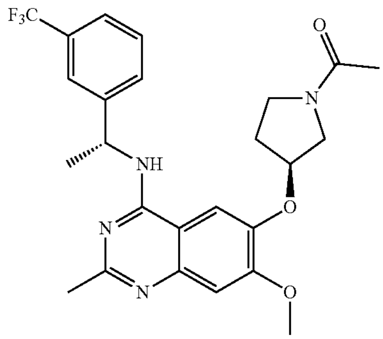 [SMILES: COc1cc2nc(C)nc(N[C@H](C)c3cccc(C(F)(F)F)c3)c2cc1O[C@H]1CCN(C(C)=O)C1] | M + H = 489; t_ret = 1.21 | LCMSBAS-1 | 13 |
| I-6 | 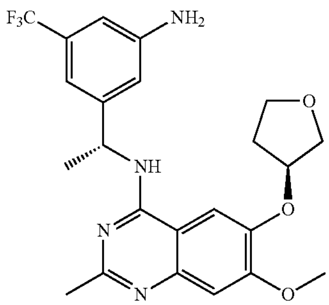 [SMILES: COc1cc2nc(C)nc(N[C@H](C)c3cc(N)cc(C(F)(F)F)c3)c2cc1O[C@H]1CCOC1] | M + H = 463; t_ret = 1.19 | LCMSBAS-1 | 6 |
| I-7 | 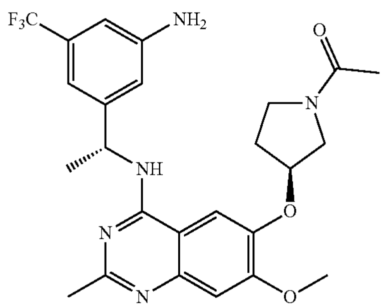 [SMILES: COc1cc2nc(C)nc(N[C@H](C)c3cc(N)cc(C(F)(F)F)c3)c2cc1O[C@H]1CCN(C(C)=O)C1] | M + H = 504; t_ret = 1.09 | LCMSBAS-1 | 3 |
| I-8 | 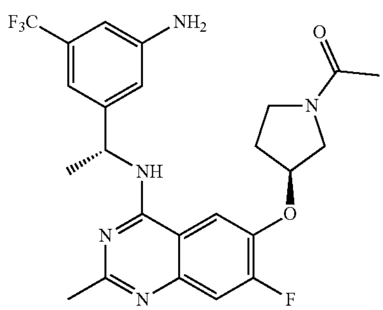 [SMILES: CC(=O)N1CC[C@H](Oc2cc3c(N[C@H](C)c4cc(N)cc(C(F)(F)F)c4)nc(C)nc3cc2F)C1] | M + H = 492; t_ret = 1.16 | LCMSBAS-1 | 6 |
| I-9 | 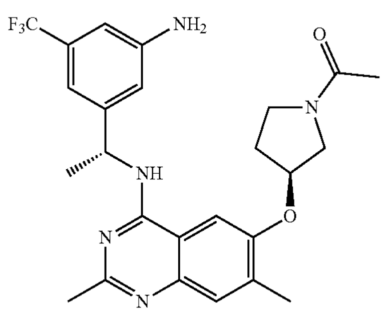 [SMILES: CC(=O)N1CC[C@H](Oc2cc3c(N[C@H](C)c4cc(N)cc(C(F)(F)F)c4)nc(C)nc3cc2C)C1] | M + H = 488; t_ret = 1.15 | LCMSBAS-1 | 3 |

TABLE 29-continued

| # | structure | [M + H]+ t$_{ret}$ [min] | HPLC method | IC$_{50}$ (SOS1) [nM] |
|---|---|---|---|---|
| I-10 | 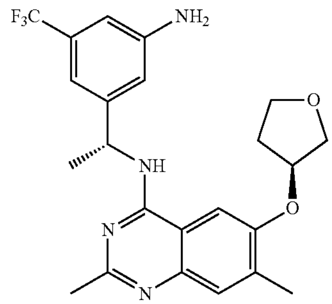 [SMILES: Cc1nc(N[C@H](C)c2cc(N)cc(C(F)(F)F)c2)c2cc(O[C@H]3CCOC3)c(C)cc2n1] | M + H = 447; t$_{ret}$ = 1.27 | LCMSBAS-1 | 7 |
| I-11 | 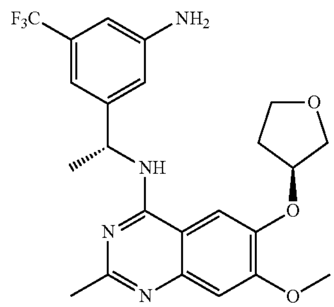 | M + H = 477; t$_{ret}$ = 1.25 | LCMSBAS-1 | 4 |
| I-12 | 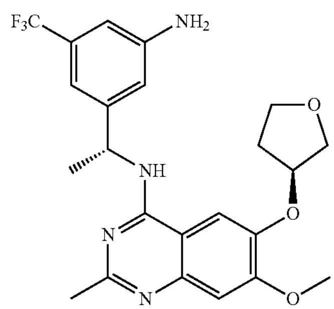 | M + H = 481; t$_{ret}$ = 1.19 | LCMSBAS-1 | 5 |
| I-13 | 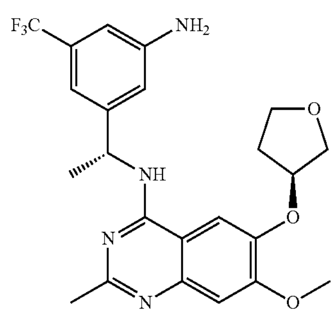 [SMILES: COc1cc2nc(C)nc(N[C@H](C)c3cc(N)cc(C(F)(F)F)c3)c2cc1O[C@H]1CCOC1] | M + H = 463; t$_{ret}$ = 1.16 | LCMSBAS-1 | 5 |
| I-14 | 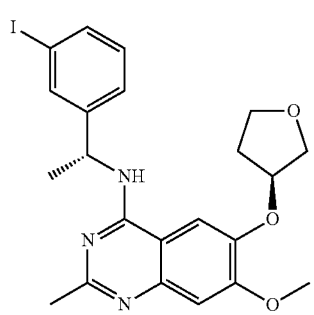 [SMILES: COc1cc2nc(C)nc(N[C@H](C)c3cccc(I)c3)c2cc1O[C@H]1CCOC1] | M + H = 506.2; t$_{ret}$ = 0.734 | BFEC | |

TABLE 29-continued

| # | structure | [M + H]+ $t_{ret}$ [min] | HPLC method | IC$_{50}$ (SOS1) [nM] |
|---|---|---|---|---|
| I-384 | 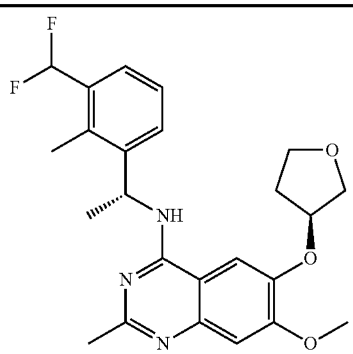 | n.a. | — | |

Experimental Procedure for the Synthesis of I-15

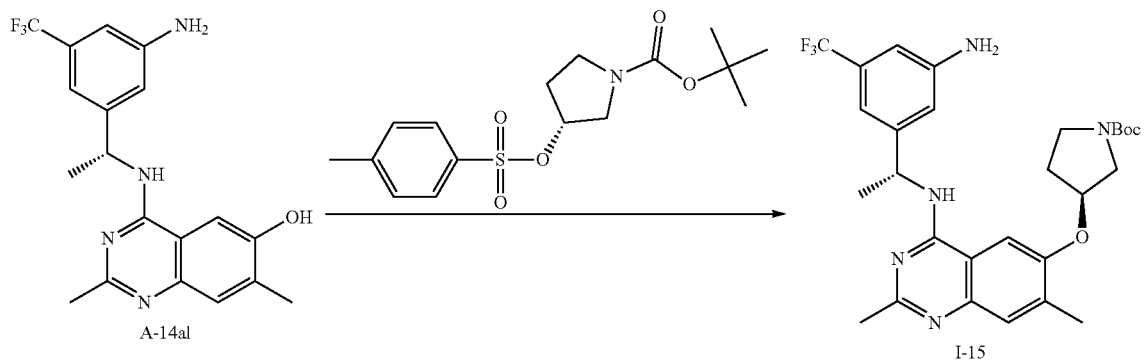

A-14al (292.0 mg, 0.8 mmol, 1.0 equiv.) is dissolved in dry NMP (3 mL) and cooled down to 0° C. Then NaH (37.0 mg, 0.9 mmol, 1.2 equiv., 60% in mineral oil) is added and the reaction mixture stirred for 5 min at rt. Tert-butyl (3R)-3-[(4-methylbenzenesulfonyl)oxy]pyrrolidine-1-carboxylate (397.0 mg, 1.2 mmol, 1.2 equiv.) is added dissolved in dry NMP (1 mL) and the reaction mixture heated to 100° C. for 5 h. The crude reaction mixture is purified by chromatography using acetonitrile/water giving the desired product I-15.

TABLE 30

| # | structure | [M + H]+ $t_{ret}$ [min] | HPLC method | IC$_{50}$ (SOS1) [nM] |
|---|---|---|---|---|
| I-15 | 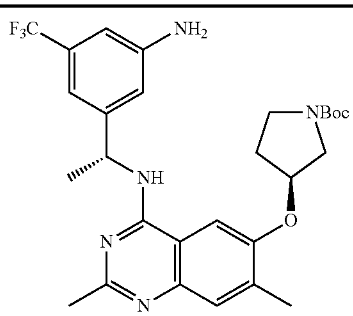 | M + H = 546.2; $t_{ret}$ = 1.07 | VAB | |

Experimental Procedure for the Synthesis of I-16

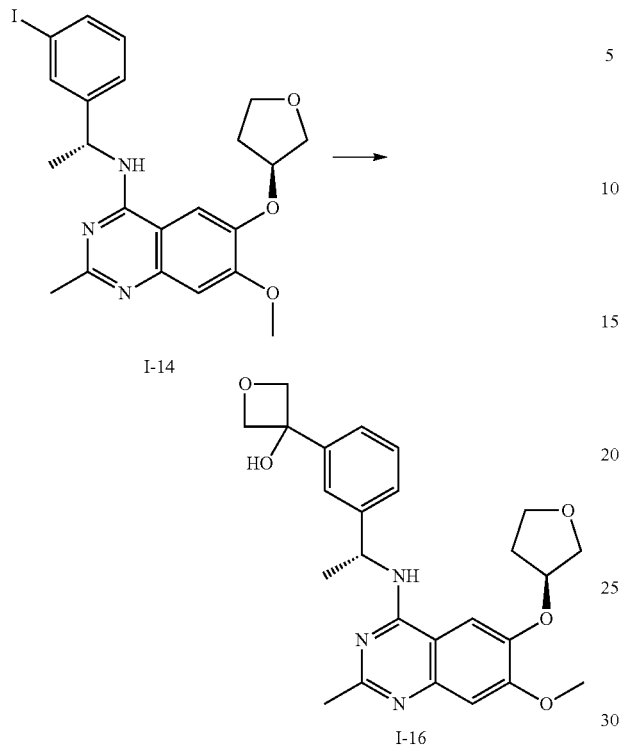

I-14

I-16

The reaction is performed under inert atmosphere. I-14 (50.0 mg, 0.1 mmol, 1.0 equiv.) is dissolved in dry THF (2 mL) and 1,3-dimethyl-3,4,5,6-tetrahydro-2(1H)-pyrimidinone (23.9 µL, 0.2 mmol, 2.0 equiv.) and cooled to −20° C. Then isopropylmagnesium bromid (0.2 mL, 0.7 mmol, 7.0 equiv.) is added dropwise and the reaction mixture stirred for 1 h at −20° C. 3-Oxetanone (11.0 mg, 0.15 mmol, 1.5 equiv.) is added and the reaction mixture stirred for 12 h at rt. The reaction is quenched with $NH_4Cl$ (sat.) and extracted with DCM. The solvent is removed under reduced pressure and the residue dissolved in DMF. The crude product is purified by chromatography using acetonitrile/water giving the desired product I-16.

The following compounds (I) (table 31) are available in an analogous manner starting from different quinazolines. The crude product (I) is purified by chromatography if necessary.

TABLE 31

| # | structure | $[M + H]^+$ $t_{ret}$ [min] | HPLC method | $IC_{50}$ (SOS1) [nM] |
|---|---|---|---|---|
| I-16 | 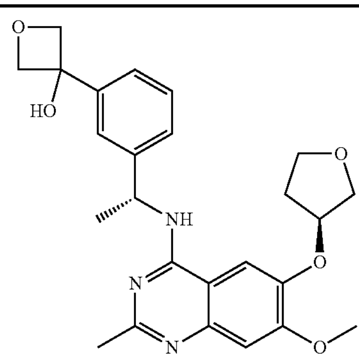 | M + H = 452; $t_{ret}$ = 0.96 | LCMSBAS1 | 38 |

TABLE 31-continued

| # | structure | [M + H]+ $t_{ret}$ [min] | HPLC method | $IC_{50}$ (SOS1) [nM] |
|---|---|---|---|---|
| I-17 | 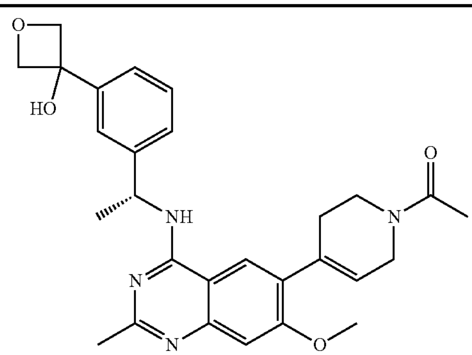 | M + H = 489; $t_{ret}$ = 0.99 | LCMSBAS1 | 34 |

Experimental Procedure for the Synthesis of I-18

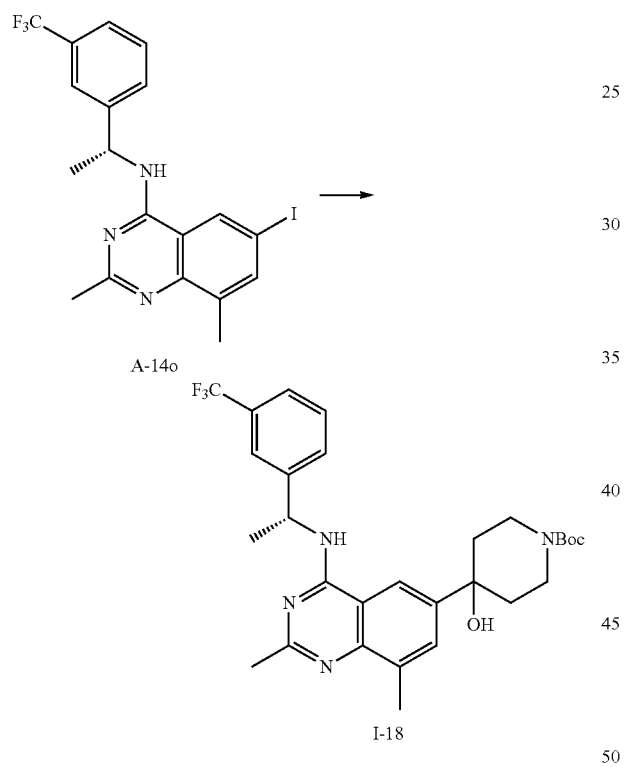

The reaction is performed under inert atmosphere. A-14o (118.3 mg, 0.3 mmol, 1.0 equiv.) is dissolved in dry THE (2 mL) and 1,3-dimethyl-3,4,5,6-tetrahydro-2(1)-pyrimidinone (58.5 µL, 0.5 mmol, 2.0 equiv.) and cooled to −20° C. Then isopropylmagnesium bromid (0.3 mL, 0.9 mmol, 3.0 equiv.) is added dropwise and the reaction mixture is stirred for 1 h. Boc-4-piperidone (75.0 mg, 0.4 mmol, 1.5 euqiv.) is added and the reaction mixture stirred for 12 h at rt. The reaction is quenched with $NH_4C$ (sat.) and extracted with DCM. The solvent is removed under reduced pressure and the residue dissolved in DMF. The crude product is purified by chromatography using acetonitrile/water giving the desired product I-18.

The following compounds (I) (table 32) are available in an analogous manner starting from different quinazolines A-14. The crude product is purified by chromatography if necessary.

TABLE 32

| # | structure | [M + H]+ t_ret [min] | HPLC method | IC_50 (SOS1) [nM] |
|---|---|---|---|---|
| I-18 | 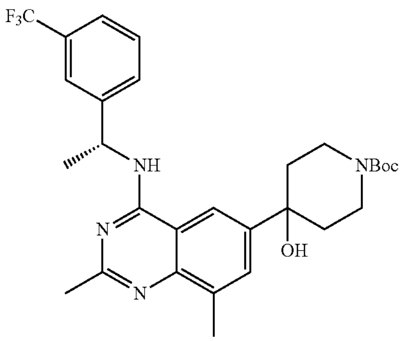 [SMILES: Cc1nc(N[C@H](C)c2cccc(C(F)(F)F)c2)c2cc(C3(O)CCN(C(=O)OC(C)(C)C)CC3)cc(C)c2n1] | M + H = 545.4; t_ret = 0.916 | BFEC | |
| I-19 | 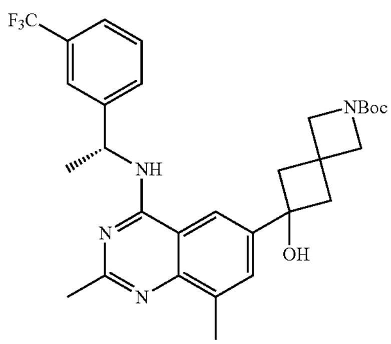 [SMILES: Cc1nc(N[C@H](C)c2cccc(C(F)(F)F)c2)c2cc(C3(O)CC4(CN(C(=O)OC(C)(C)C)C4)C3)cc(C)c2n1] | M + H = 557.4; t_ret = 0.897 | BFEC | |
| I-20 | 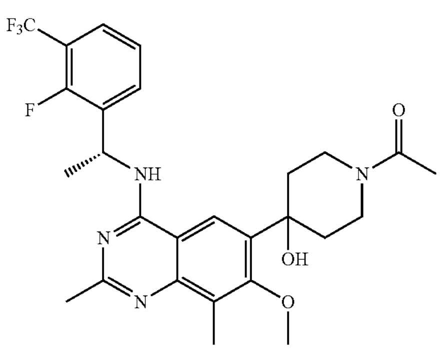 [SMILES: COc1c(C2(O)CCN(C(C)=O)CC2)cc2c(N[C@H](C)c3cccc(C(F)(F)F)c3F)nc(C)nc2c1C] | M + H = 535; t_ret = 1.34 | LCMSBAS1 | 7 |
| I-21 | 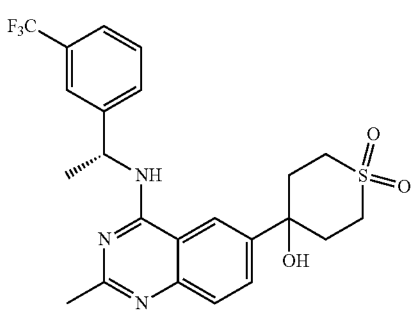 [SMILES: Cc1nc(N[C@H](C)c2cccc(C(F)(F)F)c2)c2cc(C3(O)CCS(=O)(=O)CC3)ccc2n1] | M + H = 480; t_ret = 1.23 | LCMSBAS1 | 20 |

TABLE 32-continued

| # | structure | [M + H]+ t_ret [min] | HPLC method | IC50 (SOS1) [nM] |
|---|---|---|---|---|
| I-22 | 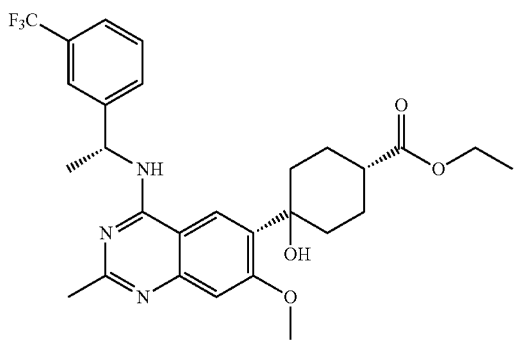 | M + H = 532; t_ret = 1.44 | LCMSBAS1 | |
| I-23 | 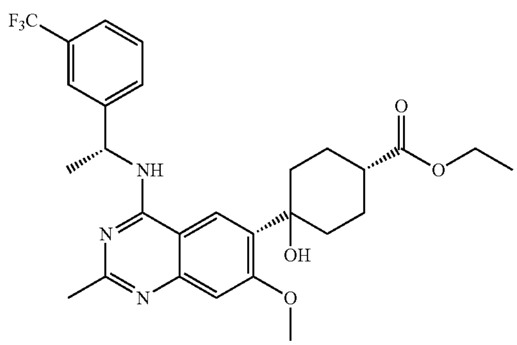 | M + H = 532; t_ret = 1.46 | LCMSBAS1 | |
| I-24 | 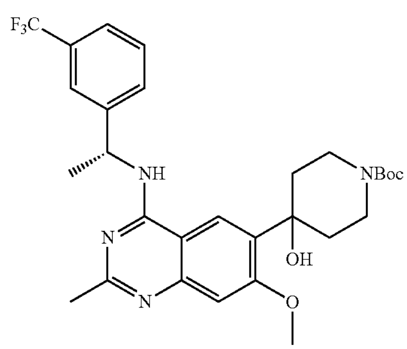 [SMILES: COc1cc2nc(C)nc(N[C@H](C)c3cccc(C(F)(F)F)c3)c2cc1C1(O)CCN(C(=O)OC(C)(C)C)CC1] | M + H = 561.4; t_ret = 0.85 | BFEC | |
| I-25 | 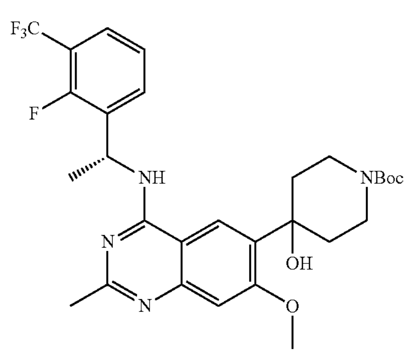 [SMILES: COc1cc2nc(C)nc(N[C@H](C)c3cccc(C(F)(F)F)c3F)c2cc1C1(O)CCN(C(=O)OC(C)(C)C)CC1] | M + H = 579; t_ret = 0.76 | BFEC | |

TABLE 32-continued

| # | structure | [M + H]+ t$_{ret}$ [min] | HPLC method | IC$_{50}$ (SOS1) [nM] |
|---|-----------|--------------------------|-------------|------------------------|
| I-26 | 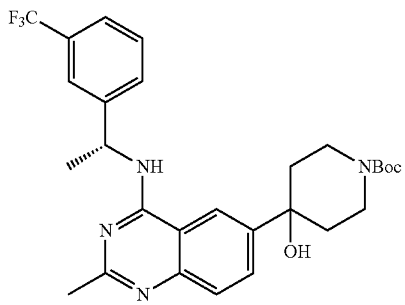 [SMILES: Cc1nc(N[C@H](C)c2cccc(C(F)(F)F)c2)c2cc(C3(O)CCN(C(=O)OC(C)(C)C)CC3)ccc2n1] | M + H = 531; t$_{ret}$ = 0.82 | BFEC | |
| I-27 | 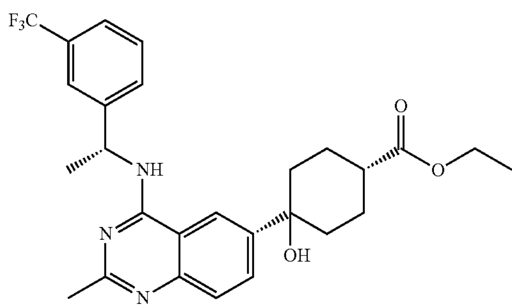 | M + H = 502; t$_{ret}$ = 0.79 | BFEC | |
| I-28 | 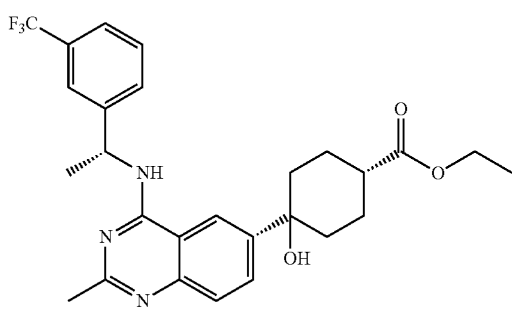 | M + H = 502; t$_{ret}$ = 0.82 | BFEC | |
| I-29 | 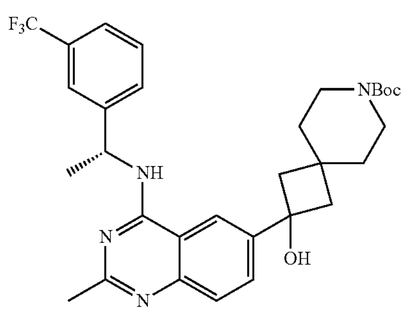 [SMILES: Cc1nc(N[C@H](C)c2cccc(C(F)(F)F)c2)c2cc(C3(O)CC4(CCN(C(=O)OC(C)(C)C)CC4)C3)ccc2n1] | M + H = 572; t$_{ret}$ = 0.86 | BFEC | |
| I-30 | 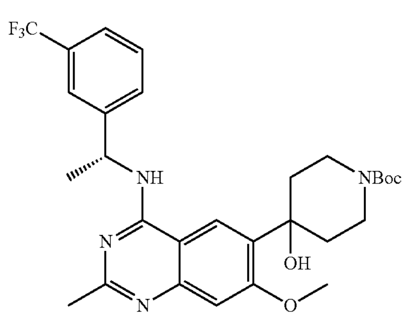 | M + H = 579; t$_{ret}$ = 0.76 | BFEC | |

TABLE 32-continued

| # | structure | [M + H]+ $t_{ret}$ [min] | HPLC method | IC$_{50}$ (SOS1) [nM] |
|---|---|---|---|---|
| I-31 | 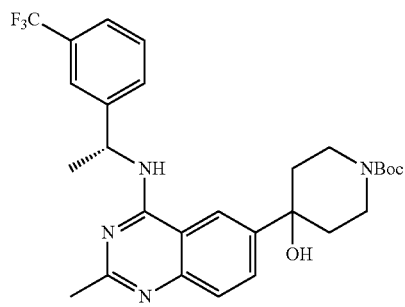 | M + H = 531; $t_{ret}$ = 0.82 | BFEC | |
| I-32 | 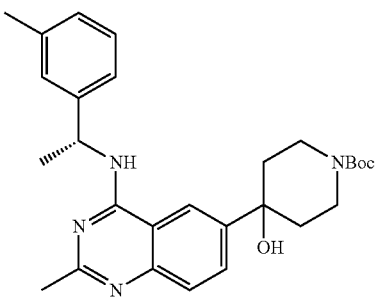 [SMILES: Cc1cccc([C@@H](C)Nc2nc(C)nc3ccc(C4(O)CCN(C(=O)OC(C)(C)C)CC4)cc23)c1] | M + H = 477; $t_{ret}$ = 0.79 | BFEC | |

Experimental Procedure for the Synthesis of I-33

I-18 (40.2 mg, 0.1 mmol, 1.0 equiv.) is dissolved in dioxane (3 mL) and treated with HCl (73.9 µL, 4 M in dioxane, 4.0 equiv.). The reaction mixture is stirred at rt for 4 d. The solvent is removed under reduced pressure to give the desired product I-33.

The following compounds (I) (table 33) are available in an analogous manner starting from different quinazolines (I) initially obtained (tables 30 and 32). The crude product (I) is purified by chromatography if necessary.

TABLE 33

| # | structure | [M + H]+ t$_{ret}$ [min] | HPLC method | IC$_{50}$ (SOS1) [nM] |
|---|---|---|---|---|
| I-33 | 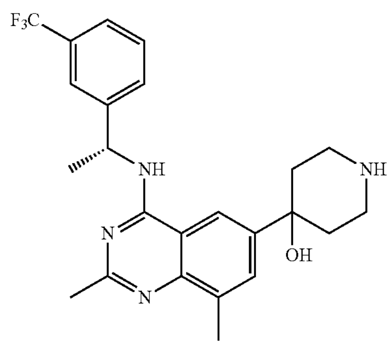 [SMILES: Cc1nc(N[C@H](C)c2cccc(C(F)(F)F)c2)c2cc(C3(O)CCNCC3)cc(C)c2n1] | M + H = 445.4; t$_{ret}$ = 0.630 | BFEC | |
| I-34 | 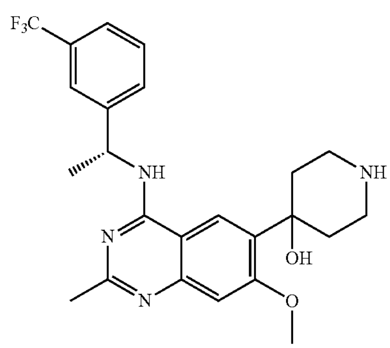 [SMILES: COc1cc2nc(C)nc(N[C@H](C)c3cccc(C(F)(F)F)c3)c2cc1C1(O)CCNCC1] | M + H = 461; t$_{ret}$ = 0.62 | BFEC | |
| I-35 | 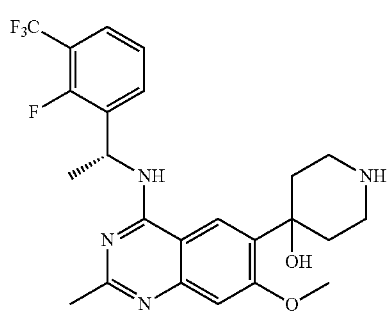 [SMILES: COc1cc2nc(C)nc(N[C@H](C)c3cccc(C(F)(F)F)c3F)c2cc1C1(O)CCNCC1] | M + H = 479; t$_{ret}$ = 0.63 | BFEC | |
| I-36 | 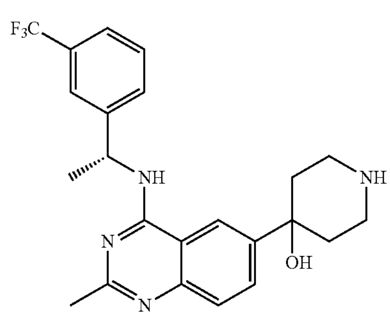 [SMILES: Cc1nc(N[C@H](C)c2cccc(C(F)(F)F)c2)c2cc(C3(O)CCNCC3)ccc2n1] | n.a. | — | |

TABLE 33-continued

| # | structure | [M + H]+ t_ret [min] | HPLC method | IC$_{50}$ (SOS1) [nM] |
|---|---|---|---|---|
| I-37 | 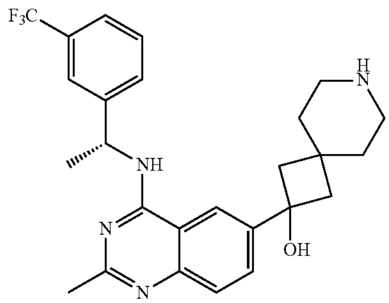 [SMILES: Cc1nc(N[C@H](C)c2cccc(C(F)(F)F)c2)c2cc(C3(O)CC4(CCNCC4)C3)ccc2n1] | M + H = 471; t_ret = 0.59 | BFEC | |
| I-38 | 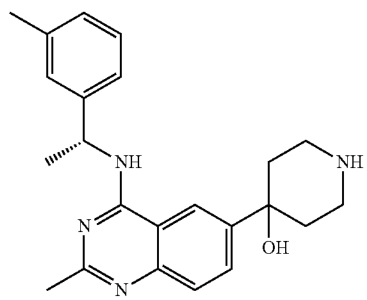 [SMILES: Cc1cccc([C@@H](C)Nc2nc(C)nc3ccc(C4(O)CCNCC4)cc23)c1] | M + H = 377; t_ret = 0.53 | BFEC | |
| I-39 | 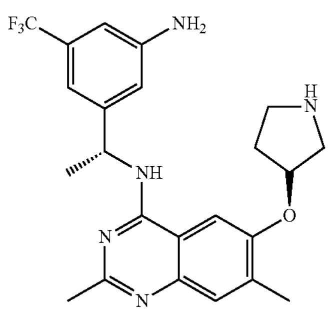 | M + H = 446; t_ret = 1.09 | LCMSBAS1 | |

Experimental Procedure for the Synthesis of I-40

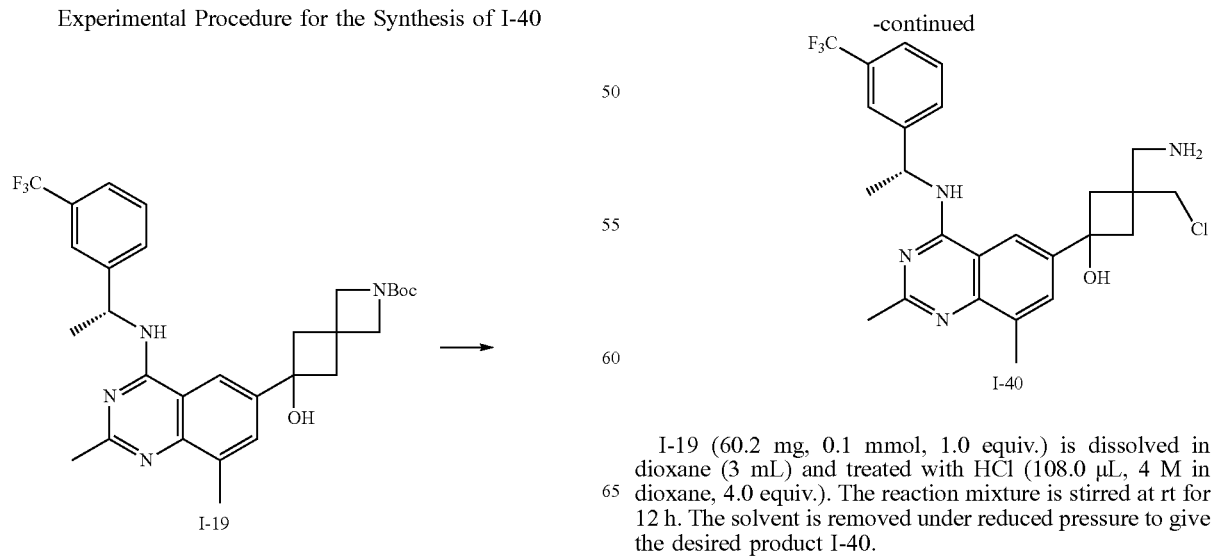

I-19 (60.2 mg, 0.1 mmol, 1.0 equiv.) is dissolved in dioxane (3 mL) and treated with HCl (108.0 μL, 4 M in dioxane, 4.0 equiv.). The reaction mixture is stirred at rt for 12 h. The solvent is removed under reduced pressure to give the desired product I-40.

Experimental Procedure for the Synthesis of I-41

Experimental Procedure for the Synthesis of I-42

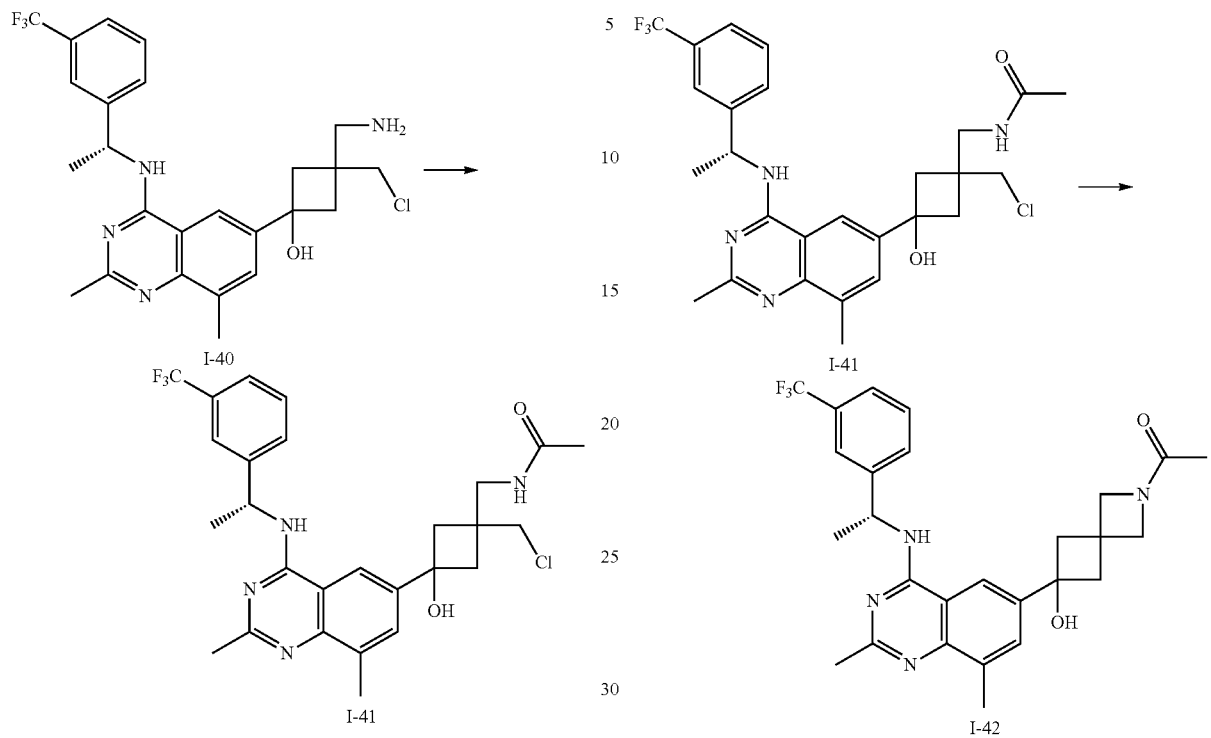

I-40 (68.0 mg, 138.0 μmol, 1.0 equiv.) is dissolved in DMF (1 mL), DIPEA (93.6 μL, 555.0 μmol, 4.0 equiv.) and TBTU (66.4 mg, 207.0 μmol, 1.5 equiv.) are added and the mixture is stirred for 15 min at rt. Then acetic acid (12.4 mg, 207.0 μmol, 1.5 equiv.) is added and the reaction mixture stirred for 1 h at rt. The crude reaction mixture is purified by chromatography using acetonitrile/water giving the desired product I-41.

I-41 (9.6 mg, 18.0 μmol, 1.0 equiv.) is dissolved in dry THF (1 mL) and treated with NaH (1.7 mg, 72.0 μmol, 4.0 equiv.). The reaction mixture is stirred at rt for 5 d, then the reaction is quenched with water, extracted with DCM and the solvent removed under reduced pressure. The crude product is purified by chromatography using acetonitrile/water giving the desired product I-42.

TABLE 34

| # | structure | $[M + H]^+$ $t_{ret}$ [min] | HPLC method | $IC_{50}$ (SOS1) [nM] |
|---|---|---|---|---|
| I-40 | 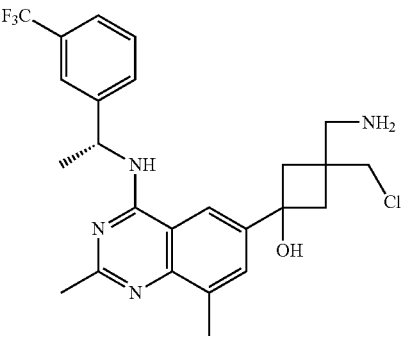 [SMILES: Cc1nc(N[C@H](C)c2cccc(C(F)(F)F)c2)c2cc(C3(O)CC(CN)(CCl)C3)cc(C)c2n1] | M + H = 493.2; $t_{ret}$ = 0.776 | BFEC | |

TABLE 34-continued
| # | structure | [M + H]+ $t_{ret}$ [min] | HPLC method | IC$_{50}$ (SOS1) [nM] |
|---|-----------|--------------------------|-------------|------------------------|
| I-41 | 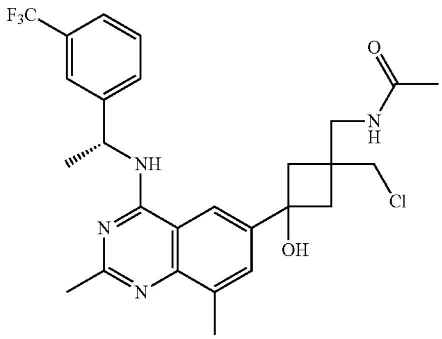 [SMILES: CC(=O)NCC1(CCl)CC(O)(c2cc(C)c3nc(C)nc(N[C@H](C)c4cccc(C(F)(F)F)c4)c3c2)C1] | M + H = 535.2; $t_{ret}$ = 0.756 | BFEC | |
| I-42 | 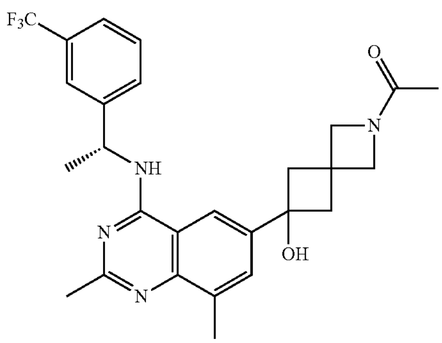 [SMILES: CC(=O)N1CC2(C1)CC(O)(c1cc(C)c3nc(C)nc(N[C@H](C)c4cccc(C(F)(F)F)c4)c3c1)C2] | M + H = 499; $t_{ret}$ = 1.32 | LCMSBAS1 | 26 |
Experimental Procedure for the Synthesis of I-43
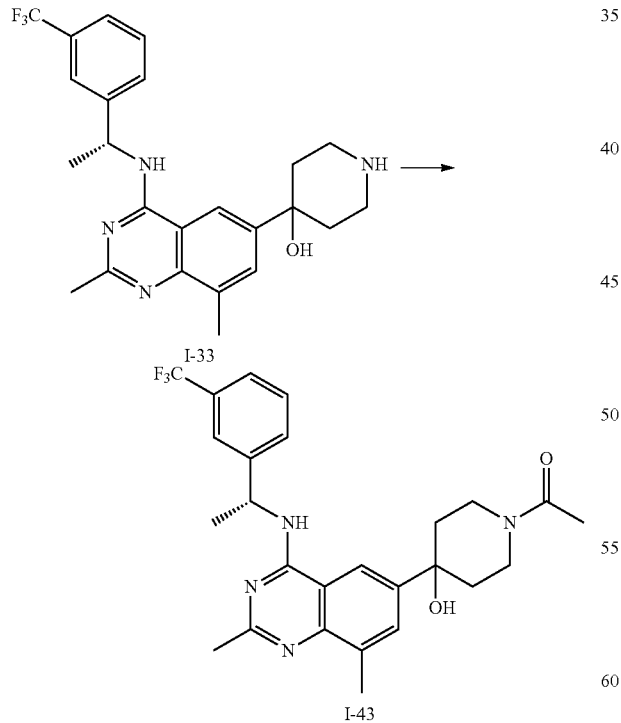
AcOH (3.9 µL, 67.0 µmol, 1.5 equiv.) is dissolved in DMF (1 mL), DIPEA (30.6 µL, 180.0 µmol, 4.0 equiv.) and HATU (25.6 mg, 67.0 µmol, 1.5 equiv.) are added and the mixture stirred for 15 min at rt. Then I-33 (20.0 mg, 45.0 µmol, 1.0 equiv.) is added and the reaction mixture stirred for 1 h at rt. The crude product is purified by chromatography using a mixture of acetonitrile/water to give the desired product I-43.

The following compounds (I) (table 35) are available in an analogous manner starting from different quinazolines (I) initially obtained (table 33). The crude product (I) is purified by chromatography if necessary.

TABLE 35

| # | structure | [M + H]⁺ $t_{ret}$ [min] | HPLC method | IC$_{50}$ (SOS1) [nM] |
|---|---|---|---|---|
| I-43 | 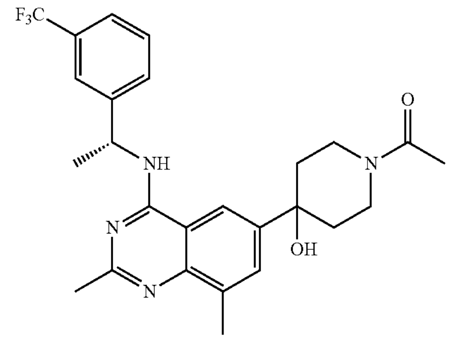 [SMILES: CC(=O)N1CCC(O)(c2cc(C)c3nc(C)nc(N[C@H](C)c4cccc(C(F)(F)F)c4)c3c2)CC1] | M + H = 487; $t_{ret}$ = 1.28 | LCMSBAS1 | 8 |
| I-44 | 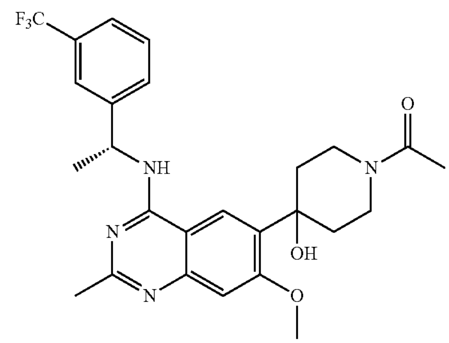 [SMILES: COc1cc2nc(C)nc(N[C@H](C)c3cccc(C(F)(F)F)c3)c2cc1C1(O)CCN(C(C)=O)CC1] | M + H = 503; $t_{ret}$ = 1.20 | LCMSBAS1 | 4 |
| I-45 | 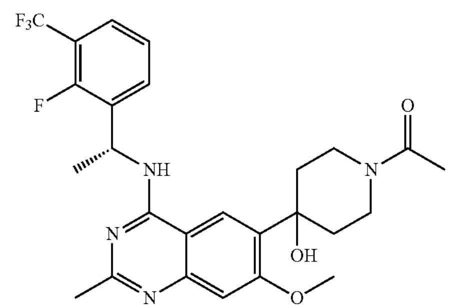 [SMILES: COc1cc2nc(C)nc(N[C@H](C)c3cccc(C(F)(F)F)c3F)c2cc1C1(O)CCN(C(C)=O)CC1] | M + H = 521; $t_{ret}$ = 1.21 | LCMSBAS1 | 2 |
| I-46 | 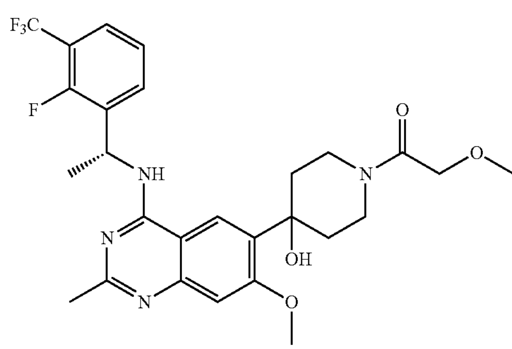 [SMILES: COCC(=O)N1CCC(O)(c2cc3c(N[C@H](C)c4cccc(C(F)(F)F)c4F)nc(C)nc3cc2OC)CC1] | M + H = 551; $t_{ret}$ = 1.22 | LCMSBAS1 | 4 |

TABLE 35-continued
| # | structure | [M + H]+ t_ret [min] | HPLC method | IC50 (SOS1) [nM] |
|---|---|---|---|---|
| I-47 | 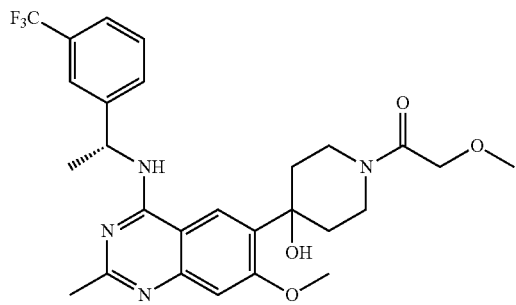 [SMILES: COCC(=O)N1CCC(O)(c2cc3c(N[C@H](C)c4cccc(C(F)(F)F)c4)nc(C)nc3cc2OC)CC1] | M + H = 533; t_ret = 1.22 | LCMSBAS1 | 5 |
| I-48 | 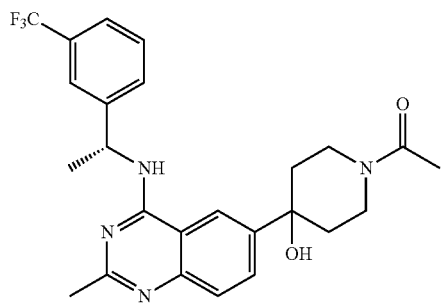 [SMILES: CC(=O)N1CCC(O)(c2ccc3nc(C)nc(N[C@H](C)c4cccc(C(F)(F)F)c4)c3c2)CC1] | M + H = 473; t_ret = 1.16 | LCMSBAS1 | 15 |
| I-49 | 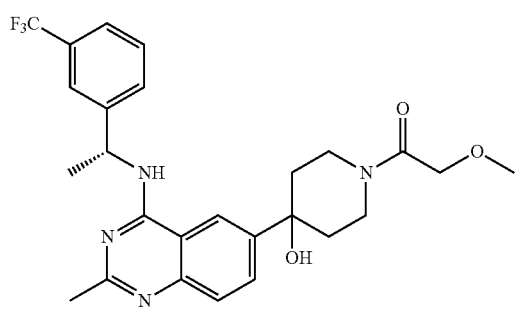 [SMILES: COCC(=O)N1CCC(O)(c2ccc3nc(C)nc(N[C@H](C)c4cccc(C(F)(F)F)c4)c3c2)CC1] | M + H = 503; t_ret = 1.17 | LCMSBAS1 | 9 |

TABLE 35-continued
| # | structure | [M + H]+ t_ret [min] | HPLC method | IC_50 (SOS1) [nM] |
|---|---|---|---|---|
| I-50 | 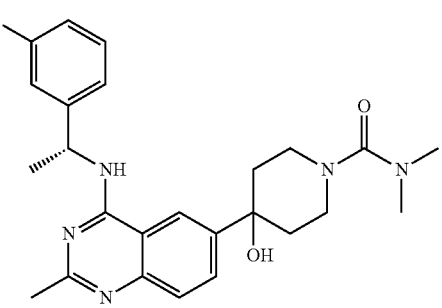 | M + H = 502; t_ret = 1.22 | LCMSBAS1 | 23 |
| I-51 | 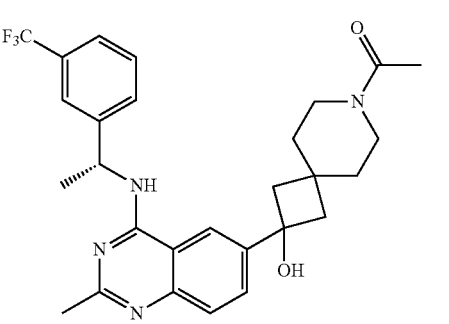 [SMILES: CC(=O)N1CCC2(CC1)CC(O)(c1ccc3nc(C)nc(N[C@H](C)c4cccc(C(F)(F)F)c4)c3c1)C2] | M + H = 513; t_ret = 1.20 | LCMSBAS1 | 23 |
| I-52 | 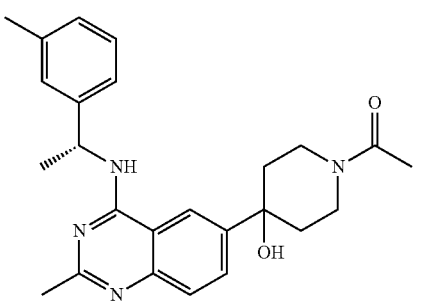 [SMILES: CC(=O)N1CCC(O)(c2ccc3nc(C)nc(N[C@H](C)c4cccc(C)c4)c3c2)CC1] | M + H = 419; t_ret = 1.09 | LCMSBAS1 | 14 |
| I-53 | 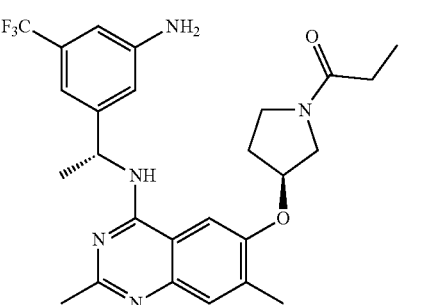 | M + H = 502; t_ret = 1.21 | LCMSBAS1 | 3 |
| I-54 | 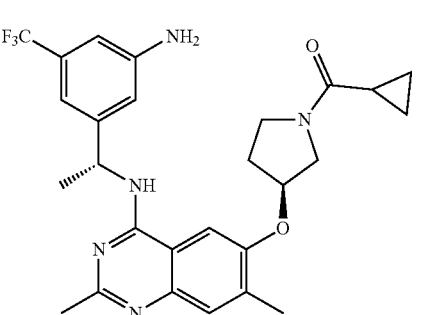 | M + H = 514; t_ret = 1.23 | LCMSBAS1 | 4 |

Experimental Procedure for the Synthesis of I-55 and I-56

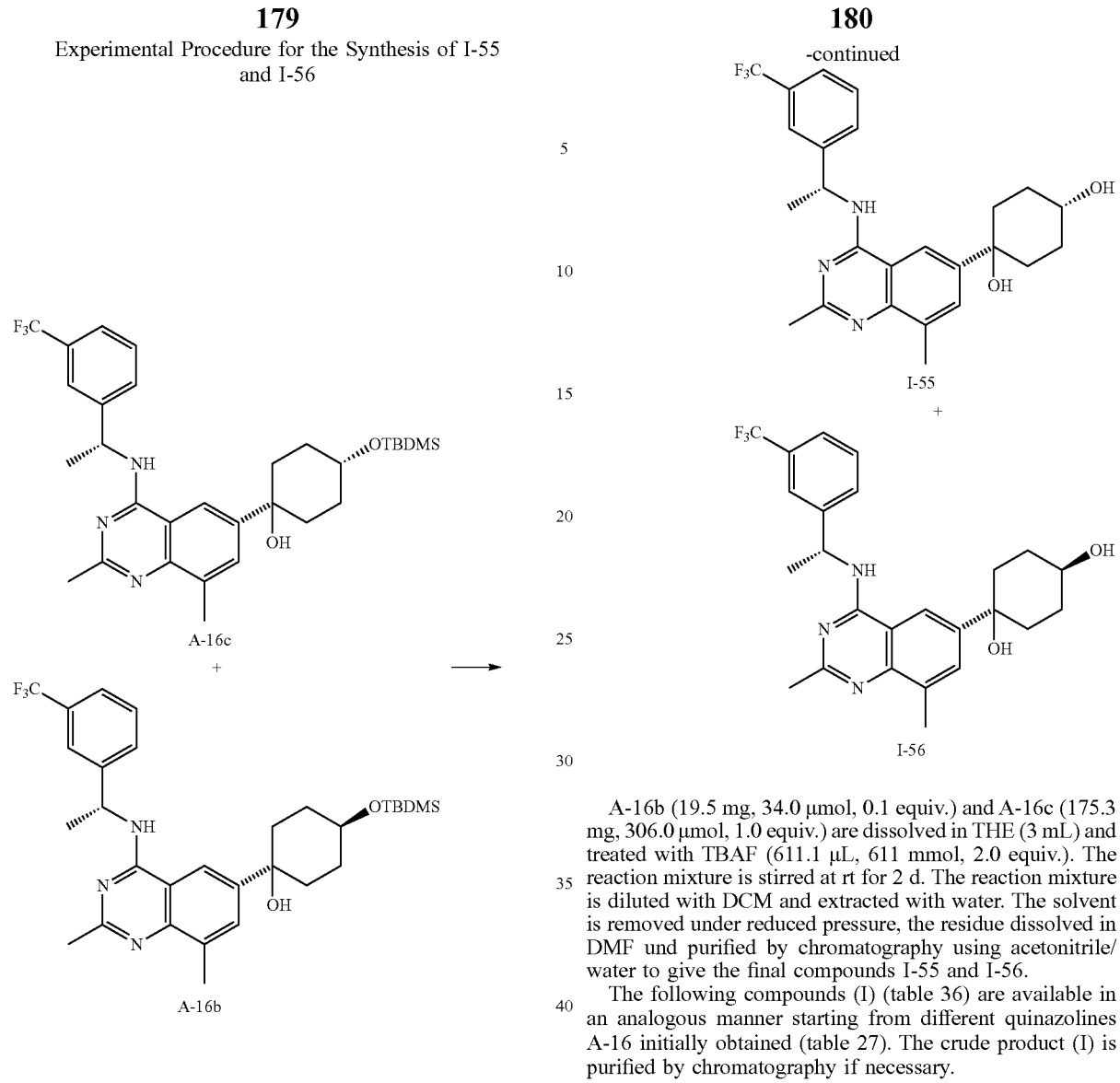

A-16b (19.5 mg, 34.0 μmol, 0.1 equiv.) and A-16c (175.3 mg, 306.0 μmol, 1.0 equiv.) are dissolved in THF (3 mL) and treated with TBAF (611.1 μL, 611 mmol, 2.0 equiv.). The reaction mixture is stirred at rt for 2 d. The reaction mixture is diluted with DCM and extracted with water. The solvent is removed under reduced pressure, the residue dissolved in DMF und purified by chromatography using acetonitrile/water to give the final compounds I-55 and I-56.

The following compounds (I) (table 36) are available in an analogous manner starting from different quinazolines A-16 initially obtained (table 27). The crude product (I) is purified by chromatography if necessary.

TABLE 36

| # | structure | [M + H]+ $t_{ret}$ [min] | HPLC method | IC$_{50}$ (SOS1) [nM] |
|---|---|---|---|---|
| I-55 | 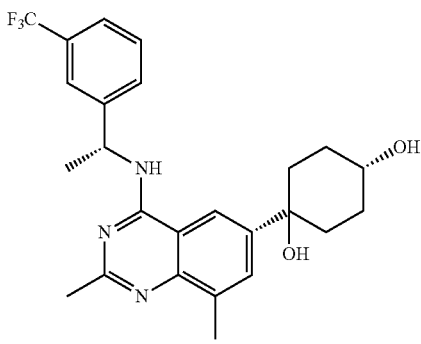 | M + H = 460; $t_{ret}$ = 1.27 | LCMSBAS1 | 20 |

TABLE 36-continued

| # | structure | [M + H]+ t_ret [min] | HPLC method | IC_50 (SOS1) [nM] |
|---|---|---|---|---|
| I-56 | 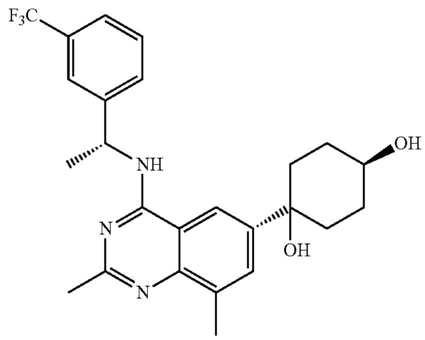 | n.a. | — | |
| I-57 | 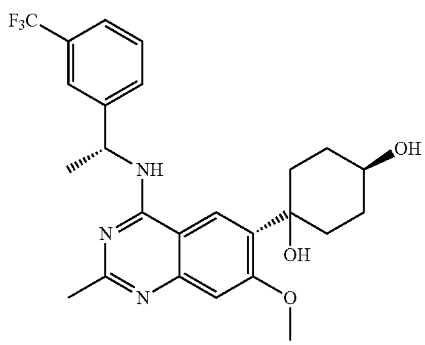 | M + H = 476; t_ret = 1.20 | LCMSBAS1 | 10 |
| I-58 | 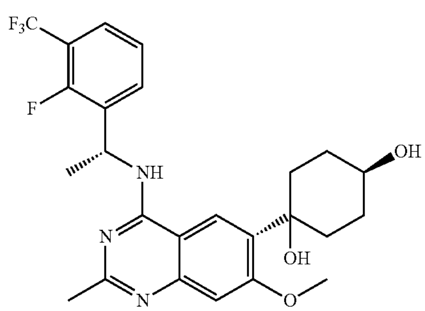 | M + H = 494; t_ret = 1.22 | LCMSBAS1 | 6 |
| I-59 | 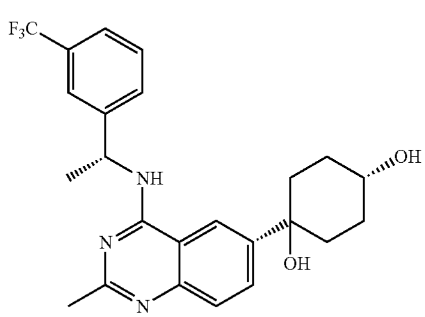 | M + H = 446; t_ret = 1.16 | LCMSBAS1 | 20 |

TABLE 36-continued

| # | structure | [M + H]+ t_ret [min] | HPLC method | IC_50 (SOS1) [nM] |
|---|---|---|---|---|
| I-60 | 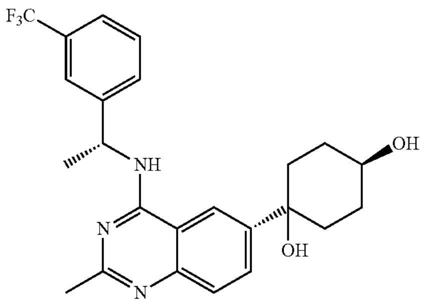 | M + H = 446; t_ret = 1.17 | LCMSBAS1 | 10 |
| I-61 | 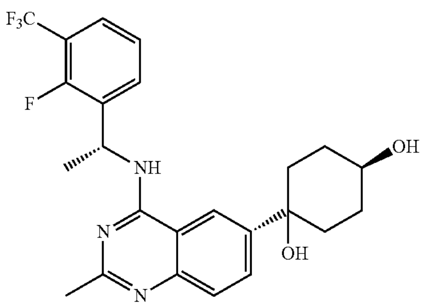 | M + H = 464; t_ret = 1.18 | LCMSBAS1 | 8 |
| I-62 | 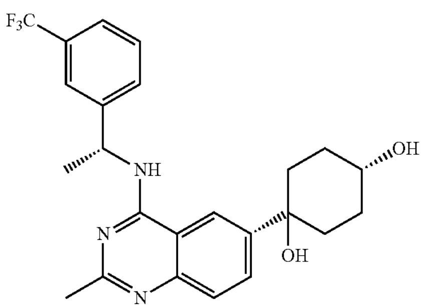 | M + H = 464; t_ret = 1.18 | LCMSBAS1 | 27 |
| I-63 | 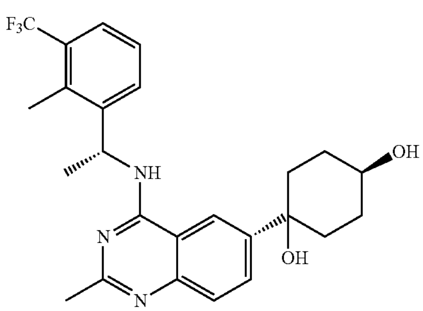 | M + H = 460; t_ret = 1.23 | LCMSBAS1 | 9 |
| I-64 | 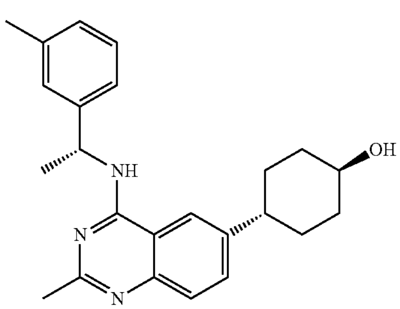 [SMILES: Cc1cccc([C@@H](C)Nc2nc(C)nc3ccc([C@H]4CC[C@H](O)CC4)cc23)c1] | M + H = 376; t_ret = 1.26 | LCMSBAS1 | 34* |

TABLE 36-continued

| # | structure | [M + H]⁺ t$_{ret}$ [min] | HPLC method | IC$_{50}$ (SOS1) [nM] |
|---|---|---|---|---|
| I-65 | 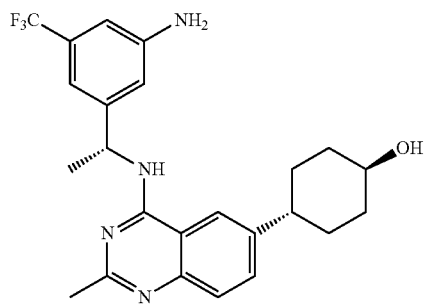 [SMILES: Cc1nc(N[C@H](C)c2cc(N)cc(C(F)(F)F)c2)c2cc([C@H]3CC[C@H](O)CC3)ccc2n1] | M + H = 445; t$_{ret}$ = 0.45 | AFEC | 8 |
| I-66 | 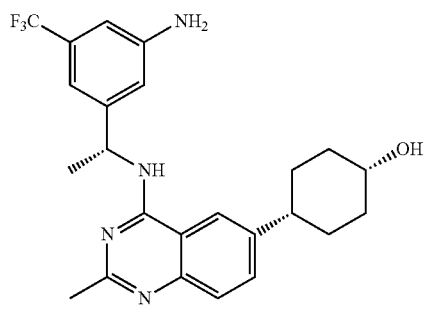 [SMILES: Cc1nc(N[C@H](C)c2cc(N)cc(C(F)(F)F)c2)c2cc([C@H]3CC[C@@H](O)CC3)ccc2n1] | M + H = 445; t$_{ret}$ = 0.47 | AFEC | 43 |

Experimental Procedure for the Synthesis of I-67

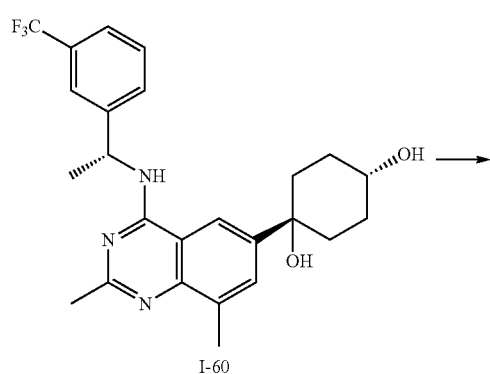

I-60

→

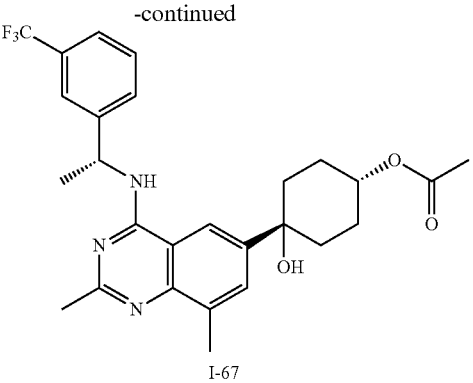

I-67

I-60 (10.0 mg, 22.0 µmol, 1.0 equiv.) is dissolved in THF (0.5 mL) and treated with DIPEA (14.0 µL, 49.0 µmol, 4.4 equiv.) and acetyl acetate (4.0 µL, 21.0 µmol, 1.8 equiv.). The reaction mixture is stirred at rt for 2 weeks. During this period additional acetyl acetate (4×4 µL) and DIPEA (4×17 µL) are added. The solvent is removed under reduced pressure and the crude product purified by chromatography using acetonitrile/water giving the desired product I-67.

TABLE 37
| # | structure | [M + H]+ t_ret [min] | HPLC method | IC$_{50}$ (SOS1) [nM] |
|---|---|---|---|---|
| I-67 | 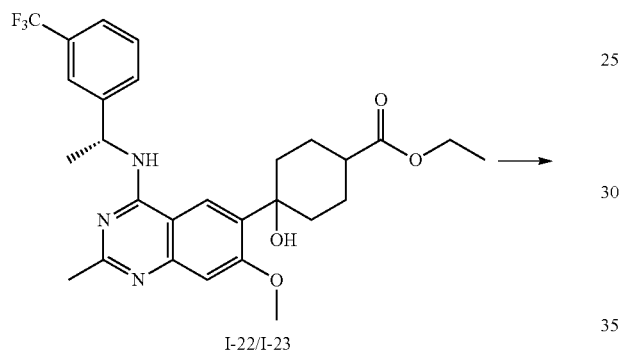 | M + H = 488; t_ret = 1.35 | LCMSBAS1 | 26 |
Experimental Procedure for the Synthesis of I-68 and I-69
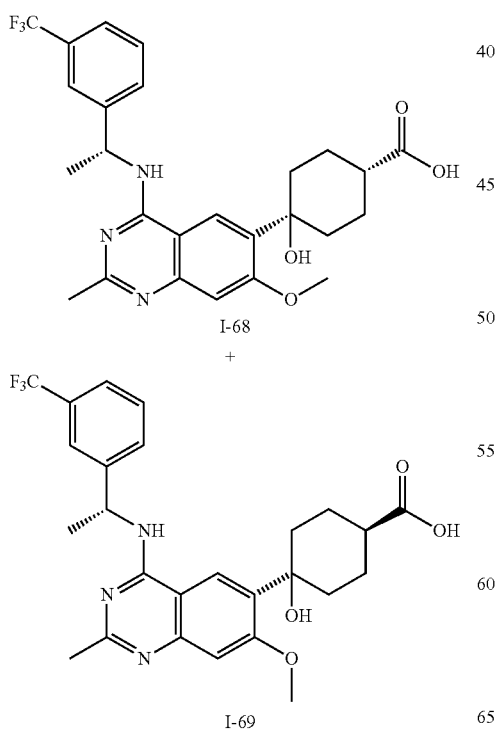

Mixture of I-22/I-23 (95.2 mg, 0.2 mmol, 1.0 equiv.) is dissolved in THF (2 mL) and treated with LiOH (100.0 mg, 4.3 mmol, 24.0 equiv.). The reaction mixture is stirred at rt for 12 h. The reaction is neutralized with HCl (1M), diluted with DCM and extracted with water. The organic layer is concentrated in vacuo giving the desired products I-68 and I-69. The following compounds (I) (table 38) are available in an analogous manner starting from different quinazolines (I) initially obtained (table 32). The crude product (I) is purified by chromatography if necessary.

TABLE 38

| # | structure | [M + H]$^+$ $t_{ret}$ [min] | HPLC method | IC$_{50}$ (SOS1) [nM] |
|---|---|---|---|---|
| I-68 | 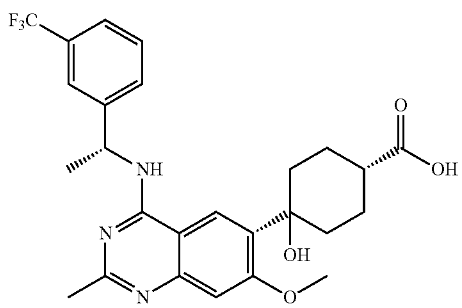 | M + H = 504; $t_{ret}$ = 0.94 | LCMSBAS1 | |
| I-69 | 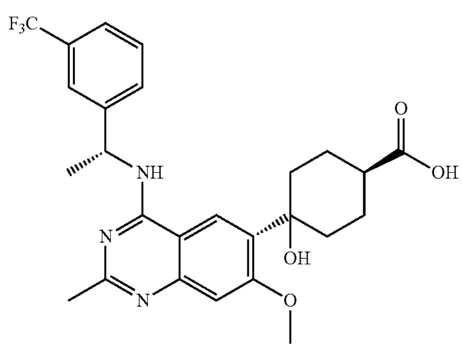 | M + H = 504; $t_{ret}$ = 0.98 | LCMSBAS1 | |
| I-70 | 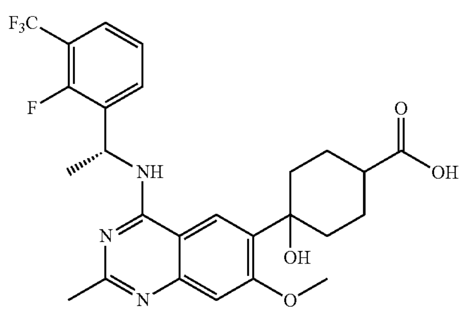 [SMILES: COc1cc2nc(C)nc(N[C@H](C)c3cccc(C(F)(F)F)c3F)c2cc1C1(O)CCC(C(=O)O)CC1] | M + H = 522; $t_{ret1}$ = 0.49 $t_{ret2}$ = 0.51 | BFEC | |
| I-71 | 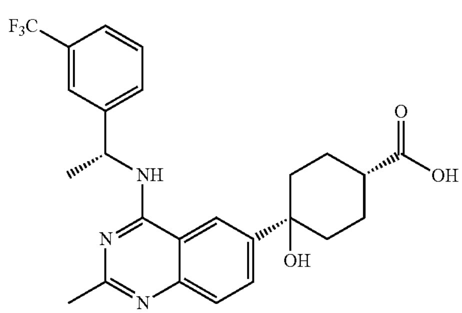 [SMILES: Cc1nc(N[C@H](C)c2cccc(C(F)(F)F)c2)c2cc([C@]3(O)CC[C@H](C(=O)O)CC3)ccc2n1] | M + H = 474; $t_{ret}$ = 0.47 | BFEC | |

TABLE 38-continued

| # | structure | [M + H]+ $t_{ret}$ [min] | HPLC method | IC$_{50}$ (SOS1) [nM] |
|---|---|---|---|---|
| I-72 | 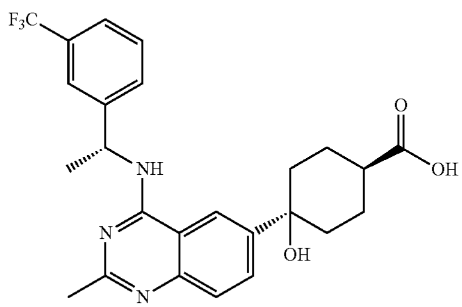 [SMILES: Cc1nc(N[C@H](C)c2cccc(C(F)(F)F)c2)c2cc([C@]3(O)CC[C@@H](C(=O)O)CC3)ccc2n1] | M + H = 474; $t_{ret}$ = 0.51 | BFEC | |

Experimental Procedure for the Synthesis of I-73

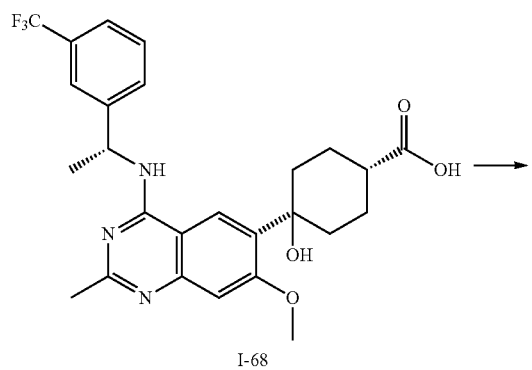

I-68 (20.0 mg, 40.0 μmol, 1.0 equiv.) is dissolved in DMF (1 mL), DIPEA (24.2 μL, 139.0 μmol, 3.5 equiv.) and HATU (18.1 mg, 48.0 μmol, 1.2 equiv.) are added and the mixture stirred for 10 min at rt. Then (2R)-1-(methylamino)propan-2-ol hydrochloride (7.8 mg, 60.0 μmol, 1.5 equiv.) is added and the reaction mixture stirred for 1 h at rt. The crude product is purified by chromatography using a mixture of acetonitrile/water to give the desired product I-73.

The following compounds (I) (table 39) are available in an analogous manner starting from different quinazolines (I) initially obtained (table 38). The crude product (I) is purified by chromatography if necessary.

TABLE 39

| # | structure | [M + H]+ $t_{ret}$ [min] | HPLC method | IC$_{50}$ (SOS1) [nM] |
|---|---|---|---|---|
| I-73 | 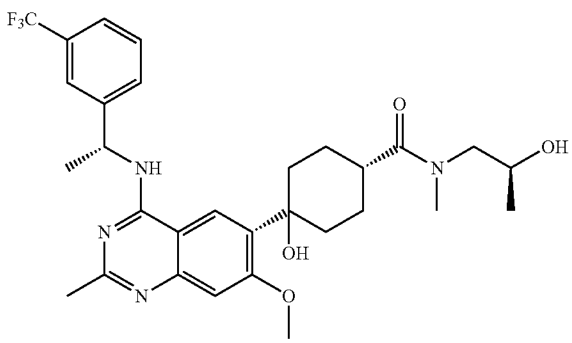 | M + H = 575; $t_{ret}$ = 1.20 | LCMSBAS1 | 41 |

TABLE 39-continued

| # | structure | [M + H]+ t_ret [min] | HPLC method | IC50 (SOS1) [nM] |
|---|---|---|---|---|
| I-74 | 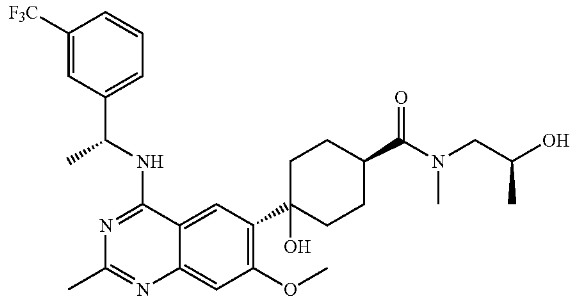 | n.a. | — | |
| I-75 | 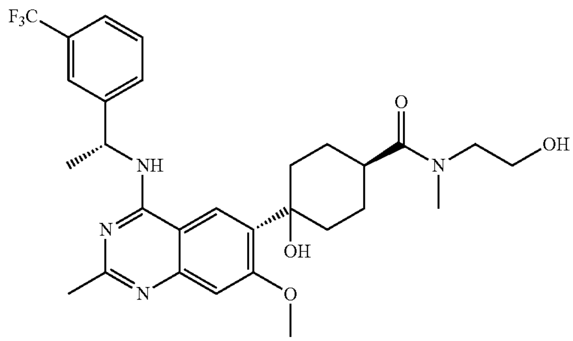 | M + H = 561; t_ret = 1.19 | LCMSBAS1 | 7 |
| I-76 | 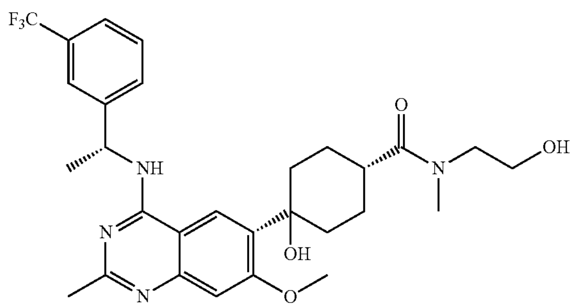 | n.a. | — | |
| I-77 | 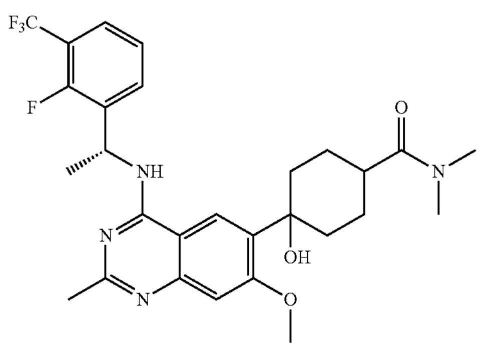 [SMILES: COc1cc2nc(C)nc(N[C@H](C)c3cccc(C(F)(F)F)c3F)c2cc1C1(O)CCC(C(=O)N(C)C)CC1] | M + H = 549; t_ret = 1.28 | LCMSBAS1 | 5 |
| I-78 | 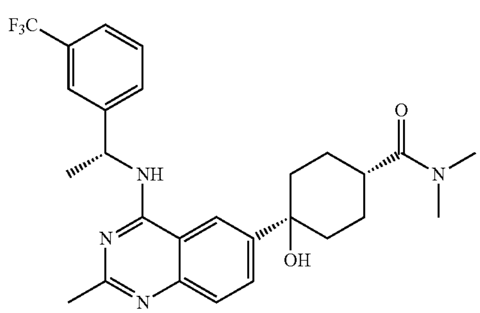 [SMILES: Cc1nc(N[C@H](C)c2cccc(C(F)(F)F)c2)c2cc([C@]3(O)CC[C@H](C(=O)N(C)C)CC3)ccc2n1] | M + H = 501; t_ret = 1.21 | LCMSBAS1 | 27 |

TABLE 39-continued

| # | structure | [M + H]+ t_ret [min] | HPLC method | IC50 (SOS1) [nM] |
|---|---|---|---|---|
| I-79 | 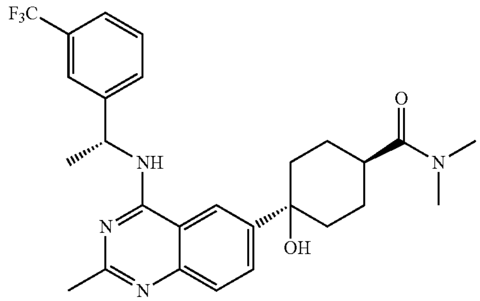 [SMILES: Cc1nc(N[C@H](C)c2cccc(C(F)(F)F)c2)c2cc([C@]3(O)CC[C@@H](C(=O)N(C)C)CC3)ccc2n1] | n.a. | — | |

Experimental Procedure for the Synthesis of I-80

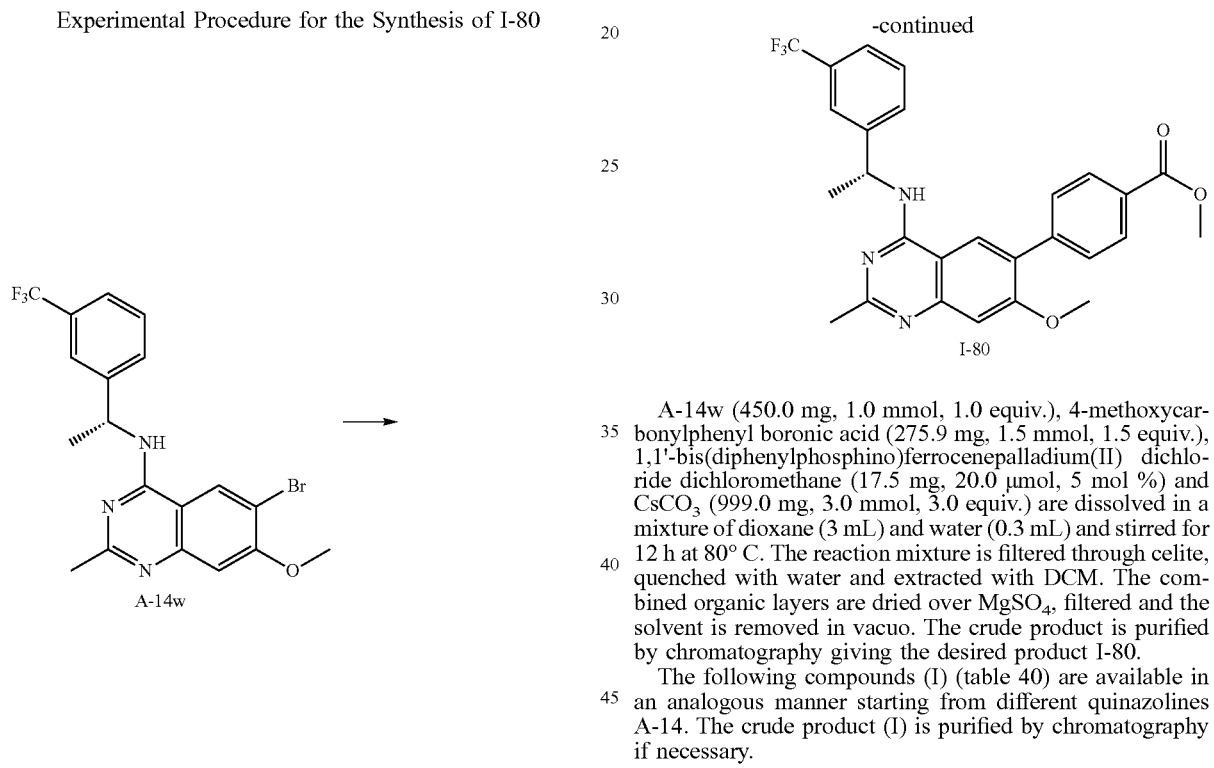

A-14w (450.0 mg, 1.0 mmol, 1.0 equiv.), 4-methoxycarbonylphenyl boronic acid (275.9 mg, 1.5 mmol, 1.5 equiv.), 1,1'-bis(diphenylphosphino)ferrocenepalladium(II) dichloride dichloromethane (17.5 mg, 20.0 µmol, 5 mol %) and CsCO₃ (999.0 mg, 3.0 mmol, 3.0 equiv.) are dissolved in a mixture of dioxane (3 mL) and water (0.3 mL) and stirred for 12 h at 80° C. The reaction mixture is filtered through celite, quenched with water and extracted with DCM. The combined organic layers are dried over MgSO₄, filtered and the solvent is removed in vacuo. The crude product is purified by chromatography giving the desired product I-80.

The following compounds (I) (table 40) are available in an analogous manner starting from different quinazolines A-14. The crude product (I) is purified by chromatography if necessary.

TABLE 40

| # | structure | [M + H]+ t_ret [min] | HPLC method | IC50 (SOS1) [nM] |
|---|---|---|---|---|
| I-80 | 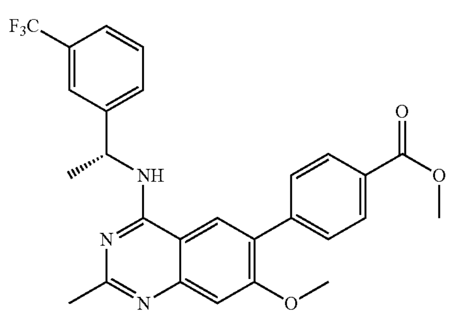 [SMILES: COC(=O)c1ccc(-c2cc3c(N[C@H](C)c4cccc(C(F)(F)F)c4)nc(C)nc3cc2OC)cc1] | M + H = 496; t_ret = 0.88 | BFEC | |

TABLE 40-continued

| # | structure | [M + H]⁺ t_ret [min] | HPLC method | IC₅₀ (SOS1) [nM] |
|---|---|---|---|---|
| I-81 | 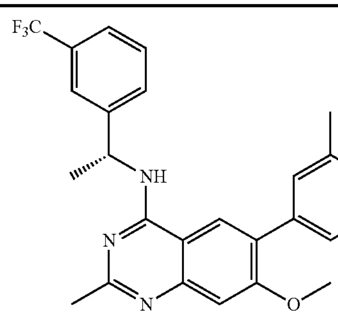 | M + H = 511; t_ret = 0.91 | BFEC | |
| I-82 | 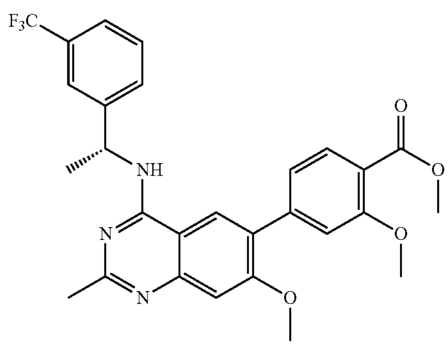 [SMILES: COC(=O)c1ccc(-c2cc3c(N[C@H](C)c4cccc(C(F)(F)F)c4)nc(C)nc3cc2OC)cc1OC] | M + H = 527; t_ret = 0.84 | BFEC | |
| I-83 | 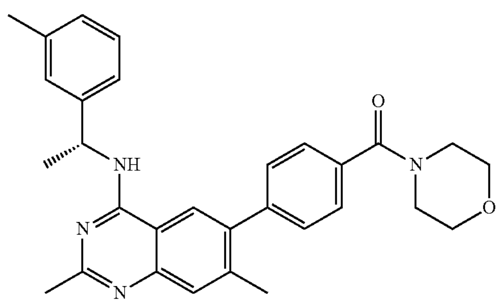 [SMILES: Cc1cccc([C@@H](C)Nc2nc(C)nc3cc(C)c(-c4ccc(C(=O)N5CCOCC5)cc4)cc23)c1] | M + H = 481; t_ret = 1.34 | LCMSBAS1 | 44 |
| I-84 | 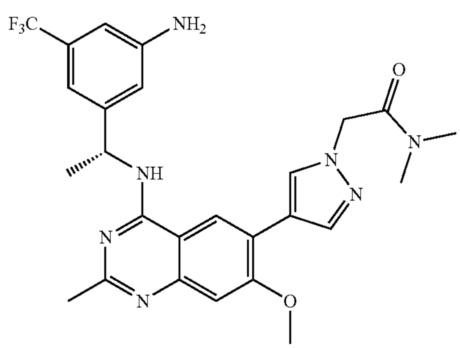 [SMILES: COc1cc2nc(C)nc(N[C@H](C)c3cc(N)cc(C(F)(F)F)c3)c2cc1-c1cnn(CC(=O)N(C)C)c1] | M + H = 528; t_ret = 1.12 | LCMSBAS1 | 6 |
| I-85 | 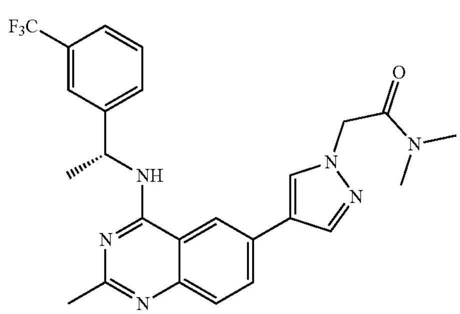 [SMILES: Cc1nc(N[C@H](C)c2cccc(C(F)(F)F)c2)c2cc(-c3cnn(CC(=O)N(C)C)c3)ccc2n1] | M + H = 483; t_ret = 1.25 | LCMSBAS1 | 41* |

TABLE 40-continued

| # | structure | [M + H]+ $t_{ret}$ [min] | HPLC method | IC$_{50}$ (SOS1) [nM] |
|---|---|---|---|---|
| I-86 | 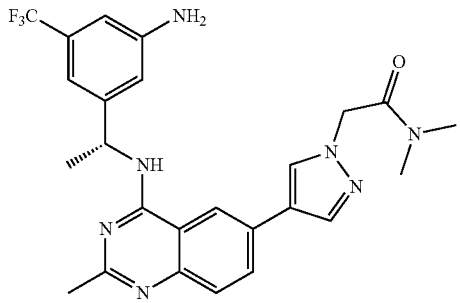 [SMILES: Cc1nc(N[C@H](C)c2cc(N)cc(C(F)(F)F)c2)c2cc(-c3cnn(CC(=O)N(C)C)c3)ccc2n1] | M + H = 498; $t_{ret}$ = 1.12 | LCMSBAS1 | 8 |
| I-87 | 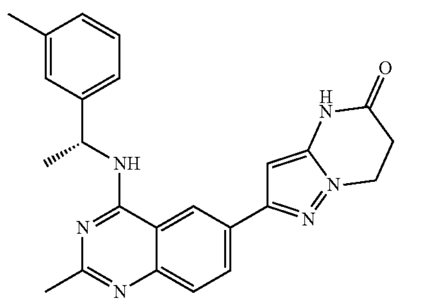 | M + H = 413; $t_{ret}$ = 1.16 | LCMSBAS1 | 18* |
| I-88 | 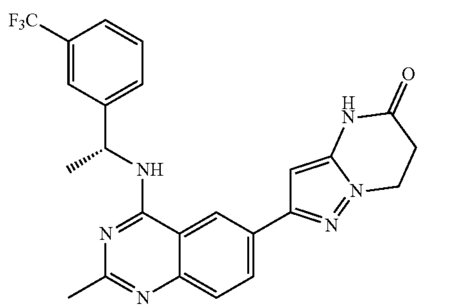 | M + H = 467; $t_{ret}$ = 1.19 | LCMSBAS1 | 30* |
| I-89 | 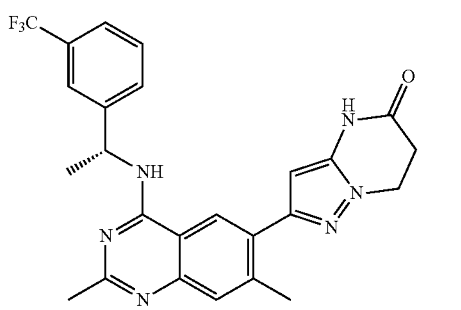 | M + H = 481; $t_{ret}$ = 1.20 | LCMSBAS1 | 34* |
| I-90 | 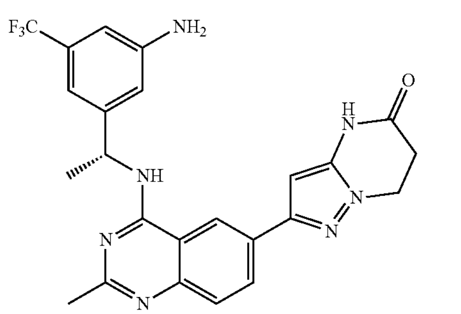 | M + H = 482; $t_{ret}$ = 1.11 | LCMSBAS1 | 7 |

TABLE 40-continued
| # | structure | [M + H]+ t_ret [min] | HPLC method | IC$_{50}$ (SOS1) [nM] |
|---|---|---|---|---|
| I-91 | 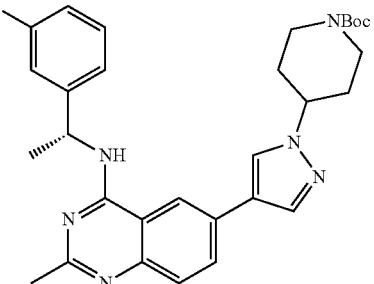 | M + H = 581; t_ret = 0.884 | BFEC | |
| I-92 | 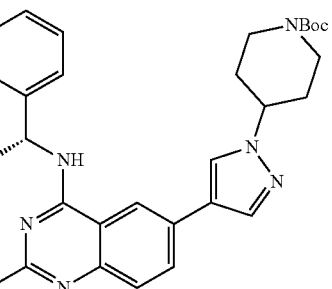 | M + H = 527; t_ret = 1.52 | LCMSBAS1 | |
| I-93 | 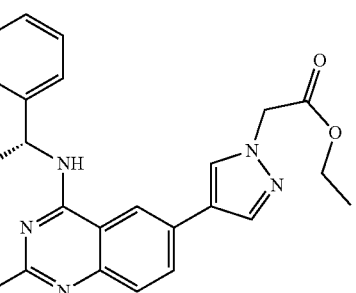 | M + H = 430.2; t_ret = 0.742 | BFEC | |
| I-94 | 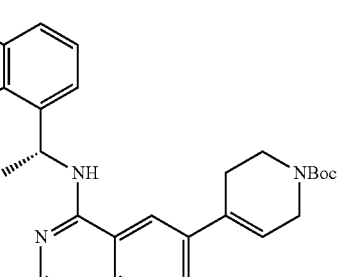 | M + H = 479; t_ret = 0.92 | BFEC | |
| I-95 | 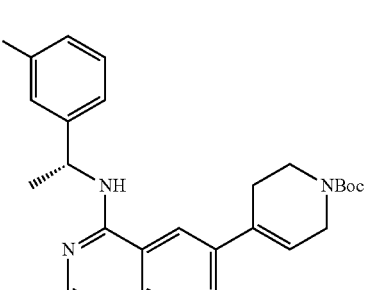 | M + H = 513; t_ret = 1.57 | LCMSBAS1 | |

TABLE 40-continued

| # | structure | [M + H]+ $t_{ret}$ [min] | HPLC method | IC$_{50}$ (SOS1) [nM] |
|---|---|---|---|---|
| I-96 | 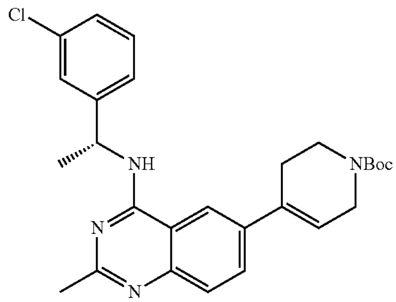 [SMILES: Cc1nc(N[C@H](C)c2cccc(Cl)c2)c2cc(C3=CCN(C(=O)OC(C)(C)C)CC3)ccc2n1] | M + H = 379; $t_{ret}$ = 1.22 | LCMSBAS1 | |
| I-97 | 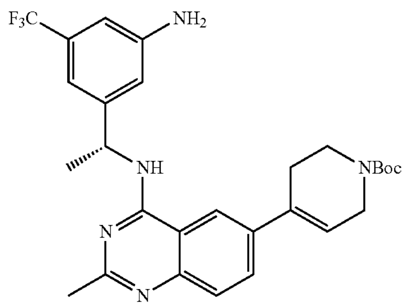 | M + H = 528; $t_{ret}$ = 1.49 | LCMSBAS1 | |
| I-98 | 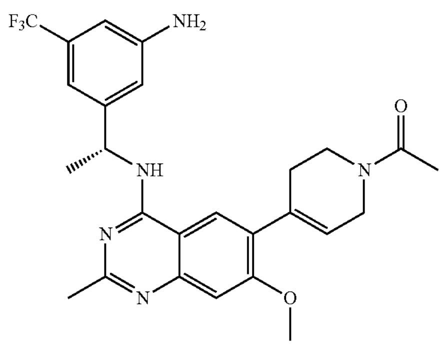 [SMILES: COc1cc2nc(C)nc(N[C@H](C)c3cc(N)cc(C(F)(F)F)c3)c2cc1C1=CCN(C(C)=O)CC1] | M + H = 500; $t_{ret}$ = 1.16 | LCMSBAS1 | |
| I-99 | 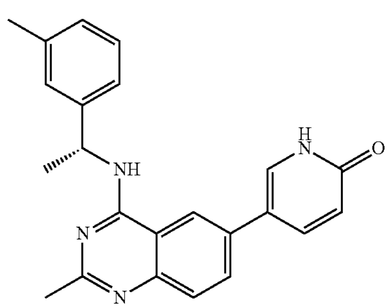 [SMILES: Cc1cccc([C@@H](C)Nc2nc(C)nc3ccc(-c4ccc(=O)[nH]c4)cc23)c1] | M + H = 371; $t_{ret}$ = 1.13 | LCMSBAS1 | 29* |
| I-100 | 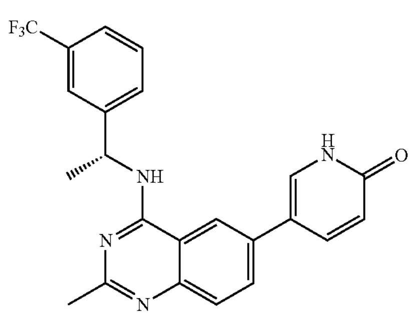 [SMILES: Cc1nc(N[C@H](C)c2cccc(C(F)(F)F)c2)c2cc(-c3ccc(=O)[nH]c3)ccc2n1] | M + H = 425; $t_{ret}$ = 1.20 | LCMSBAS1 | 48* |

TABLE 40-continued

| # | structure | [M + H]⁺ t_ret [min] | HPLC method | IC₅₀ (SOS1) [nM] |
|---|---|---|---|---|
| I-101 | 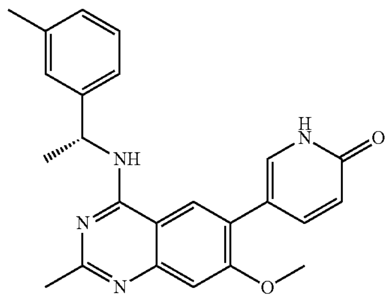 [SMILES: COc1cc2nc(C)nc(N[C@H](C)c3cccc(C)c3)c2cc1-c1ccc(=O)[nH]c1] | M + H = 401; t_ret = 1.13 | LCMSBAS1 | 28* |
| I-102 | 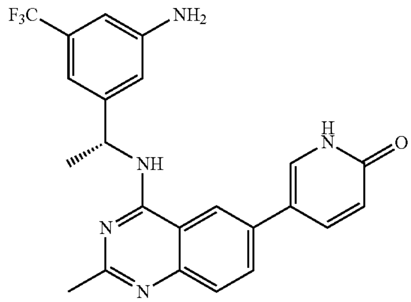 | M + H = 440; t_ret = 1.08 | LCMSBAS1 | 9 |
| I-103 | 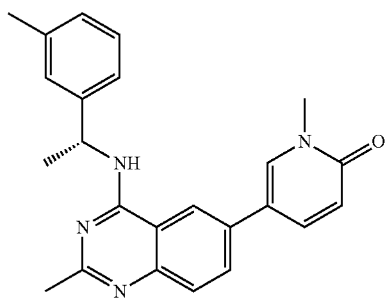 [SMILES: Cc1cccc([C@@H](C)Nc2nc(C)nc3ccc(-c4ccc(=O)n(C)c4)cc23)c1] | M + H = 385; t_ret = 1.18 | LCMSBAS1 | 46* |
| I-104 | 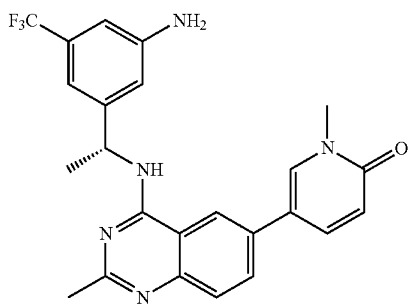 [SMILES: Cc1nc(N[C@H](C)c2cc(N)cc(C(F)(F)F)c2)c2cc(-c3ccc(=O)n(C)c3)ccc2n1] | M + H = 454; t_ret = 1.12 | LCMSBAS1 | 6* |
| I-105 | 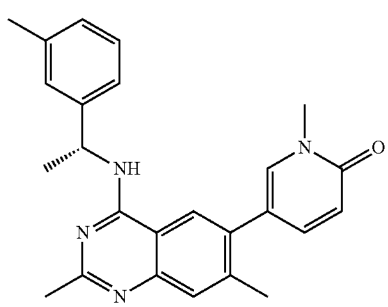 [SMILES: Cc1cccc([C@@H](C)Nc2nc(C)nc3cc(C)c(-c4ccc(=O)n(C)c4)cc23)c1] | M + H = 399; t_ret = 1.19 | LCMSBAS1 | 36* |

TABLE 40-continued

| # | structure | [M + H]+ $t_{ret}$ [min] | HPLC method | IC$_{50}$ (SOS1) [nM] |
|---|---|---|---|---|
| I-106 | 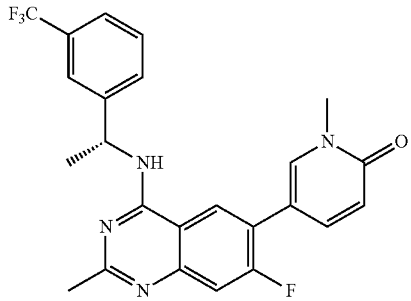 | M + H = 472; $t_{ret}$ = 1.17 | LCMSBAS1 | 18* |
| I-107 | 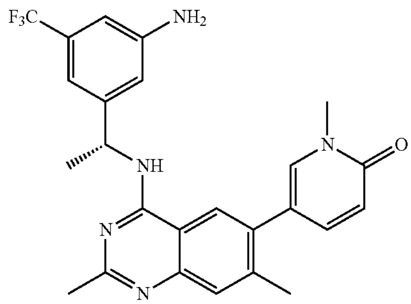 [SMILES: Cc1nc(N[C@H](C)c2cc(N)cc(C(F)(F)F)c2)c2cc(-c3ccc(=O)n(C)c3)c(C)cc2n1] | M + H = 468; $t_{ret}$ = 1.13 | LCMSBAS1 | 4* |
| I-108 | 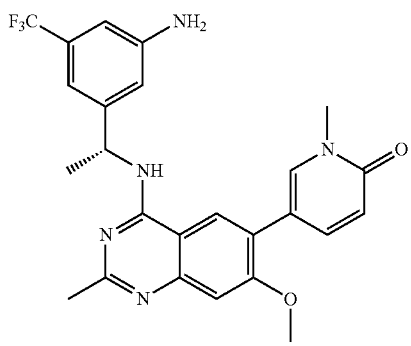 [SMILES: COc1cc2nc(C)nc(N[C@H](C)c3cc(N)cc(C(F)(F)F)c3)c2cc1-c1ccc(=O)n(C)c1] | M + H = 484; $t_{ret}$ = 1.12 | LCMSBAS1 | 8 |
| I-109 | 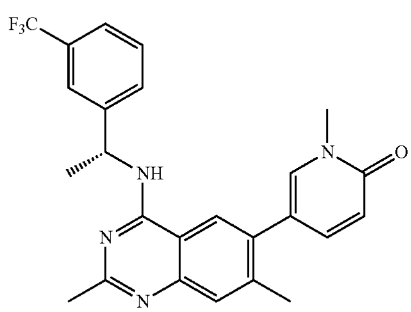 [SMILES: Cc1nc(N[C@H](C)c2cccc(C(F)(F)F)c2)c2cc(-c3ccc(=O)n(C)c3)c(C)cc2n1] | M + H = 453; $t_{ret}$ = 1.25 | LCMSBAS1 | 25 |
| I-110 | 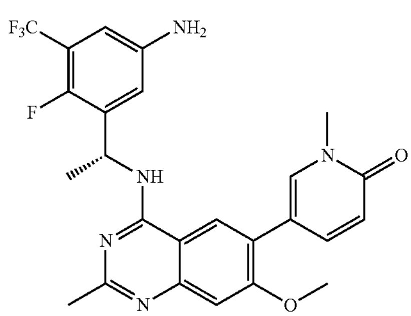 [SMILES: COc1cc2nc(C)nc(N[C@H](C)c3cc(N)cc(C(F)(F)F)c3F)c2cc1-c1ccc(=O)n(C)c1] | M + H = 502; $t_{ret}$ = 1.14 | LCMSBAS1 | 8 |

TABLE 40-continued
| # | structure | [M + H]+ $t_{ret}$ [min] | HPLC method | IC$_{50}$ (SOS1) [nM] |
|---|---|---|---|---|
| I-111 | 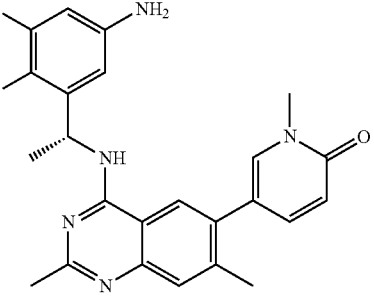 | M + H = 486; $t_{ret}$ = 1.15 | LCMSBAS1 | |
| I-112 | 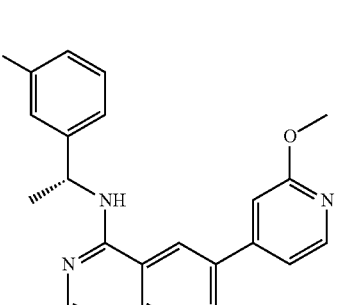 | M + H = 439; $t_{ret}$ = 1.51 | LCMSBAS1 | |
| I-113 | 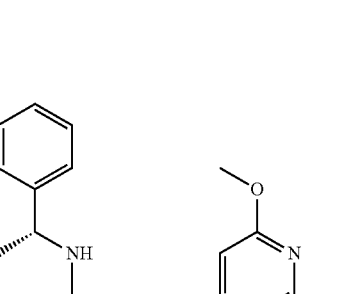 | M + H = 415; $t_{ret}$ = 1.45 | LCMSBAS1 | |
| I-114 | 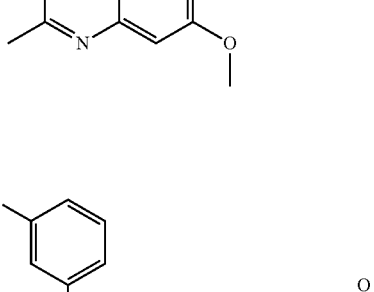 | M + H = 484; $t_{ret}$ = 0.915 | BFEC | |

TABLE 40-continued

| # | structure | [M + H]+ $t_{ret}$ [min] | HPLC method | IC$_{50}$ (SOS1) [nM] |
|---|---|---|---|---|
| I-115 | 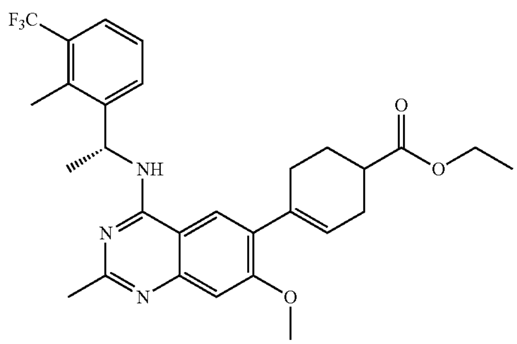 [SMILES: CCOC(=O)C1CC=C(c2cc3c(N[C@H](C)c4cccc(C(F)(F)F)c4C)nc(C)nc3cc2OC)CC1] | M + H = 528; $t_{ret}$ = 0.96 | BFEC | |
| I-116 | 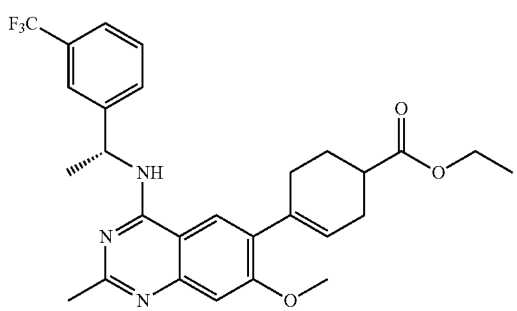 [SMILES: CCOC(=O)C1CC=C(c2cc3c(N[C@H](C)c4cccc(C(F)(F)F)c4)nc(C)nc3cc2OC)CC1] | M + H = 514; $t_{ret}$ = 0.917 | BFEC | |
| I-117 | 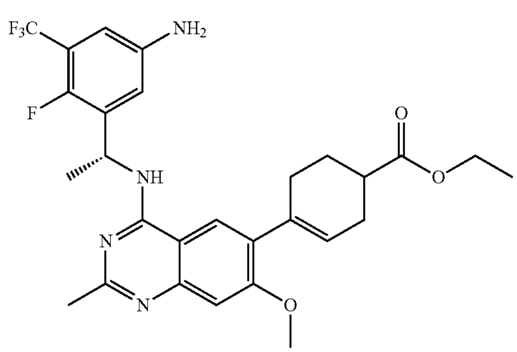 | M + H = 531; $t_{ret}$ = 0.69 | BFEC | |
| I-118 | 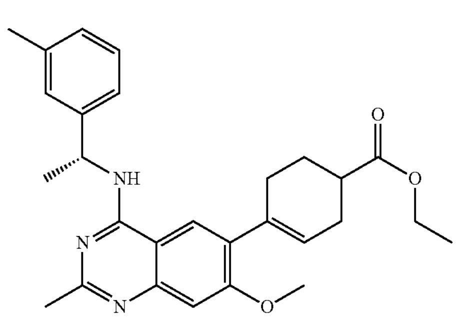 [SMILES: CCOC(=O)C1CC=C(c2cc3c(N[C@H](C)c4cccc(C)c4)nc(C)nc3cc2OC)CC1] | M + H = 460; $t_{ret}$ = 0.89 | BFEC | |

TABLE 40-continued
| # | structure | [M + H]+ $t_{ret}$ [min] | HPLC method | IC$_{50}$ (SOS1) [nM] |
|---|---|---|---|---|
| I-119 | 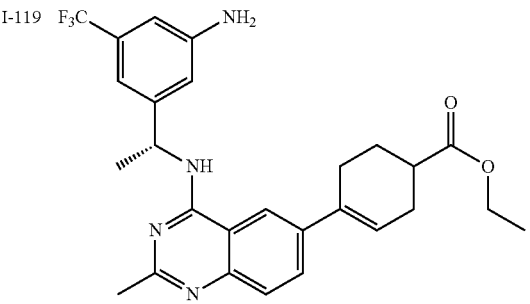 | M + H = 471; $t_{ret}$ = 0.49 | BFEC | |
| I-120 | 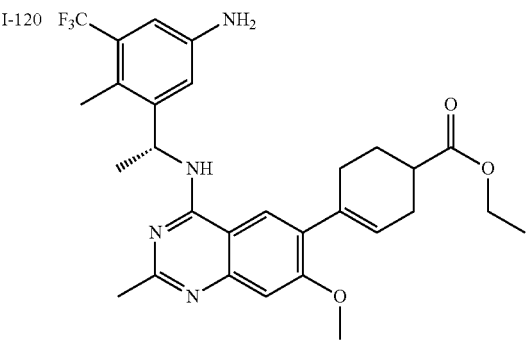 | M + H = 543; $t_{ret}$ = 0.86 | BFEC | |
| I-121 | 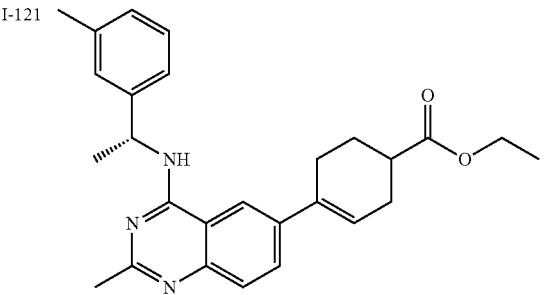 | M + H = 430; $t_{ret}$ = 0.89 | BFEC | |
| I-122 | 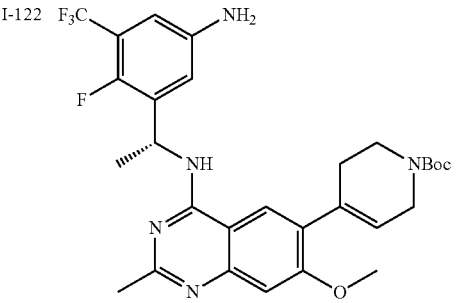 | M + H = 543; $t_{ret}$ = 0.86 | BFEC | |
| I-123 | 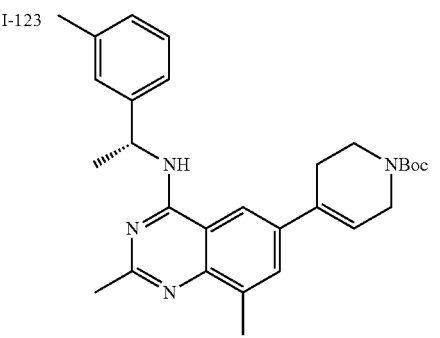 | M + H = 473; $t_{ret}$ = 1.02 | BFEC | |

TABLE 40-continued

| # | structure | [M + H]+ t_ret [min] | HPLC method | IC_50 (SOS1) [nM] |
|---|---|---|---|---|
| I-124 | 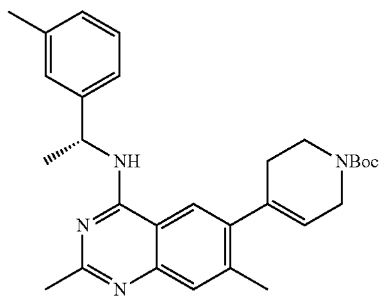 [SMILES: Cc1cccc([C@@H](C)Nc2nc(C)nc3cc(C)c(C4=CCN(C(=O)OC(C)(C)C)CC4)cc23)c1] | M + H = 473; t_ret = 0.94 | BFEC | |
| I-125 | 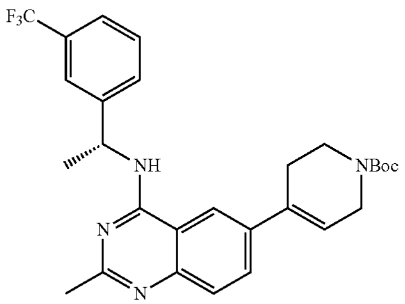 [SMILES: Cc1nc(N[C@H](C)c2cccc(C(F)(F)F)c2)c2cc(C3=CCN(C(=O)OC(C)(C)C)CC3)ccc2n1] | M + H = 513; t_ret = 1.57 | LCMSBAS1 | |
| I-126 | 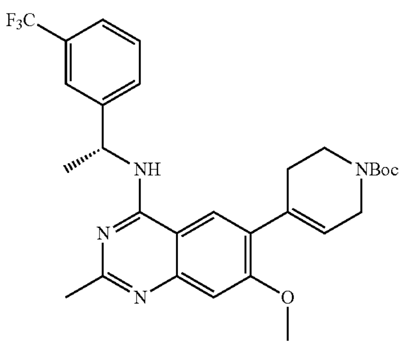 [SMILES: COc1cc2nc(C)nc(N[C@H](C)c3cccc(C(F)(F)F)c3)c2cc1C1=CCN(C(=O)OC(C)(C)C)CC1] | M + H = 543.2; t_ret = 0.937 | BFEC | |
| I-127 | 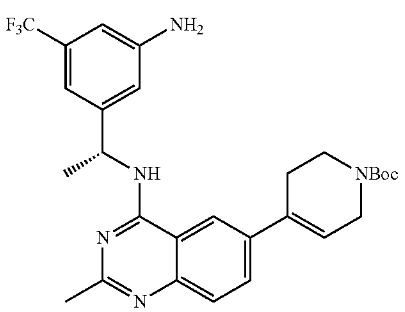 | M + H = 528; t_ret = 1.49 | LCMSBAS1 | |
| I-128 | 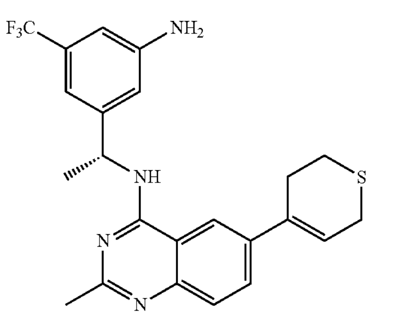 [SMILES: Cc1nc(N[C@H](C)c2cc(N)cc(C(F)(F)F)c2)c2cc(C3=CCSCC3)ccc2n1] | M + H = 445; t_ret = 0.77 | BFEC | |

TABLE 40-continued

| # | structure | [M + H]+ $t_{ret}$ [min] | HPLC method | IC$_{50}$ (SOS1) [nM] |
|---|-----------|--------------------------|-------------|------------------------|
| I-129 | 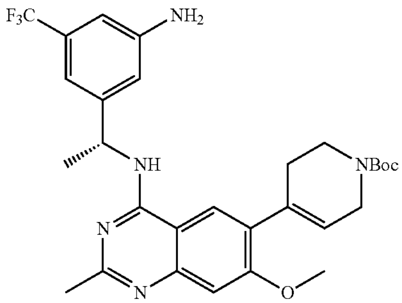 [SMILES: COc1cc2nc(C)nc(N[C@H](C)c3cc(N)cc(C(F)(F)F)c3)c2cc1C1=CCN(C(=O)OC(C)(C)C)CC1] | M + H = 558; $t_{ret}$ = 0.84 | BFEC | |
| I-130 | 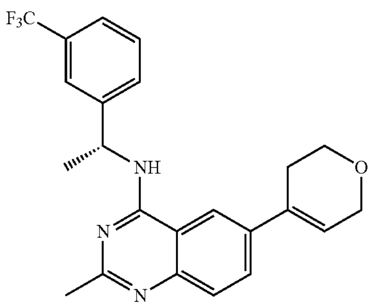 [SMILES: Cc1nc(N[C@H](C)c2cccc(C(F)(F)F)c2)c2cc(C3=CCOCC3)ccc2n1] | M + H = 414; $t_{ret}$ = 1.36 | LCMSBAS1 | |
| I-131 | 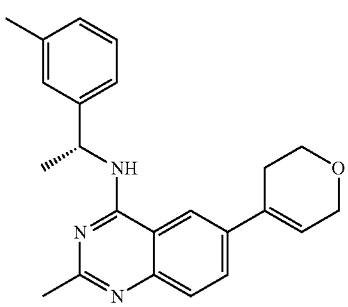 [SMILES: Cc1cccc([C@@H](C)Nc2nc(C)nc3ccc(C4=CCOCC4)cc23)c1] | M + H = 360; $t_{ret}$ = 0.74 | BFEC | |
| I-132 | 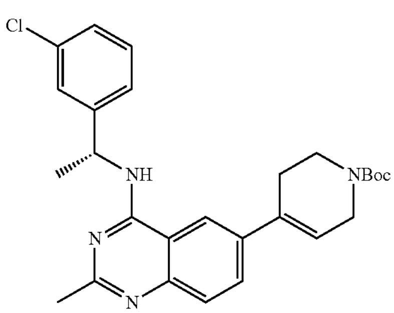 [SMILES: Cc1nc(N[C@H](C)c2cccc(Cl)c2)c2cc(C3=CCN(C(=O)OC(C)(C)C)CC3)ccc2n1] | M + H = 479; $t_{ret}$ = 0.92 | BFEC | |
| I-133 | 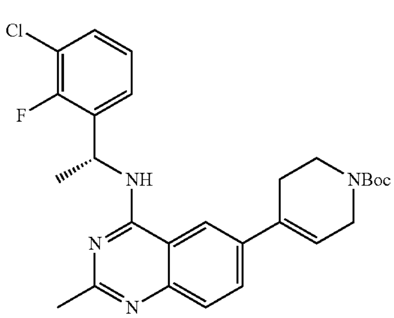 [SMILES: Cc1nc(N[C@H](C)c2cccc(Cl)c2F)c2cc(C3=CCN(C(=O)OC(C)(C)C)CC3)ccc2n1] | M + H = 497; $t_{ret}$ = 0.92 | BFEC | |

TABLE 40-continued
| # | structure | [M + H]+ t_ret [min] | HPLC method | IC$_{50}$ (SOS1) [nM] |
|---|---|---|---|---|
| I-134 | 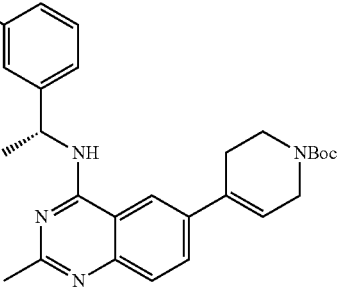 | M + H = 513; t_ret = 1.57 | LCMSBAS1 | |
| I-135 | 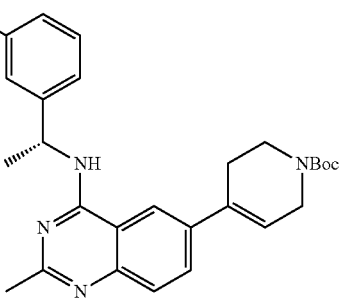 | M + H = 459; t_ret = 1.60 | LCMSBAS1 | |
| I-136 | 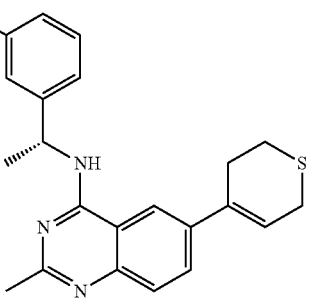 | M + H = 376; t_ret = 0.84 | BFEC | |
| I-137 | 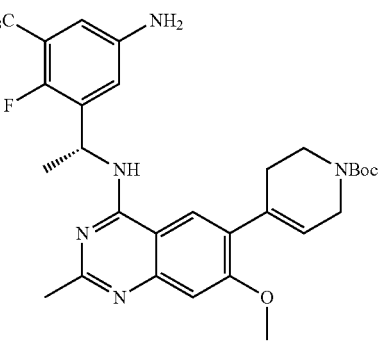 | M + H = 576; t_ret = 0.85 | BFEC | |
| I-138 | 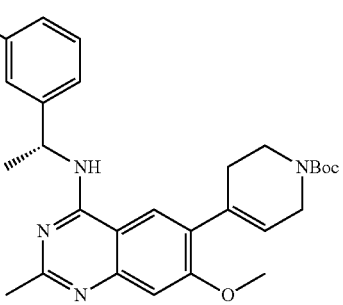 | M + H = 490; t_ret = 1.91 | BFEC | |

TABLE 40-continued

| # | structure | [M + H]$^+$ t$_{ret}$ [min] | HPLC method | IC$_{50}$ (SOS1) [nM] |
|---|---|---|---|---|
| I-139 | 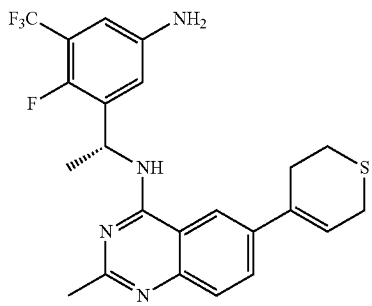 [SMILES: Cc1nc(N[C@H](C)c2cc(N)cc(C(F)(F)F)c2F)c2cc(C3=CCSCC3)ccc2n1] | M + H = 463; t$_{ret}$ = 0.78 | BFEC | |
| I-140 | 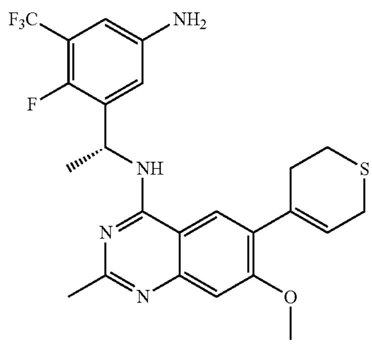 | M + H = 439; t$_{ret}$ = 0.81 | BFEC | |
| I-141 | 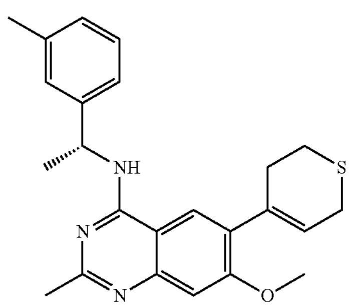 [SMILES: COc1cc2nc(C)nc(N[C@H](C)c3cccc(C)c3)c2cc1C1=CCSCC1] | M + H = 406; t$_{ret}$ = 0.84 | BFEC | |
| I-142 | 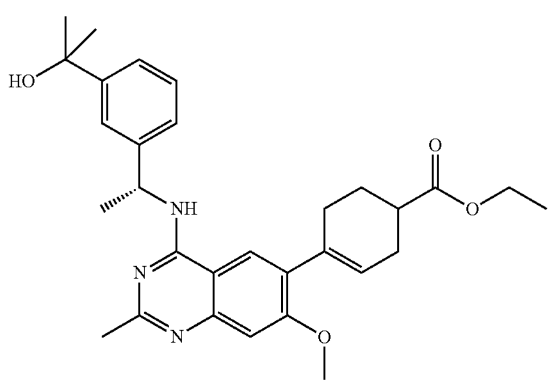 [SMILES: CCOC(=O)C1CC=C(c2cc3c(N[C@H](C)c4cccc(C(C)(C)O)c4)nc(C)nc3cc2OC)CC1] | M + H = 504; t$_{ret}$ = 0.767 | BFEC | |

TABLE 40-continued

| # | structure | [M + H]+ $t_{ret}$ [min] | HPLC method | IC$_{50}$ (SOS1) [nM] |
|---|---|---|---|---|
| I-143 | 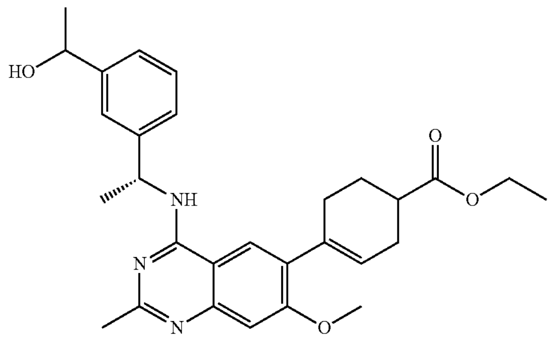 [SMILES: CCOC(=O)C1CC=C(c2cc3c(N[C@H](C)c4cccc(C(C)O)c4)nc(C)nc3cc2OC)CC1] | M + H = 490; $t_{ret}$ = 0.739 | BFEC | |
| I-144 | 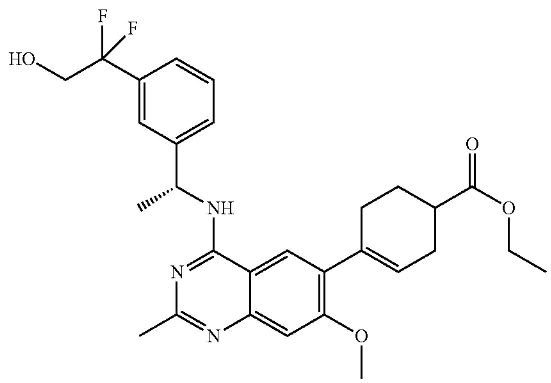 [SMILES: CCOC(=O)C1CC=C(c2cc3c(N[C@H](C)c4cccc(C(F)(F)CO)c4)nc(C)nc3cc2OC)CC1] | M + H = 526; $t_{ret}$ = 0.76 | BFEC | |
| I-145 | 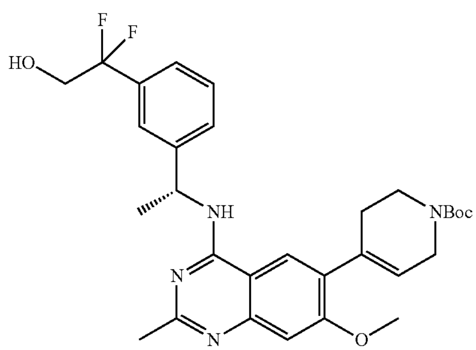 [SMILES: COc1cc2nc(C)nc(N[C@H](C)c3cccc(C(F)(F)CO)c3)c2cc1C1=CCN(C(=O)OC(C)(C)C)CC1] | M + H = 555; $t_{ret}$ = 0.78 | BFEC | |
| I-146 | 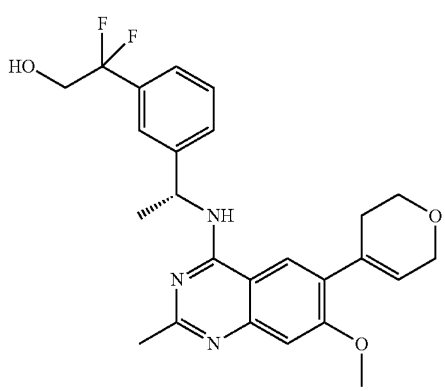 [SMILES: COc1cc2nc(C)nc(N[C@H](C)c3cccc(C(F)(F)CO)c3)c2cc1C1=CCOCC1] | M + H = 456; $t_{ret}$ = 1.15 | LCMSBAS1 | |

TABLE 40-continued

| # | structure | [M + H]+ t_ret [min] | HPLC method | IC50 (SOS1) [nM] |
|---|-----------|----------------------|-------------|------------------|
| I-147 | 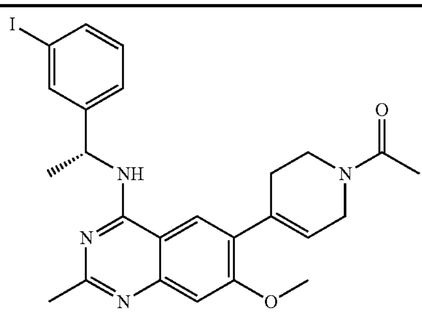 | M + H = 543.2; t_ret = 0.727 | BFEC | |

Experimental Procedure for the Synthesis of I-148

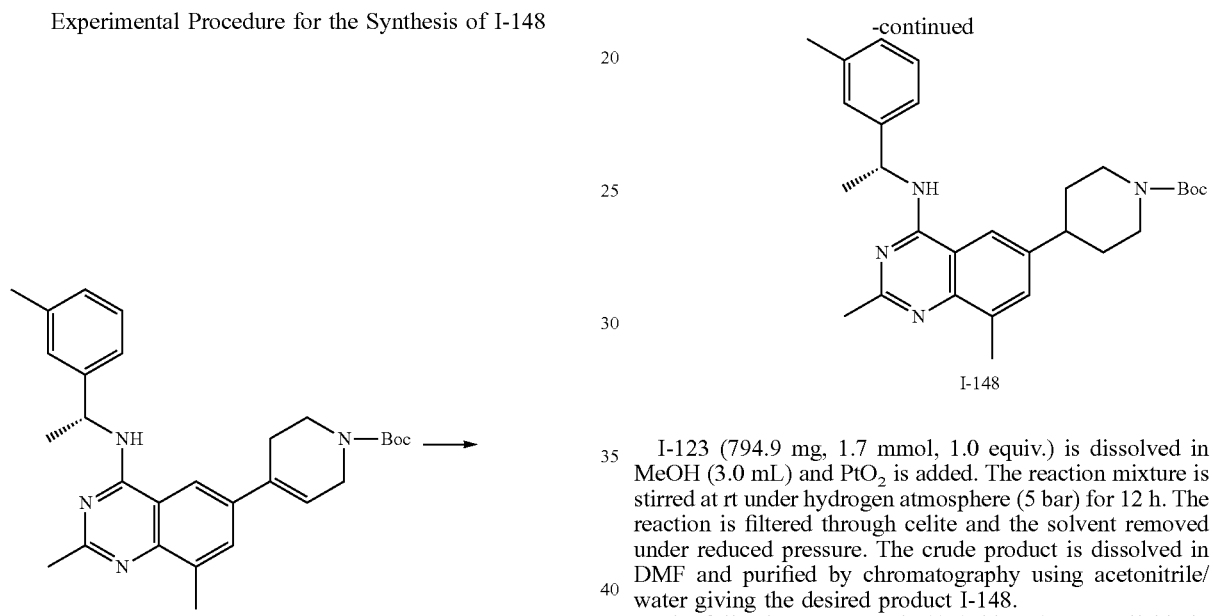

I-123 (794.9 mg, 1.7 mmol, 1.0 equiv.) is dissolved in MeOH (3.0 mL) and PtO$_2$ is added. The reaction mixture is stirred at rt under hydrogen atmosphere (5 bar) for 12 h. The reaction is filtered through celite and the solvent removed under reduced pressure. The crude product is dissolved in DMF and purified by chromatography using acetonitrile/water giving the desired product I-148.

The following compounds (I) (table 41) are available in an analogous manner starting from different quinazolines (I) initially obtained (table 40). The crude product (I) is purified by chromatography if necessary.

TABLE 41

| # | structure | [M + H]+ t_ret [min] | HPLC method | IC50 (SOS1) [nM] |
|---|-----------|----------------------|-------------|------------------|
| I-148 | 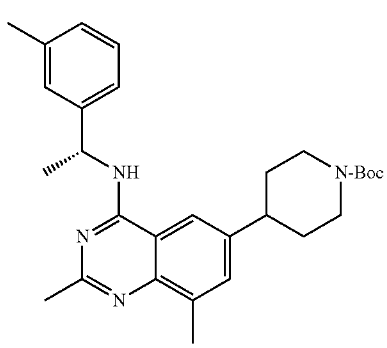 | M + H = 475; t_ret = 1.67 | LCMSBAS1 | |

TABLE 41-continued

| # | structure | [M + H]⁺ t_ret [min] | HPLC method | IC₅₀ (SOS1) [nM] |
|---|---|---|---|---|
| I-149 | 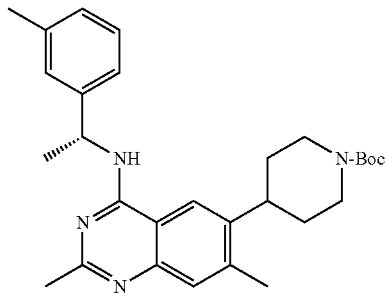 | M + H = 473; t_ret = 0.94 | BFEC | |
| I-150 | 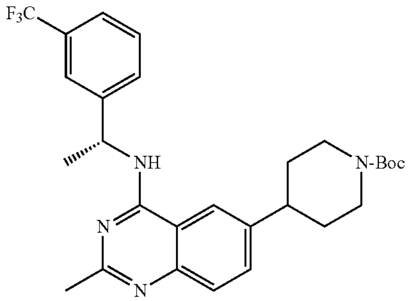 | M + H = 515; t_ret = 1.65 | LCMSBAS1 | |
| I-151 | 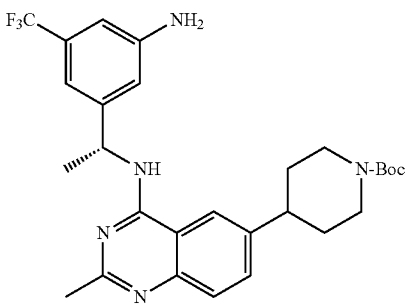 | M + H = 530; t_ret = 0.84 | BFEC | |
| I-152 | 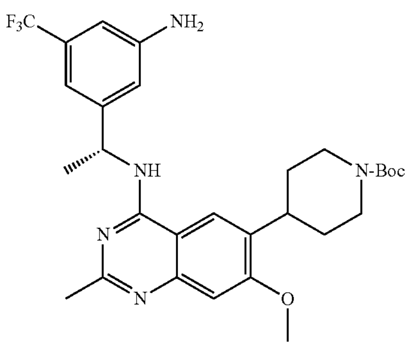 | M + H = 560; t_ret = 0.86 | BFEC | |
| I-153 | 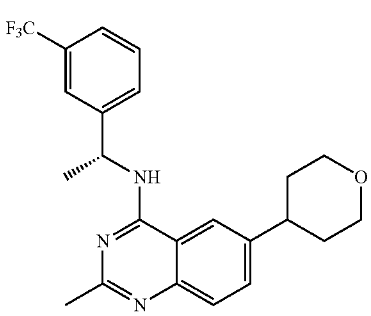 [SMILES: Cc1nc(N[C@H](C)c2cccc(C(F)(F)F)c2)c2cc(C3CCOCC3)ccc2n1] | M + H = 416; t_ret = 1.36 | LCMSBAS1 | 33 |

TABLE 41-continued

| # | structure | [M + H]+ $t_{ret}$ [min] | HPLC method | IC$_{50}$ (SOS1) [nM] |
|---|---|---|---|---|
| I-154 | 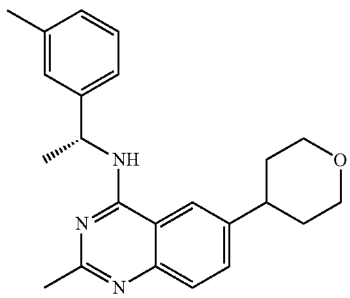 [SMILES: Cc1cccc([C@@H](C)Nc2nc(C)nc3ccc(C4CCOCC4)cc23)c1] | M + H = 362; $t_{ret}$ = 1.30 | LCMSBAS1 | 43 |
| I-155 | 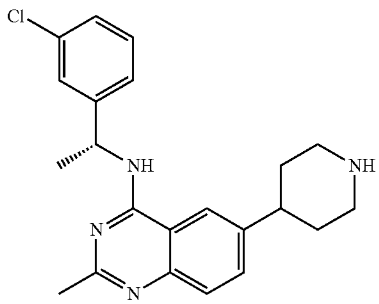 [SMILES: Cc1nc(N[C@H](C)c2cccc(Cl)c2)c2cc(C3CCNCC3)ccc2n1] | M + H = 381; $t_{ret}$ = 1.25 | LCMSBAS1 | |
| I-156 | 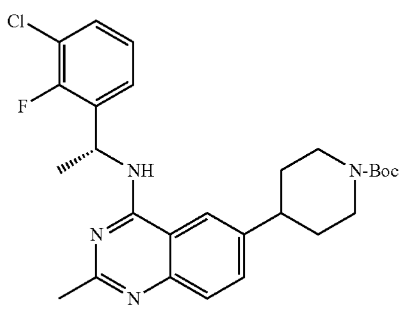 | M + H = 499; $t_{ret}$ = 0.93 | BFEC | |
| I-157 | 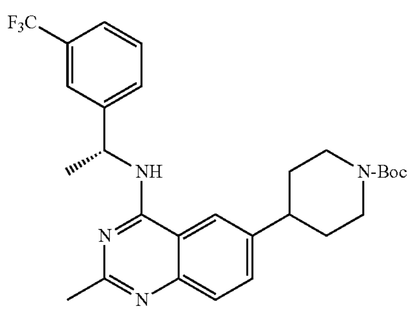 | M + H = 515; $t_{ret}$ = 1.63 | LCMSBAS1 | |
| I-158 | 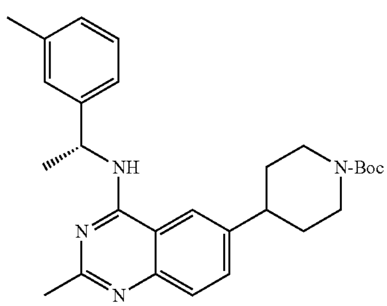 | M + H = 461; $t_{ret}$ = 0.91 | BFEC | |

TABLE 41-continued

| # | structure | [M + H]+ tret [min] | HPLC method | IC50 (SOS1) [nM] |
|---|---|---|---|---|
| I-159 | 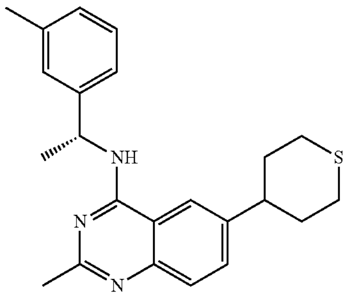 [SMILES: Cc1cccc([C@@H](C)Nc2nc(C)nc3ccc(C4CCSCC4)cc23)c1] | M + H = 378; tret = 0.85 | BFEC | |
| I-160 | 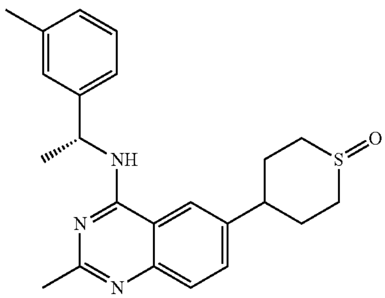 [SMILES: Cc1cccc([C@@H](C)Nc2nc(C)nc3ccc(C4CCS(=O)CC4)cc23)c1] | M + H = 394; tret = 1.12 | LCMSBAS1 | 22* |
| I-161 | 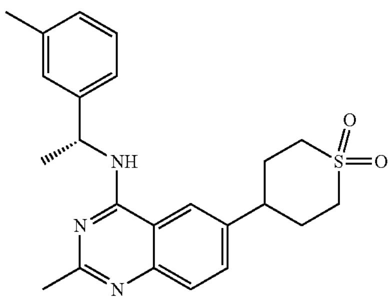 [SMILES: Cc1cccc([C@@H](C)Nc2nc(C)nc3ccc(C4CCS(=O)(=O)CC4)cc23)c1] | M + H = 410; tret = 1.19 | LCMSBAS1 | 29* |
| I-162 | 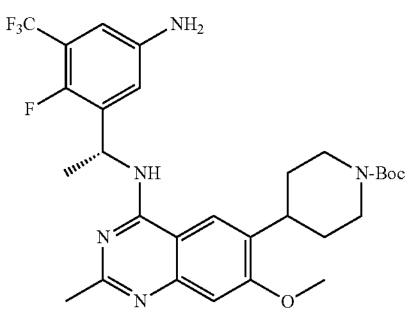 | M + H = 578; tret = 0.87 | BFEC | |
| I-163 | 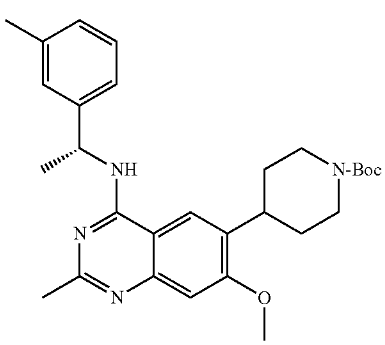 | M + H = 491; tret = 0.92 | BFEC | |

TABLE 41-continued

| # | structure | [M + H]+ t_ret [min] | HPLC method | IC50 (SOS1) [nM] |
|---|---|---|---|---|
| I-164 | 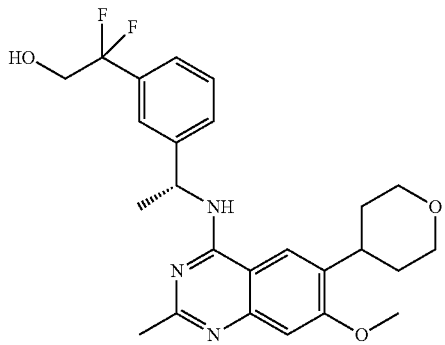 [SMILES: COc1cc2nc(C)nc(N[C@H](C)c3cccc(C(F)(F)CO)c3)c2cc1C1CCOCC1] | M + H = 458; t_ret = 1.22 | LCMSBAS1 | 3 |
| I-165 | 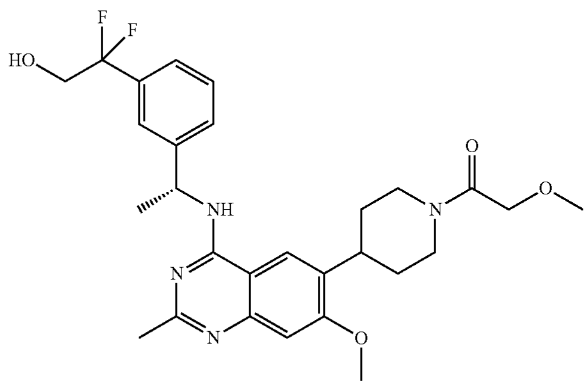 [SMILES: COCC(=O)N1CCC(c2cc3c(N[C@H](C)c4cccc(C(F)(F)CO)c4)nc(C)nc3cc2OC)CC1] | M + H = 529; t_ret = 1.08 | LCMSBAS1 | 2 |
| I-166 | 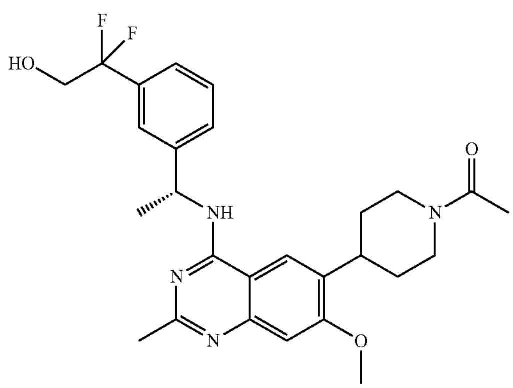 [SMILES: COc1cc2nc(C)nc(N[C@H](C)c3cccc(C(F)(F)CO)c3)c2cc1C1CCN(C(C)=O)CC1] | M + H = 499; t_ret = 1.08 | LCMSBAS1 | 2 |
| I-167 | 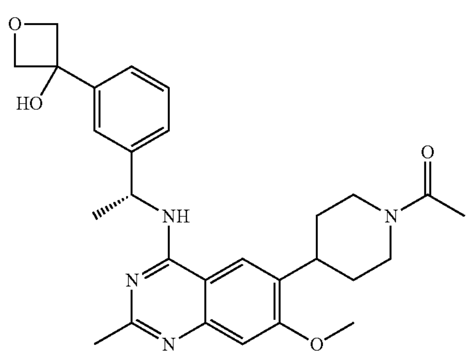 [SMILES: COc1cc2nc(C)nc(N[C@H](C)c3cccc(C4(O)COC4)c3)c2cc1C1CCN(C(C)=O)CC1] | M + H = 491; t_ret = 0.99 | LCMSBAS1 | 18 |

Experimental Procedure for the Synthesis of I-168

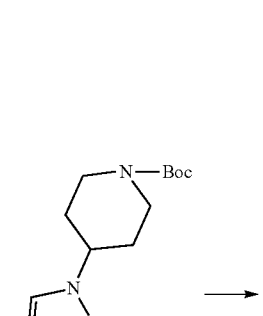

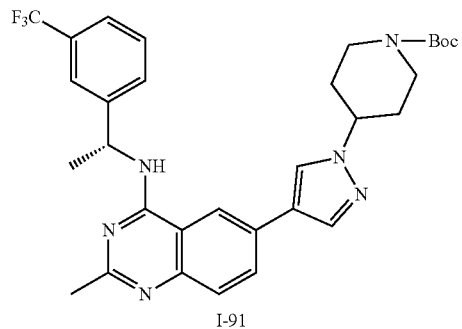

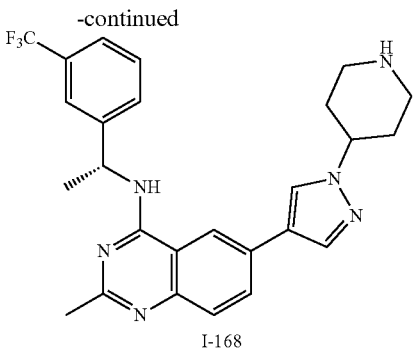

I-91 (145.3 mg, 250.0 µmol, 1.0 equiv.) is dissolved in dioxane (2 mL) and treated with HCl (250 µL, 1.0 mmol, 4.0 equiv., 4M in dioxane). The reaction mixture is heated to 40° C. for 4 h. The solvent is removed under reduced pressure giving the desired product I-168.

The following compounds (I) (table 42) are available in an analogous manner starting from different quinazolines (I) initially obtained (tables 40 and 41). The crude product (I) is purified by chromatography if necessary.

TABLE 42

| # | structure | [M + H]$^+$ $t_{ret}$ [min] | HPLC method | IC$_{50}$ (SOS1) [nM] |
|---|---|---|---|---|
| I-168 | 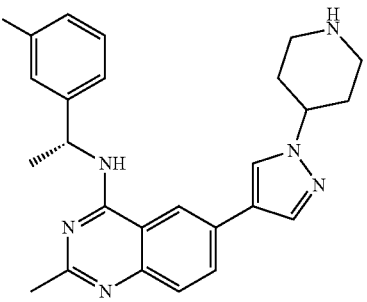 | M + H = 481; $t_{ret}$ = 1.55 | LCMSBAS1 | 48* |
| I-169 | 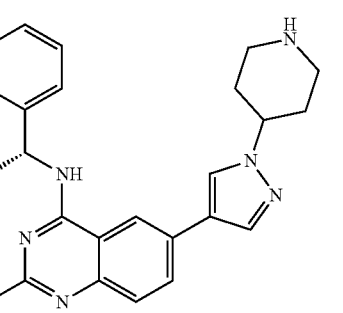 | M + H = 481; $t_{ret}$ = 1.55 | LCMSBAS1 | |
| I-170 | 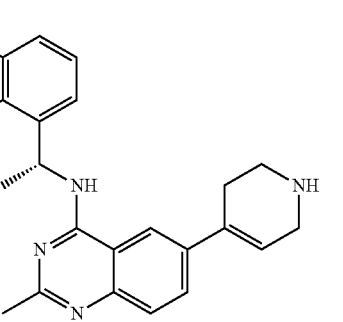 | M + H = 397; $t_{ret}$ = 1.25 | LCMSBAS1 | 24* |

TABLE 42-continued

| # | structure | [M + H]+ $t_{ret}$ [min] | HPLC method | IC$_{50}$ (SOS1) [nM] |
|---|---|---|---|---|
| I-171 | 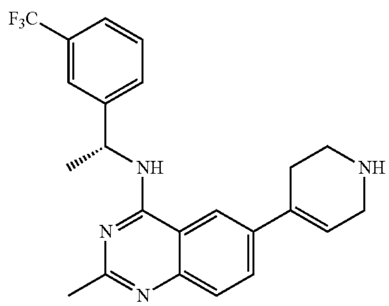 | M + H = 413; $t_{ret}$ = 1.29 | LCMSBAS1 | 18* |
| I-172 | 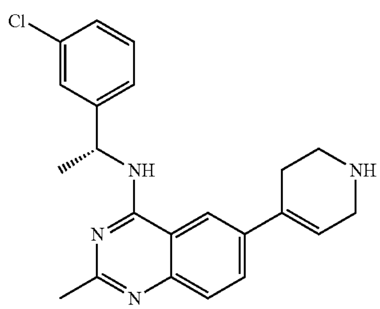 [SMILES: Cc1nc(N[C@H](C)c2cccc(Cl)c2F)c2cc(C3=CCNCC3)ccc2n1] | M + H = 379; $t_{ret}$ = 1.22 | LCMSBAS1 | 39* |
| I-173 | 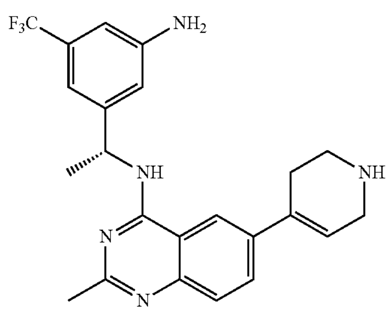 | M + H = 428; $t_{ret}$ = 0.588 | BFEC | |
| I-174 | 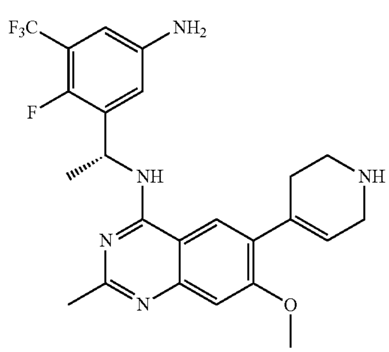 [SMILES: COc1cc2nc(C)nc(N[C@H](C)c3cc(N)cc(C(F)(F)F)c3F)c2cc1C1=CCNCC1] | M + H = 476; $t_{ret}$ = 0.61 | BFEC | |

TABLE 42-continued

| # | structure | [M + H]+ $t_{ret}$ [min] | HPLC method | IC$_{50}$ (SOS1) [nM] |
|---|---|---|---|---|
| I-175 | 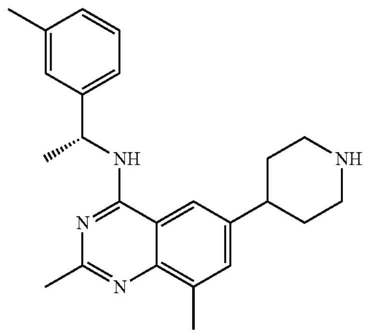 [SMILES: Cc1cccc([C@@H](C)Nc2nc(C)nc3c(C)cc(C4CCNCC4)cc23)c1] | M + H = 375; $t_{ret}$ = 1.34 | LCMSBAS1 | |
| I-176 | 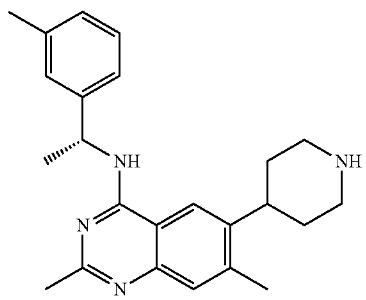 [SMILES: Cc1cccc([C@@H](C)Nc2nc(C)nc3cc(C)c(C4CCNCC4)cc23)c1] | M + H = 375; $t_{ret}$ = 1.33 | LCMSBAS1 | 46 |
| I-177 | 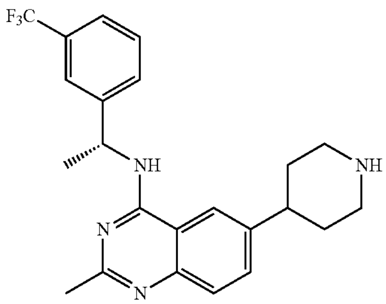 [SMILES: Cc1nc(N[C@H](C)c2cccc(C(F)(F)F)c2)c2cc(C3CCNCC3)ccc2n1] | M + H = 415; $t_{ret}$ = 1.31 | LCMSBAS1 | |
| I-178 | 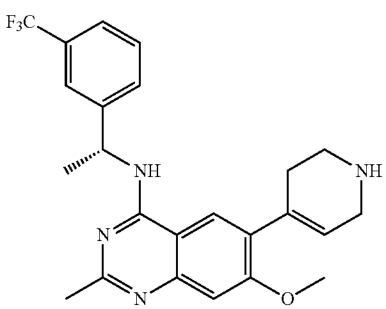 [SMILES: COc1cc2nc(C)nc(N[C@H](C)c3cccc(C(F)(F)F)c3)c2cc1C1=CCNCC1] | M + H = 443; $t_{ret}$ = 0.676 | BFEC | |
| I-179 | 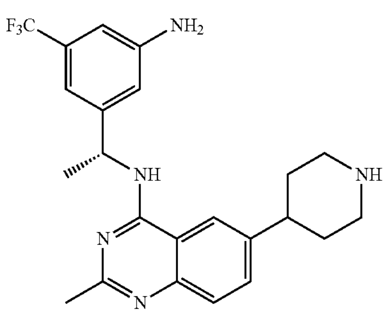 [SMILES: Cc1nc(N[C@H](C)c2cc(N)cc(C(F)(F)F)c2)c2cc(C3CCNCC3)ccc2n1] | M + H = 430; $t_{ret}$ = 0.57 | BFEC | |

TABLE 42-continued

| # | structure | [M + H]+ t_ret [min] | HPLC method | IC_50 (SOS1) [nM] |
|---|---|---|---|---|
| I-180 | 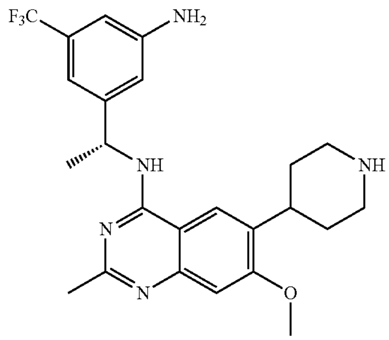 [SMILES: COc1cc2nc(C)nc(N[C@H](C)c3cc(N)cc(C(F)(F)F)c3)c2cc1C1CCNCC1] | M + H = 460; $t_{ret}$ = 0.55 | BFEC | |
| I-181 | 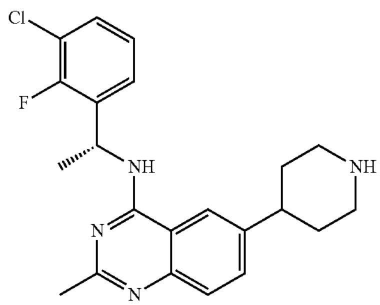 [SMILES: Cc1nc(N[C@H](C)c2cccc(Cl)c2F)c2cc(C3CCNCC3)ccc2n1] | M + H = 399; $t_{ret}$ = 1.24 | LCMSBAS1 | |
| I-182 | 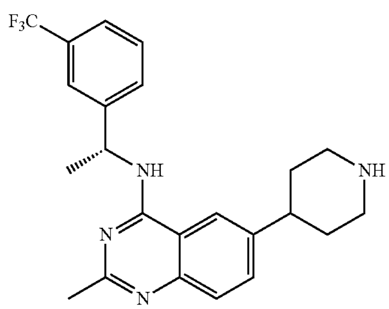 [SMILES: Cc1nc(N[C@H](C)c2cccc(C(F)(F)F)c2)c2cc(C3CCNCC3)ccc2n1] | M + H = 415; $t_{ret}$ = 1.31 | LCMSBAS1 | 22* |
| I-183 | 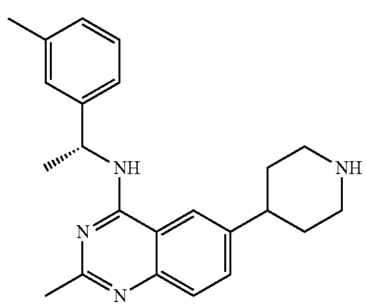 [SMILES: Cc1cccc([C@@H](C)Nc2nc(C)nc3ccc(C4CCNCC4)cc23)c1] | M + H = 361; $t_{ret}$ = 1.17 | LCMSBAS1 | 38* |
| I-184 | 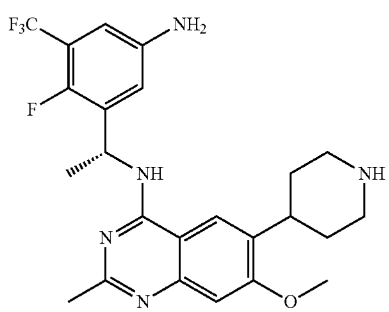 [SMILES: COc1cc2nc(C)nc(N[C@H](C)c3cc(N)cc(C(F)(F)F)c3F)c2cc1C1CCNCC1] | M + H = 478; $t_{ret}$ = 0.59 | BFEC | |

TABLE 42-continued
| # | structure | [M + H]+ $t_{ret}$ [min] | HPLC method | IC$_{50}$ (SOS1) [nM] |
|---|---|---|---|---|
| I-185 | 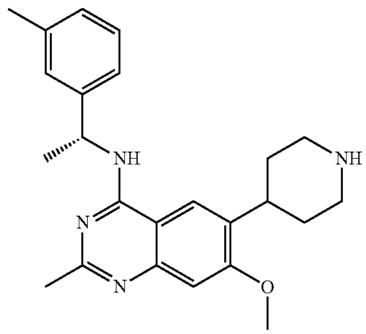 [SMILES: COc1cc2nc(C)nc(N[C@H](C)c3cccc(C)c3)c2cc1C1CCNCC1] | M + H = 391; $t_{ret}$ = 0.58 | BFEC | |
| I-186 | 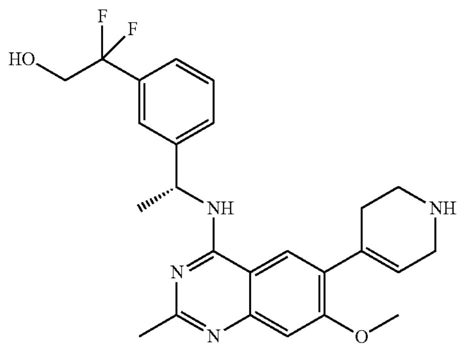 [SMILES: COc1cc2nc(C)nc(N[C@H](C)c3cccc(C(F)(F)CO)c3)c2cc1C1=CCNCC1] | M + H = 455; $t_{ret}$ = 0.51 | BFEC | |
Experimental Procedure for the Synthesis of I-187
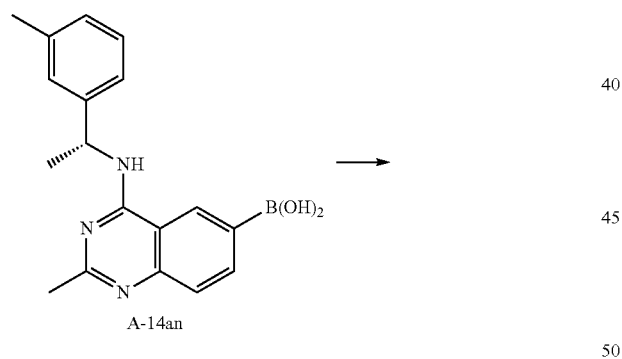
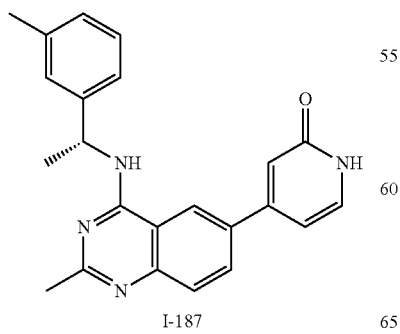

A-14an (30.0 mg, 93.0 mol, 1.0equiv.), 4-bromo-1,2-dihydropyridin-2-one hydrochloride (23.6 mg, 112.0 µmol, 1.2 equiv.), bis(di-tert-butyl(4-dimethylaminophenyl)phosphine) dichloropalladium(II) (6.6 mg, 9.0 µmol, 0.1 equiv.) and sodium carbonate (29.7 mg, 280.2 µmol, 3.0 equiv.) are dissolved in a mixture of dioxane (0.4 mL), MeOH (0.2 mL) and water (0.2 mL) and the reaction mixture is heated to 80° C. for 2 h. The crude reaction mixture is purified by chromatography using acetonitrile/water giving the desired product.

The following compounds (I) (table 43) are available in an analogous manner starting from different quinazolines A-14. The crude product (I) is purified by chromatography if necessary.

TABLE 43

| # | structure | [M + H]+ $t_{ret}$ [min] | HPLC method | IC$_{50}$ (SOS1) [nM] |
|---|---|---|---|---|
| I-187 | 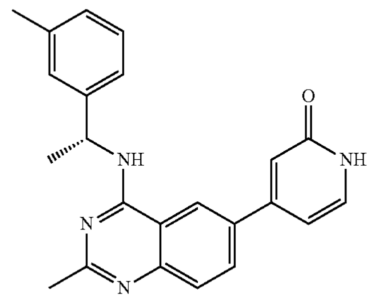 [SMILES: Cc1cccc([C@@H](C)Nc2nc(C)nc3ccc(-c4cc[nH]c(=O)c4)cc23)c1] | M + H = 371; $t_{ret}$ = 1.13 | LCMSBAS1 | |
| I-188 | 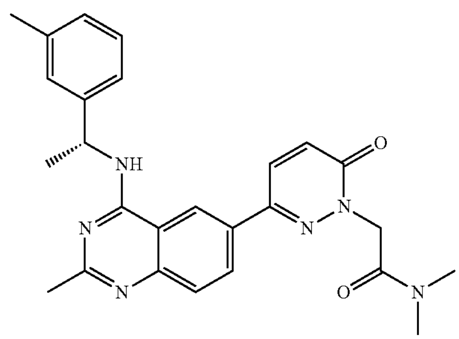 | M + H = 457; $t_{ret}$ = 1.16 | LCMSBAS1 | |
| I-189 | 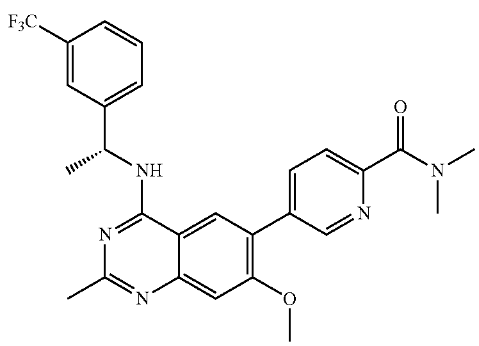 [SMILES: COc1cc2nc(C)nc(N[C@H](C)c3cccc(C(F)(F)F)c3)c2cc1-c1ccc(C(=O)N(C)C)nc1] | M + H = 510; $t_{ret}$ = 1.29 | LCMSBAS1 | 23 |
| I-190 | 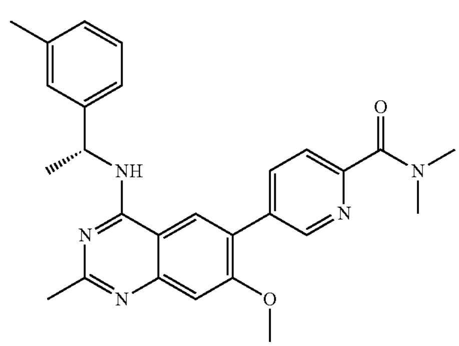 | M + H = 456; $t_{ret}$ = 1.23 | LCMSBAS1 | 34 |

TABLE 43-continued

| # | structure | [M + H]+ $t_{ret}$ [min] | HPLC method | IC$_{50}$ (SOS1) [nM] |
|---|---|---|---|---|
| I-191 | 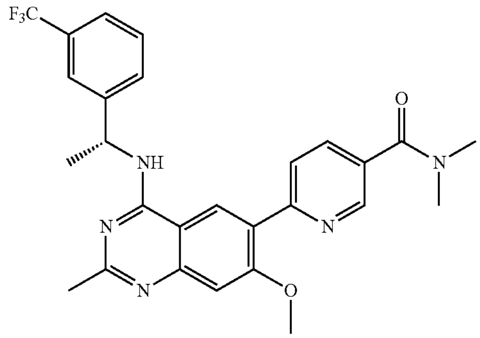 [SMILES: COc1cc2nc(C)nc(N[C@H](C)c3cccc(C(F)(F)F)c3)c2cc1-c1ccc(C(=O)N(C)C)cn1] | M + H = 510; $t_{ret}$ = 1.27 | LCMSBAS1 | 35 |
| I-192 | 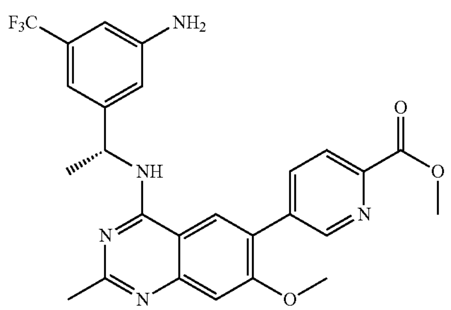 [SMILES: COC(=O)c1ccc(-c2cc3c(N[C@H](C)c4cc(N)cc(C(F)(F)F)c4)nc(C)nc3cc2OC)cn1] | M + H = 512; $t_{ret}$ = 0.68 | BFEC | |
| I-193 | 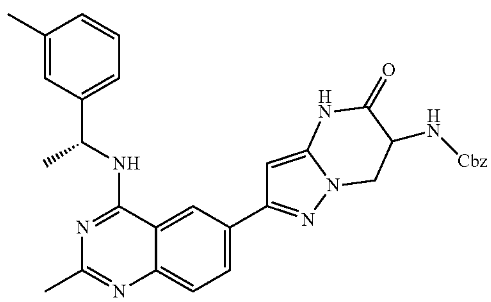 [SMILES: Cc1cccc([C@@H](C)Nc2nc(C)nc3ccc(-c4cc5n(n4)CC(NC(=O)OCc4ccccc4)C(=O)N5)cc23)c1] | M + H = 562; $t_{ret}$ = 1.35 | LCMSBAS1 | |

Experimental Procedure for the Synthesis of I-194

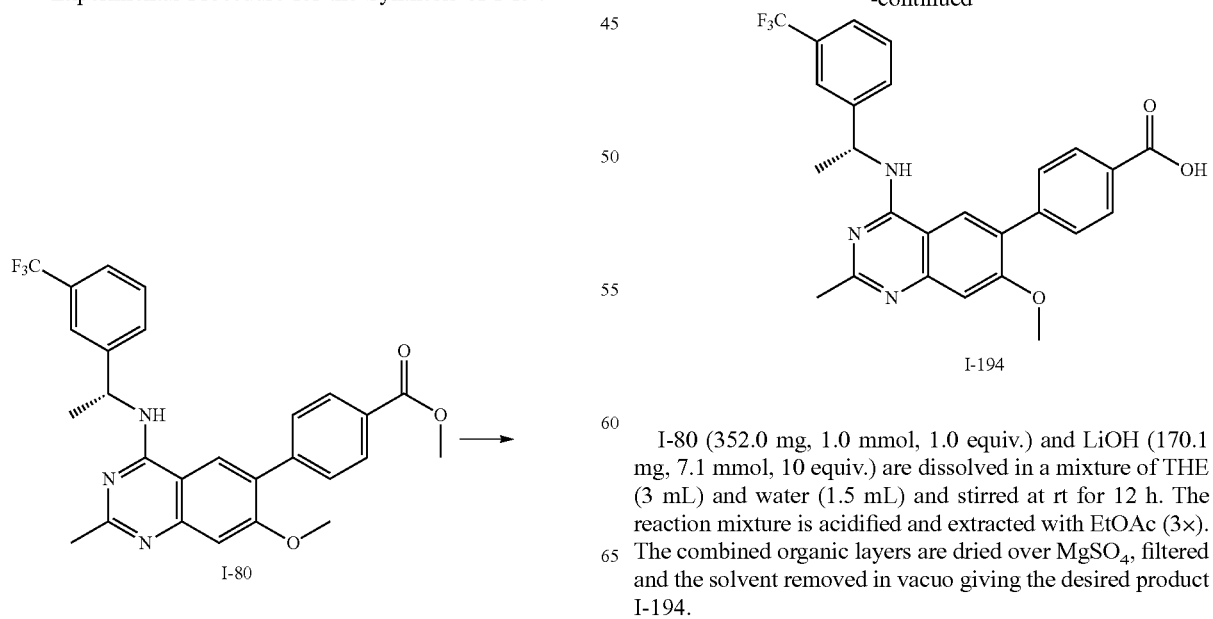

I-80 (352.0 mg, 1.0 mmol, 1.0 equiv.) and LiOH (170.1 mg, 7.1 mmol, 10 equiv.) are dissolved in a mixture of THF (3 mL) and water (1.5 mL) and stirred at rt for 12 h. The reaction mixture is acidified and extracted with EtOAc (3×). The combined organic layers are dried over MgSO$_4$, filtered and the solvent removed in vacuo giving the desired product I-194.

The following compounds (I) (table 44) are available in an analogous manner starting from different quinazolines (I) initially obtained (table 40). The crude product (I) is purified by chromatography if necessary.

TABLE 44

| # | structure | [M + H]+ $t_{ret}$ [min] | HPLC method | IC$_{50}$ (SOS1) [nM] |
|---|---|---|---|---|
| I-194 | 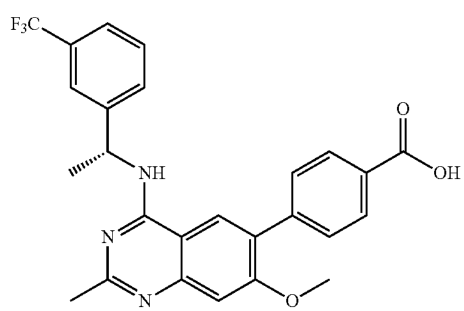 [SMILES: COc1cc2nc(C)nc(N[C@H](C)c3cccc(C(F)(F)F)c3)c2cc1-c1ccc(C(=O)O)cc1] | M + H = 482; $t_{ret}$ = 0.55 | BFEC | |
| I-195 | 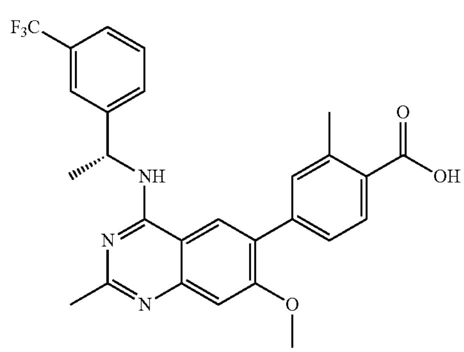 [SMILES: COc1cc2nc(C)nc(N[C@H](C)c3cccc(C(F)(F)F)c3)c2cc1-c1ccc(C(=O)O)c(C)c1] | M + H = 496; $t_{ret}$ = 0.55 | BFEC | |
| I-196 | 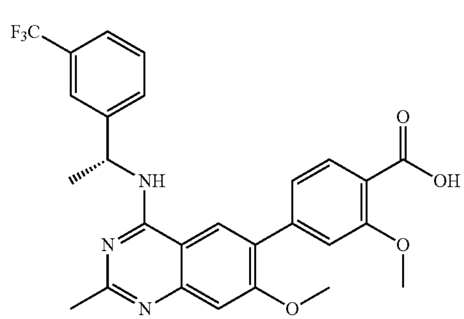 [SMILES: COc1cc(-c2cc3c(N[C@H](C)c4cccc(C(F)(F)F)c4)nc(C)nc3cc2OC)ccc1C(=O)O] | M + H = 512; $t_{ret}$ = 0.54 | BFEC | |
| I-197 | 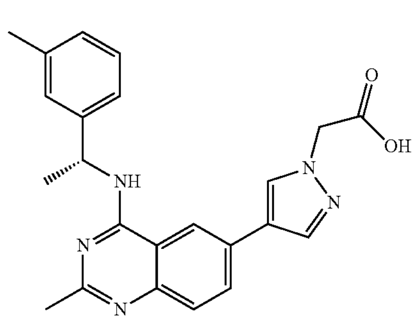 [SMILES: Cc1cccc([C@@H](C)Nc2nc(C)nc3ccc(-c4cnn(CC(=O)O)c4)cc23)c1] | M + H = 402; $t_{ret}$ = 0.94 | LCMSBAS1 | |

TABLE 44-continued

| # | structure | [M + H]+ t$_{ret}$ [min] | HPLC method | IC$_{50}$ (SOS1) [nM] |
|---|---|---|---|---|
| I-198 | 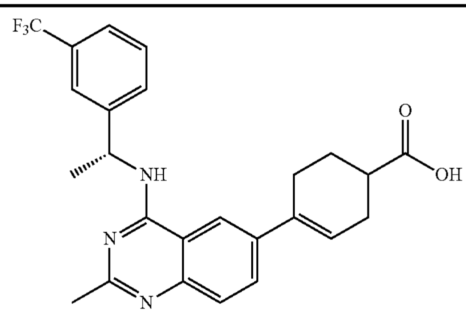 | M + H = 456; t$_{ret}$ = 0.541 | BFEC | |
| I-199 | 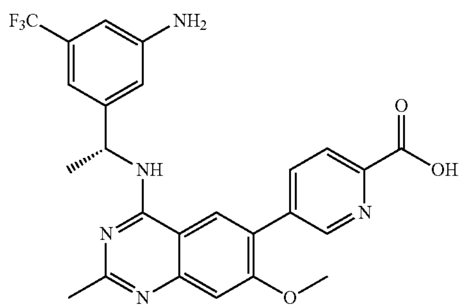 [SMILES: COc1cc2nc(C)nc(N[C@H](C)c3cc(N)cc(C(F)(F)F)c3)c2cc1-c1ccc(C(=O)O)nc1] | M + H = 498; t$_{ret}$ = 0.93 | LCMSBAS1 | |
| I-200 | 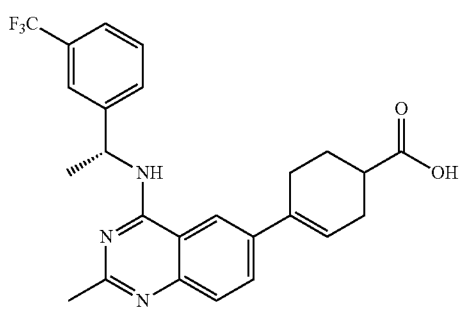 | M + H = 351; t$_{ret}$ = 0.63 | BFEC | |
| I-201 | 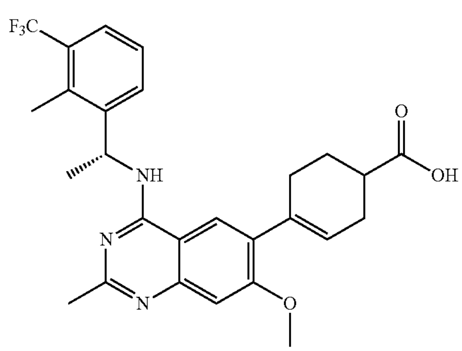 [SMILES: COc1cc2nc(C)nc(N[C@H](C)c3cccc(C(F)(F)F)c3C)c2cc1C1=CCC(C(=O)O)CC1] | M + H = 500; t$_{ret}$ = 0.59 | BFEC | |
| I-202 | 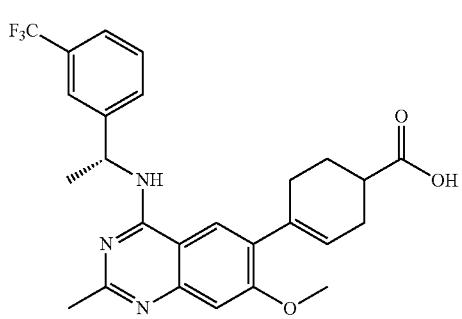 [SMILES: COc1cc2nc(C)nc(N[C@H](C)c3cccc(C(F)(F)F)c3)c2cc1C1=CCC(C(=O)O)CC1] | M + H = 486; t$_{ret}$ = 0.54 | BFEC | |

TABLE 44-continued

| # | structure | [M + H]⁺ $t_{ret}$ [min] | HPLC method | IC$_{50}$ (SOS1) [nM] |
|---|---|---|---|---|
| I-203 | 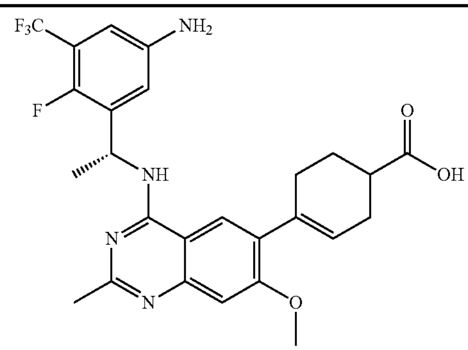 | M + H = 519; $t_{ret}$ = 0.51 | BFEC | |
| I-204 | 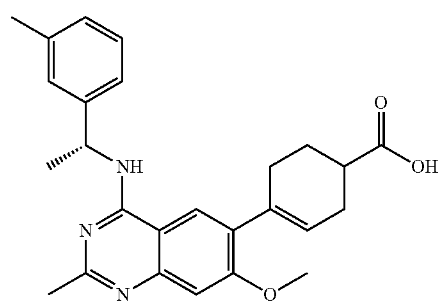 [SMILES: COc1cc2nc(C)nc(N[C@H](C)c3cccc(C)c3)c2cc1C1=CCC(C(=O)O)CC1] | M + H = 432; $t_{ret}$ = 0.50 | BFEC | |
| I-205 | 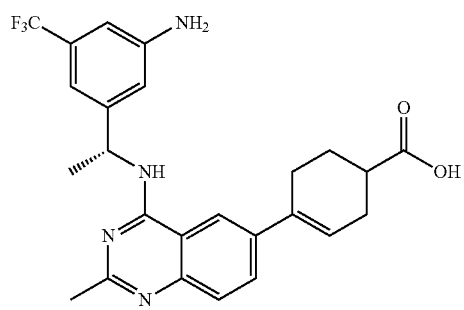 [SMILES: Cc1nc(N[C@H](C)c2cc(N)cc(C(F)(F)F)c2)c2cc(C3=CCC(C(=O)O)CC3)ccc2n1] | M + H = 471; $t_{ret}$ = 0.49 | BFEC | |
| I-206 | 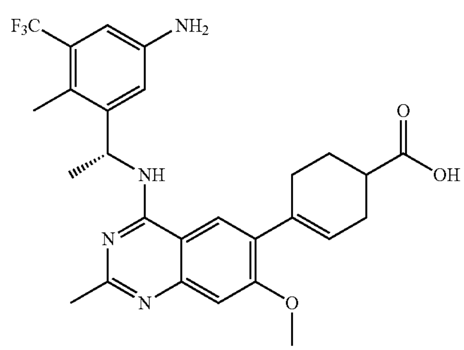 [SMILES: COc1cc2nc(C)nc(N[C@H](C)c3cc(N)cc(C(F)(F)F)c3C)c2cc1C1=CCC(C(=O)O)CC1] | M + H = 515; $t_{ret}$ = 0.53 | BFEC | |
| I-207 | 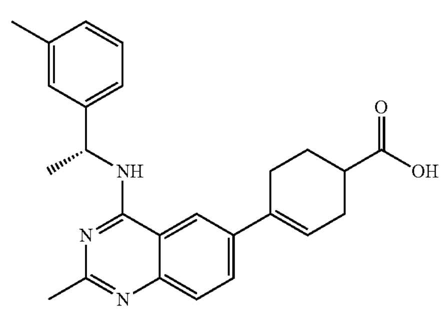 [SMILES: Cc1cccc([C@@H](C)Nc2nc(C)nc3ccc(C4=CCC(C(=O)O)CC4)cc23)c1] | M + H = 402; $t_{ret}$ = 0.48 | BFEC | |

TABLE 44-continued

| # | structure | [M + H]+ t$_{ret}$ [min] | HPLC method | IC$_{50}$ (SOS1) [nM] |
|---|---|---|---|---|
| I-208 | 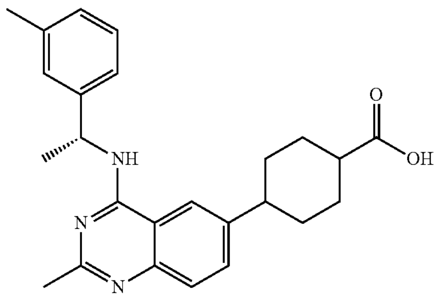 [SMILES: Cc1cccc([C@@H](C)Nc2nc(C)nc3ccc(C4CCC(C(=O)O)CC4)cc23)c1] | M + H = 404.4; t$_{ret}$ = 0.505 | BFEC | |
| I-209 | 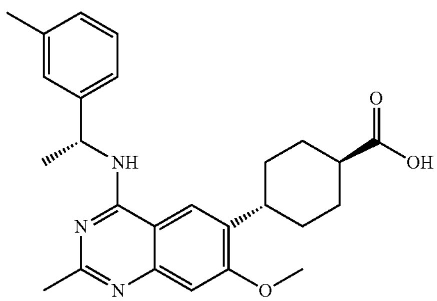 [SMILES: COc1cc2nc(C)nc(N[C@H](C)c3cccc(C)c3)c2cc1[C@H]1CC[C@H](C(=O)O)CC1] | M + H = 434; t$_{ret}$ = 0.50 | BFEC | |
| I-210 | 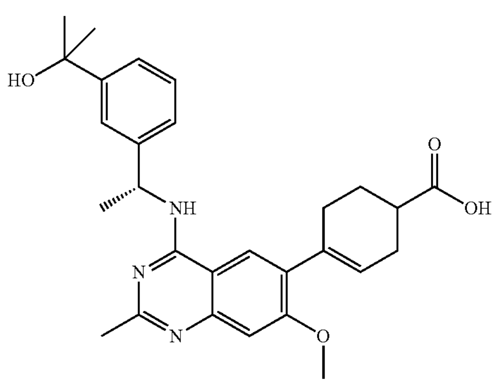 [SMILES: COc1cc2nc(C)nc(N[C@H](C)c3cccc(C(C)(C)O)c3)c2cc1C1=CCC(C(=O)O)CC1] | M + H = 476; t$_{ret}$ = 0.42 | BFEC | |
| I-211 | 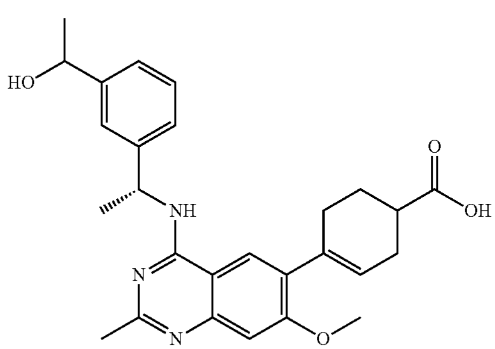 [SMILES: COc1cc2nc(C)nc(N[C@H](C)c3cccc(C(C)O)c3)c2cc1C1=CCC(C(=O)O)CC1] | M + H = 462; t$_{ret}$ = 0.39 | BFEC | |

TABLE 44-continued

| # | structure | [M + H]+ $t_{ret}$ [min] | HPLC method | IC$_{50}$ (SOS1) [nM] |
|---|---|---|---|---|
| I-212 | 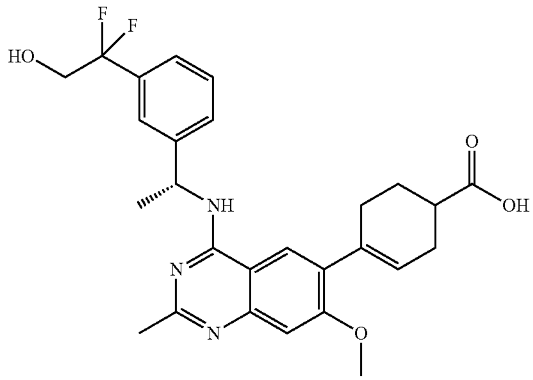 [SMILES: COc1cc2nc(C)nc(N[C@H](C)c3cccc(C(F)(F)CO)c3)c2cc1C1=CCC(C(=O)O)CC1] | M + H = 498; $t_{ret}$ = 0.42 | BFEC | |

Experimental Procedure for the Synthesis of I-213

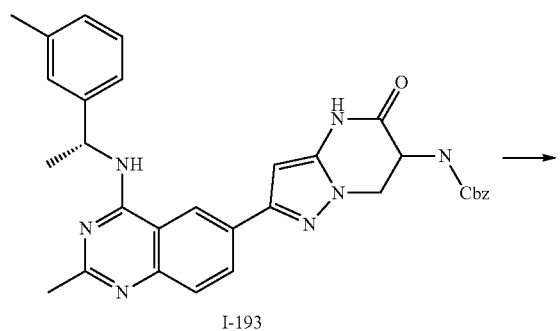

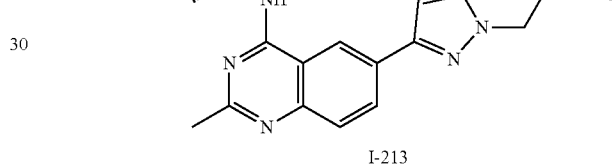

I-193 (41.0 mg, 73.0 µmol, 1.0 equiv.) is dissolved in MeOH (2 mL), treated with Pd/C (20.0 mg) and stirred at rt for 12 h. The reaction is performed in an autoclave under H$_2$ (5 bar) atmosphere. The reaction is filtered through celite and purified by chromatography using acetonitrile/water giving the desired product I-213.

TABLE 45

| # | structure | [M + H]+ $t_{ret}$ [min] | HPLC method | IC$_{50}$ (SOS1) [nM] |
|---|---|---|---|---|
| I-213 | 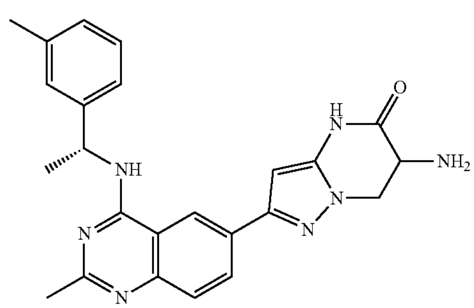 [SMILES: Cc1cccc([C@@H](C)Nc2nc(C)nc3ccc(-c4cc5n(n4)CC(N)C(=O)N5)cc23)c1] | M + H = 428; $t_{ret}$ = 1.08 | LCMSBAS1 | |

Experimental Procedure for the Synthesis of I-214

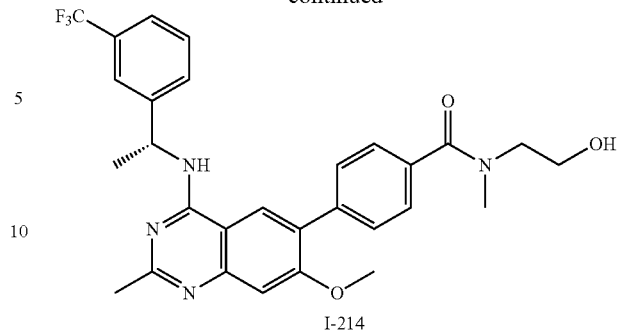

I-214

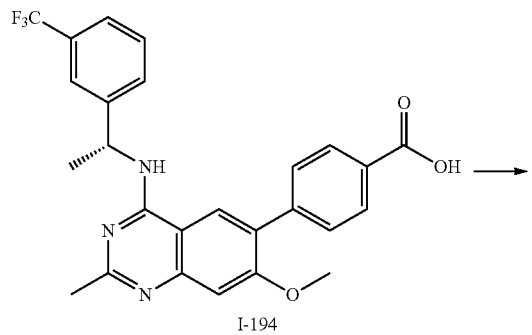

I-194

I-194 (40.0 mg, 83.0 μmol, 1.0 equiv.) is dissolved in DMF (0.4 mL), DIPEA (56.5 μL, 125.0 μmol, 4.0 equiv.) and HATU (47.3 mg, 125.0 μmol, 1.5 equiv.) are added and the mixture is stirred for 20 min at rt. Then 2-(methylamino)ethanol (12.5 mg, 166.0 μmol, 2.0 equiv.) is added and the reaction mixture stirred for 2 h at rt. The crude product is purified by chromatography using a mixture of acetonitrile/water to give the desired product I-214.

The following compounds (I) (table 46) are available in an analogous manner starting from different quinazolines (I) initially obtained (tables 42 and 44). The crude product (I) is purified by chromatography if necessary.

TABLE 46

| # | structure | [M + H]$^+$ $t_{ret}$ [min] | HPLC method | IC$_{50}$ (SOS1) [nM] |
|---|-----------|------------------------------|-------------|------------------------|
| I-214 | 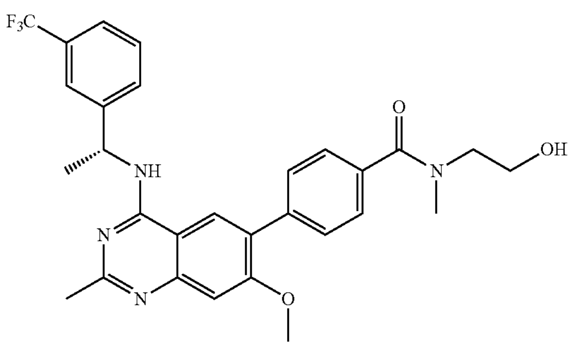 [SMILES: COc1cc2nc(C)nc(N[C@H](C)c3cccc(C(F)(F)F)c3)c2cc1-c1ccc(C(=O)N(C)CCO)cc1] | M + H = 539; $t_{ret}$ = 1.27 | LCMSBAS1 | 40 |
| I-215 | 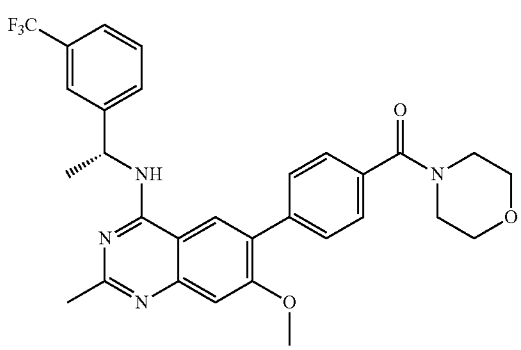 [SMILES: COc1cc2nc(C)nc(N[C@H](C)c3cccc(C(F)(F)F)c3)c2cc1-c1ccc(C(=O)N2CCOCC2)cc1] | M + H = 551; $t_{ret}$ = 1.35 | LCMSBAS1 | 37 |

TABLE 46-continued

| # | structure | [M + H]+ t_ret [min] | HPLC method | IC_50 (SOS1) [nM] |
|---|---|---|---|---|
| I-216 | 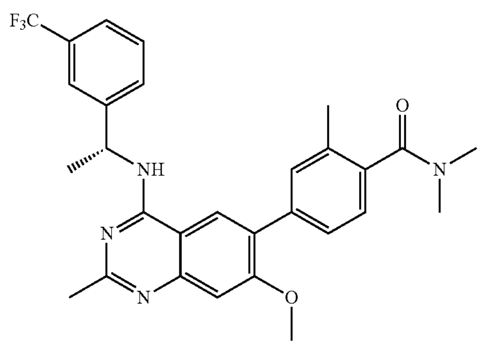 [SMILES: COc1cc2nc(C)nc(N[C@H](C)c3cccc(C(F)(F)F)c3)c2cc1-c1ccc(C(=O)N(C)C)c(C)c1] | M + H = 523; t_ret = 1.40 | LCMSBAS1 | 48 |
| I-217 | 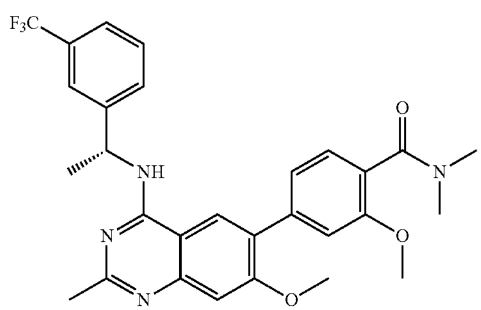 [SMILES: COc1cc(-c2cc3c(N[C@H](C)c4cccc(C(F)(F)F)c4)nc(C)nc3cc2OC)ccc1C(=O)N(C)C] | M + H = 539; t_ret = 1.36 | LCMSBAS1 | 43 |
| I-218 | 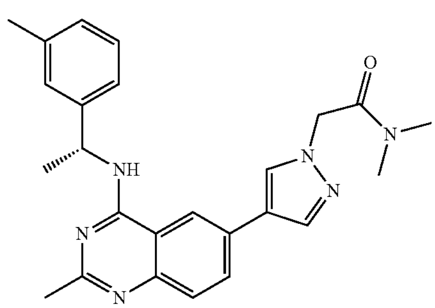 | M + H = 401; t_ret = 1.12 | LCMSBAS1 | 49* |
| I-219 | 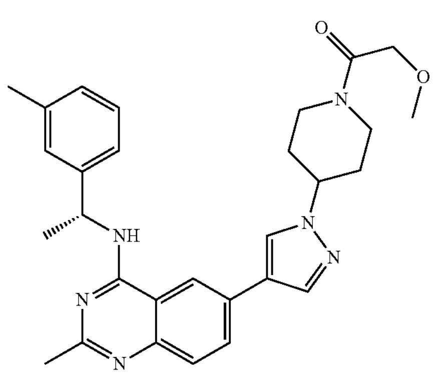 [SMILES: COCC(=O)N1CCC(n2cc(-c3ccc4nc(C)nc(N[C@H](C)c5cccc(C)c5)c4c3)cn2)CC1] | M + H = 499; t_ret = 1.21 | LCMSBAS1 | 34* |

TABLE 46-continued

| # | structure | [M + H]+ $t_{ret}$ [min] | HPLC method | IC$_{50}$ (SOS1) [nM] |
|---|---|---|---|---|
| I-220 | 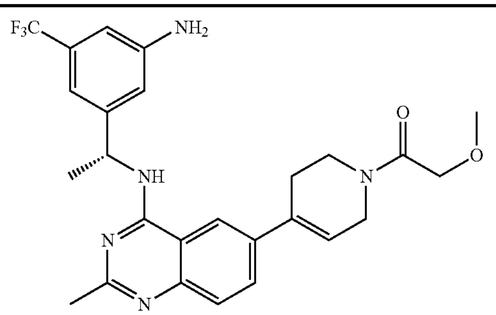 | M + H = 500; $t_{ret}$ = 1.17 | LCMSBAS1 | 3 |
| I-221 | 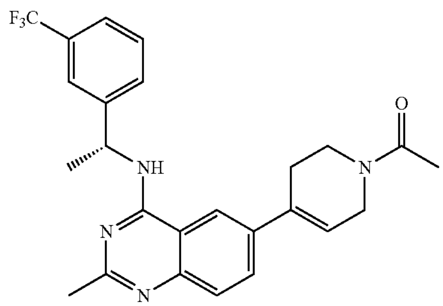 [SMILES: CC(=O)N1CC=C(c2ccc3nc(C)nc(N[C@H](C)c4cccc(C(F)(F)F)c4)c3c2)CC1] | M + H = 455; $t_{ret}$ = 1.29 | LCMSBAS1 | 11 |
| I-222 | 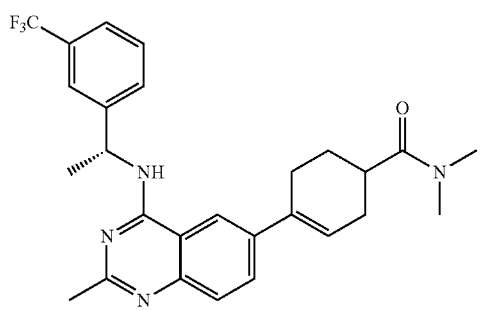 [SMILES: Cc1nc(N[C@H](C)c2cccc(C(F)(F)F)c2)c2cc(C3=CCC(C(=O)N(C)C)CC3)ccc2n1] | M + H = 483; $t_{ret}$ = 1.38 | LCMSBAS1 | 19 |
| I-223 | 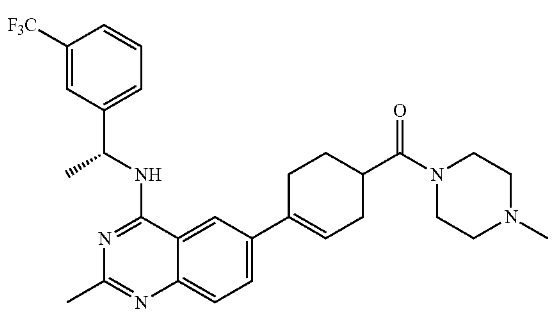 [SMILES: Cc1nc(N[C@H](C)c2cccc(C(F)(F)F)c2)c2cc(C3=CCC(C(=O)N4CCN(C)CC4)CC3)ccc2n1] | M + H = 538; $t_{ret}$ = 1.33 | LCMSBAS1 | 27 |
| I-224 | 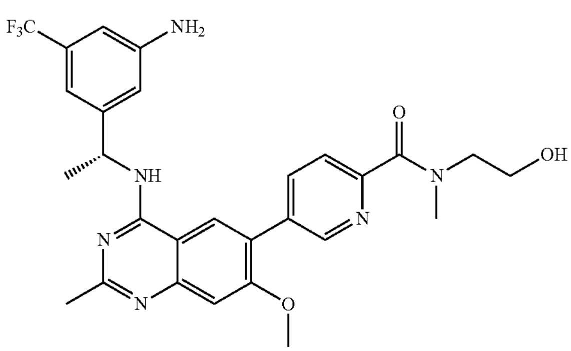 [SMILES: COc1cc2nc(C)nc(N[C@H](C)c3cc(N)cc(C(F)(F)F)c3)c2cc1-c1ccc(C(=O)N(C)CCO)nc1] | M + H = 555; $t_{ret}$ = 1.11 | LCMSBAS1 | 4 |

TABLE 46-continued

| # | structure | [M + H]+ t_ret [min] | HPLC method | IC50 (SOS1) [nM] |
|---|---|---|---|---|
| I-225 | 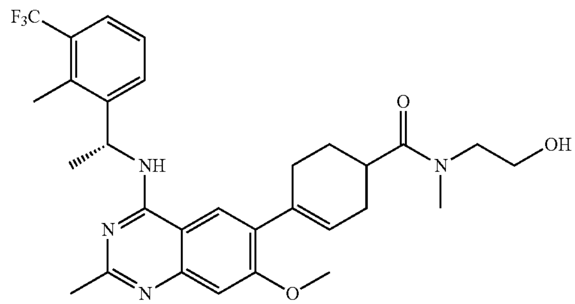 [SMILES: COc1cc2nc(C)nc(N[C@H](C)c3cccc(C(F)(F)F)c3C)c2cc1C1=CCC(C(=O)N(C)CCO)CC1] | M + H = 557; t_ret = 0.75 | BFEC | |
| I-226 | 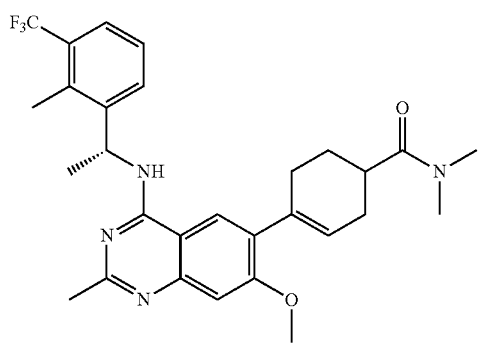 [SMILES: COc1cc2nc(C)nc(N[C@H](C)c3cccc(C(F)(F)F)c3C)c2cc1C1=CCC(C(=O)N(C)C)CC1] | M + H = 527; t_ret = 0.82 | BFEC | |
| I-227 | 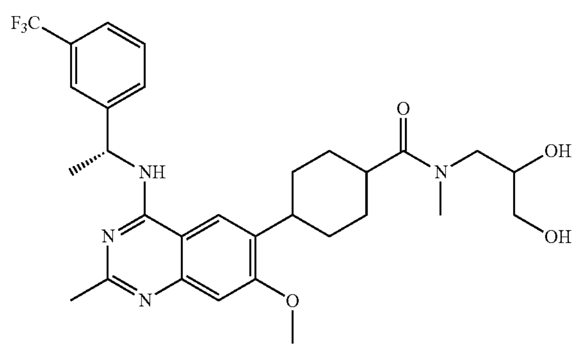 [SMILES: COc1cc2nc(C)nc(N[C@H](C)c3cccc(C(F)(F)F)c3)c2cc1C1CCC(C(=O)N(C)CC(O)CO)CC1] | M + H = 575; t_ret = 1.27 | LCMSBAS1 | 27 |
| I-228 | 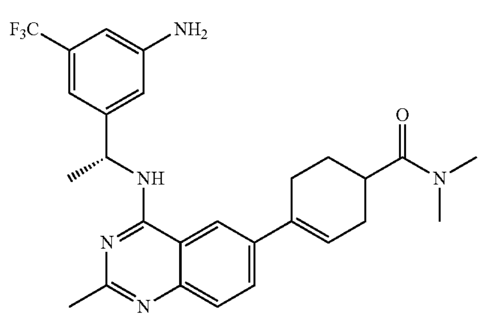 [SMILES: Cc1nc(N[C@H](C)c2cc(N)cc(C(F)(F)F)c2)c2cc(C3=CCC(C(=O)N(C)C)CC3)ccc2n1] | M + H = 498; t_ret = 0.68 | BFEC | |

TABLE 46-continued

| # | structure | [M + H]⁺ t_ret [min] | HPLC method | IC₅₀ (SOS1) [nM] |
|---|---|---|---|---|
| I-229 | 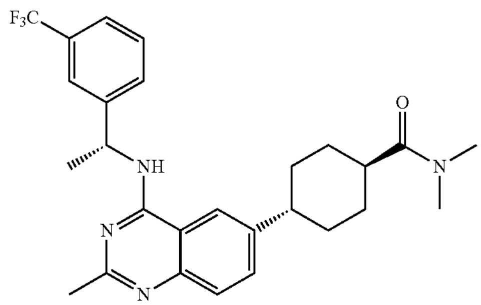 [SMILES: Cc1nc(N[C@H](C)c2cccc(C(F)(F)F)c2)c2cc([C@H]3CC[C@H](C(=O)N(C)C)CC3)ccc2n1] | M + H = 485; t_ret = 1.37 | LCMSBAS1 | 7 |
| I-230 | 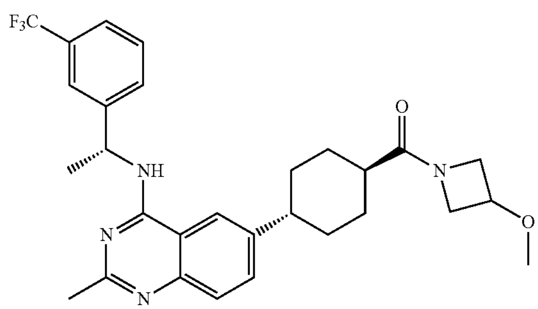 [SMILES: COC1CN(C(=O)[C@H]2CC[C@H](c3ccc4nc(C)nc(N[C@H](C)c5cccc(C(F)(F)F)c5)c4c3)CC2)C1] | M + H = 527; t_ret = 1.35 | LCMSBAS1 | 32 |
| I-231 | 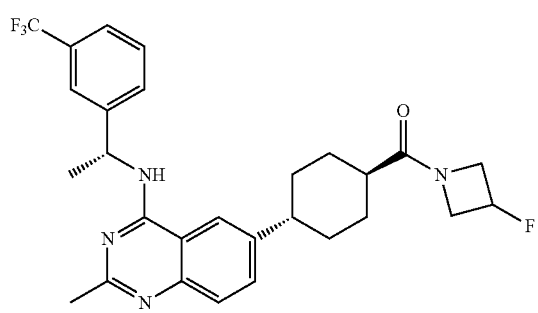 [SMILES: Cc1nc(N[C@H](C)c2cccc(C(F)(F)F)c2)c2cc([C@H]3CC[C@H](C(=O)N4CC(F)C4)CC3)ccc2n1] | M + H = 515; t_ret = 1.38 | LCMSBAS1 | 19 |
| I-232 | 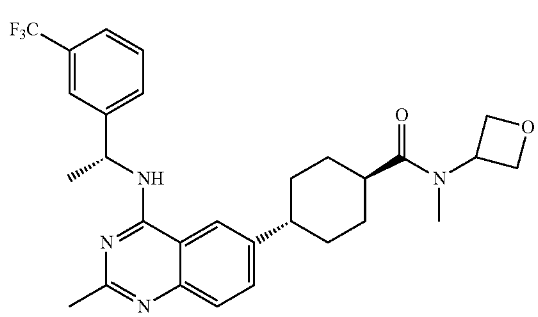 [SMILES: Cc1nc(N[C@H](C)c2cccc(C(F)(F)F)c2)c2cc([C@H]3CC[C@H](C(=O)N(C)C4COC4)CC3)ccc2n1] | M + H = 527; t_ret = 1.34 | LCMSBAS1 | |

TABLE 46-continued
| # | structure | [M + H]+ $t_{ret}$ [min] | HPLC method | IC$_{50}$ (SOS1) [nM] |
|---|---|---|---|---|
| I-233 | 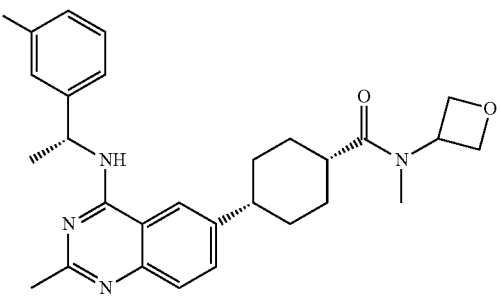 | M + H = 527; $t_{ret}$ = 1.39 | LCMSBAS1 | 38 |
| I-234 | 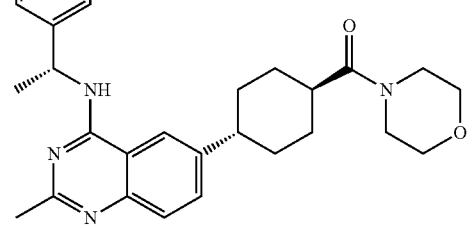 | M + H = 542; $t_{ret}$ = 1.22 | LCMSBAS1 | 2 |
| I-235 | 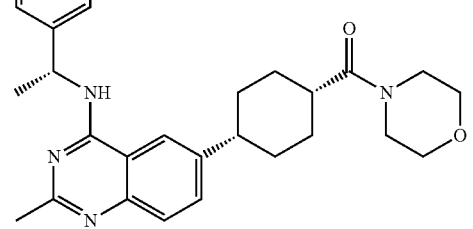 | M + H = 542; $t_{ret}$ = 1.27 | LCMSBAS1 | 8 |
| I-236 | 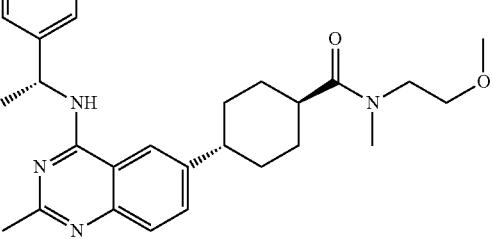 | M + H = 544; $t_{ret}$ = 1.26 | LCMSBAS1 | 2 |
| I-237 | 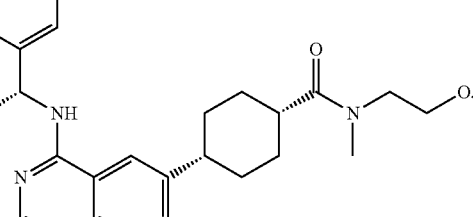 | M + H = 544; $t_{ret}$ = 1.26 | LCMSBAS1 | 9 |

TABLE 46-continued
| # | structure | [M + H]⁺ t_ret [min] | HPLC method | IC₅₀ (SOS1) [nM] |
|---|---|---|---|---|
| I-238 | 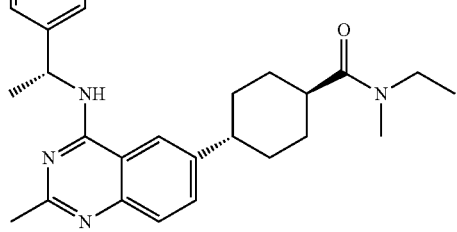 | M + H = 514; t_ret = 1.29 | LCMSBAS1 | 3 |
| I-239 | 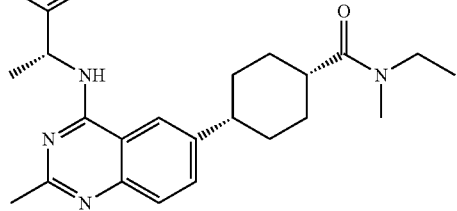 | M + H = 514; t_ret = 1.38 | LCMSBAS1 | 15 |
| I-240 | 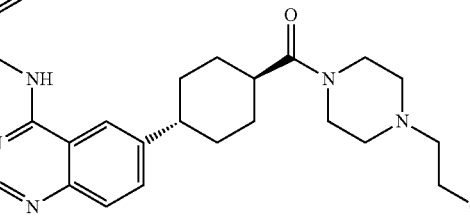 | M + H = 599; t_ret = 1.21 | LCMSBAS1 | 2 |
| I-241 | 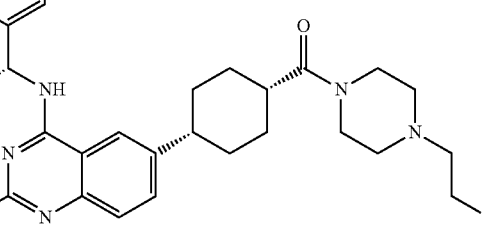 | M + H = 599; t_ret = 1.27 | LCMSBAS1 | 7 |
| I-242 | 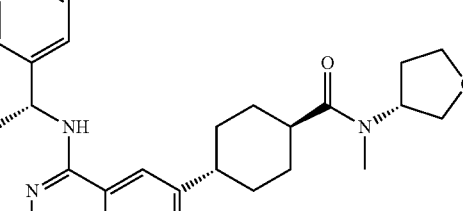 | M + H = 556; t_ret = 1.24 | LCMSBAS1 | 5 |

TABLE 46-continued
| # | structure | [M + H]+ t_ret [min] | HPLC method | IC50 (SOS1) [nM] |
|---|---|---|---|---|
| I-243 | 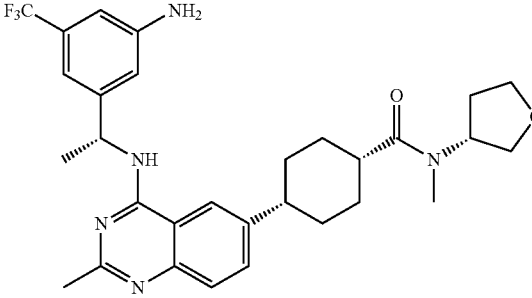 | M + H = 556; t_ret = 1.30 | LCMSBAS1 | 9 |
| I-244 | 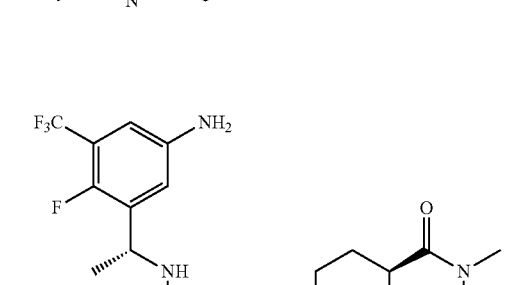 | M + H = 548; t_ret = 1.27 | LCMSBAS1 | 2 |
| I-245 | 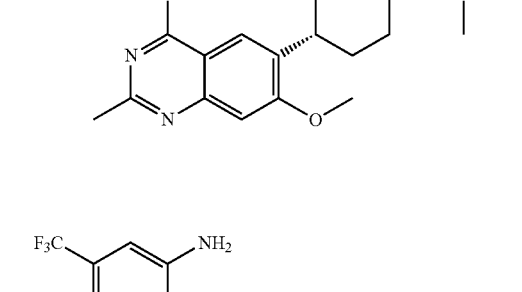 | M + H = 548; t_ret = 1.36 | LCMSBAS1 | 35 |
| I-246 | 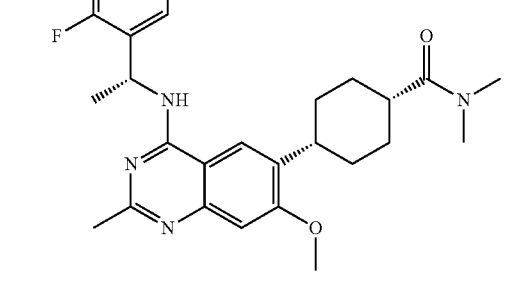 | M + H = 647; t_ret = 1.26 | LCMSBAS1 | 2 |

TABLE 46-continued
| # | structure | [M + H]+ $t_{ret}$ [min] | HPLC method | IC$_{50}$ (SOS1) [nM] |
|---|---|---|---|---|
| I-247 | 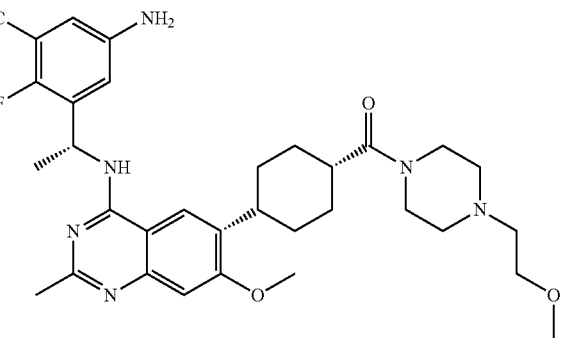 | M + H = 647; $t_{ret}$ = 1.33 | LCMSBAS1 | 18 |
| I-248 | 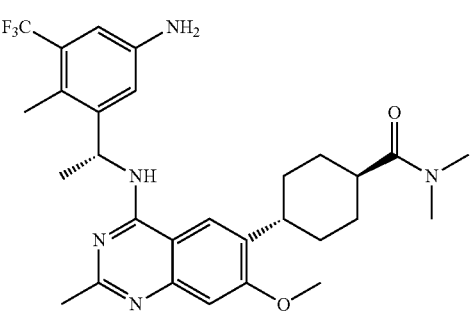 | M + H = 544; $t_{ret}$ = 1.32 | LCMSBAS1 | 2 |
| I-249 | 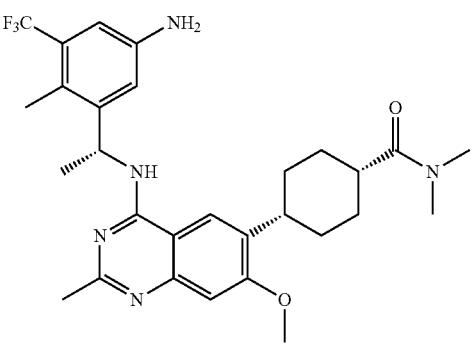 [SMILES: COc1cc2nc(C)nc(N[C@H](C)c3cc(N)cc(C(F)(F)F)c3C)c2cc1[C@H]1CC[C@@H](C(=O)N(C)C)CC1] | M + H = 544; $t_{ret}$ = 1.40 | LCMSBAS1 | 38 |
| I-250 | 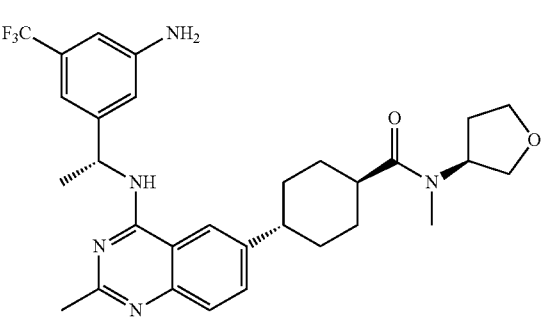 [SMILES: Cc1nc(N[C@H](C)c2cc(N)cc(C(F)(F)F)c2)c2cc([C@H]3CC[C@H](C(=O)N(C)[C@H]4CCOC4)CC3)ccc2n1] | M + H = 556; $t_{ret}$ = 1.22 | LCMSBAS1 | 4 |

TABLE 46-continued

| # | structure | [M + H]+ t$_{ret}$ [min] | HPLC method | IC$_{50}$ (SOS1) [nM] |
|---|---|---|---|---|
| I-251 | 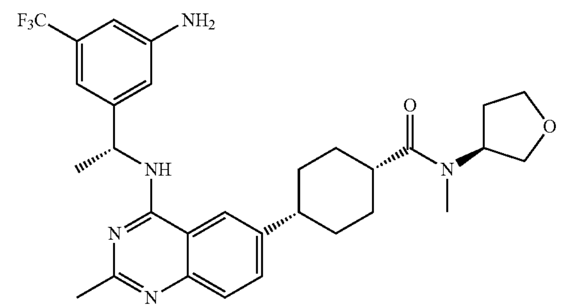 [SMILES: Cc1nc(N[C@H](C)c2cc(N)cc(C(F)(F)F)c2)c2cc([C@H]3CC[C@@H](C(=O)N(C)[C@H]4CCOC4)CC3)ccc2n1] | M + H = 556; t$_{ret}$ = 1.27 | LCMSBAS1 | 10 |
| I-252 | 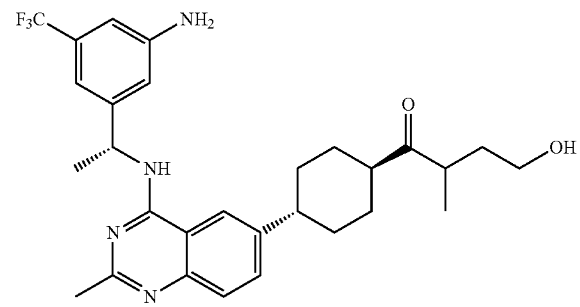 [SMILES: Cc1nc(N[C@H](C)c2cc(N)cc(C(F)(F)F)c2)c2cc([C@H]3CC[C@H](C(=O)C(C)CCO)CC3)ccc2n1] | M + H = 530; t$_{ret}$ = 1.14 | LCMSBAS1 | 3 |
| I-253 | 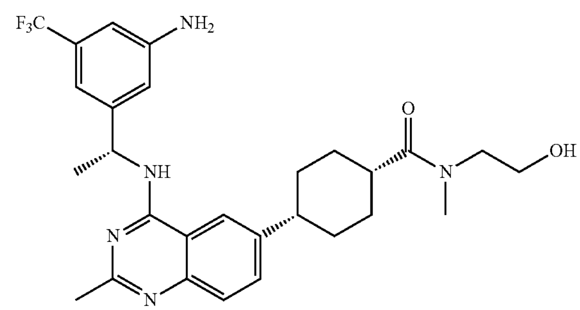 [SMILES: Cc1nc(N[C@H](C)c2cc(N)cc(C(F)(F)F)c2)c2cc([C@H]3CC[C@@H](C(=O)N(C)CCO)CC3)ccc2n1] | M + H = 530; t$_{ret}$ = 1.18 | LCMSBAS1 | 7 |
| I-254 | 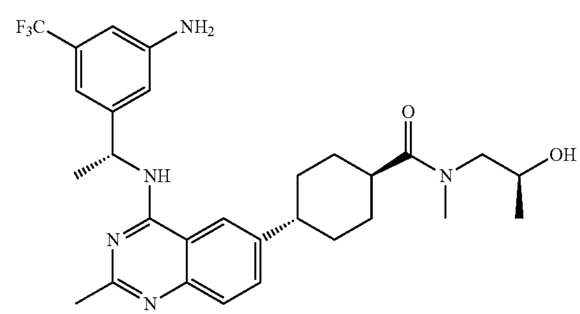 [SMILES: Cc1nc(N[C@H](C)c2cc(N)cc(C(F)(F)F)c2)c2cc([C@H]3CC[C@H](C(=O)N(C)C[C@H](C)O)CC3)ccc2n1] | M + H = 544; t$_{ret}$ = 1.18 | LCMSBAS1 | 2 |
| I-255 | 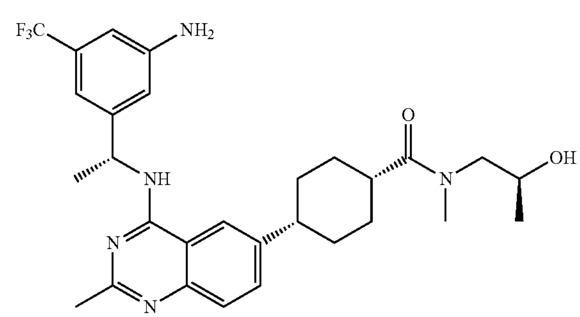 [SMILES: Cc1nc(N[C@H](C)c2cc(N)cc(C(F)(F)F)c2)c2cc([C@H]3CC[C@@H](C(=O)N(C)C[C@H](C)O)CC3)ccc2n1] | M + H = 544; t$_{ret}$ = 1.22 | LCMSBAS1 | 8 |

TABLE 46-continued
| # | structure | [M + H]+ t_ret [min] | HPLC method | IC$_{50}$ (SOS1) [nM] |
|---|---|---|---|---|
| I-256 | 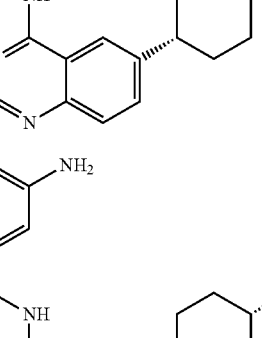 | M + H = 544; t_ret = 1.18 | LCMSBAS1 | 3 |
| I-257 | 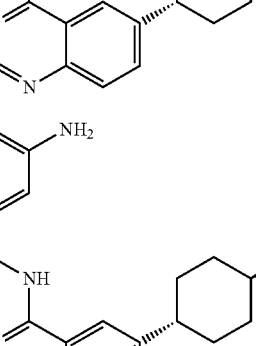 | M + H = 558; t_ret = 1.22 | LCMSBAS1 | 7 |
| I-258 | 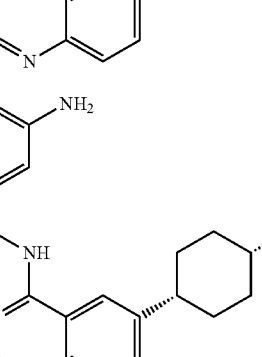 | M + H = 558; t_ret = 1.27 | LCMSBAS1 | 3 |
| I-259 | 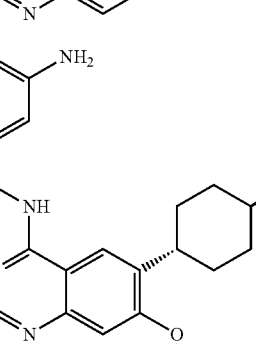 | M + H = 505; t_ret = 1.16 | LCMSBAS1 | 10 |
| I-260 | 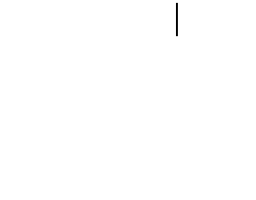 | M + H = 592; t_ret = 1.22 | LCMSBAS1 | 2 |

TABLE 46-continued

| # | structure | [M + H]+ $t_{ret}$ [min] | HPLC method | IC$_{50}$ (SOS1) [nM] |
|---|---|---|---|---|
| I-261 | 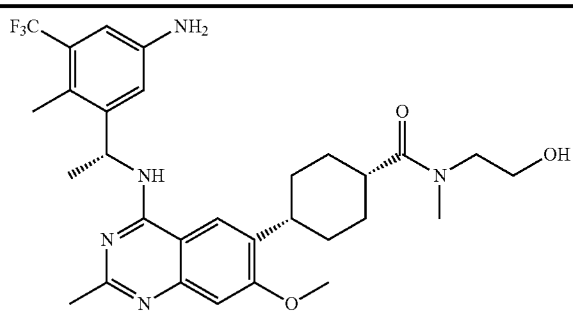 | M + H = 592; $t_{ret}$ = 1.23 | LCMSBAS1 | 2 |
| I-262 | 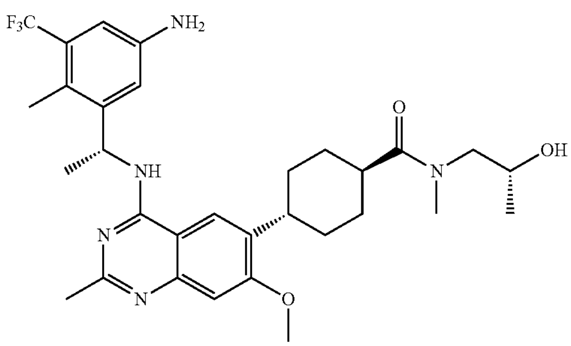 [SMILES: COc1cc2nc(C)nc(N[C@H](C)c3cc(N)cc(C(F)(F)F)c3C)c2cc1[C@H]1CC[C@H](C(=O)N(C)C[C@@H](C)O)CC1] | M + H = 606; $t_{ret}$ = 1.26 | LCMSBAS1 | 2 |
| I-263 | 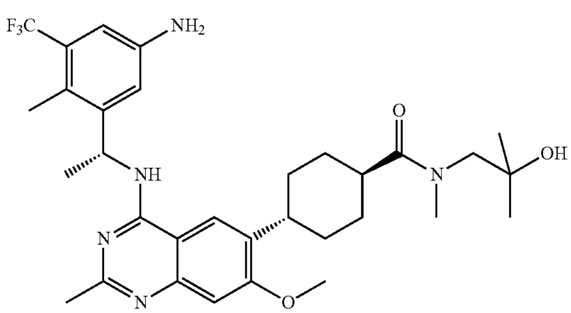 | M + H = 606; $t_{ret}$ = 1.26 | LCMSBAS1 | 3 |
| I-264 | 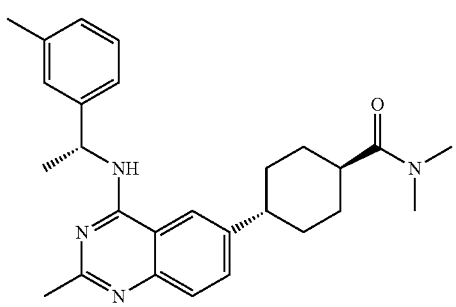 | M + H = 431; $t_{ret}$ = 1.32 | LCMSBAS1 | 13 |
| I-265 | 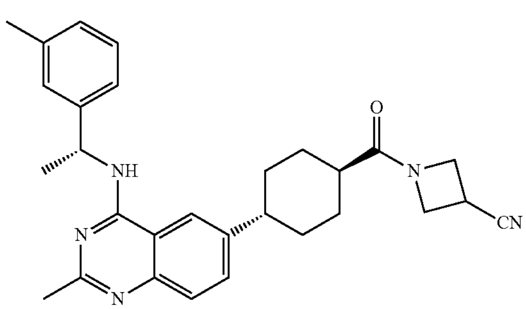 [SMILES: Cc1cccc([C@@H](C)Nc2nc(C)nc3ccc([C@H]4CC[C@H](C(=O)N5CC(C#N)C5)CC4)cc23)c1] | M + H = 468; $t_{ret}$ = 1.30 | LCMSBAS1 | 36 |

TABLE 46-continued

| # | structure | [M + H]+ $t_{ret}$ [min] | HPLC method | IC$_{50}$ (SOS1) [nM] |
|---|---|---|---|---|
| I-266 | 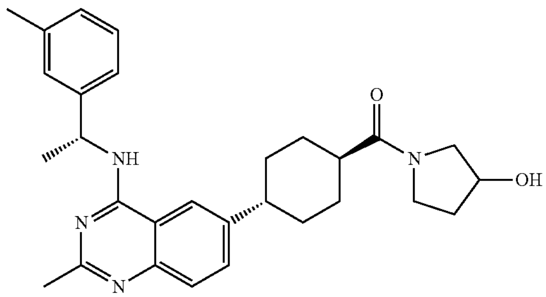 [SMILES: Cc1cccc([C@@H](C)Nc2nc(C)nc3ccc([C@H]4CC[C@H](C(=O)N5CCC(O)C5)CC4)cc23)c1] | M + H = 473; $t_{ret}$ = 1.19 | LCMSBAS1 | 25 |
| I-267 | 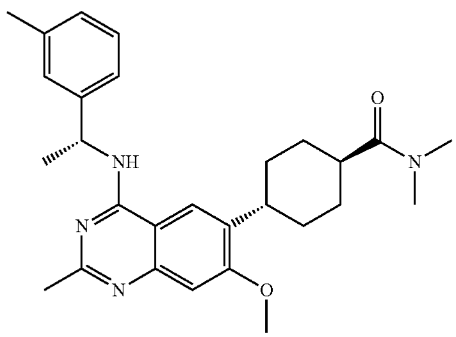 | M + H = 461; $t_{ret}$ = 1.32 | LCMSBAS1 | 9 |
| I-268 | 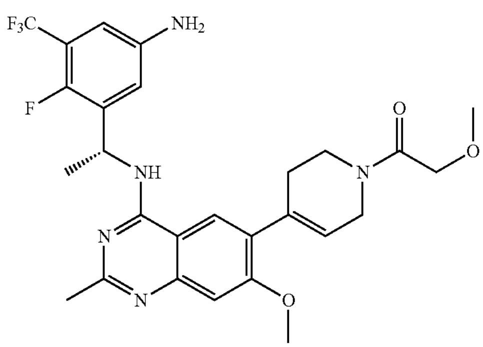 [SMILES: COCC(=O)N1CC=C(c2cc3c(N[C@H](C)c4cc(N)cc(C(F)(F)F)c4F)nc(C)nc3cc2OC)CC1] | M + H = 548; $t_{ret}$ = 0.65 | BFEC | |
| I-269 | 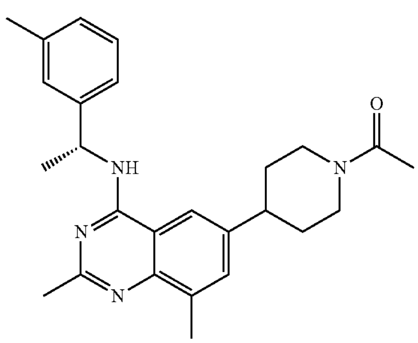 [SMILES: CC(=O)N1CCC(c2cc(C)c3nc(C)nc(N[C@H](C)c4cccc(C)c4)c3c2)CC1] | M + H = 417; $t_{ret}$ = 1.35 | LCMSBAS1 | 24 |

TABLE 46-continued

| # | structure | [M + H]⁺ t_ret [min] | HPLC method | IC₅₀ (SOS1) [nM] |
|---|---|---|---|---|
| I-270 | 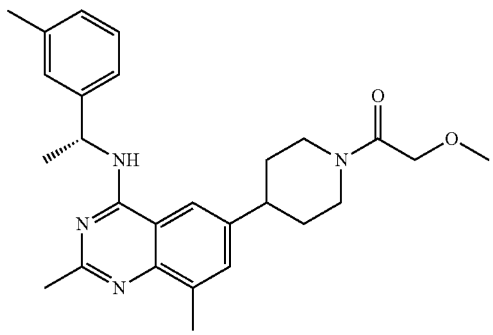 | M + H = 447; t_ret = 1.34 | LCMSBAS1 | 21 |
| I-271 | 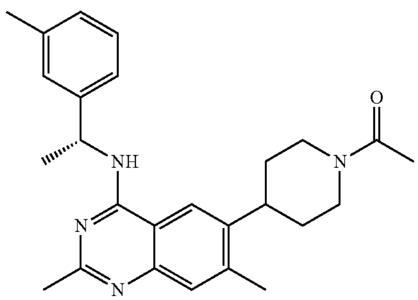 [SMILES: CC(=O)N1CCC(c2cc3c(N[C@H](C)c4cccc(C)c4)nc(C)nc3cc2C)CC1] | M + H = 417; t_ret = 1.23 | LCMSBAS1 | 24 |
| I-272 | 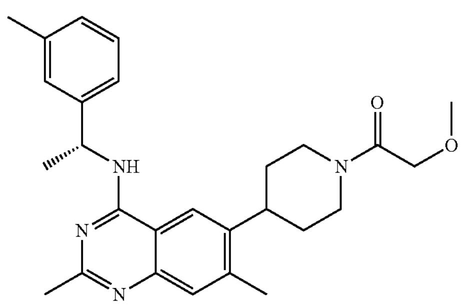 | M + H = 447; t_ret = 1.23 | LCMSBAS1 | 34 |
| I-273 | 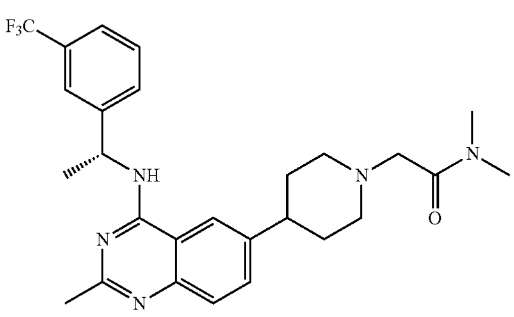 [SMILES: Cc1nc(N[C@H](C)c2cccc(C(F)(F)F)c2)c2cc(C3CCN(CC(=O)N(C)C)CC3)ccc2n1] | M + H = 500; t_ret = 1.32 | LCMSBAS1 | 11 |
| I-274 | 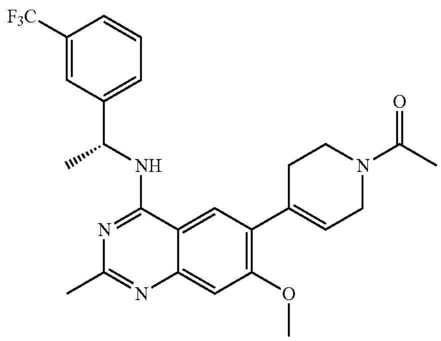 [SMILES: COc1cc2nc(C)nc(N[C@H](C)c3cccc(C(F)(F)F)c3)c2cc1C1=CCN(C(C)=O)CC1] | M + H = 485 t_ret = 0.719 | BFEC | |

TABLE 46-continued

| # | structure | [M + H]+ $t_{ret}$ [min] | HPLC method | IC$_{50}$ (SOS1) [nM] |
|---|---|---|---|---|
| I-275 | 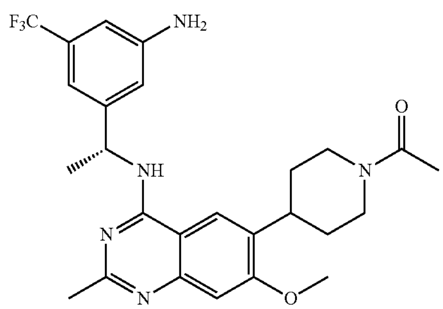 | M + H = 532; $t_{ret}$ = 1.18 | LCMSBAS1 | 2 |
| I-276 | 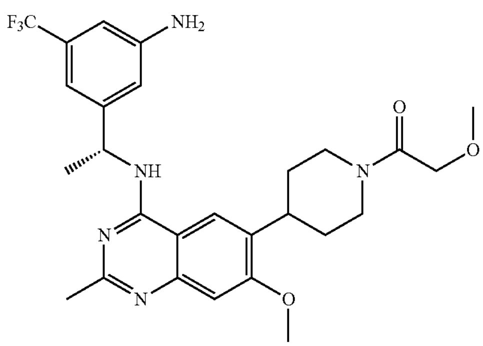 | M + H = 578; $t_{ret}$ = 1.19 | LCMSBAS1 | 3 |
| I-277 | 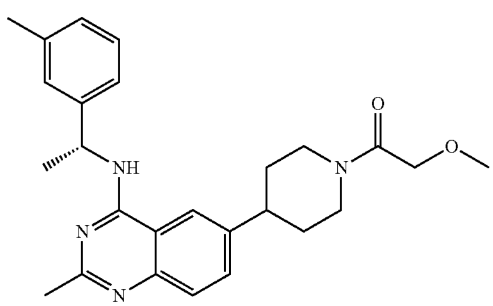 | M + H = 433; $t_{ret}$ = 1.20 | LCMSBAS1 | 22* |
| I-278 | 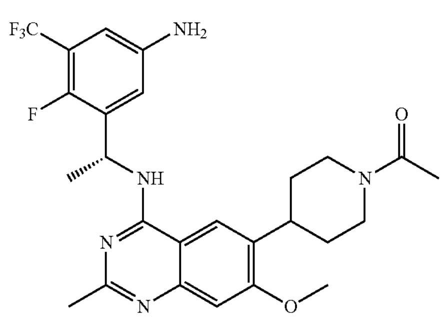 [SMILES: COc1cc2nc(C)nc(N[C@H](C)c3cc(N)cc(C(F)(F)F)c3F)c2cc1C1CCN(C(C)=O)CC1] | M + H = 520; $t_{ret}$ = 1.20 | LCMSBAS1 | 2 |
| I-279 | 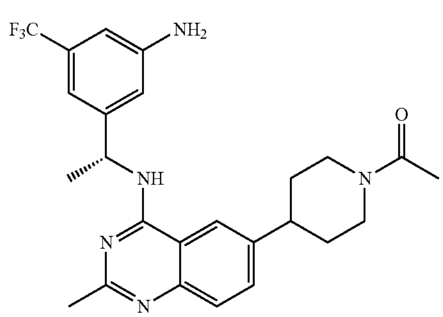 [SMILES: CC(=O)N1CCC(c2ccc3nc(C)nc(N[C@H](C)c4cc(N)cc(C(F)(F)F)c4)c3c2)CC1] | M + H = 472; $t_{ret}$ = 1.14 | LCMSBAS1 | |

TABLE 46-continued

| # | structure | [M + H]+ t_ret [min] | HPLC method | IC_50 (SOS1) [nM] |
|---|---|---|---|---|
| I-280 | 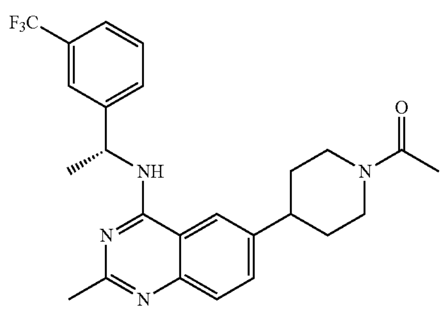 [SMILES: CC(=O)N1CCC(c2ccc3nc(C)nc(N[C@H](C)c4cccc(C(F)(F)F)c4)c3c2)CC1] | M + H = 457; t_ret = 1.28 | LCMSBAS1 | 17 |
| I-281 | 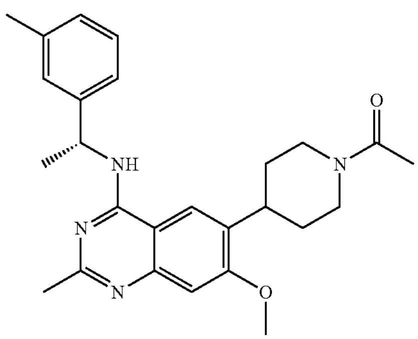 [SMILES: COc1cc2nc(C)nc(N[C@H](C)c3cccc(C)c3)c2cc1C1CCN(C(C)=O)CC1] | M + H = 433; t_ret = 1.24 | LCMSBAS1 | 12 |
| I-282 | 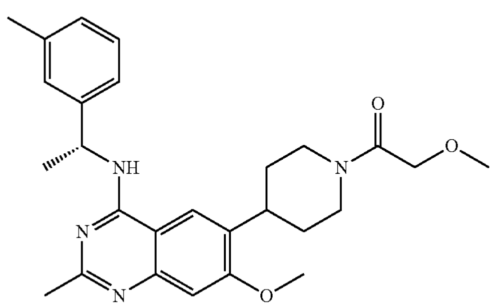 | M + H = 463; t_ret = 1.24 | LCMSBAS1 | 20 |
| I-283 | 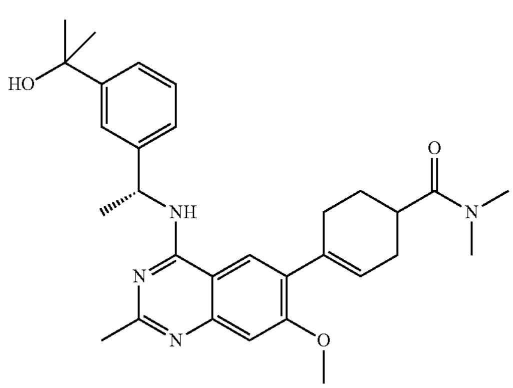 [SMILES: COc1cc2nc(C)nc(N[C@H](C)c3cccc(C(C)(C)O)c3)c2cc1C1=CCC(C(=O)N(C)C)CC1] | M + H = 503; t_ret = 0.61 | BFEC | |

TABLE 46-continued

| # | structure | [M + H]+ t$_{ret}$ [min] | HPLC method | IC$_{50}$ (SOS1) [nM] |
|---|---|---|---|---|
| I-284 | 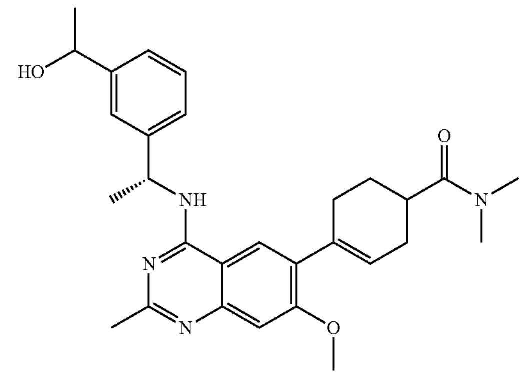 [SMILES: COc1cc2nc(C)nc(N[C@H](C)c3cccc(C(C)O)c3)c2cc1C1=CCC(C(=O)N(C)C)CC1] | M + H = 489; t$_{ret}$ = 0.58 | BFEC | |
| I-285 | 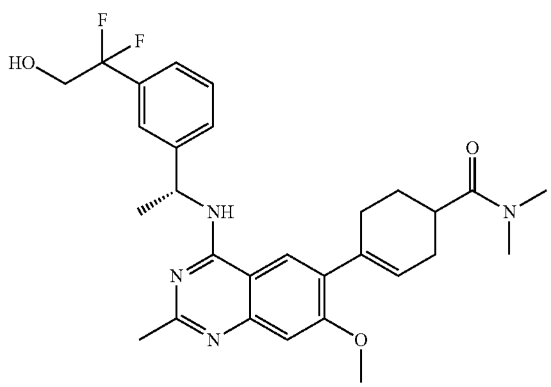 [SMILES: COc1cc2nc(C)nc(N[C@H](C)c3cccc(C(F)(F)CO)c3)c2cc1C1=CCC(C(=O)N(C)C)CC1] | M + H = 525; t$_{ret}$ = 1.18 | LCMABAS1 | 2 |
| I-286 | 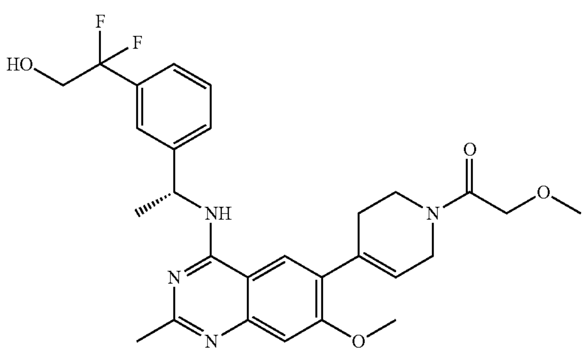 [SMILES: COCC(=O)N1CC=C(c2cc3c(N[C@H](C)c4cccc(C(F)(F)CO)c4)nc(C)nc3cc2OC)CC1] | M + H = 527; t$_{ret}$ = 1.10 | LCMABAS1 | 2 |
| I-287 | 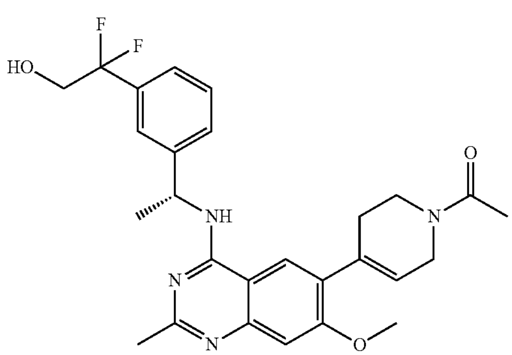 [SMILES: COc1cc2nc(C)nc(N[C@H](C)c3cccc(C(F)(F)CO)c3)c2cc1C1=CCN(C(C)=O)CC1] | M + H = 497; t$_{ret}$ = 1.11 | LCMABAS1 | 2 |

Experimental Procedure for the Synthesis of I-288

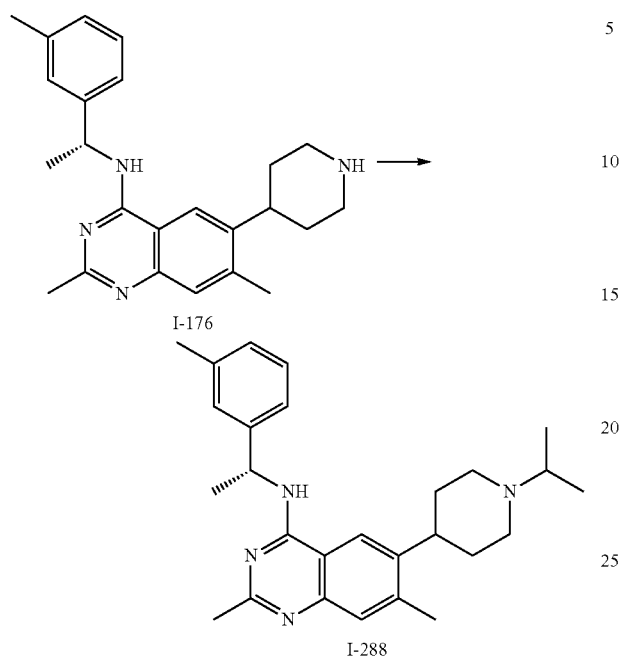

I-176 (45.0 mg, 120.0 µmol, 1.0 equiv.), propane-2-one (1.1 mL, 19.8 mmol, 164.5 equiv.) and acetic acid (15.0 µL) are dissolved in DCE (1 mL) and the reaction mixture is stirred for 30 min at rt. Then sodium triacetoxyborohydride (157.5 mg, 0.7 mmol, 6.0 equiv.) is added and the reaction mixture stirred at rt for 12 h. The reaction mixture is quenched with NaHCO$_3$ and extracted with DCM. The combined organic layers are dried over MgSO$_4$ filtered through celite and concentrated under reduced pressure. The crude product is purified by chromatography using acetonitrile/water giving the desired product I-288.

The following compounds (I) (table 47) are available in an analogous manner starting from different quinazolines (I) initially obtained (table 42). The crude product (I) is purified by chromatography if necessary.

TABLE 47

| # | structure | [M + H]$^+$ $t_{ret}$ [min] | HPLC method | IC$_{50}$ (SOS1) [nM] |
|---|---|---|---|---|
| I-288 | 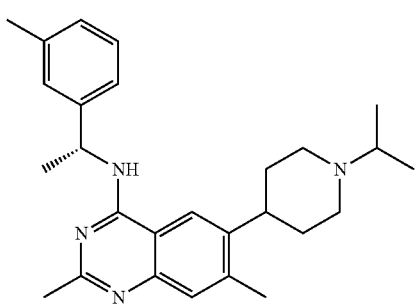 [SMILES: Cc1cccc([C@@H](C)Nc2nc(C)nc3cc(C)c(C4CCN(C(C)C)CC4)cc23)c1] | M + H = 417; $t_{ret}$ = 1.45 | LCMSBAS1 | 22 |

TABLE 47-continued

| # | structure | [M + H]+ $t_{ret}$ [min] | HPLC method | IC$_{50}$ (SOS1) [nM] |
|---|---|---|---|---|
| I-289 | 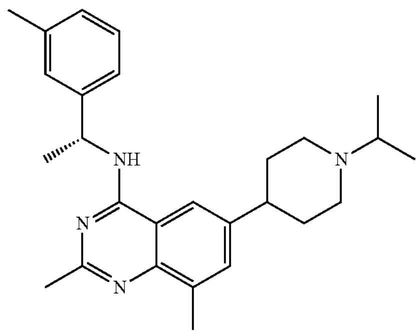 [SMILES: Cc1cccc([C@@H](C)Nc2nc(C)nc3c(C)cc(C4CCN(C(C)C)CC4)cc23)c1] | M + H = 417; $t_{ret}$ = 1.57 | LCMSBAS1 | 18 |
| I-290 | 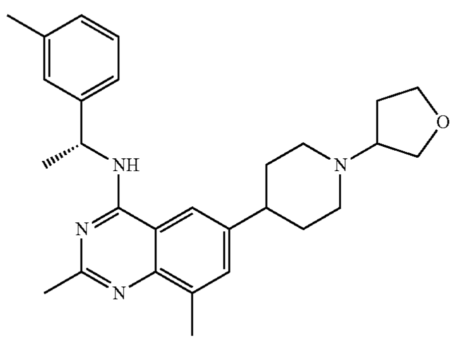 [SMILES: Cc1cccc([C@@H](C)Nc2nc(C)nc3c(C)cc(C4CCN(C5CCOC5)CC4)cc23)c1] | M + H = 445; $t_{ret}$ = 1.43 | LCMSBAS1 | 28 |
| I-291 | 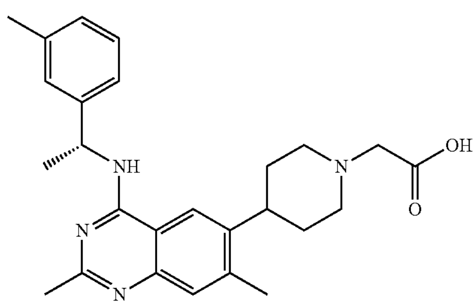 [SMILES: Cc1cccc([C@@H](C)Nc2nc(C)nc3cc(C)c(C4CCN(CC(=O)O)CC4)cc23)c1] | M + H = 433; $t_{ret}$ = 0.96 | LCMSBAS1 | 10 |
| I-292 | 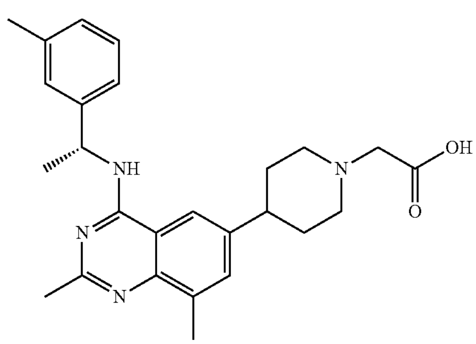 [SMILES: Cc1cccc([C@@H](C)Nc2nc(C)nc3c(C)cc(C4CCN(CC(=O)O)CC4)cc23)c1] | M + H = 433; $t_{ret}$ = 1.05 | LCMSBAS1 | 28 |

TABLE 47-continued
| # | structure | [M + H]+ $t_{ret}$ [min] | HPLC method | IC$_{50}$ (SOS1) [nM] |
|---|---|---|---|---|
| I-293 | 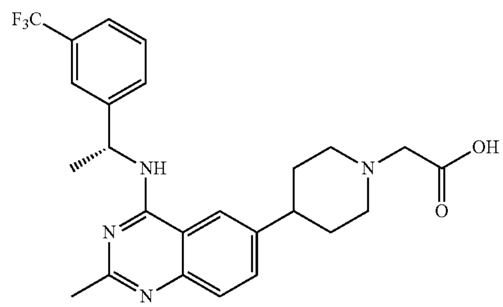 [SMILES: Cc1nc(N[C@H](C)c2cccc(C(F)(F)F)c2)c2cc(C3CCN(CC(=O)O)CC3)ccc2n1] | M + H = 473; $t_{ret}$ = 1.04 | LCMSBAS1 | 11 |
Experimental Procedure for the Synthesis of I-294 and I-295
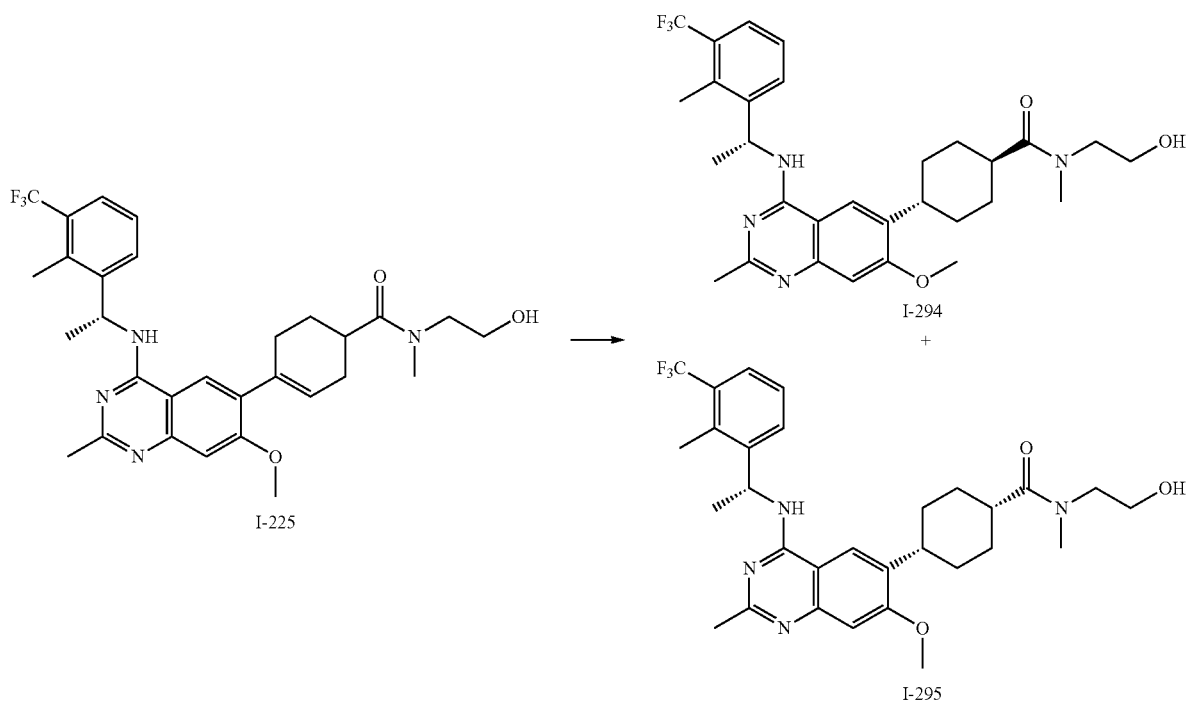 [SMILES: COc1cc2nc(C)nc(N[C@H](C)c3cccc(C(F)(F)F)c3C)c2cc1C1=CCC(C(=O)N(C)CCO)CC1 ; COc1cc2nc(C)nc(N[C@H](C)c3cccc(C(F)(F)F)c3C)c2cc1[C@H]1CC[C@@H](C(=O)N(C)CCO)CC1 ; COc1cc2nc(C)nc(N[C@H](C)c3cccc(C(F)(F)F)c3C)c2cc1[C@H]1CC[C@H](C(=O)N(C)CCO)CC1]

I-225 (43.0 mg, 73.0 μmol, 1.0 equiv.) is dissolved in MeOH (1 mL), Pd (20 mg, 10% on charcoal) is added and the reaction mixture is stirred for 12 h under $H_2$ (5 bar) atmosphere. The reaction mixture is filtered through celite and purified by chromatography using acetonitrile/water giving the desired products I-294 and I-295.

The following compounds (I) (table 48) are available in an analogous manner starting from different quinazolines (I) initially obtained (tables 27, 40, 44 and 46). The crude product (I) is purified by chromatography if necessary.

TABLE 47

| # | structure | $[M + H]^+$ $t_{ret}$ [min] | HPLC method | $IC_{50}$ (SOS1) [nM] |
|---|---|---|---|---|
| I-294 | 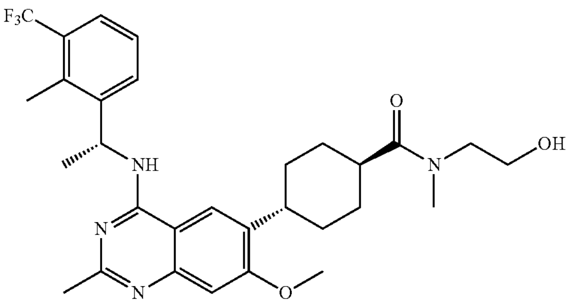 [SMILES: COc1cc2nc(C)nc(N[C@H](C)c3cccc(C(F)(F)F)c3C)c2cc1[C@H]1CC[C@H](C(=O)N(C)CCO)CC1] | M + H = 559; $t_{ret}$ = 1.35 | LCMSBAS1 | 5 |
| I-295 | 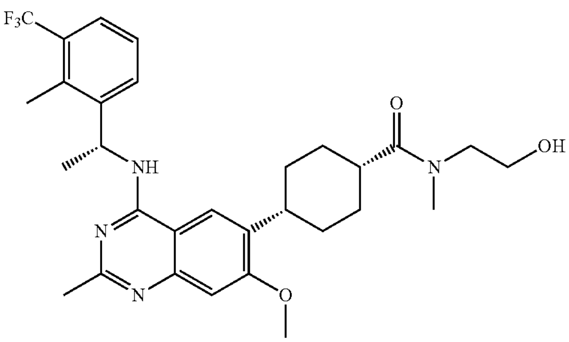 [SMILES: COc1cc2nc(C)nc(N[C@H](C)c3cccc(C(F)(F)F)c3C)c2cc1[C@H]1CC[C@@H](C(=O)N(C)CCO)CC1] | M + H = 559; $t_{ret}$ = 1.39 | LCMSBAS1 | |
| I-296 | 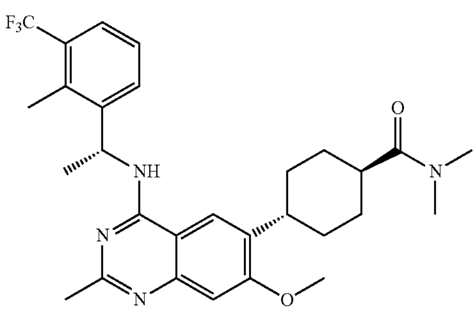 [SMILES: COc1cc2nc(C)nc(N[C@H](C)c3cccc(C(F)(F)F)c3C)c2cc1[C@H]1CC[C@H](C(=O)N(C)C)CC1] | M + H = 529; $t_{ret}$ = 1.44 | LCMSBAS1 | 7 |
| I-297 | 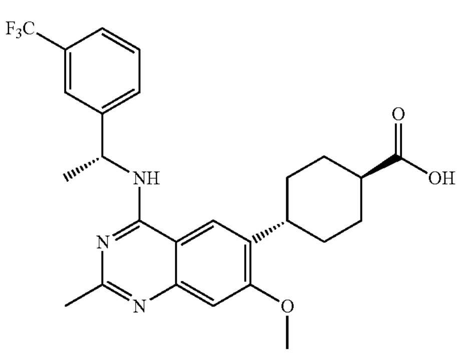 [SMILES: COc1cc2nc(C)nc(N[C@H](C)c3cccc(C(F)(F)F)c3)c2cc1[C@H]1CC[C@H](C(=O)O)CC1] | M + H = 488; $t_{ret}$ = 0.53 | BFEC | |

TABLE 47-continued

| # | structure | [M + H]+ t_ret [min] | HPLC method | IC_50 (SOS1) [nM] |
|---|---|---|---|---|
| I-298 | 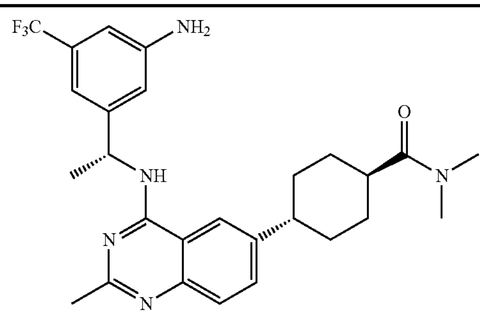 | M + H = 500; t_ret = 1.24 | LCMSBAS1 | 3 |
| I-299 | 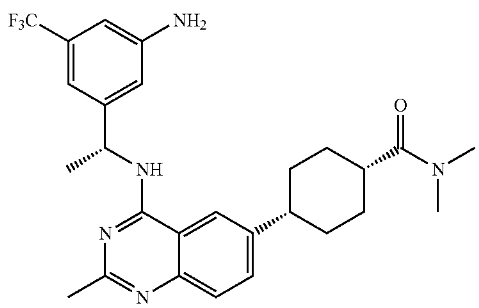 | M + H = 500; t_ret = 1.32 | LCMSBAS1 | 10 |
| I-300 | 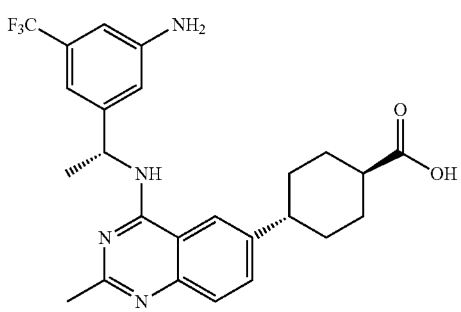 [SMILES: Cc1nc(N[C@H](C)c2cc(N)cc(C(F)(F)F)c2)c2cc([C@H]3CC[C@H](C(=O)O)CC3)ccc2n1] | M + H = 473; t_ret = 0.48 | BFEC | |
| I-301 | 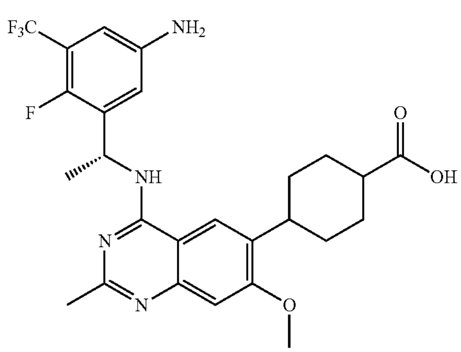 [SMILES: COc1cc2nc(C)nc(N[C@H](C)c3cc(N)cc(C(F)(F)F)c3F)c2cc1C1CCC(C(=O)O)CC1] | M + H = 521; t_ret = 0.49 | BFEC | |
| I-302 | 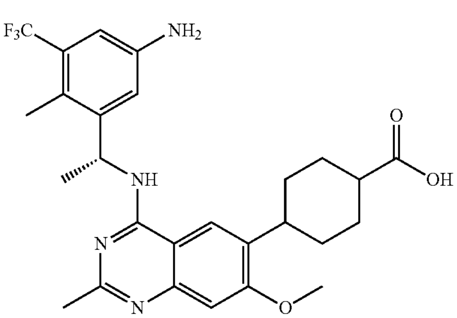 [SMILES: COc1cc2nc(C)nc(N[C@H](C)c3cc(N)cc(C(F)(F)F)c3C)c2cc1C1CCC(C(=O)O)CC1] | M + H = 517; t_ret = 0.53 | BFEC | |

TABLE 47-continued

| # | structure | [M + H]+ t_ret [min] | HPLC method | IC50 (SOS1) [nM] |
|---|---|---|---|---|
| I-303 | 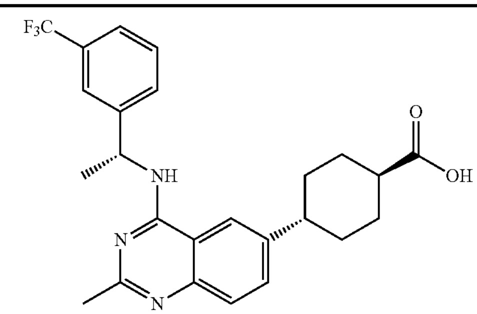 | M + H = 459; t_ret = 0.55 | BFEC | |
| I-304 | 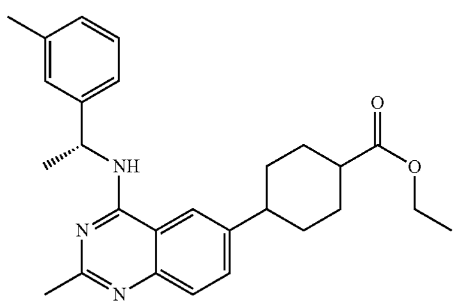 [SMILES: CCOC(=O)C1CCC(c2ccc3nc(C)nc(N[C@H](C)c4cccc(C)c4)c3c2)CC1] | M + H = 432.2; t_ret = 0.91 | BFEC | |
| I-305 | 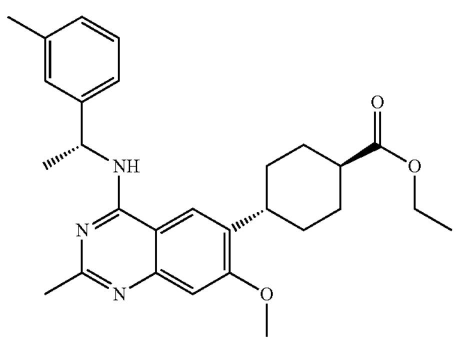 [SMILES: CCOC(=O)[C@H]1CC[C@H](c2cc3c(N[C@H](C)c4cccc(C)c4)nc(C)nc3cc2OC)CC1] | M + H = 462; t_ret = 0.90 | BFEC | |
| I-306 | 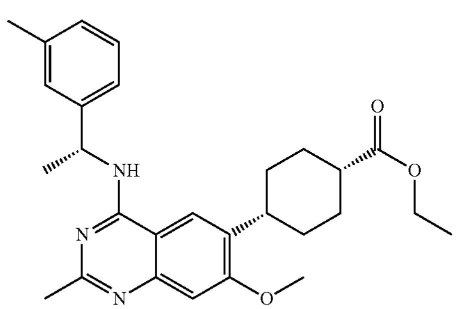 [SMILES: CCOC(=O)[C@H]1CC[C@@H](c2cc3c(N[C@H](C)c4cccc(C)c4)nc(C)nc3cc2OC)CC1] | M + H = 462; t_ret = 0.92 | BFEC | |
| I-307 | 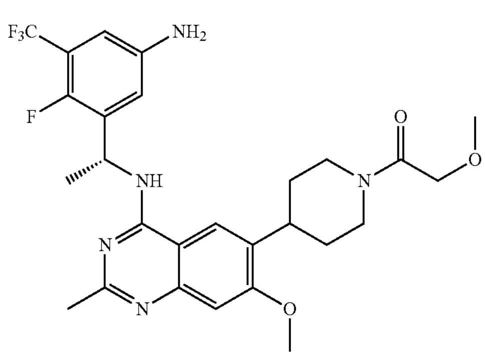 [SMILES: COCC(=O)N1CCC(c2cc3c(N[C@H](C)c4cc(N)cc(C(F)(F)F)c4F)nc(C)nc3cc2OC)CC1] | M + H = 550; t_ret = 1.21 | LCMSBAS1 | 3 |

TABLE 47-continued
| # | structure | [M + H]+ t_ret [min]; HPLC method | IC_50 (SOS1) [nM] |
|---|---|---|---|
| I-308 | 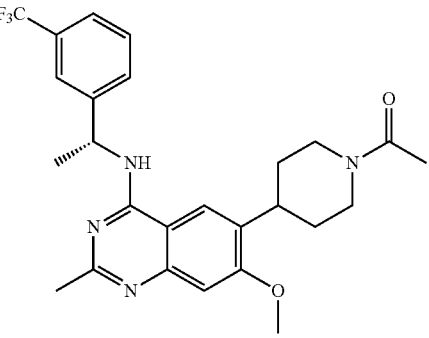 | M + H = 487; LCMSBAS1<br>t_ret = 1.30 | 9 |
| I-309 | 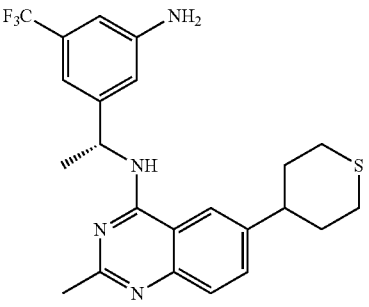 [SMILES: Cc1nc(N[C@H](C)c2cc(N)cc(C(F)(F)F)c2)c2cc(C3CCSCC3)ccc2n1] | M + H = 447; LCMSBAS1<br>t_ret = 1.41 | |
| I-310 | 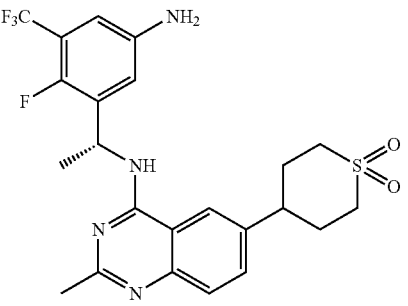 [SMILES: Cc1nc(N[C@H](C)c2cc(N)cc(C(F)(F)F)c2F)c2cc(C3CCS(=O)(=O)CC3)ccc2n1] | M + H = 497; LCMSBAS1<br>t_ret = 1.16 | 7 |
| I-311 | 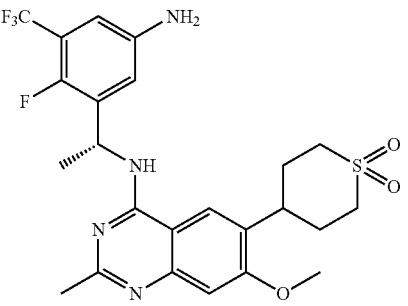 [SMILES: COc1cc2nc(C)nc(N[C@H](C)c3cc(N)cc(C(F)(F)F)c3F)c2cc1C1CCS(=O)(=O)CC1] | M + H = 527; LCMSBAS1<br>t_ret = 1.20 | 6 |

TABLE 47-continued

| # | structure | [M + H]+ $t_{ret}$ [min] | HPLC method | IC$_{50}$ (SOS1) [nM] |
|---|---|---|---|---|
| I-312 | 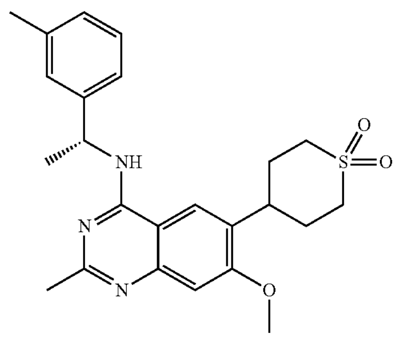 [SMILES: COc1cc2nc(C)nc(N[C@H](C)c3cccc(C)c3)c2cc1C1CCS(=O)(=O)CC1] | M + H = 440; $t_{ret}$ = 1.24 | LCMSBAS1 | 18 |
| I-313 | 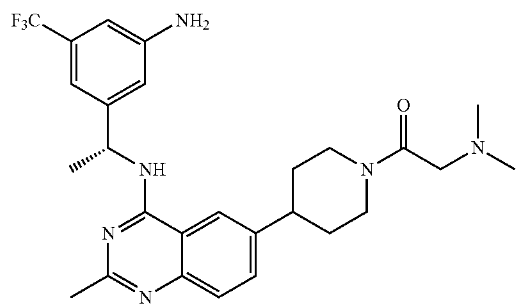 [SMILES: Cc1nc(N[C@H](C)c2cc(N)cc(C(F)(F)F)c2)c2cc(C3CCN(C(=O)CN(C)C)CC3)ccc2n1] | M + H = 515; $t_{ret}$ = 1.17 | LCMSBAS1 | 3 |
| I-314 | 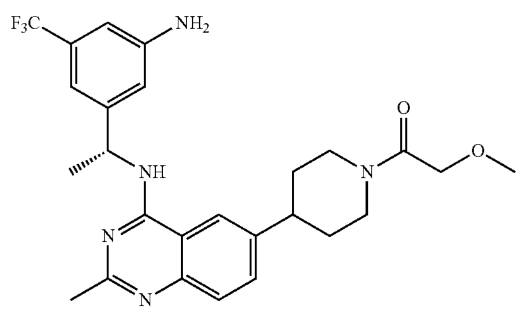 [SMILES: COCC(=O)N1CCC(c2ccc3nc(C)nc(N[C@H](C)c4cc(N)cc(C(F)(F)F)c4)c3c2)CC1] | M + H = 502; $t_{ret}$ = 1.16 | LCMSBAS1 | 2 |
| I-315 | 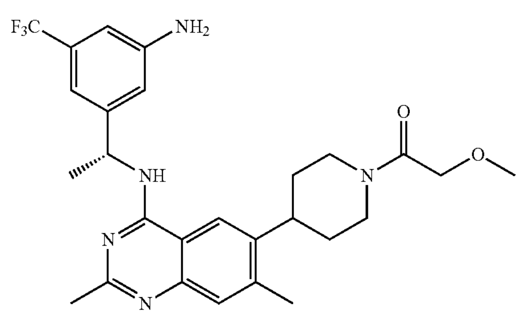 [SMILES: COCC(=O)N1CCC(c2cc3c(N[C@H](C)c4cc(N)cc(C(F)(F)F)c4)nc(C)nc3cc2C)CC1] | M + H = 516; $t_{ret}$ = 1.19 | LCMSBAS1 | 3 |

TABLE 47-continued

| # | structure | [M + H]+ $t_{ret}$ [min] | HPLC method | IC$_{50}$ (SOS1) [nM] |
|---|---|---|---|---|
| I-316 | 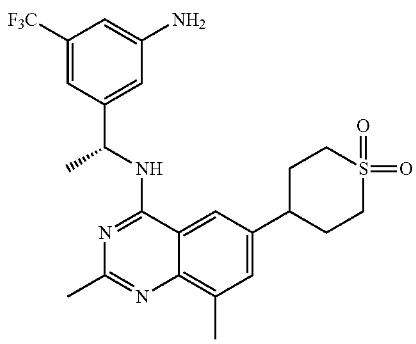 [SMILES: Cc1nc(N[C@H](C)c2cc(N)cc(C(F)(F)F)c2)c2cc(C3CCS(=O)(=O)CC3)cc(C)c2n1] | M + H = 493; $t_{ret}$ = 1.30 | LCMSBAS1 | 6 |
| I-317 | 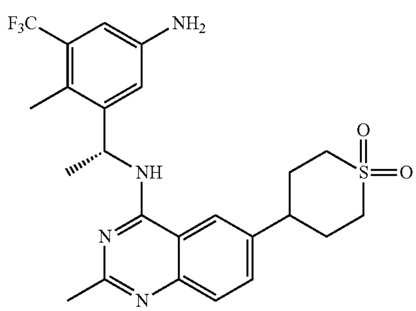 [SMILES: Cc1nc(N[C@H](C)c2cc(N)cc(C(F)(F)F)c2C)c2cc(C3CCS(=O)(=O)CC3)ccc2n1] | M + H = 493; $t_{ret}$ = 1.25 | LCMSBAS1 | 4 |
| I-318 | 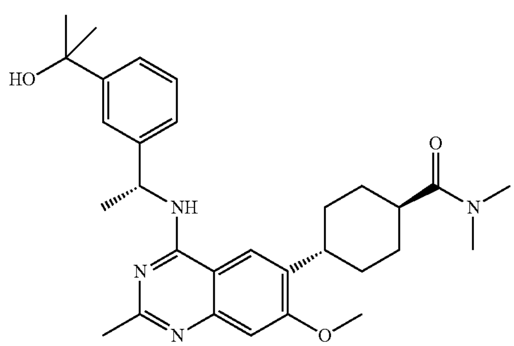 | M + H = 491; $t_{ret}$ = 1.12 | LCMSBAS1 | 8 |
| I-319 | 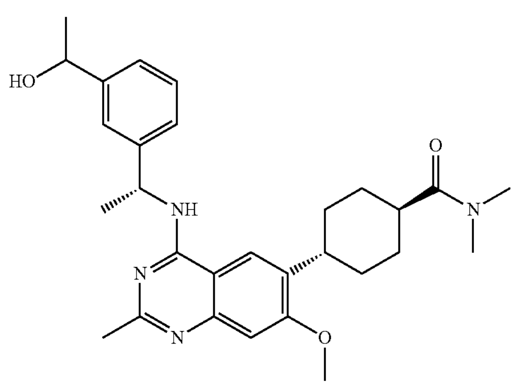 | M + H = 502; $t_{ret}$ = 1.18 | LCMSBAS1 | 13 |

TABLE 47-continued

| # | structure | [M + H]+ $t_{ret}$ [min] | HPLC method | IC$_{50}$ (SOS1) [nM] |
|---|---|---|---|---|
| I-320 | 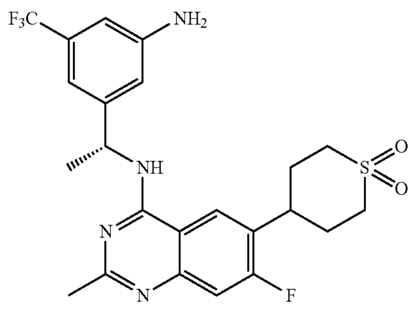 [SMILES: Cc1nc(N[C@H](C)c2cc(N)cc(C(F)(F)F)c2)c2cc(C3CCS(=O)(=O)CC3)c(F)cc2n1] | M + H = 497; $t_{ret}$ = 1.23 | LCMSBAS1 | 4 |
| I-321 | 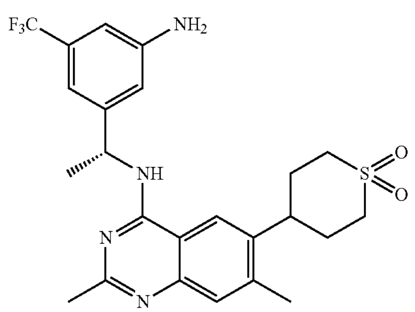 [SMILES: Cc1nc(N[C@H](C)c2cc(N)cc(C(F)(F)F)c2)c2cc(C3CCS(=O)(=O)CC3)c(C)cc2n1] | M + H = 493; $t_{ret}$ = 1.21 | LCMSBAS1 | 3 |

Experimental Procedure for the Synthesis of I-322

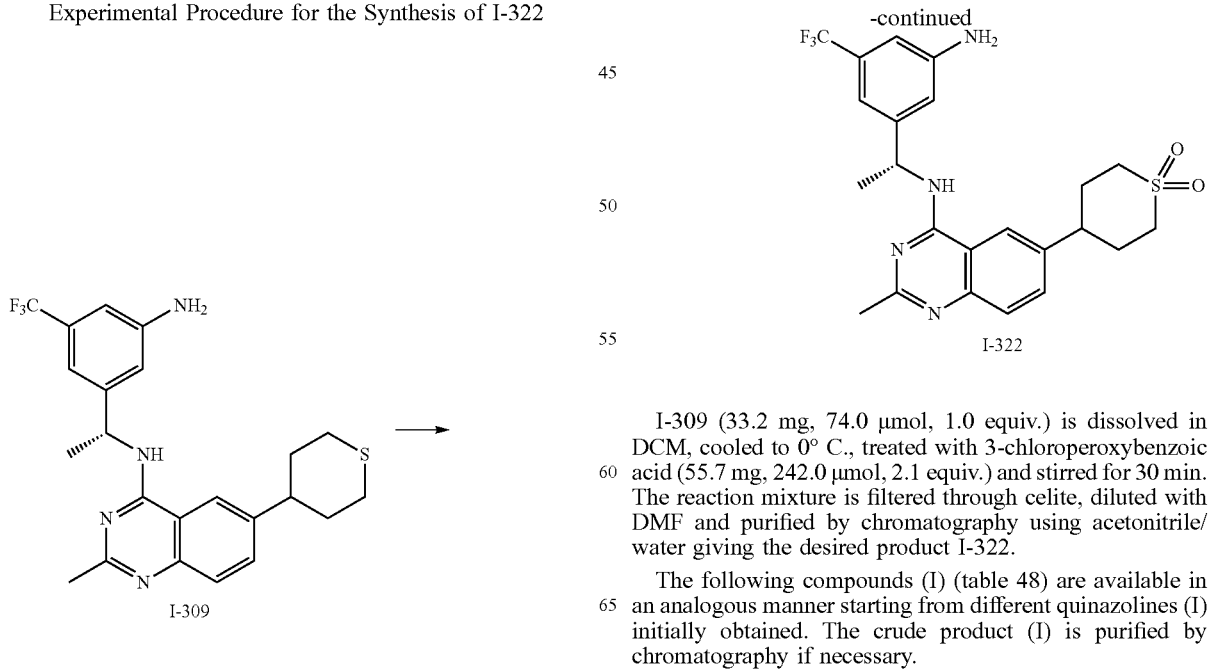

I-309 (33.2 mg, 74.0 µmol, 1.0 equiv.) is dissolved in DCM, cooled to 0° C., treated with 3-chloroperoxybenzoic acid (55.7 mg, 242.0 µmol, 2.1 equiv.) and stirred for 30 min. The reaction mixture is filtered through celite, diluted with DMF and purified by chromatography using acetonitrile/water giving the desired product I-322.

The following compounds (I) (table 48) are available in an analogous manner starting from different quinazolines (I) initially obtained. The crude product (I) is purified by chromatography if necessary.

TABLE 48

| # | structure | [M + H]+ $t_{ret}$ [min] | HPLC method | IC$_{50}$ (SOS1) [nM] |
|---|---|---|---|---|
| I-322 | 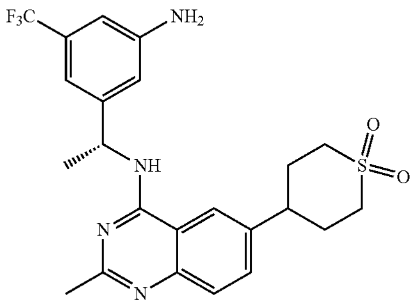 [SMILES: Cc1nc(N[C@H](C)c2cc(N)cc(C(F)(F)F)c2)c2cc(C3CCS(=O)(=O)CC3)ccc2n1] | M + H = 479; $t_{ret}$ = 1.17 | LCMSBAS1 | 3 |
| I-323 | 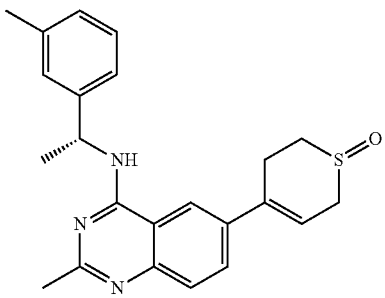 [SMILES: Cc1cccc([C@@H](C)Nc2nc(C)nc3ccc(C4=CCS(=O)CC4)cc23)c1] | M + H = 392; $t_{ret}$ = 0.60 | BFEC | |
| I-324 | 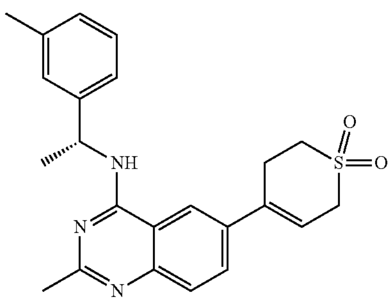 [SMILES: Cc1cccc([C@@H](C)Nc2nc(C)nc3ccc(C4=CCS(=O)(=O)CC4)cc23)c1] | M + H = 410; $t_{ret}$ = 1.19 | LCMSBAS1 | |
| I-325 | 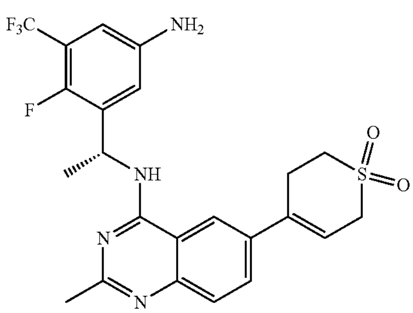 [SMILES: Cc1nc(N[C@H](C)c2cc(N)cc(C(F)(F)F)c2F)c2cc(C3=CCS(=O)(=O)CC3)ccc2n1] | M + H = 495; $t_{ret}$ = 0.65 | BFEC | |
| I-326 | 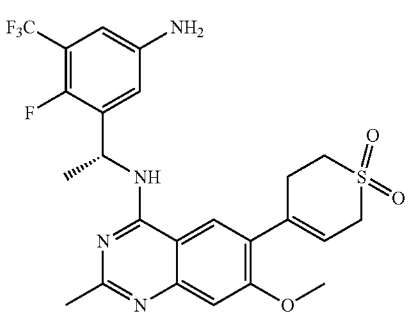 [SMILES: COc1cc2nc(C)nc(N[C@H](C)c3cc(N)cc(C(F)(F)F)c3F)c2cc1C1=CCS(=O)(=O)CC1] | M + H = 525; $t_{ret}$ = 0.68 | BFEC | |

TABLE 48-continued

| # | structure | [M + H]+ $t_{ret}$ [min] HPLC method | IC$_{50}$ (SOS1) [nM] |
|---|---|---|---|
| I-327 | 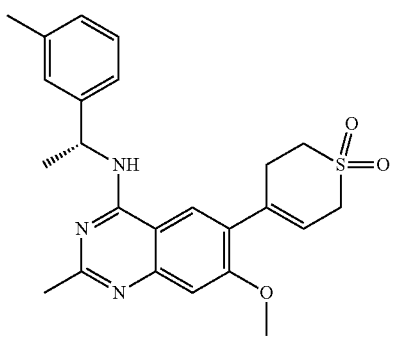 [SMILES: COc1cc2nc(C)nc(N[C@H](C)c3cccc(C)c3)c2cc1C1=CCS(=O)(=O)CC1] | M + H = 438; BFEC $t_{ret}$ = 0.67 | |
| I-328 | 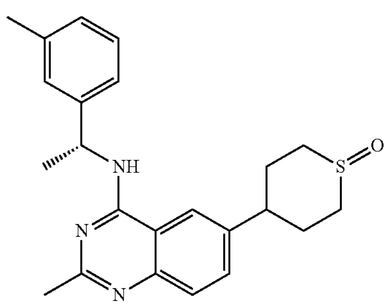 [SMILES: Cc1cccc([C@@H](C)Nc2nc(C)nc3ccc(C4CCS(=O)CC4)cc23)c1] | M + H = 394; LCMSBAS1 $t_{ret}$ = 1.11 | |

Experimental Procedure for the Synthesis of I-329

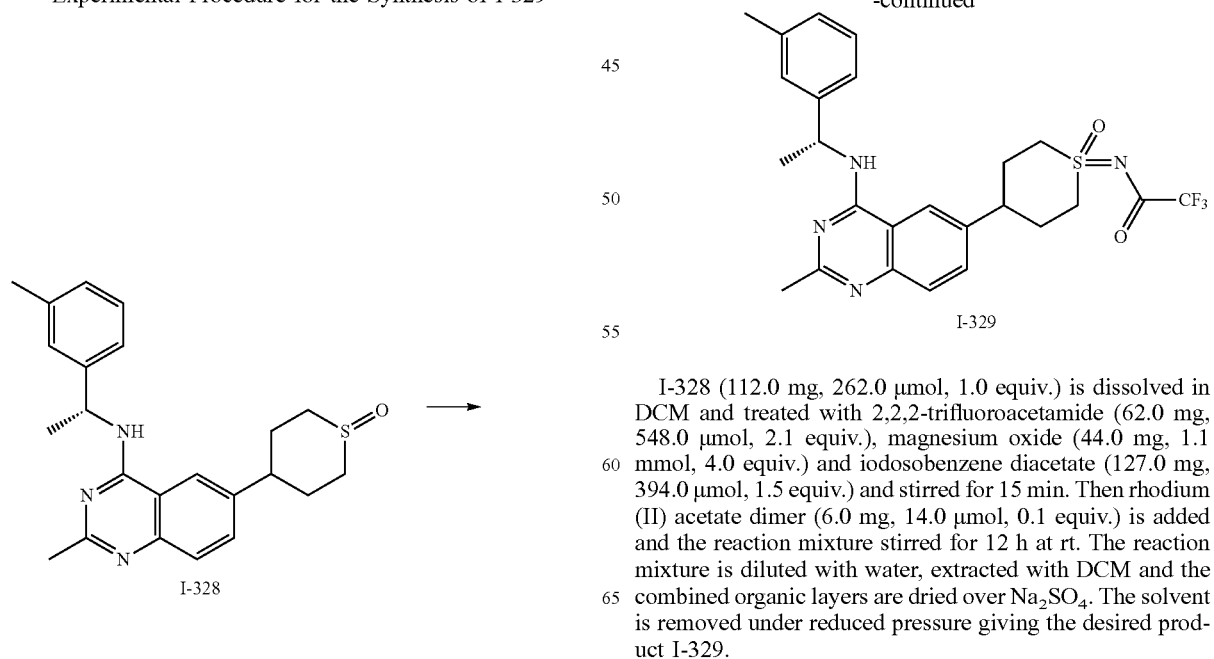

I-328 (112.0 mg, 262.0 µmol, 1.0 equiv.) is dissolved in DCM and treated with 2,2,2-trifluoroacetamide (62.0 mg, 548.0 µmol, 2.1 equiv.), magnesium oxide (44.0 mg, 1.1 mmol, 4.0 equiv.) and iodosobenzene diacetate (127.0 mg, 394.0 µmol, 1.5 equiv.) and stirred for 15 min. Then rhodium (II) acetate dimer (6.0 mg, 14.0 µmol, 0.1 equiv.) is added and the reaction mixture stirred for 12 h at rt. The reaction mixture is diluted with water, extracted with DCM and the combined organic layers are dried over Na$_2$SO$_4$. The solvent is removed under reduced pressure giving the desired product I-329.

TABLE 49

| # | structure | [M + H]+ $t_{ret}$ [min] | HPLC method | IC$_{50}$ (SOS1) [nM] |
|---|---|---|---|---|
| I-329 | 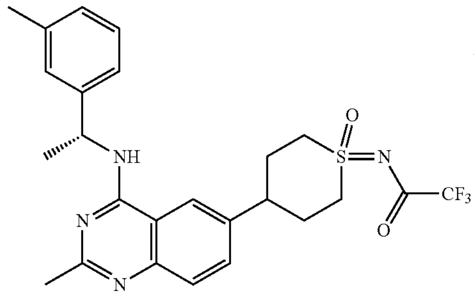 [SMILES: Cc1cccc([C@@H](C)Nc2nc(C)nc3ccc(C4CCS(=O)(=NC(=O)C(F)(F)F)CC4)cc23)c1] | M + H = 505; $t_{ret}$ = 0.80 | BFEC | |

Experimental Procedure for the Synthesis of I-330

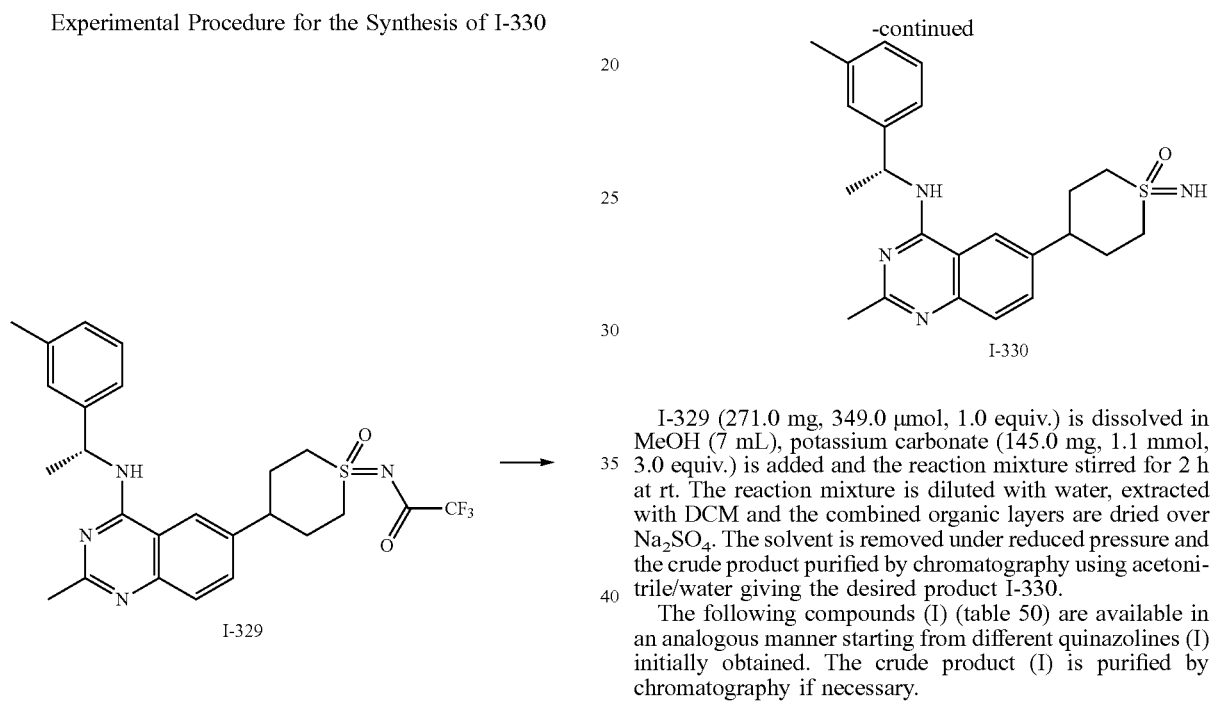

I-329 (271.0 mg, 349.0 µmol, 1.0 equiv.) is dissolved in MeOH (7 mL), potassium carbonate (145.0 mg, 1.1 mmol, 3.0 equiv.) is added and the reaction mixture stirred for 2 h at rt. The reaction mixture is diluted with water, extracted with DCM and the combined organic layers are dried over Na$_2$SO$_4$. The solvent is removed under reduced pressure and the crude product purified by chromatography using acetonitrile/water giving the desired product I-330.

The following compounds (I) (table 50) are available in an analogous manner starting from different quinazolines (I) initially obtained. The crude product (I) is purified by chromatography if necessary.

TABLE 50

| # | structure | [M + H]+ $t_{ret}$ [min] | HPLC method | IC$_{50}$ (SOS1) [nM] |
|---|---|---|---|---|
| I-330 | 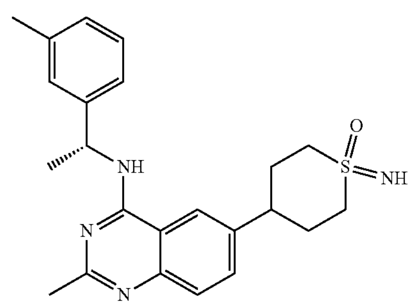 [SMILES: Cc1cccc([C@@H](C)Nc2nc(C)nc3ccc(C4CCS(=N)(=O)CC4)cc23)c1] | M + H = 409; $t_{ret}$ = 1.08 | LCMSBAS1 | 20* |

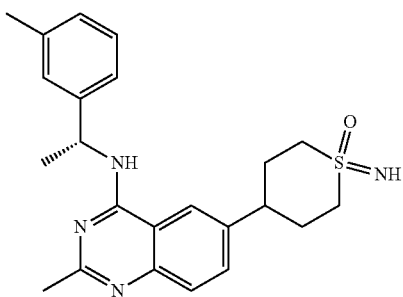

TABLE 50-continued

| # | structure | [M + H]+ $t_{ret}$ [min] | HPLC method | IC$_{50}$ (SOS1) [nM] |
|---|---|---|---|---|
| I-331 | 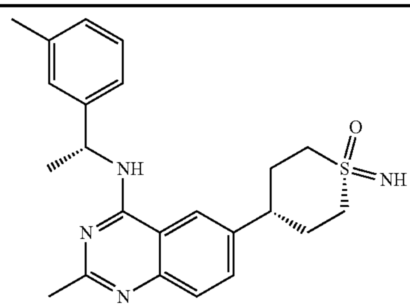 | M + H = 409; $t_{ret}$ = 1.10 | LCMSBAS1 | 25* |
| I-332 | 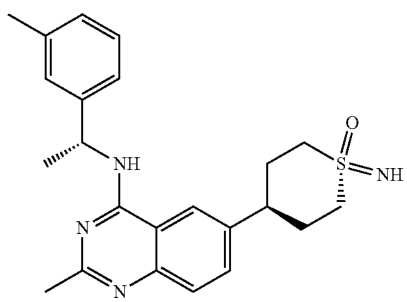 [SMILES: Cc1cccc([C@@H](C)Nc2nc(C)nc3ccc([C@H]4CC[S@](=N)(=O)CC4)cc23)c1] | M + H = 409; $t_{ret}$ = 1.10 | LCMSBAS1 | 18* |

Experimental Procedure for the Synthesis of I-333

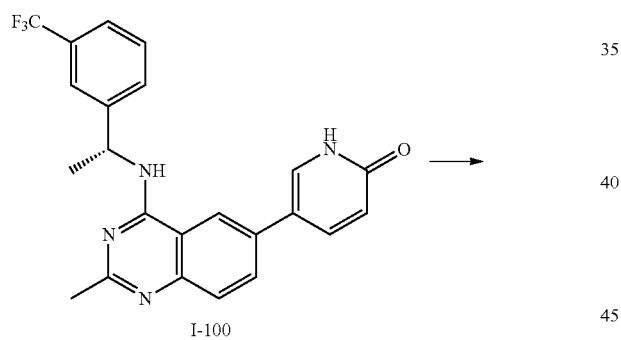

I-100

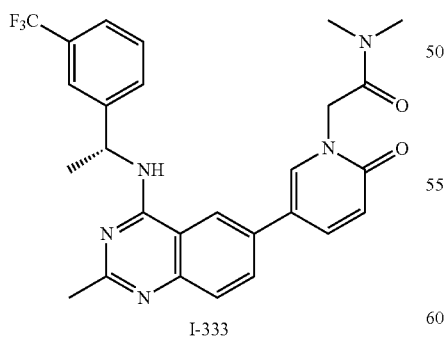

I-333

I-100 (40.0 mg, 94.0 μmol, 1.0 equiv.) is dissolved in DMF, NaH (15.0 mg, 350.0 μmol, 3.8 equiv.) is added and the reaction mixture stirred at rt for 10 min. 2-Bromo-N,N-dimethylacetamide (16.5 mg, 99.0 μmol, 1.1 equiv.) is added dropwise and the reaction mixture stirred 1 h at rt. The reaction is quenched with MeOH, filtered through celite and the solvent removed under reduced pressure. The crude product is purified by chromatography using acetonitrile/water giving the desired product I-333.

The following compounds (I) (table 51) are available in an analogous manner starting from different quinazolines (I) initially obtained (table 40). The crude product (I) is purified by chromatography if necessary.

TABLE 51

| # | structure | [M + H]+ $t_{ret}$ [min] | HPLC method | IC$_{50}$ (SOS1) [nM] |
|---|---|---|---|---|
| I-333 | 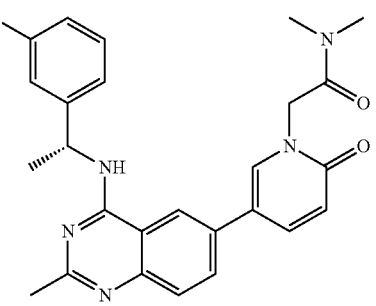 | M + H = 510; $t_{ret}$ = 1.20 | LCMSBAS1 | 26* |
| I-334 | 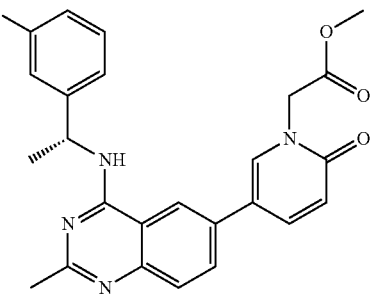 | M + H = 497; $t_{ret}$ = 1.28 | LCMSBAS1 | |
| I-335 | 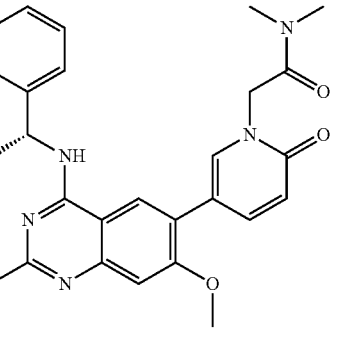 | M + H = 486; $t_{ret}$ = 1.15 | LCMSBAS1 | 27* |
| I-336 | 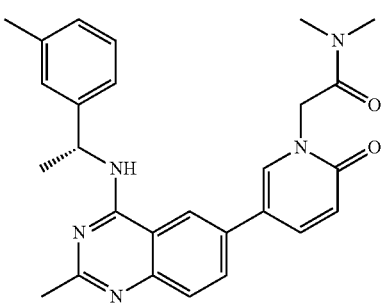 | M + H = 456; $t_{ret}$ = 1.14 | LCMSBAS1 | 26* |

TABLE 51-continued

| # | structure | [M + H]+ t_ret [min] | HPLC method | IC_50 (SOS1) [nM] |
|---|---|---|---|---|
| I-337 | 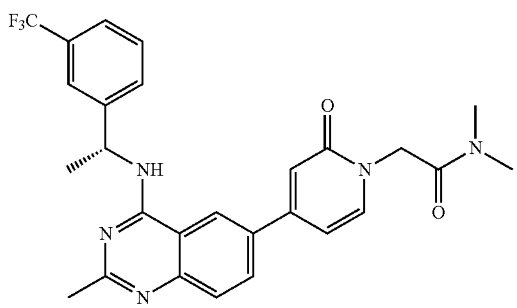 [SMILES: Cc1nc(N[C@H](C)c2cccc(C(F)(F)F)c2)c2cc(-c3ccn(CC(=O)N(C)C)c(=O)c3)ccc2n1] | M + H = 510; t_ret = 1.21 | LCMSBAS1 | 37* |
| I-338 | 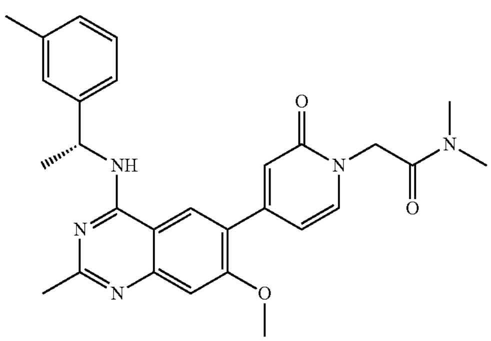 | M + H = 486; t_ret = 1.15 | LCMSBAS1 | 39* |
| I-339 | 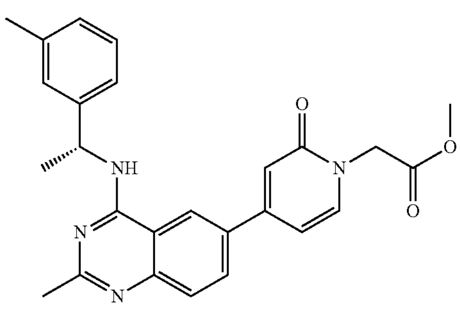 | M + H = 443; t_ret = 0.95 | VAB | |
| I-340 | 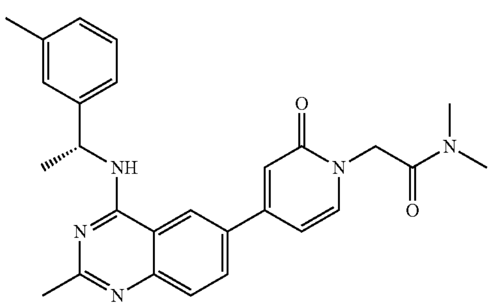 | M + H = 456; t_ret = 1.14 | LCMSBAS1 | 1* |

Experimental Procedure for the Synthesis of I-341

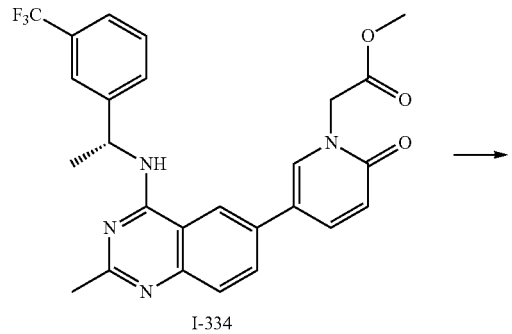

I-334

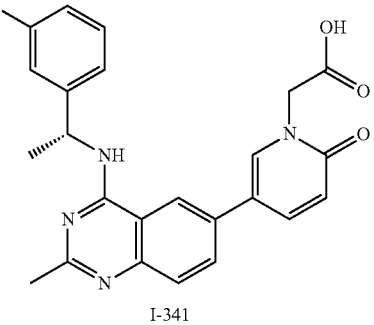

I-341

I-334 (200.0 mg, 0.4 mmol, 1.0 equiv.) is dissolved in MeOH (10 mL), NaOH (1.0 mL, 1M, 1.0 mmol, 1.0 equiv.) is added and the reaction mixture stirred at rt for 18 h. The reaction is acidified with HCl and the precipitate filtered off giving the desired product I-341.

The following compounds (I) (table 52) are available in an analogous manner starting from different quinazolines (I) initially obtained. The crude product (I) is purified by chromatography if necessary.

TABLE 52

| # | structure | [M + H]+ t_ret [min] | HPLC method | IC50 (SOS1) [nM] |
|---|-----------|----------------------|-------------|------------------|
| I-341 | 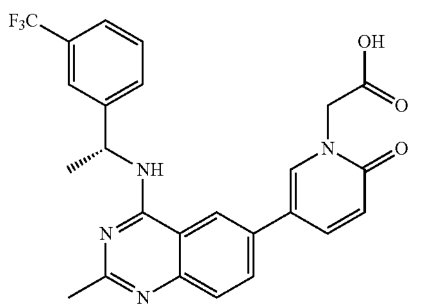 [SMILES: Cc1nc(N[C@H](C)c2cccc(C(F)(F)F)c2)c2cc(-c3ccc(=O)n(CC(=O)O)c3)ccc2n1] | M + H = 483; t_ret = 0.98 | LCMSBAS1 | 35* |
| I-342 | 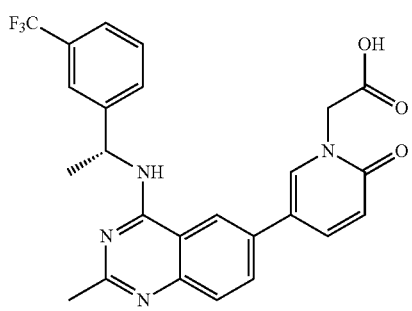 | M + H = 429; t_ret = 0.94 | LCMSBAS1 | 48* |
| | 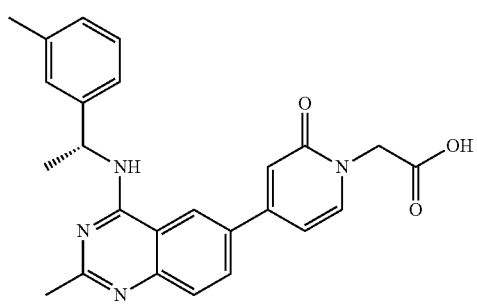 [SMILES: Cc1cccc([C@@H](C)Nc2nc(C)nc3ccc(-c4ccn(CC(=O)O)c(=O)c4)cc23)c1] | | | |

Experimental Procedure for the Synthesis of I-343

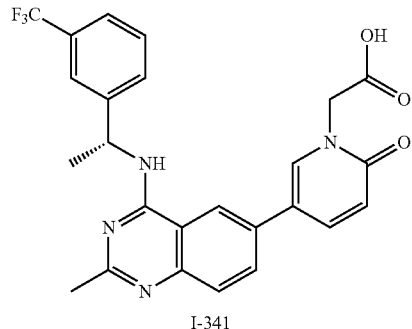

I-341

→

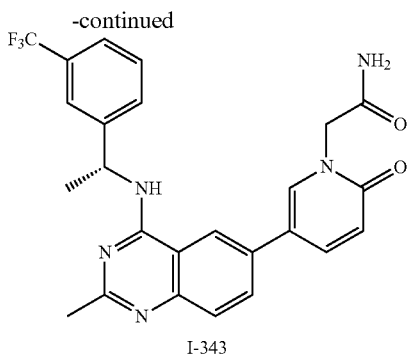

I-343

I-341 (40.0 mg, 0.08 mmol, 1.0 equiv.) is dissolved in DMF (0.8 mL), treated with TEA (23.0 μL, 0.16 mmol, 2.0 equiv.) and TBTU (33.0 mg, 0.1 mmol, 1.3 equiv.) and stirred for 15 min at rt. Then $NH_3$ (27.5 μL, 0.4 mmol, 5.0 equiv.) is added and the reaction mixture stirred at rt for 18 h. The reaction is filtered through celite and purified by chromatography giving the desired product I-343.

The following compounds I (table 53) are available in an analogous manner starting from different quinazolines (I) initially obtained. The crude product (I) is purified by chromatography if necessary.

TABLE 53

| # | structure | $[M + H]^+$ $t_{ret}$ [min] | HPLC method | $IC_{50}$ (SOS1) [nM] |
|---|-----------|------------------------------|-------------|------------------------|
| I-343 | 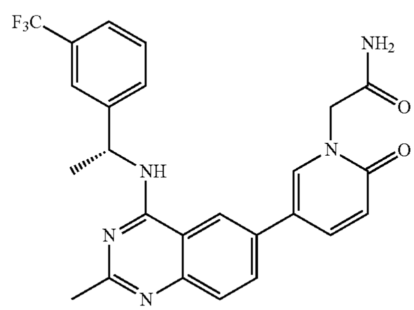 [SMILES: Cc1nc(N[C@H](C)c2cccc(C(F)(F)F)c2)c2cc(-c3ccc(=O)n(CC(N)=O)c3)ccc2n1] | M + H = 482; $t_{ret}$ = 1.15 | LCMSBAS1 | 40* |
| I-344 | 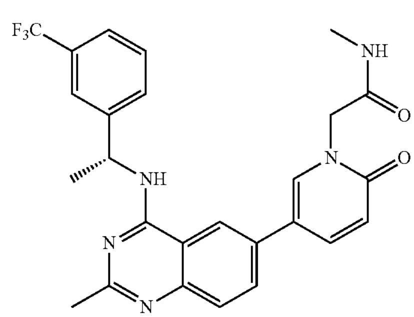 [SMILES: CNC(=O)Cn1cc(-c2ccc3nc(C)nc(N[C@H](C)c4cccc(C(F)(F)F)c4)c3c2)ccc1=O] | M + H = 496; $t_{ret}$ = 1.18 | LCMSBAS1 | 37* |

Experimental Procedure for the Synthesis of I-345

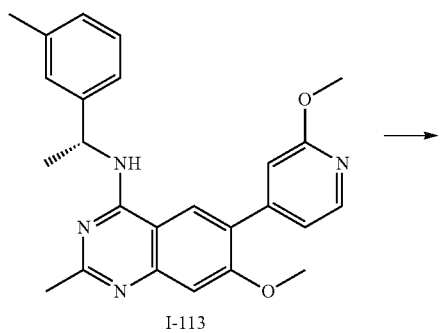
I-113

I-113 (100.0 mg, 241.0 µmol, 1.0 equiv.), lithium chloride (51.1 mg, 1.2 mmol, 5.0 equiv.) and p-toluene sulfonic acid (202.7 mg, 1.2 mmol, 5.0 equiv.) are dissolved in DMF (0.5 mL) and stirred at 120° C. for 1 h. The reaction mixture is basified with $NH_3$, filtered through celite and purified by chromatography using acetonitrile/water giving the desired product I-345.

The following compounds (I) (table 54) are available in an analogous manner starting from different quinazolines (I) initially obtained. The crude product (I) is purified by chromatography if necessary.

TABLE 54

| # | structure | [M + H]$^+$ $t_{ret}$ [min] | HPLC method | IC$_{50}$ (SOS1) [nM] |
|---|---|---|---|---|
| I-345 | 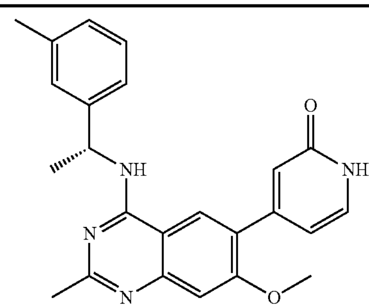 | M + H = 401; $t_{ret}$ = 1.14 | LCMSBAS1 | |
| I-346 | 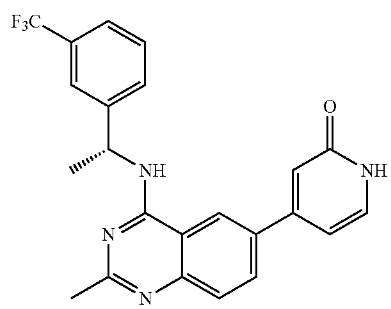 [SMILES: Cc1nc(N[C@H](C)c2cccc(C(F)(F)F)c2)c2cc(-c3cc[nH]c(=O)c3)ccc2n1] | M + H = 425; $t_{ret}$ = 1.20 | LCMSBAS1 | |

-continued

I-345

Experimental Procedure for the Synthesis of I-347

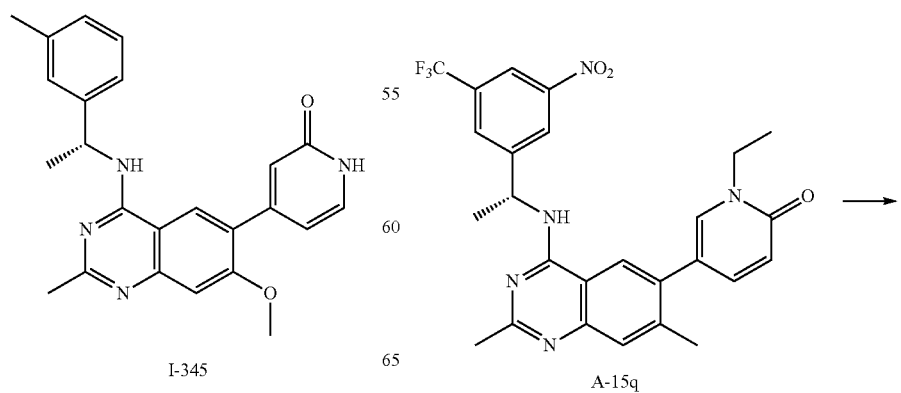
A-15q

-continued

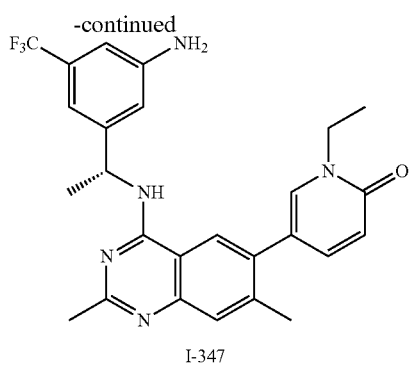

I-347

Iron (36.8 mg, 66.0 μmol, 7.5 equiv.) is suspended in EtOH (0.5 mL), treated with 1M HCl (88.0 μL, 88.0 μmol, 1.0 equiv.) and stirred for 10 min at 50° C. Then A-15q (45.0 mg, 88.0 μmol, 1.0 equiv.) is added and the reaction mixture stirred for 4 h at 80° C. The reaction is diluted with DCM and extracted with NaHCO$_3$ solution. The combined organic layers are dried over MgSO$_4$, filtered and the solvent removed under reduced pressure giving the desired product I-347.

The following compounds (I) (table 55) are available in an analogous manner starting from different quinazolines A-15. The crude product (I) is purified by chromatography if necessary.

TABLE 55

| structure | [M + H]$^+$ <br> t$_{ret}$ [min] | HPLC method | IC$_{50}$ (SOS1) [nM] |
|---|---|---|---|
| I-347 | M + H = 482; <br> t$_{ret}$ = 1.18 | LCMSBAS1 | 6 |
| I-348 | M + H = 468; <br> t$_{ret}$ = 1.14 | LCMSBAS1 | 7 |
| I-349 | M + H = 482; <br> t$_{ret}$ = 1.19 | LCMSBAS1 | 5 |

TABLE 55-continued

| structure | [M + H]+ $t_{ret}$ [min] | HPLC method | IC$_{50}$ (SOS1) [nM] |
|---|---|---|---|
| I-350 | M + H = 498; $t_{ret}$ = 1.17 | LCMSBAS1 | 9 |
| I-351 | M + H = 512; $t_{ret}$ = 1.21 | LCMSBAS1 | 13 |
| I-352 | M + H = 514; $t_{ret}$ = 1.24 | LCMSBAS1 | 2 |
| I-353 | M + H = 585; $t_{ret}$ = 1.20 | LCMSBAS1 | 2 |

TABLE 55-continued

| structure | [M + H]+ $t_{ret}$ [min] | HPLC method | IC$_{50}$ (SOS1) [nM] |
|---|---|---|---|
| I-354 | M + H = 585; $t_{ret}$ = 1.27 | LCMSBAS1 | 22 |
| I-355 | M + H = 530; $t_{ret}$ = 1.26 | LCMSBAS1 | 2 |
| I-356 | M + H = 530; $t_{ret}$ = 1.36 | LCMSBAS1 | 34 |
| I-357 | M + H = 574; $t_{ret}$ = 1.29 | LCMSBAS1 | 3 |

TABLE 55-continued
| structure | [M + H]+ t_ret [min] | HPLC method | IC$_{50}$ (SOS1) [nM] |
|---|---|---|---|
| I-358 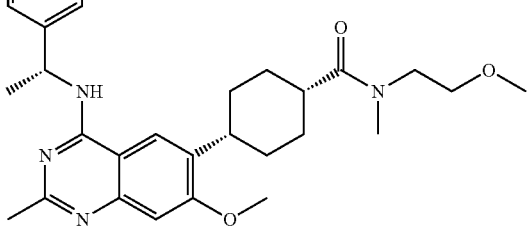 | M + H = 574; t_ret = 1.39 | LCMSBAS1 | 49 |
| I-359 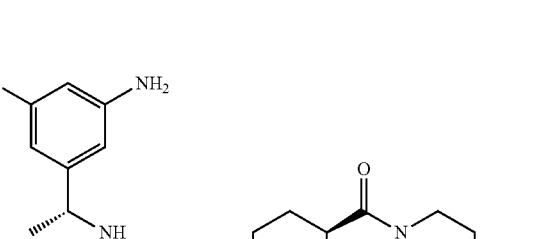 | M + H = 572; t_ret = 1.24 | LCMSBAS1 | 2 |
| I-360 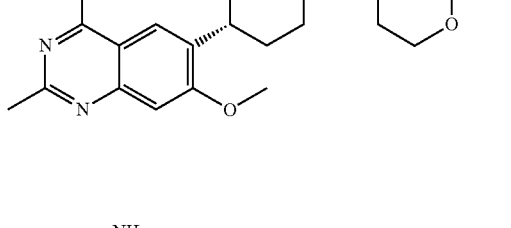 | M + H = 572; t_ret = 1.31 | LCMSBAS1 | 25 |
| I-361 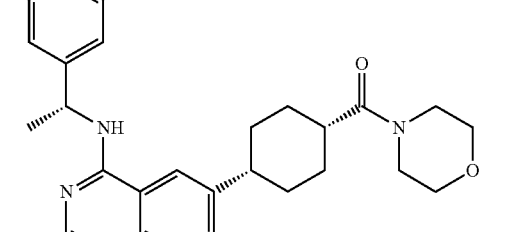 | t_ret = 1.32 | LCMSBAS1 | 5 |

TABLE 55-continued
| structure | [M + H]+ $t_{ret}$ [min] | HPLC method | IC$_{50}$ (SOS1) [nM] |
|---|---|---|---|
| I-362 | M + H = 569; $t_{ret}$ = 1.38 | LCMSBAS1 | 8 |
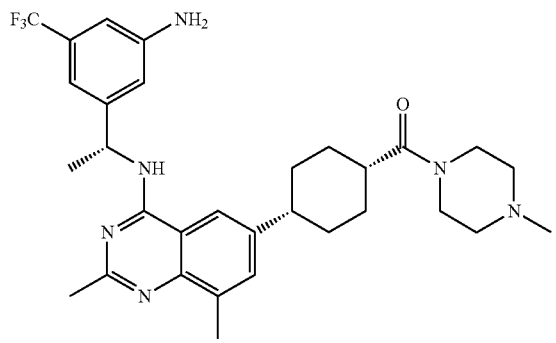
| | [M + H]+ $t_{ret}$ [min] | HPLC method | IC$_{50}$ (SOS1) [nM] |
|---|---|---|---|
| I-363 | M + H = 514; $t_{ret}$ = 1.37 | LCMSBAS1 | 4 |
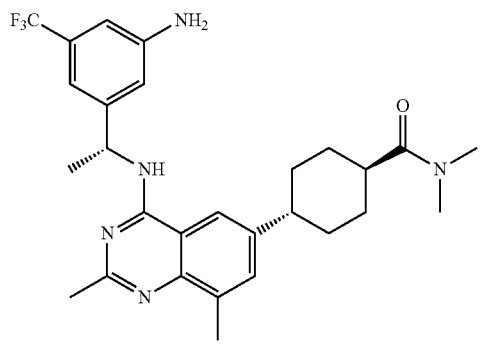 [SMILES: Cc1nc(N[C@H](C)c2cc(N)cc(C(F)(F)F)c2)c2cc([C@H]3CC[C@H](C(=O)N(C)C)CC3)cc(C)c2n1]
Experimental Procedure for the Synthesis of I-364
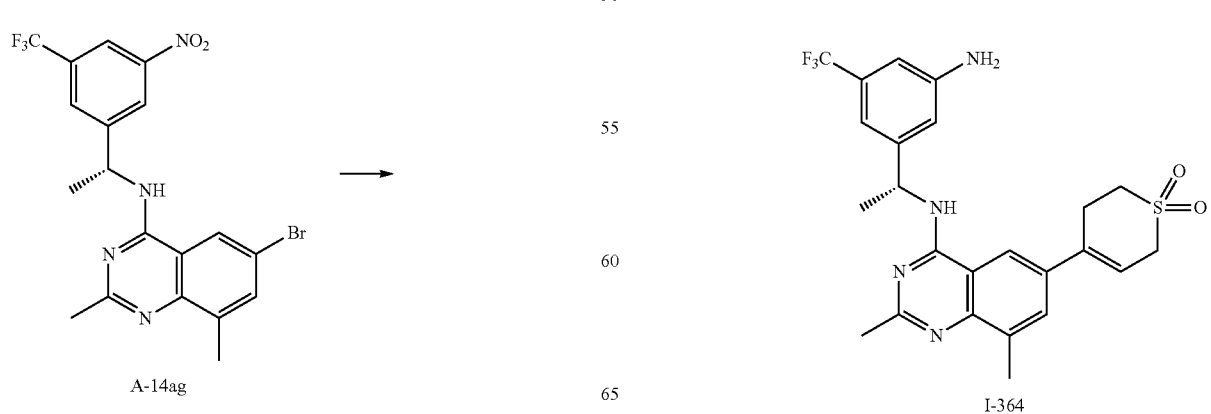
-continued A-14ag (148.2 mg, 469.0 µmol, 2.2 equiv.), N'-(1,1-dioxo-1-thian-4-ylidene)-4-methylbenzene-1-sulfonohydrazide (100.0 mg, 213.0 µmol, 1.0 equiv.) and lithium tert-butoxide (80.9 mg, 980.0 µmol, 4.6 equiv.) are dissolved in dioxane (1 mL). The reaction mixture is stirred at 100° C. for 3 d. The reaction is diluted with water, extracted with DCM, dried over MgSO$_4$, filtered and the solvent removed under reduced pressure. The crude product is dissolved in DMF and purified by chromatography using acetonitrile/water giving the desired product I-364.

The following compounds (I) (table 56) are available in an analogous manner starting from different quinazolines A-14. The crude product (I) is purified by chromatography if necessary.

TABLE 56

| # | structure | [M + H]$^+$ $t_{ret}$ [min] | HPLC method | IC$_{50}$ (SOS1) [nM] |
|---|---|---|---|---|
| I-364 | ![structure] | M + H = 491; $t_{ret}$ = 1.31 | LCMSBAS1 | 11 |
| I-365 | ![structure] | M + H = 491; $t_{ret}$ = 0.675 | BFEC | |

Experimental Procedure for the Synthesis of I-366

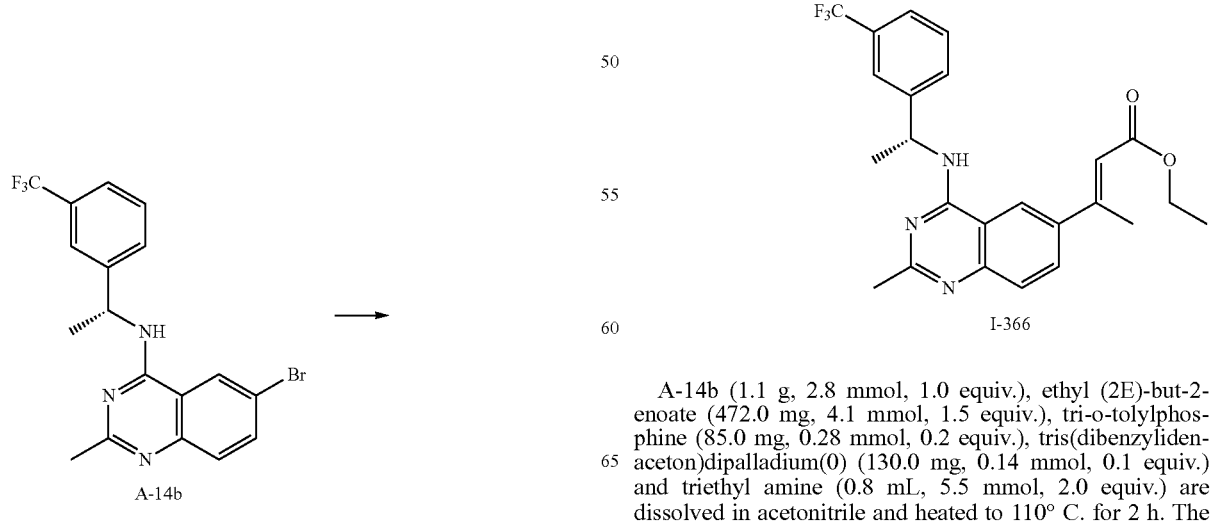

A-14b (1.1 g, 2.8 mmol, 1.0 equiv.), ethyl (2E)-but-2-enoate (472.0 mg, 4.1 mmol, 1.5 equiv.), tri-o-tolylphosphine (85.0 mg, 0.28 mmol, 0.2 equiv.), tris(dibenzylidenaceton)dipalladium(0) (130.0 mg, 0.14 mmol, 0.1 equiv.) and triethyl amine (0.8 mL, 5.5 mmol, 2.0 equiv.) are dissolved in acetonitrile and heated to 110° C. for 2 h. The reaction mixture is filtered through celite and the solvent removed under reduced pressure. The crude product is dissolved in DMF and purified by chromatography using acetonitrile/water giving the desired product I-366.

The following compounds (I) (table 57) are available in an analogous manner starting from different quinazolines A-14. The crude product (I) is purified by chromatography if necessary.

TABLE 57

| # | structure | [M + H]$^+$ $t_{ret}$ [min] | HPLC method | IC$_{50}$ (SOS1) [nM] |
|---|---|---|---|---|
| I-366 | 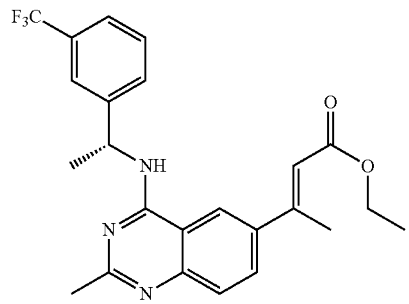 [SMILES: CCOC(=O)/C=C(\C)c1ccc2nc(C)nc(N[C@H](C)c3cccc(C(F)(F)F)c3)c2c1] | M + H = 444.0; $t_{ret}$ = 1.11 | VAB | |
| I-367 | 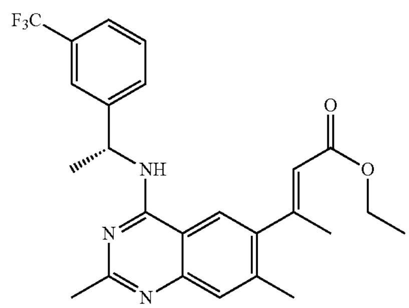 [SMILES: CCOC(=O)/C=C(\C)c1cc2c(N[C@H](C)c3cccc(C(F)(F)F)c3)nc(C)nc2cc1C] | M + H = 458.3; $t_{ret}$ = 1.16 | VAB | |
| I-368 | 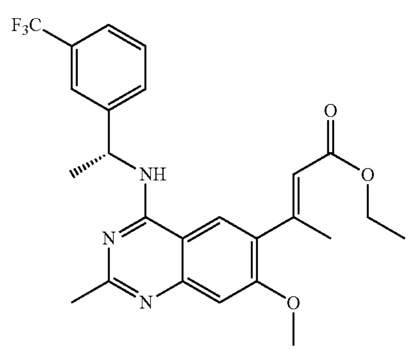 [SMILES: CCOC(=O)/C=C(\C)c1cc2c(N[C@H](C)c3cccc(C(F)(F)F)c3)nc(C)nc2cc1OC] | M + H = 474.2; $t_{ret}$ = 1.13 | VAB | |

Experimental Procedure for the Synthesis of I-369

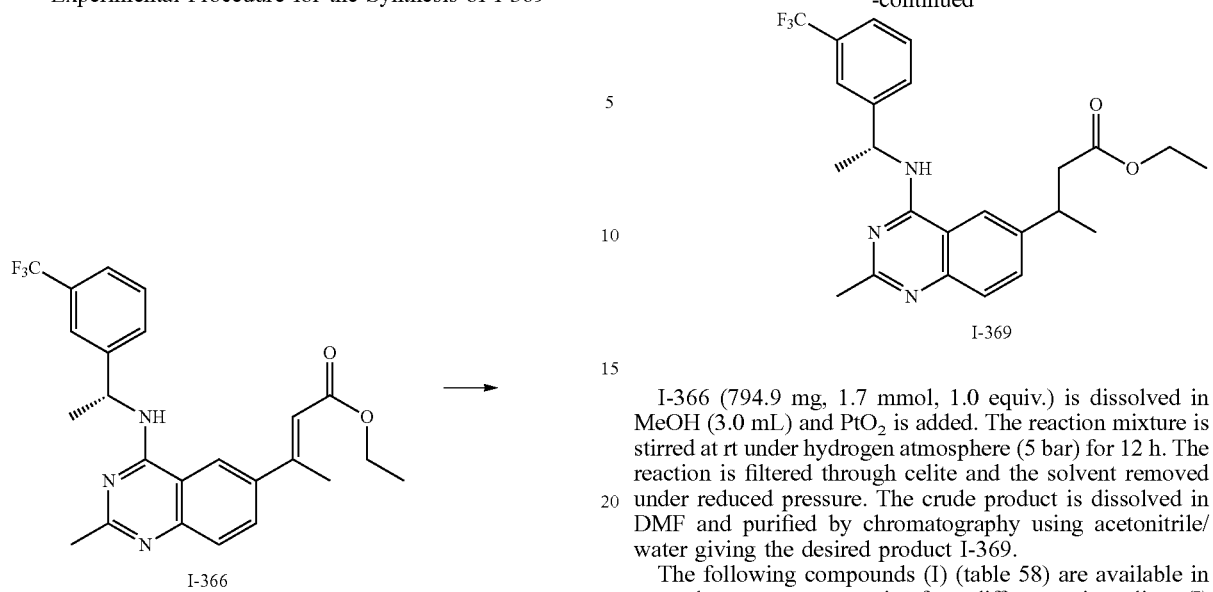

I-366 (794.9 mg, 1.7 mmol, 1.0 equiv.) is dissolved in MeOH (3.0 mL) and PtO$_2$ is added. The reaction mixture is stirred at rt under hydrogen atmosphere (5 bar) for 12 h. The reaction is filtered through celite and the solvent removed under reduced pressure. The crude product is dissolved in DMF and purified by chromatography using acetonitrile/water giving the desired product I-369.

The following compounds (I) (table 58) are available in an analogous manner starting from different quinazolines (I) initially obtained (table 57). The crude product (I) is purified by chromatography if necessary.

TABLE 58

| # | structure | [M + H]$^+$ $t_{ret}$ [min] | HPLC method | IC$_{50}$ (SOS1) [nM] |
|---|-----------|---|---|---|
| I-369 | 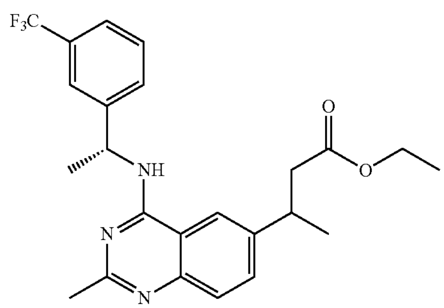 [SMILES: CCOC(=O)CC(C)c1ccc2nc(C)nc(N[C@H](C)c3cccc(C(F)(F)F)c3)c2c1] | M + H = 446.3; $t_{ret}$ = 1.10 | VAB | |
| I-370 | 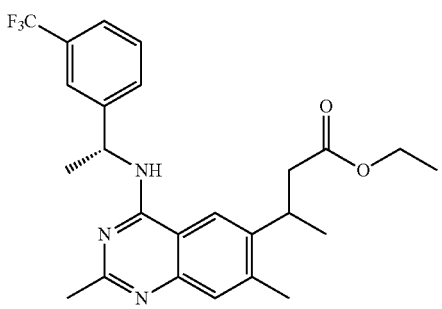 [SMILES: CCOC(=O)CC(C)c1cc2c(N[C@H](C)c3cccc(C(F)(F)F)c3)nc(C)nc2cc1C] | M + H = 460.3; $t_{ret}$ = 1.13 | VAB | |

TABLE 58-continued

| # | structure | [M + H]+ $t_{ret}$ [min] | HPLC method | IC$_{50}$ (SOS1) [nM] |
|---|---|---|---|---|
| I-371 | 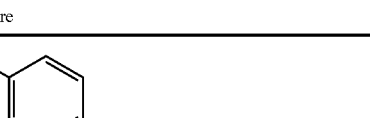 | M + H = 476.3; $t_{ret}$ = 1.12 | VAB | |

Experimental Procedure for the Synthesis of I-372

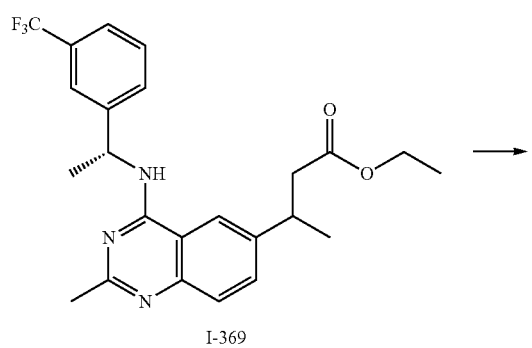

I-369

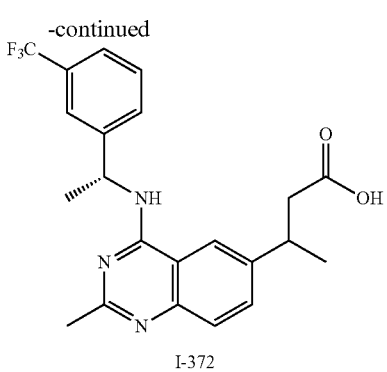

I-372

I-369 (500.0 mg, 1.1 mmol, 1.0 equiv.) is dissolved in an aqueous solution of LiOH (20 mL, 20 mmol, 1M, 17.8 equiv.) and stirred at rt for 1 h. The crude product is purified by chromatography using acetonitrile/water giving the desired product I-372.

The following intermediates (I) (table 59) are available in an analogous manner starting from different quinazolines (I) initially obtained (table 58). The crude product (I) is purified by chromatography if necessary.

TABLE 59

| # | structure | [M + H]+ $t_{ret}$ [min] | HPLC method | IC$_{50}$ (SOS1) [nM] |
|---|---|---|---|---|
| I-372 | 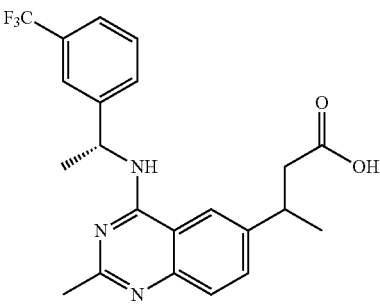 [SMILES: Cc1nc(N[C@H](C)c2cccc(C(F)(F)F)c2)c2cc(C(C)CC(=O)O)ccc2n1] | M + H = 418.3; $t_{ret}$ = 0.80 | VAB | |

TABLE 59-continued
| # | structure | [M + H]+ $t_{ret}$ [min] | HPLC method | IC$_{50}$ (SOS1) [nM] |
|---|---|---|---|---|
| I-373 | 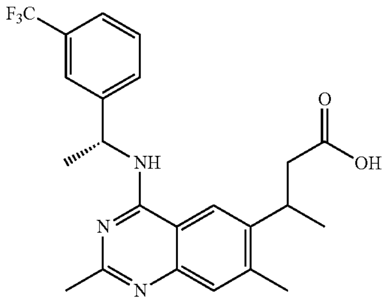 | M + H = 432.2; $t_{ret}$ = 0.79 | VAB | |
| I-374 | 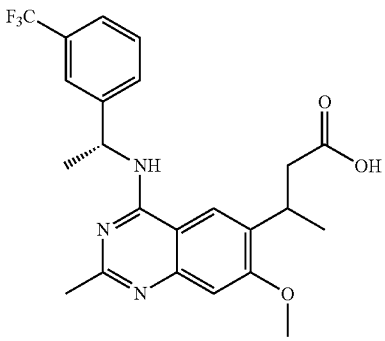 [SMILES: COc1cc2nc(C)nc(N[C@H](C)c3cccc(C(F)(F)F)c3)c2cc1C(C)CC(=O)O] | M + H = 448.1; $t_{ret}$ = 0.78 | VAB | |
Experimental Procedure for the Synthesis of I-375
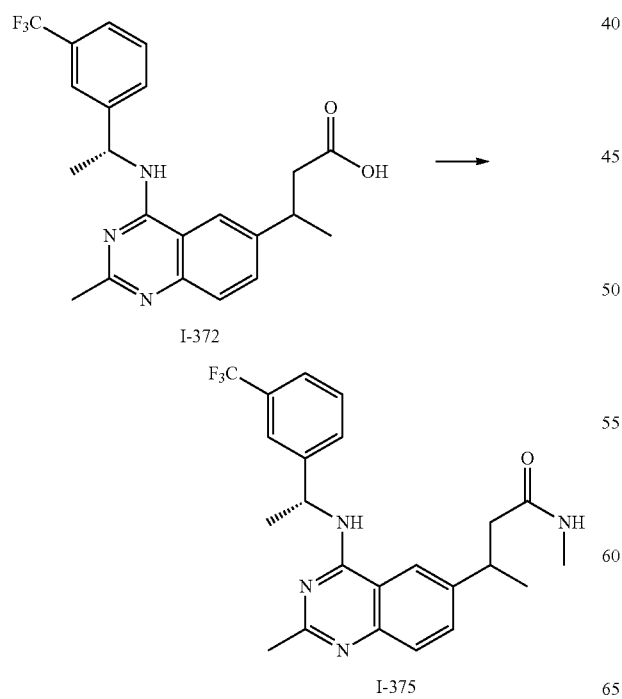

I-372 (50.0 mg, 120.0 µmol, 1.0 equiv.) is dissolved in NMP (1.0 mL), DIPEA (82.0 µL, 479.0 µmol, 4.0 equiv.) and HATU (68 mg, 180.0 µmol, 1.5 equiv.) are added and the mixture is stirred for 10 min at rt. Then methyl amine (0.12 mL, 2M, 2.0 equiv.) is added and the reaction mixture is stirred for 12 h at rt. The crude product is purified by chromatography using a mixture of acetonitrile/water to give the desired product I-375.

The following compounds (I) (table 60) are available in an analogous manner starting from different quinazolines (I) initially obtained (table 59). The crude product (I) is purified by chromatography if necessary.

TABLE 60

| structure | [M + H]$^+$ $t_{ret}$ [min] | HPLC method | IC$_{50}$ (SOS1) [nM] |
|---|---|---|---|
| I-375 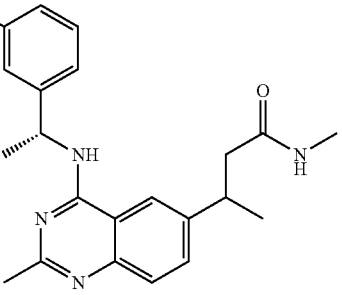 | M + H = 431; $t_{ret}$ = 1.25 | LCMSBAS1 | 36 |
| I-376 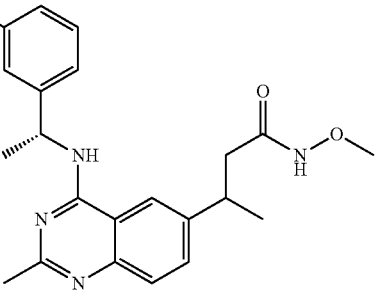 | M + H = 447; $t_{ret}$ = 1.24 | LCMSBAS1 | 34 |
| I-377 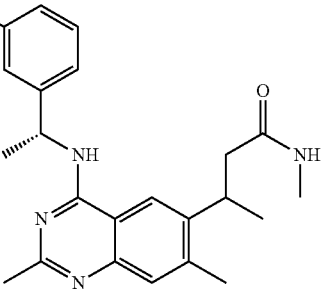 | M + H = 445; $t_{ret}$ = 1.25 | LCMSBAS1 | 10 |
| I-378 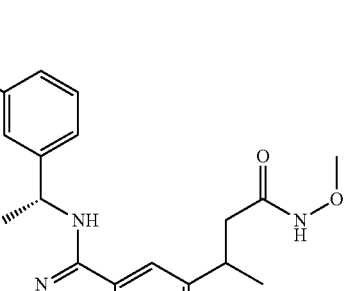 | M + H = 461; $t_{ret}$ = 1.24 | LCMSBAS1 | 8 |

TABLE 60-continued

| structure | [M + H]+ $t_{ret}$ [min] | HPLC method | IC$_{50}$ (SOS1) [nM] |
|---|---|---|---|
| I-379 | M + H = 471; $t_{ret}$ = 1.29 | LCMSBAS1 | 12 |
| I-380 | M + H = 513; $t_{ret}$ = 1.37 | LCMSBAS1 | 42 |
| I-381 | M + H = 461; $t_{ret}$ = 1.25 | LCMSBAS1 | 17 |
| I-382 | M + H = 477; $t_{ret}$ = 1.24 | LCMSBAS1 | 16 |
| I-383 | M + H = 487; $t_{ret}$ = 1.29 | LCMSBAS1 | 21 |

The following Examples describe the biological activity of the compounds according to the invention, without restricting the invention to these Examples.

Compounds of formula (I) are characterized by their many possible applications in the therapeutic field.

KRAS::SOS1 AlphaScreen Binding Assay

This assay can be used to examine the potency with which compounds inhibit the protein-protein interaction between SOS1 and KRAS G12D. This demonstrates the molecular mode of action of compounds. Low $IC_{50}$ values are indicative of high potency of the SOS1 inhibitor compound in this assay setting:

Reagents:
- GST-tagged SOS1 (564_1049_GST_TEV_ECO) produced in-house
- GST-TEV-SOS1 (564-1049) is purchased from Viva Biotech Ltd.
- 6×His-Tev-K-RasG12D(1-169)Avi is purchased from Xtal BioStructures, Inc. (Lot #X129-110)
- GDP (Sigma Cat No G7127)
- AlphaLISA Glutathione Acceptor Beads (PerkinElmer, Cat No AL109)
- AlphaScreen Streptavidin Donor Beads (PerkinElmer Cat No 6760002)
- Assay plates: Proxiplate-384 PLUS, white (PerkinElmer, Cat No 6008289)

Assay Buffer:
- 1×PBS
- 0.1% BSA
- 100 µM EDTA or without EDTA ($IC_{50}$s in the tables are measured without EDTA unless they are marked with an asterisk)
- 0.05% Tween 20

KRAS::SOS1 GDP Mix:
10 nM (final assay concentration) KRAS G12D, 10 µM (final assay concentration) GDP and 5 nM (final assay concentration) GST-SOS1 are mixed in assay buffer prior to use and kept at room temperature.

Bead Mix:
AlphaLSA Glutathione Acceptor Beads and AlphaScreen Streptavidin Donor Beads are mixed in assay buffer at a concentration of 10 µg/mL (final assay concentration) each prior to use and kept at room temperature.

Assay Protocol:
Compounds are diluted to a final start concentration of 100 µM and are tested in duplicate. Assay-ready plates (ARPs) are generated using an Access Labcyte Workstation with a Labcyte Echo 550 or 555 accoustic dispenser. For compound a start concentration of 100 µM, 150 nL of compound solution is transferred per well in 11 concentrations in duplicate with serial 1:5 dilutions.

The assay is run using a fully automated robotic system in a darkened room below 100 Lux. 10 µL of KRAS::SOS1 GDP mix is added into columns 1-24 to the 150 nL of compound solution (final dilution in the assay 1:100, final DMSO concentration 1%).

After a 30 minute incubation time 5 µL of bead mix is added into columns 1-23. Plates are kept at room temperature in a darkened incubator. After a further 60 minute incubation, the signal is measured using a PerkinElmer Envision HTS Multilabel Reader using the AlphaScreen specifications from PerkinElmer. Each plate contains the following controls:
- diluted DMSO+KRAS::SOS1 GDP mix+bead mix
- diluted DMSO+KRAS::SOS1 GDP mix Result Calculation:
$IC_{50}$ values are calculated and analyzed using a 4 parametric logistic model.

Tables of example compounds disclosed herein contain $IC_{50}$ values determined using the above assay.

Cell Proliferation Assays

Cell proliferation assays are used to examine the potency with which compounds inhibit the SOS1-mediated proliferation, growth and apoptosis of cancer cell lines in vitro. This demonstrates the molecular mode of action of compounds. Low $IC_{50}$ values are indicative of high potency of the SOS1 inhibitor compounds in this assay setting. In particular, it is observed that SOS1 inhibitor compounds demonstrate a potent inhibitory effect on the proliferation of KRAS mutant human cancer cell lines and not on BRAF mutant cancer cell lines or non-addicted KRAS wild-type human cancer cell lines. This confirms the molecular mode of action of the SOS1 inhibitor compounds as selectively targeting cancer cells dependent on RAS-family protein function.

Cell proliferation assays are performed in three-dimensional (3D) anchorage-independent soft-agar conditions with the following human cell lines:
- NCI-H358: human non-small cell lung cancer (NSCLC) with a KRAS G12C mutation;
- PC-9: human non-small cell lung cancer (NSCLC) with wild-type KRAS and an EGFR del 19 mutation;
- NCI-H1792: human non-small cell lung cancer (NSCLC) with a KRAS G12C mutation;
- SW900: human non-small cell lung cancer (NSCLC) with a KRAS G12V mutation;
- A-549: human non-small cell lung cancer (NSCLC) with a KRAS G12S mutation;
- NCI-H2122: human non-small cell lung cancer (NSCLC) with a KRAS G12C mutation;
- NCI-H520: human non-small cell lung cancer (NSCLC) with wild-type KRAS; MIA PaCa-2: human pancreatic cancer cell (PAC) with a KRAS G12C mutation;
- DLD-1: human colon cancer with a KRAS G13D mutation;
- A-375: human melanoma cancer with wildtype KRAS but a BRAFV600E mutation, which is used as a cell line being non-responsive following treatment with a SOS1 inhibitor compound;
- All cell lines but PC-9 can be purchased from the American Type Culture Collection (ATCC). PC-9 can be purchased from the European Collection of Authenticated Cell Cultures (ECACC).

Materials Used:
96-well Ultra low binding plates from Corning (CLS2474-24EA);
4% Agarose Gel 1× liquid 40 mL from Gibco (18300-012);
RPMI-1640 Medium (ATCC® 30-2001™);
Leibovitz's L-15 (Gibco, Cat #11415);
F-12K (ATCC, Catalog No. 30-2004);
DMEM (Lonza BE12-604F); Fetal Bovine Serum (FBS) from HyClone (SH30071.03);
Alamar Blue from Invitrogen (DAL1100CSTM1)

Cell Culture:
NCI-H358 cells (ATCC HTB-182), DLD-1 cells (ATCC CCL-221), NCI-H520 cells (ATCC HTB-182), PC-9 cells (ECACC 90071810), NCI-H1792 cells (ATCC CRL-5895) and NCI-H2122 cells (ATCC CRL-5985) are grown in cell culture flasks (175 cm²) using RPMI medium. SW900 cells (ATCC HTB-59) are grown in Leibovitz's L-15 medium, A-549 cells (ATCC CCL-185) are grown in F12K medium, MIA PaCa-2 cells (ATCC CRL-1420) and A-375 (ATCC- CRL-1619) are grown in DMEM medium. Cell culture medium for all listed cell lines is supplemented with 10% FBS. Cultures are incubated at 37° C. and 5% $CO_2$ in a humidified atmosphere, with medium change or subcultivation performed 2-3 times a week. SW900 cells are cultured without addition of $CO_2$.

Assay Conditions:

The assay set-up is composed of the following:
A bottom layer consisting of 90 µL medium including 1.2% agarose
A cell-layer consisting of 60 µL medium including 0.3% agarose
A top-layer consisting of 30 µL medium including the test compounds (without agarose)

For preparation of the bottom layer, 4% agarose (microwave-heated) is mixed with culture medium (incl. 2% FBS for all cell lines but SW900, for SW900 10% FCS was used to achieve cellular growth) to a final dilution of 1.2% agarose in medium. Each well is filled with 90 µL of the bottom layer suspension and cooled to room temperature for 1 h. For the cell-layer, cells are trypsinized, counted and plated in 60 µL culture medium (2% FBS) including 0.3% agarose (1500 cells per well). After cooling to room temperature for 1 h, plates are incubated overnight at 37° C. and 5% $CO_2$ in a humidified atmosphere. The next day the compounds (30 µL of serial dilutions) are added in triplicates. The concentration of the test compounds covers a range between 10 micromolar and 0.13 nanomolar minimum. Compounds (Stock: 10 mM in 100% DMSO) are diluted in medium. Cells are incubated at 37° C. and 5% $CO_2$ in a humidified atmosphere for 14 days.

Detection:

20 µL/well of AlamarBlue suspension is added per well and incubated 4-24 hours in the incubator. Fluorescence intensity is determined using a fluorescence reader (2030 VICTOR X5, Perkin Elmer). The excitation wavelength is 544/15 nm, emission 590 nm. In monotherapy data is fitted by iterative calculation using a sigmoidal curve analysis program (GraphPAD Prism) with variable hill slope to ascertain $IC_{50}$ values.

Data Analysis for Combinations:

The data is analyzed with the Boehringer Ingelheim proprietary software MegaLab (curve fitting based on drc package from R). The AlamarBlue® assay output for vehicle-treated control cells after 3 days of incubation, corresponding to 100% cell viability, is taken as the reference signal for all subsequent calculations. Relative cell viability in compound-treated cultures (signal percent of control, "POC") is calculated according to the following formula: POC (t=time of incubation until readout) =100*fluorescence (compound wells)/fluorescence (control wells). In addition, for each compound-treated culture, the fluorescent signal after incubation of cells until readout (POC (t=time of incubation until readout)) is related to the signal at the start of treatment (POC (t=0 h)):POC (t=0 h)=100*fluorescence at t=0 (control wells)/fluorescence at (t=time of incubation until readout) (control wells).

To calculate concentration-response curves, the POC data are analyzed using a four-parameter log-logistic function without any upper or lower limitation. Relative cell growth inhibition (CGI %) in compound-treated cultures is calculated according to the following formula:

$$\% CGI^{72h} = \begin{cases} s_t^{72} \geq s_c^0 : \left[1 - \dfrac{s_t^{72h} - s_c^{0h}}{s_c^{72h} - s_c^{0h}}\right] \times 100\% \\ s_t^{72} < s_c^0 : \left[1 - \dfrac{s_t^{72h} - s_c^{0h}}{s_c^{0h}}\right] \times 100\% \end{cases}$$

-continued $$S_t^{72} = POC_{(t=72\,h)}$$
$$S_c^0 = POC_{(t=0\,h)}$$

A CGI of >0% and <100% reflects a partial growth-inhibitory effect relative to vehicle-treated controls, a CGI of 100% is equivalent of complete blockade of growth, and a CGI of >100% is indicative of net cell death. Results are evaluated by a CGI matrix, plotting multiple compound concentrations of test compound 1 against different concentrations of test compound 2.

Combinatorial effects are calculated according to the Bliss independence model (Bliss C.I. Ann. Appl. Biol. 1939; 26: 585-615 (R14-2910)).

Expected CGI values for each drug concentration combination are derived from the POC (t=72 h) of the single dose treatment data of the two compounds.

$$a_x = 1 - (0.01 * POC^{comp\ 1, conc\ x})$$

$$b_y = 1 - (0.01 * POC^{comp\ 2, conc\ y})$$

$$c_{x,y} = \text{predicted } POC^{comp\ 1, conc\ x, comp\ 2, conc\ y} = a_x + b_y - a_x * b_y$$

The predicted CGI of the combination of the two compounds with concentration x and y, respectively can be calculated with formula 1 by using $c_{x,y}$ as $S_t^{72h}$, 100 as $S_c^{72h}$ and $POC_{(t=0h)}$ as $S_c^{0h}$.

The Bliss excess CGI is the difference between the experimentally observed CGI and the predicted CGI at various compound concentration combinations. Bliss excess CGI values of >0 are indicative of more than additive effects on cell growth inhibition.

In Vivo Efficacy Experiments

Tumor xenografts are established by injection of cells into the right flanks of female BomTacNMRI-Foxn1$^{nu}$ mice with an age between 6 to 8 weeks purchased from Taconic, Denmark.

MIA PaCa-2 Xenograft

In case of the s.c. MIA PaCa-2 xenograft mouse models MIA PaCa-2 cells (ATCC CRL-1420) cells are grown in cell culture flasks (175 cm$^2$) using DMEM medium supplemented with 10% FBS. Cultures are incubated at 37° C. and 5% $CO_2$ in a humidified atmosphere, with medium change or subcultivation performed 2-3 times a week. For injection tumor cells are mixed with PBS including 5% FCS and Matrigel in a ratio of 1:1. 1×10EXP7 cells in a volume of 100 µL are injected subcutaneous in each mouse to establish tumors. Mice are randomized into treatment groups of 7-10 mice once tumors reach a size between 115-170 mm$^3$ in case of the trametinib and paclitaxel combination experiment and a size between 86-170 mm$^3$ in case of the gemcitabine combination experiment. Treatment starts on day of randomization and was continued until end of the study as described in the results. The vehicle control, trametinib, 1-13 or the respective combination is administered intragastrically using a gavage needle at an application volume of 10 mL/kg in a volume of 10 mL/kg per mouse daily twice with a 6 h difference. Trametinib is dissolved in 0.5% DMSO and 0.5% Natrosol. Paclitaxel is formulated in 0.9% NaCl and is applied intravenously once a week at 10 mg/kg in a volume of 10 mL/kg. Gemcitabine is diluted for formulation in sodium chloride 0.9%. and dosed every 4$^{th}$ day intraperitoneally at 10 mg/kg.

Figure 16:
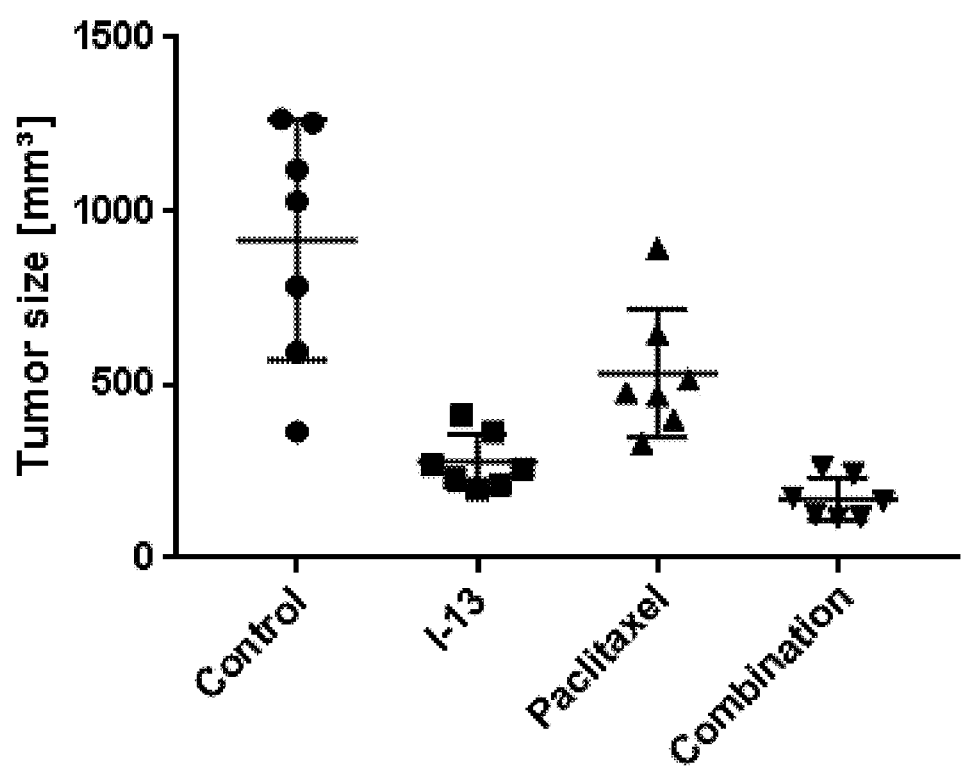
FIG. 16 shows the in vivo effect of SOS1 inhibitor compound I-13 and paclitaxel, alone or in combination, on a KRAS G12C mutant MIA PaCa-2 pancreatic xenograft mouse model. The figure shows the tumour volume after 22 days of continuous treatment.
Figure 17:
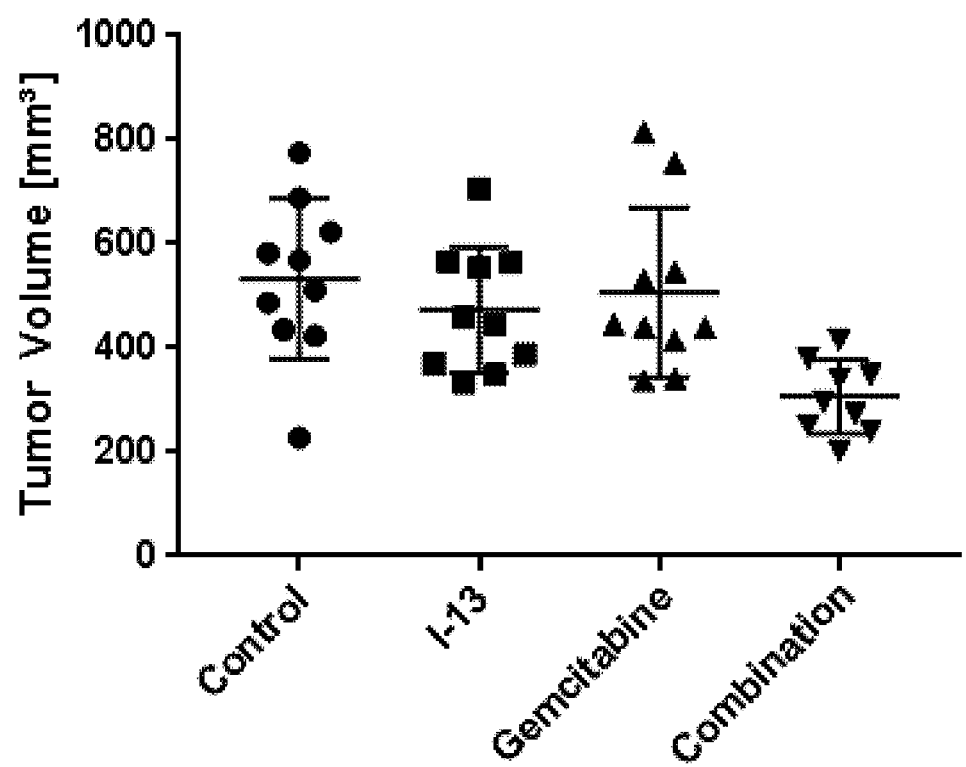
FIG. 17 shows the in vivo effect of SOS1 inhibitor compound I-13 and gemcitabine, alone or in combination, on a KRAS G12C mutant MIA PaCa-2 pancreatic xenograft mouse model. The figure shows the tumour volume after 22 days of continuous treatment.

Treatment with a combination of a SOS1 inhibitor and trametinib is described in combination example 5 (FIG. 8), treatment with a combination of a SOS1 inhibitor and paclitaxel is described in combination example 10 (FIG. 16) and treatment with a combination of a SOS1 inhibitor and gemcitabine is described in combination example 11 (FIG. 17).

Mice are housed in Macrolon® type III cages in groups of ten under standardized conditions at 21.5±1.5° C. and 55±10% humidity. Standardized irradiated diet (PROVIMI KLIBA) and autoclaved tap water are provided ad libitum. Microchips implanted subcutaneously under isoflurane anesthesia are used to identify each mouse. Cage cards showing the study number, the animal number, the compound and dose level, the administration route as well as the schedule remain with the animals throughout the study. The tumor diameter is measured two-three times a week with a caliper. The volume of each tumor [in mm$^3$] is calculated according to the formula "tumor volume=length*diameter2*π/6". To monitor side effects of treatment, mice are inspected daily for abnormalities and body weight is determined daily. Animals are sacrificed at the end of the study. Animals with necrotic tumors or tumor sizes exceeding 1500 mm$^3$ are sacrificed early during the study for ethical reasons.

Apoptosis Assay (PARP Cleavage)

Cleaved PARP is used as a marker for apoptosis of cancer cells. Apoptosis assays are used to analyze the potency of compounds to induce apoptosis in combination with SOS1 inhibitors. This demonstrates the molecular mode of action of the compounds. High arbitrary units are indicative for a strong apoptosis induction. Apoptosis assays are performed in three-dimensional (3D) anchorage-independent conditions using 24-well Scivax plates (#Cat. NCP-LH24-10) with NCI-H358 and A-549 cells. Cell culture medium and conditions are the same as described for the cell proliferation assays.

Assay Conditions:
The assay set-up is composed of the following:
200000 cells are seeded in each well of the 24-well plate;
Cells are incubated with the respective concentration of the inhibitor in monotherapy or in combination for 24 h, 48 h and 72 h;
At the respective time point complete medium is aspirated and cells are lysed by using 100 µL lysate buffer from a commercially available assay whole lysate kit (Mesoscale, Cat #K151DWD);
Protein concentration in the lysates is determined using a Bradford Assay Quick Start Bradford 1× Rye Reagent (Biorad, Cat #500-0205);
MSD Multi-Spot Assay System (Apoptosis Panel Whole Cell Lysate Kit, Mesoscale Cat #K15102D-2) is used to measure levels of cleaved PARP;
In this assay 10 µL of complete Lysis Buffer and 20 µL of sample is added to each well and incubated for 1 h. The signal values are normalized to 1 µg protein.

Detection:
Data is measured using the SECTOR S 600 Reader from mesoscales.

ERK Phosphorylation Assay

ERK phosphorylation assays are used to examine the potency with which compounds inhibit the SOS1-mediated signal transduction in a KRAS mutant human cancer cell line in vitro. This demonstrates the molecular mode of action of compounds by interfering with the RAS-family protein signal transduction cascade. Low IC$_{50}$ values are indicative of high potency of the SOS1 inhibitor compounds in this assay setting. It is observed that SOS1 inhibitor compounds demonstrate an inhibitory effect on ERK phosphorylation in a KRAS mutant human cancer cell line, thus confirming the molecular mode of action of the SOS1 inhibitor compounds on RAS-family protein signal transduction.

ERK phosphorylation assays are performed using the following human cell lines:
DLD-1 (ATCC CCL-221): human colon cancer with a KRAS G13D mutation;

Materials Used:
RPMI-1640 Medium (ATCC® 30-2001™);
Fetal Bovine Serum (FBS) from HyClone (SH30071.03);
Non-essential amino acids from Thermo Fischer Scientific (11140035);
Pyruvate from Thermo Fischer Scientific (11360039);
Glutamax from Thermo Fischer Scientific (35050061);
384 plates from Greiner Bio-One (781182);
Proxiplate™ 384 from PerkinElmer Inc. (6008280);
AlphaLISA SureFire Ultra p-ERK1/2 (Thr202/Tyr204) Assay Kit (ALSU-PERK-A500);
EGF from Sigma (E4127);
Acceptor Mix: Protein A Acceptor Beads from PerkinElmer (6760137M);
Donor Mix: AlphaScreen Streptavidin-coated Donor Beads from PerkinElmer (6760002);
Trametinib;
Staurosporine from Sigma Aldrich (S6942);

Assay Setup:
DLD-1 cells (ATCC CCL-221) are seeded at 50,000 cells per well in/60 µL of RPMI with 10% FBS, non-essential amino acids, pyruvate and glutamax in Greiner TC 384 plates. The cells are incubated for 1 h at room temperature and then incubated overnight in an incubator at 37° C. and 5% CO$_2$ in a humidified atmosphere. 60 nL compound solution (10 mM DMSO stock solution) is then added using a Labcyte Echo 550 device. After a 1 h incubation in the aforementioned incubator, 3 µL Epidermal Growth Factor (EGF, final concentration 50 ng/mL) is added. 10 minutes later the medium is removed and the cells lysed by addition of 20 µL of 1.6-fold lysis buffer from the AlphaLSA SureFire Ultra pERK1/2 (Thr202/Tyr204) Assay Kit with added protease inhibitors, 100 nM trametinib+100 nM staurosporine. After 20 minutes of incubation at room temperature with shaking, 6 µL of each lysate sample is transferred to a 384-well Proxiplate and analyzed for pERK (Thr202/Tyr204) with the AlphaLISA SureFire Ultra pERK1/2 (Thr202/Tyr204) Assay Kit. 3 µL Acceptor Mix and 3 µL Donor Mix are added under subdued light and incubated for 2 h at room temperature in the dark, before the signal is measured on a Perkin Elmer Envision plate reader using 384 AlphaScreen settings for Proxiplates. Data are fitted by iterative calculation with variable hill slope. The sigmoidal curve slope is fitted using a default fitting curve to ascertain IC$_{50}$ values.

ERK and MEK Phosphorylation to Investigate the Combinatorial Effect of SOS1 Inhibitors with MEK Inhibitors ERK and MEK phosphorylation assays are also used to investigate combinatorial effects of SOS1 inhibitors with MEK inhibitors, e.g. in MIA PaCa-2 cells.

Materials Used:
96-well Ultra low binding plates from Corning (CLS2474-24EA);
DMEM (Lonza BE12-604F);
Fetal Bovine Serum (FBS) from HyClone (SH30071.03);
Cell lysate buffer (CLB):10× (Cell Signaling, Cat #9803)
For lysis of the cells a 1.2 fold concentrated CLB is used including the following supplements: 120 µL Cell Lysis Buffer 10×(Cell Signaling, Cat #9803)+870 µL H$_2$O is supplemented with 10 µL HALT Protease & Phosphatase Inhibitor Cocktail (Thermo Scientific, Prod #1861281)+1 µL PMSF Stock sol. (Sigma, Cat #P7626)

Bradford Assay Quick Start Bradford 1×Dye Reagent (Biorad, Cat #500-0205).

Westernblot (Semidry technique): Criterion XT Precast Gel, 4-12% Bis-Tris, 26 Well Comb (Biorad, Cat #345-0125);

Running buffer: 1×XT MOPS (Biorad, Cat #161-0788);

Usage of Trans-Blot Turbo, Blots:Trans-Blot Turbo Transfer Pack, Midi format 0.2 µm PVDF (Biorad, Cat #170-4157, Bio-Rad);

TBS-T buffer: Tris buffered Saline (Biorad, Cat #170-6435) is supplemented with 0.05% Tween-20;

Blocking buffer consists of TBS-T plus 4% milk powder;

Primary antibody (incubated over night at 4° C.): Use of blocking buffer with a 1:1000 diluted of one of the primary antibodies:
a) Phospho-(Erk1/2) (Thr202/Tyr204) Rabbit Ab (Cell Signaling, Cat #9101) or
b) Phospho-MEK1/2 (Ser217/221) Rabbit mAb (Cell Signaling, Cat #9154) or
c) total protein p44/42 MAPK (Erk1/2) Rb Ab (Cell Signaling, Cat #9102 or
d) total protein MEK1/2 Rb Ab (Cell Signaling, Cat #9122)

Secondary Antibody (incubated 1 h at room temperature): Use a blocking buffer with a 1:1000 dilution of the anti-Rabbit IgG-HRP (Dako, Cat #P0448)

ECL Detection and Quantification:

ECL Western Blotting Detection Reagents (GE Healthcare, Cat #RPN2106)

ImageQuant LAS 4000 is used to induce a Chemilumescence signal that is detected with an Amersham Hyperfilm MP (GE Healthcare, Cat #28906847). The film is developed with the device Protec Optimax. Band quantification is performed by using the software "Image Quant TL" from GE Health.

Assay Setup:

MIA PaCa-2 cells are seeded at 1.16×E6 cells per 6 well plate in 2 mL DMEM medium supplemented with 2% FCS in 6 well plates. Cells are incubated over night at 37° C. with 5% $CO_2$. The next day inhibitors are added with a HP D300 digital Dispenser. Following addition of the respective inhibitor the 6-well plate is incubated for 24 h, 48 h or 72 h, respectively. At the respective timepoint cells are lysed. For this medium is aspirated and 100 µL cell lysate buffer (CLB, 1.2 fold concentrated) is added and incubated for five minutes on ice. Following this the lysate is centrifuged (16000 rpm, 4° C. for 15 minutes) and the supernatant is stored at −80° C. and used for subsequent steps. The protein concentration of the cell lysate is quantified by Bradford protein assay according to the manufacturer's instructions. 15 µg of total protein is separated on a 4-12% Bis-Tris gel and blotted on a PVDF membrane with the BIO-RAD Trans-Blot® Turbo™ Instrument. Membranes are blocked for 1 h in 5% skim milk or 5% BSA in 1×TBS/0.1% Tween 20 at room temperature and then probed overnight at 4° C. with primary antibodies as mentioned above. Antibody dilutions are prepared in 5% skim milk or 5% BSA. After washing of the membranes and incubation with secondary antibody, the proteins are visualized using the ECL Western blotting detection reagent according to the manufacturer's instructions.

Combination Example 1

Figure 2:
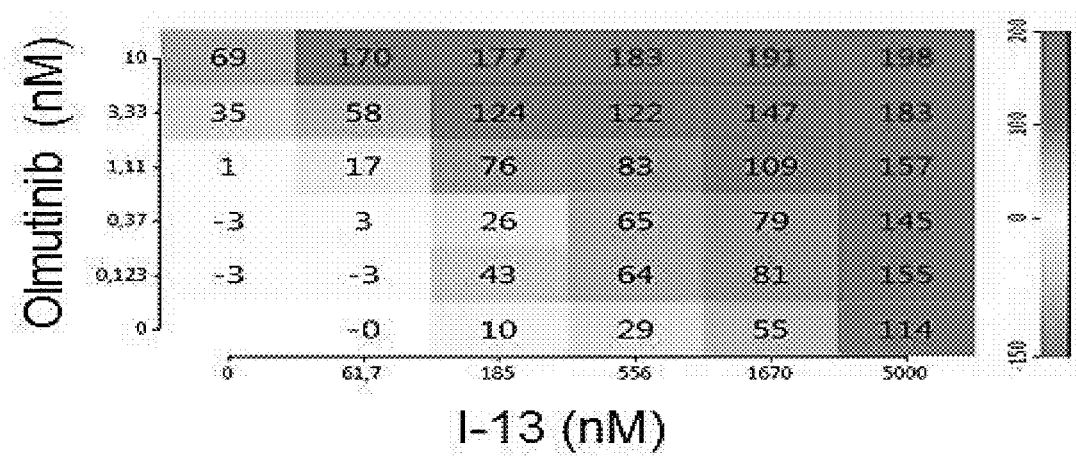
FIG. 2 shows the effect of SOS1 inhibitor compound I-13 and olmutinib, alone or in combination, on the in vitro growth of PC-9 cells (EGFR del19; KRAS wt).
Figure 2:
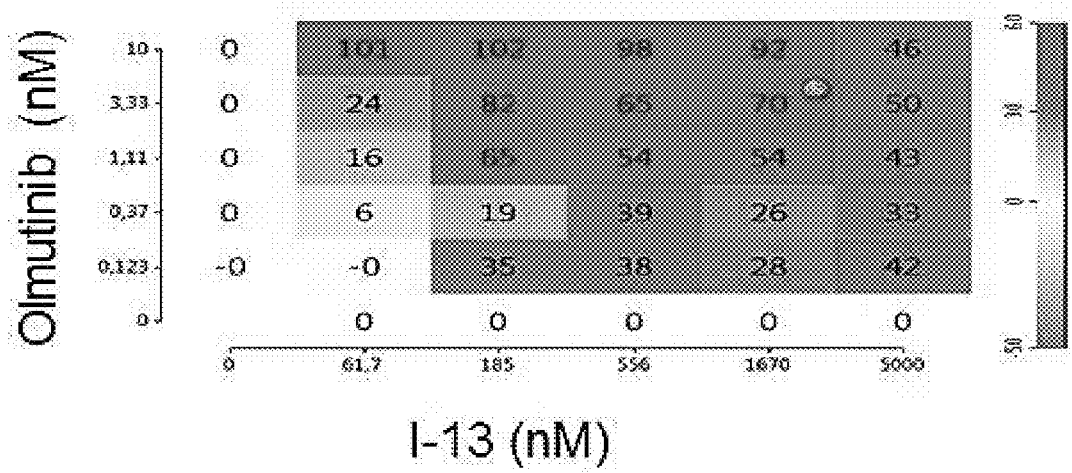
Figure 3:
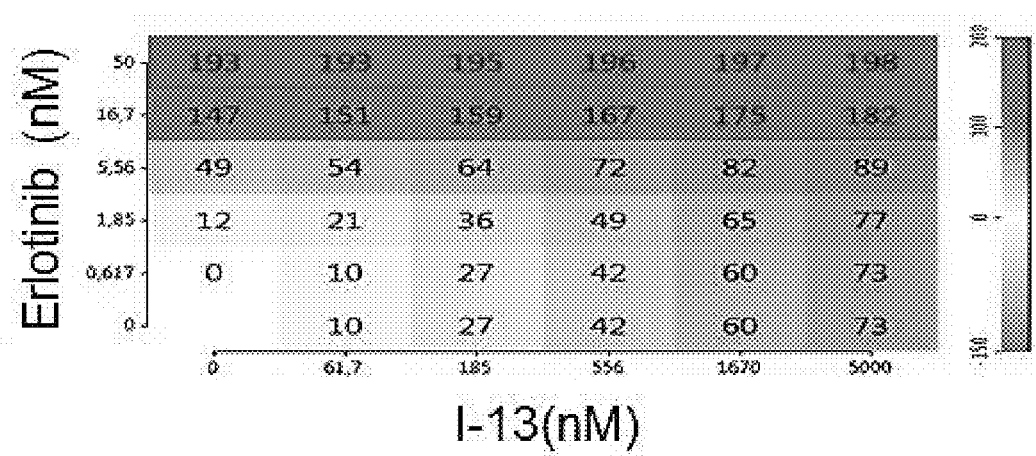
FIG. 3 shows the effect of SOS1 inhibitor compound I-13 and erlotinib, alone or in combination, on the in vitro growth of PC-9 cells (EGFR del19; KRAS wt).
Figure 3:
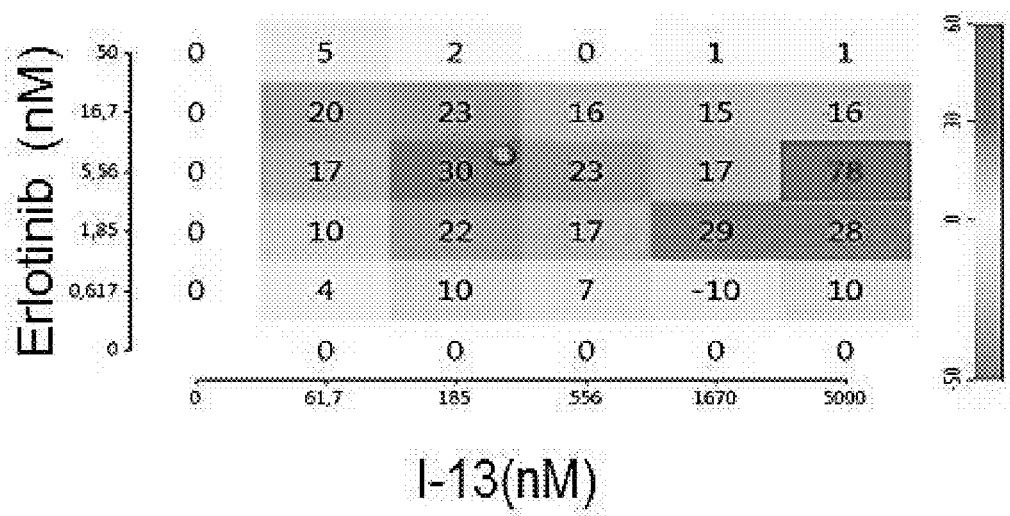

The aim of this study was to explore the effects of the combination of the SOS1 inhibitor compound I-13 with EGFR inhibitors in cell lines derived from non-small cell lung cancer. PC9 NSCLC cancer cells (EGFR del19, KRAS wt) were cultured in vitro in a 3D cell proliferation assay. The cells were embedded in softagar with medium containing 2% FCS. The cells were incubated with different concentrations of compound I-13 and with different concentrations of either afatinib (FIG. 1), olmutinib (FIG. 2) or erlotinib (FIG. 3). A CGI of >0% and <100% reflects a partial growth-inhibitory effect relative to vehicle-treated controls, a CGI of 100% is equivalent of complete blockade of growth, and a CGI of >100% is indicative of net cell death.

In this setup afatinib in monotherapy achieved with rising concentrations a CGI between 0 and 196% and compound I-13 in monotherapy CGI between 0 and 156% (FIG. 1 a)). The combination resulted in enhanced cancer cell growth inhibition reflected in an increase of the CGI values already at lower concentration of both compounds compared to both monotherapies.

Olmutinib in monotherapy achieved with rising concentrations a CGI between 0 and 114% (FIG. 2a)). The combination resulted in enhanced cancer cell growth inhibition reflected in an increase of the CGI value of up to 198% at the highest concentrations and an increase of the CGI values already at lower concentration of both compounds compared to both monotherapies.

Erlotinib in monotherapy achieved with rising concentrations a CGI between 0 and 198% and compound I-13 achieved in this experiment in monotherapy a CGI between 0 and 73% (FIG. 3 a)). The combination resulted in enhanced cancer cell growth inhibition reflected in and an increase of the CGI values already at lower concentration of both compounds compared to both monotherapies.

The Bliss excess CGI is the difference between the experimentally observed CGI and the predicted CGI at various compound concentration combinations. Bliss excess CGI values of >0 are indicative of more than additive effects on cell growth inhibition (the higher the value the stronger is the combinatorial effect). Assessment of the combinatorial effect using the Bliss independence model revealed a more than additive anti-proliferative effects of the combined drugs, over a range of concentrations around the individual inhibitor's $IC_{50}$ values. The maximum Bliss excess values increased up to 90 in case of afatinib (FIG. 1 b)), 102 in case of olmutinib (FIG. 2 b)) and 78 in case of erlotinib (FIG. 3 b)). This more than additive effect observed in combination with CGI values>100 describes an anti-proliferative effect and in addition induction of apoptosis in these three combinations.

Combination Example 2

Figure 4:
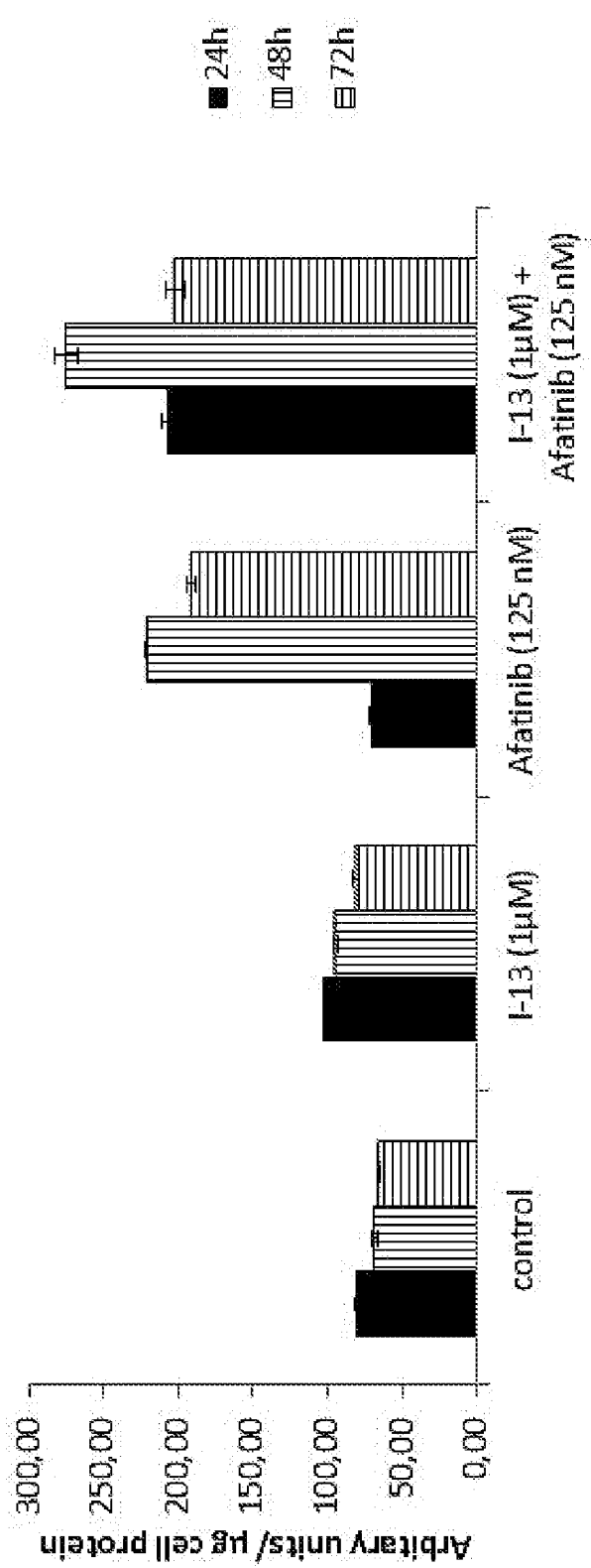
FIG. 4 shows the effect of SOS1 inhibitor compound I-13 and afatinib, alone or in combination, on the levels of cleaved PARP, a marker for apoptosis, in NCI-H358 (KRAS G12C) cells.

For validation of apoptosis induction, levels of cleaved PARP were determined with a commercially available mesoscale assay. For this assay NCI-H358 (KRAS G12C) NSCLC cells were cultured in 3D using low binding Scivax Plates, with 10% serum in the cell culture medium and cells were treated with 1 µM of compound I-13 or 125 nM of afatinib as single agents or in combination for 24 h, 48 h and 72 h. Combination of compound I-13 with afatinib resulted already in apoptosis induction at the 24 h timepoint. I-13 in monotherapy showed no apoptosis induction and afatinib in monotherapy needed 48 h to show apoptosis induction (FIG. 4).

Combination Example 3

Figure 5:
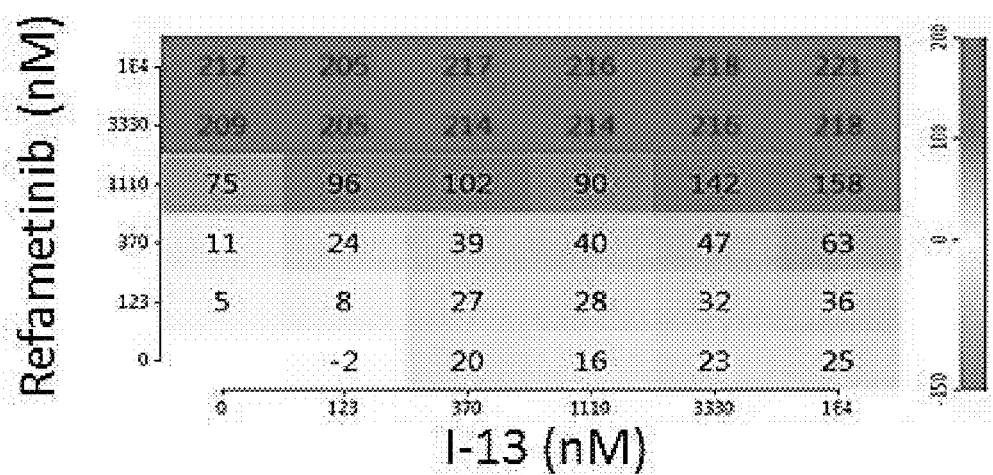
FIG. 5 shows the effect of SOS1 inhibitor compound I-13 and refametinib, alone or in combination, on the in vitro growth of A-549 (KRAS G12S) NSCLC cells.
Figure 5:
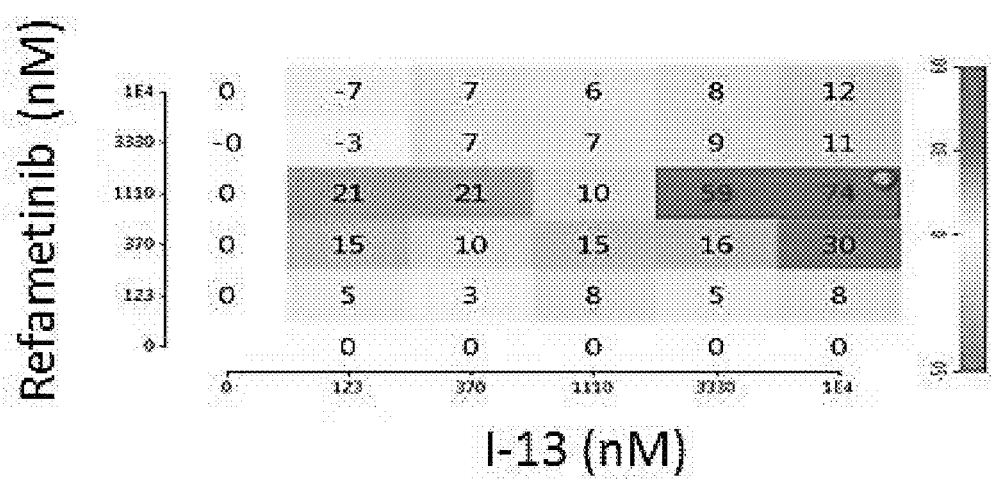

The aim of this study was to explore the effects of the combination of SOS1 inhibitor compound I-13 with MEK inhibitor refametinib in A-549 (KRAS G12S) NSCLC cells. The cells were embedded in softagar with medium containing 2% FCS and incubated with different concentrations of compound I-13 and refametinib. Assessment of the combinatorial effect using the Bliss independence model revealed a more than additive anti-proliferative effect of the combined drugs over a range of concentrations around the individual inhibitor's $IC_{50}$ values. The maximum Bliss excess values increased up to a value of 74 (FIG. 5 *a*)) indicating synergy of the combination compared to both monotherapies at relevant doses.

Combination Example 4

Figure 6:
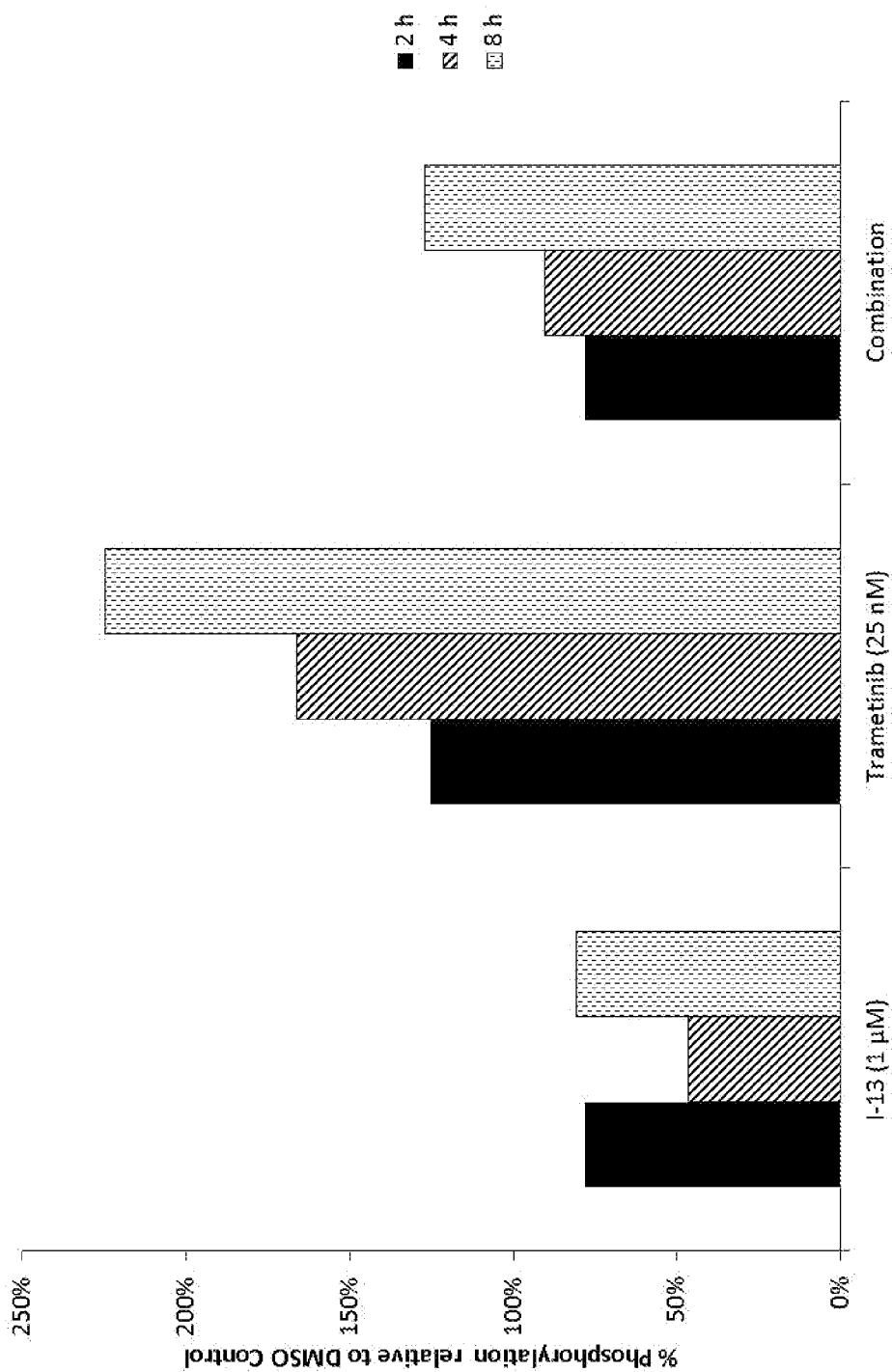
FIG. 6 shows the effect of SOS1 inhibitor compound I-13 and trametinib, alone or in combination, on phosphorylation of MEK1 (Ser217/221) in MIA PaCa-2 cells (control is set as 100% (DMSO control)).
Figure 7:
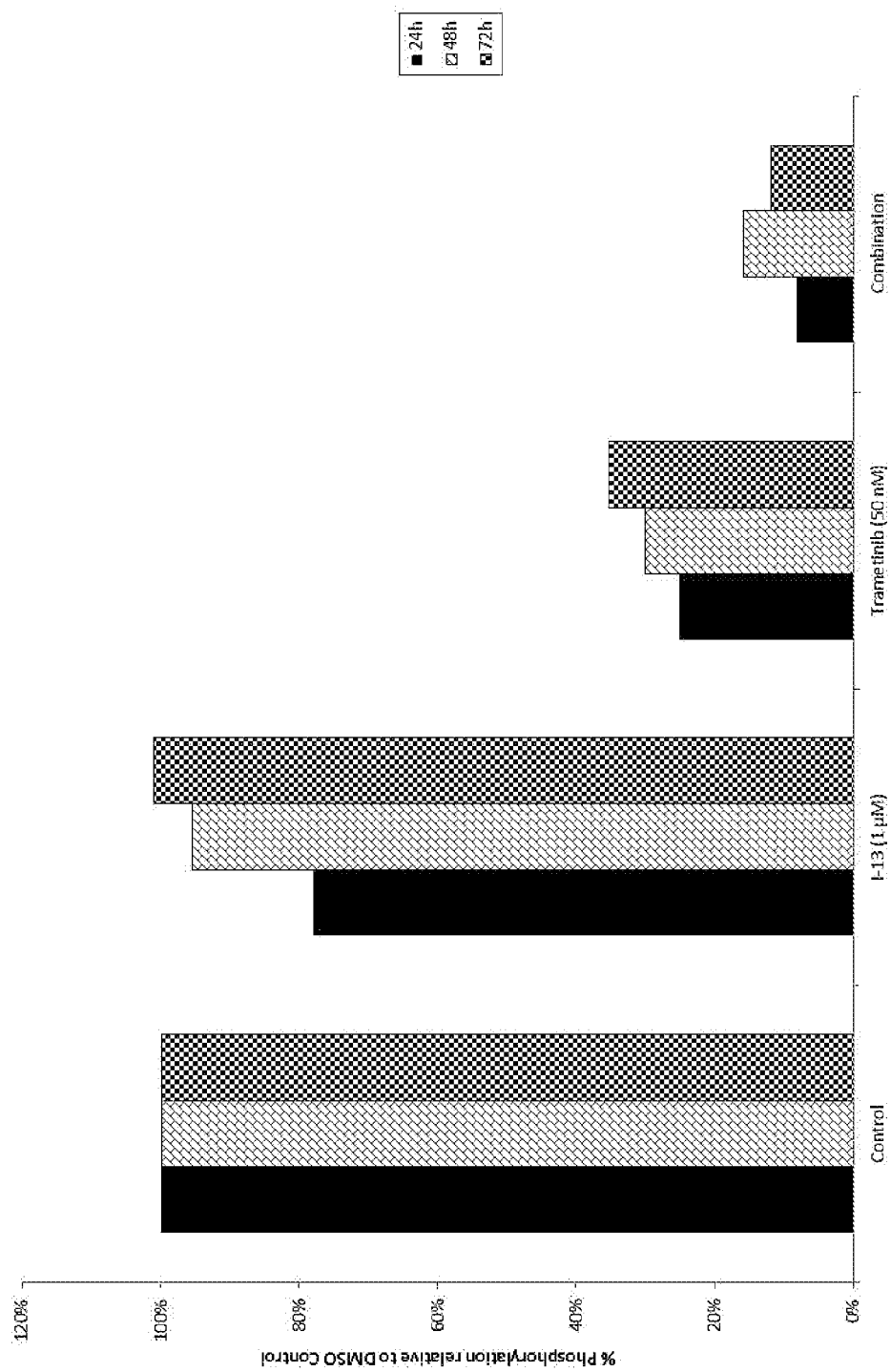
FIG. 7 shows the effect of SOS1 inhibitor compound I-13 and trametinib, alone or in combination, on phosphorylation of ERK1/2 (p42; Thr202/Tyr204) in MIA PaCa-2 cells.

Aim of this experiment was to analyse signaling modulation in the MAPK pathway mediated by compound I-13, the MEK inhibitor trametinib or the combination in MIA PaCa-2 cells, a human pancreatic cancer cell line carrying a KRAS G12C mutation. The experiment was performed by culturing the cells in 2D. For this experiment cells were treated with either 1 μM of compound I-13 alone, trametinib (either 25 nM or 50 nM) alone or with the combination of both for 2 h, 4 h and 8 h to analyse phosphorylation of MEK1/2, or treatment was performed for 24 h, 48 h and 96 h to analyse phosphorylation of ERK1/2. Cell lysate was generated at the respective timepoints and the effect on ERK or MEK phosphorylation was analysed using Western-blotting. Treatment with 25 nM trametinib resulted in increased levels of MEK1/2 (Ser 217/221) that can be explained by the release of negative feedback mechanism due to blockade of ERK1/2. This reactivation of the pathway due to inhibition by trametinib was antagonized in the combination with compound I-13. In the combination no increase of phosphorylated MEK is observed (FIG. 6). In case of ERK phosphorylation levels, in 2D culture conditions, treatment with 50 nM of trametinib resulted in around 65-75% reduction of ERK1/2 (Thr 202/Tyr 204) phosphorylation levels compared to untreated control cells. Combination of 50 nM of trametinib with 1 μM of compound I-13 resulted in a 3 fold increased reduction of p-ERK compared to monotherapy of trametinib. In the combination only 8-16% of ERK is phosphorylated compared to untreated control cells, which indicates complete blockade of the MAPK-pathway by the combination (FIG. 7).

Combination Example 5

The observed in vitro effects of the combination of I-13 with trametinib translated into a strong combinatorial effect in vivo:

In a MIA PaCa-2 (KRAS G12C) pancreatic xenograft mouse model following randomization the mice in the treatment groups were either treated with only vehicle control (0.5% Natrosol) or trametinib (high dose: 0.125 mg/kg or low dose: 0.05 mg/kg) or with the compound I-13 (50 mg/kg) or the respective combinations of I-13 plus trametinib. All compounds were applied twice daily per os (p.o.).

Figure 8:
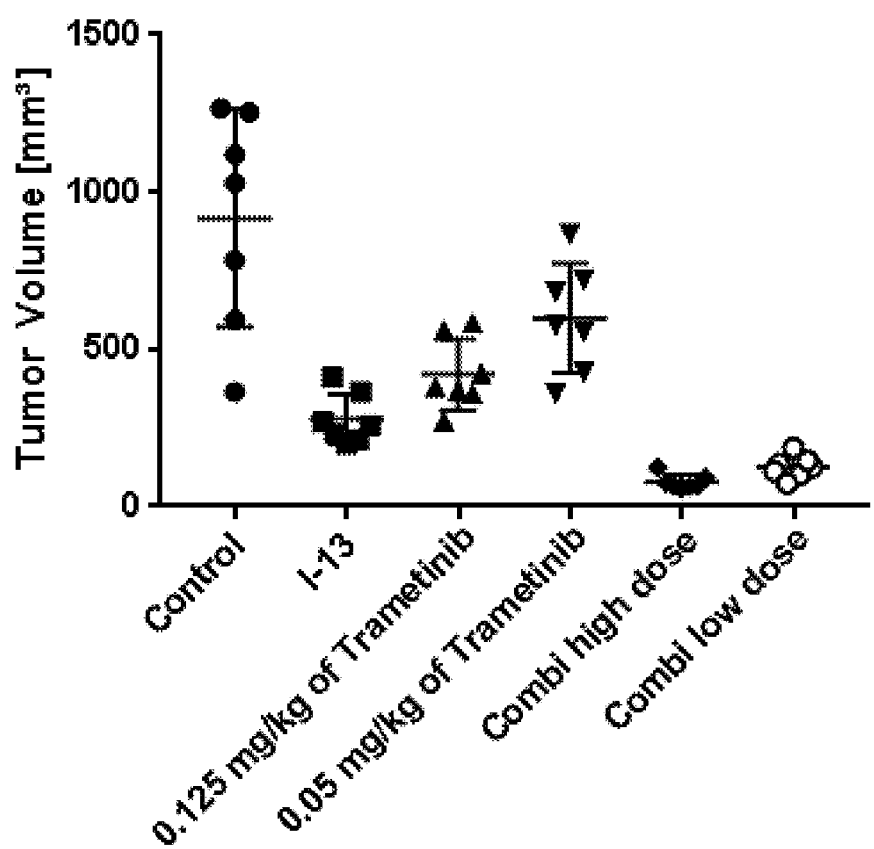
FIG. 8 shows the in vivo effect of SOS1 inhibitor compound I-13 and trametinib, alone or in combination, on a KRAS G12C mutant MIA PaCa-2 pancreatic xenograft mouse model. The figure shows the tumour volume after 22 days of continuous treatment.

In monotherapy treatment with compound I-13 achieved a TGI of 86% and no tumors showed regressions. Treatment with either 0.125 mg/kg or 0.05 mg/kg of trametinib achieved a TGI of 73% and 50%, respectively, and no regressions in any tumors. The combination of both compounds was well tolerated, showing body weight increase and resulted in a TGI of 101% (lower dose of trametinib combined with I-13) and 107% (higher dose of trametinib combined with I-13), respectively. The effect in combination was significantly stronger compared to both monotherapies. In the group treated with the combination of I-13 with 0.125 mg/kg of trametinib 7/7 tumors went into regression and in the group treated with the combination of 0.05 mg/kg of trametinib with I-13 4/7 tumors went into regression (FIG. 8). The effect in the low and high dose combination was significantly stronger compared to both monotherapies.

Combination Example 6

Figure 9:
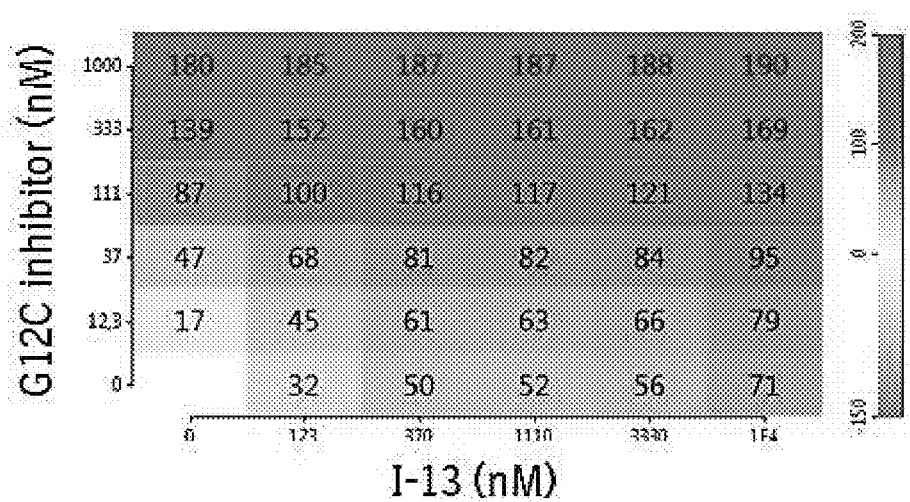
FIG. 9 shows the effect of SOS1 inhibitor compound I-13 and a KRAS G12C inhibitor (example I-272 in WO 2016/044772), alone or in combination, on the in vitro growth of NCI-H358 (KRAS G12C) NSCLC cells.
Figure 9:
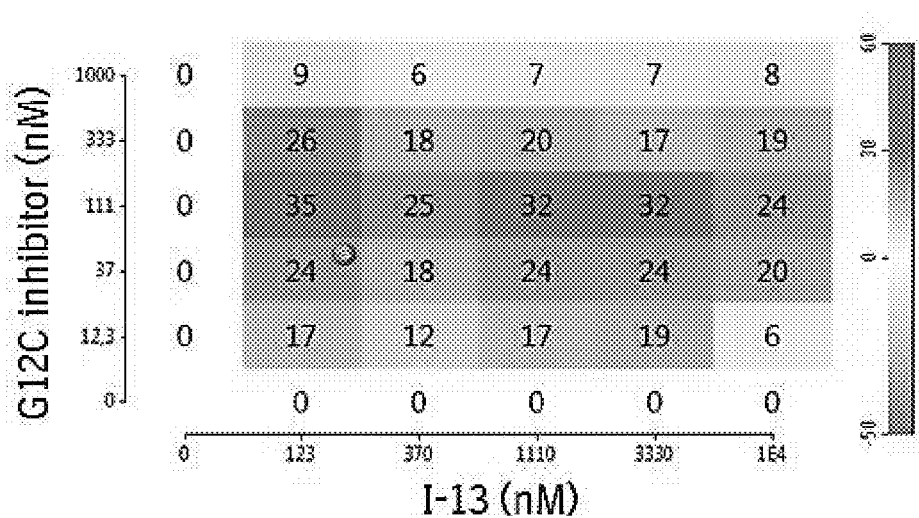
Figure 10:
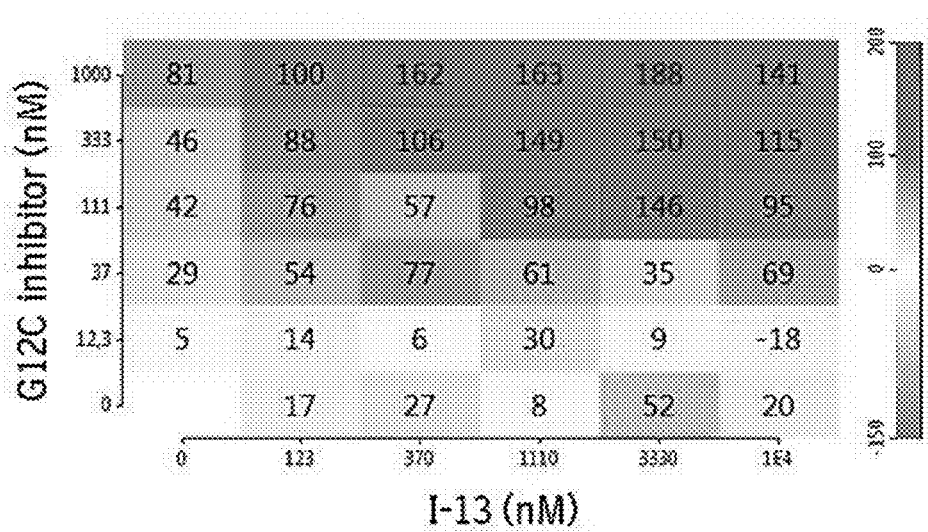
FIG. 10 shows the effect of SOS1 inhibitor compound I-13 and a KRAS G12C inhibitor (example I-272 in WO 2016/044772), alone or in combination, on the in vitro growth of NCI-H1792 (KRAS G12C) NSCLC cells.
Figure 10:
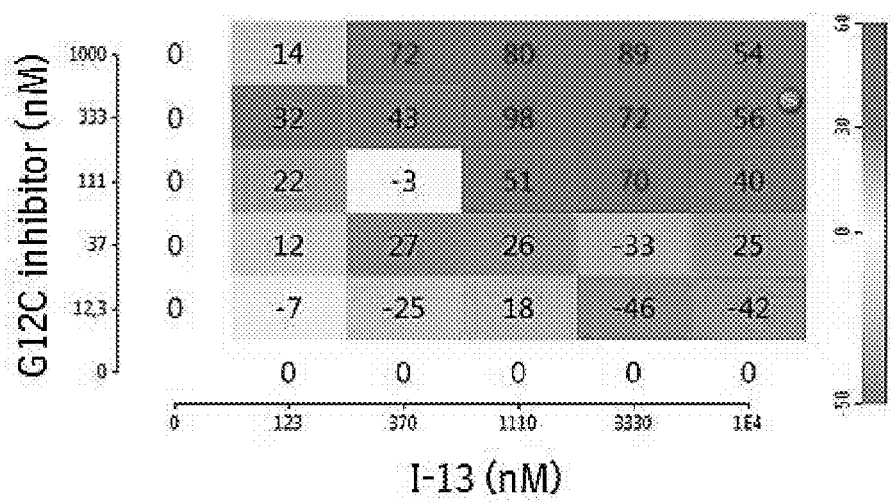

The combination of compound I-13 with a KRAS G12C inhibitor (example I-272 in WO 2016/044772) was tested in a 3D proliferation assay (with softagar) and this resulted in a more than additive effect compared to both monotherapies. The maximum Bliss excess values increased for the SOS1 inhibitor I-13 plus G12C inhibitor combination up to a value of 35 in NCI-H358 cells (FIG. 9 *b*)) and up to a value of 98 in NCI-H1792 cells (FIG. 10 *b*)), which indicates synergy.

Combination Example 7

Figure 11:
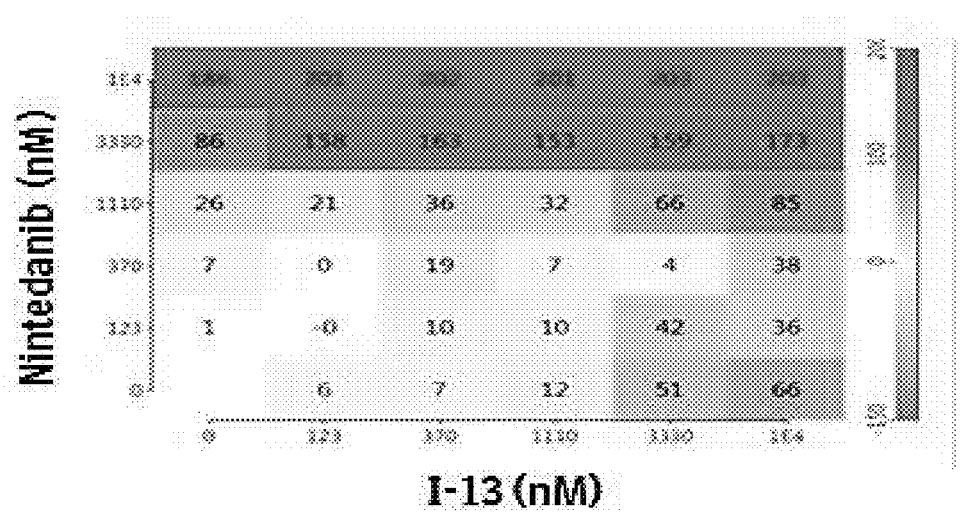
FIG. 11 shows the effect of SOS1 inhibitor compound I-13 and nintedanib, alone or in combination, on the in vitro growth of NCI-H1792 (KRAS G12C) NSCLC cells.
Figure 11:
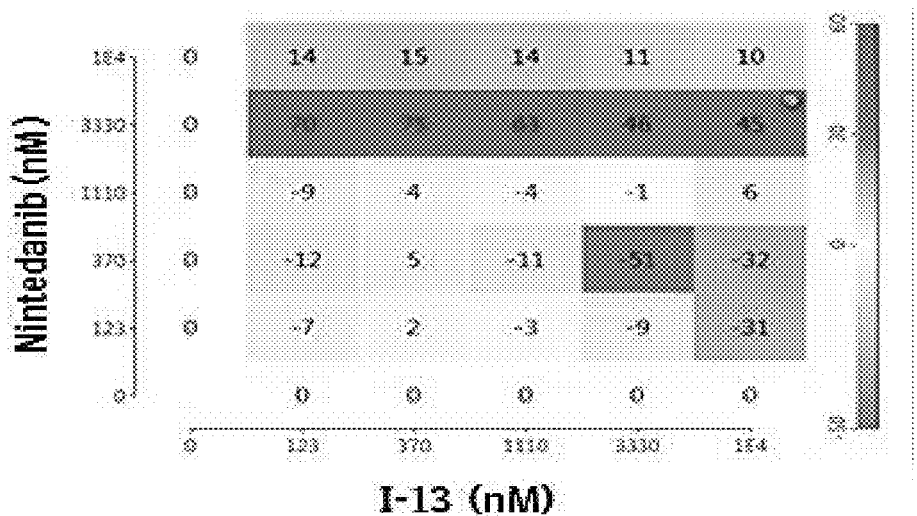
Figure 12:
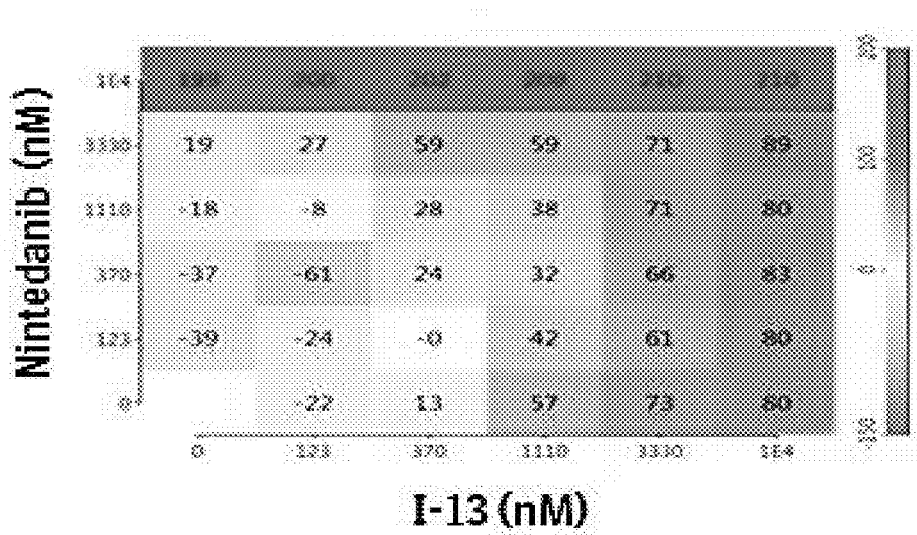
FIG. 12 shows the effect of SOS1 inhibitor compound I-13 and nintedanib, alone or in combination, on the in vitro growth of SW 900 (KRAS G12V) NSCLC cells.
Figure 12:
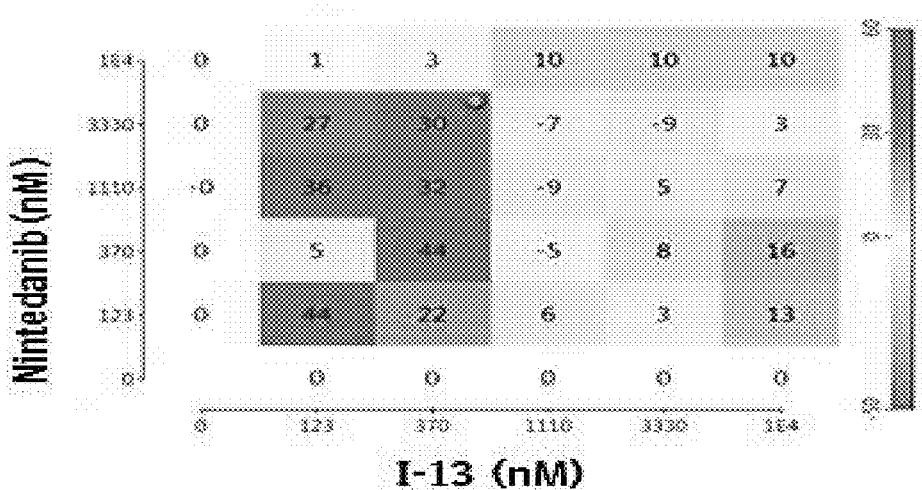

The combination of compound I-13 with nintedanib was tested in a 3D proliferation assay with softagar and this resulted in a more than additive effect in combination compared to both monotherapies. The maximum Bliss excess values increased for the SOS inhibitor I-13 plus nintedanib combination up to a value of 75 in NCI-H1792 cells (FIG. 11 *b*)) and up to a value of 44 in SW 900 cells (FIG. 12 *b*)), which indicates synergy.

Combination Example 8

Figure 13:
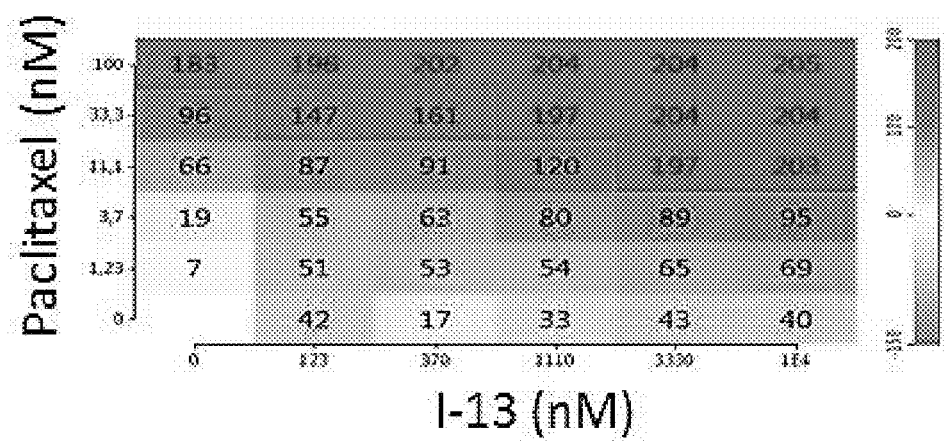
FIG. 13 shows the effect of SOS1 inhibitor compound I-13 and paclitaxel, alone or in combination, on the in vitro growth of NCI-H1792 (KRAS G12C) NSCLC cells.
Figure 13:
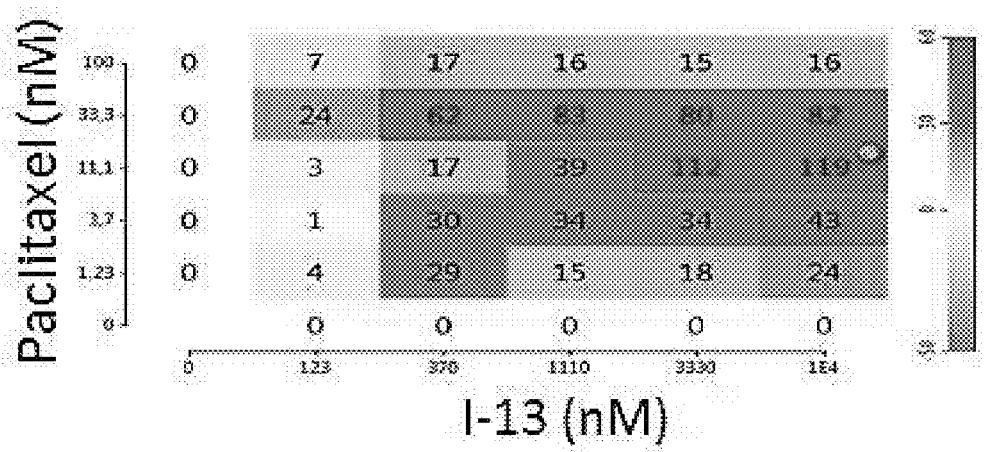
Figure 14:
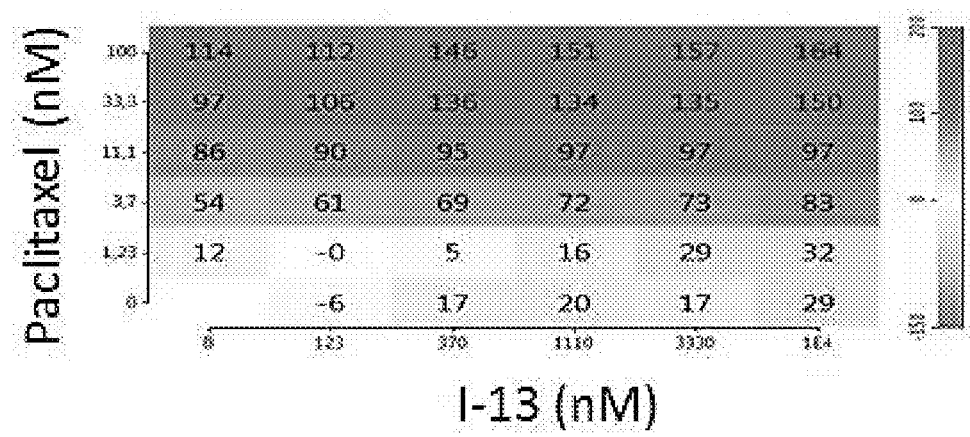
FIG. 14 shows the effect of SOS1 inhibitor compound I-13 and paclitaxel, alone or in combination, on the in vitro growth of A-549 (KRAS G12S) NSCLC cells.
Figure 14:
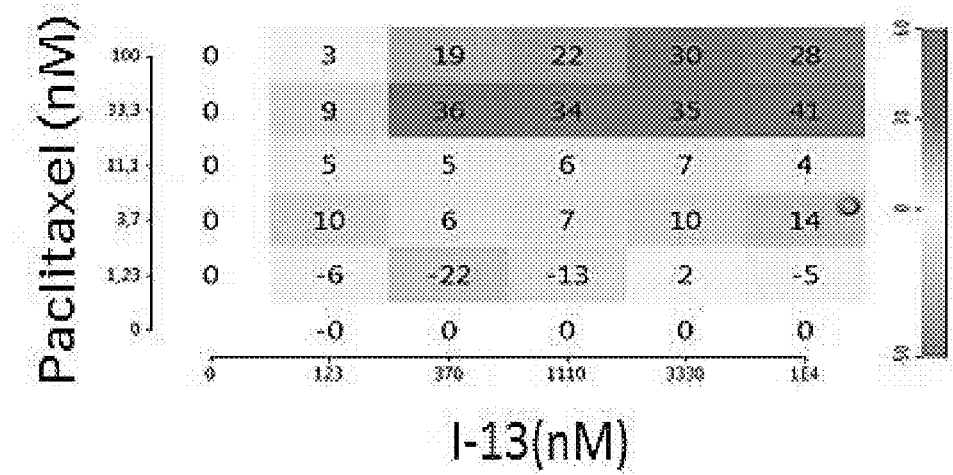

The combination of compound I-13 with paclitaxel was tested in a 3D proliferation assay and this resulted in a more than additive effect in combination compared to both monotherapies. The maximum Bliss excess values increased up to a value of 119 in case of the SOS1 inhibitor plus paclitaxel combination in NCI-H1792 cells (FIG. 13 *b*)) and a value of 41 in A-549 cells (FIG. 14 *b*)), which indicates synergy in the combination.

Combination Example 9

Figure 15:
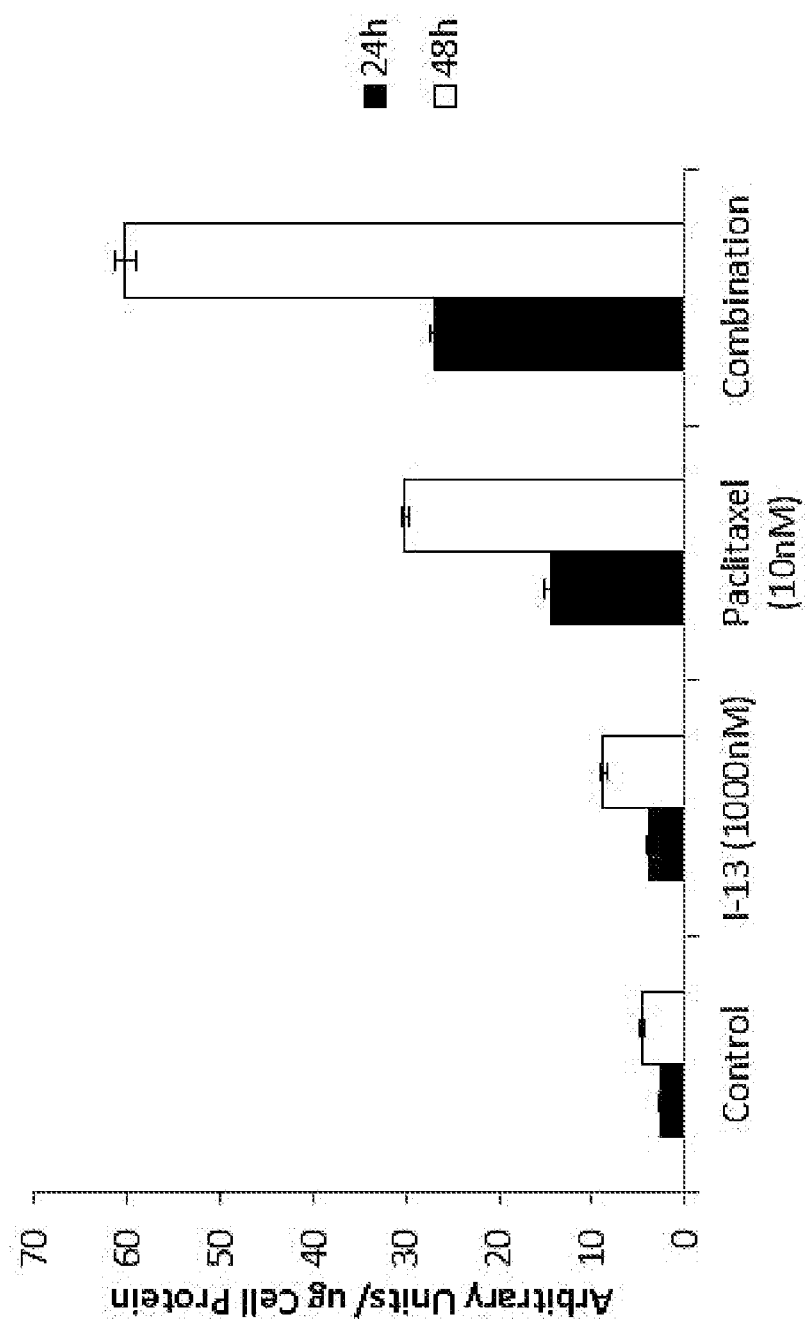
FIG. 15 shows the effect of SOS1 inhibitor compound I-13 and paclitaxel, alone or in combination, on the levels of cleaved PARP, a marker for apoptosis, in A-549 (KRAS G12S) NSCLC cells.

For validation of apoptosis induction, levels of cleaved PARP were determined with a commercially available mesoscale assay. For this assay cell were cultured in 3D using low binding Scivax Plates, with 10% serum in the cell culture medium. A459 NSCLC cells were treated with 1 μM of compound I-13 or 10 nM of paclitaxel as single agents or in combination for either 24 h or 48 h. Combination of compound I-13 with paclitaxel resulted in a stronger induction of apoptosis at the 24 h and 48 h timepoint compared to both monotherapies (FIG. 15).

Combination Example 10

Observed in vitro effects of the combination of I-13 with paclitaxel translated into a strong combinatorial effect in vivo:

Paclitaxel (10 mg/kg, q7d, i.v.) was combined with compound I-13 (50 mg/kg, bid, p.o.) in a pancreatic cancer xenograft mouse model (MIA PaCa-2 (KRAS G12C)). The combination of both compounds was well tolerated and resulted (on day 22) in a TGI of 97% and 2/7 tumors going into regressions compared to only a TGI of 62% for paclitaxel in monotherapy and a TGI of 86% for compound I-13 in monotherapy with no regressions (FIG. 16). The effect in combination is significantly stronger compared to compound I-13 in monotherapy (p=0.0131) and paclitaxel in monotherapy (p=0.0003).

Combination Example 11

Gemcitabine (50 mg/kg, q4d, i.p.) was combined with compound I-13 (50 mg/kg of I-13 was applied but in this experiment plasma levels comparable to only 12 mg/kg were achieved due to suboptimal formulation, bid, p.o.) in a pancreatic cancer xenograft mouse model (MIA PaCa-2 (KRAS G12C)). The combination of both compounds was well tolerated and resulted in a TGI of 42% compared to only a TGI of 4% for gemcitabine and 11% for compound I-13 in monotherapy. The effect in combination is significantly stronger compared to compound I-13 in monotherapy (p=0.0015) and gemcitabine in monotherapy (p=0.0011) (FIG. 17).

Combination Example 12

Figure 18:
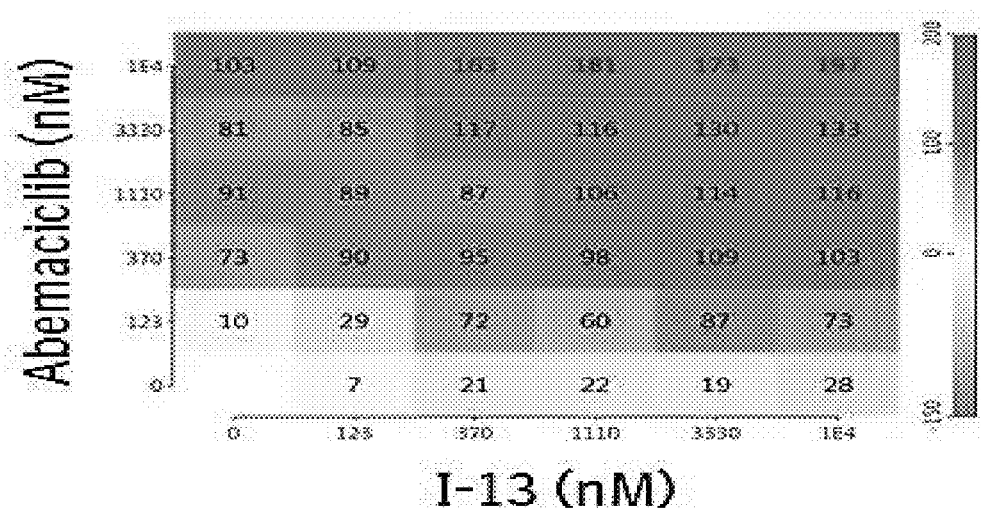
FIG. 18 shows the effect of SOS1 inhibitor compound I-13 and CDK4/6 inhibitor abemaciclib, alone or in combination, on the in vitro growth of NCI-H2122 (KRAS G12C) NSCLC cells.
Figure 18:
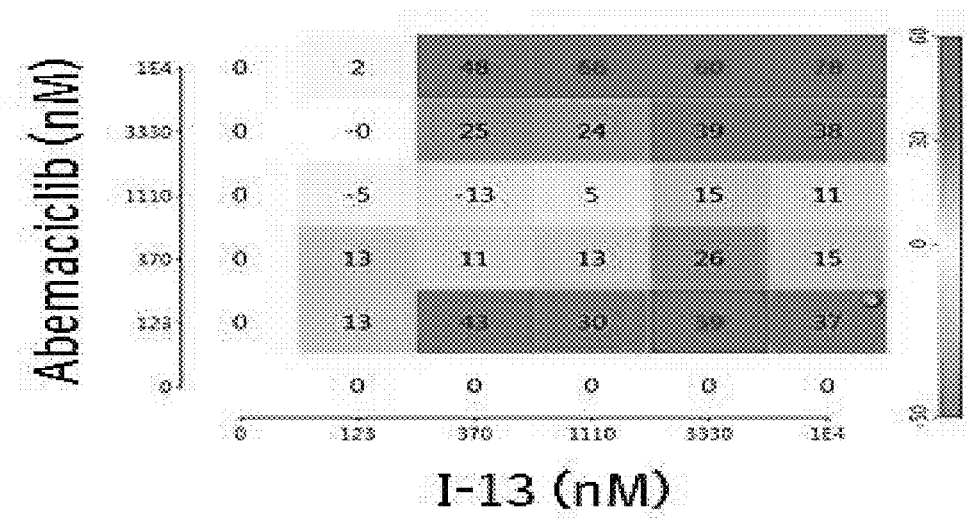

The combination of compound I-13 with the CDK4/6 inhibitor abemaciclib was tested in a 3D proliferation assay and this resulted in a more than additive effect in combination compared to both monotherapies. The maximum Bliss excess values increased up to a value of 78 in case of the SOS1 inhibitor plus abemaciclib combination in NCI-H2122 cells (FIG. 18 b)), which indicates synergy in this combination.

Therapeutic Use

Due to their biological properties the compounds of the invention, their tautomers, racemates, enantiomers, diastereomers, mixtures thereof and the salts of all the above-mentioned forms may be suitable for treating diseases characterised by excessive or abnormal cell proliferation such as cancer.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas,

Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, iymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery.

Of course, the above also includes the use of the compounds of the invention in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Combinations with Other Active Substances

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Pharmacologically active substances which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Ka inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpont inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation and methods of preparing, the compounds of the invention for the combined use with the above combination partners. Also included are the preparation, and methods of preparing, the above-mentioned combination partners for the combined use with the compounds of the invention.

Furthermore, the invention also encompasses kits comprising at least one compound of the invention and one or more other components selected from the group consisting of other drugs used for the treatment of the diseases and disorders as described above, and devices as described below.

Formulations

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 500 to 1500 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Tablets | per tablet |
|---|---|---|
| | active substance according to formula (I) | 25 mg |
| | lactose | 50 mg |
| | microcrystalline cellulose | 24 mg |
| | magnesium stearate | 1 mg |
| | | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) | Ampoule solution | |
|---|---|---|
| | active substance according to formulae (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound selected from the group consisting of:
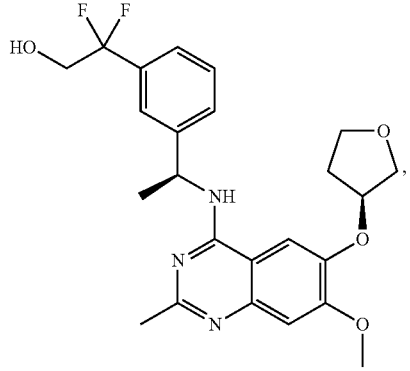
I-1
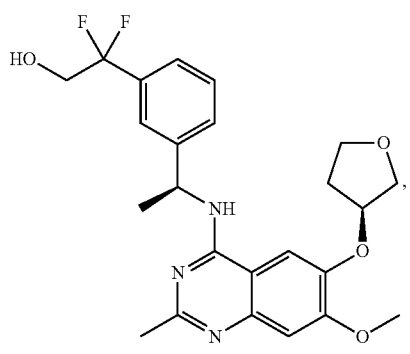
I-2
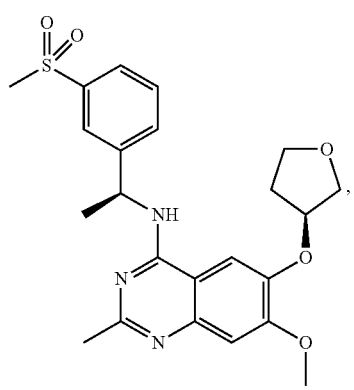
I-3
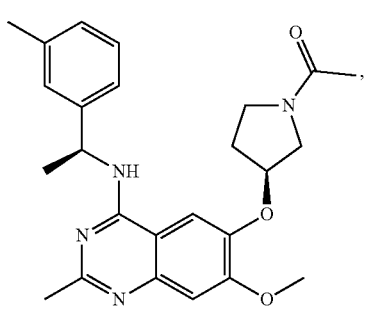
I-4
-continued
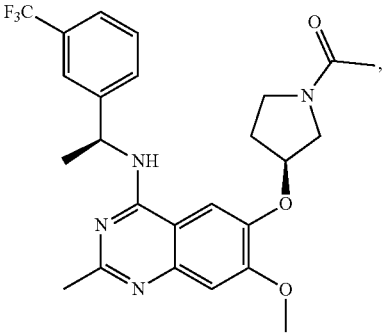
I-5
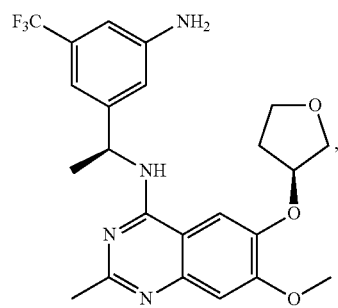
I-6
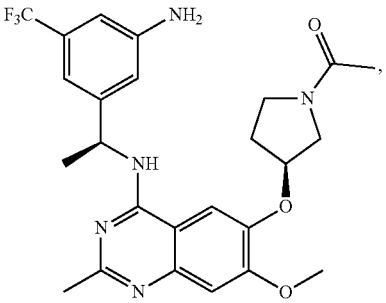
I-7
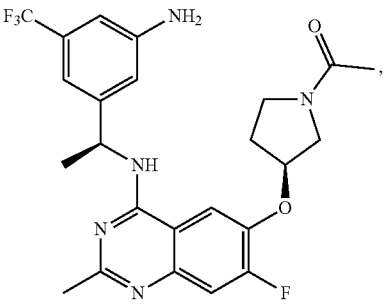
I-8
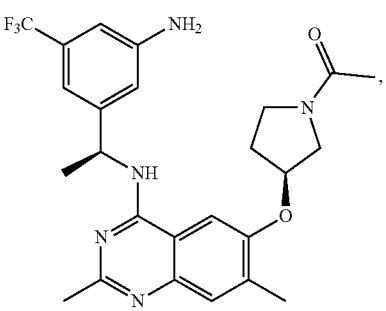
I-9

I-10
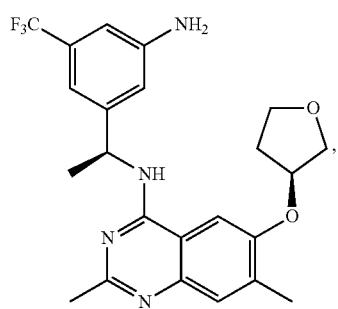
I-11
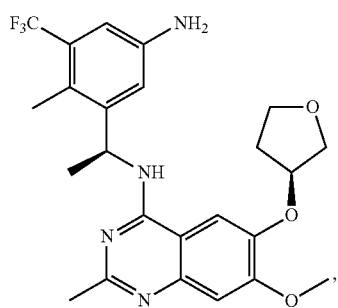
I-12
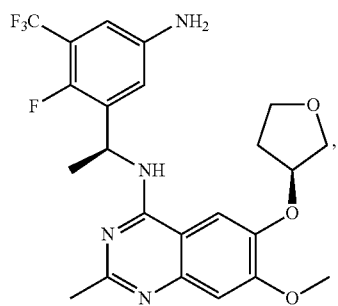
I-13
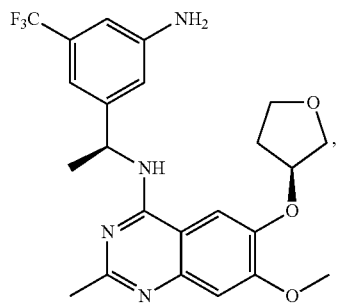
I-16
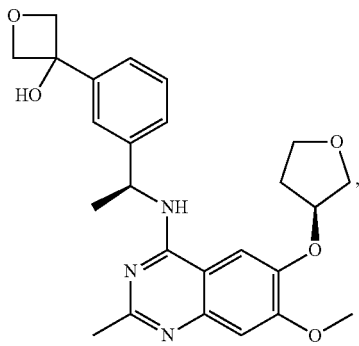
I-17
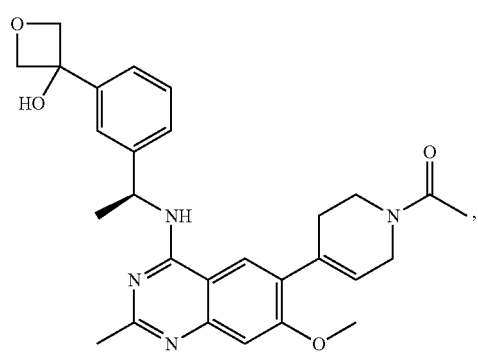
I-20
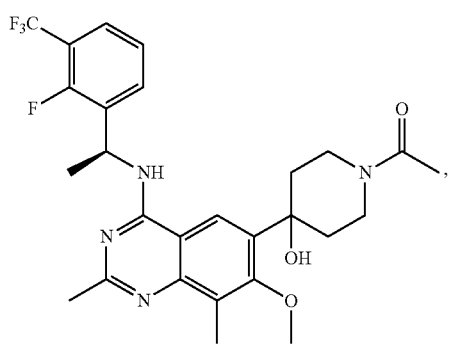
I-21
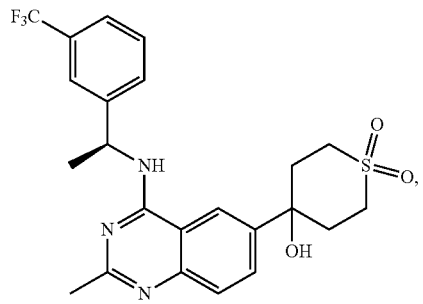
I-42
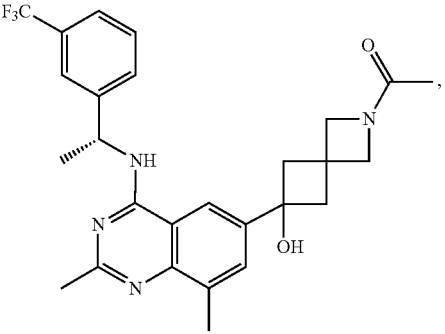

I-43
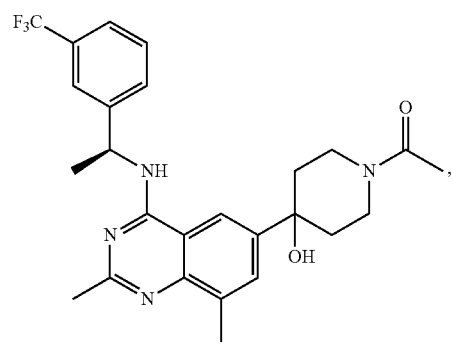
I-44
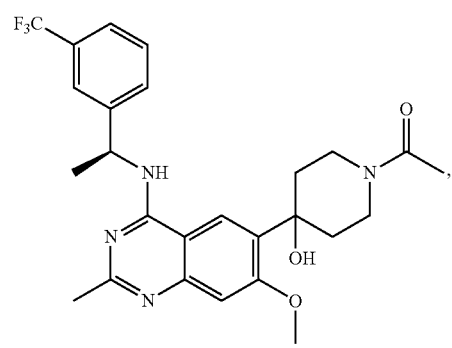
I-45
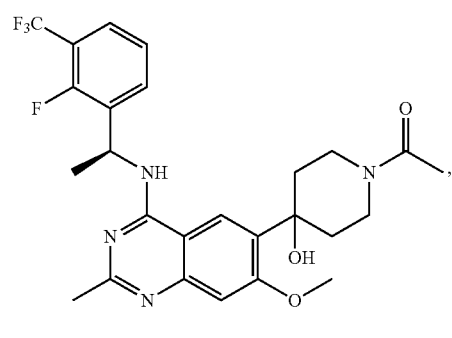
I-46
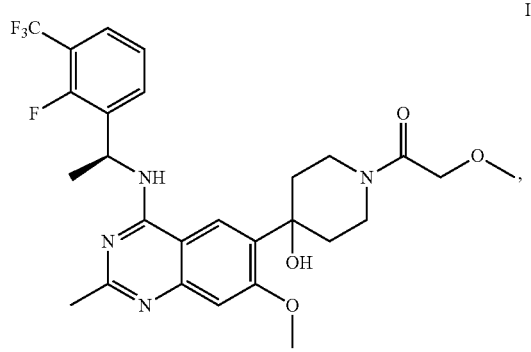
I-47
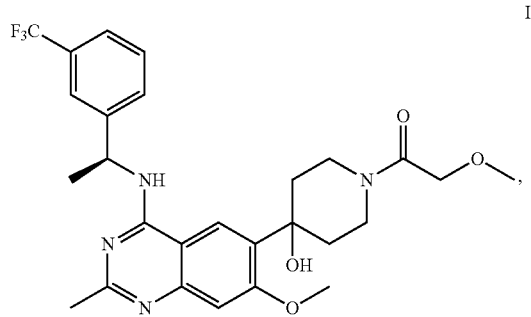
I-48
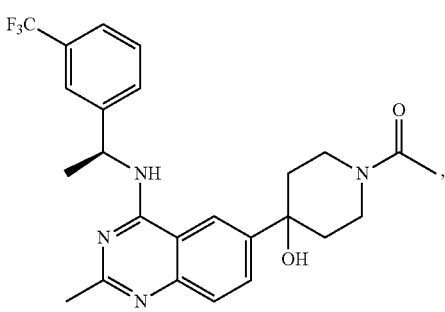
I-49
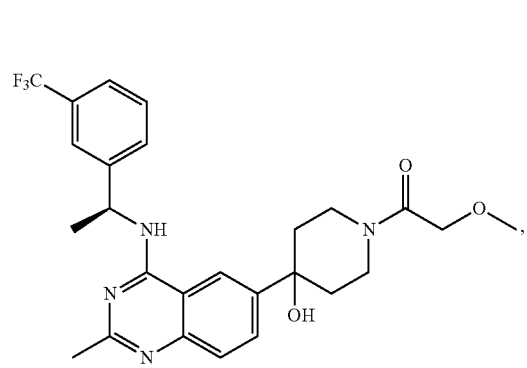
I-50
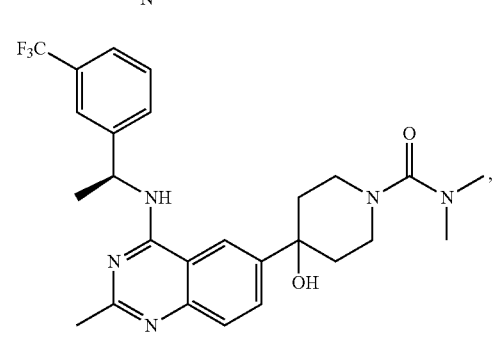
I-51
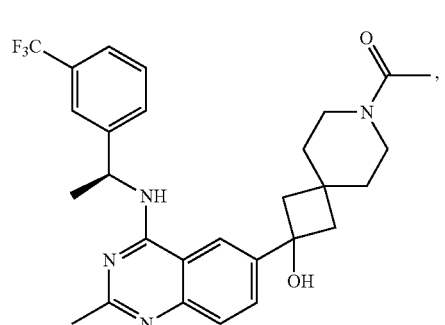
I-52
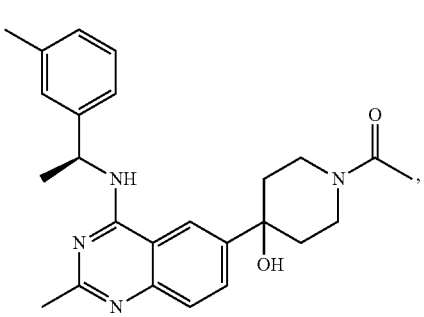

I-53
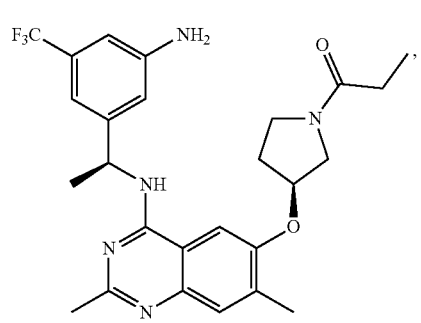
I-54
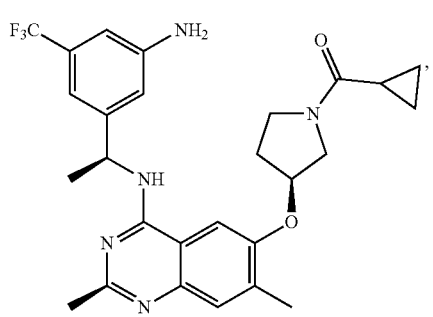
I-55
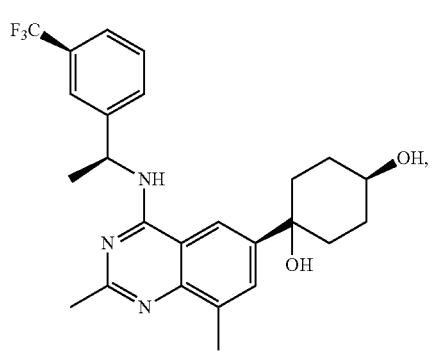
I-57
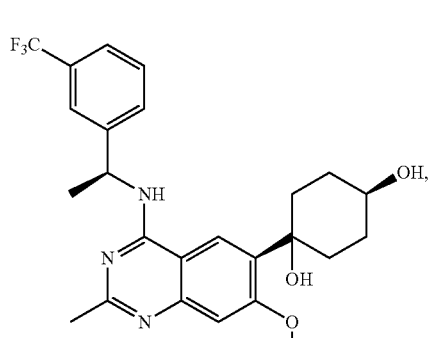
I-58
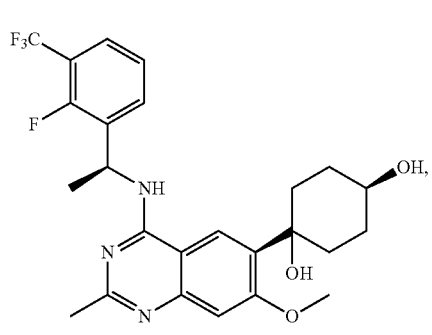
I-59
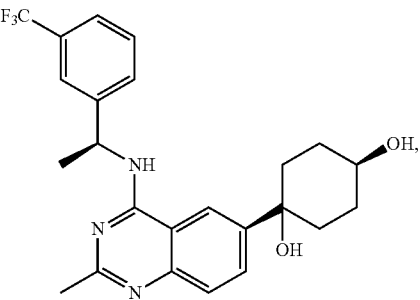
I-60
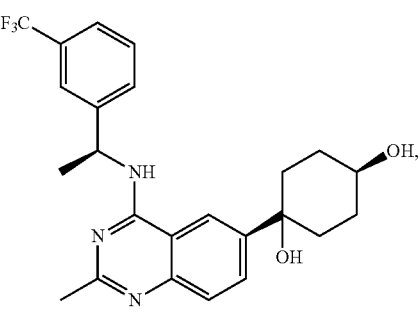
I-61
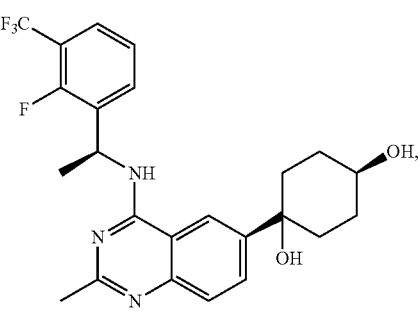
I-62
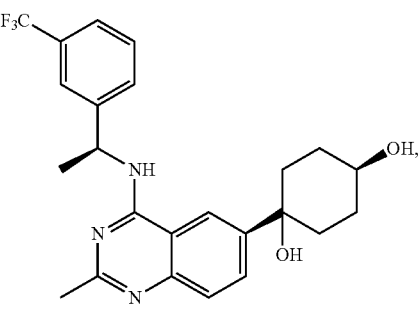
I-63
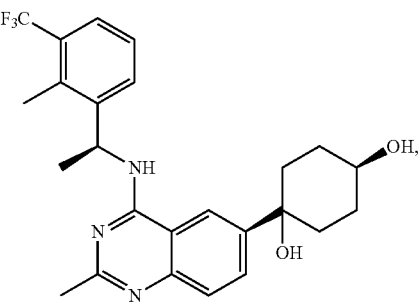

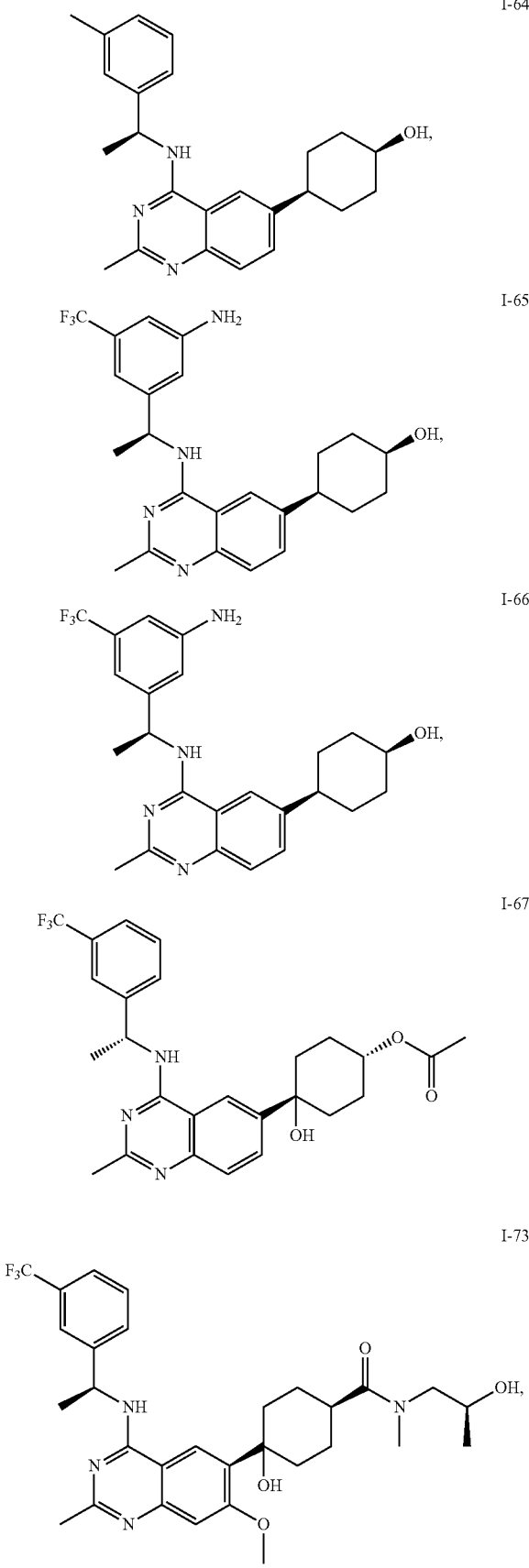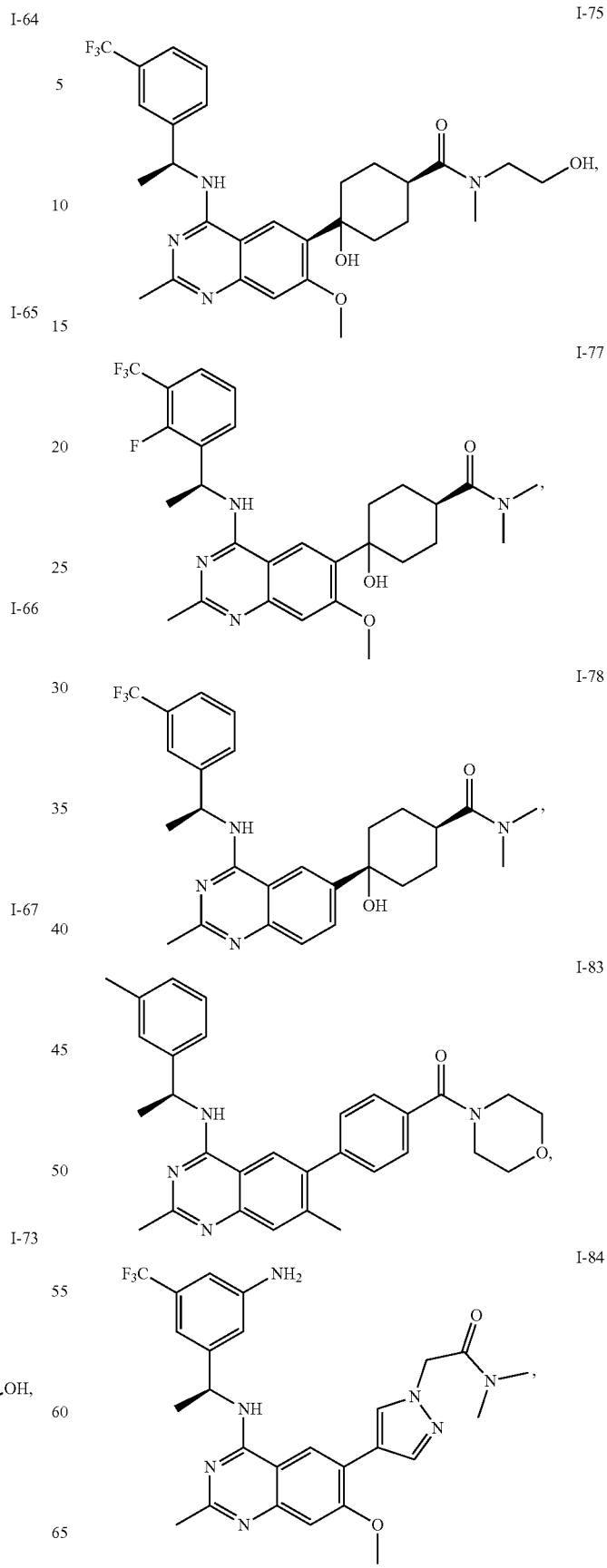

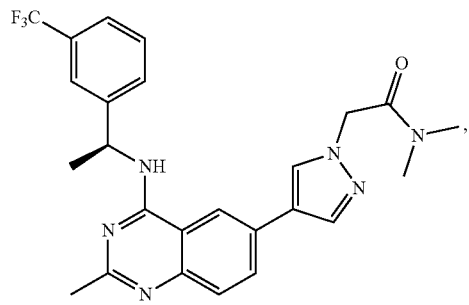 I-85
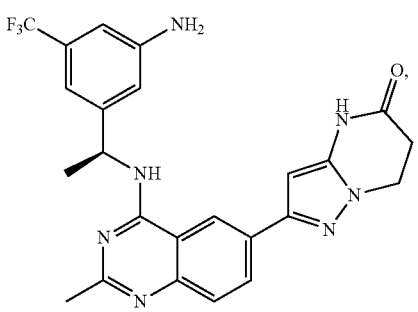 I-90
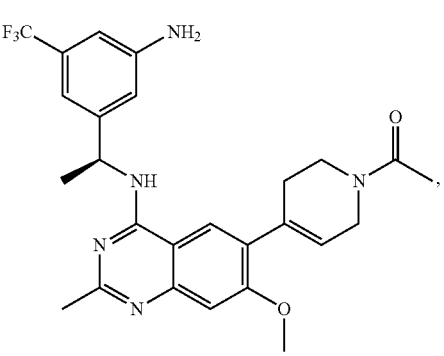 I-98
I-86
I-87
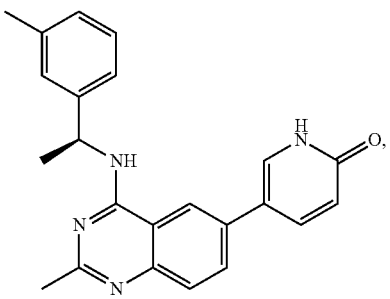 I-99
I-88
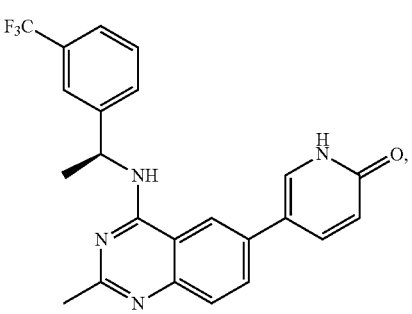 I-100
I-89
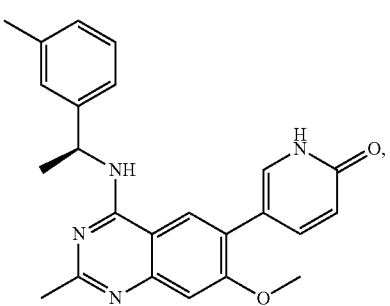 I-101

I-102
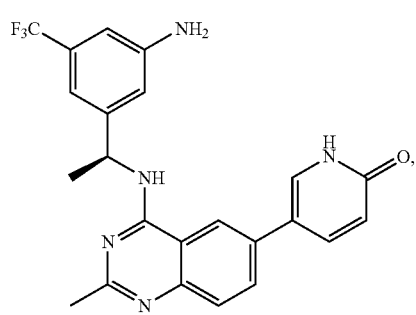
I-103
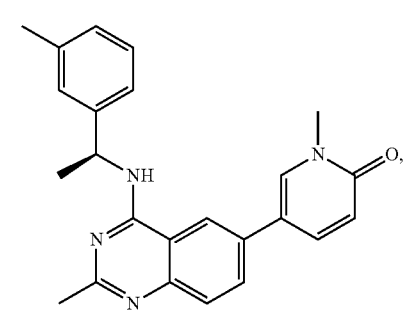
I-104
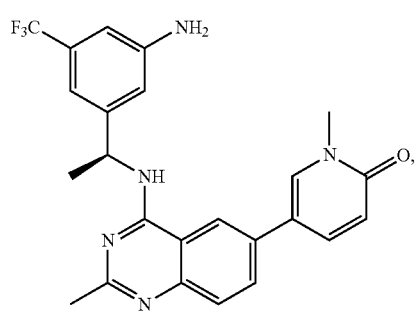
I-105
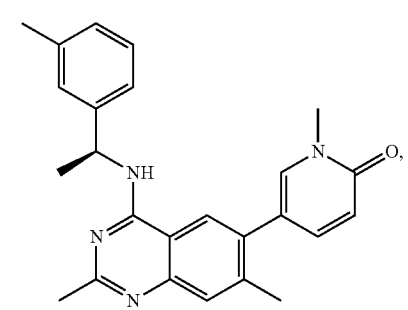
I-106
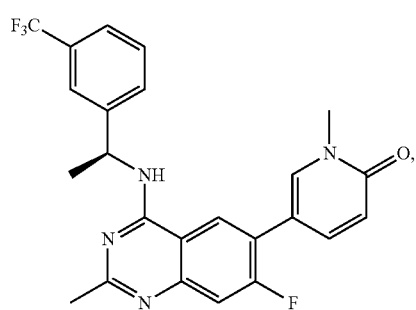
I-107
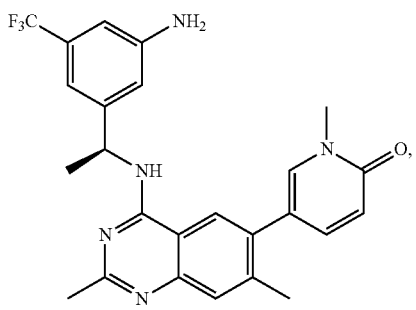
I-108
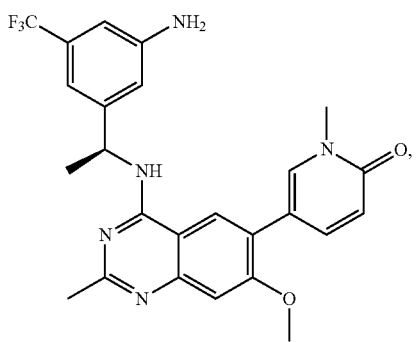
I-109
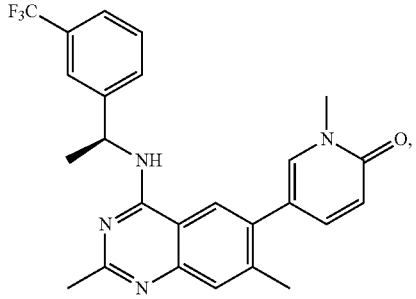
I-110
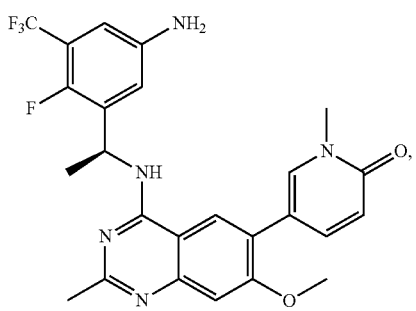
I-111
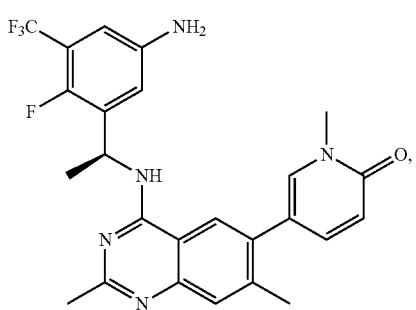

-continued
I-146
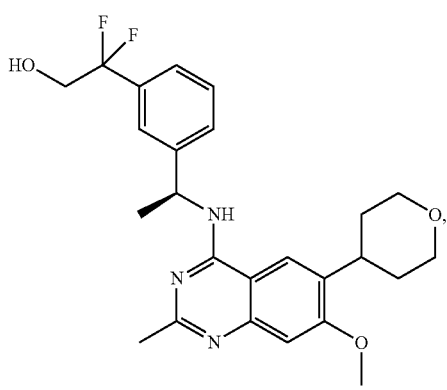
I-153
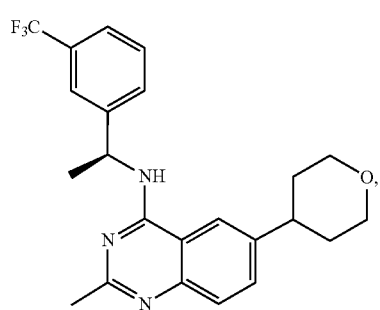
I-154
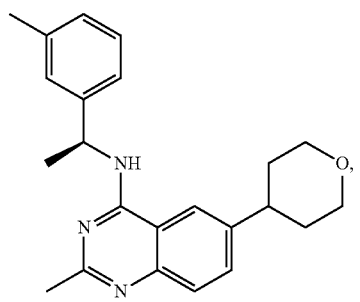
I-155
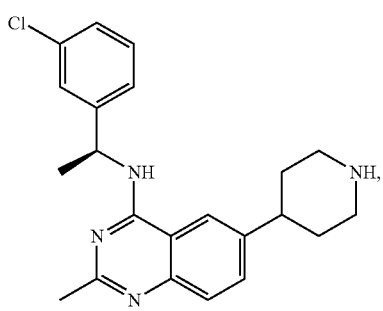
I-160
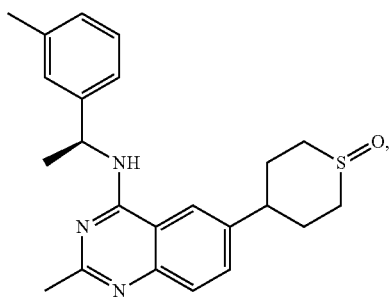
-continued
I-161
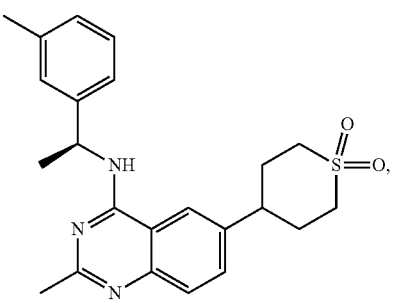
I-164
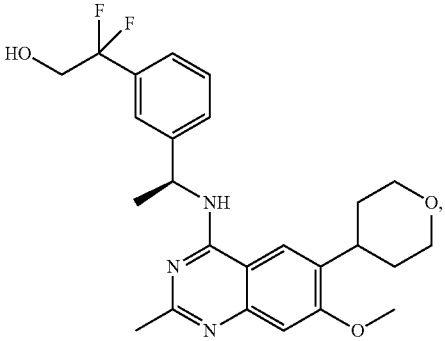
I-165
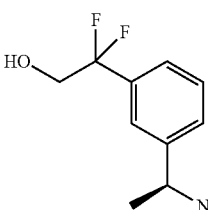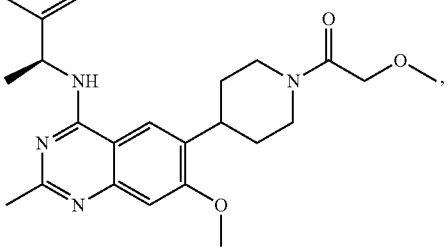
I-166
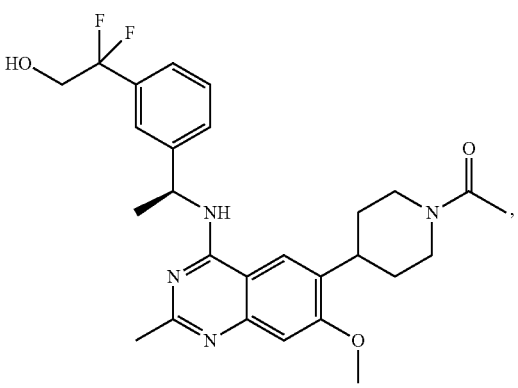

I-167
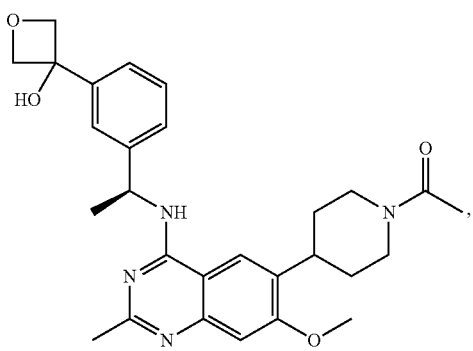
I-168
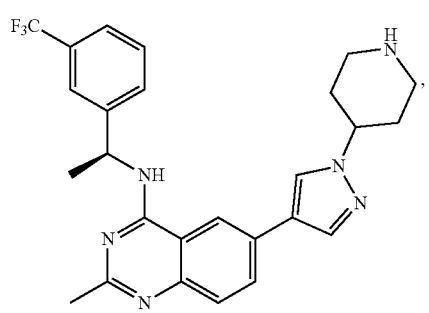
I-170
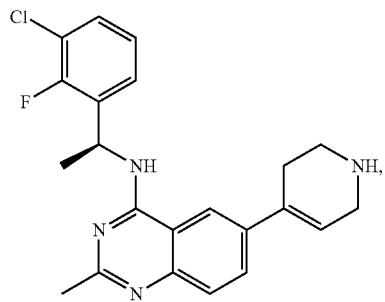
I-171
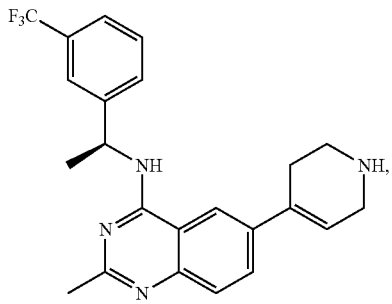
I-172
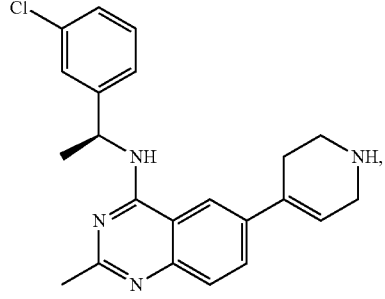
I-175
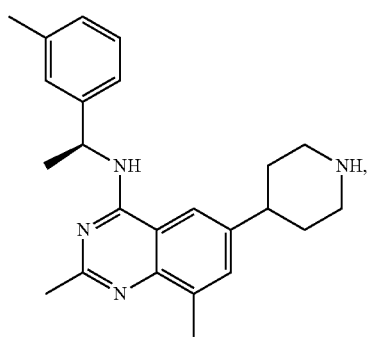
I-176
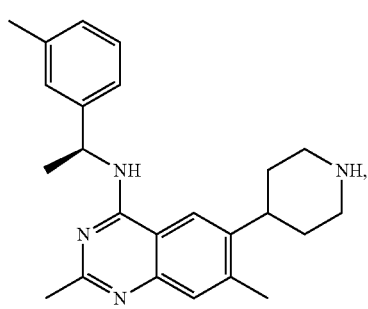
I-182
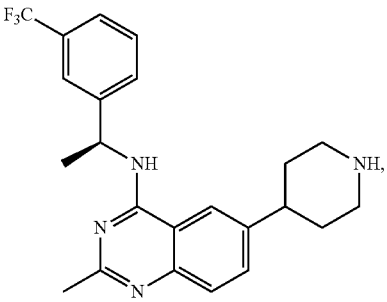
I-181
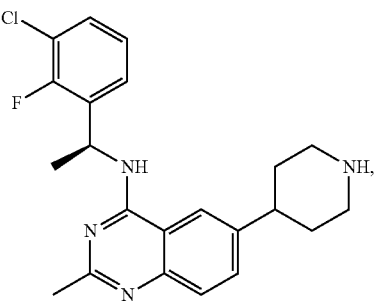
I-183
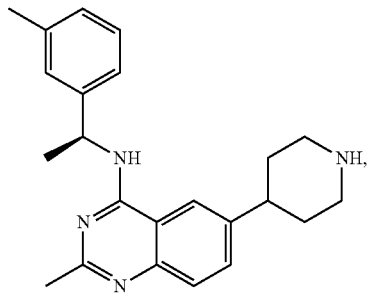

I-189
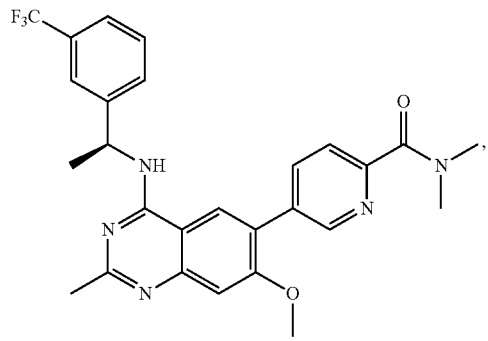
I-190
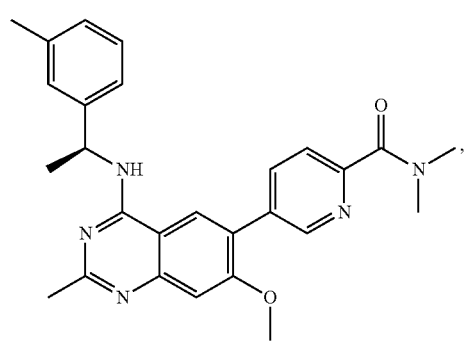
I-191
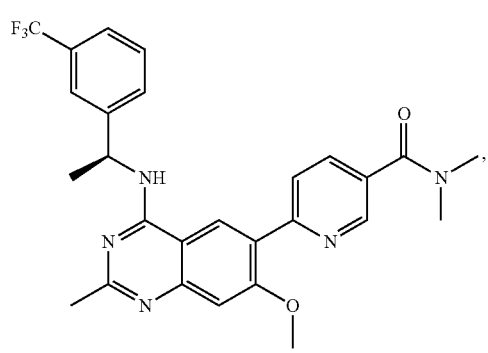
I-199
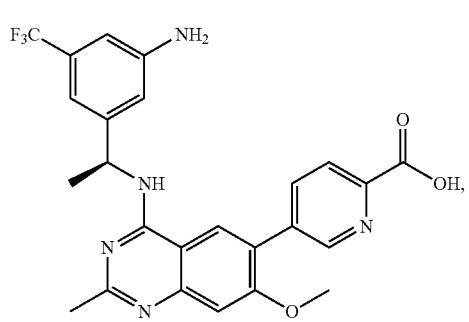
I-213
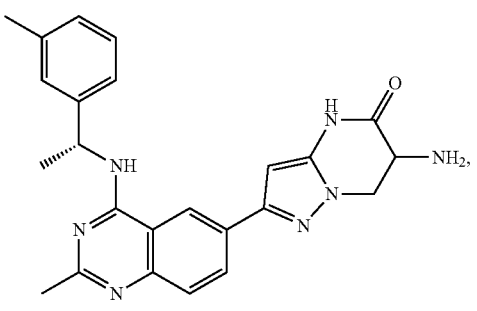
I-214
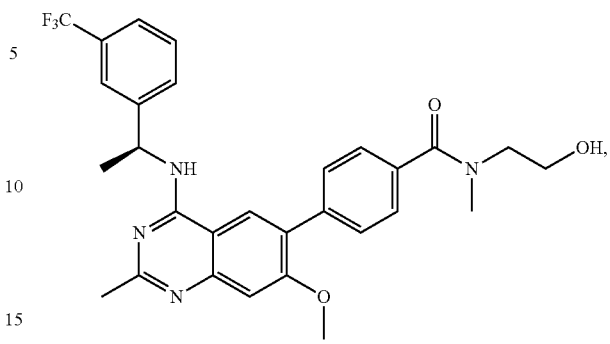
I-215
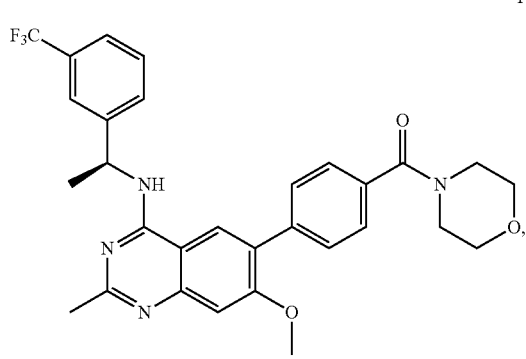
I-216
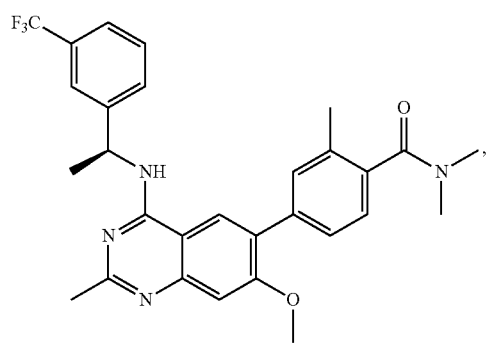
I-217
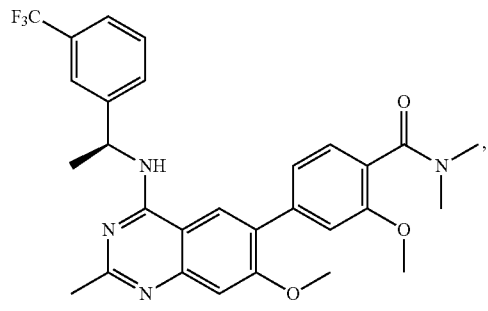

I-218
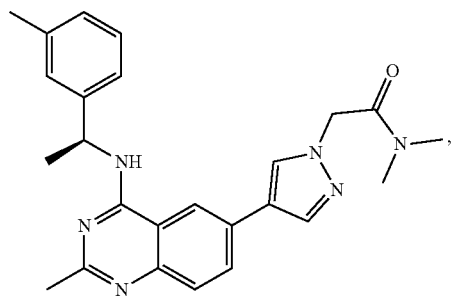
I-219
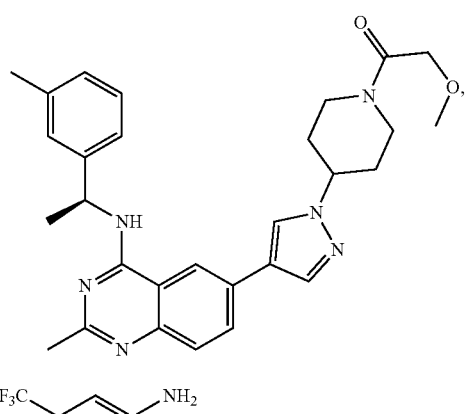
I-220
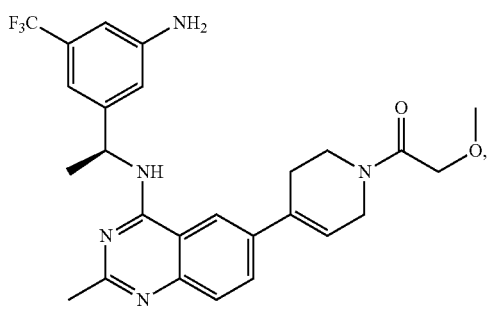
I-221
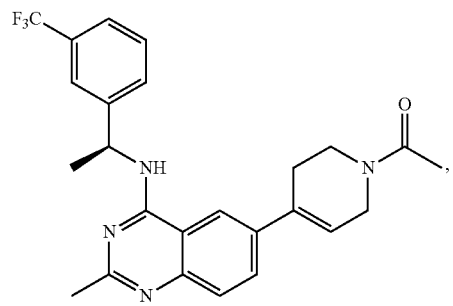
I-222
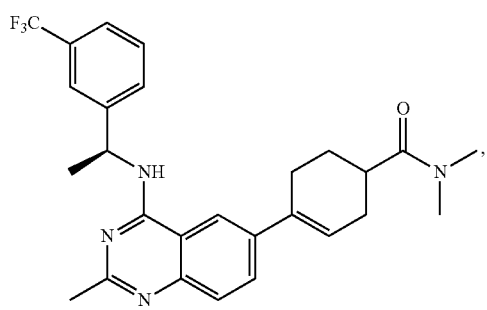
I-223
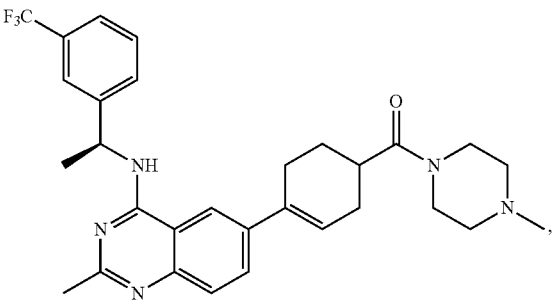
I-224
I-227
I-229
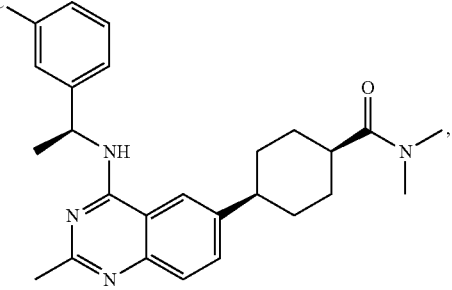

I-230
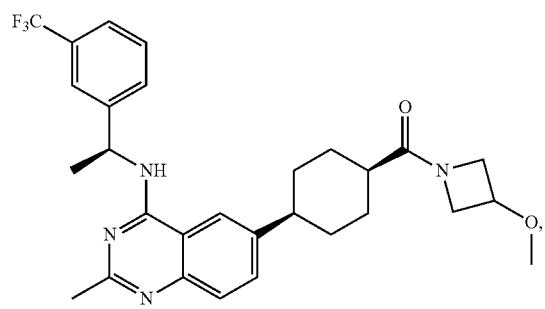
I-231
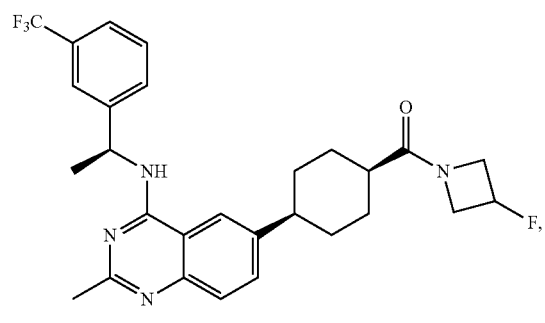
I-232
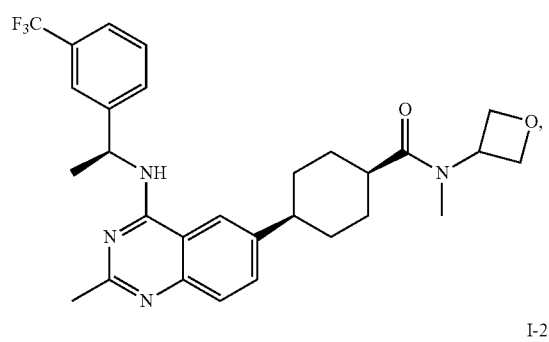
I-233
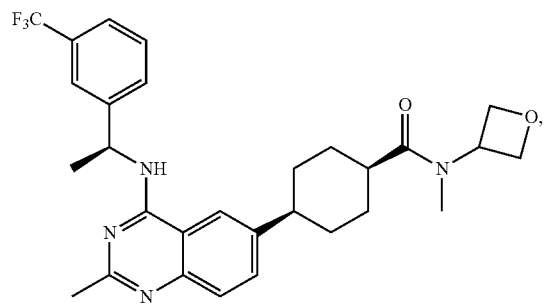
I-234
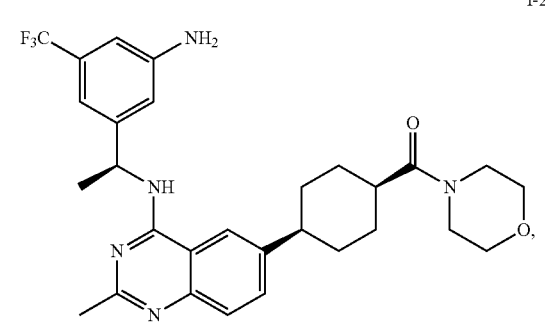
I-235
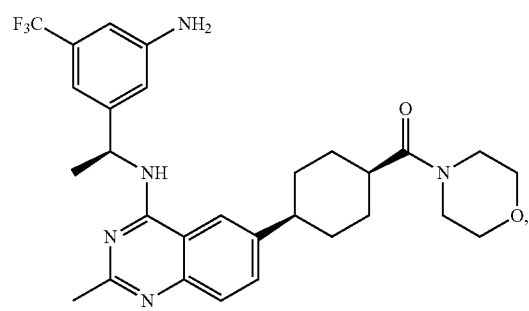
I-236
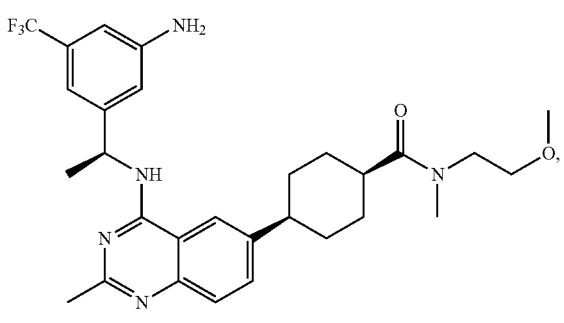
I-237
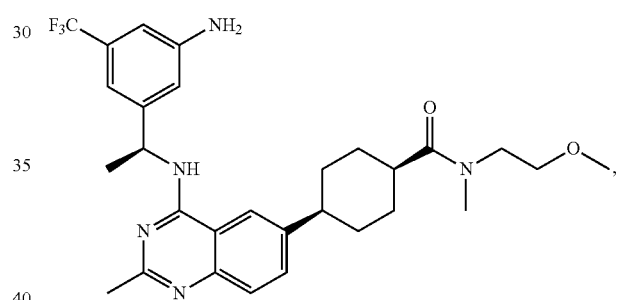
I-238
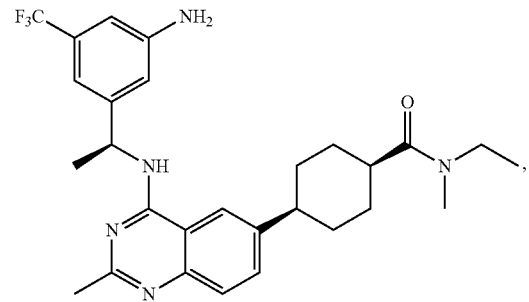
I-239
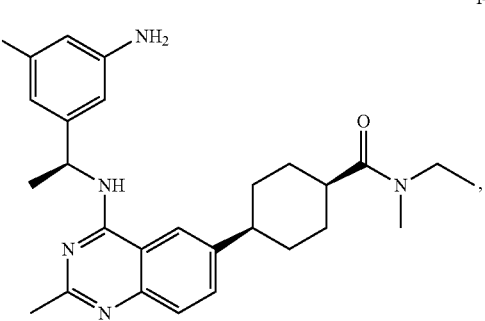

I-240
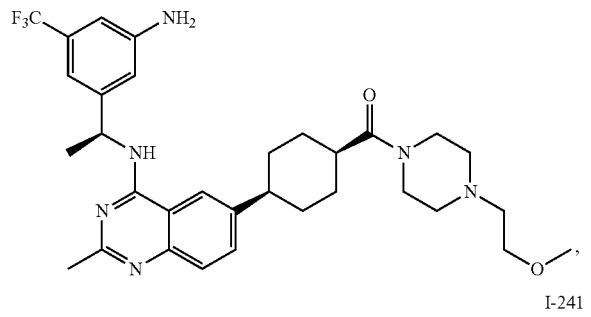
I-241
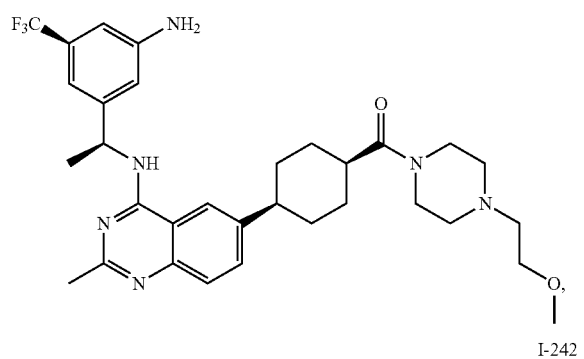
I-242
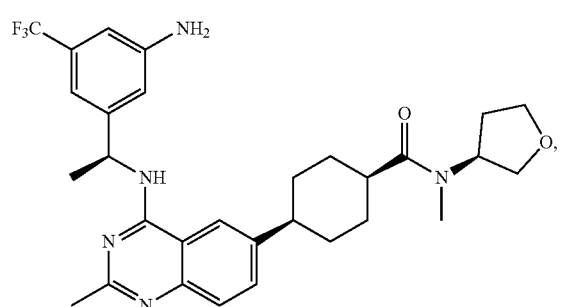
I-243
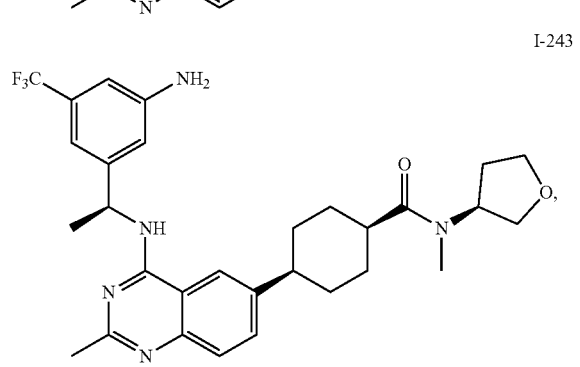
I-244
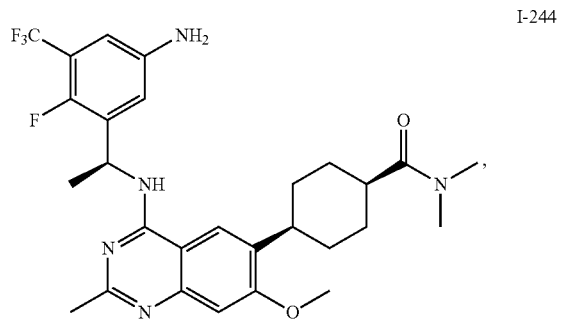
I-245
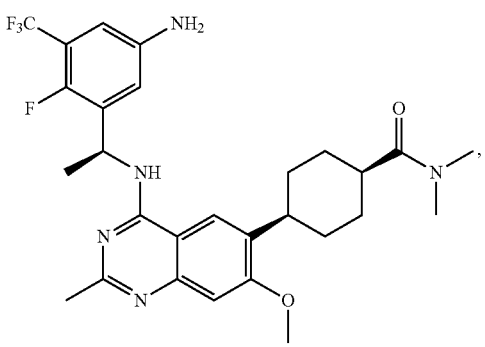
I-246
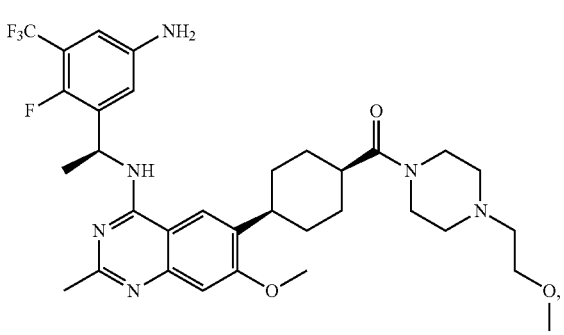
I-247
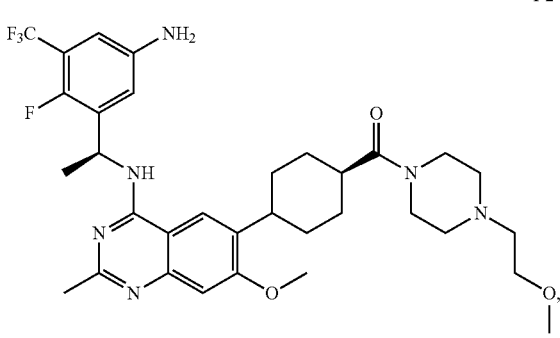
I-248
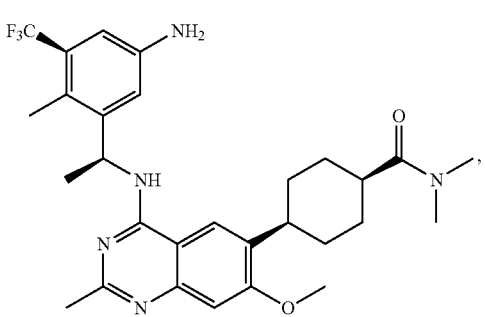

I-249
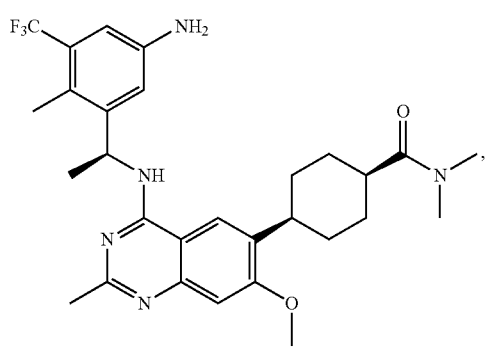
I-250
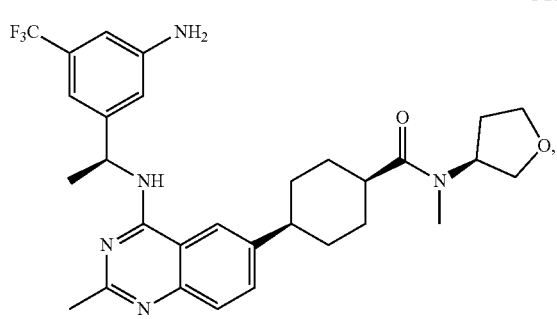
I-251
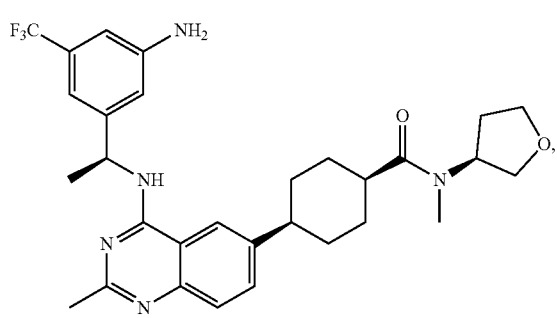
I-252
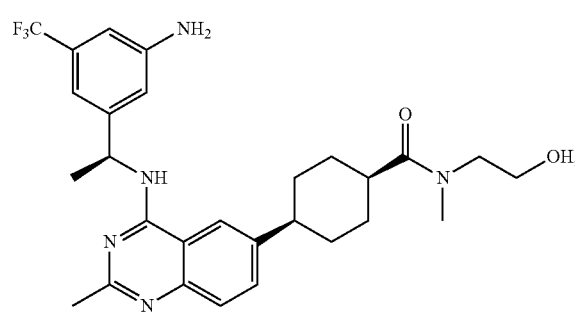
I-253
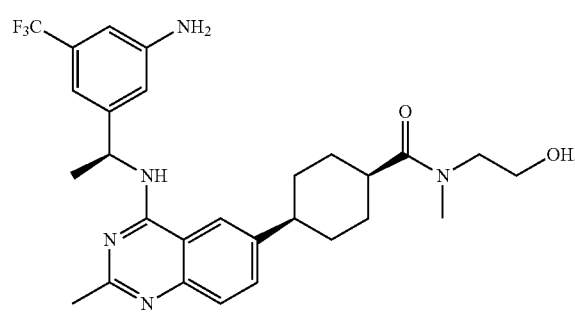
I-254
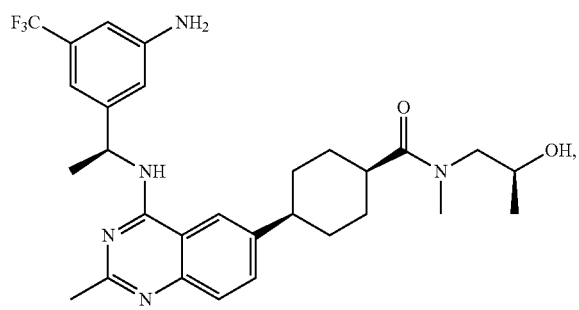
I-255
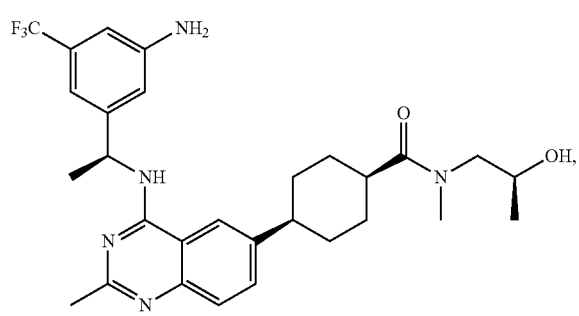
I-256
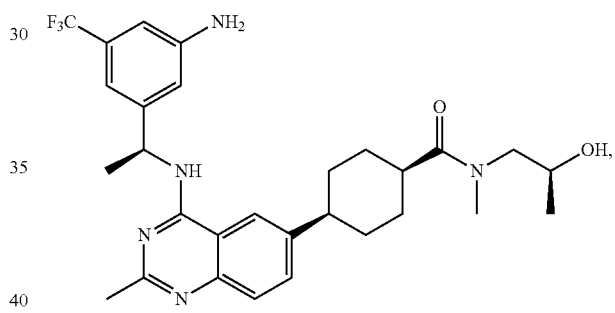
I-257
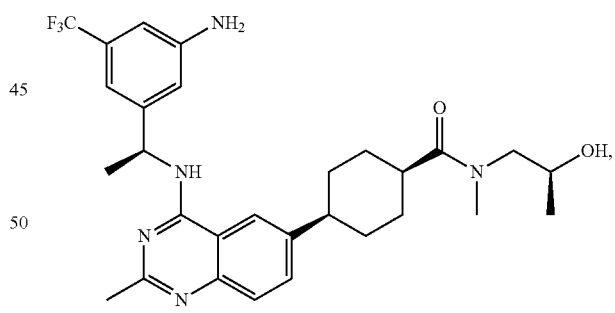
I-258
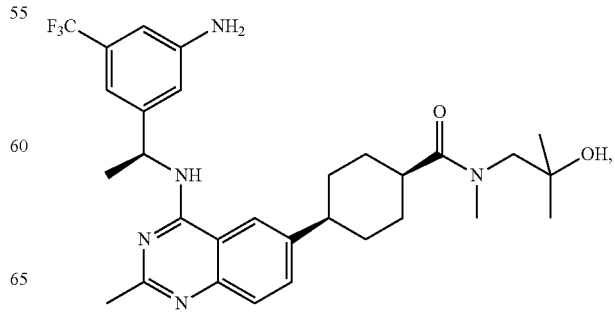

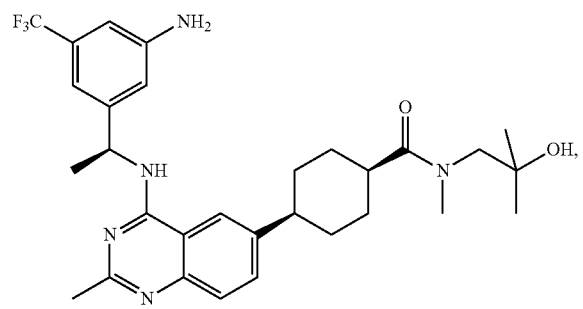
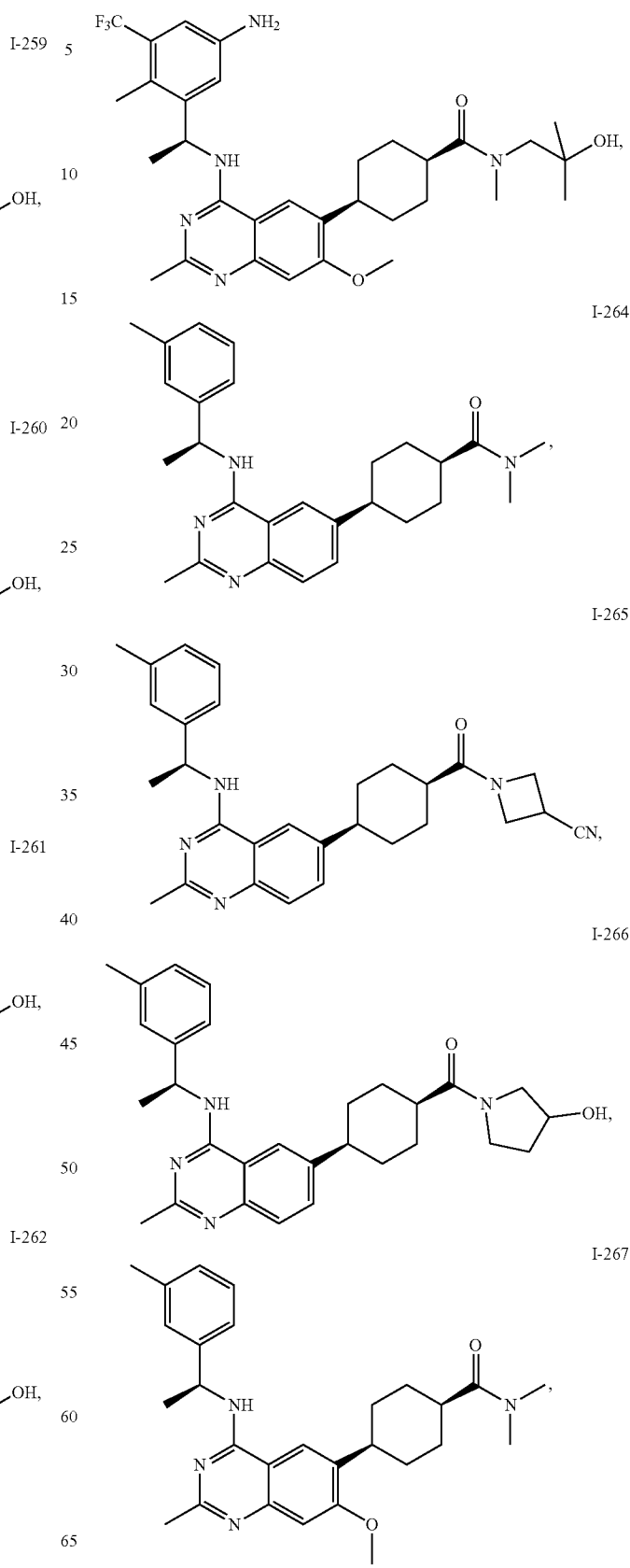

I-269
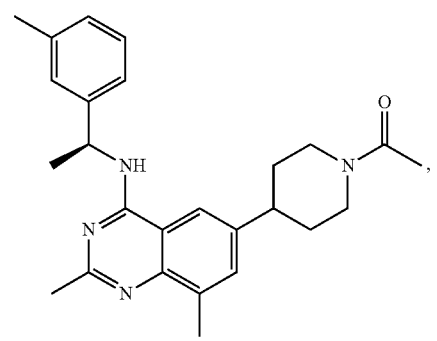
I-274
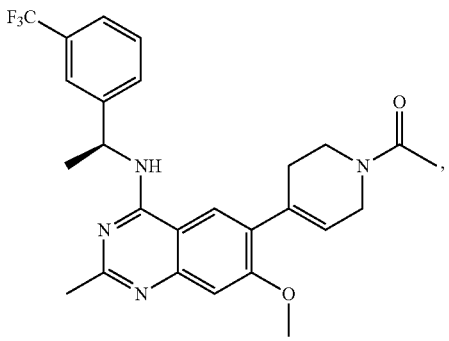
I-270
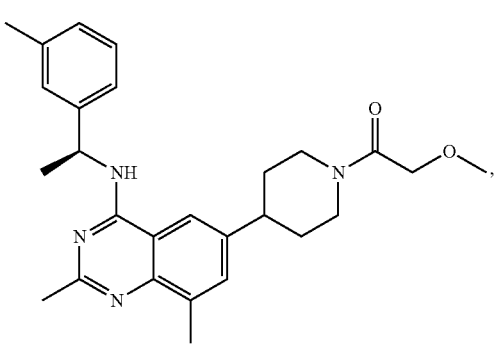
I-275
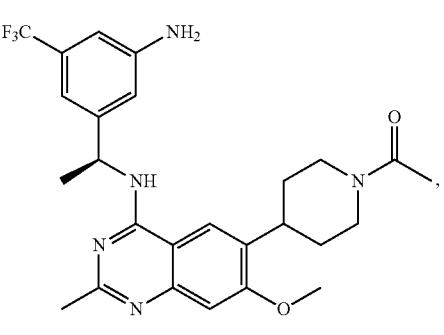
I-271
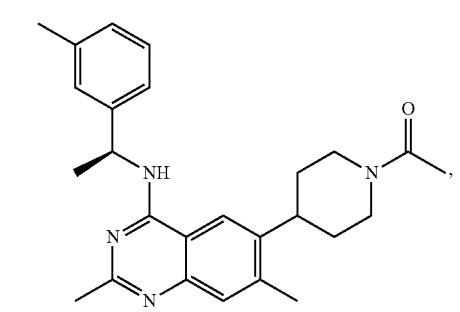
I-276
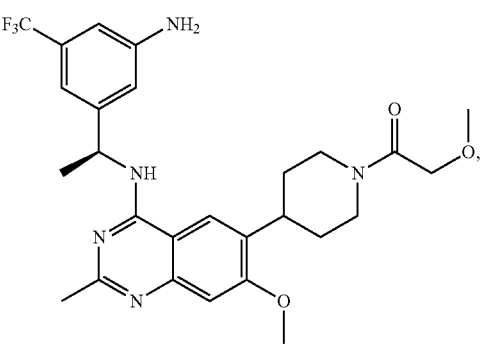
I-272
I-277
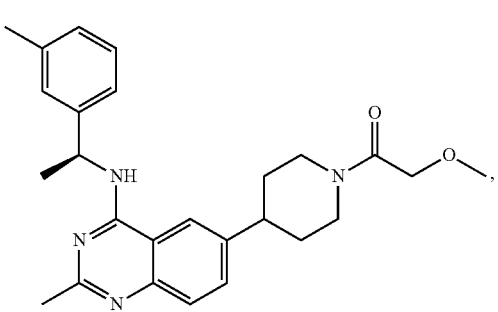
I-273
I-278
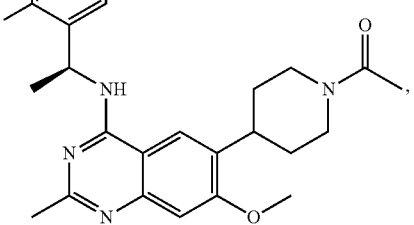

I-279
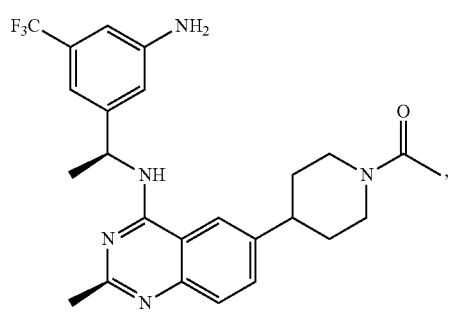
I-280
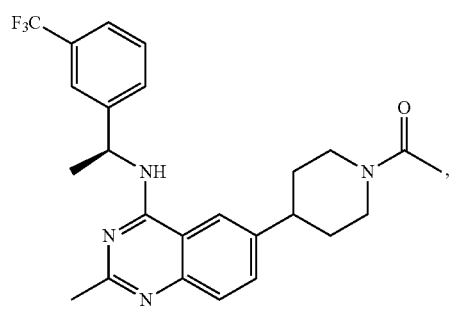
I-281
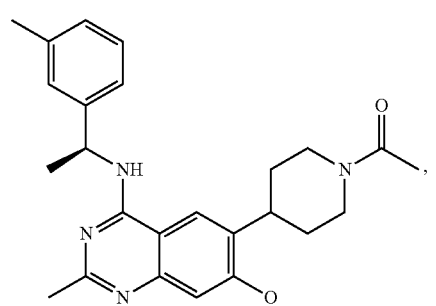
I-282
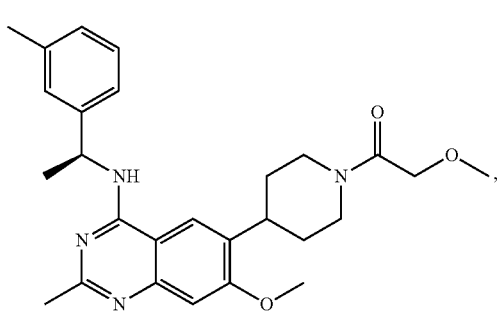
I-285
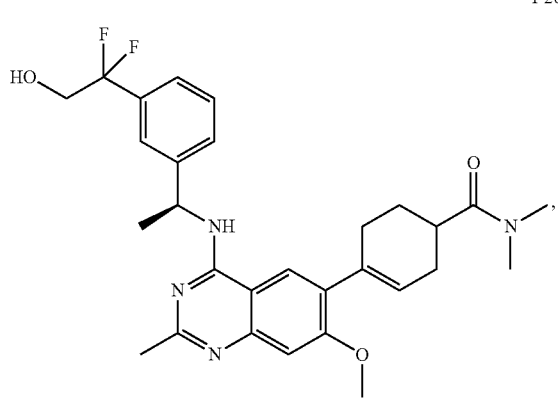
I-286
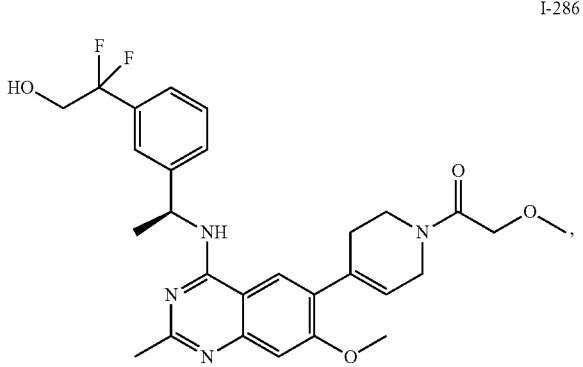
I-287
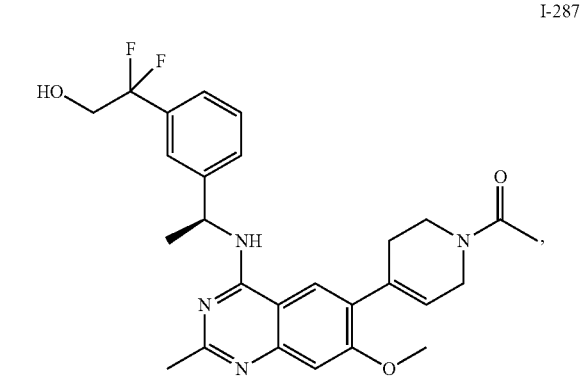
I-288
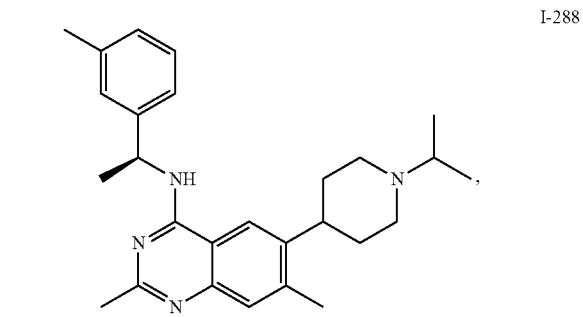
I-289
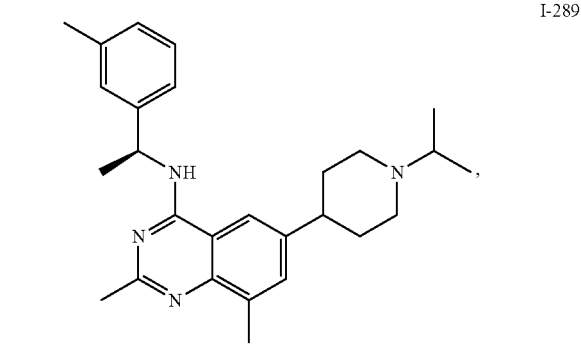

I-290 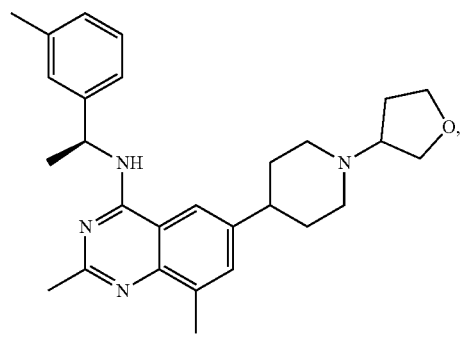
I-291 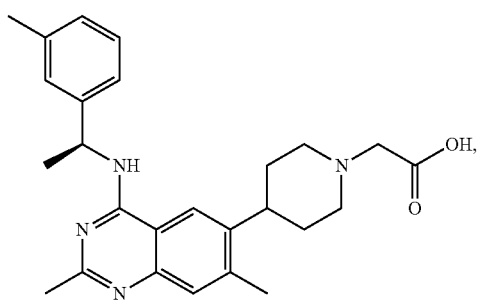
I-292 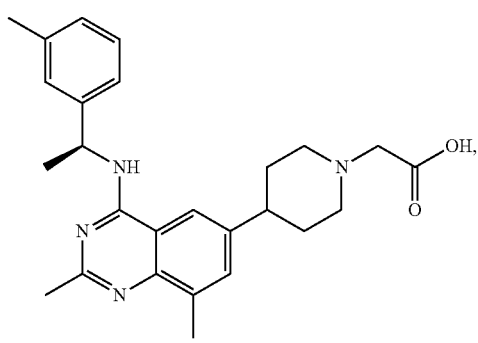
I-293 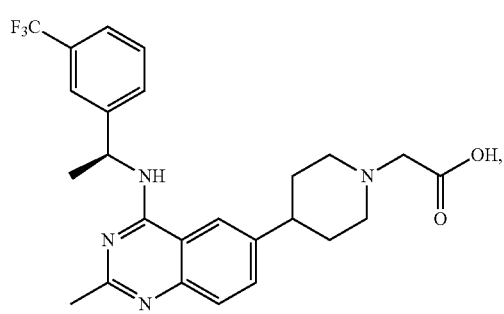
I-294 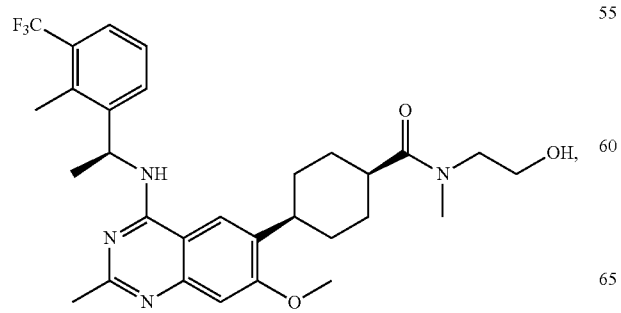
I-295 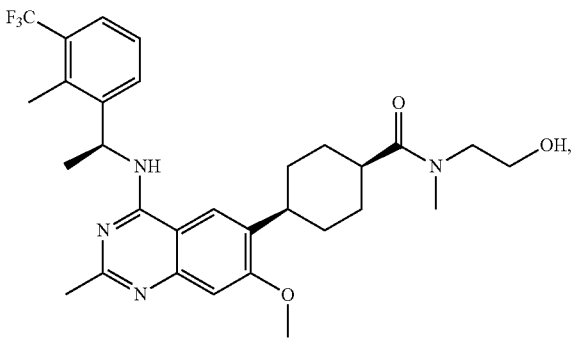
I-296 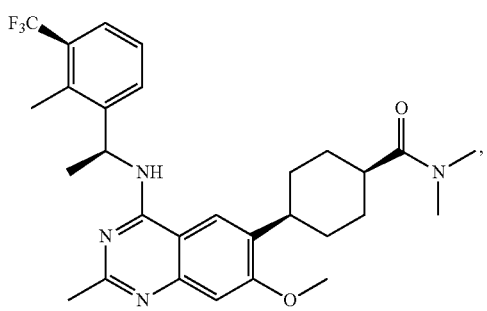
I-298 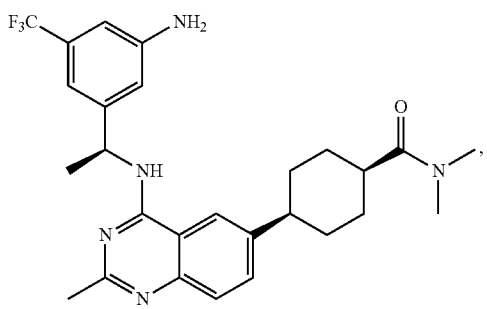
I-299 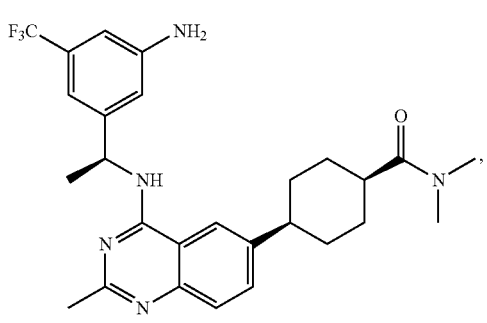
I-307 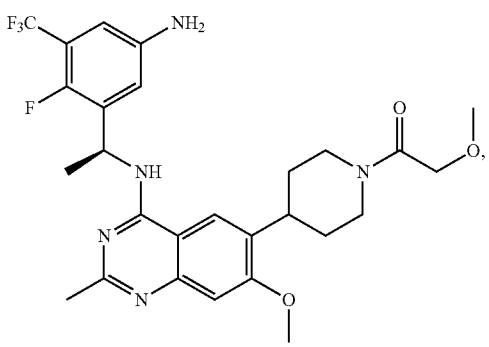

I-308
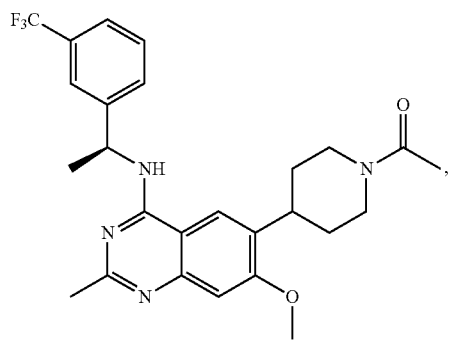
I-310
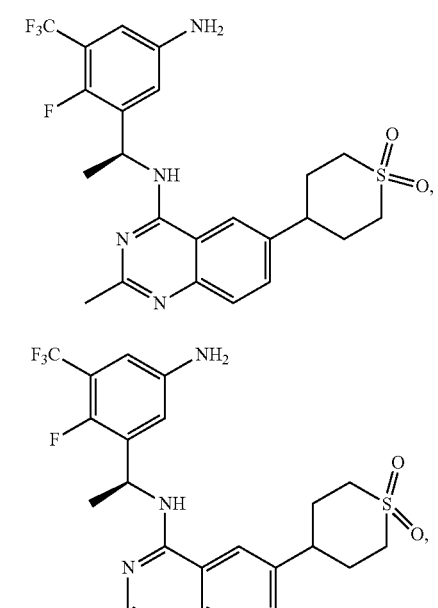
I-311
I-312
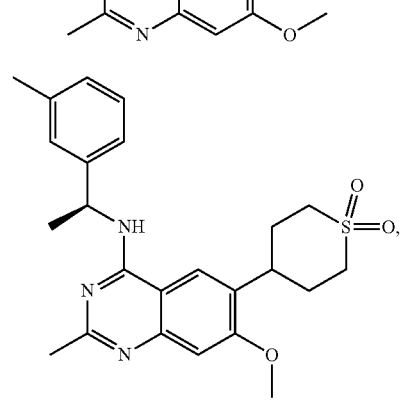
I-313
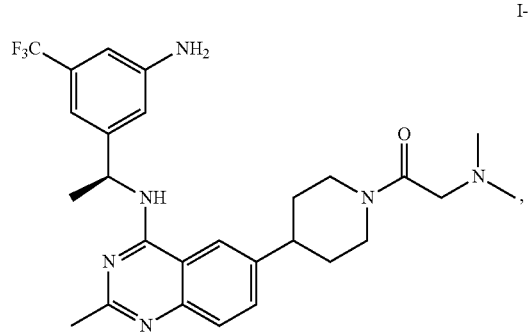
I-3134
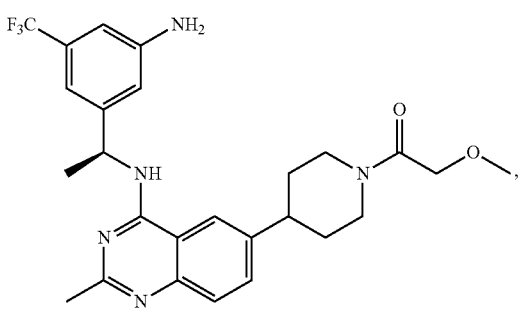
I-315
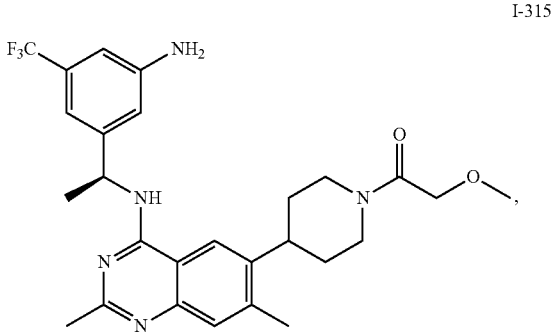
I-316
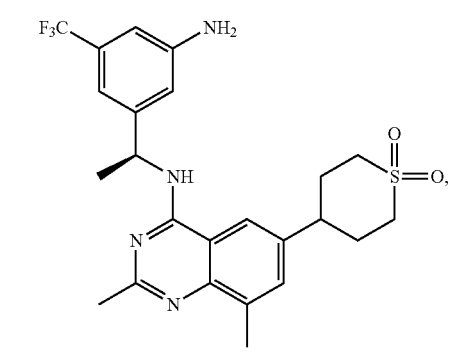
I-317
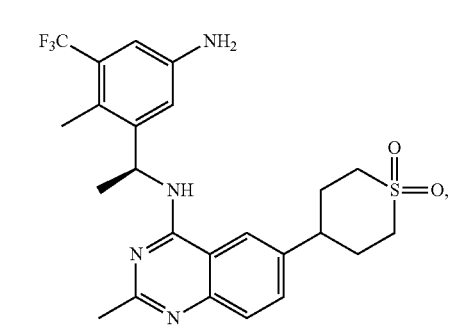

411
-continued
I-318
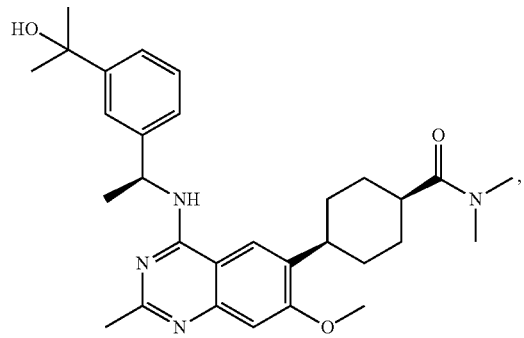
I-319
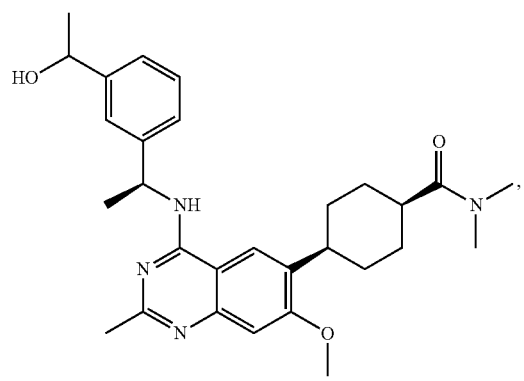
I-320
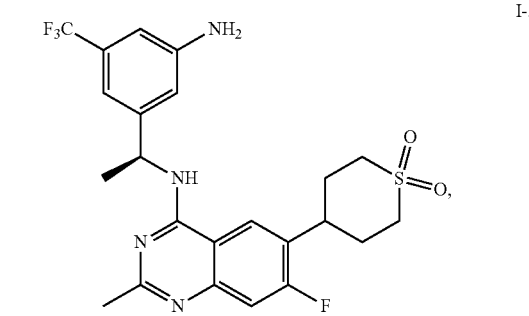
I-321
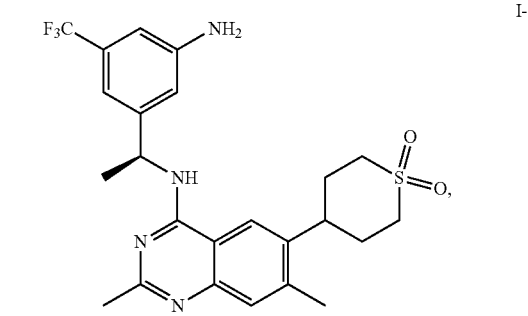
412
-continued
I-322
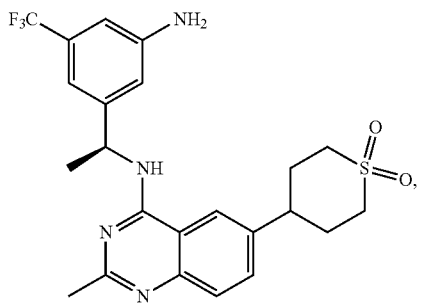
I-330
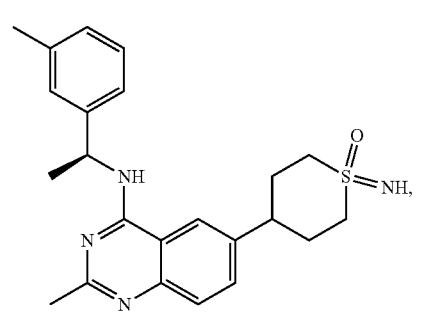
I-331
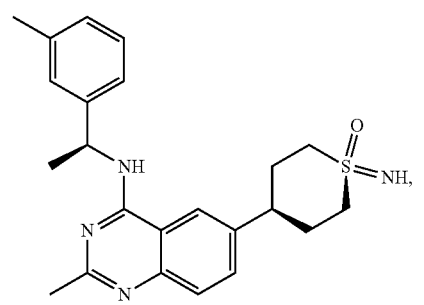
I-332
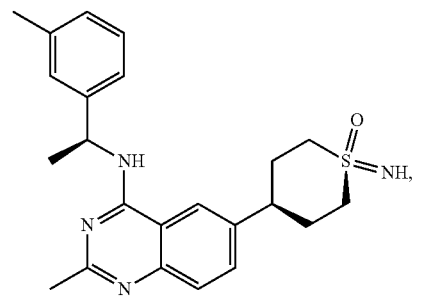
I-333
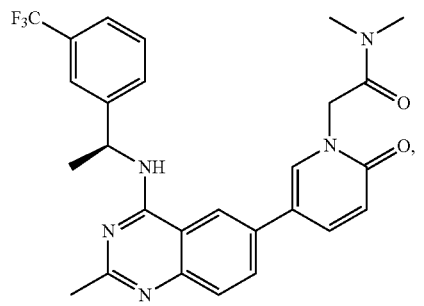

I-335 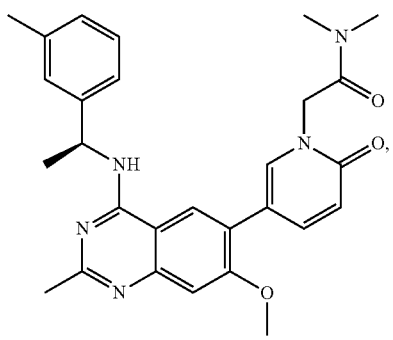
I-336 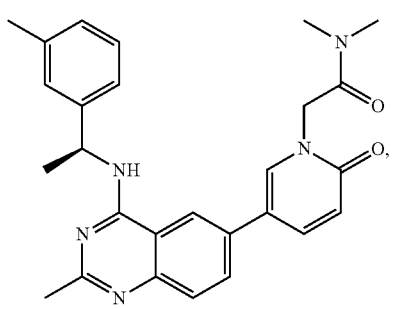
I-337 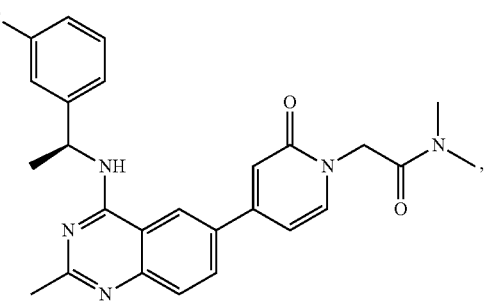
I-338 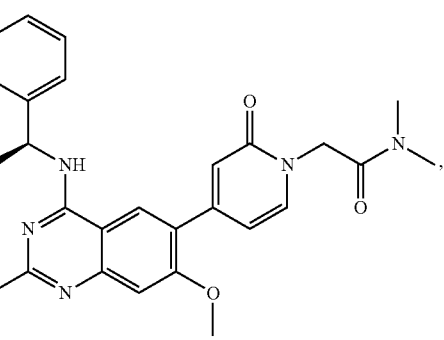
I-340 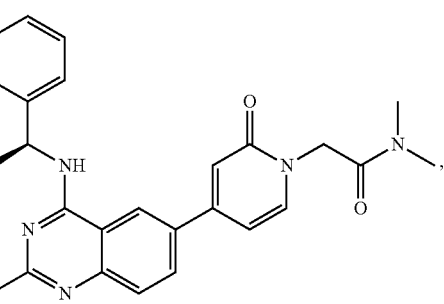
I-341 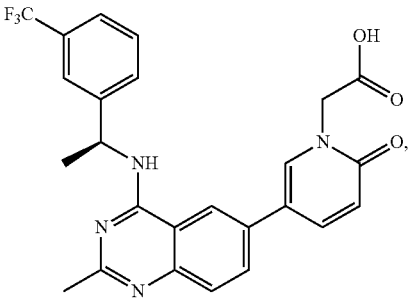
I-342 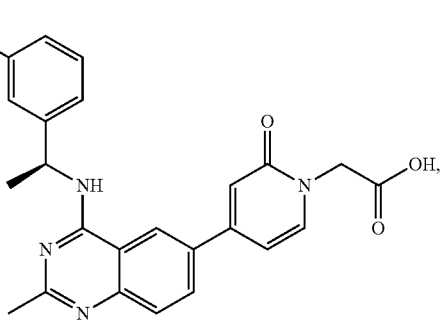
I-343 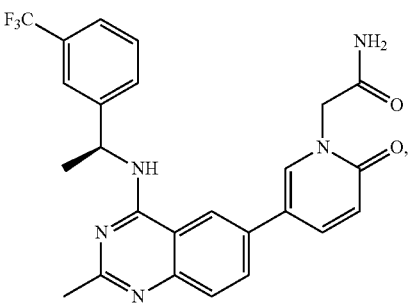
I-344 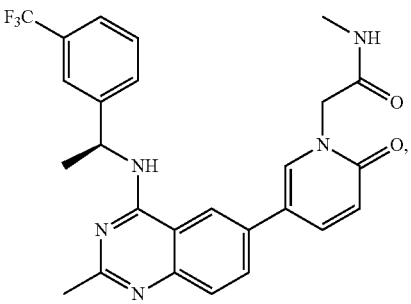
I-345 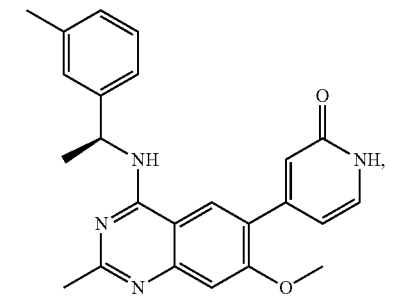

I-346
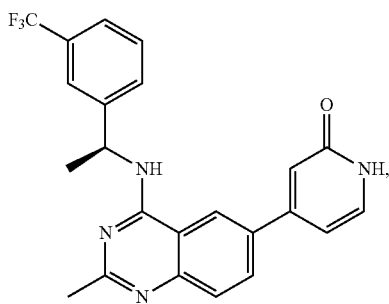
I-347
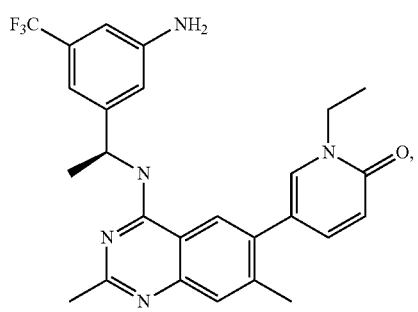
I-348
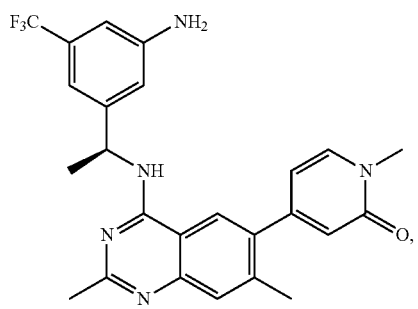
I-349
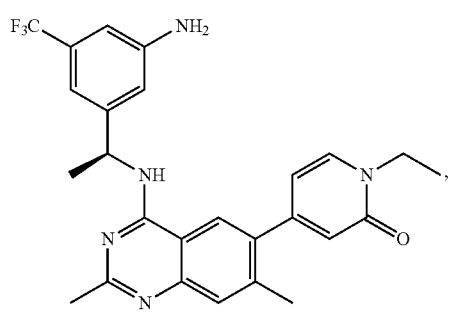
I-350
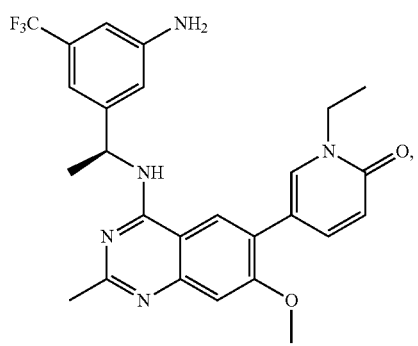
I-351
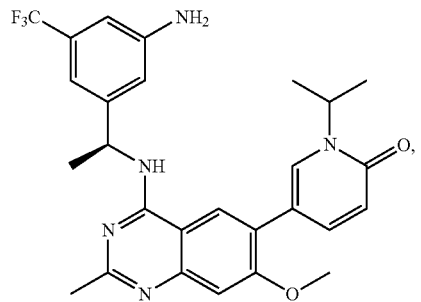
I-352
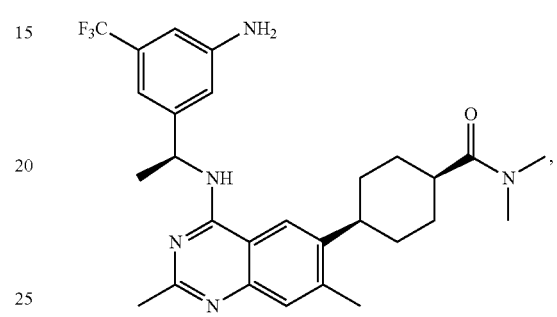
I-353
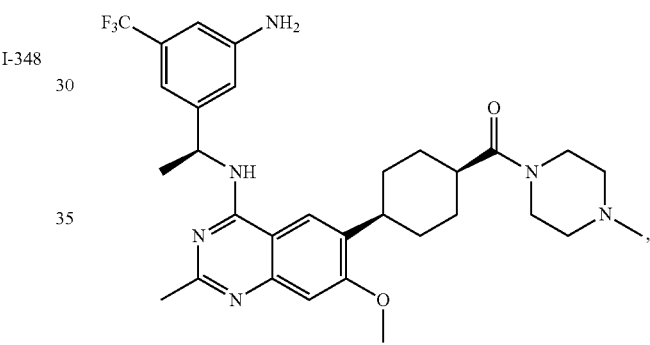
I-354
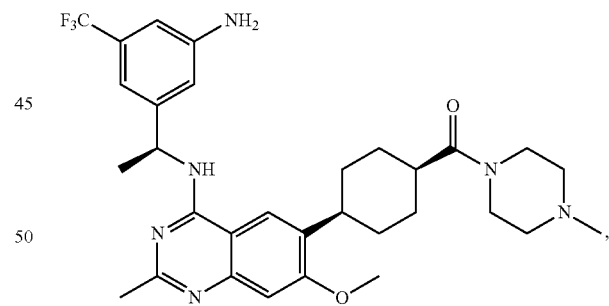
I-355
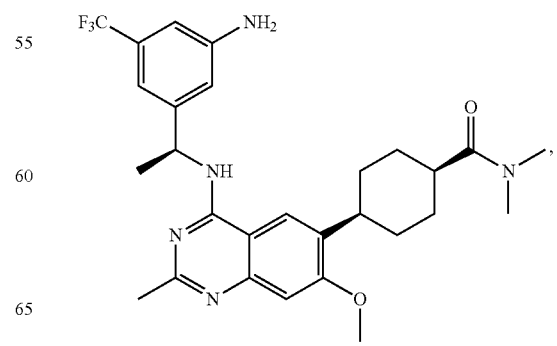

417
-continued
I-356
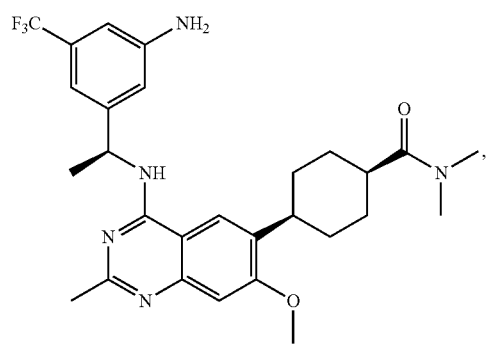
I-357
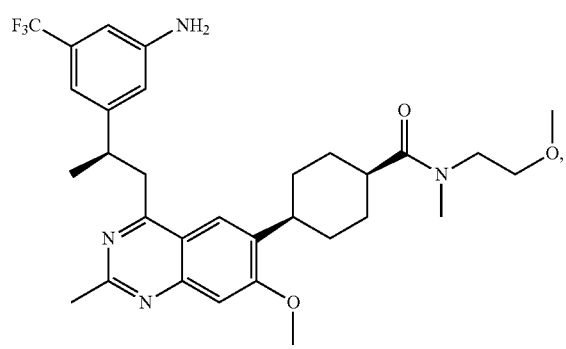
I-358
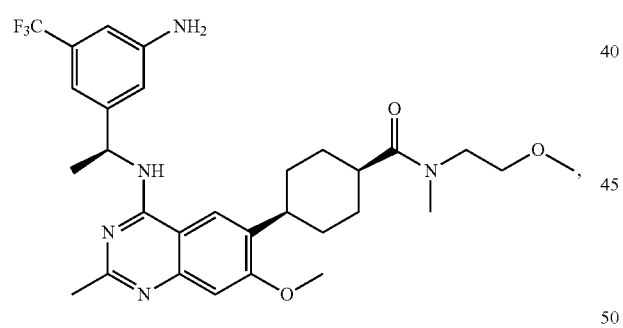
I-359
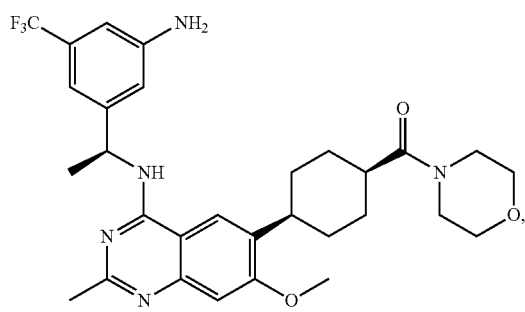
418
-continued
I-360
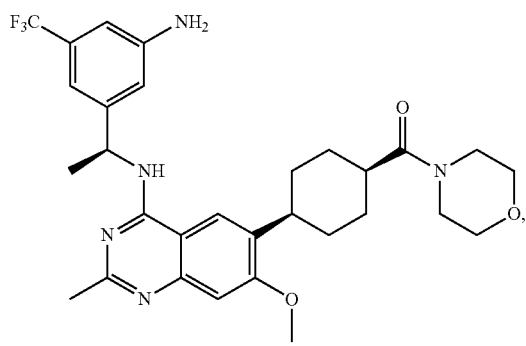
I-361
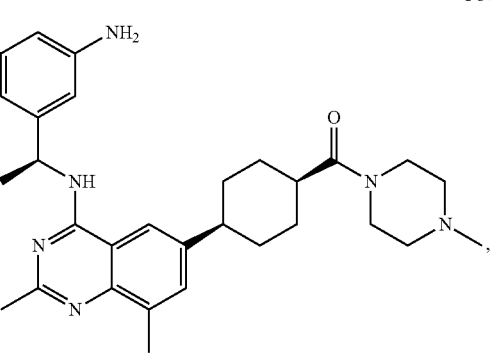
I-362
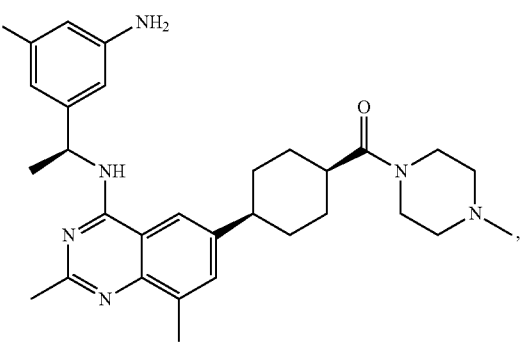
I-363
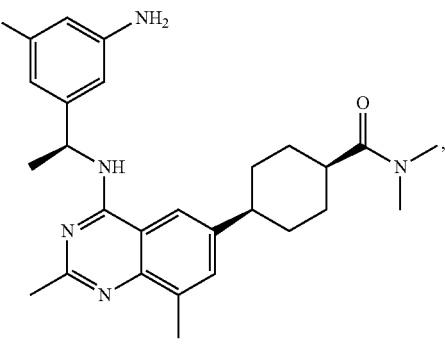

I-364
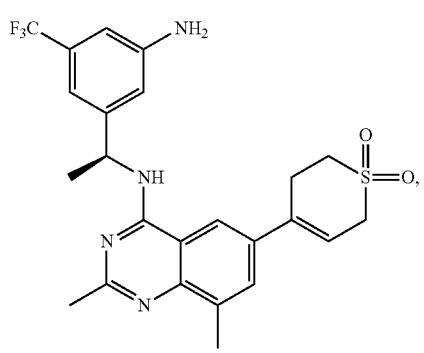
I-375
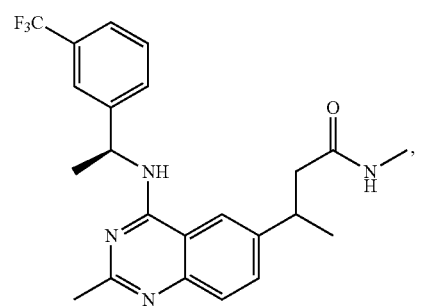
I-376
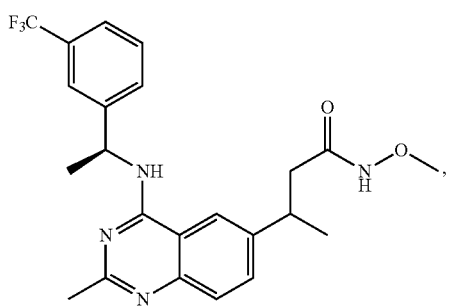
I-377
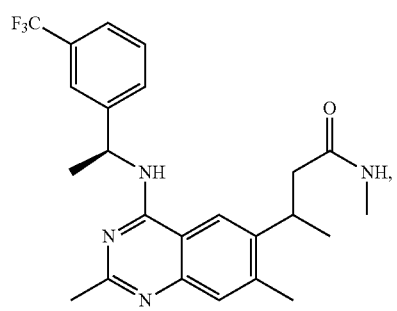
I-378
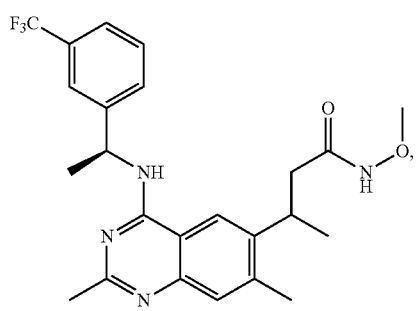
I-379
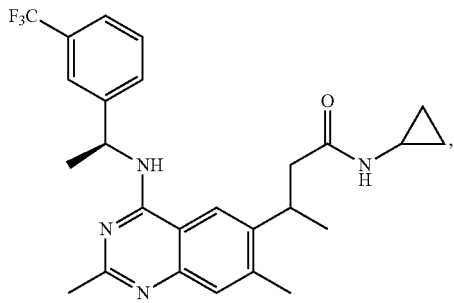
I-380
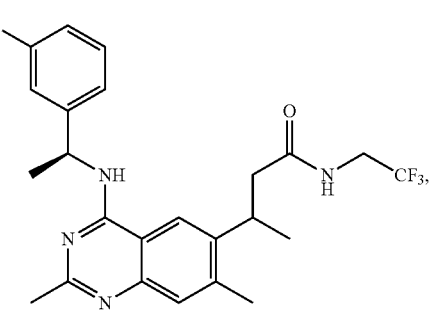
I-381
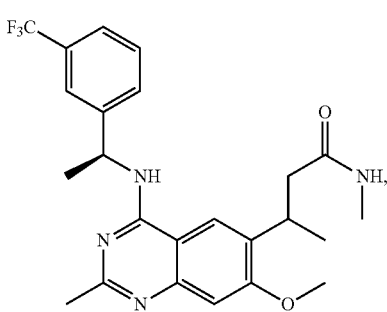
I-382
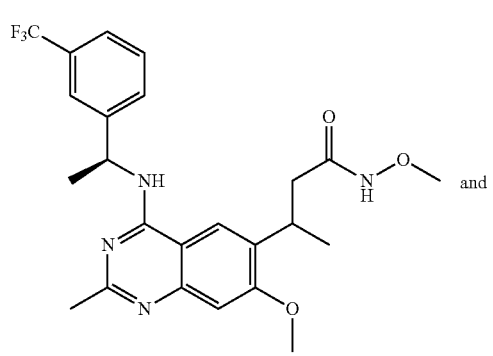
and
I-383
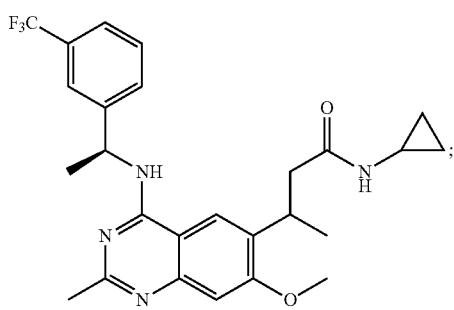
or a pharmaceutically acceptable salt thereof.
2. A method for the treatment of a disease and/or condition wherein the inhibition of the interaction of SOS1 and a RAS-family protein and/or RAC1 is of therapeutic benefit comprising administering to a patient a compound according to claim 1.

3. A method the treatment of cancer comprising administering to a patient a compound according to claim 1.

4. A method according to claim 2, wherein the disease and/or condition is selected from the group consisting of pancreatic cancer, lung cancer, colorectal cancer, cholangiocarcinoma, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas.

5. A method according to claim 2 for the treatment of a RASopathy (the RASopathy preferably selected from the group consisting of Neurofibromatosis type 1 (NF1), Noonan Syndrome (NS), Noonan Syndrome with Multiple Lentigines (NSML), Capillary Malformation-Arteriovenous Malformation Syndrome (CM-AVM), Costello Syndrome (CS), Cardio-Facio-Cutaneous Syndrome (CFC), Legius Syndrome and Hereditary gingival fibromatosis).

* * * * *